US012788808B2

(12) United States Patent
Stewart-Jones et al.

(10) Patent No.: US 12,788,808 B2
(45) Date of Patent: Nov. 10, 2026

(54) SARS-CoV-2 mRNA DOMAIN VACCINES

(71) Applicant: ModernaTX, Inc., Cambridge, MA (US)

(72) Inventors: Guillaume Stewart-Jones, Cambridge, MA (US); Andrea Carfi, Cambridge, MA (US); Sayda Mahgoub Elbashir, Cambridge, MA (US); Mihir Metkar, Cambridge, MA (US)

(73) Assignee: ModernaTX, Inc., Cambridge, MA (US)

( * ) Notice: Subject to any disclaimer, the term of this patent is extended or adjusted under 35 U.S.C. 154(b) by 880 days.

(21) Appl. No.: 17/797,784

(22) PCT Filed: Feb. 6, 2021

(86) PCT No.: PCT/US2021/016979

§ 371 (c)(1),
(2) Date: Aug. 5, 2022

(87) PCT Pub. No.: WO2021/159040

PCT Pub. Date: Aug. 12, 2021

(65) Prior Publication Data

US 2023/0346914 A1 Nov. 2, 2023

Related U.S. Application Data

(60) Provisional application No. 63/063,137, filed on Aug. 7, 2020, provisional application No. 63/044,330, filed on Jun. 25, 2020, provisional application No. 63/016,175, filed on Apr. 27, 2020, provisional application No. 62/971,825, filed on Feb. 7, 2020.

(51) Int. Cl.

| | |
|---|---|
| ***A61K 39/215*** | (2006.01) |
| ***A61K 39/00*** | (2006.01) |
| ***A61K 39/145*** | (2006.01) |
| ***A61K 47/10*** | (2017.01) |
| ***A61P 37/04*** | (2006.01) |

(52) U.S. Cl.

CPC .......... *A61K 39/215* (2013.01); *A61K 39/145* (2013.01); *A61K 47/10* (2013.01); *A61P 37/04* (2018.01); *A61K 2039/53* (2013.01)

(58) Field of Classification Search

CPC .... A61K 39/215; A61K 39/145; A61K 47/10; A61P 37/04; A61K 2039/53

See application file for complete search history.

(56) References Cited

U.S. PATENT DOCUMENTS

| | | | |
|---|---|---|---|
| 4,790,987 | A | 12/1988 | Compans et al. |
| 5,169,628 | A | 12/1992 | Wathen |
| 5,256,555 | A | 10/1993 | Milburn et al. |
| 5,427,782 | A | 6/1995 | Compans et al. |
| 5,756,264 | A | 5/1998 | Schwartz et al. |
| 5,824,497 | A | 10/1998 | Andrews et al. |
| 5,861,501 | A | 1/1999 | Benseler et al. |
| 5,989,911 | A | 11/1999 | Fournier et al. |
| 6,022,715 | A | 2/2000 | Merenkova et al. |
| 6,040,427 | A | 3/2000 | Locht et al. |
| 6,096,503 | A | 8/2000 | Sutcliffe et al. |
| 6,100,024 | A | 8/2000 | Hudson et al. |
| 6,225,091 | B1 | 5/2001 | Klein et al. |
| 6,500,419 | B1 | 12/2002 | Hone et al. |
| 6,514,948 | B1 | 2/2003 | Raz et al. |
| 6,528,262 | B1 | 3/2003 | Gilad et al. |
| 6,534,312 | B1 | 3/2003 | Shiver et al. |
| 6,610,044 | B2 | 8/2003 | Mathiesen |
| 6,652,886 | B2 | 11/2003 | Ahn et al. |
| 6,696,038 | B1 | 2/2004 | Mahato et al. |
| 6,924,365 | B1 | 8/2005 | Miller et al. |
| 7,001,890 | B1 | 2/2006 | Wagner et al. |
| 7,208,161 | B1 | 4/2007 | Murphy et al. |
| 7,316,925 | B2 | 1/2008 | Draghia-Akli et al. |
| 7,371,404 | B2 | 5/2008 | Panzner et al. |
| 7,449,324 | B2 | 11/2008 | Fouchier et al. |
| 7,491,397 | B2 | 2/2009 | Chong et al. |
| 7,531,342 | B2 | 5/2009 | Fouchier et al. |
| 7,566,454 | B2 | 7/2009 | Lu et al. |
| 7,671,186 | B2 | 3/2010 | Klein et al. |
| 7,704,720 | B2 | 4/2010 | Tang et al. |
| 7,776,523 | B2 | 8/2010 | Garcia et al. |
| 7,884,184 | B2 | 2/2011 | De Groot et al. |
| 7,943,168 | B2 | 5/2011 | Schlesinger et al. |
| 8,058,069 | B2 | 11/2011 | Yaworski et al. |

(Continued)

FOREIGN PATENT DOCUMENTS

| | | | |
|---|---|---|---|
| AU | 652831 | B2 | 9/1994 |
| AU | 2015210364 | A1 | 3/2017 |

(Continued)

OTHER PUBLICATIONS

Shamriz S. et al., "Effect of linker length and residues on the structure and stability of a fusion protein with malaria vaccine application", Comput Biol Med. Sep. 1, 2016:76:24-9 (Year: 2016).*

[No Author Listed], "2022 Breakthrough Prize in Life Sciences Awarded to Penn Medicine mRNA Pioneers Drew Weissman and Katalin Karikó," Press Release, Sep. 9, 2021, 3 pages.

[No Author Listed], "3rd International mRNA Health Conference Program," mRNA Conference, Berlin, Germany, Nov. 11, 2015, 28 pages.

[No Author Listed], "An Audience with Moncef Slaoui," Nat Rev Drug Discov., Jul. 1, 2015, 14:452-453.

(Continued)

*Primary Examiner* — Samira J Jean-Louis
*Assistant Examiner* — Peter Johansen
(74) *Attorney, Agent, or Firm* — Fish & Richardson P.C.

(57) ABSTRACT

The disclosure relates to coronavirus ribonucleic acid (RNA) vaccines as well as methods of using the vaccines and compositions comprising the vaccines. The RNA vaccines encode domains and subunits of coronavirus.

20 Claims, 11 Drawing Sheets

Specification includes a Sequence Listing.

(56) References Cited

U.S. PATENT DOCUMENTS

| | | | |
|---|---|---|---|
| 8,158,601 B2 | 4/2012 | Chen et al. | |
| 8,178,660 B2 | 5/2012 | Weiner et al. | |
| 8,217,016 B2 | 7/2012 | Hoerr et al. | |
| 8,252,289 B2 | 8/2012 | Eleouët et al. | |
| 8,278,036 B2 | 10/2012 | Kariko et al. | |
| 8,383,340 B2 | 2/2013 | Ketterer et al. | |
| 8,470,771 B2 | 6/2013 | Gao et al. | |
| 8,506,966 B2 | 8/2013 | Podda et al. | |
| 8,569,256 B2 | 10/2013 | Heyes et al. | |
| 8,609,142 B2 | 12/2013 | Troiano et al. | |
| 8,613,954 B2 | 12/2013 | Zale et al. | |
| 8,617,608 B2 | 12/2013 | Zale et al. | |
| 8,628,801 B2 | 1/2014 | Garreta et al. | |
| 8,642,076 B2 | 2/2014 | Manoharan et al. | |
| 8,658,354 B2 | 2/2014 | Kida et al. | |
| 8,663,599 B1 | 3/2014 | Sung et al. | |
| 8,691,223 B2 | 4/2014 | Van Den Brink et al. | |
| 8,691,750 B2 | 4/2014 | Constien et al. | |
| 8,691,966 B2 | 4/2014 | Kariko et al. | |
| 8,692,292 B2 | 4/2014 | Umeda et al. | |
| 8,710,200 B2 | 4/2014 | Schrum et al. | |
| 8,722,341 B2 | 5/2014 | Fouchier et al. | |
| 8,734,832 B2 | 5/2014 | O'Hagan et al. | |
| 8,734,853 B2 | 5/2014 | Sood et al. | |
| 8,754,062 B2 | 6/2014 | De Fougerolles et al. | |
| 8,822,663 B2 | 9/2014 | Schrum et al. | |
| 8,841,433 B2 | 9/2014 | Fouchier et al. | |
| 8,877,206 B2 | 11/2014 | Chen et al. | |
| 8,883,202 B2 | 11/2014 | Manoharan et al. | |
| 8,889,146 B2 | 11/2014 | Blais et al. | |
| 8,927,206 B2 | 1/2015 | De Jong et al. | |
| 8,927,692 B2 | 1/2015 | Weiner et al. | |
| 8,980,864 B2 | 3/2015 | Hoge et al. | |
| 8,999,380 B2 | 4/2015 | Bancel et al. | |
| 9,008,142 B2 | 4/2015 | Minneman et al. | |
| 9,018,089 B2 | 4/2015 | Liniger et al. | |
| 9,139,554 B2 | 9/2015 | Hope et al. | |
| 9,192,651 B2 | 11/2015 | Chakraborty et al. | |
| 9,192,661 B2 | 11/2015 | Jain et al. | |
| 9,220,683 B2 | 12/2015 | Manoharan et al. | |
| 9,221,891 B2 | 12/2015 | Bancel et al. | |
| 9,226,959 B2 | 1/2016 | Kramps et al. | |
| 9,234,013 B2 | 1/2016 | Thess et al. | |
| 9,271,996 B2 | 3/2016 | de Fougerolles et al. | |
| 9,283,287 B2 | 3/2016 | Bancel et al. | |
| 9,295,689 B2 | 3/2016 | de Fougerolles et al. | |
| 9,303,079 B2 | 4/2016 | Bancel et al. | |
| 9,376,726 B2 | 6/2016 | Fouchier et al. | |
| 9,464,124 B2 | 10/2016 | Bancel et al. | |
| 9,512,456 B2 | 12/2016 | Wang et al. | |
| 9,533,047 B2 | 1/2017 | de Fougerolles et al. | |
| 9,567,653 B2 | 2/2017 | Fouchier et al. | |
| 9,572,896 B2 | 2/2017 | Bancel et al. | |
| 9,597,380 B2 | 3/2017 | Chakraborty et al. | |
| 9,623,095 B2 | 4/2017 | Kallen et al. | |
| 9,629,804 B2 | 4/2017 | Heartlein et al. | |
| 9,669,089 B2 | 6/2017 | Thess et al. | |
| 9,675,668 B2 | 6/2017 | Bancel et al. | |
| 9,693,958 B2 | 7/2017 | Zhu | |
| 9,790,531 B2 | 10/2017 | Wang et al. | |
| 9,803,199 B2 | 10/2017 | Koizumi et al. | |
| 9,868,691 B2 | 1/2018 | Benenato et al. | |
| 9,872,900 B2 | 1/2018 | Ciaramella et al. | |
| 9,937,196 B2 | 4/2018 | Jain et al. | |
| 10,022,435 B2 | 7/2018 | Ciaramella et al. | |
| 10,023,626 B2 | 7/2018 | Bolen et al. | |
| 10,064,934 B2 | 9/2018 | Ciaramella et al. | |
| 10,064,935 B2 | 9/2018 | Ciaramella et al. | |
| 10,124,055 B2 | 11/2018 | Ciaramella et al. | |
| 10,207,010 B2 | 2/2019 | Besin et al. | |
| 10,232,055 B2 | 3/2019 | Kariko et al. | |
| 10,272,150 B2 | 4/2019 | Ciaramella et al. | |
| 10,273,269 B2 | 4/2019 | Ciaramella | |
| 10,286,086 B2 | 5/2019 | Roy et al. | |
| 10,323,076 B2 | 6/2019 | Ellsworth et al. | |
| 10,385,088 B2 | 8/2019 | Fraley et al. | |
| 10,449,244 B2 | 10/2019 | Ciaramella et al. | |
| 10,465,190 B1 | 11/2019 | Chen et al. | |
| 10,493,143 B2 | 12/2019 | Ciaramella et al. | |
| 10,526,629 B2 | 1/2020 | Rabideau et al. | |
| 10,543,269 B2 | 1/2020 | Ciaramella et al. | |
| 10,653,712 B2 | 5/2020 | Hoge | |
| 10,653,767 B2 | 5/2020 | Ciaramella et al. | |
| 10,695,419 B2 | 6/2020 | Ciaramella et al. | |
| 10,702,599 B2 | 7/2020 | Ciaramella et al. | |
| 10,702,600 B1 | 7/2020 | Ciaramella et al. | |
| 10,857,105 B2 | 12/2020 | Benenato et al. | |
| 10,906,944 B2 | 2/2021 | He et al. | |
| 10,912,826 B2 | 2/2021 | Thess et al. | |
| 10,925,958 B2 | 2/2021 | Ciaramella | |
| 10,933,127 B2 | 3/2021 | Ciaramella et al. | |
| 10,953,089 B1 * | 3/2021 | Smith | A61K 39/215 |
| 10,960,070 B2 | 3/2021 | Graham et al. | |
| 11,027,025 B2 | 6/2021 | Hoge et al. | |
| 11,045,540 B2 | 6/2021 | Ciaramella | |
| 11,103,578 B2 | 8/2021 | Ciaramella et al. | |
| 11,266,735 B2 | 3/2022 | Kallen et al. | |
| 11,351,242 B1 | 6/2022 | Lori et al. | |
| 11,384,352 B2 | 7/2022 | Miracco | |
| 11,406,703 B2 | 8/2022 | Kramarczyk et al. | |
| 11,421,248 B2 | 8/2022 | Ko | |
| 11,464,848 B2 | 10/2022 | Ciaramella et al. | |
| 11,485,960 B2 | 11/2022 | Dousis et al. | |
| 11,497,807 B2 | 11/2022 | Ciaramella et al. | |
| 11,547,673 B1 | 1/2023 | Sahin et al. | |
| 11,564,893 B2 | 1/2023 | Smith | |
| 11,566,051 B2 | 1/2023 | Zhang et al. | |
| 11,576,961 B2 | 2/2023 | Ciaramella et al. | |
| 11,638,693 B2 | 5/2023 | Geall | |
| 11,638,694 B2 | 5/2023 | Geall | |
| 11,643,441 B1 | 5/2023 | Ciaramella et al. | |
| 11,666,534 B2 | 6/2023 | Geall | |
| 11,696,946 B2 | 7/2023 | Ciaramella | |
| 11,752,206 B2 | 9/2023 | Ciaramella et al. | |
| 11,766,401 B2 | 9/2023 | Geall | |
| 11,786,467 B2 | 10/2023 | Geall | |
| 11,786,607 B2 | 10/2023 | Hoge et al. | |
| 11,851,694 B1 | 12/2023 | Mauger et al. | |
| 11,866,696 B2 | 1/2024 | Issa et al. | |
| 11,872,278 B2 | 1/2024 | Ciaramella et al. | |
| 11,905,525 B2 | 2/2024 | Brito et al. | |
| 11,911,453 B2 | 2/2024 | Ciaramella et al. | |
| 11,912,982 B2 | 2/2024 | Issa et al. | |
| 12,070,495 B2 | 8/2024 | Lusso et al. | |
| 12,133,899 B2 | 11/2024 | Sahin et al. | |
| 12,151,029 B2 | 11/2024 | Hennessy et al. | |
| 12,318,443 B2 | 6/2025 | Ciaramella | |
| 12,329,811 B2 | 6/2025 | Nachbagauer et al. | |
| 12,383,508 B2 | 8/2025 | Almarsson et al. | |
| 12,403,335 B2 | 9/2025 | Ciaramella et al. | |
| 12,453,766 B2 | 10/2025 | Ciaramella et al. | |
| 12,491,260 B2 | 12/2025 | Besin et al. | |
| 2001/0001066 A1 | 5/2001 | Cezayirli et al. | |
| 2001/0005506 A1 | 6/2001 | Cezayirli et al. | |
| 2002/0137720 A1 | 9/2002 | Ertl et al. | |
| 2003/0032615 A1 | 2/2003 | Felgner et al. | |
| 2003/0073619 A1 | 4/2003 | Mahato et al. | |
| 2003/0083272 A1 | 5/2003 | Wiederholt et al. | |
| 2003/0092653 A1 | 5/2003 | Kisich et al. | |
| 2003/0135040 A1 | 7/2003 | Eritja et al. | |
| 2003/0165849 A1 | 9/2003 | Zhang et al. | |
| 2003/0232061 A1 | 12/2003 | Fouchier et al. | |
| 2004/0005545 A1 | 1/2004 | Fouchier et al. | |
| 2004/0096451 A1 | 5/2004 | Young et al. | |
| 2004/0132683 A1 | 7/2004 | Felgner et al. | |
| 2004/0167090 A1 | 8/2004 | Monahan et al. | |
| 2005/0032730 A1 | 2/2005 | Von Der Mulbe et al. | |
| 2005/0059624 A1 | 3/2005 | Hoerr et al. | |
| 2005/0250723 A1 | 11/2005 | Hoerr et al. | |
| 2005/0287540 A1 | 12/2005 | Murphy et al. | |
| 2006/0002958 A1 | 1/2006 | Naylor et al. | |
| 2006/0024668 A1 | 2/2006 | Hoek | |
| 2006/0083780 A1 | 4/2006 | Heyes et al. | |
| 2006/0172003 A1 | 8/2006 | Meers et al. | |

(56) References Cited

U.S. PATENT DOCUMENTS

| | | | |
|---|---|---|---|
| 2006/0172966 | A1 | 8/2006 | Lipford et al. |
| 2006/0188490 | A1 | 8/2006 | Hoerr et al. |
| 2006/0217338 | A1 | 9/2006 | Lu et al. |
| 2006/0228367 | A1 | 10/2006 | Ulbrandt et al. |
| 2006/0247195 | A1 | 11/2006 | Ray |
| 2007/0105193 | A1 | 5/2007 | Vilalta et al. |
| 2007/0141030 | A1 | 6/2007 | Yu et al. |
| 2007/0252295 | A1 | 11/2007 | Panzner et al. |
| 2007/0280929 | A1 | 12/2007 | Hoerr et al. |
| 2007/0281336 | A1 | 12/2007 | Jendrisak et al. |
| 2007/0292453 | A1 | 12/2007 | Floyd et al. |
| 2008/0025914 | A1 | 1/2008 | Bjork |
| 2008/0025944 | A1 | 1/2008 | Hoerr et al. |
| 2008/0057080 | A1 | 3/2008 | Luke et al. |
| 2008/0076174 | A1 | 3/2008 | Selden et al. |
| 2008/0171079 | A1 | 7/2008 | Hanon et al. |
| 2008/0171711 | A1 | 7/2008 | Hoerr et al. |
| 2008/0220471 | A1 | 9/2008 | Davis et al. |
| 2008/0267873 | A1 | 10/2008 | Hoerr et al. |
| 2008/0274463 | A1 | 11/2008 | Chen et al. |
| 2009/0042825 | A1 | 2/2009 | Matar et al. |
| 2009/0093433 | A1 | 4/2009 | Woolf et al. |
| 2009/0104226 | A1 | 4/2009 | Perri et al. |
| 2009/0123529 | A1 | 5/2009 | Xiaomao |
| 2009/0148467 | A1 | 6/2009 | Friedman et al. |
| 2009/0162395 | A1 | 6/2009 | Crowe et al. |
| 2009/0286852 | A1 | 11/2009 | Kariko et al. |
| 2009/0304683 | A1 | 12/2009 | Dimitrov et al. |
| 2010/0015232 | A1 | 1/2010 | Besenbacher et al. |
| 2010/0028943 | A1 | 2/2010 | Thomas et al. |
| 2010/0047261 | A1 | 2/2010 | Hoerr et al. |
| 2010/0048883 | A1 | 2/2010 | Ketterer et al. |
| 2010/0068226 | A1 | 3/2010 | Taylor et al. |
| 2010/0112042 | A1 | 5/2010 | Polisky et al. |
| 2010/0130588 | A1 | 5/2010 | Yaworski et al. |
| 2010/0189729 | A1 | 7/2010 | Hoerr et al. |
| 2010/0203076 | A1 | 8/2010 | Fotin-Mleczek et al. |
| 2010/0239608 | A1 | 9/2010 | Von Der Mulbe et al. |
| 2010/0260817 | A1 | 10/2010 | Slobodkin et al. |
| 2010/0272747 | A1 | 10/2010 | Chow et al. |
| 2010/0273220 | A1 | 10/2010 | Yanik et al. |
| 2010/0285135 | A1 | 11/2010 | Wendorf et al. |
| 2010/0291156 | A1 | 11/2010 | Barner et al. |
| 2010/0303851 | A1 | 12/2010 | Hoerr et al. |
| 2010/0305196 | A1 | 12/2010 | Probst et al. |
| 2011/0045022 | A1 | 2/2011 | Tsai |
| 2011/0053829 | A1 | 3/2011 | Baumhof et al. |
| 2011/0065095 | A1 | 3/2011 | Kida et al. |
| 2011/0077287 | A1 | 3/2011 | Mulbe et al. |
| 2011/0086904 | A1 | 4/2011 | Russell |
| 2011/0135645 | A1 | 6/2011 | Williamson et al. |
| 2011/0143397 | A1 | 6/2011 | Kariko et al. |
| 2011/0143436 | A1 | 6/2011 | Dahl et al. |
| 2011/0184160 | A1 | 7/2011 | Weiner et al. |
| 2011/0200582 | A1 | 8/2011 | Baryza et al. |
| 2011/0244026 | A1 | 10/2011 | Guild et al. |
| 2011/0250225 | A1 | 10/2011 | Fotin-Mleczek et al. |
| 2011/0256175 | A1 | 10/2011 | Hope et al. |
| 2011/0269950 | A1 | 11/2011 | Von Der Mulbe et al. |
| 2011/0300205 | A1 | 12/2011 | Geall et al. |
| 2011/0311472 | A1 | 12/2011 | Hoerr et al. |
| 2012/0009221 | A1 | 1/2012 | Hoerr et al. |
| 2012/0021042 | A1 | 1/2012 | Panzner et al. |
| 2012/0027813 | A1 | 2/2012 | Podda et al. |
| 2012/0045471 | A1 | 2/2012 | Haller et al. |
| 2012/0046346 | A1 | 2/2012 | Rossi et al. |
| 2012/0053333 | A1 | 3/2012 | Mauro et al. |
| 2012/0058153 | A1 | 3/2012 | Ilyinskii et al. |
| 2012/0069014 | A1 | 3/2012 | Wong et al. |
| 2012/0101148 | A1 | 4/2012 | Aking et al. |
| 2012/0177701 | A1 | 7/2012 | Ilyinskii et al. |
| 2012/0177724 | A1 | 7/2012 | Irvine et al. |
| 2012/0178702 | A1 | 7/2012 | Huang et al. |
| 2012/0189700 | A1 | 7/2012 | Aguilar et al. |
| 2012/0195917 | A1 | 8/2012 | Sahin et al. |
| 2012/0213812 | A1 | 8/2012 | Lipford et al. |
| 2012/0213818 | A1 | 8/2012 | Hoerr et al. |
| 2012/0219573 | A1 | 8/2012 | Baumhof et al. |
| 2012/0237975 | A1 | 9/2012 | Schrum et al. |
| 2012/0252117 | A1 | 10/2012 | Selden et al. |
| 2012/0258046 | A1 | 10/2012 | Mutzke |
| 2012/0263648 | A1 | 10/2012 | Shapiro et al. |
| 2012/0276209 | A1 | 11/2012 | Cullis et al. |
| 2012/0295832 | A1 | 11/2012 | Constien et al. |
| 2012/0301955 | A1 | 11/2012 | Thomas et al. |
| 2013/0007828 | A1 | 1/2013 | Kister et al. |
| 2013/0017223 | A1 | 1/2013 | Hope et al. |
| 2013/0022538 | A1 | 1/2013 | Rossi |
| 2013/0064894 | A1 | 3/2013 | Martin et al. |
| 2013/0065942 | A1 | 3/2013 | Matar et al. |
| 2013/0078281 | A1 | 3/2013 | He et al. |
| 2013/0090372 | A1 | 4/2013 | Budzik et al. |
| 2013/0102034 | A1 | 4/2013 | Schrum et al. |
| 2013/0111615 | A1 | 5/2013 | Kariko et al. |
| 2013/0115274 | A1 | 5/2013 | Knopov et al. |
| 2013/0116307 | A1 | 5/2013 | Heyes et al. |
| 2013/0121988 | A1 | 5/2013 | Hoerr et al. |
| 2013/0123338 | A1 | 5/2013 | Heyes et al. |
| 2013/0129785 | A1 | 5/2013 | Manoharan et al. |
| 2013/0142818 | A1 | 6/2013 | Baumhof et al. |
| 2013/0149375 | A1 | 6/2013 | Geall |
| 2013/0150625 | A1 | 6/2013 | Budzik et al. |
| 2013/0156845 | A1 | 6/2013 | Manoharan et al. |
| 2013/0158021 | A1 | 6/2013 | Dong et al. |
| 2013/0164400 | A1 | 6/2013 | Knopov et al. |
| 2013/0171241 | A1 | 7/2013 | Geall |
| 2013/0177587 | A1 | 7/2013 | Robinson et al. |
| 2013/0177639 | A1 | 7/2013 | Geall et al. |
| 2013/0177640 | A1 | 7/2013 | Geall et al. |
| 2013/0178541 | A1 | 7/2013 | Stanton et al. |
| 2013/0183355 | A1 | 7/2013 | Jain et al. |
| 2013/0189351 | A1 | 7/2013 | Geall |
| 2013/0195867 | A1 | 8/2013 | Hoerr et al. |
| 2013/0195967 | A1 | 8/2013 | Guild et al. |
| 2013/0195968 | A1 | 8/2013 | Geall et al. |
| 2013/0195969 | A1 | 8/2013 | Geall et al. |
| 2013/0197068 | A1 | 8/2013 | Kariko et al. |
| 2013/0202645 | A1 | 8/2013 | Barner et al. |
| 2013/0202684 | A1 | 8/2013 | Geall et al. |
| 2013/0236533 | A1 | 9/2013 | Von Andrian et al. |
| 2013/0236974 | A1 | 9/2013 | De Fougerolles |
| 2013/0243848 | A1 | 9/2013 | Lobovkina et al. |
| 2013/0245103 | A1 | 9/2013 | de Fougerolles et al. |
| 2013/0245104 | A1 | 9/2013 | De Fougerolles et al. |
| 2013/0245107 | A1 | 9/2013 | De Fougerolles et al. |
| 2013/0259923 | A1 | 10/2013 | Bancel et al. |
| 2013/0266640 | A1 | 10/2013 | De Fougerolles et al. |
| 2013/0274504 | A1 | 10/2013 | Colletti et al. |
| 2013/0274523 | A1 | 10/2013 | Bawiec, III et al. |
| 2013/0280283 | A1 | 10/2013 | Lorenz et al. |
| 2013/0287832 | A1 | 10/2013 | O'Hagan et al. |
| 2013/0295043 | A1 | 11/2013 | Kallen et al. |
| 2013/0330401 | A1 | 12/2013 | Payne et al. |
| 2013/0336998 | A1 | 12/2013 | Kallen et al. |
| 2014/0024076 | A1 | 1/2014 | Tang et al. |
| 2014/0037660 | A1 | 2/2014 | Folin-Mleczek et al. |
| 2014/0039032 | A1 | 2/2014 | Kuboyama et al. |
| 2014/0044772 | A1 | 2/2014 | MacLachlan et al. |
| 2014/0044791 | A1 | 2/2014 | Basilion et al. |
| 2014/0045913 | A1 | 2/2014 | Kuboyama et al. |
| 2014/0050759 | A1 | 2/2014 | Falkner et al. |
| 2014/0065204 | A1 | 3/2014 | Hayes et al. |
| 2014/0065228 | A1 | 3/2014 | Yaworski et al. |
| 2014/0105966 | A1 | 4/2014 | Bancel et al. |
| 2014/0112950 | A1 | 4/2014 | Singh et al. |
| 2014/0121393 | A1 | 5/2014 | Manoharan et al. |
| 2014/0127248 | A1 | 5/2014 | Ross et al. |
| 2014/0134129 | A1 | 5/2014 | Thalhamer et al. |
| 2014/0134201 | A1 | 5/2014 | Tureci et al. |
| 2014/0141042 | A1 | 5/2014 | Vitelli et al. |
| 2014/0141070 | A1 | 5/2014 | Geall et al. |
| 2014/0142290 | A1 | 5/2014 | Madden et al. |
| 2014/0147432 | A1 | 5/2014 | Bancel et al. |
| 2014/0147454 | A1 | 5/2014 | Chakraborty et al. |

(56) References Cited

U.S. PATENT DOCUMENTS

2014/0148502 A1 5/2014 Bancel et al.
2014/0193482 A1 7/2014 Bancel et al.
2014/0193484 A1 7/2014 Bertholet Girardin et al.
2014/0200257 A1 7/2014 Rajeev et al.
2014/0206752 A1 7/2014 Afeyan et al.
2014/0212498 A1 7/2014 Brito et al.
2014/0220083 A1 8/2014 Brito et al.
2014/0227346 A1 8/2014 Geall et al.
2014/0242152 A1 8/2014 Geall et al.
2014/0248314 A1 9/2014 Swanson et al.
2014/0248320 A1 9/2014 Tsai
2014/0255472 A1 9/2014 Geall et al.
2014/0271699 A1 9/2014 Kwong et al.
2014/0271829 A1 9/2014 Lilja et al.
2014/0275227 A1 9/2014 Hoge et al.
2014/0302079 A1 10/2014 Nabel et al.
2014/0308304 A1 10/2014 Manoharan et al.
2014/0328825 A1 11/2014 Meis et al.
2014/0348924 A1 11/2014 Pascolo
2014/0370497 A1 12/2014 Fouchier et al.
2014/0378538 A1 12/2014 Bancel
2015/0030622 A1 1/2015 Marshall et al.
2015/0030669 A1 1/2015 Platscher et al.
2015/0051268 A1 2/2015 Bancel et al.
2015/0056253 A1 2/2015 Bancel et al.
2015/0064233 A1 3/2015 Shih et al.
2015/0079121 A1 3/2015 Weiner et al.
2015/0086612 A1 3/2015 Sahin et al.
2015/0086613 A1 3/2015 DeRosa et al.
2015/0093413 A1 4/2015 Thess et al.
2015/0118183 A1 4/2015 Baumhof
2015/0118264 A1 4/2015 Baumhof et al.
2015/0126589 A1 5/2015 Geiger et al.
2015/0140027 A1 5/2015 Cardosa et al.
2015/0141499 A1 5/2015 Bancel et al.
2015/0184195 A1 7/2015 Thess et al.
2015/0202153 A1 7/2015 Frank et al.
2015/0203446 A1 7/2015 Manoharan et al.
2015/0307542 A1 10/2015 Roy et al.
2015/0315541 A1 11/2015 Bancel et al.
2015/0335728 A1 11/2015 Wong et al.
2015/0376115 A1 12/2015 Ansell et al.
2016/0022580 A1 1/2016 Ramsay et al.
2016/0022806 A1 1/2016 Weiner et al.
2016/0024139 A1 1/2016 Berlanda Scorza et al.
2016/0024140 A1 1/2016 Issa et al.
2016/0024141 A1 1/2016 Issa et al.
2016/0032273 A1 2/2016 Shahrokh et al.
2016/0032284 A1 2/2016 Chen et al.
2016/0032316 A1 2/2016 Weissman et al.
2016/0038612 A1 2/2016 Hoge et al.
2016/0039884 A1 2/2016 Li et al.
2016/0046675 A1 2/2016 Kwong et al.
2016/0151284 A1 6/2016 Heyes et al.
2016/0151474 A1 6/2016 Kallen et al.
2016/0166678 A1 6/2016 Kallen et al.
2016/0194368 A1 7/2016 Hoge et al.
2016/0194625 A1 7/2016 Hoge et al.
2016/0243221 A1 8/2016 Hoge et al.
2016/0271272 A1 9/2016 Bancel et al.
2016/0296617 A1 10/2016 Jiang et al.
2016/0317647 A1 11/2016 Ciaramella et al.
2016/0331828 A1 11/2016 Ciaramella et al.
2016/0331844 A1 11/2016 Fotin-Mleczek et al.
2016/0361411 A1 12/2016 Gindy et al.
2016/0376224 A1 12/2016 Du et al.
2016/0376321 A1 12/2016 Hotez et al.
2017/0002041 A1 1/2017 Hauser et al.
2017/0009244 A1 1/2017 Sahin et al.
2017/0016026 A1* 1/2017 Florkiewicz ........... A61K 39/00
2017/0043037 A1 2/2017 Kariko et al.
2017/0065675 A1 3/2017 Bancel et al.
2017/0130255 A1 5/2017 Wang et al.
2017/0202979 A1 7/2017 Chakraborty et al.
2017/0204152 A1 7/2017 Nelson et al.
2017/0210697 A1 7/2017 Benenato et al.
2017/0210698 A1 7/2017 Benenato et al.
2017/0224844 A1* 8/2017 Benenato ................ A61P 25/00
2017/0239371 A1 8/2017 Guild et al.
2017/0340724 A1 11/2017 Ciaramella et al.
2017/0340725 A1 11/2017 Ciaramella et al.
2018/0000953 A1 1/2018 Almarsson et al.
2018/0002393 A1 1/2018 Bancel et al.
2018/0008694 A1 1/2018 Ciaramella et al.
2018/0021258 A1 1/2018 Graham et al.
2018/0028645 A1 2/2018 Ciaramella et al.
2018/0028664 A1 2/2018 Besin et al.
2018/0147298 A1 5/2018 Besin et al.
2018/0161422 A1 6/2018 Probst et al.
2018/0237849 A1 8/2018 Thompson
2018/0243225 A1 8/2018 Ciaramella
2018/0243230 A1 8/2018 Smith
2018/0244756 A1 8/2018 Graham
2018/0256628 A1 9/2018 Hoge et al.
2018/0271795 A1 9/2018 Martini et al.
2018/0271970 A1 9/2018 Ciaramella et al.
2018/0273977 A1 9/2018 Mousavi et al.
2018/0274009 A1 9/2018 Marquardt et al.
2018/0280496 A1 10/2018 Ciaramella et al.
2018/0289792 A1 10/2018 Ciaramella et al.
2018/0296663 A1 10/2018 Hipp et al.
2018/0303925 A1 10/2018 Weissman et al.
2018/0303929 A1 10/2018 Ciaramella et al.
2018/0311336 A1 11/2018 Ciaramella et al.
2018/0311343 A1 11/2018 Huang et al.
2018/0312549 A1 11/2018 Ciaramella
2018/0318409 A1 11/2018 Valiante et al.
2018/0326039 A1 11/2018 Haruta
2018/0334480 A1 11/2018 Gershoni
2018/0351057 A1 12/2018 Bollman et al.
2018/0351843 A1 12/2018 Bollman et al.
2018/0363019 A1 12/2018 Hoge
2018/0369374 A1 12/2018 Frederick et al.
2018/0371047 A1 12/2018 Ticho et al.
2019/0002890 A1 1/2019 Martini et al.
2019/0008938 A1 1/2019 Ciaramella et al.
2019/0008948 A1 1/2019 Ciaramella et al.
2019/0015501 A1 1/2019 Ciaramella et al.
2019/0085368 A1 3/2019 Bancel et al.
2019/0099481 A1 4/2019 Ciaramella et al.
2019/0125839 A1 5/2019 Frederick et al.
2019/0167811 A1 6/2019 Benenato et al.
2019/0175517 A1 6/2019 Martini et al.
2019/0175727 A1 6/2019 Huang et al.
2019/0192646 A1 6/2019 Cohen et al.
2019/0192653 A1 6/2019 Hoge et al.
2019/0240317 A1 8/2019 Ciaramella et al.
2019/0241633 A1 8/2019 Fotin-Mleczek et al.
2019/0274968 A1* 9/2019 Weissman .............. A61K 39/21
2019/0275170 A1 9/2019 Benenato et al.
2019/0298657 A1 10/2019 Martini et al.
2019/0298658 A1 10/2019 Benenato
2019/0300906 A1 10/2019 Martini et al.
2019/0309337 A1 10/2019 Rabideau et al.
2019/0314292 A1 10/2019 Benenato et al.
2019/0314493 A1 10/2019 Ciaramella et al.
2019/0328865 A1 10/2019 Du et al.
2019/0336452 A1 11/2019 Brader
2019/0336595 A1 11/2019 Ciaramella
2019/0351040 A1 11/2019 Valiante et al.
2019/0351047 A1 11/2019 Jasny et al.
2019/0351048 A1* 11/2019 Rauch .................. C07K 14/165
2019/0382774 A1 12/2019 Hoge et al.
2019/0390181 A1 12/2019 Benenato et al.
2020/0030432 A1 1/2020 Ciaramella et al.
2020/0032274 A1 1/2020 Mauger et al.
2020/0038499 A1 2/2020 Narayanan et al.
2020/0054737 A1 2/2020 Ciaramella et al.
2020/0061185 A1 2/2020 Graham et al.
2020/0069599 A1 3/2020 Smith et al.
2020/0069793 A1 3/2020 Ciaramella
2020/0069794 A1 3/2020 Ciaramella et al.
2020/0071689 A1 3/2020 Miracco
2020/0085916 A1 3/2020 Martini et al.

(56) References Cited

U.S. PATENT DOCUMENTS

| | | | |
|---|---|---|---|
| 2020/0109420 | A1 | 4/2020 | Brito et al. |
| 2020/0129445 | A1 | 4/2020 | Patel et al. |
| 2020/0129608 | A1 | 4/2020 | Ciaramella et al. |
| 2020/0129615 | A1 | 4/2020 | Ciaramella et al. |
| 2020/0163878 | A1 | 5/2020 | Baumhof et al. |
| 2020/0239869 | A1 | 7/2020 | Issa et al. |
| 2020/0254086 | A1 | 8/2020 | Hoge et al. |
| 2020/0282046 | A1 | 9/2020 | Ciaramella et al. |
| 2020/0282047 | A1 | 9/2020 | Ciaramella et al. |
| 2020/0297634 | A1 | 9/2020 | Karmali et al. |
| 2020/0306191 | A1 | 10/2020 | Schariter et al. |
| 2020/0338004 | A1 | 10/2020 | Hansson et al. |
| 2020/0368162 | A1 | 11/2020 | Martini |
| 2020/0368343 | A1 | 11/2020 | Ciaramella et al. |
| 2020/0399322 | A1 | 12/2020 | Baumhof et al. |
| 2020/0405844 | A1 | 12/2020 | Ciaramella et al. |
| 2020/0407402 | A1 | 12/2020 | He et al. |
| 2021/0023199 | A1 | 1/2021 | Kallen et al. |
| 2021/0030866 | A1 | 2/2021 | Kallen et al. |
| 2021/0046173 | A1 | 2/2021 | Ciaramella et al. |
| 2021/0060175 | A1 | 3/2021 | Baumhof et al. |
| 2021/0087135 | A1 | 3/2021 | Benenato et al. |
| 2021/0128716 | A1 | 5/2021 | Probst et al. |
| 2021/0139543 | A1 | 5/2021 | He et al. |
| 2021/0145982 | A1 | 5/2021 | Hoge et al. |
| 2021/0162037 | A1 | 6/2021 | Jasny et al. |
| 2021/0163919 | A1 | 6/2021 | Issa et al. |
| 2021/0187097 | A1 | 6/2021 | Ciaramella et al. |
| 2021/0206818 | A1 | 7/2021 | Huang et al. |
| 2021/0217484 | A1 | 7/2021 | Giessel et al. |
| 2021/0220467 | A1 | 7/2021 | Ciaramella et al. |
| 2021/0228707 | A1 | 7/2021 | Mektar et al. |
| 2021/0228708 | A1 | 7/2021 | Smith et al. |
| 2021/0268086 | A1 | 9/2021 | Zhong et al. |
| 2021/0268102 | A1 | 9/2021 | Yan et al. |
| 2021/0275665 | A1 | 9/2021 | Cho |
| 2021/0309976 | A1 | 10/2021 | Dousis et al. |
| 2021/0322541 | A1 | 10/2021 | Akahata et al. |
| 2021/0340225 | A1 | 11/2021 | Grosveld et al. |
| 2021/0378980 | A1 | 12/2021 | Horhota et al. |
| 2021/0379181 | A1 | 12/2021 | Rauch et al. |
| 2022/0031631 | A1 | 2/2022 | Almarsson et al. |
| 2022/0047518 | A1 | 2/2022 | Hennessy et al. |
| 2022/0054653 | A1 | 2/2022 | Martini et al. |
| 2022/0062175 | A1 | 3/2022 | Smith et al. |
| 2022/0062408 | A1 | 3/2022 | Kramarczyk et al. |
| 2022/0125899 | A1 | 4/2022 | Ashburn et al. |
| 2022/0145381 | A1 | 5/2022 | Elich et al. |
| 2022/0175906 | A1 | 6/2022 | Ciaramella et al. |
| 2022/0193223 | A1 | 6/2022 | Ciaramella et al. |
| 2022/0211838 | A1 | 7/2022 | Oostvogels et al. |
| 2022/0236253 | A1 | 7/2022 | Hopson |
| 2022/0241399 | A1 | 8/2022 | Lusso et al. |
| 2022/0257746 | A1 | 8/2022 | Ciaramella et al. |
| 2022/0347292 | A1 | 11/2022 | Panther et al. |
| 2022/0348900 | A1 | 11/2022 | Shamashkin et al. |
| 2022/0349006 | A1 | 11/2022 | Amato et al. |
| 2022/0370616 | A1 | 11/2022 | Hennessy |
| 2022/0378904 | A1 | 12/2022 | Panther et al. |
| 2022/0401551 | A1 | 12/2022 | Kramarczyk et al. |
| 2022/0409720 | A1 | 12/2022 | Ciaramella |
| 2023/0000970 | A1 | 1/2023 | Nachbagauer et al. |
| 2023/0020362 | A1 | 1/2023 | Ciaramella et al. |
| 2023/0044692 | A1 | 2/2023 | Ciaramella et al. |
| 2023/0090422 | A1 | 3/2023 | Zhang et al. |
| 2023/0114180 | A1 | 4/2023 | Ciaramella et al. |
| 2023/0116376 | A1 | 4/2023 | Ciaramella |
| 2023/0141153 | A1 | 5/2023 | Zhang et al. |
| 2023/0142529 | A1 | 5/2023 | White et al. |
| 2023/0142780 | A1 | 5/2023 | Stedman et al. |
| 2023/0173060 | A1 | 6/2023 | Benmohamed |
| 2023/0181481 | A1 | 6/2023 | White et al. |
| 2023/0190761 | A1 | 6/2023 | Brader et al. |
| 2023/0212645 | A1 | 7/2023 | Marquardt et al. |
| 2023/0270836 | A1 | 8/2023 | Ciaramella et al. |
| 2023/0285539 | A1* | 9/2023 | Joyce ..................... A61K 39/12 |
| 2023/0287437 | A1 | 9/2023 | Smith et al. |
| 2023/0303632 | A1 | 9/2023 | Ciaramella |
| 2023/0310576 | A1 | 10/2023 | Ciaramella et al. |
| 2023/0338506 | A1 | 10/2023 | Shaw et al. |
| 2023/0338512 | A1 | 10/2023 | Muik et al. |
| 2023/0346907 | A1 | 11/2023 | Ciaramella et al. |
| 2023/0346914 | A1 | 11/2023 | Stewart-Jones et al. |
| 2023/0355743 | A1 | 11/2023 | Stewart-Jones et al. |
| 2023/0374079 | A1 | 11/2023 | Ciaramella |
| 2023/0381301 | A1 | 11/2023 | Ciaramella et al. |
| 2023/0390379 | A1 | 12/2023 | Ciaramella et al. |
| 2024/0000917 | A1 | 1/2024 | Ciaramella |
| 2024/0100145 | A1 | 3/2024 | Bollman et al. |
| 2024/0100151 | A1 | 3/2024 | Carfi et al. |
| 2024/0139309 | A1 | 5/2024 | Carfi et al. |
| 2024/0156952 | A1 | 5/2024 | Ciaramella et al. |
| 2024/0173400 | A1 | 5/2024 | Ciaramella et al. |
| 2024/0181030 | A1 | 6/2024 | Himansu et al. |
| 2024/0207392 | A1 | 6/2024 | Chandramouli et al. |
| 2024/0209068 | A1 | 6/2024 | Deal et al. |
| 2024/0216500 | A1 | 7/2024 | Nachbagauer et al. |
| 2024/0226028 | A1 | 7/2024 | Goldman et al. |
| 2024/0226277 | A1 | 7/2024 | Nachbagauer et al. |
| 2024/0229109 | A1 | 7/2024 | Rabideau et al. |
| 2024/0238211 | A1 | 7/2024 | Brader et al. |
| 2024/0263226 | A1 | 8/2024 | Schmitt |
| 2024/0277831 | A1 | 8/2024 | King et al. |
| 2024/0285754 | A1 | 8/2024 | Stewart-Jones |
| 2024/0293534 | A1 | 9/2024 | Stewart-Jones |
| 2024/0299525 | A1 | 9/2024 | Ciaramella et al. |
| 2024/0299531 | A1 | 9/2024 | Stewart-Jones |
| 2024/0335526 | A1 | 10/2024 | Ciaramella et al. |
| 2024/0358819 | A1 | 10/2024 | Stewart-Jones |
| 2024/0366745 | A1 | 11/2024 | Ciaramella et al. |
| 2024/0382581 | A1 | 11/2024 | Stewart-Jones |
| 2024/0398927 | A9 | 12/2024 | Ciaramella et al. |
| 2025/0041407 | A1 | 2/2025 | Ciaramella |
| 2025/0067729 | A1 | 2/2025 | Brader |
| 2025/0073327 | A1 | 3/2025 | Lusso et al. |
| 2025/0082748 | A1 | 3/2025 | Ciaramella et al. |
| 2025/0099569 | A1 | 3/2025 | Ciaramella et al. |
| 2025/0121220 | A1 | 4/2025 | Ciaramella et al. |
| 2025/0121221 | A1 | 4/2025 | Ciaramella et al. |
| 2025/0281418 | A1 | 9/2025 | Smith |
| 2025/0360194 | A1 | 11/2025 | Bahl et al. |

FOREIGN PATENT DOCUMENTS

| | | | |
|---|---|---|---|
| CA | 2473135 | A1 | 6/2003 |
| CA | 3194325 | A1 | 5/2022 |
| CN | 102076847 | A | 5/2011 |
| CN | 102177236 | A | 9/2011 |
| CN | 102573901 | A | 7/2012 |
| CN | 106244608 | A | 12/2016 |
| CN | 108366604 | A | 8/2018 |
| CN | 110951756 | A | 4/2020 |
| CN | 110974950 | A | 4/2020 |
| CN | 110974954 | A | 4/2020 |
| CN | 111032863 | A | 4/2020 |
| CN | 111088283 | A | 5/2020 |
| CN | 111218458 | A | 6/2020 |
| CN | 111218459 | A | 6/2020 |
| CN | 111303254 | A | 6/2020 |
| CN | 111518175 | A | 8/2020 |
| CN | 111592602 | A | 8/2020 |
| CN | 111848753 | A | 10/2020 |
| CN | 111939250 | A | 11/2020 |
| CN | 111978377 | A | 11/2020 |
| CN | 112023035 | A | 12/2020 |
| CN | 112028976 | A | 12/2020 |
| CN | 112043825 | A | 12/2020 |
| CN | 112048005 | A | 12/2020 |
| CN | 112094327 | A | 12/2020 |
| CN | 112220920 | A | 1/2021 |
| CN | 112226445 | A | 1/2021 |
| CN | 112266411 | A | 1/2021 |
| CN | 112321688 | A | 2/2021 |
| CN | 112358533 | A | 2/2021 |

(56) References Cited

FOREIGN PATENT DOCUMENTS

| | | | |
|---|---|---|---|
| CN | 112480217 | A | 3/2021 |
| CN | 112546211 | A | 3/2021 |
| CN | 112626089 | A | 4/2021 |
| CN | 112794884 | A | 5/2021 |
| CN | 113999128 | A | 2/2022 |
| EP | 0204401 | A1 | 12/1986 |
| EP | 1026253 | A2 | 8/2000 |
| EP | 1083232 | A1 | 3/2001 |
| EP | 1383556 | A1 | 1/2004 |
| EP | 1083232 | B1 | 2/2005 |
| EP | 1619254 | A1 | 1/2006 |
| EP | 1301614 | B1 | 11/2006 |
| EP | 1383556 | B1 | 10/2007 |
| EP | 1905844 | A2 | 2/2008 |
| EP | 2092064 | B1 | 9/2010 |
| EP | 1619254 | B1 | 12/2010 |
| EP | 1026253 | B2 | 12/2012 |
| EP | 2188379 | B1 | 1/2013 |
| EP | 2548960 | A1 | 1/2013 |
| EP | 3083578 | A1 | 10/2016 |
| EP | 2548960 | B1 | 1/2018 |
| EP | 3452101 | A2 | 3/2019 |
| EP | 3608308 | A | 2/2020 |
| EP | 3901261 | A1 | 10/2021 |
| EP | 4008357 | B1 | 12/2022 |
| JP | 2008-500399 | A | 1/2008 |
| JP | 2014-504634 | A | 2/2014 |
| JP | 2015-518472 | A | 7/2015 |
| JP | 2016-515815 | A | 6/2016 |
| JP | 2016-539944 | A | 12/2016 |
| JP | 2017-513956 | A | 6/2018 |
| JP | 7438604 | B2 | 2/2024 |
| WO | WO 1987/005326 | A1 | 9/1987 |
| WO | WO 1990/011092 | A2 | 10/1990 |
| WO | WO 1992/019752 | A1 | 11/1992 |
| WO | WO 1993/014778 | A1 | 8/1993 |
| WO | WO 1995/008626 | A1 | 3/1995 |
| WO | WO 1995/024485 | A2 | 9/1995 |
| WO | WO 1995/026204 | A1 | 10/1995 |
| WO | WO 1995/033835 | A1 | 12/1995 |
| WO | WO 1996/040945 | A2 | 12/1996 |
| WO | WO 1997/048370 | A2 | 12/1997 |
| WO | WO 1998/000547 | A1 | 1/1998 |
| WO | WO 1998/012207 | A1 | 3/1998 |
| WO | WO 1998/058956 | A1 | 12/1998 |
| WO | WO 1999/014346 | A2 | 3/1999 |
| WO | WO 1999/033982 | A2 | 7/1999 |
| WO | WO 1999/052503 | A2 | 10/1999 |
| WO | WO 2000/029561 | A2 | 5/2000 |
| WO | WO 2000/050586 | A2 | 8/2000 |
| WO | WO 2001/021810 | A1 | 3/2001 |
| WO | WO 2001/093836 | A2 | 12/2001 |
| WO | WO 2002/048310 | A2 | 6/2002 |
| WO | WO 2002/064799 | A2 | 8/2002 |
| WO | WO 2003/059381 | A2 | 7/2003 |
| WO | WO 2003/072720 | A2 | 9/2003 |
| WO | WO 2004/058166 | A2 | 7/2004 |
| WO | WO 2004/076645 | A1 | 9/2004 |
| WO | WO 2005/000235 | A2 | 1/2005 |
| WO | WO 2005/007689 | A1 | 1/2005 |
| WO | WO 2005/009346 | A2 | 2/2005 |
| WO | WO 2005/027825 | A2 | 3/2005 |
| WO | WO 2005/027936 | A2 | 3/2005 |
| WO | WO 2005/027963 | A2 | 3/2005 |
| WO | WO 2005/034992 | A2 | 4/2005 |
| WO | WO 2005/118813 | A2 | 12/2005 |
| WO | WO 2005/118857 | A2 | 12/2005 |
| WO | WO 2005/120152 | A2 | 12/2005 |
| WO | WO 2006/020071 | A2 | 2/2006 |
| WO | WO 2006/050280 | A2 | 5/2006 |
| WO | WO 2006/056027 | A1 | 6/2006 |
| WO | WO 2006/071255 | A2 | 7/2006 |
| WO | WO 2006/071903 | A2 | 7/2006 |
| WO | WO 2006/074341 | A2 | 7/2006 |
| WO | WO 2006/078294 | A2 | 7/2006 |
| WO | WO 2006/095259 | A2 | 9/2006 |
| WO | WO 2007/024708 | A2 | 3/2007 |
| WO | WO 2007/064952 | A2 | 3/2007 |
| WO | WO 2007/038862 | A1 | 4/2007 |
| WO | WO 2007/051303 | A1 | 5/2007 |
| WO | WO 2007/094854 | A2 | 8/2007 |
| WO | WO 2007/095976 | A2 | 8/2007 |
| WO | WO 2008/011609 | A2 | 1/2008 |
| WO | WO 2008/014979 | A2 | 2/2008 |
| WO | WO 2008/043052 | A2 | 4/2008 |
| WO | WO 2008/014979 | A3 | 5/2008 |
| WO | WO 2008/052770 | A2 | 5/2008 |
| WO | WO 2008/077592 | A1 | 7/2008 |
| WO | WO 2008/083949 | A2 | 7/2008 |
| WO | WO 2008/103276 | A2 | 8/2008 |
| WO | WO 2008/143640 | A1 | 11/2008 |
| WO | WO 2008/145129 | A2 | 12/2008 |
| WO | WO 2008/151049 | A2 | 12/2008 |
| WO | WO 2009/030254 | A1 | 3/2009 |
| WO | WO 2009/030481 | A1 | 3/2009 |
| WO | WO 2009/046738 | A1 | 4/2009 |
| WO | WO 2009/046739 | A1 | 4/2009 |
| WO | WO 2009/095226 | A1 | 8/2009 |
| WO | WO 2009/127060 | A1 | 10/2009 |
| WO | WO 2009/127230 | A1 | 10/2009 |
| WO | WO 2010/037408 | A1 | 4/2010 |
| WO | WO 2010/037539 | A1 | 4/2010 |
| WO | WO 2010/042877 | A1 | 4/2010 |
| WO | WO 2010/053572 | A2 | 5/2010 |
| WO | WO 2010/054401 | A1 | 5/2010 |
| WO | WO 2010/054406 | A1 | 5/2010 |
| WO | WO 2010/060430 | A2 | 6/2010 |
| WO | WO 2010/077717 | A1 | 7/2010 |
| WO | WO 2010/088537 | A3 | 8/2010 |
| WO | WO 2010/088927 | A1 | 8/2010 |
| WO | WO 2010/115046 | A2 | 10/2010 |
| WO | WO 2010/129709 | A1 | 11/2010 |
| WO | WO 2010/144740 | A1 | 12/2010 |
| WO | WO 2010/148013 | A2 | 12/2010 |
| WO | WO 2010/149743 | A2 | 12/2010 |
| WO | WO 2011/005799 | A2 | 1/2011 |
| WO | WO 2011/017548 | A1 | 2/2011 |
| WO | WO 2011/026641 | A9 | 3/2011 |
| WO | WO 2011/068810 | A1 | 6/2011 |
| WO | WO 2011/069529 | A1 | 6/2011 |
| WO | WO 2011/069586 | A1 | 6/2011 |
| WO | WO 2011/071931 | A2 | 6/2011 |
| WO | WO 2012/024629 | A1 | 8/2011 |
| WO | WO 2011/106607 | A2 | 9/2011 |
| WO | WO 2011/127255 | A1 | 10/2011 |
| WO | WO 2011/130624 | A2 | 10/2011 |
| WO | WO 2011/140627 | A1 | 11/2011 |
| WO | WO 2011/144358 | A1 | 11/2011 |
| WO | WO 2011/150264 | A2 | 12/2011 |
| WO | WO 2012/006359 | A1 | 1/2012 |
| WO | WO 2012/006369 | A2 | 1/2012 |
| WO | WO 2012/006372 | A1 | 1/2012 |
| WO | WO 2012/006376 | A2 | 1/2012 |
| WO | WO 2012/006377 | A2 | 1/2012 |
| WO | WO 2012/006378 | A1 | 1/2012 |
| WO | WO 2012/006380 | A2 | 1/2012 |
| WO | WO 2012/019630 | A1 | 2/2012 |
| WO | WO 2012/019780 | A1 | 2/2012 |
| WO | WO 2012/030683 | A2 | 3/2012 |
| WO | WO 2012/030901 | A1 | 3/2012 |
| WO | WO 2012/031043 | A1 | 3/2012 |
| WO | WO 2012/031046 | A2 | 3/2012 |
| WO | WO 2012/038450 | A1 | 3/2012 |
| WO | WO 2012/045075 | A1 | 4/2012 |
| WO | WO 2012/045082 | A2 | 4/2012 |
| WO | WO 2012/051211 | A2 | 4/2012 |
| WO | WO 2012/068295 | A1 | 5/2012 |
| WO | WO 2012/072269 | A1 | 6/2012 |
| WO | WO 2012/075040 | A2 | 6/2012 |
| WO | WO 2012/089225 | A1 | 7/2012 |
| WO | WO 2012/092569 | A2 | 7/2012 |
| WO | WO 2012/099805 | A2 | 7/2012 |
| WO | WO 2012/104820 | A1 | 8/2012 |
| WO | WO 2012/113413 | A1 | 8/2012 |

(56) References Cited

FOREIGN PATENT DOCUMENTS

| | | | |
|---|---|---|---|
| WO | WO 2012/113513 | A1 | 8/2012 |
| WO | WO 2012/116714 | A1 | 9/2012 |
| WO | WO 2012/116715 | A1 | 9/2012 |
| WO | WO 2012/116810 | A1 | 9/2012 |
| WO | WO 2012/116811 | A1 | 9/2012 |
| WO | WO 2012/135805 | A2 | 10/2012 |
| WO | WO 2012/138453 | A1 | 10/2012 |
| WO | WO 2012/149045 | A2 | 11/2012 |
| WO | WO 2012/149376 | A2 | 11/2012 |
| WO | WO 2012/159754 | A2 | 11/2012 |
| WO | WO 2012/170889 | A1 | 12/2012 |
| WO | WO 2012/170930 | A1 | 12/2012 |
| WO | WO 2012/177760 | A1 | 12/2012 |
| WO | WO 2013/006825 | A1 | 1/2013 |
| WO | WO 2013/006834 | A1 | 1/2013 |
| WO | WO 2013/006837 | A1 | 1/2013 |
| WO | WO 2013/006838 | A1 | 1/2013 |
| WO | WO 2013/006842 | A2 | 1/2013 |
| WO | WO 2013/024865 | A1 | 2/2013 |
| WO | WO 2013/030778 | A2 | 3/2013 |
| WO | WO 2013/052167 | A2 | 4/2013 |
| WO | WO 2013/052523 | A1 | 4/2013 |
| WO | WO 2013/055905 | A1 | 4/2013 |
| WO | WO 2013/056132 | A2 | 4/2013 |
| WO | WO 2013/059496 | A1 | 4/2013 |
| WO | WO 2013/075266 | A1 | 5/2013 |
| WO | WO 2013/078199 | A2 | 5/2013 |
| WO | WO 2013/090186 | A1 | 6/2013 |
| WO | WO 2013/090648 | A1 | 6/2013 |
| WO | WO 2013/093648 | A2 | 6/2013 |
| WO | WO 2013/102203 | A1 | 7/2013 |
| WO | WO 2013/113326 | A1 | 8/2013 |
| WO | WO 2013/113502 | A1 | 8/2013 |
| WO | WO 2013/120498 | A1 | 8/2013 |
| WO | WO 2013/120628 | A1 | 8/2013 |
| WO | WO 2013/120629 | A1 | 8/2013 |
| WO | WO 2013/143555 | A1 | 10/2013 |
| WO | WO 2013/151663 | A1 | 10/2013 |
| WO | WO 2013/151736 | A2 | 10/2013 |
| WO | WO 2013/174409 | A1 | 11/2013 |
| WO | WO 2013/182683 | A1 | 12/2013 |
| WO | WO 2013/185069 | A1 | 12/2013 |
| WO | WO 2014/028487 | A1 | 2/2014 |
| WO | WO 2014/028763 | A1 | 2/2014 |
| WO | WO 2014/035457 | A1 | 3/2014 |
| WO | WO 2014/071219 | A1 | 5/2014 |
| WO | WO 2014/071963 | A1 | 5/2014 |
| WO | WO 2014/072061 | A1 | 5/2014 |
| WO | WO 2014/074912 | A1 | 5/2014 |
| WO | WO 2014/081507 | A1 | 5/2014 |
| WO | WO 2014/089239 | A1 | 6/2014 |
| WO | WO 2014/089486 | A1 | 6/2014 |
| WO | WO 2014/093574 | A1 | 6/2014 |
| WO | WO 2014/108515 | A1 | 7/2014 |
| WO | WO 2014/127917 | A1 | 8/2014 |
| WO | WO 2014/136086 | A1 | 9/2014 |
| WO | WO 2014/140211 | A1 | 9/2014 |
| WO | WO 2014/144196 | A1 | 9/2014 |
| WO | WO 2014/144711 | A1 | 9/2014 |
| WO | WO 2014/145038 | A1 | 9/2014 |
| WO | WO 2014/152027 | A1 | 9/2014 |
| WO | WO 2014/152030 | A1 | 9/2014 |
| WO | WO 2014/152200 | A1 | 9/2014 |
| WO | WO 2014/152211 | A1 | 9/2014 |
| WO | WO 2014/152540 | A1 | 9/2014 |
| WO | WO 2014/152774 | A1 | 9/2014 |
| WO | WO 2014/152940 | A1 | 9/2014 |
| WO | WO 2014/152966 | A1 | 9/2014 |
| WO | WO 2014/159813 | A1 | 10/2014 |
| WO | WO 2014/160243 | A1 | 10/2014 |
| WO | WO 2014/160463 | A1 | 10/2014 |
| WO | WO 2014/174018 | A1 | 10/2014 |
| WO | WO 2014/182661 | A2 | 11/2014 |
| WO | WO 2014/202570 | A1 | 12/2014 |
| WO | WO 2014/210356 | A1 | 12/2014 |
| WO | WO 2015/005253 | A1 | 1/2015 |
| WO | WO 2015/006747 | A2 | 1/2015 |
| WO | WO 2015/013551 | A1 | 1/2015 |
| WO | WO 2015/023461 | A2 | 2/2015 |
| WO | WO 2015/024667 | A1 | 2/2015 |
| WO | WO 2015/024668 | A2 | 2/2015 |
| WO | WO 2015/024669 | A1 | 2/2015 |
| WO | WO 2015/048744 | A2 | 4/2015 |
| WO | WO 2015/061467 | A1 | 4/2015 |
| WO | WO 2015/062738 | A1 | 5/2015 |
| WO | WO 2015/081155 | A1 | 6/2015 |
| WO | WO 2015/085318 | A2 | 6/2015 |
| WO | WO 2015/095340 | A1 | 6/2015 |
| WO | WO 2015/095346 | A1 | 6/2015 |
| WO | WO 2015/101414 | A2 | 7/2015 |
| WO | WO 2015/101415 | A1 | 7/2015 |
| WO | WO 2015/130584 | A2 | 9/2015 |
| WO | WO 2015/135558 | A1 | 9/2015 |
| WO | WO 2015/143335 | A1 | 9/2015 |
| WO | WO 2015/149944 | A2 | 10/2015 |
| WO | WO 2015/164674 | A1 | 10/2015 |
| WO | WO 2015/177312 | A1 | 11/2015 |
| WO | WO 2015/188933 | A1 | 12/2015 |
| WO | WO 2015/189425 | A1 | 12/2015 |
| WO | WO 2015/199952 | A1 | 12/2015 |
| WO | WO 2016/012800 | A1 | 1/2016 |
| WO | WO 2016/031986 | A1 | 3/2016 |
| WO | WO 2016/037053 | A1 | 3/2016 |
| WO | WO 2016/103238 | A1 | 6/2016 |
| WO | WO 2016/116398 | A1 | 7/2016 |
| WO | WO 2016/123864 | A1 | 8/2016 |
| WO | WO 2016/128376 | A1 | 8/2016 |
| WO | WO 2016/138160 | A1 | 9/2016 |
| WO | WO 2016/164762 | A1 | 10/2016 |
| WO | WO 2016/174227 | A1 | 11/2016 |
| WO | WO 2016/176330 | A1 | 11/2016 |
| WO | WO 2016/184822 | A1 | 11/2016 |
| WO | WO 2016/201377 | A1 | 12/2016 |
| WO | WO 2016/203025 | A1 | 12/2016 |
| WO | WO 2017/011773 | A2 | 1/2017 |
| WO | WO 2017/015457 | A1 | 1/2017 |
| WO | WO 2017/015463 | A2 | 1/2017 |
| WO | WO 2017/019935 | A1 | 2/2017 |
| WO | WO 2017/020026 | A1 | 2/2017 |
| WO | WO 2017/031232 | A1 | 2/2017 |
| WO | WO 2017/031241 | A1 | 2/2017 |
| WO | WO 2017/049245 | A2 | 3/2017 |
| WO | WO 2017/053297 | A1 | 3/2017 |
| WO | WO 2017/153936 | A1 | 3/2017 |
| WO | WO 2017/172890 | A1 | 3/2017 |
| WO | WO 2017/062513 | A1 | 4/2017 |
| WO | WO 2017/066789 | A1 | 4/2017 |
| WO | WO 2017/070601 | A1 | 4/2017 |
| WO | WO 2017/070616 | A2 | 4/2017 |
| WO | WO 2017/070618 | A1 | 4/2017 |
| WO | WO 2017/070620 | A2 | 4/2017 |
| WO | WO 2017/070622 | A1 | 4/2017 |
| WO | WO 2017/070623 | A1 | 4/2017 |
| WO | WO 2017/070626 | A2 | 4/2017 |
| WO | WO 2017/182524 | A1 | 4/2017 |
| WO | WO 2017/075038 | A1 | 5/2017 |
| WO | WO 2017/075531 | A1 | 5/2017 |
| WO | WO 2017/081082 | A1 | 5/2017 |
| WO | WO 2017/112865 | A1 | 6/2017 |
| WO | WO 2017/127750 | A1 | 7/2017 |
| WO | WO 2017/174564 | A1 | 10/2017 |
| WO | WO 2018/081318 | A1 | 10/2017 |
| WO | WO 2017/191258 | A1 | 11/2017 |
| WO | WO 2017/191274 | A2 | 11/2017 |
| WO | WO 2017/201333 | A1 | 11/2017 |
| WO | WO 2017/201340 | A2 | 11/2017 |
| WO | WO 2017/201342 | A1 | 11/2017 |
| WO | WO 2017/201347 | A1 | 11/2017 |
| WO | WO 2017/201349 | A1 | 11/2017 |
| WO | WO 2018/006052 | A1 | 1/2018 |
| WO | WO 2018/053209 | A1 | 3/2018 |
| WO | WO 2018/075592 | A1 | 4/2018 |
| WO | WO 2018/075980 | A1 | 4/2018 |
| WO | WO 2018/078053 | A1 | 5/2018 |

(56) References Cited

FOREIGN PATENT DOCUMENTS

| | | | |
|---|---|---|---|
| WO | WO 2018/081459 | A1 | 5/2018 |
| WO | WO 2018/081462 | A1 | 5/2018 |
| WO | WO 2018/081638 | A1 | 5/2018 |
| WO | WO 2018/089801 | A1 | 5/2018 |
| WO | WO 2018/089851 | A2 | 5/2018 |
| WO | WO 2018/107088 | A2 | 6/2018 |
| WO | WO 2018/111967 | A1 | 6/2018 |
| WO | WO 2018/115527 | A2 | 6/2018 |
| WO | WO 2018/144082 | A1 | 8/2018 |
| WO | WO 2018/144778 | A1 | 8/2018 |
| WO | WO 2018/151816 | A1 | 8/2018 |
| WO | WO 2018/157009 | A1 | 8/2018 |
| WO | WO 2018/170245 | A1 | 9/2018 |
| WO | WO 2018/170256 | A1 | 9/2018 |
| WO | WO 2018/170260 | A1 | 9/2018 |
| WO | WO 2018/170270 | A1 | 9/2018 |
| WO | WO 2018/170347 | A1 | 9/2018 |
| WO | WO 2018/175783 | A1 | 9/2018 |
| WO | WO 2018/140826 | A9 | 10/2018 |
| WO | WO 2018/187590 | A1 | 10/2018 |
| WO | WO 2018/200737 | A1 | 11/2018 |
| WO | WO 2018/232355 | A1 | 12/2018 |
| WO | WO 2018/232357 | A1 | 12/2018 |
| WO | WO 2019/018765 | A1 | 1/2019 |
| WO | WO 2019/036670 | A2 | 2/2019 |
| WO | WO 2019/036682 | A1 | 2/2019 |
| WO | WO 2019/036683 | A1 | 2/2019 |
| WO | WO 2019/036685 | A1 | 2/2019 |
| WO | WO 2019/055807 | A1 | 3/2019 |
| WO | WO 2019/081750 | A1 | 5/2019 |
| WO | WO 2019/092153 | A1 | 5/2019 |
| WO | WO 2019/103993 | A1 | 5/2019 |
| WO | WO 2019/148101 | A1 | 8/2019 |
| WO | WO 2019/202035 | A1 | 10/2019 |
| WO | WO 2020/006242 | A1 | 1/2020 |
| WO | WO 2020/056370 | A1 | 3/2020 |
| WO | WO 2020/061284 | A1 | 3/2020 |
| WO | WO 2020/061295 | A1 | 3/2020 |
| WO | WO 2020/061367 | A1 | 3/2020 |
| WO | WO 2020/097291 | A1 | 5/2020 |
| WO | WO 2020/163719 | A2 | 8/2020 |
| WO | WO 2020/172239 | A1 | 8/2020 |
| WO | WO 2020/185811 | A1 | 9/2020 |
| WO | WO 2020/190750 | A1 | 9/2020 |
| WO | WO 2020/243561 | A1 | 12/2020 |
| WO | WO 2021/016430 | A1 | 1/2021 |
| WO | WO 2021/030533 | A1 | 2/2021 |
| WO | WO 2021/178971 | A1 | 2/2021 |
| WO | WO 2021/050864 | A1 | 3/2021 |
| WO | WO 2021/055811 | A1 | 3/2021 |
| WO | WO 2021/138447 | A1 | 7/2021 |
| WO | WO 2021/147025 | A1 | 7/2021 |
| WO | WO 2021/154763 | A1 | 8/2021 |
| WO | WO 2021/154812 | A1 | 8/2021 |
| WO | WO 2021/154828 | A1 | 8/2021 |
| WO | WO 2021/155243 | A1 | 8/2021 |
| WO | WO 2021/155274 | A1 | 8/2021 |
| WO | WO 2021/155323 | A1 | 8/2021 |
| WO | WO 2021/155733 | A1 | 8/2021 |
| WO | WO 2021/156267 | A1 | 8/2021 |
| WO | WO 2021/159040 | A1 | 8/2021 |
| WO | WO 2021/159118 | A2 | 8/2021 |
| WO | WO 2021/159130 | A2 | 8/2021 |
| WO | WO 2021/160346 | A1 | 8/2021 |
| WO | WO 2021/160850 | A1 | 8/2021 |
| WO | WO 2021/163365 | A1 | 8/2021 |
| WO | WO 2021/163622 | A1 | 8/2021 |
| WO | WO 2021/174128 | A1 | 9/2021 |
| WO | WO 2021/174567 | A1 | 9/2021 |
| WO | WO 2021/178623 | A1 | 9/2021 |
| WO | WO 2021/178886 | A1 | 9/2021 |
| WO | WO 2021/188906 | A1 | 9/2021 |
| WO | WO 2021/189056 | A2 | 9/2021 |
| WO | WO 2021/198706 | A2 | 10/2021 |
| WO | WO 2021/202971 | A1 | 10/2021 |
| WO | WO 2021/203053 | A1 | 10/2021 |
| WO | WO 2021/204175 | A1 | 10/2021 |
| WO | WO 2021/204179 | A1 | 10/2021 |
| WO | WO 2021/205183 | A1 | 10/2021 |
| WO | WO 2021/205455 | A1 | 10/2021 |
| WO | WO 2021/207014 | A2 | 10/2021 |
| WO | WO 2021/207420 | A1 | 10/2021 |
| WO | WO 2021/210984 | A1 | 10/2021 |
| WO | WO 2021/211279 | A1 | 10/2021 |
| WO | WO 2021/211343 | A1 | 10/2021 |
| WO | WO 2021/211688 | A1 | 10/2021 |
| WO | WO 2021/211748 | A1 | 10/2021 |
| WO | WO 2021/213924 | A1 | 10/2021 |
| WO | WO 2021/213945 | A1 | 10/2021 |
| WO | WO 2021/216575 | A1 | 10/2021 |
| WO | WO 2021/216729 | A1 | 10/2021 |
| WO | WO 2021/222304 | A1 | 11/2021 |
| WO | WO 2021/226436 | A1 | 11/2021 |
| WO | WO 2021/231901 | A1 | 11/2021 |
| WO | WO 2021/231929 | A1 | 11/2021 |
| WO | WO 2021/231963 | A1 | 11/2021 |
| WO | WO 2021/237084 | A1 | 11/2021 |
| WO | WO 2021/237174 | A1 | 11/2021 |
| WO | WO 2021/239880 | A1 | 12/2021 |
| WO | WO 2021/247817 | A1 | 12/2021 |
| WO | WO 2021/262672 | A1 | 12/2021 |
| WO | WO 2022/009121 | A1 | 1/2022 |
| WO | WO 2022/032154 | A2 | 2/2022 |
| WO | WO 2022/043551 | A2 | 3/2022 |
| WO | WO 2022/046898 | A1 | 3/2022 |
| WO | WO 2022/067010 | A1 | 3/2022 |
| WO | WO 2022/076562 | A1 | 4/2022 |
| WO | WO 2022/081544 | A1 | 4/2022 |
| WO | WO 2022/099003 | A1 | 5/2022 |
| WO | WO 2022/101469 | A1 | 5/2022 |
| WO | WO 2022/104265 | A1 | 5/2022 |
| WO | WO 2022/137133 | A1 | 6/2022 |
| WO | WO 2022/150717 | A1 | 7/2022 |
| WO | WO 2022/155524 | A1 | 7/2022 |
| WO | WO 2022/155530 | A1 | 8/2022 |
| WO | WO 2022/162027 | A2 | 8/2022 |
| WO | WO 2022/187698 | A1 | 9/2022 |
| WO | WO 2022/197624 | A1 | 9/2022 |
| WO | WO 2022/204491 | A1 | 9/2022 |
| WO | WO 2022/212191 | A1 | 10/2022 |
| WO | WO 2022/212442 | A1 | 10/2022 |
| WO | WO 2022/212711 | A1 | 10/2022 |
| WO | WO 2022/221335 | A1 | 10/2022 |
| WO | WO 2022/221336 | A1 | 10/2022 |
| WO | WO 2022/221359 | A1 | 10/2022 |
| WO | WO 2022/221440 | A1 | 10/2022 |
| WO | WO 2022/226277 | A1 | 10/2022 |
| WO | WO 2022/226318 | A1 | 10/2022 |
| WO | WO 2022/232585 | A1 | 11/2022 |
| WO | WO 2022/233629 | A1 | 11/2022 |
| WO | WO 2022/241103 | A1 | 11/2022 |
| WO | WO 2022/245888 | A1 | 11/2022 |
| WO | WO 2022/266010 | A1 | 12/2022 |
| WO | WO 2022/266012 | A1 | 12/2022 |
| WO | WO 2022/266389 | A1 | 12/2022 |
| WO | WO 2023/283642 | A1 | 1/2023 |
| WO | WO 2023/283642 | A2 | 1/2023 |
| WO | WO 2023/283645 | A1 | 1/2023 |
| WO | WO 2023/283651 | A1 | 1/2023 |
| WO | WO 2023/006920 | A1 | 2/2023 |
| WO | WO 2023/014649 | A1 | 2/2023 |
| WO | WO 2023/018773 | A1 | 2/2023 |
| WO | WO 2023/018923 | A1 | 2/2023 |
| WO | WO 2023/019181 | A1 | 2/2023 |
| WO | WO 2023/056401 | A1 | 4/2023 |
| WO | WO 2023/069625 | A1 | 4/2023 |
| WO | WO 2023/069895 | A1 | 4/2023 |
| WO | WO 2023/069900 | A1 | 4/2023 |
| WO | WO 2023/076358 | A1 | 5/2023 |
| WO | WO 2023/076658 | A1 | 5/2023 |
| WO | WO 2023/081311 | A1 | 5/2023 |
| WO | WO 2023/092069 | A1 | 5/2023 |
| WO | WO 2023/094713 | A2 | 6/2023 |
| WO | WO 2023/107999 | A2 | 6/2023 |

(56) References Cited

FOREIGN PATENT DOCUMENTS

| | | |
|---|---|---|
| WO | WO 2023/114307 A1 | 6/2023 |
| WO | WO 2023/132885 A1 | 7/2023 |
| WO | WO 2023/135333 A1 | 7/2023 |
| WO | WO 2023/137149 A1 | 7/2023 |
| WO | WO 2023/147091 A1 | 8/2023 |
| WO | WO 2023/150256 A1 | 8/2023 |
| WO | WO 2023/154818 A1 | 8/2023 |
| WO | WO 2023/196914 A1 | 10/2023 |
| WO | WO 2023/201204 A1 | 10/2023 |
| WO | WO 2023/201294 A1 | 10/2023 |
| WO | WO 2023/201296 A1 | 10/2023 |
| WO | WO 2023/212696 A1 | 11/2023 |
| WO | WO 2023/225524 A1 | 11/2023 |
| WO | WO 2023/239836 A1 | 12/2023 |
| WO | WO 2023/250119 A1 | 12/2023 |
| WO | WO 2024/010993 A1 | 1/2024 |
| WO | WO 2024/015890 A1 | 1/2024 |
| WO | WO 2024/026005 A1 | 2/2024 |
| WO | WO 2024/030369 A1 | 2/2024 |
| WO | WO 2024/050483 A1 | 3/2024 |
| WO | WO 2024/097874 A1 | 5/2024 |
| WO | WO 2024/123978 A1 | 6/2024 |
| WO | WO 2024/151811 A1 | 7/2024 |
| WO | WO 2024/163465 A1 | 8/2024 |
| WO | WO 2024/191860 A2 | 9/2024 |
| WO | WO 2024/206835 A1 | 10/2024 |

OTHER PUBLICATIONS

[No Author Listed], "BioNTech Expands Clinical Oncology Portfolio with First Patient Dosed in Phase 2 Trial of mRNA-based Individualized Immunotherapy BNT122 in Colorectal Cancer Patients," Press Release, BioNTech, Oct. 1, 2021, 2 pages.

[No Author Listed], "BioNTech Fourth Quarter and Full-Year 2019 Results," BioNTech, Mar. 31, 2020, 15 pages.

[No Author Listed], "BioNTech SE Annual Report (Form 20-F) 179, F-12," United States Securities and Exchange Commission, Mar. 30, 2021, 739 pages.

[No Author Listed], "BioNTech SE Annual Report (Form 20-F) 81," United States Securities and Exchange Commission, Mar. 30, 2022, 700 pages.

[No Author Listed], "BioNTech Signs Collaboration Agreement with Pfizer to Develop mRNA-based Vaccines for Prevention of Influenza," Press Release, Aug. 16, 2018, 3 pages.

[No Author Listed], "BNT162 COVID-19 Vaccine Program Update," BioNTech, Apr. 23, 2020, 15 pages.

[No Author Listed], "Center for Drug Evaluation and Research Approval Package for New Drug Application No. 50-718/S-50 for Doxil®," Approved Dec. 28, 2015, 97 pages.

[No Author Listed], "Clinical trial NCT04528719: A Dose Escalation Study to Evaluate Safety, Reactogenicity, and Immunogenicity of mRNA-1345 in Healthy Adults and in Children Who Are Respiratory Syncytial Virus Seropositive," (ModernaTX, Inc.), Aug. 27, 2020, retrieved on 15 Mar. 15, 2021, retrieved from URL https://www.clinicaltrials.gov/ct2/show/NCT04528719?term=NCT04528719&draw=2&rank=1>, 9 pages.

[No Author Listed], "Comirnaty (mRNA-1273) EMA SmPC," Summary of Product Characteristics, Dec. 1, 2021, 276 pages.

[No Author Listed], "Comirnaty Dosing Schedule for People 12 Years of Age & Older (2023-2024 Formula)," Pfizer-BioNTech, Oct. 2023, 2 pages.

[No Author Listed], "Coronavirus (COVID-19) Update: FDA Authorizes Changes to Simplify Use of Bivalent mRNA COVID-19 Vaccines," FDA News Release, Apr. 18, 2023, 3 pages.

[No Author Listed], "COVID-19 Vaccine Development Program," Pfizer, Jul. 1, 2020, 18 pages.

[No Author Listed], "DARPA Awards Moderna Therapeutics a Grant for up to $25 Million to Develop Messenger RNA Therapeutics," News Release, Moderna, Oct. 2, 2013, 1 page.

[No Author Listed], "Delivery means to avoid degradation of RNA preparations: Lipid nanoparticles (LNPs) for RNA delivery," CosmoBio, Retrieved from the Internet: <https://www.cosmobio.co.jp/product/detail/lipid-nanoparticles-for-rna-delivery-ecl.asp?entry_id=43081>, Last Accessed: Oct. 23, 2023, 10 pages (Machine Translation).

[No Author Listed], "Dosing Schedule for Ages 12 Years of Age and Older with Pfizer-BioNTech COVID-19 Vaccine," Bivalent (Original and Omicron BA.4/BA.5), Apr. 2023, 7-9.

[No Author Listed], "European Commission Authorizes COVID 19 Vaccine Moderna in Europe," Jan. 6, 2021, Accessed from <https://www.drugs.com/clinical_trials/european-commission-authorizes-covid-19-vaccine-moderna-europe-19152.html>, 5 pages.

[No Author Listed], "Fact Sheet for Healthcare Providers Administering Vaccine: Emergency Use Authorization of Pfizer-BioNTech COVID-19 Vaccine (2023-2024 Formula) for 6 Months through 11 Years of Age," Pfizer-BioNTech, Sep. 2023, 59 pages.

[No Author Listed], "Goldman Sachs Virtual 41st Annual Global Healthcare Conference," Pfizer Inc., Jun. 9, 2020, 13 pages.

[No Author Listed], History of Changes for Study: NCT04405076, Dose-Confirmation Study to Evaluate the Safety, Reactogenicity, and Immunogenicity of mRNA-1273 COVID-19 Vaccine in Adults Aged 18 Years and Older, Version submitted Dec. 6, 2022, 6 pages.

[No Author Listed], "Increase in Manufacturing Capacity for COVID-19 Vaccines from Janssen, Moderna, and BioNTech/Pfizer," European Medicines Agency, Dec. 16, 2021, 4 pages.

[No Author Listed], "Katalin Karikó and Drew Weissman awarded Horwitz Prize for pioneering research on COVID-19 vaccines," Columbia University Irving Medical Center, Aug. 16, 2021, <https://www.cuimc.columbia.edu/news/horwitz-prize-2021> (last accessed Aug. 24, 2023), 12 pages.

[No Author Listed], "Katalin Karikó Laureate de la Grande Medaille 2021 de L'Academie des Sciences,Press Release," De L'Academie des Sciences, Sep. 28, 2021, 2 pages.

[No Author Listed], "Messenger RNA Pioneer Katalin Karikó Receives European Inventor Award 2022 for Lifetime Achievement," Press Release, European Patent Office, Jun. 21, 2022, 4 pages.

[No Author Listed], "Messenger RNA" definition, Collins Dictionary of Science, 2005, p. 514.

[No Author Listed], "Messenger RNA" definition, The Penguin Dictionary of Science, 2009, 3 pages.

[No Author Listed], "Messenger RNA" definition, Webster's New World Medical Dictionary, 3rd Ed., 2008, p. 271.

[No Author Listed], "Messenger RNA," Jun. 19, 2013, retrieved from URL <http://en.wikipedia.org/wiki/Messenger RNA>, 10 pages.

[No Author Listed], "Moderna Announces First Participant Dosed in Phase 2 Study of Omicron-Specific Booster Candidate and Publication of Data on Booster Durability Against Omicron Variant," News Release, Moderna, Jan. 26, 2022, 4 pages.

[No Author Listed], "Moderna Announces First Participant Dosed in Phase 2 Study of Omicron-Specific Booster Candidate," News Release, Mar. 10, 2022, 2 pages.

[No Author Listed], "Moderna Announces Funding Award from CEPI to Accelerate Development of Messenger RNA (mRNA) Vaccine Against Novel Coronavirus," News Release, Moderna, Jan. 23, 2020, 2 pages.

[No Author Listed], "Moderna Announces Strategy to Address Omicron (B.1.1.529) SARS-CoV-2 Variant," Press Release, Moderna, Nov. 26, 2021, 2 pages.

[No Author Listed], "Moderna has no plans to share its COVID-19 vaccine recipe," Associated Press, Oct. 11, 2021, 2 pages.

[No Author Listed], "Moderna Inc to Discuss Updates on Respiratory Syncytial Virus (RSV) Vaccine Program Call," Edited Transcript. Refinitiv., Oct. 8, 2020, 14 pages.

[No Author Listed], "Moderna Provides Business Update and Announces Three New Development Programs in Infectious Disease Vaccines," Press Release, Jan. 11, 2021, 5 pages.

[No Author Listed], "Moderna Receives FDA Authorization for Emergency Use of Omicron-Targeting Bivalent COVID-19 Booster Vaccine for Adults 18 Years and Older," News Release, Moderna, Aug. 31, 2022, 5 pages.

(56) References Cited

OTHER PUBLICATIONS

[No Author Listed], "Moderna Reports Fourth Quarter and Fiscal Year 2020 Financial Results and Provides Business Updates," Press Release, Feb. 25, 2021, 9 pages.
[No Author Listed], "Moderna's Update Patent Pledge," Press Release, Moderna, Mar. 7, 2022, 2 pages.
[No Author Listed], "Modified mRNA Vaccines, 2021 Lasker-DeBakey Clinical Medicial Research Award," 2021, retrieved on Nov. 14, 2022, retrieved from URL <https://laskerfoundation.org/winners/modified-mrna-vaccines/>, 17 pages.
[No Author Listed], "Penn mRNA Scientists Drew Weissman and Katalin Karikó Receive 2021 Lasker Award, America's Top Biomedical Research Prize," Penn News Release, Sep. 24, 2021, 6 pages.
[No Author Listed], "Pfizer and BioNTech Announce Early Positive Data from an Ongoing Phase 1/2 Study of mRNA-based Vaccine Candidate against SARS-CoV-2," Press Release, Jul. 1, 2020, 8 pages.
[No Author Listed], "Pfizer and BioNTech Announce Early Positive Update from German Phase 1/2 Study of COVID-19 Vaccine Study, Including First T Cell Response Data," Press Release, Jul. 20, 2020, 6 pages.
[No Author Listed], "Pfizer and BioNTech Announce Phase 3 Trial Data Showing High Efficacy of a Booster Dose of Their COVID-19 Vaccine," Press Release, Pfizer, Oct. 21, 2021, 10 pages.
[No Author Listed], "Pfizer and BioNTech Choose Lead mRNA Vaccine Candidate Against COVID-19 and Commence Pivotal Phase 2/3 Global Study," Press Release, Jul. 27, 2020, 7 pages.
[No Author Listed], "Pfizer and BioNTech Granted FDA Emergency Use Authorization of Omicron BA.4/BA.5-Adapted Bivalent COVID-19 Vaccine Booster for Ages 12 Years and Older," Pfizer, Aug. 31, 2022, 12 pages.
[No Author Listed], "Pfizer and BioNTech Receive Expanded U.S. Emergency Use Authorization for an Additional COVID-19 Vaccine Booster in Individuals Aged 50 Years and Older," Press Release, Pfizer, Mar. 29, 2022, 12 pages.
[No Author Listed], "Pfizer and BioNTech Submit Applications to U.S. FDA for Omicron XBB.1.5-Adapted Monovalent COVID-19 Vaccine," Pfizer, Jun. 23, 2023, 8 pages.
[No Author Listed], "Pfizer and BioNTech Submit Supplemental Biologics License Application for U.S. FDA Approval of Omicron BA.4/BA.5-Adapted Bivalent COVID-19 Vaccine for Ages 12 Years and Older as Primary Series or Booster," Pfizer, Feb. 24, 2023, 12 pages.
[No Author Listed], "Pfizer Inc to discuss data from an ongoing phase 1/2 study of mRNA-based vaccine candidate against SARS_CoV-2 Call," Edited Transcript, Thomson Reuters, Jul. 1, 2020, 15 pages.
[No Author Listed], "Pfizer reports fourth-quarter and full-year 2021 results," Pfizer, Feb. 8, 2022, 41 pages.
[No Author Listed], "Pfizer/BioNTech COVID-19 mRNA vaccine (BNT162, PF-07302048)," TGA Pre-Submission Meeting, Sep. 18, 2020, retrieved on Oct. 3, 2024, retrieved from URL <https://www.tga.gov.au/sites/default/files/foi-2389-03-1.pdf>, 180 pages.
[No Author Listed], "Pioneering Scientists Awarded the Albany Prize, America's Most Distinguished Prize in Medicine, for Research Leading to Covid-19 Vaccines," The Albany Prize, Aug. 26, 2021, 4 pages.
[No Author Listed], "RBC capital Markets Global Healthcare Conference," Pfizer Inc., May 19, 2020, 9 pages.
[No Author Listed], "Remarks by President Trump and Members of the Coronavirus Task Force in Meeting with Pharmaceutical Companies," The White House, Mar. 2, 2022, 31 pages.
[No Author Listed], "Statement by Moderna on Intellectual Property Matters during the COVID-19 Pandemic," Press Release, Moderna, Oct. 8, 2020, 1 page.
[No Author Listed], "Statement from NIH and BARDA on the FDA Emergency Use Authorization of the Moderna COVID-19 Vaccines," COVID.gov, Dec. 18, 2020, 3 pages.
[No Author Listed], "The species Severe acute respiratory syndromerelated coronavirus: classifying 2019-nCoV and naming it SARS-CoV-2: Classifying 2019-nCoV and Naming it SARS-CoV-2, 5," Nature Microbiology, Mar. 2020, 5(4):536-544.
[No Author Listed], "Two Pioneering RNA Scientists Win the 2021 Dr. Paul Janssen Award for Biomedical Research," Press Release, Johnson & Johnson, Sep. 28, 2021, 2 pages.
[No Author Listed], "Vaccine information fact sheet for recipients and caregivers about Comirnaty (COVID-19 Vaccine, mRNA) and the Pfizer-BioNTech COVID-19 vaccine to prevent coronavirus disease 2019 (COVID-19) for use in individuals 12 years of age and older," Pfizer-BioNTech, Jul. 8, 2022, 9 pages.
[No Author Listed], Comirnaty, "Highlights of Prescribing Information," FDA Label, Jul. 2022, 27 pages.
[No Author Listed], Comirnaty, "Highlights of Prescribing Information," FDA Label, Oct. 2023, 36 pages.
[No Author Listed], Moderna Patents, retrieved on Jul. 1, 2024, retrieved from URL <https://www.modernatx.com/en-US/patents>, 1 page.
[No Author Listed], Pfizer-BioNTech COVID-19 Vaccine Information Sheet, Sep. 11, 2023, 3 pages.
[No Author Listed], Q2 2020 Earnings Call, BioNTech SE, Aug. 11, 2020, 26 pages.
[No Author Listed], WHO Drug Information, 2021, 35(2), 341 pages.
[No Author Listed], WHO Drug Information, 2021, 35(2):578-579.
Agnihothram, "Summary Basis for Regulatory Action—STN 125752/0," Review Committee Chair, Jan. 30, 2022, 30 pages.
Agrawal et al., "Immunization with inactivated Middle East Respiratory Syndrome coronavirus vaccine leads to lung immunopathology on challenge with live virus," Hum Vaccin Immunother., Sep. 2016, 12(9):2351-2356.
Ahmad et al., "New multivalent cationic lipids reveal bell curve for transfection efficiency versus membrane charge density: lipid-DNA complexes for gene delivery," J Gene Med., Jun. 2005, 7(6):739-748.
Ahmed et al., "Biochemistry, Lipids," Statpearls Publishing, May 1, 2023, retrieved from URL <https://www.ncbi.nlm.nih.gov/books/NBK525952>, 5 pages.
Akinc et al., "A combinatorial library of lipid-like materials for delivery of RNAi therapeutics," Nat Biotechnol., May 2008, 26(5):561-569.
Akinc et al., "Targeted Delivery of RNAi Therapeutics With Endogenous and Exogenous Ligand-Based Mechanisms," Molecular Therapy, 2010, 18(7):1357-1364.
Aliprantis et al., "A phase 1, randomized, placebo-controlled study to evaluate the safety and immunogenicity of an mRNA-based RSV prefusion F protein vaccine in healthy younger and older adults," Hum Vaccin Immunother., May 4, 2021, 17(5):1248-1261.
Allen et al., "Liposomal drug delivery systems: From concept to clinical applications," Adv. Drug Deliv. Rev., 2013, 65:36-48.
Altieri et al., "The influence of 4-thiouridine labeling on pre-mRNA splicing outcomes," PLoS One., Dec. 13, 2021, 16(12):e0257503, 13 pages.
Archer, "Induction of a T-cell specific antigen on bone marrow lymphocytes with thymus RNA," Immunology, Jan. 1978, 34(1):123-9.
Arthur, "Pfizer predicts $54bn in 2022 revenue from Comirnaty and Paxlovid," BioPharmaReporter, Feb. 8, 2022, retrieved from Internet Archive: Wayback Machine URL <https://web.archive.org/web/20220208163637/https://www.biopharma-reporter.com/Article/2022/02/08/Pfizer-predicts-54bn-in-2022-sales-from-Comirnaty-and-Paxlovid>, 3 pages.
Ashley et al., "Bone Marrow-generated Dendritic Cells Pulsed with Tumor Extracts or Tumor RNA Induce Antitumor Immunity against Central Nervous System Tumors," J Exp Med., Oct. 6, 1997, 186(7):1177-82.
Atkins et al., "The molecular pathogenesis of Semliki Forest virus: a model virus made useful?," Journal of General Virology, Sep. 1999, 80(9):2287-2297.
Atsmon et al., "Safety and Immunogenicity of Multimeric-001—a Novel Universal Influenza Vaccine," J Clin Immunol., Jun. 2012, 32(3):595-603.

(56) References Cited

OTHER PUBLICATIONS

Austin et al., "Split-Dose Administration Enhances Immune Responses Elicited by a mRNA/Lipid Nanoparticle Vaccine Expressing Respiratory Syncytial Virus F Protein," Mol Pharm., Jan. 2, 2023, 20(1):279-289.
Bahl et al., "Preclinical and Clinical Demonstration of Immunogenicity by mRNA Vaccines against H10N8 and H7N9 Influenza Viruses," Molecular Therapy, Jun. 7, 2017, 25(6):1316-27.
Bancel, "Our Global Commitment to Vaccine Access," Moderna, Oct. 8, 2021, 1 page.
Bangham et al., "Diffusion of univalent ions across the lamellae of swollen phospholipids," J Mol Biol., Aug. 1965, 13(1):238-52.
Barbier et al., "The clinical progress of mRNA vaccines and immunotherapies," Nature Biotechnology, Jun. 2022, 40(6):840-54.
Bear, "Gene expression and regulation," Lewin's Cells, 2011, Chapter 4:105-68.
Bennett et al., "Cholesterol Enhances Cationic Liposome Mediated DNA Transfection of Human Respiratory Epithelial Cells" Biosci Rep., Feb. 1995, 15(1):47-53.
Bermudez, "We decided not to enforce our patent during the pandemic," Noubar Afeyan, co-founder of Moderna, BBC News World, May 6, 2021, 11 pages.
Bettinger et al., "Peptide-mediated RNA delivery: a novel approach for enhanced transfection of primary and post-mitotic cells," Nucleic Acids Res., Sep. 15, 2001, 29(18):3882-91.
Bharali et al., "Nanoparticles and cancer therapy: a concise review with emphasis on dendrimers," Int J Nanomedicine., 2009, 4:1-7.
Bisht et al., "Severe acute respiratory syndrome coronavirus spike protein expressed by attenuated vaccinia virus protectively immunizes mice," PNAS, Apr. 27, 2004, 101(17):6641-6646.
Bogers et al., "Potent immune responses in rhesus macaques induced by nonviral delivery of a self-amplifying RNA vaccine expressing HIV type 1 envelope with a cationic nanoemulsion," J Infect Dis., Mar. 15, 2015, 211(6):947-955.
Bok et al., "Accelerated COVID-19 vaccine development: milestones, lessons, and prospects," Immunity, Aug. 10, 2021, 54(8):1636-1651.
Bonehill et al., "Single-step antigen loading and activation of dendritic cells by mRNA electroporation for the purpose of therapeutic vaccination in melanoma patients," Clin Cancer Res., May 2009, 15(10):3366-3375.
Bose et al., "Role of nucleolin in human parainfluenza virus type 3 infection of human lung epithelial cells," J Viral., Aug. 2004, 78(15):8146-8158.
Bourla, "An Open Letter from Pfizer Chairman and CEO to Colleagues," Pfizer, May 7, 2021, 3 pages.
Brito et al., "A Cationic Nanoemulsion for the Delivery of Next-generation RNA Vaccines," The American Society of Gene & Cell Therapy, Dec. 2014, 22(12):2118-2129.
Buchholz et al., "Contributions of the structural proteins of severe acute respiratory syndrome coronavirus to protective immunity," PNAS, Jun. 29, 2004, 101(26):9804-9809.
Buschmann et al., "Chitosans for Delivery of Nucleic Acids," Advanced Drug Delivery Reviews, Aug. 2013, 65(9):1234-1270.
Byoung-Shik et al., "Intranasal immunization with plasmid DNA encoding spike protein of SARS-coronavirus/polyethylenimine nanoparticles elicits antigen-specific humoral and cellular immune responses," BMC Immunol., Dec. 31, 2010, 11:65, 9 pages.
Carvalho et al., "The first 12 months of COVID-19: a timeline of immunological insights," Nat Rev Immunol., Apr. 2021, 21(4):245-256.
Cassimeris et al., "Lewin's Cells, Second Edition" 2011, Jones and Bartlett Publishers, 109 Pages.
Chalkias et al., "Safety, immunogenicity and antibody persistence of a bivalent Beta-containing booster vaccine against COVID-19: a phase 2/3 trial," Nature Medicine, Oct. 6, 2022, 28:2388-2397.
Chan et al., "Genomic characterization of the 2019 novel human-pathogenic coronavirus isolated from a patient with atypical pneumonia after visiting Wuhan," Emerg Microbes Infect., Jan. 28, 2020, 9(1):221-236.
Chang et al., "Recent Insights into the Developments of Therapeutics Against Coronavirus Disease by Targeting N Protein," Drug Discovery Today, Apr. 2016, 21(4):562-572.
Chen et al., "Receptor-binding domain of SARS-Cov spike protein: Soluble expression in *E. coli*, purification and functional characterization," World J. Gastroenterol., Oct. 21, 2005, 11(39):6159-6164.
Chen et al., "Vaccine design of hemagglutinin glycoprotein against influenza," Trends Biotechnol., Sep. 2011, 29(9):426-434.
Cheng et al., "Selective ORgan Targeting (SORT) nanoparticles for tissue specific mRNA delivery and CRISPR/Cas gene editing," Nat Nanotechnol., Apr. 2020, 15(4):313-320.
Cherry et al., "SARS: The First Pandemic of the 21st Century," Pediatric Research, 2004, 56(1):1-5.
Choi et al., "2'-O-methylation in mRNA disrupts tRNA decoding during translation elongation," Nat Struct Mol Biol., Mar. 2018, 25(3):208-216.
Clancy et al., "Translation: DNA to mRNA to Protein," Nature Education, 2008, 1(1):101, 7 pages.
Cobb et al., "Who discovered messenger RNA?," Curr Biol., Jun. 29, 2015, 25(13):R526-32.
Coelho et al., "Safety and Efficacy of RNAi Therapy for Transthyretin Amyloidosis," New Engl J Med., Aug. 29, 2013, 369(9):819-829.
Cohen, "New crop of mRNA vaccines aim for accessibility," Science, Apr. 7, 2022, 376(6589):120-121.
Cohen, "Scientists are moving at record speed to create new coronavirus vaccines—but they may come too late," Science Insider, Jan. 27, 2020, 7 pages.
Cohen, "Scientists question Moderna invention claim in COVID-19 vaccine dispute," Science Insider, Aug. 29, 2022, 3 pages.
Comirnaty, "Highlights of Prescribing Information," FDA Label, Oct. 2024, 37 pages.
Conry et al., "Characterization of a messenger RNA polynucleotide vaccine vector," Cancer Res., Apr. 1995, 55(7):1397-1400.
Cooper et al., "Chapters 1, 7, and 8," in The Cell: A Molecular Approach, 5th Ed., 2009, 163 pages.
CosmoBio.Co.Jp [online], "Lipid Nanoparticles (LNPs) for RNA Delivery," available on or before Dec. 2021, retrieved on Jun. 4, 2025, retrieved from URL <https://www.cosmobio.co.jp/product/detail/lipid-nanoparticles-for-rna-delivery-ecl.aspx?entry_id-43081>, 8 pages (with English Translation).
Cox et al., "FluBlok, a recombinant hemagglutinin influenza vaccine," Influenza Other Respir Viruses., Nov. 2008, 2(6):211-219.
Cross, "Without these lipid shells, there would be no mRNA vaccines for COVID-19," Chem Eng News., Mar. 6, 2021, 99(8), 8 pages.
Curriculum Vitae of Daniel O. Griffin, M.D., Ph.D., Aug. 23, 2023, 22 pages.
Curriculum Vitae of Deborah Fuller (Deposition Exhibit), filed in IPR2023-01359 on Aug. 30, 2024, 2 pages.
Curriculum Vitae of James J. Moon, Ph.D., filed in IPR2023-01359 on Aug. 28, 2023, 28 pages.
Dahlman et al., "In vivo endothelial siRNA delivery using polymeric nanoparticles with low molecular weight," Nature Nanotechnology, May 11, 2014, 9(8):648-655.
De Groot et al., "Part II—The Positive Sense Single Stranded RNA Viruses—Family Coronaviridae," Virus Taxonomy: Ninth Report of the International Committee on Taxonomy of Viruses, 2012, pp. 806-828.
Declaration of Amy K. Wigmore in IPR2023-01358 dated Apr. 16, 2024, 5 pages.
Declaration of Amy K. Wigmore in IPR2023-01359 dated Apr. 16, 2024, 5 pages.
Declaration of Andrew J. Danford in IPR2023-01358 dated Jul. 1, 2024, 5 pages.
Declaration of Daniel O. Griffin, M.D., Ph.D. in IPR2023-01358 dated Aug. 27, 2023, 99 pages.
Declaration of Daniel O. Griffin, M.D., Ph.D. in IPR2023-01359 dated Aug. 27, 2023, 119 pages.
Declaration of Deborah H. Fuller, Ph.D., in IPR2023-01358 dated May 30, 2024 (public redacted version of Ex. 2199), 517 pages.
Declaration of Deborah H. Fuller, Ph.D., in IPR2023-01359 dated May 30, 2024. (public redacted version of Ex. 2199), 523 pages.

(56) References Cited

OTHER PUBLICATIONS

Declaration of Douglas L. Sawyer in IPR2023-01358 dated Jul. 17, 2024, 3 pages.
Declaration of Douglas L. Sawyer in IPR2023-01359 dated Jul. 17, 2024, 3 pages.
Declaration of Gabrielle Landes in IPR2023-01358 dated Apr. 25, 2024, 3 pages.
Declaration of Gabrielle Landes in IPR2023-01359 dated Apr. 25, 2024, 3 pages.
Declaration of James E. Malackowski in IPR2023-01358 dated May 29, 2024, 84 pages.
Declaration of James E. Malackowski in IPR2023-01359 dated May 29, 2024, 84 pages.
Declaration of James J. Moon, Ph.D. in IPR2023-01358 dated Apr. 25, 2023, 64 pages.
Declaration of James J. Moon, Ph.D. in IPR2023-01359 dated Apr. 25, 2023, 57 pages.
Declaration of Joshua L. Stern in IPR2023-01358 dated Apr. 17, 2024, 4 pages.
Declaration of Kathryn S. Kayali in IPR2023-01358 dated Apr. 16, 2024, 5 pages.
Declaration of Kathryn S. Kayali in IPR2023-01359 dated Apr. 26, 2024, 5 pages.
Declaration of Kevin S. Prussia in IPR2023-01358 dated Apr. 17, 2024, 4 pages.
Declaration of Kevin S. Prussia in IPR2023-01359 dated Apr. 17, 2024, 4 pages.
Declaration of L. Ross Pierce in IPR2023-01358 dated Aug. 30, 2024 (Redacted public version), 54 pages.
Declaration of L. Ross Pierce in IPR2023-01359 dated Aug. 30, 2024 (Redacted public version), 54 pages.
Declaration of M. Ryan Meuth in IPR2023-01358 dated Apr. 25, 2024, 3 pages.
Declaration of M. Ryan Meuth in IPR2023-01359 dated Apr. 25, 2024, 3 pages.
Declaration of Philp Krause, M.D., in IPR2023-01358 dated May 28, 2024 (public redacted version of Ex. 2200), 330 pages.
Declaration of Philp Krause, M.D., in IPR2023-01359 dated May 28, 2024 (public redacted version of Ex. 2200), 330 pages.
Declaration of Thomas H. L. Selby in IPR2023-01359 dated Apr. 26, 2024, 5 pages.
Declaration of W. Christopher Bakewell in IPR2023-01358 dated Aug. 30, 2024, 110 pages.
Declaration of W. Christopher Bakewell in IPR2023-01359 dated Aug. 30, 2024, 110 pages.
Declaration of Warren C.W. Chan, Ph.D. in IPR2023-01358 dated May 29, 2024, 136 pages.
Declaration of Warren C.W. Chan, Ph.D. in IPR2023-01359 dated May 29, 2024, 136 pages.
Deering et al., "Nucleic acid vaccines: prospects for non-viral delivery of mRNA vaccines," Expert Opin Drug Deliv., Jun. 2014 Jun. 11(6):885-99.
Defendants' Supplemental Patent-Related Disclosures, Exhibit C—Invalidity Contentions of U.S. Pat. No. 10,702,600, dated Jun. 27, 2023 (Excerpts), 100 pages.
Defendants' Patent-Related Disclosures, Exhibit C—Invalidity Contentions of U.S. Pat. No. 10,702,600, dated Mar. 31, 2023 (Excerpts), 5 pages.
Defendants' Patent-Related Disclosures, Exhibit D—Invalidity Contentions of U.S. Pat. No. 10,933,127, dated Mar. 31, 2023 (Excerpts), 5 pages.
Defendants' Supplemental Patent-Related Disclosures, Exhibit D—Invalidity Contentions of U.S. Pat. No. 10,933,127, Jun. 27, 2023 (Excerpts), 110 pages.
DeFrancesco, "The 'anti-hype' vaccine," Nat Biotechnol., Mar. 2017, 35(3):193-197.
Del Pozo-Rodríguez et al., "Lipid Nanoparticles as Vehicles for Macromolecules: Nucleic Acids and Peptides," Recent Pat Drug Deliv Formul., Sep. 2011, 5(3):214-226.
Deming et al, "Vaccine Efficacy in Senescent Mice Challenged with Recombinant SARS-CoV Bearing Epidemic and Zoonotic Spike Variants," PLoS Medicine, Dec. 2006, 3(12):e525, 17 pages.
Deposition of Daniel O. Griffin, M.D., Ph.D. in *BioNTech SE and Pfizer Inc.* v. *Moderna TX, Inc.*, in IPR2023-01358 and IPR2023-01359, May 22, 2024, 317 pages.
Deposition of Daniel O. Griffin, M.D., Ph.D. in *BioNTech SE and Pfizer Inc.* v. *Moderna TX, Inc.*, in IPR2023-01358 and IPR2023-01359, Sep. 20, 2024, 77 pages.
Deposition of Deborah Fuller, Ph.D. in *BioNTech SE and Pfizer Inc.* v. *Moderna TX, Inc.*, in IPR2023-01358 and IPR2023-01359, Aug. 2, 2024, 130 pages.
Deposition of James E. Malackowski in *BioNTech SE and Pfizer Inc.* v. *Moderna TX, Inc.*, in IPR2023-01358 and IPR2023-01359, Jul. 22, 2024, and Errata Sheet dated Aug. 27, 2024, 65 pages.
Deposition of James J. Moon, Ph.D. in *BioNTech SE and Pfizer Inc.* v. *Moderna TX, Inc.*, in IPR2023-01358 and IPR2023-01359, May 10, 2024, 190 pages.
Deposition of James J. Moon, Ph.D. in *BioNTech SE and Pfizer Inc.* v. *Moderna TX, Inc.*, in IPR2023-01358 and IPR2023-01359, Sep. 13, 2024, 51 pages.
Deposition of L. Ross Pierce, M.D., in *BioNTech SE and Pfizer Inc.* v. *Moderna TX, Inc.*, in IPR2023-01358 and IPR2023-01359, Oct. 4, 2024 (redacted version of Ex. 2256), 56 pages.
Deposition of Philip Krause, M.D. in *BioNTech SE and Pfizer Inc.* v. *Moderna TX, Inc.*, in IPR2023-01358 and IPR2023-01359, Aug. 14, 2024 (redacted), 158 pages.
Deposition of W. Christopher Bakewell in *BioNTech SE and Pfizer Inc.* v. *Moderna TX, Inc.*, in IPR2023-01358 and IPR2023-01359, Oct. 3, 2024, 64 pages.
Deposition of Warren C.W. Chan Ph.D. in *BioNTech SE and Pfizer Inc.* v. *Moderna TX, Inc.*, in IPR2023-01358 and IPR2023-01359, Jul. 30, 2024, 375 pages.
Diken et al., "Current Developments in Actively Personalized Cancer Vaccination with a Focus on RNA as the Drug Format," Prog Tumor Res., Sep. 4, 2015, 42:44-54.
Dimitriadis et al., "Translation of rabbit globin mRNA introduced by liposomes into mouse lymphocytes," Nature, Aug. 31, 1978, 274(5674):923-924.
Division of Microbiology and Infectious Diseases (DMID) Protocol No. 20-0003—mRMA-1273, Version 1.0 (Excerpts—Exhibit No. 2150 in IPR2023-01359), dated Feb. 14, 2020, 14 pages.
Division of Microbiology and Infectious Diseases (DMID) Protocol No. 20-0003—mRMA-1273, Version 3.0 (Excerpts—Exhibit No. 2149 in IPR2023-01358), dated Mar. 30, 2020, 13 pages.
Division of Microbiology and Infectious Diseases (DMID) Protocol No. 20-0003—mRMA-1273, Version 4.0 (Excerpts—Exhibit No. 2151 in IPR2023-01359), dated May 20, 2020, 16 pages.
Division of Microbiology and Infectious Diseases (DMID) Protocol, "Phase I, Open-Label, Dose-Ranging Study of the Safety and Immunogenicity of 2019-nCoV Vaccine (mRNA-1273) in Healthy Adults (Excerpts—Exhibit No. 2053 in IPR2023-01359)," dated Mar. 30, 2020, 8 pages.
Division of Microbiology and Infectious Diseases (DMID) Protocol, "Phase I, Open-Label, Dose-Ranging Study of the Safety and Immunogenicity of 2019-nCoV Vaccine (mRNA-1273) in Healthy Adults (Excerpts—Exhibit No. 2054 in IPR2023-01359)," dated Feb. 14, 2020, 10 pages.
Division of Microbiology and Infectious Diseases (DMID) Protocol, "Phase I, Open-Label, Dose-Ranging Study of the Safety and Immunogenicity of 2019-nCoV Vaccine (mRNA-1273) in Healthy Adults (Excerpts—Exhibit No. 2055 in IPR2023-01359)," dated May 20, 2020, 12 pages.
Dolgin, "Business: The billion-dollar biotech," Nature, Jun. 4, 2015, 522(7554):26-28.
Dormitzer, "Synthetic Vaccinology at Novartis," Presentation at The National Academy of Sciences Forum on Synthetic Biology, The Keck Center, Washington, D.C., Oct. 21, 2013, 12 pages.
Drummond et al., "The Evolutionary Consequences of Erroneous Protein Synthesis," Nature Reviews Genetics, Oct. 2009, 10(10:715-724.
Du et al., "Recombinant adeno-associated virus expressing the receptor-binding domain of severe acute respiratory syndrome

(56) References Cited

OTHER PUBLICATIONS coronavirus S protein elicits neutralizing antibodies: Implication for developing SARS vaccines," Virology, Sep. 15, 2006, 353(1):6-16.
Dufourc, "Sterols and membrane dynamics," J Chem Biol., Nov. 2008, 1(1-4):63-77.
Ellebedy et al., "Influenza Vaccines," Vaccine, Nov. 5, 2009, 27(Suppl 4):D65-D68.
Engler et al., "Half- vs Full-Dose Trivalent Inactivated Influenza Vaccine (2004-2005)—Age, Dose, and Sex Effects on Immune Responses," Arch Intern Med., Dec. 8, 2008, 168(22):2405-2414.
Erasmus et al., "A Nanostructured Lipid Carrier for Delivery of a Replicating Viral RNA Provides Single, Low-Dose Protection against Zika," Mol Ther., Oct. 3, 2018, 26(10):2507-2522.
Erasmus et al., "An Alphavirus-derived replicon RNA vaccine induces SARS-CoV-2 neutralizing antibody and T cell responses in mice and nonhuman primates," Science Translational Medicine, Aug. 5, 2020, 12(555):eabc9396, 11 pages.
Ernsting et al., "Factors Controlling the Pharmacokinetics, Biodistribution and Intratumoral Penetration of Nanoparticles," J. Control Release., Dec. 28, 2013, 172(3):782-794.
Escriou et al., "Protection from SARS coronavirus conferred by live measles vaccine expressing the spike glycoprotein," Virology, Mar. 2014, 452-453:32-41.
European Medicines Agency, "Assessment Report for COVID-19 Vaccine Moderna," dated Mar. 11, 2021, 169 pages.
European Medicines Agency, "Assessment Report for Spikevax," dated Sep. 14, 2023, 48 pages.
European Medicines Agency, "Nuvaxovid," retrieved on Jul. 11, 2024, retrieved from URL <https://www.ema.europa.eu/en/medicines/human/EPAR/nuvaxovid>, 12 pages.
Fauquet, "Taxonomy, Classification and Nomenclature of Viruses," Encyclopedia of Virology, Third Ed., 2008, pp. 9-23.
FDA, "E6(R2) Good Clinical Practice: Integrated Addendum to ICH E6(R1—Guidance for Industry," U.S. Department of Health and Human Services, Mar. 2018, 68 pages.
FDA, "Guidance for Industry E6 Good Clinical Practice: Consolidated Guidance," U.S. Department of Health and Human Services, Apr. 1996, 63 pages.
Felgner et al., "Lipofection: A highly efficient, lipid-mediated DNA-transfection procedure," PNAS, Nov. 1987, 84(21):7413-7417.
Final Written Decision in *BioNTech SE and Pfizer Inc.* v. *Moderna TX, Inc.*, IPR2023-01358, dated Mar. 5, 2025, 124 pages.
Final Written Decision in *BioNTech SE and Pfizer Inc.* v. *Moderna TX, Inc.*, IPR2023-01358, dated Mar. 5, 2025, 133 pages.
Fleeton et al., "Self-replicative RNA vaccines elicit protection against influenza A virus, respiratory syncytial virus, and a tickborne encephalitis virus," J Infect Dis., May 2001, 183(9):1395-1398.
Fujimori, "How this Once Little-Known Molecule is Disrupting Medicine," Pfizer, Jun. 2022, 7 pages.
Fuller, "How mRNA and DNA vaccines could soon treat cancers, HIV, autoimmune disorders and genetic diseases," The Conversation, Jan. 24, 2022, 5 pages.
Gandhi et al., "Immunization of HIV-1-Infected Persons with Autologous Dendritic Cells Transfected with mRNA Encoding HIV-1 Gag and Nef: Results of a Randomized, Placebo-Controlled Clinical Trial," JAIDS Journal of Acquired Immune Deficiency Syndromes, Mar. 2016, 71(3):246-253.
Gao et al., "Nonviral Gene Delivery: What We Know and What Is Next," The AAPS Journal, Mar. 2007, 9(1):E92-E104.
Garde et al., "The story of mRNA: How a once-dismissed idea became a leading technology in the Covid vaccine race," STAT News, Nov. 10, 2020, 23 pages.
Geall et al., "Nonviral delivery of self-amplifying RNA vaccines," PNAS, Sep. 4, 2012, 109(36):14604-14609.
Geall et al., "Using self-amplifying mRNA vaccines to facilitate a rapid response to pandemic influenza," Eur Pharm Rev., Jul. 3, 2014, 5 pages.
GenBank Accession No. AGN52936.1, "spike glycoprotein [Middle East respiratory syndrome coronavirus]," Jun. 10, 2013, 3 pages.
GenBank Accession No. AHX22069, "fusion glycoprotein F0 [Human respirovirus 3]," May 14, 2014, 2 pages.
Geneseq Accession No. BCI53556, First entry: Jan. 14, 2016, 2 pages.
Geneseq Accession No. BGP67180, First entry: Sep. 19, 2019, 2 pages.
Gilboa et al., "Cancer immunotherapy with mRNA-transfected dendritic cells," Immunol Rev., Jun. 2004, 199:251-263.
Gilleron et al., "Image-Based Analysis of Lipid Nanoparticle-Mediated siRNA Delivery, Intracellular Trafficking and Endosomal Escape," Nature Biotech., Jul. 2013, 31(7):638-646.
Ginn et al., "Gene Therapy Clinical Trials Worldwide to 2017: An Update," The Journal of Gene Medicine, May 2018, 20(5):e3015, 16 pages.
Glenn et al., "Safety and immunogenicity of a Sf9 insect cell-derived respiratory syncytial virus fusion protein nanoparticle vaccine," Vaccine, Jan. 7, 2013, 31(3):524-532.
Gorbalenya, A., E., "The species *Severe acute respiratory syndrome related coronavirus*: classifying 2019-nCoV and naming it SARS-CoV-2," Nature Microbiology, Mar. 2020, 5(4):536-544.
Greer et al., "Long-term protection in hamsters against human parainfluenza virus type 3 following mucosal or combinations of mucosal and systemic immunizations with chimeric alphavirus-based replicon particles," Scand J Immunol., Dec. 2007, 66(6):645-653.
Griffin et al., "A small $CD11b^+$ human B1 cell subpopulation stimulates T cells and is expanded in lupus," Journal of Experimental Medicine, Dec. 19, 2011, 208(13):2591-2598.
Griffin et al., "Co-infection with Hepatitis C Virus Increases Mortality in HIV-1 Infected Patients Through Increased Liver-Related Deaths Rather Than By Increasing Malignancy Related Deaths," J. AIDS and Clin. Res., 2016, 7(4): 3 pages.
Griffin et al., "Cytokine storm of a different flavour: the different cytokine signature of SARS-CoV-2 the cause of COVID-19 from the original SARS outbreak," Journal of Global Antimicrobial Resistance, Mar. 2021, 24:90-92.
Griffin et al., "Human B1 cells in umbilical cord and adult peripheral blood express the novel phenotype $CD20^+$ $CD27^+$ $CD43^+$ $CD70^-$," Journal of Experimental Medicine., Jan. 2011, 208(1):67-80.
Guevara et al., "Advances in Lipid Nanoparticles for mRNA-Based Cancer Immunotherapy," Front Chem., Oct. 23, 2020, 8:589959, 17 pages.
Guo et al., "Nanoparticles escaping RES and endosome: Challenges for siRNA delivery for cancer therapy," J Nanomat., Jan. 2011, 742895:1-12.
Hartmann et al., "Part I RNA Synthesis and Detection," Handbook of RNA Biochemistry, Second Edition, 2014, pp. 1-27.
Hashiba et al., "The use of design of experiments with multiple responses to determine optimal formulations for in vivo hepatic mRNA delivery," J Control Release., Nov. 10, 2020, 327:467-476.
Hattinger et al., "Prophylactic mRNA Vaccination against Allergy Confers Long-Term Memory Responses and Persistent Protection in Mice," Journal of Immunology Research, 2015, 2015(1):797421, 12 pages.
Hatziantoniou et al., "Anaphylactic reactions to mRNA COVID-19 vaccines: A call for further study," Vaccine, May 6, 2021, 39(19):2605-2607.
He et al., "Single-component, self-assembling, protein nanoparticles presenting the receptor binding domain and stabilized spike as SARS-CoV-2 vaccine candidates," Sci Adv., Mar. 19, 2021, 7(12):eabf1591, 17 pages.
Hecker et al., "Non-Viral DNA and mRNA Gene Delivery to the CNS Pre-Operatively for Neuroprotection and Following Neurotrauma—681," Molecular Therapy, May 2004, 9(S1):S258.
Heiser et al., "Induction of Polyclonal Prostate Cancer-Specific CTL Using Dendritic Cells Transfected with Amplified Tumor RNA1," J Immunol., Mar. 2001, 166(5):2953-2960.
Hekele et al., "Rapidly produced SAM? vaccine against H7N9 influenza is immunogenic in mice," Emerging Microbes & Infections, Jan. 2013, 2:1-7.

(56) References Cited

OTHER PUBLICATIONS

Hemmer et al., "Minimal peptide length requirements for CD4+ T cell clones—implications for molecular mimicry and T cell survival," Int Immunol., Mar. 2000, 12(3):375-383.
Heyes et al., "Cationic lipid saturation influences intracellular delivery of encapsulated nucleic acids," Journal of Controlled Release, Oct. 2005, 107(2):276-287.
Hoernes et al., "Nucleotide modifications within bacterial messenger RNAs regulate their translation and are able to rewire the genetic code," Nucleic Acids Res., Jan. 29, 2016, 44(2):852-862.
Hoerr et al., "In vivo application of RNA leads to induction of specific cytotoxic T lymphocytes and antibodies—Abstract No. OP 57" European Journal of Immunology, Jan. 2000, 30:1-7.
Hoerr et al., Stabilized Messenger RNA (RNActiveTM) as a Tool for Innovative Gene Delivery. Tissue Engineering. Apr. 2007; 13(4): 865-925.
Hoerr, "More than a messenger: A new class of drugs—mRNA-based therapeutics," Genetic Engineering & Biotechnology News, Jun. 18, 2013, retrieved on Mar. 25, 2016, retrieved from URL <http://www.genengnews.com/gen-articles/more-than-a-messenger-a-new-class-of-drugs-mrna-based-therapeutics/4916/>, 3 pages.
Holtkamp et al., "Modification of antigen-encoding RNA increases stability, translational efficacy, and T-cell stimulatory capacity of dendritic cells," Gene Therapy, Dec. 2006, 108(13):4009-4017.
Hope et al., "Reduction of Liposome Size and Preparation of Unilamellar Vesicles by Extrusion Techniques," Liposome Technology, 1993, Chapter 8, pp. 123-139.
Horr, "RNA vaccine for the induction of specific cytotoxic T lymphocytes (CTL) and antibodies," Dissertation for the degree of Doctor of Natural Sciences, Eberhard Karls University of Tübingen, 1999, 138 pages (English translation).
Houser et al., "Influenza Vaccines: Challenges and Solutions," Cell Host Microbe., Mar. 11, 2015, 17(3):295-300.
Hu et al., "Cytosolic delivery mediated via electrostatic surface binding of protein, virus, or siRNA cargos to pH-responsive core-shell gel particles," Biomacromolecules, Apr. 2009, 10(4):756-765.
Huang et al., "Asymmetric 1-alkyl-2-acyl phosphatidylcholine: a helper lipid for enhanced non-viral gene delivery," Int J Pharm., May 2012, 427(1):64-70.
Huang et al., "Construction and biological characterisation of recombinant porcine circovirus type 2 expressing the V5 epitope tag," Virus Res., Nov. 2011, 161(2):115-123.
Huang et al., "Structural and functional properties of SARS-CoV-2 spike protein: potential antivirus drug development for COVID-19," Acta Pharmacologica Sinica, Aug. 3, 2020, 41(9):1141-1149.
Huang, "In Vivo Delivery of RNAi with Lipid-Based Nanoparticles," Ann. Rev. Biomed. Eng., 2011, 13:507-530.
Human Metapneumovirus (HM PV) Clinical Features, CDC Website, Sep. 5, 2019, retrieved from URL <https://www.cdc.gov/surveillance/nrevss/hmpv/clinical.html>, 5 pages.
Institution Decision in IPR2023-01358, dated Mar. 19, 2024, 97 pages.
Institution Decision in IPR2023-01359, dated Mar. 19, 2024, 96 pages.
International Preliminary Report on Patentability in International Application No. PCT/US2021/016979, mailed on Aug. 18, 2022, 13 pages.
International Search Report and Written Opinion for Application No. PCT/US2016/058327, mailed on Jun. 29, 2017, 25 pages.
Invitation to Pay Additional Fees in International Application No. PCT/US2021/016979, mailed on Jun. 11, 2021, 13 pages.
Jaimes et al., "Phylogenetic Analysis and Structural Modeling of SARS-CoV-2 Spike Protein Reveals an Evolutionary Distinct and Proteolytically Sensitive Activation Loop," J Mol Biol., May 2020, 432(10):3309-3325.
Japanese Package Insert for Spikevax Intramuscular Injection (Monovalent: Omicron XBB.1.5), Oct. 2023, 17 pages (with English translation).
Jaume et al., "Anti-Severe Acute Respiratory Syndrome Coronavirus Spike Antibodies Trigger Infection of Human Immune Cells via a pH- and Cysteine Protease-Independent FcγR Pathway," Journal of Virology, Oct. 2011, 85(20):10582-10597.
Jayaraman et al., "Maximizing the potency of siRNA lipid nanoparticles for hepatic gene silencing in vivo," Angew Chem Int Ed Engl., Aug. 20, 2012,51(34):8529-8533.
Jeffs et al., "A Scalable, Extrusion-Free Method for Efficient Liposomal Encapsulation of Plasmid DNA," Pharmaceutical research., Mar. 2005, 22(2):362-372.
Jirikowski et al., "Reversal of diabetes insipidus in Brattleboro Rats: Intrahypothalamic injection of vasopressin mRNA," Science, Feb. 21, 1992, 255(5047):996-998.
Johanning et al., "A Sindbis virus mRNA polynucleotide vector achieves prolonged and high level heterologous gene expression in vivo," Nucleic Acids Res., May 11, 1995, 23(9):1495-1501.
Johansson et al., "Intradermal Electroporation of Naked Replicon RNA Elicits Strong Immune Responses," PLoS One, Jan. 2012, 1: Article e29732 , 7 pages.
Jorquera et al., "Nanoparticle Vaccines Encompassing the Respiratory Syncytial Virus (RSV) G Protein CX3C Chemokine Motif Induce Robust Immunity Protecting from Challenge and Disease," PLoS One, Sep. 10, 2013;8(9):e74905, 13 pages.
Kallen et al., "A novel, disruptive vaccination technology: self-adjuvanted RNActive(®) vaccines," Hum Vaccin Immunother., Oct. 2013, 9(10):2263-2276.
Kalra et al., "Virosomes: As a Drug Delivery Carrier," American Journal of Advanced Drug Delivery, 2013, 1:29-35.
Kam et al., "Antibodies against trimeric S glycoprotein protect hamsters against SARS-CoV challenge despite their capacity to mediate FcgammaRII-dependent entry into B cells in vitro," Vaccine, Jan. 8, 2007, 25(4):729-740.
Kanapathipillai et al., "Nanoparticle targeting of anti-cancer drugs that alter intracellular signaling or influence the tumor microenvironment," Adv. Drug Deliv. Rev., Dec. 15, 2014, 79-80, pp. 107-118.
Kanasty et al., "Delivery materials for siRNA therapeutics," Nat Mater., Nov. 2013, 12(11):967-977.
Kansensho.or.jp [online], "Novel Coronavirus Infection," The Japanese Association for Infectious Diseases, last updated on May 23, 2024, retrieved on Jun. 4, 2025, retrieved from URL <https://www.kansensho.or.jp/modules/topics/index.php?content_id=31>, 16 pages (with English Translation).
Kansensho.or.jp [online], "Response to Novel Coronavirus (2019—nCoV) Infection (as of Jan. 28, 2020)," General incorporated foundation Japanese Association for Infectious Diseases, Jan. 28, 2020, retrieved on Jun. 4, 2025, retrieved from URL <https://www.kansensho.or.jp/uploads/files/topics/2019ncov/2019ncov_taiou 200128.pdf>, 6 pages (with English Translation).
Kansteiner, "It's the end of the line for J&J's COVID shot in the US, CDC says," Fiercepharma, May 16, 2023, 2 pages.
Karikó et al., "Generating the optimal mRNA for therapy: HPLC purification eliminates immune activation and improves translation of nucleoside-modified, protein-encoding mRNA," Nucleic Acids Res., Nov. 2011, 39(21):e142, 10 pages.
Karikó et al., "Incorporation of Pseudouridine Into mRNA Yields Superior Nonimmunogenic Vector With Increased Translational Capacity and Biological Stability," Mol Ther., Nov. 2008, 16(11):1833-1840.
Karikó et al., "Increased eythropoiesis in mice injected with submicrogram quantities of pseudouridine-containing mRNA encoding erythropoietin," Molecular Therapy, 20(5):948-953.
Karikó et al., "Modified Uridines Are the Key to a Successful Message," Nature Reviews Immunology, Oct. 2021, 21(10):619.
Karikó et al., "Naturally occurring nucleoside modifications suppress the immunostimulatory activity of RNA: Implication for therapeutic RNA development," Current Opinion in Drug Discovery and Development, Sep. 2007, 10(5):523- 532.
Karikó et al., "Suppression of RNA recognition by Toll-like receptors: The impact of nucleoside modification and the evolutionary origin of RNA," Immunity, Aug. 2005, 23:165-175.
Kauffman et al., "Optimization of Lipid Nanoparticle Formulations for mRNA Delivery in Vivo with Fractional Factorial and Definitive Screening Designs," Nano Lett., Nov. 11, 2015, 15(11):7300-7306.
Keegan, "The Lasker Awards: A History of "America's Nobels"," Cell Mentor, Sep. 11, 2018, 7 pages.

(56) References Cited

OTHER PUBLICATIONS

Keshwara et al., "Rabies-based vaccine induces potent immune responses against Nipah virus," NPJ Vaccines, Apr. 15, 2019, 4:15; Erratum in: NPJ Vaccines, May 13, 2019, 4:18, 10 pages.
Kim et al., "Generation and Characterization of DNA Vaccines Targeting the Nucleocapsid Protein of Severe Acute Respiratory Syndrome Coronavirus," Virology, May 2004, 78(9):4638-4645.
King et al., "Virus Taxonomy: Classification and Nomenclature of Viruses. Ninth Report of the International Committee on Taxonomy of Viruses," Int Union of Microbiol Soc., 2012, 50 pages.
Kisich et al., "Antimycobacterial agent based on mRNA encoding human beta-defensin 2 enables primary macrophages to restrict growth of *Mycobacterium tuberculosis*," Infect Immun., Apr. 2001, 69(4):2692-9.
Kolata, "Kati Karikó Helped Shield the World from the Coronavirus," New York Times, Apr. 8, 2021, Updated Sep. 24, 2021, 5 pages.
Konwarh, "Nanobodies: Prospects of Expanding the Gamut of Neutralizing Antibodies Against the Novel Coronavirus, SARS-CoV-2," Frontiers in immunology, Jun. 23, 2020, 11:1531, 6 pages.
Kozielski et al., "Bioreducible cationic polymer-based nanoparticles for efficient and environmentally triggered cytoplasmic siRNA delivery to primary human brain cancer cells," ACS Nano, Apr. 22, 2014, 8(4):3232-41.
Krammer et al., "Chimeric hemagglutinin influenza virus vaccine constructs elicit broadly protective stalk-specific antibodies," J Virol., Jun. 2013, ;87(12):6542-50.
Kranz et al., "Systemic RNA Delivery to Dendritic Cells Exploits Antiviral Defense for Cancer Immunotherapy," Nature, 2016, 534:396-411.
Kreiter et al., "Intranodal Vaccination with Naked Antigen-Encoding RNA Elicits Potent Prophylactic and Therapeutic Antitumoral Immunity," Cancer Research, Nov. 2010, 70:9031-9040.
Kreiter et al., "Tumor vaccination using messenger RNA: prospects of a future therapy," Curr Opinion in Immun., Jun. 2011, 23(3):399-406.
Kresge, "The messenger RNA pioneers everyone ignored," Bloomberg, Nov. 23, 2021, last accessed Aug. 24, 2023, retrieved from URL <https://www.bloomberg.com/news/newsletters/2021-11-23/themessenger-rna-pioneers-everyone-ignored>, 4 pages.
Kuhn et al., "mRNA as a versatile tool for exogenous protein expression," Current Gene Therapy, Oct. 2012, 12(5):347-361.
Kumari et al., "A critical overview of current progress for COVID-19: development of vaccines, antiviral drugs, and therapeutic antibodies," J. Biomed Sci., Sep. 2022, 29:68, 36 pages.
Kutzler et al., "DNA Vaccines: Ready for Prime Time?," Nature Reviews Genetics, 2008, 9:776-788.
Langer, "New methods of drug delivery," Science, Sep. 28, 1990, 249:1527-1533.
Leal et al., "Phase I clinical trial of an intranodally administered mRNA-based therapeutic vaccine against HIV-1 infection," AIDS, 2018, 32(17):2533-2545.
Leitner et al., "DNA and RNA-based vaccines: principles, progress and prospects," Vaccine, Dec. 10, 1999, 18(9-10):765-77.
Leung et al., "Chapter Four—Lipid nanoparticles for short interfering RNA delivery," Advances in Genetic, Jan. 2014, 88:71-110.
Leuschner et al., "Therapeutic siRNA silencing in inflammatory monocytes in mice," Nat Biotechnol., Oct. 9, 2011, 29(11):1005-10.
Li et al., "Application of ultra-high performance liquid chromatography for chemical characterization of liposome-based therapeutic small-interfering RNA," American Pharmaceutical Review, Sep.-Oct. 2010, 13(6), 13 pages.
Li et al., "Cell Attachment Domains of the Porcine Epidemic Diarrhea Virus Spike Protein Are Key Targets of Neutralizing Antibodies," J Virol., May 26, 2017, 91(12):e00273-17, 16 pages.
Li et al., "Effects of local structural transformation of lipid-like compounds on delivery of messenger RNA," Sci Rep., Feb. 26, 2016, 6:22137, 8 pages.
Li et al., "Overcoming obstacles to develop effective and safe siRNA therapeutics," Expert Opin Biol Ther., May 2009, 9(5):609-19.
Li, "Receptor recognition mechanisms of coronaviruses: a decade of structural studies," J Virol., Feb. 2015, 89(4):1954-64.
Liang et al., "Efficient Targeting and Activation of Antigen-Presenting Cells In Vivo after Modified mRNA Vaccine Administration in Rhesus Macaques," Molecular Therapy, Dec. 2017, 25(12):2635-2647.
Liang et al., "Enhanced Neutralizing Antibody Response Induced by Respiratory Syncytial Virus Prefusion F Protein Expressed by a Vaccine Candidate," J Virol., Sep. 2015, 89(18):9499-510.
Lin et al., "Progress and challenges of mRNA vaccines," Interdisc Med., Dec. 22, 2022, 1(1):e20220008, 5 pages.
Lin et al., "Three-dimensional imaging of lipid gene-carriers: membrane charge density controls universal transfection behavior in lamellar cationic liposome-DNA complexes," Biophys J., May 2003, 84(5):3307-16.
Liu et al., "Chimeric severe acute respiratory syndrome coronavirus (SARS-CoV) S glycoprotein and influenza matrix 1 efficiently form virus-like particles (VLPs) that protect mice against challenge with SARS-CoV," Vaccine, Sep. 2, 2011, 29(38):6606-13.
Liu et al., "Influence of polyethylene glycol density and surface lipid on pharmacokinetics and biodistribution of lipid-calcium-phosphate nanoparticles," Biomaterials, Mar. 2014, 35(9):3027-34.
Liu et al., "The Membrane Protein of Severe Acute Respiratory Syndrome Coronavirus Acts as a Dominant Immunogen Revealed by a Clustering Region of Novel Functionally and Structurally Defined Cytotoxic T-Lymphocyte Epitopes," The Journal of infectious diseases, Oct. 15, 2010, 202(8):1171-80.
Liu, "AstraZeneca withdraws US COVID vaccine application, shifts focus to antibody treatments," Fierce Pharma, Nov. 10, 2022, 2 pages.
Loftus, "Moderna Signals It May Enforce Covid-19 Vaccine Patents in Wealthy Nations," Wall Street Journal, Mar. 7, 2022, last accessed Jul. 1, 2024, retrieved from URL <https://www.wsj.com/articles/moderna-signals-it-may-enforce-covid-19-vaccine-patents-in-wealthy-nations-11646699609>, 4 pages.
Lorenzi et al., "Intranasal vaccination with messenger RNA as a new approach in gene therapy: Use against tuberculosis," BMC Biotechnol., Oct. 2010, 10(77):1-11.
Lovelace Jr., et al., "Dr. Anthony Fauci says chance of coronavirus vaccine being highly effective is 'not great'," CNBC.com, Aug. 7, 2020, retrieved on Sep. 16, 2025, retrieved from URL <https://www.cnbc.com/2020/08/07/coronavirus-vaccine-dr-fauci-says-chances-of-it-being-highly-effective-is-not-great.html>, 4 pages.
Lu et al., "Bat-to-human: spike features determining 'host jump' of coronaviruses SARS-CoV, MERS-CoV, and beyond," Trends Microbiol., Aug. 2015, 23(8):468-78.
Lu et al., "Immunogenicity of DNA Vaccines Expressing Human Immunodeficiency Virus Type 1 Envelope Glycoprotein With and Without Deletions in the V1/2 and V3 Regions," AIDS Research & Human Retroviruses, Jan. 1998, 14(2):151-155.
Lutz et al., "Unmodified mRNA in LNPs constitutes a competitive technology for prophylactic vaccines," NPJ Vaccines, Oct. 19, 2017, 2:29, 9 pages.
Ma et al., "Intranasal vaccination with recombinant receptor-binding domain of MERS-CoV spike protein induces much stronger local mucosal immune responses than subcutaneous immunization: Implication for designing novel mucosal MERS vaccines," Vaccine, Apr. 11, 2014, 32(18):2100-8.
Maclachlan, "Lipid Nanoparticle-mediated delivery of messenger RNA," Presentation, 1st International mRNA Health Conference, Tubingen, Germany, Oct. 24, 2013, retrieved on Oct. 3, 2025, retrieved from URL <https://paperzz.com/doc/6840698/lipid-nanoparticle-mediated-delivery-of-messenger-rna>, 32 pages.
Magini et al., "Self-Amplifying mRNA Vaccines Expressing Multiple Conserved Influenza Antigens Confer Protection against Homologous and Heterosubtypic Viral Challenge," PLoS One, Aug. 15, 2016, 11(8):e0161193, 25 pages.
Mandal et al., "Reprogramming human fibroblasts to pluripotency using modified mRNA," Nat Protoc., Mar. 2013, 8(3):568-82.

(56) References Cited

OTHER PUBLICATIONS

Marshall et al., "Ch. 79: Regulation and Testing of Vaccines," Plotkin's Vaccines, 7th edition, 2018, pp. 1547-1565.
Martin et al., "A SARS DNA Vaccine Induces Neutralizing Antibody and Cellular Immune Responses in Healthy Adults in a Phase I Clinical Trial," Vaccine, Nov. 25, 26(50):6338-43.
Martinon et al., "Induction of virus-specific cytotoxic T lymphocytes in vivo by liposome-entrapped mRNA," EurJ Immunol., Jul. 1993, 23(7):1719-22.
Mas et al., "Engineering, Structure and Immunogenicity of the Human Metapneumovirus F Protein in the Postfusion Conformation," PLoS Pathog., Sep. 9, 2016, 12(9):e1005859, 21 pages.
Mcdonnell et al. "Molecular Medicine: DNA vaccines," N Engl J Med., Jan. 4, 1996, 334(1):42-5.
Mclellan et al., "Structure and function of respiratory syncytial virus surface glycoproteins," Curr Top Microbiol Immunol., Dec. 21, 2013;372:83-104.
Mclellan et al., "Structure of respiratory syncytial virus fusion glycoprotein in the postfusion conformation reveals preservation of neutralizing epitopes," J Virol., Aug. 2011, 85(15):7788-96.
Mclellan et al., "Structure-based design of a fusion glycoprotein vaccine for respiratory syncytial virus," Science, Nov. 2013, 342(6158):592-8.
Mendonca et al., "Design of lipid-based nanoparticles for delivery of therapeutic nucleic acids," Drug Discov Today., Mar. 2023, 28(3):103505, 17 pages.
Miao et al., "Delivery of mRNA vaccines with heterocyclic lipids increases anti-tumor efficacy by STING-mediated immune cell activation," Nat Biotechnol., Oct. 2019, 37(10):1174-1185.
Mitchell et al., "RNA transfected dendritic cells as cancer vaccines," Curr Opin Mal Ther., Apr. 2000, 2(2):176-81.
Mitchell et al., "RNA-transfected dendritic cells in cancer immunotherapy," J Clin Invest., Nov. 2000, 106 (9):1065-9.
Mockey et al., "mRNA-based cancer vaccine: prevention of B16 melanoma progression and metastasis by systemic injection of MART1 mRNA histidylated lipopolyplexes," Cancer Gene Therapy, Jun. 2007, 14:802-814.
Moderna Form 10-K for the fiscal year ended Dec. 31, 2018, 308 pages.
Moderna Form 10-K for the fiscal year ended Dec. 31, 2022, 182 pages.
Moderna Form 10-Q for the quarterly period ended Jun. 30, 2024, 44 pages.
Moderna Form 8-K, Mar. 16, 2020, 11 pages.
Moderna, Inc. Form 10-K, 2020, 330 pages.
Moderna, Inc. Form 10-K, 2023, 219 pages.
Moderna, Inc., Patents, retrieved on Oct. 31, 2023, retrieved from URL <https://www.modernatx.com/patents>, 3 pages.
Moderna, Science & Technology Day, dated May 17, 2022, 136 pages.
Moderna, Vaccines and Related Biological Products Advisory Committee Presentation: Moderna COVID-19 Variant Vaccines; MOD_000767652-MOD_000767686, dated Jun. 15, 2023, 35 pages.
Modjarrad, "MERS-CoV vaccine candidates in development: The current landscape," Vaccine, Jun. 3, 2016, 34(26):2982-2987.
Mok et al., "An Alphavirus Replicon-Based Human Metapneumovirus Vaccine Is Immunogenic and Protective in Mice and Cotton Rats," J Virol., Nov. 2008, 82(22):11410-11418.
Mullard, "COVID-19 vaccine success enables a bolder vision for mRNA cancer vaccines, says BioNTech CEO," Nat Rev Drug Discov., Jul. 2021, 20(7):500-501.
Muller et al., "Transfection of dendritic cells with RNA induces CD4- and COB-mediated T cell immunity against breast carcinomas and reveals the immunodominance of presented T cell epitopes," J Immunol., Jun. 15, 2003, 170(12):5892-6.
Murphy, Excerpts from "Janeway's Immunobiology," 8th Ed., 2012, 250 pages.
Muthumani et al., "A synthetic consensus anti-spike protein DNA vaccine induces protective immunity against Middle East respiratory syndrome coronavirus in nonhuman primates," Sci Transl Med., Aug. 19, 2015, 7(301):301ra132, 29 pages.
Nakayama et al., "Comparison of Current Regulatory Status for Gene-Based Vaccines in the U.S., Europe and Japan," Vaccines, Mar. 2015, 3(1):186-202.
Narayanan et al., "Interplay between viruses and host mRNA degradation," Biochim Biophys Acta., Jun.-Jul. 2013, 1829(6-7):732-741.
National Human Genome Research Institute, "Central Dogma," 2023, NIH, URL: <https://www.genome.gov/geneticsglossary/Central-Dogma>, 4 pages.
National Human Genome Research Institute, "Double Helix," 2023, NIH, URL <https://www.genome.gov/geneticsglossary/Double-Helix>, 2 pages.
Non-Final Office Action in U.S. Appl. No. 18/762,384, dated Apr. 21, 2025, 9 pages.
Non-Final Office Action in U.S. Appl. No. 18/762,384, dated Sep. 11, 2024, 17 pages.
Notice of Allowance in U.S. Appl. No. 18/762,384, dated Feb. 5, 2025, 7 pages.
Notice of Allowance in U.S. Appl. No. 18/762,384, dated Oct. 17, 2024, 7 pages.
Onpattro, "Highlights of Prescribing Information," FDA Prescribing Label, Aug. 2018, 14 pages.
Openshaw et al., "Immune Responses and Disease Enhancement During Respiratory Syncytial Virus Infection," Clinical Microbiology Reviews, Jul. 2005, 18(13):541-555.
Opposition against European Patent No. 3324979 B1, filed by BioNTech SE (Opponent) against ModernaTX, Inc. (Patentee) on Jul. 10, 2023, 86 pages.
Ostro et al., "Evidence for translation of rabbit globin mRNA after liposome-mediated insertion into a human cell line," Nature, Aug. 31, 1978, 274(5674):921-3.
Paoletti, "Applications of Pox Virus Vectors to Vaccination: An Update," PNAS, Oct. 1996, 93(21):11349-11353.
Paramasivam et al., "Endosomal Escape of Delivered mRNA from Endosomal Recycling Tubules Visualized at the Nanoscale," Journal of Cell Biology, Dec. 9, 2021, 221(2):e202110137, 20 pages.
Pardi et al., "Nucleoside-modified mRNA vaccines induce potent T follicular helper and germinal center B cell responses," J Exp Med., Jun. 4, 2018, 215(6):1571-1588.
Park et al., "Non-Viral COVID-19 Vaccine Delivery Systems," Advanced Drug Delivery Reviews, Feb. 2021, 169:137-151.
Park et al., "The Miracle Workers. Heroes of the Year.," Time Magazine, Dec. 27, 2021, 17 pages.
Pascolo, "Messenger RNA-based vaccines," Expert Opin Biol Ther., Aug. 2004, 4(8):1285-94.
Pascolo, "Vaccination with messenger RNA (mRNA)," Handb Exp Pharmacol., 2008, 183:221-235.
Patel et al., "Naturally-occurring cholesterol analogues in lipid nanoparticles induce polymorphic shape and enhance intracellular delivery of mRNA," Nat Commun., Feb. 20, 2020, 11(1):983, 13 pages.
Patent Owner's Preliminary Response in IPR2023-01358 dated Dec. 8, 2023, 82 pages.
Patent Owner's Preliminary Response in IPR2023-01359 dated Dec. 7, 2023, 83 pages.
Patent Owner's Preliminary Statement Regarding Alleged Inconsistent Positions in IPR2023-01359 dated Jan. 16, 2024, 14 pages.
Patent Owner's Preliminary Statement Regarding Petitioner's Inconsistent Positions in IPR2023-01358 dated Jan. 16, 2024, 14 pages.
Patent Owner's Response in IPR2023-01358 dated May 31, 2024, 103 pages.
Patent Owner's Response in IPR2023-01359 dated May 31, 2024, 103 pages.
Patent Owner's Sur-Reply in IPR2023-01358 dated Oct. 16, 2024, 63 pages.
Patent Owner's Sur-Reply in IPR2023-01359 dated Oct. 16, 2024, 63 pages.
Patent Owner's Sur-Reply in Support of Preliminary Response in IPR2023-01358 dated Jan. 25, 2024, 13 pages.
Patent Owner's Sur-Reply in Support of Preliminary Response in IPR2023-01359 dated Jan. 25, 2024, 13 pages.

(56) References Cited

OTHER PUBLICATIONS

Patent Sublicense Agreement Between Cellscript, LLC and ModernaTx, Inc., dated Jun. 26, 2017, 36 pages.
Peabody et al., "Termination-reinitiation occurs in the translation of mammalian cell mRNAs," Mol Cell Biol., Jul. 1986, 6(7):2695-703.
Peek et al., "Nanotechnology in vaccine delivery," Adv Drug Deliv Rev., May 22, 2008, 60(8):915-28.
Petitioner's Preliminary Statement Regarding Patent Owner's Inconsistent Positions in IPR-2023-01358 dated Jan. 23, 2024, 8 pages.
Petitioner's Reply to Patent Owner's Preliminary Response in IPR2023-01358 dated Jan. 12, 2024, 15 pages.
Petitioner's Reply to Patent Owner's Preliminary Response in IPR2024-01359 dated Jan. 12, 2024, 15 pages.
Petitioner's Reply to Patent Owner's Response in IPR2023-01358 dated Aug. 30, 2024, 68 pages.
Petitioner's Reply to Patent Owner's Response in IPR2023-01359 dated Aug. 30, 2024, 69 pages.
Phua et al., "Mesenger RNA (mRNA) nanoparticle tumour vaccination," Nanoscale., Jul. 21, 2014, 6(14):7715-29.
Plotkin, "Vaccines: Past, Present and Future," Nature Medicine, Historical Perspective, Apr. 2005, 11(Suppl. 4):S5-S11.
Press Release, Novavax, "U.S. FDA Grants Emergency Use Authorization for Novavax COVID-19 Vaccine, Adjuvanted for Individuals Aged 18 and Over," Jul. 13, 2022, 5 pages.
Probst et al., "Characterization of the ribonuclease activity on the skin surface," Genet Vaccines Ther., May 29, 2006, 4:4, 9 pages.
Pulford et al., "Liposome-siRNA-peptide complexes cross the blood-brain barrier and significantly decrease PrP'C on neuronal cells and PrP'RES in infected cell cultures," PLoS One, Jun. 2010, 5(6):e11085, 13 pages.
Rabinovich et al., "Synthetic messenger RNA as a tool for gene therapy," Hum. Gene Ther., Oct. 2006, 17:1027-1035.
Raj et al., "Dipeptidyl peptidase 4 is a functional receptor for the emerging human coronavirus-EMC," Nature, Mar. 14, 2013, 495(7440):251-4.
Ramamoorth et al., "Nonviral vectors in gene therapy—an overview," J Clin Diagn Res., Jan. 2015, 9(1):GE01-GE06.
Regla-Nava et al., "Severe Acute Respiratory Syndrome Coronaviruses with Mutations in the E Protein Are Attenuated and Promising Vaccine Candidates," Journal of Virology, Apr. 2015, 89(7):3870-3887.
Ren et al., "Recent vaccine development for human metapneumovirus," J Gen Virol., Jul. 2015, 96(Pt 7):1515-20.
Reply Declaration of Daniel Griffin in IPR2023-01358 dated Aug. 30, 2024, 280 pages (Redacted public version).
Reply Declaration of Daniel Griffin in IPR2023-01359 dated Aug. 30, 2024, 281 pages (Redacted public version).
Reply Declaration of James Moon in IPR2023-01358 dated Aug. 30, 2024, 70 pages (Redacted public version).
Reply Declaration of James Moon in IPR2023-01359 dated Aug. 30, 2024, 70 pages (Redacted public version).
Rittig et al., "Intradermal vaccinations with RNA coding for TAA generate CD8+ and CD4+ immune responses and induce clinical benefit in vaccinated patients," Mol Ther., May 2011, 19(5):990-9.
Robbins et al., "Moderna Backs down in its Vaccine Patent Fight with the NIH," New York Times, Dec. 17, 2021, 1 page.
Rodriguez-Gascon et al., "Development of nucleic acid vaccines: use of self-amplifying RNA in lipid nanoparticles," Int J Nanomedicine., Apr. 10, 2014, 9:1833-1843.
Rossi et al., "IRES-based Venezuelan equine encephalitis vaccine candidate elicits protective immunity in mice," Virology, Mar. 15, 2013, 437(2):81-8.
Sahdev et al., "Biomaterials for Nanoparticle Vaccine Delivery Systems," Pharmaceutical Research, Oct. 2014, 31(10):2563-2582.
Sahin et al., "Personalized RNA mutanome vaccines mobilize poly-specific therapeutic immunity against cancer," Nature, Jul. 13, 2017, 547(7662):222-226.
Salomon et al., "A liposomal RNA vaccine inducing neoantigen-specific CD4+ T cells augments the antitumor activity of local radiotherapy in mice," Oncoimmunology, Jun. 22, 2020, 9(1):1771925, 13 pages.
Santoro et al., "An efficient system for the evolution of aminoacyl-tRNA synthetase specificity," Nat Biotechnol., Oct. 2002, 20(10):1044-8.
Schmitt et al., "In vitro induction of a bladder cancer-specific T-cell response by mRNA-transfected dendritic cells," J Cancer Res Clin Oncol., Feb. 2001, 127(3):203-6.
Schumann et al., "Multiple links between 5-methylcytosine content of mRNA and translation," BMC Biol., Apr. 15, 2020, 18(40):1-23.
Schuurhuis et al., "Ins and outs of dendritic cells," Int Arch Allergy Immunol., Mar. 2006, 140(1):53-72.
Segura et al., "Monitoring gene therapy by external imaging of mRNA: Pilot study on murine erythropoietin," Ther Drug Monit., Oct. 2007, 29(5):612-8.
Semple et al., "Efficient encapsulation of antisense oligonucleotides in lipid vesicles using ionizable aminolipids: Formation of novel small multilamellar vesicle structures," Biochimica Et Biophysica Acta, Feb. 2001, 1510(1-2):152-166.
Semple et al., "Rational design of cationic lipids for siRNA delivery," Nature Biotechnology, Feb. 2010, 28(2):172-178.
Shaw et al., "The Path to an RSV Vaccine," Current Opinion in Virology, Jun. 2013, 3(3):332-342.
Shidhadye et al., "Solid lipid nanoparticles and nanostructured lipid carriers—innovative generations of solid lipid carriers," Curr Drug Deliv., Oct. 2008, 5(4):324-31.
Shim et al., "Intranasal immunization with plasmid DNA encoding spike protein of SARS-coronavirus/polyethylenimine nanoparticles elicits antigen-specific humoral and cellular immune responses," BMC Immunol., Dec. 31, 2010, 11:65, 9 pages.
Slimko et al., "Codon optimization of Caenorhabditis elegans GluCl ion channel genes for mammalian cells dramatically improves expression levels," Journal of Neuroscience Methods, Mar. 30, 2003, 124(1):75-81.
Smits et al., "RNA-based gene transfer for adult stem cells and T cells," Leukemia, Nov. 2004, 18(11):1898-1902.
Song et al., "Middle East Respiratory Syndrome Coronavirus Spike Protein Delivered by Modified Vaccinia Virus Ankara Efficiently Induces Virus-Neutralizing Antibodies," Journal of Virology, Nov. 2013, 87(21):11950-4.
Spikevax (COVID-19 Vaccine, mRNA), "Highlights of Prescribing Information," FDA Label, Apr. 2024, 45 pages.
Spikevax (COVID-19 Vaccine, mRNA), "Highlights of Prescribing Information," FDA Label, Jan. 2025, 43 pages.
Spikevax (COVID-19 Vaccine, mRNA), "Highlights of Prescribing Information," FDA Label, Sep. 2023, 45 pages.
Stanton et al., "Messenger RNA as a Novel Therapeutic Approach," Topics in Medicinal Chemistry RNA Therapeutics, Mar. 2017, 2 pages (Excerpts).
Steitz et al., "Effective Induction of Anti-Melanoma Immunity Following Genetic Vaccination with Synthetic mRNA Coding for the Fusion Protein EGFP.TRP2," Cancer Immunology, Mar. 2006, 55(3):246-253.
Stenler et al., "Safety and efficacy of DNA vaccines: Plasmids vs. minicircles," Human Vaccines & Immunotherapeutics, May 2014, 10(5):1306-8.
Stephenson et al., "Cross-reactivity to highly pathogenic avian influenza H5N1 viruses after vaccination with nonadjuvanted and MF59-adjuvanted influenza A/Duck/Singapore/97 (H5N3) vaccine: a potential priming strategy," J Infect Dis., Apr. 15, 2005, 191(8):1210-5.
Stewart-Jones et al., "Domain-based mRNA vaccines encoding spike protein N-terminal and receptor binding domains confer protection against SARS-CoV-2," Science Translational Medicine, Sep. 13, 2023, 15(713):eadf4100, 16 pages.
Strong et al., "Incorporation of beta-globin untranslated regions into a Sindbis virus vector for augmentation of heterologous mRNA expression," Gene Ther., Jun. 1997, 4(6):624-7.
Sullenger et al., "Emerging clinical applications of RNA," Nature, Jul. 11, 2002, 418(6894):252-8.

(56) References Cited

OTHER PUBLICATIONS

Szebeni et al., "Activation of complement by therapeutic liposomes and other lipid excipient-based therapeutic products: prediction and prevention," Adv Drug Deliv Rev., Sep. 16, 2011, 63(12):1020-30.
Szebeni et al., "Complement activation as a bioequivalence issue relevant to the development of generic liposomes and other nanoparticulate drugs," Biochem Biophys Res Commun., Dec. 18, 2015, 468(3):490-7.
Szebeni J. Complement activation-related pseudoallergy: a stress reaction in blood triggered by nanomedicines and biologicals, Mol Immunol., Oct. 2014, 61(2):163-73.
Tai et al., "Characterization of the receptor-binding domain (RBD) of 2019 novel coronavirus: implication for development of RBD protein as a viral attachment inhibitor and vaccine," Cellular and Molecular Immunology, Mar. 19, 2020, 17:613-620.
Tam et al., "Advances in Lipid Nanoparticles for siRNA Delivery," Pharmaceutics, Sep. 18, 2013, 5(3):498-507.
Tavernier, G., et al., "mRNA as gene therapeutic: How to control protein expression, J. of Controlled Release," Mar. 2011, 150(3):238-247.
Tenchov et al., "Lipid nanoparticles 2014 From liposomes to mRNA vaccine delivery, a landscape of research diversity and advancement," ACS Nano, Jun. 28, 2021, 15(11):16982-7015.
Terada et al., "Characterization of Lipid Nanoparticles Containing Ionizable Cationic Lipids Using Design-of-Experiments Approach," Langmuir., Jan. 26, 2021, 37(3):1120-1128.
Teufel et al., "Human peripheral blood mononuclear cells transfected with messenger RNA stimulate antigen-specific cytotoxic T-lymphocytes in vitro," Cell Mol Life Sci., Aug. 2005, 62(15):1755-62.
Tews et al., "Chapter 2: Self-Replicating RNA," RNA Vaccines: Methods and Protocols, 2017, 1499:15-35.
Thery et al., "The cell biology of antigen presentation in dendritic cells," Curr Opin Immunol., Feb. 2001, 13(1):45-51.
Thess et al., "Sequence-engineered mRNA Without Chemical Nucleoside Modifications Enables an Effective Protein Therapy in Large Animals," Mol Ther., Sep. 2015, 23(9):1456-64.
UniProt KB Accession No. P59594, "SPIKE_CVHSA," Oct. 14, 2015, 9 pages.
UniProtKB Accession: A0A059T4A1, "Influenza A virus A/Jiangxi/IPB13/2013(H10N8) hemagglutinin protein," Sep. 3, 2014, 5 pages.
Updated Curriculum Vitae of Daniel O. Griffin, Ph.D., dated Aug. 23, 2024, 24 pages.
Van Boheemen et al., "Genomic characterization of a newly discovered coronavirus associated with acute respiratory distress syndrome in humans," mBio., Nov. 20, 2012, 3(6):e00473-12, 9 pages.
Vardi et al., "Moderna's Mysterious Medicines," Forbes, Dec. 14, 2016, 5 pages.
Vardi, "Moderna's Mysterious Coronavirus Vaccine Delivery System," Forbes, Jul. 29, 2020, 9 pages.
Vennema et al., "Early death after feline Infectious Peritonitis Virus Challenge due to Recombinant Vaccinia Virus Immunization," Journal of Virology, Mar. 1990, 64(3):1407-1409.
Vergati et al., "Strategies for Cancer Vaccine Development," Journal of Biomedicine and Biotechnology, 2010, 2010:596432, 13 pages.
Verma et al., "Double-headed nucleosides: Synthesis and applications," Beilstein J Org Chem., Jun. 8, 2021, 17:1392-1439.
Vogel et al., "BNT162b vaccines protect rhesus macaques from SARS-CoV-2," Nature, Apr. 2021, 592(7853):283-289.
Von Niessen et al., "Improving mRNA-Based Therapeutic Gene Delivery by Expression-Augmenting 3' UTRs Identified by Cellular Library Screening," Mol Ther., Apr. 10, 2019, 27(4):824-836.
Walls et al., "Crucial steps in the structure determination of a coronavirus spike glycoprotein using cryo-electron microscopy," Protein Sci., Jan. 2017, 26(1):113-121.
Walls et al., "Tectonic conformational changes of a coronavirus spike glycoprotein promote membrane fusion," Proc Natl Acad Sci U S A., Oct. 17, 2017, 114(42):11157-11162.
Walter et al., "Evaluation of the BNT162b2 COVID-19 Vaccine in Children 5 to 11 Years of Age," New England J. Med., Jan. 6, 2022, 386:35-46.
Wan et al., "Comparison of Immunogenicity Between Codon Optimized HIV-1 Thailand Subtype B gp140 and gp145 Vaccines," Vaccine, Jun. 21, 2007, 25(26):4949-4959.
Wang et al., "Evaluation of candidate vaccine approaches for MERS-CoV," Nature Communications, Jul. 2015, 6(1):7712, 11 pages.
Wang et al., "Lipid Nanoparticles for the Delivery of Nucleic Acids," Nanoparticulate Drug Delivery Systems: Strategies, Technologies, and Applications, 2013, Chapter 3: 29 pages.
Wang et al., "Systemic delivery of modified mRNA encoding herpes simplex virus 1 thymidine kinase for targeted cancer gene therapy," Mol Ther., Feb. 2013, 21(2):358-367.
Weide et al., "Direct Injection of Protamine-protected mRNA: Results of a Phase 1/2 Vaccination Trial in Metastatic Melanoma Patients," Immunotherapy, Jun. 2009, 32(5):498-507.
Weide et al., "Results of the First Phase I/II Clinical Vaccination Trial with Direct Injection of mRNA," J. Immunotherapy, Feb. 2008, 31(2):180-188.
Wen et al., "New Approaches for Immunization and Therapy against Human Metapneumovirus," Clin Vaccine Immunol., Aug. 2015, 22(8):858-866.
Whitehead et al., "Knocking down barriers: advances in siRNA delivery," Nat Rev Drug Discov., Feb. 2009, 8(2):129-138.
Whitt, "Generation of VSV pseudotypes using recombinant ΔG-VSV for studies on virus entry, identification of entry inhibitors, and immune responses to vaccines," J Virol Methods., Nov. 2010, 169(2):365-374.
Williams et al., "Human metapneumovirus isolate TN/92-4 fusion protein gene, complete cds," GenBank Accession No. EF051124.1, Nov. 29, 2007, 2 pages.
Withoff et al., "Replication-defective Recombinant Semliki Forest Virus Encoding GM-CSF as a Vector System for Rapid and Facile Generation of Autologous Human Tumor Cell Vaccines," Gene Therapy, 2001, (8):1515-1523.
Wolff et al., "Direct Gene Transfer into Mouse Muscle in Vivo," Science, Mar. 1990, 247(4949):1465-1468.
Wong et al., "An mRNA vaccine for influenza," Nat Biotechnol., Dec. 2012, 30(12):1202-1204.
Xia, "Detailed Dissection and Critical Evaluation of the Pfizer/BioNTech and Moderna mRNA Vaccines," Vaccines (Basel), Jul. 3, 2021, 9(7):734, 19 pages.
Yamamoto et al., "Current prospects for mRNA gene delivery," European Journal of Pharmaceutics and Biopharmaceutics, Mar. 2009, 71(3):484-489.
Yang et al., "A DNA vaccine induces SARS coronavirus neutralization and protective immunity in mice," Nature, Apr. 2004, 428(6982):561-564.
Yang et al., "A vaccine targeting the RBD of the S protein of SARS-CoV-2 induces protective immunity," Nature, Jul. 29, 2020, 586:572-577.
Yang et al., "Evasion of Antibody Neutralization in Emerging Severe Acute Respiratory Syndrome Coronaviruses," PNAS, Jan. 18, 2005, 102(3):797-801.
Yang et al., "The structure and functions of coronavirus genomic 3' and 5' ends," Virus Res., Aug. 3, 2015, 206:120-133.
Yin et al., "Immunogenicity and protective efficacy of recombinant fusion proteins containing spike protein of infectious bronchitis virus and hemagglutinin of H3N2 influenza virus in chickens," Virus Res., Sep. 2, 2016, 223:206-212.
Yin et al., "Non-viral vectors for gene-based therapy," Nat Rev Genet., Aug. 2014, 15(8):541-555.
Yoo et al., "Synthesis and Processing of the Haemagglutinin-Esterase Glycoprotein of Bovine Coronavirus Encoded in the E3 Region of Adenovirus," J. Gen. Virology, 1992, 73:2591-2600.
Youn et al., "Modified mRNA as an alternative to plasmid DNA (pDNA) for transcript replacement and vaccination therapy," Expert Opin Biol Ther., Sep. 2015, 15(9):1337-1348.
Zangi et al., "Modified mRNA directs the fate of heart progenitor cells and induces vascular regeneration after myocardial infarction," Nat Biotechnol., Oct. 2013, 31(10):898-907.

(56) References Cited

OTHER PUBLICATIONS

Zhang et al., "Delivery of mRNA vaccine with a lipid-like material potentiates antitumor efficacy through Toll-like receptor 4 signaling," Proc Natl Acad Sci U S A, Feb. 9, 2021, 118(6):e2005191118, 12 pages.
Zhao et al., "Key Aspects of Coronavirus Avian Infectious Bronchitis Virus," Pathogens, May 11, 2023, 12(5):698, 14 pages.
Zhao et al., "Lipid Nanoparticles for Gene Delivery," Advances in Genetics, Elsevier, 2014, Chapter 2: 24 pages.
Zhou et al., "Current RNA-Based Therapeutics in Clinical Trials," Current Gene Therapy, 2019, 19:172-196.
Zhou et al., "RNA Melanoma Vaccine: Induction of Antitumor Immunity by Human Glycoprotein 100 mRNA Immunization," Hum Gene Ther., Nov. 1999, 10(16):2719-2724.
Zhu et al., "Receptor-binding domain as a target for developing SARS vaccines," Journal of Thoracic Disease, Aug. 2013, 5(Suppl 2):S142-S148.
Zhukovsky et al., "Heterogeneity of Early Intermediates in Cell-Liposome Fusion Mediated by Influenza Hemagglutinin," Biophys J., Nov. 2006, 91(9):3349-3358.
Ziganshina et al., "Antibody-Dependent Enhancement with a Focus on SARS-CoV-2 and Anti-Glycan Antibodies," Viruses, Jul. 20, 2023, 15(7):1584, 20 pages.
Zumla et al., "Middle East respiratory syndrome," Lancet, Sep. 5, 2015, 386(9997):995-1007.
U.S. Appl. No. 62/972,886, Wrapp et al., Feb. 11, 2020.
U.S. Appl. No. 63/032,502, Hsieh et al.
International Search Report and Written Opinion for International Application No. PCT/US2021/016979, mailed Oct. 6, 2021.
[No Author Listed] Lineage list. Last accessed Oct. 17, 2023 at https://cov-lineages.org/lineage_list.html. 77 pages.
[No Author Listed], A Phase 3, Randomized, Stratified, Observer-Blind, Placebo-Controlled Study to Evaluate the Efficacy, Safety, and Immunogenicity of mRNA-1273 SARS-CoV-2 Vaccine in Adults Aged 18 Years and Older. ModernaTX, Inc. Protocol mRNA-1273-P301, Amendment 3. Aug. 20, 2020. 135 pages.
[No Author Listed], Background document on the mRNA-1273 vaccine (Moderna) against COVID-19. World Health Organization. Feb. 3, 2021. Accessed from <https://www.who.int/publications/i/item/background-document-on-the-mrna-1273-vaccine-(moderna)-against-covid-19>. 41 pages.
[No Author Listed], Canada Exercises Increased Option for 20 Million Doses of mRNA Vaccine Against COVID-19 (mRNA-1273). Moderna Press Release. Sep. 22, 2020. 2 pages.
[No Author Listed], CDC. SARS-CoV-2 Variant Classifications and Definitions. https://www.cdc.gov/coronavirus/2019-ncov/variants/variant-classifications.html. Updated Sep. 1, 2023. 5 pages.
[No Author Listed], Coronavirus (COVID-19) Update: FDA Issues Policies to Guide Medical Product Developers Addressing Virus Variants. FDA News Release. Feb. 22, 2021. 5 pages.
[No Author Listed], Could COVID-19 vaccines be tweaked to cover new coronavirus variants? I Gavi, the Vaccine Alliance. Published Jan. 14, 2021. URL:https://www.gavi.org/vaccineswork/could-covid-19-vaccines-be-tweaked-cover-new-coronavirus-variants: Last accessed Apr. 26, 2022. 5 pages.
[No Author Listed], Experimental COVID-19 Vaccine Protects Upper and Lower Airways in Nonhuman Primates. NIH News Release. Jul. 28, 2020. 4 pages.
[No Author Listed], Experimental COVID-19 Vaccine Safe, Generates Immune Response. NIH News Release. Jul. 14, 2020. 4 pages.
[No Author Listed], History of Changes for Study: NCT04283461, Safety and Immunogenicity Study of 2019-nCoV Vaccine (mRNA-1273) for Prophylaxis of SARS-CoV-2 Infection (COVID-19). Version submitted Dec. 8, 2022. 8 pages.
[No Author Listed], History of Changes for Study: NCT04283461, Safety and Immunogenicity Study of 2019-nCoV Vaccine (mRNA-1273) for Prophylaxis of SARS-CoV-2 Infection (COVID-19). Version submitted Mar. 11, 2021. 10 pages.
[No Author Listed], List of past and pending litigations. Prepared Oct. 24, 2023. 1 page.
[No Author Listed], Moderna Advances Late-Stage Development of its Vaccine (mRNA-1273) Against COVID-19. Moderna Press Release. Jun. 11, 2020. 3 pages.
[No Author Listed], Moderna and Lonza Announce Worldwide Strategic Collaboration to Manufacture Moderna's Vaccine (mRNA-1273) Against Novel Coronavirus. Moderna Press Release. May 1, 2020. 3 pages.
[No Author Listed], Moderna Announces Award from U.S. Government Agency BARDA for up to $483 Million to Accelerate Development of mRNA Vaccine (mRNA-1273) Against Novel Coronavirus. Moderna Press Release. Apr. 16, 2020. 3 pages.
[No Author Listed], Moderna Announces Expansion of BARDA Agreement to Support Larger Phase 3 Program for Vaccine (mRNA-1273) Against COVID-19. Moderna Press Release. Jul. 26, 2020. 3 pages.
[No Author Listed], Moderna Announces FDA Authorization of Moderna COVID 19 Vaccine in U.S. Press Release. Dec. 19, 2020. 3 pages.
[No Author Listed], Moderna Announces First Participant Dosed in NIH-led Phase 1 Study of mRNA Vaccine (mRNA-1273) Against Novel Coronavirus. Moderna Press Release. Mar. 16, 2020. 2 pages.
[No Author Listed], Moderna Announces First Participants in Each Age Cohort Dosed in Phase 2 Study of mRNA Vaccine (mRNA-1273) Against Novel Coronavirus. Moderna Press Release. May 29, 2020. 2 pages.
[No Author Listed], Moderna Announces IND Submitted to U.S. FDA for Phase 2 Study of mRNA Vaccine (mRNA-1273) Against Novel Coronavirus. Moderna Press Release. Apr. 27, 2020. 3 pages.
[No Author Listed], Moderna Announces it has Shipped Variant-Specific Vaccine Candidate, mRNA-1273.351, to NIH for Clinical Study. Moderna Press Release. Feb. 24, 2021. 3 pages.
[No Author Listed], Moderna Announces Phase 3 COVE Study of mRNA Vaccine Against COVID-19 (mRNA-1273) Begins. Moderna Press Release. Jul. 27, 2020. 3 pages.
[No Author Listed], Moderna Announces Positive Interim Phase 1 Data for its mRNA Vaccine (mRNA-1273) Against Novel Coronavirus. Moderna Press Release. May 18, 2020. 3 pages.
[No Author Listed], Moderna Announces Progress Across Broad Portfolio and all Three Clinical Stage Therapeutic Areas at 2020 R&D Day. Moderna Press Release. Sep. 17, 2020. 4 pages.
[No Author Listed], Moderna Announces Publication in The New England Journal of Medicine of Interim Results From Phase 1 Study of Its mRNA Vaccine Against COVID-19 (mRNA-1273). Moderna Press Release. Jul. 14, 2020. 5 pages.
[No Author Listed], Moderna Announces Publication in The New England Journal of Medicine of Non-Human Primate Preclinical Viral Challenge Study of its mRNA Vaccine Against COVID-19 (mRNA-1273). Moderna Press Release. Jul. 28, 2020. 3 pages.
[No Author Listed], Moderna Announces Supply Agreement with U.S. Government for Initial 100 Million Doses of mRNA Vaccine Against COVID-19 (mRNA-1273), Moderna Press Release. Aug. 11, 2020. 3 pages.
[No Author Listed], Moderna Completes Enrollment of Phase 2 Study of its mRNA Vaccine Against COVID-19 (mRNA-1273). Moderna Press Release. Jul. 8, 2020. 2 pages.
[No Author Listed], Moderna Confirms Advanced Discussions with European Commission to Supply Europe with 80 Million Doses of mRNA Vaccine Against COVID-19 (mRNA-1273). Moderna Press Release. Aug. 24, 2020. 3 pages.
[No Author Listed], Moderna Confirms Discussions with the Ministry of Health, Labour and Welfare to Supply Japan with 40 Million Doses of mRNA Vaccine Against COVID-19 (mRNA-1273). Moderna Press Release. Aug. 28, 2020. 2 pages.
[No Author Listed], Moderna Receives FDA Fast Track Designation for mRNA Vaccine (mRNA-1273) Against Novel Coronavirus. Moderna Press Release. May 12, 2020. 2 pages.
[No Author Listed], Moderna Ships mRNA Vaccine Against Novel Coronavirus (mRNA-1273) for Phase 1 Study. Moderna Press Release. Feb. 24, 2020. 2 pages.

(56) References Cited

OTHER PUBLICATIONS

[No Author Listed], Moderna's COVID-19 Vaccine Candidate Meets its Primary Efficacy Endpoint in the First Interim Analysis of the Phase 3 COVE Study. Press Release. Nov. 16, 2020. 3 pages.
[No Author Listed], NIH Clinical Trial of Investigational Vaccine for COVID-19 begins. NIH News Release. Mar. 16, 2020. 3 pages.
[No Author Listed], NIH-Moderna Investigational COVID-19 Vaccine Shows Promise in Mouse Studies. NIH News Release. Aug. 5, 2020. 4 pages.
[No Author Listed], Phase 3 Clinical Trial of Investigational Vaccine for COVID-19 Begins. NIH News Release. Jul. 27, 2020. 3 pages.
[No Author Listed], Press release, Moderna, "Moderna Announces Publication in The New England Journal of Medicine of Interim Results From Older Adult Age Cohorts in Phase 1 Study of its mRNA Vaccine Against COVID-19 (mRNA-1273)", Sep. 29, 2020. 7 pages.
[No Author Listed], SARS-CoV-2 variants of concern as of May 4, 2023. European Centre for Disease Prevention and Control. Last accessed May 16, 2023 at https://www.ecdc.europa.eu/en/covid-19/variants-concern. 7 pages.
[No Author Listed], Severe acute respiratory syndrome coronavirus 2 isolate Wuhan-Hu-1, complete genome. GenBank Accession No. 045512, published on Jul. 18, 2020. 15 pages.
[No Author Listed], Severe acute respiratory syndrome coronavirus 2 isolate Wuhan-Hu-1, complete genome. Genbank Accession No. MN908947.3. Jan. 13, 2020. 15 pages.
[No Author Listed], Spikevax (mRNA-1273) EMA SmPC (summary of product characteristics). Published Jan. 20, 2021. 137 pages.
[No Author Listed], World Health Organization. 2021. Classification of Omicron(B.1.1.529): SARS-CoV-2Variant of Concern. Nov. 26, 2021. 3 pages.
[No Author Listed]. Reflection paper on the regulatory requirements for vaccines intended to provide protection against variant strain(s) of SARS-CoV-2. European Medicines Agency. EMA/117973/2021. Feb. 23, 2021. 7 pages.
Abbasi, COVID-19 and mRNA Vaccines—First Large Test for a New Approach. JAMA. Sep. 22, 2020;324(12):1125-1127. doi: 10.1001/jama.2020.16866.
Adney et al., Efficacy of an Adjuvanted Middle East Respiratory Syndrome Coronavirus Spike Protein Vaccine in Dromedary Camels and Alpacas. Viruses. Mar. 2, 2019;11(3). pii: E212. doi: 10.3390/v11030212.
Al Kahlout et al., Comparative Serological Study for the Prevalence of Anti-MERS Coronavirus Antibodies in High- and Low-Risk Groups in Qatar. J Immunol Res. Feb. 18, 2019;2019:1386740. doi: 10.1155/2019/1386740. eCollection 2019.
*Alnylam Pharmaceuticals, Inc.* v. *Moderna, Inc.* (Fed. Circ. 2023-2357) D.I. 8—Docketing Statement, Sep. 21, 2023. 2 pages.
*Alnylam Pharmaceuticals, Inc.* v. *Moderna, Inc et al* (D. Del. 23-cv-580-CFC) D.I. 1—Complaint for Patent Infringement, May 26, 2023. 28 pages.
*Alnylam Pharmaceuticals, Inc.* v. *Moderna, Inc et al* (D. Del. 23-cv-580-CFC) D.I. 12—Answer to the Complaint, Jul. 17, 2023. 37 pages.
*Alnylam Pharmaceuticals, Inc.* v. *Moderna, Inc et al.* (D. Del. 22-cv-335-CFC) D.I. 1—Complaint for Patent Infringement, Mar. 17, 2022. 14 pages.
*Alnylam Pharmaceuticals, Inc.* v. *Moderna, Inc et al.* (D. Del. 22-cv-335-CFC) D.I. 128—Final Judgement, Aug. 30, 2023. 2 pages.
*Alnylam Pharmaceuticals, Inc.* v. *Moderna, Inc et al.* (D. Del. 22-cv-335-CFC) D.I. 130—Notice of Appeal to the U.S. Court of Appeals for the Federal Circuit, Aug. 31, 2023. 3 pages.
*Alnylam Pharmaceuticals, Inc.* v. *Moderna, Inc et al.* (D. Del. 22-cv-335-CFC) D.I. 87—Answer to the Complaint, May 10, 2023. 44 pages.
Anderson et al., Safety and Immunogenicity of SARS-CoV-2 mRNA-1273 Vaccine in Older Adults. N Engl J Med. Sep. 29, 2020;NEJMoa2028436: 1- 12. doi: 10.1056/NEJMoa2028436.
Andries et al., N(1)-methylpseudouridine-incorporated mRNA outperforms pseudouridine-incorporated mRNA by providing enhanced protein expression and reduced immunogenicity in mammalian cell lines and mice. J Control Release. Nov. 10, 2015;217:337-44. doi: 10.1016/j.jconrel.2015.08.051. Epub Sep. 3, 2015.
*Arbutus BioPharma Corp. et al.* v. *Moderna, Inc. et al.* (D. Del. 22-cv-252-MSG) D.I. 1—Complaint for Patent Infringement, Feb. 28, 2022. 51 pages.
*Arbutus BioPharma Corp. et al.* v. *Moderna, Inc. et al.* (D. Del. 22-cv-252-MSG) D.I. 31—District Court Memorandum, Nov. 2, 2022. 16 pages.
*Arbutus BioPharma Corp. et al.* v. *Moderna, Inc. et al.* (D. Del. 22-cv-252-MSG) D.I. 35—Answer to the Complaint, Nov. 30, 2022. 83 pages.
*Arbutus BioPharma Corp. et al.* v. *Moderna, Inc. et al.* (D. Del. 22-cv-252-MSG) D.I. 64—District Court Memorandum, Mar. 10, 2023. 4 pages.
Baden et al., Efficacy and Safety of the mRNA-1273 SARS-CoV-2 Vaccine. N Engl J Med. Feb. 4, 2021;384(5):403-416. doi: 10.1056/NEJMoa2035389. Epub Dec. 30, 2020.
Bhavana et al., COVID-19: Pathophysiology, treatment options, nanotechnology approaches, and research agenda to combating the SARS-CoV2 pandemic. Life Sci. Nov. 15, 2020;261:118336. doi: 10.1016/j.lfs.2020.118336. Epub Aug. 23, 2020.
Bruxvoort et al., Real-world effectiveness of the mRNA-1273 vaccine against COVID-19: Interim results from a prospective observational cohort study. Lancet Reg Health Am. Feb. 2022:6:100134. doi: 10.1016/j.lana.2021.100134. Epub Nov. 25, 2021.
Buschmann et al., Nanomaterial Delivery Systems for mRNA Vaccines. Vaccines (Basel). Jan. 19, 2021;9(1):65. doi: 10.3390/vaccines9010065.
Callaway, Omicron likely to weaken COVID vaccine protection. Nature. Dec. 2021;600(7889):367-368. doi: 10.1038/d41586-021-03672-3.
Cele et al., SARS-CoV-2 Omicron has extensive but incomplete escape of Pfizer BNT162b2 elicited neutralization and requires ACE2 for infection. medRxiv. 2021 doi: 10.1101/2021.12.08.21267417.2021.12.08.21267417. 15 pages.
Cerutti et al., Potent SARS-CoV-2 neutralizing antibodies directed against spike N-terminal domain target a single supersite. Cell Host Microbe. May 12, 2021;29(5):819-833.e7. doi: 10.1016/j.chom.2021.03.005. Epub Mar. 12, 2021.
Chaudhary et al., mRNA vaccines for infectious diseases: principles, delivery and clinical translation. Nature Reviews Drug Discovery vol. 20, pp. 817-838 (2021).
Chen et al., A novel neutralizing monoclonal antibody targeting the N-terminal domain of the MERS-CoV spike protein. Emerg Microbes Infect. Jun. 28, 2017;6(6):e60. doi: 10.1038/emi.2017.50. Erratum for: Emerg Microbes Infect. May 24, 2017;6(5):e37.
Chen et al., Emerging coronaviruses: Genome structure, replication, and pathogenesis. J. Med Virol. Apr. 2020;92(4):418-423. doi: 10.1002/jmv.25681. Epub Feb. 7, 2020. Erratum in: J Med Virol. Oct. 2020;92(10):2249.
Chi et al., A neutralizing human antibody binds to the N-terminal domain of the Spike protein of SARS-CoV-2. Science. Aug. 7, 2020;369(6504):650-655. doi: 10.1126/science.abc6952. Epub Jun. 22, 2020.
Choi et al., Safety and immunogenicity of SARS-CoV-2 variant mRNA vaccine boosters in healthy adults: an interim analysis. Nat Med. Nov. 2021;27(11):2025-2031. doi: 10.1038/s41591-021-01527-y. Epub Sep. 15, 2021.
Choi et al., Serum Neutralizing Activity of mRNA-1273 against SARS-CoV-2 Variants, J Virol. Nov. 9, 2021;95(23):e0131321. doi: 10.1128/JVI.01313-21. Epub Sep. 22, 2021.
Chu et al., Immune Memory Response After a Booster Injection of mRNA-1273 for Severe Acute Respiratory Syndrome Coronavirus-2 (SARS-CoV-2). 2021 MedRxiv doi: https://doi.org/10.1101/2021.09.29.21264089. 52 pages.

(56) References Cited

OTHER PUBLICATIONS

Corbett et al., Evaluation of the mRNA-1273 Vaccine against SARS-CoV-2 in Nonhuman Primates. N Engl J Med 2020; 383:1544-55. doi: 10.1056/NEJMoa2024671.
Corbett et al., SARS-CoV-2 mRNA vaccine design enabled by prototype pathogen preparedness. Nature. Oct. 2020;586(7830):567-571. doi: 10.1038/s41586-020-2622-0. Epub Aug. 5, 2020.
Cullis et al., Lipid Nanoparticle Systems for Enabling Gene Therapies. Mol Ther. Jul. 5, 2017;25(7):1467-1475. doi: 10.1016/j.ymthe.2017.03.013. Epub Apr. 13, 2017.
Dai et al., Viral targets for vaccines against COVID-19. Nat Rev Immunol. Feb. 2021;21(2):73-82. doi: 10.1038/s41577-020-00480-0. Epub Dec. 18, 2020.
Dejnirattisai et al., Reduced neutralisation of SARS-CoV-2 omicron B.1.1.529 variant by post-immunisation serum. Lancet. Jan. 15, 2022;399(10321):234-236. doi: 10.1016/S0140-6736(21)02844-0. Epub Dec. 20, 2021.
Du et al., The spike protein of SARS-CoV—a target for vaccine and therapeutic development. Nat Rev Microbiol. Mar. 2009;7(3):226-36. doi: 10.1038/nrmicro2090. Epub Feb. 9, 2009.
El Sahly et al., Efficacy of the mRNA-1273 SARS-CoV-2 Vaccine at Completion of Blinded Phase. N Engl J Med. Nov. 4, 2021; 385:1774-1785.
Furuichi et al., Viral and cellular mRNA capping: past and prospects. Adv Virus Res. 2000;55:135-84. doi: 10.1016/s0065-3527(00)55003-9.
Furuichi, Caps on Eukaryotic mRNAs. eLS. John Wiley & Sons. Jul. 1-2, 2014.
Gallie, D.R., The cap and poly(A) tail function synergistically to regulate mRNA translational efficiency. Genes Dev. Nov. 1991;5(11):2108-16.
Geall et al., RNA: the new revolution in nucleic acid vaccines. Semin Immunol. Apr. 2013;25(2):152-9. doi: 10.1016/j.smim.2013.05.001. Epub Jun. 2, 2013.
Graham et al., Novel Vaccine Technologies: Essential Components of an Adequate Response to Emerging Viral Diseases. JAMA. Apr. 10, 2018;319(14):1431-1432. doi: 10.1001/jama.2018.0345.
Guo et al., An Engineered Receptor-Binding Domain Improves the Immunogenicity of Multivalent SARS-CoV-2 Vaccines. mBio. May-Jun. 2021; 12(3): e00930-21.
He et al., Receptor-binding domain of SARS-CoV spike protein induces highly potent neutralizing antibodies: implication for developing subunit vaccine. Biochem Biophys Res Commun. Nov. 12, 2004;324(2):773-81. doi: 10.1016/j.bbrc.2004.09.106.
Heinz et al., Distinguishing features of current COVID-19 vaccines: knowns and unknowns of antigen presentation and modes of action. NPJ Vaccines. Aug. 16, 2021;6(1):104. doi: 10.1038/s41541-021-00369-6.
Hou et al., Lipid nanoparticles for mRNA delivery. Nature Reviews Materials vol. 6, pp. 1078-1094 (2021).
Hsieh et al., Structure-based design of prefusion-stabilized SARS-CoV-2 spikes. Science. Sep. 18, 2020;369(6510):1501-1505. doi: 10.1126/science.abd0826. Epub Jul. 23, 2020.
Huang et al., Clinical features of patients infected with 2019 novel coronavirus in Wuhan, China. Lancet. Jan. 24, 2020;395(10223)497-506.
Jackson et al., An mRNA Vaccine against SARS-CoV-2—Preliminary Report. N Engl J Med. Jul. 14, 2020; NEJMoa2022483. doi: 10.1056/NEJMoa2022483. Online ahead of print.
Javier et al., Phylogenetic Analysis and Structural Modeling of SARS-CoV-2 Spike Protein Reveals an Evolutionary Distinct and Proteolytically Sensitive Activation Loop. J Mol Biol. May 1, 2020;432(10):3309-3325. doi: 10.1016/j.jmb.2020.04.009. Epub Apr. 19, 2020.
Jiaming et al., The recombinant N-terminal domain of spike proteins is a potential vacciine against Middle East respiratory syndrome coronavirus (MERS-CoV) infection. Vaccine. Jan. 3, 2017;35(1):10-18. doi: 10.1016/j.vaccine.2016.11.064. Epub Nov. 26, 2016.
Jiang et al., The Variation of SARS-CoV-2 and Advanced Research on Current Vaccines. Front Med (Lausanne). Jan. 18, 2022:8:806641. doi: 10.3389/fmed.2021.806641. eCollection 2021.
Kallen et al., A development that may evolve into a revolution in medicine: mRNA as the basis for novel, nucleotide-based vaccines and drugs. Ther Adv Vaccines. Jan. 2014;2(1):10-31. doi: 10.1177/2051013613508729.
Kauffman et al., Materials for non-viral intracellular delivery of messenger RNA therapeutics. J Control Release. Oct. 28, 2016;240:227-234. doi: 10.1016/j.jconrel.2015.12.032. Epub Dec. 21, 2015.
Khoury et al., Neutralizing antibody levels are highly predictive of immune protection from symptomatic SARS-CoV-2 infection. Nat Med. Jul. 2021;27(7):1205-1211. doi: 10.1038/s41591-021-01377-8. Epub May 17, 2021.
Kirchdoerfer et al., Stabilized coronavirus spikes are resistant to conformational changes induced by receptor recognition or protseolysis. Sci Rep. Oct. 24, 2018;8(1):15701. doi: 10.1038/s41598-018-34171-7.
Koyama et al., Analysis on GENIE reveals novel recurrent variants that affect molecular diagnosis of sizable number of cancer patients. BMC Cancer. Feb. 1, 2019;19(1):114. doi: 10.1186/s12885-019-5313-1.
Koyama et al., Emergence of Drift Variants That May Affect COVID-19 Vaccine Development and Antibody Treatment. Pathogens. Apr. 26, 2020;9(5):324. doi: 10.3390/pathogens9050324.
Kramps et al., Messenger RNA-based vaccines: progress, challenges, applications. Wiley Interdiscip Rev RNA. Nov.-Dec. 2013;4(6):737-49. doi: 10.1002/wrna.1189. Epub Jul. 25, 2013.
Kurimoto et al., PEG-OligoRNA Hybridization of mRNA for Developing Sterically Stable Lipid Nanoparticles toward In Vivo Administration. Molecules. Apr. 3, 2019;24(7): 1303.
Li et al., Lipid-based nanoparticles for nucleic acid delivery. Pharm Res. Mar. 2007;24(3):438-49. doi: 10.1007/s11095-006-9180-5.
Li, Structure, Function, and Evolution of Coronavirus Spike Proteins. Annu Rev Virol. Sep. 29, 2016;3(1):237-261. doi: 10.1146/annurev-virology-110615-042301. Epub Aug. 25, 2016.
Lin et al., Glycan Masking of Epitopes in the NTD and RBD of the Spike Protein Elicits Broadly Neutralizing Antibodies Against SARS-CoV-2 Variants. Front Immunol. Dec. 2, 2021:12:795741. doi: 10.3389/fimmu.2021.795741. eCollection 2021.
Liu et al., Potent neutralizing antibodies against multiple epitopes on SARS-CoV-2 spike. Nature. Aug. 2020;584(7821):450-456. doi: 10.1038/s41586-020-2571-7. Epub Jul. 22, 2020.
Lu et al., Genomic characterisation and epidemiology of 2019 novel coronavirus: implications for virus origins and receptor binding. Lancet. Feb. 22, 2020;395(10224):565-574. doi: 10.1016/S0140-6736(20)30251-8. Epub Jan. 30, 2020.
Ma et al., Intranasal vaccination with recombinant receptor-binding domain of MERS-CoV spike protein induces much stronger local mucosal immune responses than subcutaneous immunization: Implication for designing novel mucosal MERS vaccines. Vaccine. Apr. 11, 2014;32(18):2100-8. doi: 10.1016/j.vaccine.2014.02.004. Epub Feb. 18, 2014.
Martinez-Flores et al., SARS-CoV-2 Vaccines Based on the Spike Glycoprotein and Implications of New Viral Variants. Front Immunol. Jul. 12, 2021;12:701501. doi: 10.3389/fimmu.2021.701501. eCollection 2021.
Mccallum et al., N-terminal domain antigenic mapping reveals a site of vulnerability for SARS-CoV-2. Cell. Apr. 29, 2021; 184(9): 2332-2347.e16.
Mckay et al., Self-amplifying RNA SARS-CoV-2 lipid nanoparticle vaccine candidate induces high neutralizing antibody titers in mice. Nat Commun. Jul. 9, 2020;11(1):3523. doi: 10.1038/s41467-020-17409-9.
Midoux et al., Lipid-based mRNA vaccine delivery systems. Expert Rev Vaccines. Feb. 2015;14(2):221-34. doi: 10.1586/14760584.2015.986104. Epub Dec. 26, 2014. Review.
*ModernaTX, Inc. et al* v. *Pfizer Inc. et al.* (D. Mass. 22-11378-RGS) D.I. 105—Memorandum and Order on Claim Construction, Aug. 1, 2023. 15 pages.
*ModernaTX, Inc. et al* v. *Pfizer Inc. et al.* (D. Mass. 22-11378-RGS) D.I. 1—Infringement, Aug. 26, 2022. 39 pages.

(56) References Cited

OTHER PUBLICATIONS

*ModernaTX, Inc. et al* v. *Pfizer Inc. et al.* (D. Mass. 22-11378-RGS) D.I. 45—Complaint, Dec. 5, 2022. 81 pages.
Mulligan et al., Phase I/II study of COVID-19 RNA vaccine BNT162b1 in adults. Nature. Oct. 2020;586(7830):589-593. doi: 10.1038/s41586-020-2639-4. Epub Aug. 12, 2020.
Nance et al., Modifications in an Emergency: The Role of N1-Methylpseudouridine in COVID-19 Vaccines. ACS Cent Sci. May 26, 2021;7(5):748-756. doi: 10.1021/acscentsci.1c00197. Epub Apr. 6, 2021.
Oostvogels et al., Phase 1 Assessment of the Safety and Immunogenicity of an mRNA-Lipid Nanoparticle Vaccine Candidate Against SARS-CoV-2 in Human Volunteers. medRxiv Nov. 9, 2020. 20228551;1-38. doi: https://doi.org/10.1101/2020.11.09.20228551.
Pallesen et al., Immunogenicity and structures of a rationally designed prefusion MERS-CoV spike antigen. Proc Natl Acad Sci U S A. Aug. 29, 2017;114(35):E7348-E7357. doi: 10.1073/pnas.1707304114. Epub Aug. 14, 2017.
Pardi et al., mRNA vaccines—a new era in vaccinology. Nat Rev Drug Discov. Apr. 2018;17(4):261-279. doi: 10.1038/nrd.2017.243. Epub Jan. 12, 2018.
Pardi et al., Zika virus protection by a single low-dose nucleoside-modified mRNA vaccination. Nature. Mar. 9, 2017;543(7644):248-251. doi: 10.1038/nature21428. Epub Feb. 2, 2017.
Pathak et al., Intra-host variability in global SARS-CoV-2 genomes as signatures of RNA editing: implications in viral and host response outcomes. bioRxiv Dec. 9, 2020; 2020.12.09.417519; doi: https://doi.org/10.1101/2020.12.09.417519. 32 pages.
Pegu et al., Durability of mRNA-1273 vaccine-induced antibodies against SARS-CoV-2 variants. Science. Sep. 17, 2021;373(6561):1372-1377. doi: 10.1126/science.abj4176. Epub Aug. 13, 2021.
Petition For Inter Partes Review of U.S. Pat. No. 10,702,600. *BioNTech SE and Pfizer Inc.* (Petitioners) v. *ModernaTX, Inc.* (Patent Owner). Filed Aug. 28, 2023. 87 pages.
Petition For Inter Partes Review of U.S. Pat. No. 10,933,127. *BioNTech SE and Pfizer Inc.* (Petitioners) v. *ModernaTX, Inc.* (Patent Owner). Filed Aug. 28, 2023. 89 pages.
Petition For Inter Partes Review of U.S. Pat. No. 8,058,069 (IPR2019-00554). *Moderna Therapeutics, Inc.* (Petitioner) v. *Arbutus Biopharma Corporation* (Patent Owner). Filed Nov. 15, 2011. 81 pages.
Petsch et al., Protective efficacy of in vitro synthesized, specific mRNA vaccines against influenza A virus infection. Nat Biotechnol. Dec. 2012;30(12):1210-6. doi: 10.1038/nbt.2436. Epub Nov. 25, 2012.
*Promosome, LLC* v. *Moderna, Inc.* (S.D. Cal. 23-cv-1047-JES-DDL) D.I. 1—Complaint for Patent Infringement, Jun. 6, 2023. 51 pages.
*Promosome, LLC* v. *Moderna, Inc.* (S.D. Cal. 23-cv-1047-JES-DDL) D.I. 30—Notice of Dismissal, Sep. 19, 2023. 4 pages.
Pulliam et al., Increased risk of SARS-CoV-2 reinfection associated with emergence of the Omicron variant in South Africa. medRxiv 2021. doi:10.1101/2021.11.11.21266068:2021.11.11.21266068. 42 pages.
Regalado, Don't panic about the latest coronavirus mutations say drug companies. MIT Technology Review. Dec. 23, 2020. 5 pages.
Regalado, Moderna believes it could update its coronavirus vaccine without a big new trial. MIT Technology Review. Jan. 13, 2021. 4 pages.
Reichmuth et al., mRNA Vaccine Delivery Using Lipid Nanoparticles. Ther Deliv. 2016;7(5):319-34. doi: 10.4155/tde-2016-0006.
Sahin et al., mRNA-based therapeutics—developing a new class of drugs. Nat Rev Drug Discov. Oct. 2014;13(10):759-80. doi: 10.1038/nrd4278. Epub Sep. 19, 2014.
Sarkar et al., S glycoprotein diversity of the Omicron variant. medRxiv 2021. doi:10.1101/2021.12.04.21267284:2021.12.04.21267284. 30 pages.
Schlake et al., Developing mRNA-vaccine technologies. RNA Biol. Nov. 2012;9(11):1319-30. doi: 10.4161/rna.22269. Epub Oct. 12, 2012.
Schoenmaker et al., mRNA-lipid nanoparticle COVID-19 vaccines: Structure and stability. Int J Pharm. May 15, 2021;601:120586. doi: 10.1016/j.ijpharm.2021.120586. Epub Apr. 9, 2021.
Schott, J.W., et al., Viral and non-viral approaches for transient delivery of mRNA and proteins. Current Gene Ther. 2011; 11 (5): 382-398.
Shin et al., Recent Advances in RNA Therapeutics and RNA Delivery Systems Based on Nanoparticles. Adv. Therap., Nov. 2018;1(7):1800065. Review.
Skidmore et al.,Genomic Sequencing of SARS-CoV-2 E484K Variant B.1.243.1, Arizona, USA. Emerg Infect Dis. Oct. 2021;27(10):2718-2720. doi: 10.3201/eid2710.211189.
Sohn, R.L., et al., In-vivo particle mediated delivery of mRNA to mammalian tissues: ballistic and biological effects. Wound Rep and Regen. Jul.-Aug. 2001; 287-296.
Tegally et al., Emergence and rapid spread of a new severe acute respiratory syndrome-related coronavirus 2 (SARS-CoV-2) lineage with multiple spike mutations in South Africa. medRxIV. Dec. 22, 2020; Preprint:19 pages. doi: 10.1101/2020.12.21.20248640. Epub Dec. 22, 2020.
Tenchov et al., Lipid Nanoparticles—From Liposomes to mRNA Vaccine Delivery, a Landscape of Research Diversity and Advancement. ACS Nano. Nov. 23, 2021;15(11):16982-17015. doi: 10.1021/acsnano.1c04996. Epub Jun. 28, 2021.
To et al., An overview of rational design of mRNA-based therapeutics and vaccines. Expert Opin Drug Discov. Nov. 2021;16(11):1307-1317. doi: 10.1080/17460441.2021.1935859. Epub Jul. 19, 2021.
Ulmer et al., RNA-based vaccines. Vaccine. Jun. 22, 2012;30(30):4414-8. doi: 10.1016/j.vaccine.2012.04.060. Epub Apr. 28, 2012.
Walsh et al., Safety and Immunogenicity of Two RNA-Based Covid-19 Vaccine Candidates. N Engl J Med. Oct. 14, 2020;NEJMoa2027906: 1-13. doi: 10.1056/NEJMoa2027906. Online ahead of print.
Wang et al., An Evidence Based Perspective on mRNA-SARS-CoV-2 Vaccine Development.Med Sci Monit. May 5, 2020;26: e924700. doi: 10.12659/MSM.924700.
Wang et al., Antibody Resistance of SARS-CoV-2 Variants B.1.351 and B.1.1.7. bioRxiv [Preprint]. Feb. 12, 2021:2021.01.25.428137. doi: 10.1101/2021.01.25.428137. Update in: Nature. May 2021;593(7857):130-135.
Wang et al., Delivery of oligonucleotides with lipid nanoparticles. Adv Drug Deliv Rev. Jun. 29, 2015;87:68-80. doi: 10.1016/j.addr.2015.02.007. Epub Feb. 27, 2015.
Wang et al., Increased Resistance of SARS-CoV-2 Variants B.1.351 and B.1.1.7 to Antibody Neutralization. bioRxiv. Jan. 26, 2021; 23 pages. doi: 10.1101 /2021.01.25.428137. Preprint.
Wang et al., mRNA vaccine-elicited antibodies to SARS-CoV-2 and circulating variants. Nature. Apr. 2021;592(7855):616-622. doi: 10.1038/s41586-021-03324-6. Epub Feb. 10, 2021. PMID: 33567448; PMCID: PMC8503938.
Wang et al., Structural Definition of a Neutralization-sensitive Epitope on the MERS-CoV S1-NTD. Cell Rep. Sep. 24, 2019;28(13):3395-3405.e6. doi: 10.1016/j.celrep.2019.08.052.
Weissman, mRNA transcript therapy. Expert Rev Vaccines. Feb. 2015;14(2):265-81. doi: 10.1586/14760584.2015.973859. Epub Oct. 31, 2014.
Wilhelm et al., Reduced Neutralization of SARS-CoV-2 Omicron Variant by Vaccine Sera and Monoclonal Antibodies. medRxiv. 2021. doi:10.1101/2021.12.07.21267432:2021.12.07.21267432. 9 pages.
Wrapp et al., Cryo-EM structure of the 2019-nCoV spike in the prefusion conformation. Science. Feb. 19, 2020. pii: eabb2507. doi: 10.1126/science.abb2507.
Wu et al., A new coronavirus associated with human respiratory disease in China. Nature. Mar. 2020;579(7798):265-269. doi: 10.1038/s41586-020-2008-3. Epub Feb. 3, 2020.
Wu et al., mRNA-1273 vaccine induces neutralizing antibodies against spike mutants from global SARS-CoV-2 variants. bioRxiv preprint. Jan. 25, 2021. doi: 10.1101/2021.01.25.427948. 20 pages.
Wu et al., Variant SARS-CoV-2 mRNA vaccines confer broad neutralization as primary or booster series in mice. bioRxiv [Preprint]. Oct. 7, 2021:2021.04.13.439482. doi: 10.1101/2021.04.13.439482. Update in: Vaccine. Dec. 17, 2021;39(51):7394-7400.

(56) References Cited

OTHER PUBLICATIONS

Wu et al.,Serum Neutralizing Activity Elicited by mRNA-1273 Vaccine. N Engl J Med. Apr. 15, 2021;384(15):1468-1470. doi: 10.1056/NEJMc2102179. Epub Mar. 17, 2021.
Ye et al., Rational development of a combined mRNA vaccine against COVID-19 and influenza. NPJ Vaccines. Jul. 26, 2022;7(1):84. doi: 10.1038/s41541-022-00478-w.
Yin et al., Immunogenicity and protective efficacy of recombinant fusion proteins containing spike protein of infectious bronchitis virus and hemagglutinin of H3N2 influenza virus in chickens. Virus Res. Sep. 2, 2016;223:206-12. doi: 10.1016/j.virusres.2016.07.010. Epub Aug. 3, 2016.
Yuan et al., Cryo-EM structures of MERS-CoV and SARS-CoV spike glycoproteins reveal the dynamic receptor binding domains. Nat Commun. Apr. 10, 2017;8:15092. doi: 10.1038/ncomms15092.
Zeng et al., Formulation and Delivery Technologies for mRNA Vaccines. Curr Top Microbiol Immunol. Jun. 2, 2020;10.1007/82_2020_217. doi: 10.1007/82_2020_217.
Zhang et al., A Thermostable mRNA Vaccine against COVID-19. Cell. Sep. 3, 2020;182(5):1271-1283.e16. doi: 10.1016/j.cell.2020.07.024. Epub Jul. 23, 2020.
Zhang et al., Prefusion spike protein stabilization through computational mutagenesis. Proteins. Apr. 2021;89(4):399-408. doi: 10.1002/prot.26025. Epub Dec. 4, 2020.
Zhao et al., Nanoparticle vaccines. Vaccine. Jan. 9, 2014;32(3):327-37. doi: 10.1016/j.vaccine.2013.11.069. Epub Dec. 2, 2013.
Zhou et al., Evidence of escape of SARS-CoV-2 variant B.1.351 from natural and vaccine-induced sera. Cell. Apr. 29, 2021; 184(9): 2348-2361.e6.
[No. Author Listed], "Aivc recommendation for the composition of influenza vaccine for Australia in 2021," Australian Government Therapeutic Goods Administration (TGA), Oct. 9, 2020, retrieved on Jul. 29, 2022, 2 pages.
[No. Author Listed], "Heroes of Chemistry' recognized for contributions to health, medicine and more," American Chemical Society, Jul. 20, 2022, 2 pages.
[No. Author Listed], "MEGAscript Kit Product Manual," Ambion/Invitrogen, Oct. 27, 2009, retrieved from URL <http://tools.invitrogen.com/contenl/sfs/manuals/cms_072987.pdf>, 29 pages.
[No. Author Listed], "mMessage mMachine Kit, User Guide by Ambion," 2012, 36 pages.
[No. Author Listed], "Moderna Announces Positive Interim Phase 1 Clinical Data Demonstrating First mRNA Vaccine Candidate, mRNA-1440, Induces High Levels of Immunogenicity," Moderna Press Release, Apr. 27, 2017, 5 pages.
[No. Author Listed], "Moderna's (MRNA) Flu Vaccine Data Fails to Impress Investors," Zacks Equity Research, Dec 13, 2021, retrieved on Apr. 29, 2026, retrieved from URL <https://finance.yahoo.com/news/modernas-mrna-flu-vaccine-data-153303228.html?guccounter=1&guce_referrer=aHR0cHM6Ly93d3cuYmluZy5jb20v&guce_referrer_sig=AQAAAKxJR4IpEGdCIMPQ8HJ-p94dZE_SlxRyXLIH9LexoZy11S1513uDzHUkatmrEWOy-5ZtpfIPHh_CqRpA9u3C1_TO3JKxSJerUr-BLOpTy8u1f_PXyfgM83VBeX1VFVRDIP-LK5_ZWiPjnRwDYv9atBO5pSjUi2HVaaDXEp4eOjwF>, 5 pages.
[No. Author Listed], "Programme of the 1st International mRNA Health Conference held in Germany," Oct. 2013, retrieved from URL <https://www.mrna-conference.com/inhalt/uploads/2019/03/International_mRNA Health Conference 2013 Program Booklet.pdf>, 32 pages.
[No. Author Listed], "Recommended composition of influenza virus vaccines for use in the 2021 southern hemisphere influenza season," World Health Organization, Sep. 25, 2020, 9 pages.
Aartse et al., "Influenza A Virus Hemagglutinin Trimer, Head and Stem Proteins Identify and Quantify Different Hemagglutinin-Specific B Cell Subsets in Humans," Vaccines, Jul. 2021, 9(7):717, 16 pages.
Alberer et al., "Safety and immunogenicity of a mRNA rabies vaccine in healthy adults: an open-label, non-randomised, prospective, first-in-human phase 1 clinical trial, " The Lancet, Jul. 25, 2017, 390(10101): 1511-1520.
Aleku et al., "Atu027, a Liposomal Small Interfering RNA Formulation Targeting Protein Kinase N3, Inhibits Cancer Progression," Cancer Research, Dec. 2008, 68(23):9788-9798.
Alfonso et al., "An Anti-Idiotype Vaccine Elicits a Specific Response to N-Glycolyl Sialic Acid Residues of Glycoconjugates in Melanoma Patients," Journal of Immunology, Mar. 2002, 168(5):2523-2529.
Anderson et al., "Incorporation of pseudouridine into mRNA enhances translation by diminishing PKR activation," Nucleic Acids Research, May 2010, 38(17):5884-5892.
Anderson et al., "Nucleoside modifications in RNA limit activation of 2'-5'- oligoadenylate synthetase and increase resistance to cleavage by RNase L," Nucleic Acids Research, Aug. 2011, 39(21):9329-9338.
Anderson et al., "Stability of mRNA/Cationic Lipid Lipoplexes in Human and Rat Cerebrospinal Fluid: Methods and Evidence for Nonviral mRNA Gene Delivery to the Central Nervous System," Human Gene Therapy, Feb. 10, 2003, 14(3):191-202.
Anderson et al., "The Bridge," National Academy Of Engineering of the National Academies, Fall 2006, 36(3):1-55.
Andrews-Pfannkoch et al., "Hydroxyapatite-Mediated Separation of Double-Stranded DNA, Single-Stranded DNA, and RNA Genomes from Natural Viral Assemblages," Applied and Environmental Microbiology, Jun. 2010, 76(15):5039-5045.
Andries et al., "Comparison of the Gene Transfer Efficiency of mRNA/GL67 and pDNA/GL67 Complexes in Respiratory Cells," Molecular Pharmaceutics, Jun. 2012, 9(8):2136-2145.
Apostolopoulos et al., "Cellular Mucins: Targets for Immunotherapy," Critical Reviews in Immunology, 1994, 14(3-4):293-309.
Ast, "How Did Alternative Splicing Evolve?," Nature Reviews Genetics, Oct. 2004, 5(10):773-782.
Aurup et al., "Translation of 2'-Modified mRNA in Vitro and in Vivo," Nucleic Acids Research, Nov. 1994, 22(23):4963-4968.
Ausar et al., "High-throughput Screening of Stabilizers for Respiratory Syncytial Virus: Identification of Stabilizers and Their Effects on the Conformational Thermostability of Viral Particles," Human Vaccines, May 2007, 3(3):94-103.
Baars et al., "A phase II study of active specific immunotherapy and 5- FU/Leucovorin as adjuvant therapy for stage III colon carcinoma," British Journal of Cancer, Apr. 2002, 86(8):1230-1234.
Badis et al., "A snoRNA that Guides the Two Most Conserved Pseudouridine Modifications within rRNA Confers a Growth Advantage in Yeast," RNA, Jul. 2003, 9(7):771-779.
Baker et al., "RNA-Guided RNA Modification: Functional Organization of the Archaeal H/Aca Rnp," Genes & Development, May 2005, 19(10):1238-1248.
Barr et al., "Epidemiological, Antigenic and Genetic Characteristics of Seasonal Influenza A(H1N1), A(H3N2) and B Influenza Virus: Basis for WHO Recommendation on the Composition of Influenza Vaccines for Use in the 2009-2010 Northern Hemisphere Season," Vaccine, Feb. 2010, 28(5):1156-1167.
Basarkar et al., "Nanoparticulate systems for polynucleotide delivery," International Journal of Nanomedicine, Sep. 2007, 2(3):353-360.
Basha et al., "Influence of Cationic Lipid Composition on Gene Silencing Properties of Lipid Nanoparticle Formulations of siRNA in Antigen-Presenting Cells," Molecular Therapy, Dec. 2011, 19(12):2186-2200.
Bauman et al., "Safety, Tolerability, and Immunogenicity of mRNA-4157 in Combination with Pembrolizumab in Subjects with Unresectable Solid Tumors (KEYNOTE-603): An Update," Abstract 798, Journal for ImmunoTherapy of Cancer, 2020, 8(Suppl 3):A477.
Belliveau et al., "Microfluidic Synthesis of Highly Potent Limit-Size Lipid Nanoparticles for In Vivo Delivery of siRNA," Molecular Therapy Nucleic Acids, Aug. 2012, 1(8):e37, 9 pages.
Bentebibel et al., "ICOS+PD-1+CXCR3+ T follicular helper cells contribute to the generation of high-avidity antibodies following influenza vaccination," Scientific Reports, May 2016, 6:26494, 8 pages.

(56) References Cited

OTHER PUBLICATIONS

Bernstein et al., "Poly(A), Poly(A) Binding Protein and the Regulation of mRNA Stability," Trends in Biochemical Sciences, Sep. 1988, 14(9):373-377.
Bevilacqua et al., "Post-Transcriptional Regulation of Gene Expression by Degradation of Messenger RNAs," Journal of Cellular Physiology, Mar. 2003, 195(3):356-372.
BIOPHAMA. "Sample Synagis (Palivizumab; MEDI-493); respiratory syncytial virus (RSV) monoclonal antibody, recombinant," BioPlan Associates, Inc, MedImmune, Inc, 2013, 19 pages.
Bloom et al., "Self-amplifying RNA vaccines for infectious diseases," Gene Therapy, Apr. 2021, 28(3-4):117-129.
Blumenthal, "QB replicase template specificity: different templates require different GTP concentrations for initiation," Proceedings of the National Academy of Sciences, May 1980, 77(5):2601-2605.
Boczkowski et al., "Induction of Tumor Immunity and Cytotoxic T Lymphocyte Responses Using Dendritic Cells Transfected with Messenger RNA Amplified from Tumor Cells," Cancer Research, Feb. 2000, 60(4):1028-1034.
Bolhassani et al., "Improvement of different vaccine delivery systems for cancer therapy," Molecular Cancer, Jan. 2011, 10:3, 20 pages.
Bommakanti et al., "Design of an HA2-Based Escherichia coli Expressed Influenza Immunogen that Protects Mice from Pathogenic Challenge," Proceedings of the National Academy of Sciences, Jul. 2010, 107(31):13701-13706.
Bose et al., "Influence of cationic lipid concentration on properties of lipid-polymer hybrid nanospheres for gene delivery," International Journal of Nanomedicine, Sep. 2015, 10:5367-5382.
Bouloy et al., "Both the 7-methyl and the 2'-O-methyl groups in the cap of mRNA strongly influence its ability to act as primer for influenza virus RNA transcription," Proceedings of the National Academy of Sciences of the United States of America, Jul. 1980, 77(7):3952-3956.
Bowie et al., "Deciphering the Message in Protein Sequences: Tolerance to Amino Acid Substitutions," Science, Mar. 1990, 247(4948):1306-1310.
Brandenburg et al., "Mechanisms of Hemagglutinin Targeted Influenza Virus Neutralization," Public Library of Science One (PLOS One), Dec. 2013, 8(12):e80034, 14 pages.
Brennan, "Ribonucleoside triphosphate concentration-dependent termination of bacteriophage SP01 transcription in vitro by Bacillus subtilis RNA polymerase," Virology, Jun. 1984, 135(2):555-560.
Brito et al., "Self-amplifying mRNA vaccines," Advances in Genetics, Dec. 2014, 89:179-233.
Burke et al., "Formulation, Stability, and Delivery of Live Attenuated Vaccines for Human Use," Critical Reviews in Therapeutic Drug Carrier Systems, 1999, 16(1):1-83.
Cannon et al., "RNA Based Vaccines," DNA and Cell Biology, Dec. 2002, 21(12):953-961.
CAPLUS Database Accession No. 1943:2081, "Synthesis of the alkaloid arecoline, the active constituent of betel nuts," Jan. 1, 1941, 1 page.
Carralot et al., "Polarization of immunity induced by direct injection of naked sequence-stabilized mRNA vaccines," Cellular and Molecular Life Sciences, Sep. 2004, 61(18):2418-2424.
Charette et al., "Pseudouridine in RNA: what, where, how, and why," International Union of Biochemistry and Molecular Biology Life, May 2000, 49(5):341-351.
Chen et al., "A Flexible RNA Backbone within the Polypyrimidine Tract Is Required for U2AF65 Binding and Pre-mRNA Splicing In Vivo," Molecular and Cellular Biology, Jul. 2010, 30(17):4108-4119.
Chen et al., "Clinical and epidemiological characteristics of a fatal case of avian influenza A H10N8 virus infection: a descriptive study," The Lancet, Feb. 2014, 383(9918):714-721.
Chen et al., "Enhanced protection against a lethal influenza virus challenge by immunization with both hemagglutinin- and neuraminidase-expressing DNAs," Vaccine, Feb. 1999, 17(7-8):653-659.
Chen et al., "Gold-loading magnetic core-shell organic/inorganic nanocomposites: Facile preparation and multiple properties," Polymers for Advanced Technologies, Jun. 2014, 25(9):1069-1076.
Chen et al., "Human monoclonal antibodies targeting the haemagglutinin glycoprotein can neutralize H7N9 influenza virus," Nature Communications, Mar. 2015, 6:6714, 10 pages.
Chen et al., "Influence of particle size on the in vivo potency of lipid nanoparticle formulations of siRNA," Journal of Controlled Release, May 2016, 235:236-244.
Chen et al., "Vaccination of monoglycosylated hemagglutinin induces cross-strain protection against influenza virus infections," Proceedings of the National Academy of Sciences, Dec. 2013, 111(7):2476-2481.
Cheng et al., "Enhancement of Sindbis Virus Self-Replicating RNA Vaccine Potency by Linkage of Herpes Simplex Virus Type 1VP22 Protein to Antigen," Journal of Virology, Mar. 2001, 75(5):2368-2376.
Cheng et al., "Multifunctional triblock copolymers for intracellular messenger RNA delivery," Biomaterials, Oct. 2012, 33(28):6868-6876.
Chinnakannan et al., "The Design and Development of a Multi-HBV Antigen Encoded in Chimpanzee Adenoviral and Modified Vaccinia Ankara Viral Vectors; A Novel Therapeutic Vaccine Strategy against HBV," Vaccines, Apr. 2020, 8(2):184, 20 pages.
Cho et al., "The PurR regulon in *Escherichia coli* K-12 MG1655," Nucleic Acids Research, May 2011, 39(15):6456-6464.
Colter et al., "Infectivity of ribonucleic acid isolated from virus-infected tissues," Virology, Dec. 1957, 4(3):522-532.
Condon et al., "DNA-based immunization by in vivo transfection of dendritic cells," Nature Medicine, Oct. 1996, 2(10):1122-1128.
Cosman et al., "ULBPs, Novel MHC Class I-Related Molecules, Bind to CMV Glycoprotein UL16 and Stimulate NK Cytotoxicity through the NKG2D Receptor," Immunity, Feb. 2001, 14(2):123-133.
Cowling, "Regulation of mRNA cap methylation," Biochemical Journal, Dec 2009, 425(2):295-302.
Cross et al., "Can mRNA disrupt the drug industry?" Chemical & Engineering News, Sep. 2018, 96(35):35-40.
Cu et al., "Enhanced Delivery and Potency of Self-Amplifying mRNA Vaccines by Electroporation in Situ," Vaccines, Aug. 2013, 1(3):367-383.
Cuburu et al., "Intravaginal immunization with HPV vectors induces tissue-resident CD8+ T cell responses," Journal of Clinical Investigation, Dec. 2012, 122(12):4606-4620.
Cunningham et al., "The Cycle of Human Herpes Simplex Virus Infection: Virus Transport and Immune Control," Journal of Infectious Diseases, Sep. 2006, 194(Suppl 1):S11-S18.
Daniels et al., "Influenza Virus Characterisation," Surveillance report for the Summary Europe, Jul. 2012, 11 pages.
Daniels, "Surveillance Report: Influenza virus characterisation," ECOC, 2012, retrieved on May 11, 2026, retrieved from URL <https://www.ecdceuropa.eu/sites/default/files/media/en/publications/Publications/In fluenza-virus-characterisation-Sep. 2012.pdf>, 13 pages.
Davis, "Stabilization of RNA stacking by pseudouridine," Nucleic Acids Research, Jan. 1995, 23(24):5020-5026.
De Jong et al., "Drug delivery and nanoparticles: applications and hazards," International Journal of Nanomedicine, Jun. 2008, 3(2):133-149.
De Marco et al., "A Non-VH1-69 Heterosubtypic Neutralizing Human Monoclonal Antibody Protects Mice against H1N1 and H5N1 Viruses," Public Library of Science One, Apr. 2012, 7(4):e34415, 9 pages.
De Pooter et al., "mRNA Therapeutic Vaccine for Hepatitis B Demonstrates Immunogenicity and Efficacy in the AAV-HBV Mouse Model," Vaccines, Feb. 2024, 12(3):237, 19 pages.
Dean et al., "Rapid Amplification of Plasmid and Phage DNA Using Phi29 DNA Polymerase and Multiply-Primed Rolling Circle Amplification," Genome Research, Jun. 2001, 11(6):1095-1099.
Decision of the Regional Court of Dusseldorf in European Patent No. EP 3718565 B1, dated Oct. 31, 2022, 2 pages.

(56) References Cited

OTHER PUBLICATIONS

Delehanty et al., "Peptides for specific intracellular delivery and targeting of nanoparticles: implications for developing nanoparticle-mediated drug delivery," Future Science: Therapeutic Delivery, Sep. 2010, 1(3):411-433.
Devoldere et al., "Evading innate immunity in nonviral mRNA delivery: don't shoot the messenger," Drug Discovery Today, Jul. 2015, 21(1):11-25.
Di Caro et al., "In Vivo Delivery of Nucleic Acid-Formulated Microparticles as a Potential Tolerogenic Vaccine for Type 1 Diabetes," Reviews in Diabetic Studies, Dec. 2012, 9(4):348-356.
Diebold et al., "Innate Antiviral Responses by Means of TLR7-Mediated Recognition of Single-Stranded RNA," Science, Feb. 2004, 303(5663):1529-1531.
Disbrow et al., "Codon optimization of the HPV-16 E5 gene enhances protein expression, " Virology, Jun. 2003, 311(1):105-114.
Dolgin, "mRNA flu shots move into trials," Nature Reviews Drug Discovery, Nov. 2021, 20(11):801-803.
Ducani et al., "Rolling circle replication requires single-stranded DNA binding protein to avoid termination and production of double-stranded DNA," Nucleic Acids Research, Aug. 2014, 42(16):10596-10604.
Dunham, "The application of nucleic acid vaccines in veterinary medicine," Research in Veterinary Science, Aug. 2002, 73(1):9-16.
Easton et al., "Rapid, nondenaturing RNA purification using weak anion-exchange fast performance liquid chromatography," RNA, Jan. 2010, 16(3):647-653.
EBI Accession No. MS954916.1, "Sequence 2 from Patent WO2017040343," Jul. 12, 2017, 1 page.
Edelheit et al., "Transcriptome-Wide Mapping of 5-methylcytidine RNA Modifications in Bacteria, Archaea, and Yeast Reveals m5 C within Archaeal mRNAs," PLOS Genetics, Jun. 2013, 9(6):e1003602, 14 pages.
El Ouahabi et al., "Double long-chain amidine liposome-mediated self replicating RNA transfection," Federation of European Biochemical Societies Letters, Feb. 1996, 380(1-2):108-112.
Espeseth et al., "Modified mRNA/lipid nanoparticle-based vaccines expressing respiratory syncytial virus F protein variants are immunogenic and protective in rodent models of RSV infection," Nature Partner Journals Vaccines, Feb. 2020, 5(1):16, 14 pages.
Ewert et al., "Cationic Liposome-Nucleic Acid Complexes for Gene Delivery and Silencing: Pathways and Mechanisms for Plasmid DNA and siRNA," Topics in Current Chemistry, Jun. 2010, 296:191-226.
Fang et al., "Development of Lipid-Shell and Polymer Core Nanoparticles with Water-Soluble Salidroside for Anti-Cancer Therapy," International Journal of Molecular Sciences, Feb. 2014, 15(3):3373-3388.
Feldman et al., "mRNA vaccines against H10N8 and H7N9 influenza viruses of pandemic potential are immunogenic and well tolerated in healthy adults in phase 1 randomized clinical trials," Vaccine, May 2019, 37(25):3326-3334.
Felgner, "Cationic lipid/polynucleotide condensates for in vitro and in vivo polynucleotide delivery—the cytofectins," Journal of Liposome Research, 1993, 3(1):3-16.
Felgner, "Particulate systems and polymers for in vitro and in vivo delivery of polynucleotides," Advanced Drug Delivery Reviews, Sep. 1990, 5(3): 163-187.
Fernandez et al., "Unusual base pairing during the decoding of a stop codon by the ribosome," Nature, Jun. 2013, 500(7460):107-110.
Fotakis et al., "Computational cancer neoantigen prediction: current status and recent advances," ImmunoOncology Technology, Nov. 2021, 12:100052, 13 pages.
Freyn et al., "A Multi-Targeting, Nucleoside-Modified mRNA Influenza Virus Vaccine Provides Broad Protection in Mice," Molecular Therapy, Apr. 2020, 28(7):1569-1584.
Fuke et al., "Role of poly(A) tail as an identity element for mRNA nuclear export," Nucleic Acids Research, Feb. 2008, 36(3):1037-1049.
Furuichi et al., "Viral and Cellular mRNA Capping: Past and Prospects," Advances in Virus Research, 2000, 55:135-184.
Furuichi, "Caps on Eukaryotic mRNAs," Encyclopedia of Life Sciences, Jul. 2014, 12 pages.
Fynan et al., "DNA vaccines: Protective immunizations by parenteral, mucosal, and gene-gun inoculations," Proceedings of the National Academy of Sciences, Dec. 1993, 90(24):11478-11482.
Gainor et al., "T-cell Responses to Individualized Neoantigen Therapy mRNA-4157 (V940) as Monotherapy or in Combination With Pembrolizumab," Poster, Presented at the Society for Immunotherapy of Cancer, San Diego, California, Nov. 3-5, 2023, 1 page.
Gao et al., Human Infection with a Novel Avian-Origin Influenza A (H7N9) Virus, The New England Journal of Medicine, Apr. 2013, 368(20):1888-1897.
GenBank Accession No. ABM67072, "fusion protein [human metapneumovirus]," Oct. 6, 2006, 2 pages.
GenBank Accession No. ATP60600, "T7RNAP [Cloning vector pTara:500*]," Nov. 4, 2017, 1 page.
GenBank Accession No. EF051125, "Pisum sativum yieldin-like protein (YLD) mRNA, complete cds," Oct. 7, 2006, 2 pages.
GenBank Accession No. FJ750874.1, "Influenza A virus (A/wild bird feces/Korea/HDR16/2003(H7N2)) segment 4 hemagglutinin (HA) gene, complete cds," Mar. 5, 2010, 2 pages.
GenBank Accession No. JN817576.1, "Influenza A virus (A/mallard/Korea/1242/2010(H10N6)) segment 4 hemagglutinin (HA) gene, complete cds," Dec. 20, 2012, 2 pages.
GenBank Accession No. KF042104.1, "Influenza A virus (A/chicken/Zhejiang/C483/2013(H7N9)) segment 4 hemagglutinin (HA) gene, complete cds," Jun. 11, 2014, 2 pages.
GenBank Accession No. KJ406543.1, "Influenza A virus (A/Jiangxi/IPB13/2013(H10N8)) segment 4 hemagglutinin (HA) gene, complete cds," Jun. 12, 2014, 2 pages.
GenPept Accession No. AAY46211.1, "hemagglutinin [Influenza A virus (A/mallard/Sweden/91/2002(H7N9))]," Sep. 30, 2005, 2 pages.
GenPept Accession No. ABO77067.1, "hemagglutinin [Influenza A virus (A/turkey/Italy/4426/2000(H7N1))]," Apr. 2, 2007, 2 pages.
GenPept Accession No. ACF25291.1, "hemagglutinin [Influenza A virus (A/ruddy turnstone/NJ/1956/2001(H10N7))]," Jul. 13, 2008, 2 pages.
GenPept Accession No. ADE75192.1, "hemagglutinin [Influenza A virus (A/mallard/Sweden/Apr. 2002(H10N2))]," Apr. 8, 2010, 2 pages.
GenPept Accession No. AEK65976.1, "hemagglutinin [Influenza A virus (A/duck/Italy/4692-Sep. 2004(H7))]," Aug. 2, 2011, 2 pages.
GenPept Accession No. AGN69400.1, "hemagglutinin [Influenza A virus (A/chicken/Zhejiang/C483/2013(H7N9))]," Jun. 11, 2014, 2 pages.
GenPept Accession No. AHK10761.1, "hemagglutinin [Influenza A virus (A/Jiangxi/IPB13/2013(H10N8))]," Jun. 12, 2014, 2 pages.
GenPept Accession No. AHZ39686.1, "hemagglutinin [Influenza A virus (A/Anhui/DEWH72-Jan. 2013(H7N9))]," May 9, 2014, 2 pages.
GenPept Accession No. BAS30426.1, "fusion protein [Human respirovirus 3]," Sep. 2, 2015, 2 pages.
Georgopoulos et al., "Use of high-performance liquid chromatographic fractionation of large RNA molecules in the assay of group I intron ribozyme activity," Journal of Chromatography A, Jan. 2000, 868(1):109-114.
GISAID Accession No. EPI443651, Dec. 11, 2013, 3 pages.
GISAID Accession No. EPI457621, Jun. 16, 2013, 1 page.
GISAID Accession No. EPI487905, Nov. 23, 2011, 3 pages.
GISAID Accession No. EPI497477, Dec. 20, 2013, 3 pages.
GISAID Accession No. EPI508781, Mar. 9, 2014, 3 pages.
Gjetting et al., "In vitro and in vivo effects of polyethylene glycol (PEG)-modified lipid in DOTAP/cholesterol-mediated gene transfection," International Journal of Nanomedicine, May 2010, 5:371-383.
Govind et al., "Primer-independent initiation of RNA synthesis by SeMV recombinant RNA-dependent RNA polymerase," Virology, Mar. 2010, 401(2):280-292.

(56) References Cited

OTHER PUBLICATIONS

Graf et al., "Codon-Optimized Genes that Enable Increased Heterologous Expression in Mammalian Cells and Elicit Efficient Immune Responses in Mice after Vaccination of Naked DNA," Methods in Molecular Medicine, 2004, 94:197-210.
Graham et al., "Novel Vaccine Technologies: Essential Components of an Adequate Response to Emerging Viral Diseases," Journal of the American Medical Association, Mar. 2018, 319(14):1431-1432.
Granstein et al., "Induction of Anti-Tumor Immunity with Epidermal Cells Pulsed with Tumor-Derived RNA or Intradermal Administration of RNA," Journal of Investigative Dermatology, Apr. 2000, 114(4):632-636.
Grosjean, "Modification and editing of RNA: historical overview and important facts to remember. Fine-tuning of RNA functions by modification and editing," Topics in Current Genetics, Jan. 2005, 12:1-22.
Gruegelsiepe et al., "Enzymatic RNA Synthesis, Ligation and Modification," Handbook of RNA Biochemistry, 2005, Chapter 1, pp. 3-21.
Guimaraes et al., "Ionizable lipid nanoparticles encapsulating barcoded mRNA for accelerated in vivo delivery screening," Journal of Controlled Release, Oct. 2019, 316:404-417.
Hadinoto et al., "Lipid-polymer hybrid nanoparticles as a new generation therapeutic delivery platform: a review," European Journal of Pharmaceutics and Biopharmaceutics, Jul. 2013, Part A, 85(3):427-443.
Hajj et al., "Tools for translation: non-viral materials for therapeutic mRNA delivery," Nature Reviews Materials, Sep. 2017, 2(10):17056, 17 pages.
Halford et al., "Herpes Simplex Virus 2 ICP02 Mutant Viruses Are Avirulent and Immunogenic: Implications for a Genital Herpes Vaccine," Public Library of Science One, Aug. 2010, 5(8):e12251, 17 pages.
Harenberg et al., "Persistence of Th1/Tcl responses one year after tetravalent dengue vaccination in adults and adolescents in Singapore," Human Vaccines & Immunotherapeutics, Jul. 2013, 9(11):2317-2325.
Harris et al., "An improved RNA amplification procedure results in increased yield of autologous RNA transfected dendritic cell-based vaccine," Biochimica et Biophysica Acta, Apr. 2005, 1724(1-2):127-136.
Hassett et al., "Optimization of Lipid Nanoparticles for Intramuscular Administration of mRNA Vaccines," Molecular Therapy: Nucleic Acids, Feb. 2019, 15:1-11.
He et al., "Low molecular weight protamine (LMWP): a nontoxic protamine substitute and an effective cell-penetrating peptide," Journal of Controlled Release, Jun. 2014, 193:63-73.
Heidenreich et al., "Chemically modified RNA: approaches and applications," The Federation of American Societies for Experimental Biology Journal, Jan. 1993, 7(1):90-96.
Heilman et al., "Internal 6-methyladenine residues increase the in vitro translation efficiency of dihydrofolate reductase messenger RNA," International Journal of Biochemistry and Cell Biology, Jul. 1996, 28(7):823-829.
Heiser et al., "Autologous dendritic cells transfected with prostate-specific antigen RNA stimulate CTL responses against metastatic prostate tumors," Journal of Clinical Investigation, Feb. 2002, 109(3):409-417.
Hsu et al., "Cationic lipid nanoparticles for therapeutic delivery of siRNA and miRNA to murine liver tumor," Nanomedicine, May 2013, 9(8): 1169-1180.
Huddleston et al., "The sequence of the nucleoprotein gene of human influenza A virus, strain A/NT/60/68," Nucleic Acids Research, Feb. 1982, 10(3): 1029-1038.
Imamura et al., "Global reemergence of enterovirus 068 as an important pathogen for acute respiratory infections," Reviews in Medical Virology, Mar. 2015, 25(2):102-114.
Impagliazzo et al., "A stable trimeric influenza hemagglutinin stem as a broadly protective immunogen," Science, Aug. 2015, 349(6254):1301-1306.
International Preliminary Report on Patentability in International Application No. PCT/US2022/020218, mailed on Sep. 28, 2023, 11 pages.
International Search Report and Written Opinion for Application No. PCT/US2022/024497, mailed on Sep. 5, 2022, 21 pages.
International Search Report and Written Opinion for Application No. PCT/US2022/024669, mailed on Sep. 26, 2022, 22 pages.
International Search Report and Written Opinion for International Application No. PCT/US2022/020218, mailed Aug. 16, 2022, 18 pages.
Invitation to Pay Additional Fees and, Where Applicable, Protest Fee in International Application No. PCT/US2022/020218, mailed on Jun. 24, 2022, 9 pages.
Ivanovska et al., "Immunization with a DNA chimeric molecule encoding a hemagglutinin peptide and a scFv CD21-specific antibody fragment induces long- lasting IgM and CTL responses to influenza virus," Vaccine, Nov. 2005, 24(11):1830-1837.
Iwasaki et al., "Enhanced CTL Responses Mediated by Plasmid DNA Immunogens Encoding Costimulatory Molecules and Cytokines," Journal of Immunology, May 1997, 158(10):4591-4601.
Jaishankar et al., "Strong synthetic stationary phase promoter-based gene expression system for *Escherichia coli*," Plasmid, Feb. 2020, 109:102491.
Jia et al., "Kinetic Mechanism of GTP Binding and RNA Synthesis during Transcription Initiation by Bacteriophage T7 Rna Polymerase," Journal of Biological Chemistry, Nov. 1997, 272(48):30147-30153.
John et al., "Multi-antigenic human cytomegalovirus mRNA vaccines that elicit potent humoral and cell-mediated immunity," Vaccine, Feb. 2018, 36(12):1689-1699.
Jorquera et al., "Nanoparticle Vaccines Encompassing the Respiratory Syncytial Virus (Rsv) G Protein CX3C Chemokine Motif Induce Robust Immunity Protecting from Challenge and Disease," Public Library of Science One, Sep. 2013, 8(9):e74905, 13 pages.
Kabanov et al., "A new class of antivirals: antisense oligonucleotides combined with a hydrophobic substituent effectively inhibit influenza virus reproduction and synthesis of virus specific proteins in MOCK cells," Federation of European Biochemical Societies Letters, Jan. 1990, 259(2):327-330.
Kanaya et al., "Codon usage and tRNA genes in eukaryotes: correlation of codon usage diversity with translation efficiency and with CG-dinucleotide usage as assessed by multivariate analysis," Journal of Molecular Evolution, Oct. 2001, 53(4-5):290-298.
Karijolich et al., "Converting nonsense codons into sense codons by targeted pseudouridylation, " Nature, Jun. 2011, 474(7351):395-398.
Karikó et al., "Impacts of Nucleoside Modification on RNA Mediated Activation of Toll-Like Receptors," Nucleic Acids in Innate Immunity, May 2008, Chapter 13, pp. 171-188.
Karikó et al., "In vivo protein expression from mRNA delivered into adult rat brain," Journal of Neuroscience Methods, Jan. 2001, 105(1):77-86.
Karikó et al., "Phosphate-enhanced transfection of cationic lipid-complexed mRNA and plasmid DNA," Biochimica et Biophysica Acta, Mar. 1998, 1369(2):320-334.
Kauffman et al., "Efficacy and immunogenicity of unmodified and pseudouridine-modified mRNA delivered systemically with lipid nanoparticles in vivo," Biomaterials, Sep. 2016, 109:78-87.
Kaukinen et al., "The reactivity of phosphodiester bonds within linear single-stranded oligoribonucleotides is strongly dependent on the base sequence," Nucleic Acids Research, Jan. 2002, 30(2):468-474.
Kern et al., "Application of a fed-batch system to produce RNA by in vitro transcription, " Biotechnology Progress, Mar. 1999, 15(2):174-184.
Khurana et al., "Recombinant HA1 produced in Escherichia coli forms functional oligomers and generates strain-specific SRID potency antibodies for pandemic influenza vaccines, " Vaccine, Jun. 2011, 29(34):5657-5665.
Kierzek et al., "The contribution of pseudouridine to stabilities and structure of RNAs, " Nucleic Acids Research, Dec. 2013, 42(5):3492-3501.

(56) References Cited

OTHER PUBLICATIONS

Kim et al., "High Cleavage Efficiency of a 2A Peptide Derived from Porcine Teschovirus-1 in Human Cell Lines, Zebrafish and Mice," Public Library of Science One, Apr. 2011, 6(4):e18556, 8 pages.
Klinman et al., "DNA vaccines: safety and efficacy issues," Springer Seminars in Immunopathology, 1997, 19(2):245-256.
Knepper et al., "The Novel Human Influenza A(H7N9) Virus Is Naturally Adapted to Efficient Growth in Human Lung Tissue," mBio, Oct. 2013, 4(5):e00601-13, 5 pages.
Koch et al., "Quantitative studies on the infectivity of ribonucleic acid from partially purified and highly purified poliovirus preparations," Virology, Mar. 1960, 10(3):329-343.
Kon et al., "A single-dose F1-based mRNA-LNP vaccine provides protection against the lethal plague bacterium," Science Advances, Mar. 2023, 9(10):eadg1036, 10 pages.
Kopera et al., "Expression, purification and characterization of glycosylated influenza H5N1 hemagglutinin produced in Pichia pastoris," Acta Biochimica Polonica, Sep. 2014, 61(3):597-602.
Kore et al., "Synthesis and biological validation of N7-(4-chlorophenoxyethyl) substituted dinucleotide cap analogs for mRNA translation," Bioorganic and Medicinal Chemistry, Jun. 2013, 21(15):4570-4574.
Kormann et al., "Expression of therapeutic proteins after delivery of chemically modified mRNA in mice, " Nature Biotechnology, Feb. 2011, 29(2):154-157.
Kowalski et al., "Delivering the Messenger: Advances in Technologies for Therapeutic mRNA Delivery, " Molecular Therapy, Apr. 2019, 27(4): 1-19.
Kozak, "Regulation of translation via mRNA structure in prokaryotes and eukaryotes," Gene, Oct. 2005, 361:13-37.
Kudla et al., "High Guanine and Cytosine Content Increases mRNA Levels in Mammalian Cells," Public Library of Science Biology, Jun. 2006, 4(6):e180, 10 pages.
Kulkarni et al., "Lipid Nanoparticles Enabling Gene Therapies: From Concepts to Clinical Utility," Nucleic Acid Therapeutics, Apr. 2018, 28(3):146-157.
Kumar et al., "Shielding of Lipid Nanoparticles for siRNA Delivery: Impact on Physicochemical Properties, Cytokine Induction, and Efficacy," Molecular Therapy: Nucleic Acids, Nov. 2014, 3(11):e210, 7 pages.
Kusakabe et al., "The Timing of GM-CSF Expression Plasmid Administration Influences the Th1/Th2 Response Induced by an HIV-1-Specific DNA Vaccine," Journal of Immunology, Mar. 2000, 164(6):3102-3111.
Kwong et al., "Broadly neutralizing antibodies and the search for an HIV-1 vaccine: the end of the beginning," Nature Reviews Immunology, Sep. 2013, 13:693- 701.
Laursen et al., "Broadly neutralizing antibodies against influenza viruses," Antiviral Research, Apr. 2013, 98(3):476-483.
Lee et al., "Lipid nanoparticle siRNA systems for silencing the androgen receptor in human prostate cancer in vivo," International Journal of Cancer, Sep. 2012, 131(5):E781-E790.
Leroueil et al., "Wide Varieties of Cationic Nanoparticles Induce Defects in Supported Lipid Bilayers," Nano Letters, Jan. 2008, 8(2):420-424.
Lewandowski et al., "Separation of the Infectious Ribonucleic Acid of Potato Spindle Tuber Virus from Double-Stranded Ribonucleic Acid of Plant Tissue Extracts," Journal of Virology, Nov. 1971, 8(5):809-812.
Lewis, "Dynamic Polyconjugates (DPC) Technology: an elegant solution to the siRNA delivery problem," Arrowhead Research Corp, Nov. 2011, 6 pages.
Li et al., "Developing Lipid Nanoparticle-Based siRNA Therapeutics for Hepatocellular Carcinoma Using an Integrated Approach," Molecular Cancer Therapeutics, Aug. 2013, 12(11):2308-2318.
Li et al., "Preparation and Gene Delivery of Alkaline Amino Acids-Based Cationic Liposomes," Archives of Pharmacal Research, Aug. 2008, 31(7):924-931.
Li et al., "Prophylactic, therapeutic and immune enhancement effect of liposome-encapsulated PolyICLC on highly pathogenic H5N1 influenza infection," Journal of Gene Medicine, Jan. 2011, 13(1):60-72.
Lian et al., "Trends and Developments in Liposome Drug Delivery Systems," Journal of Pharmaceutical Sciences, Jun. 2001, 90(6):667-680.
Limberis et al., "Intranasal Antibody Gene Transfer in Mice and Ferrets Elicits Broad Protection Against Pandemic Influenza," Science Translational Medicine, May 2013, 5(187):187ra72, 8 pages.
Lin et al., "Lipid-based nanoparticles in the systemic delivery of siRNA," Nanomedicine, Jan. 2014, 9(1):105-120.
Lin et al., "The Herpes Simplex Virus Icpo Ring Finger Domain Inhibits IRF3- and IRF7-Mediated Activation of Interferon-Stimulated Genes," Journal of Virology, Feb. 2004, 78(4): 1675-1684.
Lindgren et al., "Induction of Robust B Cell Responses after Influenza mRNA Vaccination Is Accompanied by Circulating Hemagglutinin-Specific ICOS+ PD-1+ CXCR3+ T Follicular Helper Cells," Frontiers in Immunology, Nov. 2017, 8:1539, 12 pages.
Love et al., "Lipid-like materials for low-dose, in vivo gene silencing," Proceedings of the National Academy of Sciences, Jan. 2010, 107(5):1864-1869.
Lu et al., "Production and stabilization of the trimeric influenza hemagglutinin stem domain for potentially broadly protective influenza vaccines," Proceedings of the National Academy of Sciences, Dec. 2013, 111(1):125-130.
Luo et al., "Synthetic DNA delivery systems," Nature Biotechnology, Jan. 2000, 18(1):33-37.
Ma et al., "HPV pseudovirions as DNA delivery vehicles," Therapeutic Delivery, Apr. 2011, 2(4):427-430.
Madden et al., "Systemic delivery of mRNA therapeutics using lipid nanoparticles (LNP): improved potency for novel LNP and influence of route of administration on protein expression," Poster, Presented at the 2nd International mRNA Health Conference, Nov. 12, 2014, 1 page.
Magee et al., "Marked Stimulation of Lymphocyte-mediated Attack on Tumor Cells by Target-directed Liposomes Containing Immune RNA," Cancer Research, Apr. 1978, 38(4):1173-1176.
Maier et al., "Biodegradable Lipids Enabling Rapidly Eliminated Lipid Nanoparticles for Systemic Delivery of RNAi Therapeutics," Molecular Therapy, Jun. 2013, 21(8):1570-1578.
Malone et al., "Cationic liposome-mediated RNA transfection," Proceedings of the National Academy of Sciences, Aug. 1989, 86(16):6077-6081.
Marc et al., "Nucleic acid vaccination strategies against infectious diseases," Expert Opinion on Drug Delivery, Sep. 2015, 12(12):1851-1865.
Martinon et al., "Induction of virus-specific cytotoxic T lymphocytes in vivo by liposome-entrapped mRNA," European Journal of Immunology, Jul. 1993, 23(7):1719-1722.
Maruggi et al., "mRNA as a Transformative Technology for Vaccine Development to Control Infectious Diseases, " Molecular Therapy, Feb. 2019, 27(4): 757-772.
Marzi et al., "An Ebola whole-virus vaccine is protective in non-human primates," Science, Mar. 2015, 348(6233):439-442.
Matray et al., "Synthesis and properties of RNA analogs—oligoribonucleotide N3' —> P5' phosphoramidates, " Nucleic Acids Research, Oct. 1999, 27(20):3976-3985.
Matsuda et al., "Determinants of Initiation Codon Selection during Translation in Mammalian Cells," Public Library of Science One, Nov. 2010, 5(11):e15057, 13 pages.
Maurer et al., "Spontaneous Entrapment of Polynucleotides upon Electrostatic Interaction with Ethanol-Destabilized Cationic Liposomes," Biophysical Journal, May 2001, 80(5):2310-2326.
McKenzie et al., "Nucleic Acid Vaccines: Tasks and Tactics," Immunologic Research, Dec. 2001, 24(3):225-244.
Mellits et al., "Removal of double-stranded contaminants from RNA transcripts: synthesis of adenovirus Va Rnai from a T7 vector," Nucleic Acids Research, Sep. 1990, 18(18):5401-5406.

(56) References Cited

OTHER PUBLICATIONS

Michel et al., "Cationic Nanoliposomes Meet mRNA: Efficient Delivery of Modified mRNA Using Hemocompatible and Stable Vectors for Therapeutic Applications," Molecular Therapy: Nucleic Acids, Jul. 2017, 8:459-468.
Middleton et al., "Hendra Virus Vaccine, a One Health Approach to Protecting Horse, Human, and Environmental Health," Emerging Infectious Diseases, Mar. 2014, 20(3):372-379.
Mignone et al., "Untranslated regions of mRNAs," Genome Biology, Feb. 2002, 3(3):reviews0004, 10 pages.
Mochida et al., "Exogenous mRNA encoding tetanus or botulinum neurotoxins expressed in Aplysia neurons," Proceedings of the National Academy of Sciences, Oct. 1990, 87(20): 7844-7848.
Moffat et al., "Functions of the C-Terminal Domain of Varicella-Zoster Virus Glycoprotein E in Viral Replication In Vitro and Skin and T-Cell Tropism In Vivo," Journal of Virology, Nov. 2004, 78(22):12406-12415.
Mullen et al., "Mapping of Intracellular Localization Domains and Evidence for Colocalization Interactions between the IE110 and IE175 Nuclear Transactivator Proteins of Herpes Simplex Virus," Journal of Virology, May 1994, 68(5):3250-3266.
Nagata et al., "Codon optimization effect on translational efficiency of DNA vaccine in mammalian cells: analysis of plasmid DNA encoding a CTL epitope derived from microorganisms," Biochemical and Biophysical Research Communications, Aug. 1999, 261(2):445-451.
Nagata et al., "Synthesis and biological activity of artificial mRNA prepared with novel phosphorylating reagents," Nucleic Acids Research, Jul. 2010, 38(21):7845-7857.
Nair et al., "Soluble Proteins Delivered to Dendritic Cells Via pH-sensitive Liposomes Induce Primary Cytotoxic T Lymphocyte Responses In Vitro," Journal of Experimental Medicine, Feb. 1992, 175(2):609-612.
Nedialkov et al., "NTP-driven Translocation by Human RNA Polymerase II," Journal of Biological Chemistry, Mar. 2003, 278(20):18303-18312.
Office Action in Russian Application No. 2021109685, dated Jan. 27, 2025, 31 pages (with English translation).
Office Action in U.S. Appl. No. 18/555,087, mailed on Feb. 19, 2026, 52 pages.
Office Action in U.S. Appl. No. 18/555,130, mailed on Feb. 23, 2026, 42 pages.
Okumura et al., "Antitumor activity of cationic liposome-mediated Bax mRNA transfer in HOSM-1 mandibular osteosarcoma cells: a comparative study of local administration and systemic administration," Abstract 98, Journal of Oral and Maxillofacial Surgery, Aug. 2014, 72(9):e107.
Ouranidis et al., "Pharma 4.0 Continuous mRNA Drug Products Manufacturing," Pharmaceutics, Aug. 2021, 13(9): 1371.
Painter et al., "Topical Delivery of mRNA to the Murine Lung and Nasal Epithelium, " Molecular Therapy, May 2004, 9(Suppl 1):S187.
Palese, "Making better influenza virus vaccines?," Emerging Infectious Diseases, Jan. 2006, 12(1):61-65.
Pardi et al., "Developing an influenza vaccine using lipid nanoparticle-encapsulated nucleoside-modified mRNA," Abstract 1349, Eur. J. Immunol., Aug. 2016, 46(S1):1232-1233.
Pardi et al., "Expression kinetics of nucleoside-modified mRNA delivered in lipid nanoparticles to mice by various routes," Journal of Controlled Release, Aug. 2015, 217:345-351.
Parisien et al., "Rationalization and prediction of selective decoding of pseudouridine-modified nonsense and sense codons, " RNA, Jan. 2012, 18(3):355-367.
Pearson et al., "Improved tools for biological sequence comparison," Proceedings of the National Academy of Sciences of the United States of America, Apr. 1988, 85(8):2444-2448.
Peculis, "RNA processing: Pocket guides to ribosomal RNA," Current Biology, Aug. 1997, 7(8):R480-R482.
Pfoh et al., "Crystal Structure of USP7 Ubiquitin-like Domains with an ICPO Peptide Reveals a Novel Mechanism Used by Viral and Cellular Proteins to Target USP7," Public Library of Science Pathogens, Jun. 2015, 11(6):e1004950, 23 pages.
Phue et al., "Modified *Escherichia coli* B (BL21), a superior producer of plasmid DNA compared with Escherichia coli K (DH5alpha)," Biotechnology and Bioengineering, Nov. 2008, 101(4):831-836.
Pine et al., "Development of an mRNA-lipid nanoparticle vaccine against Lyme disease, " Molecular Therapy, Aug. 2023, 31(9):2702-2714.
Polack et al., "Safety and Efficacy of the BNT162b2 mRNA Covid-19 Vaccine, " The New England Journal of Medicine, Dec. 2020, 383(27):2603-2615.
Pollard et al., "Type I Ifn Counteracts the Induction of Antigen-Specific Immune Responses by Lipid-Based Delivery of mRNA Vaccines," Molecular Therapy, Jan. 2013, 21(1):251-259.
Poveda et al., "Establishing Preferred Product Characterization for the Evaluation of RNA Vaccine Antigens, " Vaccines, Sep. 2019, 7(4):131, 14 pages.
Probst et al., "Spontaneous cellular uptake of exogenous messenger RNA in vivo is nucleic acid-specific, saturable and ion dependent," Gene Therapy, May 2007, 14(15):1175-1180.
Qu et al., "Design, synthesis and biological evaluation of multivalent glucosides with high affinity as ligands for brain targeting liposomes," European Journal of Medicinal Chemistry, Nov. 2013, 72:110-118.
Rammensee et al., "Peptides naturally presented by MHC class I molecules," Annual Review of Immunology, Apr. 1993, 11:213-244.
Read et al., "A versatile reducible polycation-based system for efficient delivery of a broad range of nucleic acids," Nucleic Acids Research, Jan. 2005, 33(9): e86, 16 pages.
Rejman et al., "mRNA transfection of cervical carcinoma and mesenchymal stem cells mediated by cationic carriers," Journal of Controlled Release, Nov. 2010, 147(3):385-391.
Ren et al., "Full Genome of Influenza A (H7N9) Virus Derived by Direct Sequencing without Culture," Emerging Infectious Diseases, Nov. 2013, 19(11):1881-1884.
Reyes-Sandoval et al., "DNA vaccines," Current Molecular Medicine, May 2001, 1(2):217-243.
Richner et al., "Modified mRNA vaccines protect against Zika virus infection," Cell, Mar. 2017, 168(6):1114-1125.
Robbins et al., "2'-O-methyl-modified RNAs act as TLR7 antagonists," Molecular Therapy, 2007, 15(9):1663-1669.
Robinson et al., "Expression of Human nPTB Is Limited by Extreme Suboptimal Codon Content," Public Library of Science One, Mar. 2008, 3(3):e1801, 11 pages.
Robinson et al., "Protection against a lethal influenza virus challenge by immunization with a haemagglutinin-expressing plasmid DNA," Vaccine, 1993, 11(9):957-960.
Rock, "A new foreign policy: MHC class I molecules monitor the outside world," Immunology Today, Mar. 1996, 17(3):131-137.
Rockoff, "Startup Moderna Shows Promise in Vaccine Trial," The Wall Street Journal, Apr. 2017, 2 pages.
Rosa et al., "mRNA vaccines manufacturing: Challenges and bottlenecks," Vaccine, Apr. 2021, 39(16):2190-2200.
Ross, "Control of messenger RNA stability in higher eukaryotes," Trends in Genetics, May 1996, 12(5):171-175.
Rozenski et al., "The RNA Modification Database: 1999 update," Nucleic Acids Research, Jan. 1999, 27(1):196-197.
Sabnis et al., "A Novel Amino Lipid Series for mRNA Delivery: Improved Endosomal Escape and Sustained Pharmacology and Safety in Non-human Primates," Molecular Therapy, Mar. 2018, 26(6):1509-1519.
Saenz-Badillos et al., "RNA as a tumor vaccine: a review of the literature," Experimental Dermatology, Jun. 2001, 10(3):143-154.
Sahin et al., "An RNA vaccine drives immunity in checkpoint-inhibitor-treated melanoma," Nature, Jul. 2020, 585(7823):107-112.
Satz et al., "Mechanism of immune transfer by RNA extracts. Immune RNA induces the synthesis of idiotype-bearing antigen receptors in noncommitted cells," Molecular and Cellular Biochemistry, Dec. 1980, 33(3):105-113.

(56) References Cited

OTHER PUBLICATIONS

Sayour et al., "RNA Nanoparticle Vaccines Facilitate and Sustain Adoptive Cellular Therapy Targeting Pediatric Intracranial Malignancies," Abstract 4012, Pediatric Blood and Cancer, Jun. 2015, 62(2):S24.

Scheel et al., "Immunostimulating capacities of stabilized RNA molecules," European Journal of Immunology, Feb. 2004, 34(2):537-547.

Schirrmacher et al., "Intra-pinna anti-tumor vaccination with self-replicating infectious RNA or with DNA encoding a model tumor antigen and a cytokine," Gene Therapy, Jul. 2000, 7(13): 1137-1147.

Schmidt et al., "Fast and Flexible mRNA Vaccine Manufacturing as a Solution to Pandemic Situations by Adopting Chemical Engineering Good Practice—Continuous Autonomous Operation in Stainless Steel Equipment Concepts," Processes, Oct. 2021, 9(11):1874-1893.

Schmidt et al., "Progress in the development of human parainfluenza virus vaccines," Expert Review of Respiratory Medicine, Aug. 2011, 5(4):515-526.

Schneider et al., "Measuring control of transcription initiation by changing concentrations of nucleotides and their derivatives," Methods in Enzymology, 2003, 370:606-617.

Schwendener, "Liposomes as vaccine delivery systems: a review of the recent advances," Therapeutic Advances in Vaccines, Nov. 2014, 2(6):159-182.

Sharp et al., "Effect of translational signals on mRNA decay in *Bacillus subtilis*," Journal of Bacteriology, Sep. 2003, 185(18):5372-5379.

Sirin et al., "AB-Bind: Antibody binding mutational database for computational affinity predictions," Protein Science, Feb. 2016, 25(2):393-409.

Squires et al., "Widespread occurrence of 5-methylcytosine in human coding and non-coding RNA," Nucleic Acids Research, Feb. 2012, 40(11):5023-5033.

Stab et al., "Protective Efficacy and Immunogenicity of a Combinatory DNA Vaccine against Influenza A Virus and the Respiratory Syncytial Virus," Public Library of Science One, Aug. 2013, 8(8):e72217, 9 pages.

Stanekova et al., "Conserved epitopes of influenza A virus inducing protective immunity and their prospects for universal vaccine development," Virology Journal, Nov. 2010, 7:351, 13 pages.

Steel et al., "Influenza Virus Vaccine Based on the Conserved Hemagglutinin Stalk Domain," mBio, May 2010, 1(1):1-10.

Steinle et al., "Concise Review: Application of In Vitro Transcribed Messenger RNA for Cellular Engineering and Reprogramming: Progress and Challenges," Stem Cells, Jun. 2016, 35(1):68-79.

Strobel et al., "Human dendritic cells transfected with either RNA or DNA encoding influenza matrix protein MI differ in their ability to stimulate cytotoxic T lymphocytes," Gene Therapy, Dec. 2000, 7(23):2028-2035.

Tang et al., "A host-range restricted parainfluenza virus type 3 (PIV3) expressing the human metapneumovirus (hMPV) fusion protein elicits protective immunity in African green monkeys," Vaccine, Feb. 2005, 23(14):1657-1667.

Torchilin et al., "Multifunctional and stimuli-sensitive pharmaceutical nanocarriers," European Journal of Pharmaceutics and Biopharmaceutics, Mar. 2009, 71(3):431-444.

Torrecilla et al., "Lipid Nanoparticles as Carriers for RNAi against Viral Infections: Current Status and Future Perspectives," BioMed Research International, Aug. 2014, 2014: 161794, 17 pages.

Tracy, "Progress in the Development of LNP Delivery for siRNA Advancing LNPs to the Clinic," International Liposome Research Days Meeting, Vancouver, Canada. Aug. 2010, 52 pages.

Triana-Alonso et al., "Self-coded 3'-Extension of Run-off Transcripts Produces Aberrant Products during in Vitro Transcription with T7 Rna Polymerase," Journal of Biological Chemistry, Mar. 1995, 270(11):6298-6307.

Trojan et al., "Immune Reactivity Against a Novel HLA-A3-Restricted Influenza Virus Peptide Identified by Predictive Algorithms and Interferon-y Quantitative PCR," Journal of Immunotherapy, Jan. 2003, 26(1):41-46.

Ueda et al., "Phosphorothioate-containing RNAs show mRNA activity in the prokaryotic translation systems in vitro," Nucleic Acids Research, Feb. 1991, 19(3):547-552.

Ulmer et al., "Heterologous protection against influenza by injection of DNA encoding a viral protein," Science, Mar. 1993, 259(5102):1745-1749.

Uzgün et al., "PEGylation Improves Nanoparticle Formation and Transfection Efficiency of Messenger RNA," Pharmaceutical Research, Sep. 2011, 28(9):2223-2232.

Valich, "COVID-19 vaccine: what's RNA research got to do with it?," University of Rochester, Dec. 2020, 11 pages.

Van Tendeloo et al., "mRNA-based gene transfer as a tool for gene and cell therapy," Current Opinion in Molecular Therapeutics, Oct. 2007, 9(5):423-431.

Vassilev et al., "Microparticle-mediated RNA immunization against bovine viral diarrhea virus," Vaccine, Feb. 2001, 19(15-16):2012-2019.

Wan et al., "Lipid nanoparticle delivery systems for siRNA-based therapeutics," Drug Delivery and Translational Research, Jun. 2013, 4(1):74-83.

Wang et al., "Enhanced bioavailability and efficiency of curcumin for the treatment of asthma by its formulation in solid lipid nanoparticles," International Journal of Nanomedicine, Jul. 2012, 7:3667-3677.

Wang et al., "Hemagglutinin (HA) Proteins from H1 and H3 Serotypes of Influenza A Viruses Require Different Antigen Designs for the Induction of Optimal Protective Antibody Responses as Studied by Codon-Optimized Ha Dna Vaccines," Journal of Virology, Sep. 2006, 80(23):11628-11637.

Wang et al., "Lymphatic-targeted cationic liposomes: A robust vaccine adjuvant for promoting long-term immunological memory," Vaccine, Aug. 2014, 32(42):5475-5483.

Wang et al., "Purification of the messenger ribonucleic acid for the lipoprotein of the Escherichia coli outer membrane," Biochemistry, Oct. 1979, 18(20):4270-4277.

Wang et al., "Structure-based development of human antibody cocktails against SARS-CoV-2," Cell Research, Jan. 2021, 31(1):101-103.

Weaver, "Post-transcriptional events II: capping and polyadenylation," Molecular Biology, 1999, Chapter 15, 38 pages.

Weber et al., "Individualised neoantigen therapy mRNA-4157 (V940) plus pembrolizumab versus pembrolizumab monotherapy in resected melanoma (KEYNOTE-942): a randomised, phase 2b study, " The Lancet, Jan. 2024, 403(10427):632-644.

Weber et al., "mRNA-4157 (V940) individualized neoantigen therapy plus pembrolizumab vs pembrolizumab in high-risk resected melanoma: clinical efficacy and correlates of response," European Society for Medical Oncology Congress, Oct. 2023, retreived from URL <https://s29.q4cdn.com/435878511/files/doc_presentations/2023/Oct. 23/esmo-2023.pdf>, 17 pages.

Wei et al., "Induction of broadly neutralizing H1N1 influenza antibodies by vaccination," Science, Aug. 2010, 329(5995): 1060-1064.

Weilhammer et al., "The use of nanolipoprotein particles to enhance the immunostimulatory properties of innate immune agonists against lethal influenza challenge," Biomaterials, Sep. 2013, 34(38):10305-10318.

Weissman et al., "HPLC Purification of In Vitro Transcribed Long RNA," Methods in Molecular Biology, Jan. 2012, Chapter 3, 969:43-54.

Who, "Communicable disease surveillance and response systems," Guide for monitoring and evaluating, 2006, 90 pages.

Who, "Serological Diagnosis Of Influenza By Microneutralization Assay," Techincal Document, Dec. 2010, 25 pages.

Who, "Who Manual on Animal Influenza Diagnosis and Surveillance," World Health Organization Global Influenza Programme, 2002, 5, 98 pages.

(56) References Cited

OTHER PUBLICATIONS

Wilson et al., "Real time measurement of PEG shedding from lipid nanoparticles in serum via NMR spectroscopy," Molecular Pharmaceutics, Jan. 2015, 12(2):386-392.
Winkler et al., "Changing the Antigen Binding Specificity by Single Point Mutations of an Anti-p24 (HIV-1) Antibody," Molecular Pharmaceutics, Oct. 2000, 165(8):4505-4514.
Wohlbold et al., "An H10N8 influenza virus vaccine strain and mouse challenge model based on the human isolate *A/Jiangxi-Donghu/346/13*," Vaccine, Jan. 2015, 33(9):1102-1106.
Woodle et al., "Sterically stabilized liposomes," Biochimica et Biophysica Acta, Aug. 1992, 1113(2): 171-199.
Wu et al., "A Sequence That Affects the Copy No. and Stability of pSW200 and ColE1," Journal of Bacteriology, May 2010, 192(14):3654-3660.
Wu et al., "Fusion Protein Vectors to Increase Protein Production and Evaluate the Immunogenicity of Genetic Vaccines," Molecular Therapy, Sep. 2000, 2(3): 288-297.
Xue et al., "Lipid-Based Nanocarriers for RNA Delivery," Current Pharmaceutical Design, Jul. 2015, 21(22):3140-3147.
Yildiz et al., "Trans-Amplifying Rna: A Journey from Alphavirus Research to Future Vaccines," Viruses, Mar. 2024, 16(4):503, 17 pages.
Ying et al., "Cancer therapy using a self-replicating RNA vaccine," Nature Medicine, Jul. 1999, 5(7):823-827.
Zavitz et al., "Dissecting the functional role of PriA protein-catalysed primosome assembly in *Escherichia coli* DNA replication," Molecular Microbiology, Dec. 1991, 5(12):2869-2873.
Ze et al., "Identification of Effective Constituents of Influenza Vaccine by Immunization with Plasmid DNAs Encoding Viral Proteins," Japanese Journal of Infectious Diseases, Dec. 2000, 53(6):219-228.
Zerboni et al., "Varicella-Zoster Virus Glycoprotein E Is a Critical Determinant of Virulence in the SCID Mouse-Human Model of Neuropathogenesis," Journal of Virology, Oct. 2010, 85(1):98-111.
Zhang et al., "Construction of Eukaryotic Expressing Plasmids Encoding HA and HA1 of Influenza A Virus and Their Transient Expression in HEK293 cells," Journal of Huazhong University of Science and Technology Medical Sciences, Mar. 2006, 26(2):225-227.
Zhao et al., "A therapeutic hepatitis B mRNA vaccine with strong immunogenicity and persistent virological suppression," Nature Partner Journals Vaccines, Feb. 2024, 9(1):22, 6 pages.
Zhao et al., "Lipid Nanoparticles for Gene Delivery," Advances in Genetics, Nov. 2014, Chapter 2, 88:13-36.
Zohra et al., "Drastic effect of nanoapatite particles on liposome-mediated mRNA delivery to mammalian cells," Analytical Biochemistry, Jul. 2005, 345(1):164-166.
Zou et al., "Lipid-mediated delivery of RNA is more efficient than delivery of DNA in non-dividing cells," International Journal of Pharmaceutics, Jan. 2010, 389(1-2):232-243.
Tai et al., "A Recombinant Receptor-Binding Domain of MERS-CoV in Trimeric Form Protects Human Dipeptidyl Peptidase 4 (hDPIP4) Transgenic Mice from MERS-CoV Infection," Virology, 2016, 499:375-382.
Wang et al., "Subunit Vaccines Against Emerging Pathogenic Human Coronaviruses, " Frontiers in Microbiology, 2020, 11:298, 19 pages.
Chen et al., "Potential for developing a SARS-CoV receptor binding domain (RBD) recombinant protein as a heterologous human vaccine against coronavirus infectious disease (COVID)-19," Human Vaccines & Immunotherapeutics, Jun. 2020, 16(6):1239-1242.
Cho et al., "Development of Middle East respiratory syndrome coronavirus vaccines—advances and challenges," Human Vaccines & Immunotherapeutics, Feb. 2018, 14(2):304-313.
U.S. Appl. No. 18/282,097, filed Sep. 14, 2023, Stewart-Jones.

* cited by examiner

```
A ------------------------------------------------------------ 0
B ------------------------------------------------------------ 0
C mfvflvllplvssQCVNLTTRTQLPPAYTNSFTRGVYYPDKVFRSSVLHSTQDLFLPFFS 60
D mfvflvllplvssQCVNLTTRTQLPPAYTNSFTRGVYYPDKVFRSSVLHSTQDLFLPFFS 60
E mfvflvllplvssQCVNLTTRTQLPPAYTNSFTRGVYYPDKVFRSSVLHSTQDLFLPFFS 60
F mfvflvllplvssQCVNLTTRTQLPPAYTNSFTRGVYYPDKVFRSSVLHSTQDLFLPFFS 60

A ------------------------------------------------------------ 0
B ------------------------------------------------------------ 0
C NVTWFHAIHVSGTNGTKRFDNPVLPFNDGVYFASTEKSNIIRGWIFGTTLDSKTQSLLIV 120
D NVTWFHAIHVSGTNGTKRFDNPVLPFNDGVYFASTEKSNIIRGWIFGTTLDSKTQSLLIV 120
E NVTWFHAIHVSGTNGTKRFDNPVLPFNDGVYFASTEKSNIIRGWIFGTTLDSKTQSLLIV 120
F NVTWFHAIHVSGTNGTKRFDNPVLPFNDGVYFASTEKSNIIRGWIFGTTLDSKTQSLLIV 120

A ------------------------------------------------------------ 0
B ------------------------------------------------------------ 0
C NNATNVVIKVCEFQFCNDPFLGVYYHKNNKSWMESEFRVYSSANNCTFEYVSQPFLMDLE 180
D NNATNVVIKVCEFQFCNDPFLGVYYHKNNKSWMESEFRVYSSANNCTFEYVSQPFLMDLE 180
E NNATNVVIKVCEFQFCNDPFLGVYYHKNNKSWMESEFRVYSSANNCTFEYVSQPFLMDLE 180
F NNATNVVIKVCEFQFCNDPFLGVYYHKNNKSWMESEFRVYSSANNCTFEYVSQPFLMDLE 180

A ------------------------------------------------------------ 0
B ------------------------------------------------------------ 0
C GKQGNFKNLREFVFKNIDGYFKIYSKHTPINLVRDLPQGFSALEPLVDLPIGINITRFQT 240
D GKQGNFKNLREFVFKNIDGYFKIYSKHTPINLVRDLPQGFSALEPLVDLPIGINITRFQT 240
E GKQGNFKNLREFVFKNIDGYFKIYSKHTPINLVRDLPQGFSALEPLVDLPIGINITRFQT 240
F GKQGNFKNLREFVFKNIDGYFKIYSKHTPINLVRDLPQGFSALEPLVDLPIGINITRFQT 240

A -------------------------------------------mysmqlascvtltlvll 17
B -------------------------------------------mysmqlascvtltlvll 17
C LLALHRSYLTPGDSSSGWTAGAAAYYVGYLQPRTFLLKYNENGTITDAVDSgggsILAIY 300
D LLALHRSYLTPGDSSSGWTAGAAAYYVGYLQPRTFLLKYNENGTITDAVDgggsggg--- 300
E LLALHRSYLTPGDSSSGWTAGAAAYYVGYLQPRTFLLKYNENGTITDAVDgggsggg--- 300
F LLALHRSYLTPGDSSSGWTAGAAAYYVGYLQPRTFLLKYNENGTITDAVDgggsggg--- 300

A vnsQPNITNLCPFGEVFNATRFASVYAWNRKRISNCVADYSVLYNSASFSTFKCYGVSPT 77
B vnsQPNITNLCPFGEVFNATRFASVYAWNRKRISNCVADYSVLYNSASFSTFKCYGVSPT 77
C STVASSLVLLVSLGAISF------------------------------------------ 318
D ----PNITNLCPFGEVFNATRFASVYAWNRKRISNCVADYSVLYNSASFSTFKCYGVSPT 353
E ----PNITNLCPFGEVFNATRFASVYAWNRKRISNCVADYSVLYNSASFSTFKCYGVSPT 353
F ----PNITNLCPFGEVFNATRFASVYAWNRKRISNCVADYSVLYNSASFSTFKCYGVSPT 353

A KLNDLCFTNVYADSFVIRGDEVRQIAPGQTGKIADYNYKLPDDFTGCVIAWNSNNLDSKV 137
B KLNDLCFTNVYADSFVIRGDEVRQIAPGQTGKIADYNYKLPDDFTGCVIAWNSNNLDSKV 137
C ------------------------------------------------------------ 318
D KLNDLCFTNVYADSFVIRGDEVRQIAPGQTGKIADYNYKLPDDFTGCVIAWNSNNLDSKV 413
E KLNDLCFTNVYADSFVIRGDEVRQIAPGQTGKIADYNYKLPDDFTGCVIAWNSNNLDSKV 413
F KLNDLCFTNVYADSFVIRGDEVRQIAPGQTGKIADYNYKLPDDFTGCVIAWNSNNLDSKV 413
```

*FIG. 3*

A GGNYNYLYRLFRKSNLKPFERDISTEIYQAGSTPCNGVEGFNCYFPLQSYGFQPTNGVGY 197
B GGNYNYLYRLFRKSNLKPFERDISTEIYQAGSTPCNGVEGFNCYFPLQSYGFQPTNGVGY 197
C ------------------------------------------------------------ 318
D GGNYNYLYRLFRKSNLKPFERDISTEIYQAGSTPCNGVEGFNCYFPLQSYGFQPTNGVGY 473
E GGNYNYLYRLFRKSNLKPFERDISTEIYQAGSTPCNGVEGFNCYFPLQSYGFQPTNGVGY 473
F GGNYNYLYRLFRKSNLKPFERDISTEIYQAGSTPCNGVEGFNCYFPLQSYGFQPTNGVGY 473

A QPYRVVVLSFELLHAPATVCGPK------------------------------------- 220
B QPYRVVVLSFELLHAPATVCGPK*sgggsILAIYSTVASSLVLLVSLGAISF*---------- 248
C ------------------------------------------------------------ 318
D QPYRVVVLSFELLHAPATVCGPKsgggs*ILAIYSTVASSLVLLVSLGAISFkrqykdmms* 533
E *QPYRVVVLSFELLHAPATVCGPK*sgggs*ILAIYSTVASSLVLLVSLGAISF*--------- 524
F QPYRVVVLSFELLHAPATVCGPKsgggs*ILAIYSTVASSLVLLVSLGAISF*kkkkrprns 533

A -------------------------------------------------- 220 SEQ ID NO: 62
B -------------------------------------------------- 248 SEQ ID NO: 77
C -------------------------------------------------- 318 SEQ ID NO: 47
D eqq-ppqaepq--------------------------------------- 543 SEQ ID NO: 98
E -------------------------------------------------- 524 SEQ ID NO: 92
F ykcgtntmereeseqtkkrekihipersdeaqrvfkssktsscdksdtcf 583 SEQ ID NO: 95

*Lowercase* – signal peptide
*UPPERCASE* – NTD
UPPERCASE – RBD
lowercase – linker
*UPPERCASE* – TM domain
lowercase – CD86
lowercase – CD11B

*FIG. 3 (continued)*

G mfvflvllplvssQCVNLTTRTQLPPAYTNSFTRGVYYPDKVFRSSVLHSTQDLFLPFFS 60
H mfvflvllplvssQCVNLTTRTQLPPAYTNSFTRGVYYPDKVCRSSVLHSTQDLFLPFFS 60
I mfvflvllplvssQCVNLTTRTQLPPAYTNSFTRGVYYPDKVFRSSVLHSTQDLFLPFFS 60
J mfvflvllplvssQCVNLTTRTQLPPAYTNSFTRGVYYPDKVFRSSVLHSTQDLFLPFFS 60
K mfvflvllplvssQCVNLTTRTQLPPAYTNSFTRGVYYPDKVFRSSVLHSTQDLFLPFFS 60
L mfvflvllplvssQCVNLTTRTQLPPAYTNSFTRGVYYPDKVFRSSVLHSTQDLFLPFFS 60
**************************************** ***************

G NVTWFHAIHVSGTNGTKRFDNPVLPFNDGVYFASTEKSNIIRGWIFGTTLDSKTQSLLIV 120
H NVTWFHAIHVSGTNGTKRFDNPVLPFNDGVYFASTEKSNIIRGWIFGTTLDSKTQSLLIV 120
I NVTWFHAIHVSGTNGTKRFDNPVLPFNDGVYFASTEKSNIIRGWIFGTTLDSKTQSLLIV 120
J NVTWFHAIHVSGTNGTKRFDNPVLPFNDGVYFASTEKSNIIRGWIFGTTLDSKTQSLLIV 120
K NVTWFHAIHVSGTNGTKRFDNPVLPFNDGVYFASTEKSNIIRGWIFGTTLDSKTQSLLIV 120
L NVTWFHAIHVSGTNGTKRFDNPVLPFNDGVYFASTEKSNIIRGWIFGTTLDSKTQSLLIV 120
************************************************************

G NNATNVVIKVCEFQFCNDPFLGVYYHKNNKSWMESEFRVYSSANNCTFEYVSQPFLMDLE 180
H NNATNVVIKVCEFQFCNDPFLGVYYHKNNKSWMESEFRVYSSANNCTFEYVSQPFLMDLE 180
I NNATNVVIKVCEFQFCNDPFLGVYYHKNNKSWMESEFRVYSSANNCTFEYVSQPFLMDLE 180
J NNATNVVIKVCEFQFCNDPFLGVYYHKNNKSWMESEFRVYSSANNCTFEYVSQPFLMDLE 180
K NNATNVVIKVCEFQFCNDPFLGVYYHKNNKSWMESEFRVYSSANNCTFEYVSQPFLMDLE 180
L NNATNVVIKVCEFQFCNDPFLGVYYHKNNKSWMESEFRVYSSANNCTFEYVSQPFLMDLE 180
************************************************************

G GKQGNFKNLREFVFKNIDGYFKIYSKHTPINLVRDLPQGFSALEPLVDLPIGINITRFQT 240
H GKQGNFKNLREFVFKNIDGYFKIYSKHTPINLVRDLPQGFSALEPLVDLPIGINITRFQT 240
I GKQGNFKNLREFVFKNIDGYFKIYSKHTPINLVRDLPQGFSALEPLVDLPIGINITRFQT 240
J GKQGNFKNLREFVFKNIDGYFKIYSKHTPINLVRDLPQGFSALEPLVDLPIGINITRFQT 240
K GKQGNFKNLREFVFKNIDGYFKIYSKHTPINLVRDLPQGFSALEPLVDLPIGINITRFQT 240
L GKQGNFKNLREFVFKNIDGYFKIYSKHTPINLVRDLPQGFSALEPLVDLPIGINITRFQT 240
************************************************************

G LLALHRSYLTPGDSSSGWTAGAAAYYVGYLQPRTFLLKYNENGTITDAVDCALDPLSETK 300
H LLALHRSYLTPGDSSSGWTAGAAAYYVGYLQPRTFLLKYNENGTITDAVDCALDPLSETK 300
I LLALHRSYLTPGDSSSGWTAGAAAYYVGYLQPRTFLLKYNENGTITDAVDCALDPLSETK 300
J LLALHRSYLTPGDSSSGWTAGAAAYYVGYLQPRTFLLKYNENGTITDAVDCALDPLSETK 300
K LLALHRSYLTPGDSSSGWTAGAAAYYVGYLQPRTFLLKYNENGTITDAVDCALDPLSETK 300
L LLALHRSYLTPGDSSSGWTAGAAAYYVGYLQPRTFLLKYNENGTITDAVDCALDPLSETK 300
************************************************************

G CTLKSFTVgsgggsgggsgggsgggsggQPTESIVRFPNITNLCPFGEVFNATRFASVYA 360
H CTLKSFTVgsgggsgggsgggsgggsggQPTESIVRFPNITNLCPFGEVFNATRFASVYA 360
I CTLKSFTVEKGIYQ--------TSNFRVQPTESIVRFPNITNLCPFGEVFNATRFASVYA 352
J CTLKSFTVEKGIYQ--------TSNFRVQPTESIVRFPNITNLCPFGEVFNATRFASVYA 352
K CTLKSFTVEKGIYQ--------TSNFRVQPTESIVRFPNITNLCPFGEVFNATRFASVYA 352
L CTLKSFTVEKGIYQ--------TSNFRVQPTESIVRFPNITNLCPFGEVFNATRFASVYA 352
******** .*  .          ..   ********************************

FIG. 5

```
G WNRKRISNCVADYSVLYNSASFSTFKCYGVSPTKLNDLCFTNVYADSFVIRGDEVRQIAP 420
H WNRKRISNCVADYSVLYNSASFSTFKCYGVSPTKLNDLCFTNVYADSFVIRGDEVRQIAP 420
I WNRKRISNCVADYSVLYNSASFSTFKCYGVSPTKLNDLCFTNVYADSFVIRGDEVRQIAP 412
J WNRKRISNCVADYSVLYNSASFSTFKCYGVSPTKLNDLCFTNVYADSFVIRGDEVRQIAP 412
K WNRKRISNCVADYSVLYNSASFSTFKCYGVSPTKLNDLCFTNVYADSFVIRGDEVRQIAP 412
L WNRKRISNCVADYSVLYNSASFSTFKCYGVSPTKLNDLCFTNVYADSFVIRGDEVRQIAP 412
  ************************************************************

G GQTGKIADYNYKLPDDFTGCVIAWNSNNLDSKVGGNYNYLYRLFRKSNLKPFERDISTEI 480
H GQTGKIADYNYKLPDDFTGCVIAWNSNNLDSKVGGNYNYLYRLFRKSNLKPFERDISTEI 480
I GQTGKIADYNYKLPDDFTGCVIAWNSNNLDSKVGGNYNYLYRLFRKSNLKPFERDISTEI 472
J GQTGKIADYNYKLPDDFTGCVIAWNSNNLDSKVGGNYNYLYRLFRKSNLKPFERDISTEI 472
K GQTGKIADYNYKLPDDFTGCVIAWNSNNLDSKVGGNYNYLYRLFRKSNLKPFERDISTEI 472
L GQTGKIADYNYKLPDDFTGCVIAWNSNNLDSKVGGNYNYLYRLFRKSNLKPFERDISTEI 472
  ************************************************************

G YQAGSTPCNGVEGFNCYFPLQSYGFQPTNGVGYQPYRVVVLSFELLHAPATVCGPKKSTN 540
H YQAGSTPCNGVEGFNCYFPLQSYGFQPTNGVGYQPYRVVVLSFELLHAPATVCGPKKSTN 540
I YQAGSTPCNGVEGFNCYFPLQSYGFQPTNGVGYQPYRVVVLSFELLHAPATVCGPKKST- 531
J YQAGSTPCNGVEGFNCYFPLQSYGFQPTNGVGYQPYRVVVLSFELLHAPATVCGPKKSTN 532
K YQAGSTPCNGVEGFNCYFPLQSYGFQPTNGVGYQPYRVVVLSFELLHAPATVCGPKKSTN 532
L YQAGSTPCNGVEGFNCYFPLQSYGFQPTNGVGYQPYRVVVLSFELLHAPATVCGPKKSTN 532
*********************************************************

G LVKNKCVNFNFNGLTGTGVLTESNKKFLPFQQFGRDIADTTDAVRDPQTLEILDITPCSF 600
H LVKNKCVNFNFNGLTGTGVLTESNKKFLPFCQFGRDIADTTDAVRDPQTLEILDITPCSF 600
I ------------------------------------------------------------ 531
J LVKNKCVNFNFNGLTGTGVLTESNKKFLPFQQFGRDIADTTDAVRDPQTLEILDITPCSF 592
K LVKNKCVNFNFNGLTGTGVLTESNKKFLPFQQFGRDIADTTDAVRDPQTLEILDITPCSF 592
L LVKNKCVNFNFNGLTGTGVLTESNKKFLPFQQFGRDIADTTDAVRDPQTLEILDITPCSF 592

G GG---------------------------------------------------------- 602
H GG---------------------------------------------------------- 602
I ------------------------------------------------------------ 531
J GG---------------------------------------------------------- 594
K GGVSVITPGTNTSNQVAVLYQDVNCTEVPVAIHADQLTPTWRVYSTGSNVFQTRAGCLIG 652
L GGVSVITPGTNTSNQVAVLYQDVNCTEVPVAIHADQLTPTWRVYSTGSNVFQTRAGCLIG 652

G ---------------------------sgggsILAIYSTVASSLVLLVSLGAISF 630 SEQ ID NO: 26
H ---------------------------sgggsILAIYSTVASSLVLLVSLGAISF 630 SEQ ID NO: 29
I ---------------------------sgggsILAIYSTVASSLVLLVSLGAISF 559 SEQ ID NO: 20
J ---------------------------sgggsILAIYSTVASSLVLLVSLGAISF 622 SEQ ID NO: 23
K AEHVNNSYECDIPIGAGICASYQTQTNS--------------------------- 680 SEQ ID NO: 5
L AEHVNNSYECDIPIGAGICASYQTQTNsgggsILAIYSTVASSLVLLVSLGAISF 707 SEQ ID NO: 17
                            *
```

*Lowercase* – signal peptide
*UPPERCASE* – NTD
UPPERCASE – RBD
lowercase – linker
<u>*UPPERCASE*</u> – TM domain G = S1-594-PolyG-TM
H = S1-594-PolyG-DS-TM
I = S1-531-TM
J = S1-594-TM
K = Soluble S1 Subunit
L = S1-666-TM

*FIG. 5 (continued)*

Serum IgG1 and IgG2a Titers at Day 36

SEQUENCE LISTING

<160> NUMBER OF SEQ ID NOS: 152

<210> SEQ ID NO 1
<211> LENGTH: 2216
<212> TYPE: RNA
<213> ORGANISM: Artificial Sequence
<220> FEATURE:
<223> OTHER INFORMATION: Synthetic

<400> SEQUENCE: 1
gggaaauaag agagaaaaga agaguaagaa gaaauauaag accccggcgc cgccaccaug 60
uucguguucc uggugcugcu gccccuggug agcagccagu gcgugaaccu gaccacccgg 120
acccagcugc caccagccua caccaacagc uucacccggg gcgucuacua ccccgacaag 180
guguuccgga gcagcguccu gcacagcacc caggaccugu uccugcccuu cuucagcaac 240
gugaccuggu uccacgccau ccacgugagc ggcaccaacg gcaccaagcg guucgacaac 300
cccgugcugc ccuucaacga cggcguguac uucgccagca ccgagaagag caacaucauc 360
cggggcugga ucuucggcac cacccuggac agcaagaccc agagccugcu gaucgugaau 420
aacgccacca acguggugau caaggugugc gaguuccagu ucugcaacga ccccuuccug 480
ggcguguacu accacaagaa caacaagagc uggauggaga gcgaguuccg gguguacagc 540
agcgccaaca acugcaccuu cgaguacgug agccagcccu uccugaugga ccuggagggc 600
aagcagggca acuucaagaa ccugcgggag uucguguuca agaacaucga cggcuacuuc 660
aagaucuaca gcaagcacac cccaaucaac cuggugcggg aucugcccca gggcuucuca 720
gcccuggagc cccuggugga ccugcccauc ggcaucaaca ucacccgguu ccagacccug 780
cuggcccugc accggagcua ccugacccca ggcgacagca gcagcgggug gacagcaggc 840
gcggcugcuu acuacguggg cuaccugcag ccccggaccu uccugcugaa guacaacgag 900
aacggcacca ucaccgacgc cguggacugc gcccuggacc cucugagcga gaccaagugc 960
acccugaaga gcuucaccgu ggagaagggc aucuaccaga ccagcaacuu ccgggugcag 1020
cccaccgaga gcaucgugcg guuccccaac aucaccaacc ugugccccuu cggcgaggug 1080
uucaacgcca cccgguucgc cagcguguac gccuggaacc ggaagcggau cagcaacugc 1140
guggccgacu acagcgugcu guacaacagc gccagcuuca gcaccuucaa gugcuacggc 1200
gugagcccca ccaagcugaa cgaccugugc uucaccaacg uguacgccga cagcuucgug 1260
auccguggcg acgaggugcg gcagaucgca cccggccaga caggcaagau cgccgacuac 1320
aacuacaagc ugcccgacga cuucaccggc ugcgugaucg ccuggaacag caacaaccuc 1380
gacagcaagg ugggcggcaa cuacaacuac cuguaccggc uguuccggaa gagcaaccug 1440
aagcccuucg agcgggacau cagcaccgag aucuaccaag ccggcuccac cccuugcaac 1500
ggcguggagg gcuucaacug cuacuucccu cugcagagcu acggcuucca gcccaccaac 1560
ggcgugggcu accagcccua ccggguggug gugcugagcu ucgagcugcu gcacgcccca 1620
gccaccgugu guggccccaa gaagagcacc aaccugguga agaacaagug cgugaacuuc 1680
aacuucaacg gccuuaccgg caccggcgug cugaccgaga gcaacaagaa auuccugccc 1740
uuucagcagu ucggccggga caucgccgac accaccgacg cugugcggga uccccagacc 1800
cuggagaucc uggacaucac cccuugcagc uucggcggcg ugagcgugau caccccaggc 1860
accaacacca gcaaccaggu ggccgugcug uaccaggacg ugaacugcac cgaggugccc 1920
guggccaucc acgccgacca gcugacaccc accuggcggg ucuacagcac cggcagcaac 1980
guguuccaga cccgggccgg uugccugauc ggcgccgagc acgugaacaa cagcuacgag 2040
ugcgacaucc ccaucggcgc cggcaucugu gccagcuacc agacccagac caauucauga 2100
uaauaggcug gagccucggu ggccuagcuu cuugccccuu gggccucccc ccagccccuc 2160
cuccccuucc ugcacccgua cccccguggu cuuugaauaa agucugagug ggcggc 2216

<210> SEQ ID NO 2
<211> LENGTH: 57
<212> TYPE: RNA
<213> ORGANISM: Artificial Sequence
<220> FEATURE:
<223> OTHER INFORMATION: Synthetic

<400> SEQUENCE: 2
gggaaauaag agagaaaaga agaguaagaa gaaauauaag accccggcgc cgccacc 57

<210> SEQ ID NO 3
<211> LENGTH: 2040
<212> TYPE: RNA
<213> ORGANISM: Artificial Sequence
<220> FEATURE:
<223> OTHER INFORMATION: Synthetic

<400> SEQUENCE: 3
auguucgugu uccuggugcu gcugccccug gugagcagcc agugcgugaa ccugaccacc 60
cggacccagc ugccaccagc cuacaccaac agcuucaccc ggggcgucua cuaccccgac 120
aagguguucc ggagcagcgu ccugcacagc acccaggacc uguuccugcc cuucuucagc 180
aacgugaccu gguuccacgc cauccacgug agcggcacca acggcaccaa gcgguucgac 240
aaccccgugc ugcccuucaa cgacggcgug uacuucgcca gcaccgagaa gagcaacauc 300
auccggggcu ggaucuucgg caccacccug gacagcaaga cccagagccu gcugaucgug 360
aauaacgcca ccaacguggu gaucaaggug ugcgaguucc aguucugcaa cgaccccuuc 420
cugggcgugu acuaccacaa gaacaacaag agcuggaugg agagcgaguu ccggguguac 480
agcagcgcca acaacugcac cuucgaguac gugagccagc ccuuccugau ggaccuggag 540
ggcaagcagg gcaacuucaa gaaccugcgg gaguucgugu ucaagaacau cgacggcuac 600
uucaagaucu acagcaagca caccccaauc aaccuggugc gggaucugcc ccagggcuuc 660
ucagcccugg agccccuggu ggaccugccc aucggcauca acaucacccg guuccagacc 720
cugcuggccc ugcaccggag cuaccugacc ccaggcgaca gcagcagcgg guggacagca 780
ggcgcggcug cuuacuacgu gggcuaccug cagccccgga ccuuccugcu gaaguacaac 840
gagaacggca ccaucaccga cgccguggac ugcgcccugg acccucugag cgagaccaag 900
ugcacccuga agagcuucac cguggagaag ggcaucuacc agaccagcaa cuuccgggug 960
cagcccaccg agagcaucgu gcgguucccc aacaucacca accugugccc cuucggcgag 1020
guguucaacg ccacccgguu cgccagcgug uacgccugga accggaagcg gaucagcaac 1080
ugcguggccg acuacagcgu gcuguacaac agcgccagcu ucagcaccuu caagugcuac 1140
ggcgugagcc ccaccaagcu gaacgaccug ugcuucacca acguguacgc cgacagcuuc 1200
gugauccgug gcgacgaggu gcggcagauc gcacccggcc agacaggcaa gaucgccgac 1260
uacaacuaca agcugcccga cgacuucacc ggcugcguga ucgccuggaa cagcaacaac 1320
cucgacagca aggugggcgg caacuacaac uaccuguacc ggcuguuccg gaagagcaac 1380
cugaagcccu ucgagcggga caucagcacc gagaucuacc aagccggcuc caccccuugc 1440
aacggcgugg agggcuucaa cugcuacuuc ccucugcaga gcuacggcuu ccagcccacc 1500

-continued aacggcgugg gcuaccagcc cuaccgggug guggugcuga gcuucgagcu gcugcacgcc 1560
ccagccaccg uguguggccc caagaagagc accaaccugg ugaagaacaa gugcgugaac 1620
uucaacuuca acggccuuac cggcaccggc gugcugaccg agagcaacaa gaaauuccug 1680
cccuuucagc aguucggccg ggacaucgcc gacaccaccg acgcugugcg ggaucccag 1740 acccuggaga uccuggacau caccccuugc agcuucggcg gcgugagcgu gaucacccca 1800
ggcaccaaca ccagcaacca gguggccgug cuguaccagg acgugaacug caccgaggug 1860
cccguggcca uccacgccga ccagcugaca cccaccuggc gggucuacag caccggcagc 1920
aacguguucc agacccgggc cgguugccug aucggcgccg agcacgugaa caacagcuac 1980
gagugcgaca uccccaucgg cgccggcauc ugugccagcu accagaccca gaccaauuca 2040

<210> SEQ ID NO 4
<211> LENGTH: 119
<212> TYPE: RNA
<213> ORGANISM: Artificial Sequence
<220> FEATURE:
<223> OTHER INFORMATION: Synthetic

<400> SEQUENCE: 4
ugauaauagg cuggagccuc gguggccuag cuucuugccc cuugggccuc cccccagccc 60
cuccuccccu uccugcaccc guacccccgu ggucuuugaa uaaagucuga gugggcggc 119

<210> SEQ ID NO 5
<211> LENGTH: 680
<212> TYPE: PRT
<213> ORGANISM: Artificial Sequence
<220> FEATURE:
<223> OTHER INFORMATION: Synthetic

<400> SEQUENCE: 5

Met Phe Val Phe Leu Val Leu Leu Pro Leu Val Ser Ser Gln Cys Val
1 5 10 15

Asn Leu Thr Thr Arg Thr Gln Leu Pro Pro Ala Tyr Thr Asn Ser Phe
20 25 30

Thr Arg Gly Val Tyr Tyr Pro Asp Lys Val Phe Arg Ser Ser Val Leu
35 40 45

His Ser Thr Gln Asp Leu Phe Leu Pro Phe Phe Ser Asn Val Thr Trp
50 55 60

Phe His Ala Ile His Val Ser Gly Thr Asn Gly Thr Lys Arg Phe Asp
65 70 75 80

Asn Pro Val Leu Pro Phe Asn Asp Gly Val Tyr Phe Ala Ser Thr Glu
85 90 95

Lys Ser Asn Ile Ile Arg Gly Trp Ile Phe Gly Thr Thr Leu Asp Ser
100 105 110

Lys Thr Gln Ser Leu Leu Ile Val Asn Asn Ala Thr Asn Val Val Ile
115 120 125

Lys Val Cys Glu Phe Gln Phe Cys Asn Asp Pro Phe Leu Gly Val Tyr
130 135 140

Tyr His Lys Asn Asn Lys Ser Trp Met Glu Ser Glu Phe Arg Val Tyr
145 150 155 160

Ser Ser Ala Asn Asn Cys Thr Phe Glu Tyr Val Ser Gln Pro Phe Leu
165 170 175

Met Asp Leu Glu Gly Lys Gln Gly Asn Phe Lys Asn Leu Arg Glu Phe
180 185 190

Val Phe Lys Asn Ile Asp Gly Tyr Phe Lys Ile Tyr Ser Lys His Thr

```
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620
```

```
His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser
        675                 680


<210> SEQ ID NO 6
<211> LENGTH: 2729
<212> TYPE: RNA
<213> ORGANISM: Artificial Sequence
<220> FEATURE:
<223> OTHER INFORMATION: Synthetic

<400> SEQUENCE: 6

gggaaauaag agagaaaaga agaguaagaa gaaauauaag accccggcgc cgccaccaug      60

uucguguucc uggugcugcu gccccuggug agcagccagu gcgugaaccu gaccacccgg     120

acccagcugc caccagccua caccaacagc uucacccggg gcgucuacua ccccgacaag     180

guguuccgga gcagcguccu gcacagcacc caggaccugu uccugcccuu cuucagcaac     240

gugaccuggu uccacgccau ccacgugagc ggcaccaacg gcaccaagcg guucgacaac     300

cccgugcugc ccuucaacga cggcguguac uucgccagca ccgagaagag caacaucauc     360

cggggcugga ucuucggcac cacccuggac agcaagaccc agagccugcu gaucgugaau     420

aacgccacca acguggugau caaggugugc gaguuccagu ucugcaacga ccccuuccug     480

ggcguguacu accacaagaa caacaagagc uggauggaga gcgaguuccg gguguacagc     540

agcgccaaca acugcaccuu cgaguacgug agccagcccu uccugaugga ccuggagggc     600

aagcagggca acuucaagaa ccugcgggag uucguguuca agaacaucga cggcuacuuc     660

aagaucuaca gcaagcacac cccaaucaac cuggugcggg aucugcccca gggcuucuca     720

gcccuggagc cccuggugga ccugcccauc ggcaucaaca ucacccgguu ccagacccug     780

cuggcccugc accggagcua ccugacccca ggcgacagca gcagcgggug gacagcaggc     840

gcggcugcuu acuacguggg cuaccugcag ccccggaccu uccugcugaa guacaacgag     900

aacggcacca ucaccgacgc cguggacugc gcccuggacc cucugagcga gaccaagugc     960

acccugaaga gcuucaccgu ggagaagggc aucuaccaga ccagcaacuu ccgggugcag    1020

cccaccgaga gcaucgugcg guuccccaac aucaccaacc ugugccccuu cggcgaggug    1080

uucaacgcca cccgguucgc cagcguguac gccuggaacc ggaagcggau cagcaacugc    1140

guggccgacu acagcgugcu guacaacagc gccagcuuca gcaccuucaa gugcuacggc    1200

gugagcccca ccaagcugaa cgaccugugc uucaccaacg uguacgccga cagcuucgug    1260

auccguggcg acgaggugcg gcagaucgca cccggccaga caggcaagau cgccgacuac    1320

aacuacaagc ugcccgacga cuucaccggc ugcgugaucg ccuggaacag caacaaccuc    1380

gacagcaagg ugggcggcaa cuacaacuac cuguaccggc uguuccggaa gagcaaccug    1440

aagcccuucg agcgggacau cagcaccgag aucuaccaag ccggcuccac cccuugcaac    1500

ggcguggagg gcuucaacug cuacuucccu cugcagagcu acggcuucca gcccaccaac    1560

ggcgugggcu accagcccua ccggguggug gugcugagcu ucgagcugcu gcacgcccca    1620

gccaccgugu guggccccaa gaagagcacc aaccugguga agaacaagug cgugaacuuc    1680
```

aacuucaacg gccuuaccgg caccggcgug cugaccgaga gcaacaagaa auuccugccc 1740
uuucagcagu ucggccggga caucgccgac accaccgacg cugugcggga uccccagacc 1800
cuggagaucc uggacaucac ccuuugcagc uucggcggcg ugagcgugau caccccaggc 1860
accaacacca gcaaccaggu ggccgugcug uaccaggacg ugaacugcac cgaggugccc 1920
guggccaucc acgccgacca gcugacaccc accuggcggg ucuacagcac cggcagcaac 1980
guguuccaga cccgggccgg uugccugauc ggcgccgagc acgugaacaa cagcuacgag 2040
ugcgacaucc ccaucggcgc cggcaucugu gccagcuacc agacccagac caauucagga 2100
ggaggcagcg gcggcgauau caucaagcuu cugaacgagc aaguuaacaa ggaaaugcag 2160
agcaguaauc ucuacaugag caugagcagc uggugcuaca cccacucccu ggacggagca 2220
ggccucuucc uguucgacca cgcagccgag gaguacgagc acgcuaagaa guugaucauu 2280
uucuugaacg agaacaacgu gcccgugcag cuaacgucaa ucagcgcacc ugagcacaag 2340
uucgagggcc ugacccagau cuuccagaag gccuacgaac acgaacagca caucuccgag 2400
agcaucaaca auauugugga ucacgcuauc aaguccaagg accacgcuac cuucaacuuc 2460
cugcaguggu acguggccga gcaacaugag gaggaggugc uguucaagga cauccuggac 2520
aagaucgagc ugaucgguaa ugagaaucac ggccuguacc uggccgacca guacgugaag 2580
ggcaucgcca agagccggaa gucaggcuca ugauaauagg cuggagccuc gguggccuag 2640
cuucuugccc cuugggccuc cccccagccc cuccuccccu uccugcaccc guacccccgu 2700
ggucuuugaa uaaagucuga gugggcggc 2729

<210> SEQ ID NO 7
<211> LENGTH: 2553
<212> TYPE: RNA
<213> ORGANISM: Artificial Sequence
<220> FEATURE:
<223> OTHER INFORMATION: Synthetic

<400> SEQUENCE: 7
auguucgugu uccuggugcu gcugccccug gugagcagcc agugcgugaa ccugaccacc 60
cggacccagc ugccaccagc cuacaccaac agcuucaccc ggggcgucua cuaccccgac 120
aagguguucc ggagcagcgu ccugcacagc acccaggacc uguuccugcc cuucuucagc 180
aacgugaccu gguuccacgc cauccacgug agcggcacca acggcaccaa gcgguucgac 240
aaccccgugc ugcccuucaa cgacggcgug uacuucgcca gcaccgagaa gagcaacauc 300
auccggggcu ggaucuucgg caccacccug gacagcaaga cccagagccu gcugaucgug 360
aauaacgcca ccaacguggu gaucaaggug ugcgaguucc aguucugcaa cgaccccuuc 420
cugggcgugu acuaccacaa gaacaacaag agcuggaugg agagcgaguu ccggguguac 480
agcagcgcca acaacugcac cuucgaguac gugagccagc ccuuccugau ggaccuggag 540
ggcaagcagg gcaacuucaa gaaccugcgg gaguucgugu ucaagaacau cgacggcuac 600
uucaagaucu acagcaagca caccccaauc aaccuggugc gggaucugcc ccagggcuuc 660
ucagcccugg agccccuggu ggaccugccc aucggcauca acaucacccg guuccagacc 720
cugcuggccc ugcaccggag cuaccugacc ccaggcgaca gcagcagcgg guggacagca 780
ggcgcggcug cuuacuacgu gggcuaccug cagccccgga ccuuccugcu gaaguacaac 840
gagaacggca ccaucaccga cgccguggac ugcgcccugg acccucugag cgagaccaag 900
ugcacccuga agagcuucac cguggagaag ggcaucuacc agaccagcaa cuuccgggug 960
cagcccaccg agagcaucgu gcgguucccc aacaucacca accugugccc cuucggcgag 1020

```
guguucaacg ccacccgguu cgccagcgug uacgccugga accggaagcg gaucagcaac   1080

ugcguggccg acuacagcgu gcuguacaac agcgccagcu ucagcaccuu caagugcuac   1140

ggcgugagcc ccaccaagcu gaacgaccug ugcuucacca acguguacgc cgacagcuuc   1200

gugauccgug gcgacgaggu gcggcagauc gcacccggcc agacaggcaa gaucgccgac   1260

uacaacuaca agcugcccga cgacuucacc ggcugcguga ucgccuggaa cagcaacaac   1320

cucgacagca aggugggcgg caacuacaac uaccuguacc ggcuguuccg gaagagcaac   1380

cugaagcccu ucgagcggga caucagcacc gagaucuacc aagccggcuc caccccuugc   1440

aacggcgugg agggcuucaa cugcuacuuc ccucugcaga gcuacggcuu ccagcccacc   1500

aacggcgugg gcuaccagcc cuaccgggug guggugcuga gcuucgagcu gcugcacgcc   1560

ccagccaccg uguguggccc caagaagagc accaaccugg ugaagaacaa gugcgugaac   1620

uucaacuuca acggccuuac cggcaccggc gugcugaccg agagcaacaa gaaauuccug   1680

cccuuucagc aguucggccg ggacaucgcc gacaccaccg acgcugugcg ggaucccag   1740

acccuggaga uccuggacau caccccuugc agcuucggcg gcgugagcgu gaucacccca   1800

ggcaccaaca ccagcaacca gguggccgug cuguaccagg acgugaacug caccgaggug   1860

cccguggcca uccacgccga ccagcugaca cccaccuggc ggguc uacag caccggcagc   1920

aacguguucc agacccgggc cgguugccug aucggcgccg agcacgugaa caacagcuac   1980

gagugcgaca uccccaucgg cgccggcauc ugugccagcu accagaccca gaccaauuca   2040

ggaggaggca gcggcggcga uaucaucaag cuucugaacg agcaaguuaa caaggaaaug   2100

cagagcagua aucucuacau gagcaugagc agcuggugcu acacccacuc ccuggacgga   2160

gcaggccucu uccuguucga ccacgcagcc gaggaguacg agcacgcuaa gaaguugauc   2220

auuuucuuga acgagaacaa cgugcccgug cagcuaacgu caaucagcgc accugagcac   2280

aaguucgagg gccugaccca gaucuuccag aaggccuacg aacacgaaca gcacaucucc   2340

gagagcauca acaauauugu ggaucacgcu aucaagucca aggaccacgc uaccuucaac   2400

uuccugcagu gguacgugge cgagcaacau gaggaggagg ugcuguucaa ggacauccug   2460

gacaagaucg agcugaucgg uaaugagaau cacggccugu accuggccga ccaguacgug   2520

aagggcaucg ccaagagccg gaagucaggc uca                                2553
```

<210> SEQ ID NO 8
<211> LENGTH: 851
<212> TYPE: PRT
<213> ORGANISM: Artificial Sequence
<220> FEATURE:
<223> OTHER INFORMATION: Synthetic

<400> SEQUENCE: 8

```
Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
```

-continued

```
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
            165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
            245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
            325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
            405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
            485                 490                 495

Phe Gln Pro Thr Asn Gly Val Gly Tyr Gln Pro Tyr Arg Val Val Val
            500                 505                 510
```

```
Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Gly Gly Gly Ser Gly Gly Asp Ile
        675                 680                 685

Ile Lys Leu Leu Asn Glu Gln Val Asn Lys Glu Met Gln Ser Ser Asn
    690                 695                 700

Leu Tyr Met Ser Met Ser Ser Trp Cys Tyr Thr His Ser Leu Asp Gly
705                 710                 715                 720

Ala Gly Leu Phe Leu Phe Asp His Ala Ala Glu Glu Tyr Glu His Ala
                725                 730                 735

Lys Lys Leu Ile Ile Phe Leu Asn Glu Asn Asn Val Pro Val Gln Leu
            740                 745                 750

Thr Ser Ile Ser Ala Pro Glu His Lys Phe Glu Gly Leu Thr Gln Ile
        755                 760                 765

Phe Gln Lys Ala Tyr Glu His Glu Gln His Ile Ser Glu Ser Ile Asn
    770                 775                 780

Asn Ile Val Asp His Ala Ile Lys Ser Lys Asp His Ala Thr Phe Asn
785                 790                 795                 800

Phe Leu Gln Trp Tyr Val Ala Glu Gln His Glu Glu Glu Val Leu Phe
                805                 810                 815

Lys Asp Ile Leu Asp Lys Ile Glu Leu Ile Gly Asn Glu Asn His Gly
            820                 825                 830

Leu Tyr Leu Ala Asp Gln Tyr Val Lys Gly Ile Ala Lys Ser Arg Lys
        835                 840                 845

Ser Gly Ser
    850
```

<210> SEQ ID NO 9
<211> LENGTH: 2762
<212> TYPE: RNA
<213> ORGANISM: Artificial Sequence
<220> FEATURE:
<223> OTHER INFORMATION: Synthetic

<400> SEQUENCE: 9

```
gggaaauaag agagaaaaga agaguaagaa gaaauauaag accccggcgc cgccaccaug     60
```

-continued

```
ggcauccugc ccagcccugg caugcccgcu cugcugagcc uggugagccu gcugagcgug    120
cugcugaugg gcugcguggc ugagaccggc augcagaucu acgagggcaa gcugaccgca    180
gagggccugc gguucggcau cguggccagc cgcgccaacc acgcucuggu ggaccggcuu    240
guggagggcg cuaucgacgc caucgugaga cacggcggcc gggaagagga caucacccug    300
gugcgggugu gcggcagcug ggagauuccc gucgccgccg gagaacuggc ccggaaggag    360
gacaucgacg ccgugaucgc caucggcgug cugugcagag gcgccacgcc cagcuucgac    420
uacaucgcca gcgaggugag caagggccug gccgaccuga gccuggagcu gcggaagccc    480
aucaccuucg gcgugaucac cgccgacacc cuggagcagg ccaucgaggc cgcaggcacc    540
ugccacggca acaagggcug ggaagccgcc cugugcgcca ucgagauggc caaccuguuc    600
aagagccugc ggggcggaag uggaggcucu gguggcagcg gaggaucugg cggcggcacc    660
acccggaccc agcugccacc agccuacacc aacagcuuca cccggggcgu cuacuacccc    720
gacaaggugu uccggagcag cguccugcac agcacccagg accuguuccu gcccuucuuc    780
agcaacguga ccugguucca cgccauccac gugagcggca ccaacggcac caagcgguuc    840
gacaaccccg ugcugcccuu caacgacggc guguacuucg ccagcaccga gaagagcaac    900
aucauccggg gcuggaucuu cggcaccacc cuggacagca agacccagag ccugcugauc    960
gugaauaacg ccaccaacgu ggugaucaag gugugcgagu uccaguucug caacgacccc   1020
uuccugggcg uguacuacca caagaacaac aagagcugga uggagagcga guuccgggug   1080
uacagcagcg ccaacaacug caccuucgag uacgugagcc agcccuuccu gauggaccug   1140
gagggcaagc agggcaacuu caagaaccug cgggaguucg uguucaagaa caucgacggc   1200
uacuucaaga ucuacagcaa gcacacccca aucaaccugg ugcgggaucu gccccagggc   1260
uucucagccc uggagccccu gguggaccug cccaucggca ucaacaucac ccgguuccag   1320
acccugcugg cccugcaccg gagcuaccug accccaggcg acagcagcag cgggugggaca   1380
gcaggcgcgg cugcuuacua cgugggcuac cugcagcccc ggaccuuccu gcugaaguac   1440
aacgagaacg gcaccaucac cgacgccgug gacugcgccc uggacccucu gagcgagacc   1500
aagugcaccc ugaagagcuu caccguggag aagggcaucu accagaccag caacuuccgg   1560
gugcagccca ccgagagcau cgugcgguuc cccaacauca ccaaccugug ccccuucggc   1620
gagguguuca acgccacccg guucgccagc guguacgccu ggaaccggaa gcggaucagc   1680
aacugcgugg ccgacuacag cgugcuguac aacagcgcca gcuucagcac cuucaagugc   1740
uacggcguga gccccaccaa gcugaacgac cugugcuuca ccaacgugua cgccgacagc   1800
uucgugaucc guggcgacga ggugcggcag aucgcacccg gccagacagg caagaucgcc   1860
gacuacaacu acaagcugcc cgacgacuuc accggcugcg ugaucgccug gaacagcaac   1920
aaccucgaca gcaagguggg cggcaacuac aacuaccugu accggcuguu ccggaagagc   1980
aaccugaagc ccuucgagcg ggacaucagc accgagaucu accaagccgg cuccaccccu   2040
ugcaacggcg uggagggcuu caacugcuac uucccucugc agagcuacgg cuuccagccc   2100
accaacggcg ugggcuacca gcccuaccgg gugguggugc ugagcuucga gcugcugcac   2160
gccccagcca ccgugugugg ccccaagaag agcaccaacc uggugaagaa caagugcgug   2220
aacuucaacu ucaacggccu uaccggcacc ggcgugcuga ccgagagcaa caagaaauuc   2280
cugcccuuuc agcaguucgg ccgggacauc gccgacacca ccgacgcugu gcgggauccc   2340
cagacccugg agauccugga caucaccccu ugcagcuucg gcggcgugag cgugaucacc   2400
ccaggcacca acaccagcaa ccagguggcc gugcuguacc aggacgugaa cugcaccgag   2460
```

gugcccgugg ccauccacgc cgaccagcug acacccaccu ggcgggucua cagcaccggc 2520
agcaacgugu uccagacccg ggccgguugc cugaucggcg ccgagcacgu gaacaacagc 2580
uacgagugcg acauccccau cggcgccggc aucugugcca gcuaccagac ccagaccaau 2640
ucaugauaau aggcuggagc cucgguggcc uagcuucuug ccccuugggc cucccccag 2700 ccccuccucc ccuuccugca cccguacccc cguggucuuu gaauaaaguc ugagugggcg 2760
gc 2762

<210> SEQ ID NO 10
<211> LENGTH: 2586
<212> TYPE: RNA
<213> ORGANISM: Artificial Sequence
<220> FEATURE:
<223> OTHER INFORMATION: Synthetic

<400> SEQUENCE: 10
augggcaucc ugcccagccc uggcaugccc gcucugcuga gccuggugag ccugcugagc 60
gugcugcuga ugggcugcgu ggcugagacc ggcaugcaga ucuacgaggg caagcugacc 120
gcagagggcc ugcgguucgg caucguggcc agccgcgcca accacgcucu gguggaccgg 180
cuuguggagg gcgcuaucga cgccaucgug agacacggcg gccgggaaga ggacaucacc 240
cuggugcggg ugugcggcag cugggagauu cccgucgccg ccggagaacu ggcccggaag 300
gaggacaucg acgccgugau cgccaucggc gugcugugca gaggcgccac gcccagcuuc 360
gacuacaucg ccagcgaggu gagcaagggc cuggccgacc ugagccugga gcugcggaag 420
cccaucaccu ucggcgugau caccgccgac acccuggagc aggccaucga ggccgcaggc 480
accugccacg gcaacaaggg cugggaagcc gcccugugcg ccaucgagau ggccaaccug 540
uucaagagcc ugcggggcgg aaguggaggc ucugguggca gcggaggauc uggcggcggc 600
accacccgga cccagcugcc accagccuac accaacagcu ucacccgggg cgucuacuac 660
cccgacaagg uguuccggag cagcguccug cacagcaccc aggaccuguu ccugcccuuc 720
uucagcaacg ugaccugguu ccacgccauc cacgugagcg gcaccaacgg caccaagcgg 780
uucgacaacc ccgugcugcc cuucaacgac ggcguguacu ucgccagcac cgagaagagc 840
aacaucaucc ggggcuggau cuucggcacc acccuggaca gcaagaccca gagccugcug 900
aucgugaaua acgccaccaa cguggugauc aaggugugcg aguuccaguu cugcaacgac 960
cccuuccugg gcguguacua ccacaagaac aacaagagcu ggauggagag cgaguuccgg 1020
guguacagca gcgccaacaa cugcaccuuc gaguacguga gccagcccuu ccugauggac 1080
cuggagggca agcagggcaa cuucaagaac cugcgggagu ucguguucaa gaacaucgac 1140
ggcuacuuca agaucuacag caagcacacc ccaaucaacc uggugcggga ucugccccag 1200
ggcuucucag cccuggagcc ccugguggac cugcccaucg gcaucaacau cacccgguuc 1260
cagacccugc uggcccugca ccggagcuac cugaccccag gcgacagcag cagcgggugg 1320
acagcaggcg cggcugcuua cuacgugggc uaccugcagc cccggaccuu ccugcugaag 1380
uacaacgaga acggcaccau caccgacgcc guggacugcg cccuggaccc ucugagcgag 1440
accaagugca cccugaagag cuucaccgug gagaagggca ucuaccagac cagcaacuuc 1500
cgggugcagc ccaccgagag caucgugcgg uuccccaaca ucaccaaccu gugccccuuc 1560
ggcgaggugu ucaacgccac ccgguucgcc agcguguacg ccuggaaccg gaagcggauc 1620
agcaacugcg uggccgacua cagcgugcug uacaacagcg ccagcuucag caccuucaag 1680
ugcuacggcg ugagccccac caagcugaac gaccugugcu ucaccaacgu guacgccgac 1740
agcuucguga uccguggcga cgaggugcgg cagaucgcac ccggccagac aggcaagauc 1800
gccgacuaca acuacaagcu gcccgacgac uucaccggcu gcgugaucgc cuggaacagc 1860
aacaaccucg acagcaaggu gggcggcaac uacaacuacc uguaccggcu guuccggaag 1920
agcaaccuga agcccuucga gcgggacauc agcaccgaga ucuaccaagc cggcuccacc 1980
ccuugcaacg gcguggaggg cuucaacugc uacuucccuc ugcagagcua cggcuuccag 2040
cccaccaacg gcgugggcua ccagcccuac cgggugugg ugcugagcuu cgagcugcug 2100
cacgccccag ccaccgugug uggccccaag aagagcacca accuggugaa gaacaagugc 2160
gugaacuuca acuucaacgg ccuuaccggc accggcgugc ugaccgagag caacaagaaa 2220
uuccugcccu uucagcaguu cggccgggac aucgccgaca ccaccgacgc ugugcgggau 2280
ccccagaccc uggagauccu ggacaucacc ccuugcagcu ucggcggcgu gagcgugauc 2340
accccaggca ccaacaccag caaccaggug gccgugcugu accaggacgu gaacugcacc 2400
gaggugcccg uggccaucca cgccgaccag cugacaccca ccuggcgggu cuacagcacc 2460
ggcagcaacg uguuccagac ccgggccggu ugccugaucg gcgccgagca cgugaacaac 2520
agcuacgagu gcgacauccc caucggcgcc ggcaucugug ccagcuacca gacccagacc 2580
aauuca 2586

<210> SEQ ID NO 11
<211> LENGTH: 862
<212> TYPE: PRT
<213> ORGANISM: Artificial Sequence
<220> FEATURE:
<223> OTHER INFORMATION: Synthetic

<400> SEQUENCE: 11

Met Gly Ile Leu Pro Ser Pro Gly Met Pro Ala Leu Leu Ser Leu Val
1 5 10 15

Ser Leu Leu Ser Val Leu Leu Met Gly Cys Val Ala Glu Thr Gly Met
20 25 30

Gln Ile Tyr Glu Gly Lys Leu Thr Ala Glu Gly Leu Arg Phe Gly Ile
35 40 45

Val Ala Ser Arg Ala Asn His Ala Leu Val Asp Arg Leu Val Glu Gly
50 55 60

Ala Ile Asp Ala Ile Val Arg His Gly Gly Arg Glu Glu Asp Ile Thr
65 70 75 80

Leu Val Arg Val Cys Gly Ser Trp Glu Ile Pro Val Ala Ala Gly Glu
85 90 95

Leu Ala Arg Lys Glu Asp Ile Asp Ala Val Ile Ala Ile Gly Val Leu
100 105 110

Cys Arg Gly Ala Thr Pro Ser Phe Asp Tyr Ile Ala Ser Glu Val Ser
115 120 125

Lys Gly Leu Ala Asp Leu Ser Leu Glu Leu Arg Lys Pro Ile Thr Phe
130 135 140

Gly Val Ile Thr Ala Asp Thr Leu Glu Gln Ala Ile Glu Ala Ala Gly
145 150 155 160

Thr Cys His Gly Asn Lys Gly Trp Glu Ala Ala Leu Cys Ala Ile Glu
165 170 175

Met Ala Asn Leu Phe Lys Ser Leu Arg Gly Gly Ser Gly Gly Ser Gly
180 185 190

Gly Ser Gly Gly Ser Gly Gly Gly Thr Thr Arg Thr Gln Leu Pro Pro

-continued

```
        195                 200                 205

Ala Tyr Thr Asn Ser Phe Thr Arg Gly Val Tyr Tyr Pro Asp Lys Val
    210                 215                 220

Phe Arg Ser Ser Val Leu His Ser Thr Gln Asp Leu Phe Leu Pro Phe
225                 230                 235                 240

Phe Ser Asn Val Thr Trp Phe His Ala Ile His Val Ser Gly Thr Asn
                245                 250                 255

Gly Thr Lys Arg Phe Asp Asn Pro Val Leu Pro Phe Asn Asp Gly Val
            260                 265                 270

Tyr Phe Ala Ser Thr Glu Lys Ser Asn Ile Ile Arg Gly Trp Ile Phe
        275                 280                 285

Gly Thr Thr Leu Asp Ser Lys Thr Gln Ser Leu Leu Ile Val Asn Asn
    290                 295                 300

Ala Thr Asn Val Val Ile Lys Val Cys Glu Phe Gln Phe Cys Asn Asp
305                 310                 315                 320

Pro Phe Leu Gly Val Tyr Tyr His Lys Asn Asn Lys Ser Trp Met Glu
                325                 330                 335

Ser Glu Phe Arg Val Tyr Ser Ser Ala Asn Asn Cys Thr Phe Glu Tyr
            340                 345                 350

Val Ser Gln Pro Phe Leu Met Asp Leu Glu Gly Lys Gln Gly Asn Phe
        355                 360                 365

Lys Asn Leu Arg Glu Phe Val Phe Lys Asn Ile Asp Gly Tyr Phe Lys
    370                 375                 380

Ile Tyr Ser Lys His Thr Pro Ile Asn Leu Val Arg Asp Leu Pro Gln
385                 390                 395                 400

Gly Phe Ser Ala Leu Glu Pro Leu Val Asp Leu Pro Ile Gly Ile Asn
                405                 410                 415

Ile Thr Arg Phe Gln Thr Leu Leu Ala Leu His Arg Ser Tyr Leu Thr
            420                 425                 430

Pro Gly Asp Ser Ser Ser Gly Trp Thr Ala Gly Ala Ala Ala Tyr Tyr
        435                 440                 445

Val Gly Tyr Leu Gln Pro Arg Thr Phe Leu Leu Lys Tyr Asn Glu Asn
    450                 455                 460

Gly Thr Ile Thr Asp Ala Val Asp Cys Ala Leu Asp Pro Leu Ser Glu
465                 470                 475                 480

Thr Lys Cys Thr Leu Lys Ser Phe Thr Val Glu Lys Gly Ile Tyr Gln
                485                 490                 495

Thr Ser Asn Phe Arg Val Gln Pro Thr Glu Ser Ile Val Arg Phe Pro
            500                 505                 510

Asn Ile Thr Asn Leu Cys Pro Phe Gly Glu Val Phe Asn Ala Thr Arg
        515                 520                 525

Phe Ala Ser Val Tyr Ala Trp Asn Arg Lys Arg Ile Ser Asn Cys Val
    530                 535                 540

Ala Asp Tyr Ser Val Leu Tyr Asn Ser Ala Ser Phe Ser Thr Phe Lys
545                 550                 555                 560

Cys Tyr Gly Val Ser Pro Thr Lys Leu Asn Asp Leu Cys Phe Thr Asn
                565                 570                 575

Val Tyr Ala Asp Ser Phe Val Ile Arg Gly Asp Glu Val Arg Gln Ile
            580                 585                 590

Ala Pro Gly Gln Thr Gly Lys Ile Ala Asp Tyr Asn Tyr Lys Leu Pro
        595                 600                 605

Asp Asp Phe Thr Gly Cys Val Ile Ala Trp Asn Ser Asn Asn Leu Asp
    610                 615                 620
```

-continued

```
Ser Lys Val Gly Gly Asn Tyr Asn Tyr Leu Tyr Arg Leu Phe Arg Lys
625                 630                 635                 640

Ser Asn Leu Lys Pro Phe Glu Arg Asp Ile Ser Thr Glu Ile Tyr Gln
                645                 650                 655

Ala Gly Ser Thr Pro Cys Asn Gly Val Glu Gly Phe Asn Cys Tyr Phe
            660                 665                 670

Pro Leu Gln Ser Tyr Gly Phe Gln Pro Thr Asn Gly Val Gly Tyr Gln
        675                 680                 685

Pro Tyr Arg Val Val Val Leu Ser Phe Glu Leu Leu His Ala Pro Ala
    690                 695                 700

Thr Val Cys Gly Pro Lys Lys Ser Thr Asn Leu Val Lys Asn Lys Cys
705                 710                 715                 720

Val Asn Phe Asn Phe Asn Gly Leu Thr Gly Thr Gly Val Leu Thr Glu
                725                 730                 735

Ser Asn Lys Lys Phe Leu Pro Phe Gln Gln Phe Gly Arg Asp Ile Ala
            740                 745                 750

Asp Thr Thr Asp Ala Val Arg Asp Pro Gln Thr Leu Glu Ile Leu Asp
        755                 760                 765

Ile Thr Pro Cys Ser Phe Gly Gly Val Ser Val Ile Thr Pro Gly Thr
    770                 775                 780

Asn Thr Ser Asn Gln Val Ala Val Leu Tyr Gln Asp Val Asn Cys Thr
785                 790                 795                 800

Glu Val Pro Val Ala Ile His Ala Asp Gln Leu Thr Pro Thr Trp Arg
                805                 810                 815

Val Tyr Ser Thr Gly Ser Asn Val Phe Gln Thr Arg Ala Gly Cys Leu
            820                 825                 830

Ile Gly Ala Glu His Val Asn Asn Ser Tyr Glu Cys Asp Ile Pro Ile
        835                 840                 845

Gly Ala Gly Ile Cys Ala Ser Tyr Gln Thr Gln Thr Asn Ser
    850                 855                 860
```

<210> SEQ ID NO 12
<211> LENGTH: 2714
<212> TYPE: RNA
<213> ORGANISM: Artificial Sequence
<220> FEATURE:
<223> OTHER INFORMATION: Synthetic

<400> SEQUENCE: 12

```
gggaaauaag agagaaaaga agaguaagaa gaaauauaag accccggcgc cgccaccaug     60

uucguguucc uggugcugcu gccccuggug agcagccagu gcgugaaccu gaccacccgg    120

acccagcugc caccagccua caccaacagc uucacccggg gcgucuacua ccccgacaag    180

guguuccgga gcagcguccu gcacagcacc caggaccugu uccugcccuu cuucagcaac    240

gugaccuggu uccacgccau ccacgugagc ggcaccaacg gcaccaagcg guucgacaac    300

cccgugcugc ccuucaacga cggcguguac uucgccagca ccgagaagag caacaucauc    360

cggggcugga ucuucggcac cacccuggac agcaagaccc agagccugcu gaucgugaau    420

aacgccacca acguggugau caaggugugc gaguuccagu ucugcaacga ccccuuccug    480

ggcguguacu accacaagaa caacaagagc uggauggaga gcgaguuccg gguguacagc    540

agcgccaaca acugcaccuu cgaguacgug agccagcccu uccugaugga ccuggagggc    600

aagcagggca acuucaagaa ccugcgggag uucguguuca agaacaucga cggcuacuuc    660

aagaucuaca gcaagcacac cccaaucaac cuggugcggg aucugcccca gggcuucuca    720
```

```
gcccuggagc cccuggugga ccugcccauc ggcaucaaca ucacccgguu ccagacccug    780

cuggcccugc accggagcua ccugacccca ggcgacagca gcagcgggug gacagcaggc    840

gcggcugcuu acuacguggg cuaccugcag ccccggaccu uccugcugaa guacaacgag    900

aacggcacca ucaccgacgc cguggacugc gcccuggacc cucugagcga gaccaagugc    960

acccugaaga gcuucaccgu ggagaagggc aucuaccaga ccagcaacuu ccgggugcag   1020

cccaccgaga gcaucgugcg guuccccaac aucaccaacc ugugccccuu cggcgaggug   1080

uucaacgcca cccgguucgc cagcguguac gccuggaacc ggaagcggau cagcaacugc   1140

guggccgacu acagcgugcu guacaacagc gccagcuuca gcaccuucaa gugcuacggc   1200

gugagcccca ccaagcugaa cgaccugugc uucaccaacg uguacgccga cagcuucgug   1260

auccguggcg acgaggugcg gcagaucgca cccggccaga caggcaagau cgccgacuac   1320

aacuacaagc ugcccgacga cuucaccggc ugcgugaucg ccuggaacag caacaaccuc   1380

gacagcaagg ugggcggcaa cuacaacuac cuguaccggc uguuccggaa gagcaaccug   1440

aagcccuucg agcgggacau cagcaccgag aucuaccaag ccggcuccac cccuugcaac   1500

ggcguggagg gcuucaacug cuacuucccu cugcagagcu acggcuucca gcccaccaac   1560

ggcgugggcu accagcccua ccggguggug gugcugagcu ucgagcugcu gcacgcccca   1620

gccaccgugu guggccccaa gaagagcacc aaccugguga agaacaagug cgugaacuuc   1680

aacuucaacg gccuuaccgg caccggcgug cugaccgaga gcaacaagaa auuccugccc   1740

uuucagcagu ucggccggga caucgccgac accaccgacg cugugcggga uccccagacc   1800

cuggagaucc uggacaucac cccuugcagc uucggcggcg ugagcgugau caccccaggc   1860

accaacacca gcaaccaggu ggccgugcug uaccaggacg ugaacugcac cgaggugccc   1920

guggccaucc acgccgacca gcugacaccc accuggcggg ucuacagcac cggcagcaac   1980

guguuccaga cccgggccgg uugccugauc ggcgccgagc acgugaacaa cagcuacgag   2040

ugcgacaucc ccaucggcgc cggcaucugu gccagcuacc agacccagac caauucagga   2100

ggaggcuccg gaggcgguag cgcugagacc ggcaugcaga ucuacgaggg caagcugacc   2160

gcagagggcc ugcgguucgg caucguggcc agccgcgcca accacgcucu gguggaccgg   2220

cuuguggagg gcgcuaucga cgccaucgug agacacggcg gccgggaaga ggacaucacc   2280

cuggugcggg ugugcggcag cugggagauu cccgucgccg ccggagaacu ggcccggaag   2340

gaggacaucg acgccgugau cgccaucggc gugcugugca gaggcgccac gcccagcuuc   2400

gacuacaucg ccagcgaggu gagcaagggc cuggccgacc ugagccugga gcugcggaag   2460

cccaucaccu ucggcgugau caccgccgac acccuggagc aggccaucga ggccgcaggc   2520

accugccacg gcaacaaggg cugggaagcc gcccugugcg ccaucgagau ggccaaccug   2580

uucaagagcc ugcggugaua auaggcugga gccucggugg ccuagcuucu ugccccuugg   2640

gccucccccc agccccuccu ccccuuccug cacccguacc cccguggucu uugaauaaag   2700

ucugaguggg cggc                                                     2714
```

<210> SEQ ID NO 13
<211> LENGTH: 2538
<212> TYPE: RNA
<213> ORGANISM: Artificial Sequence
<220> FEATURE:
<223> OTHER INFORMATION: Synthetic

<400> SEQUENCE: 13

-continued

```
auguucgugu uccuggugcu gcugccccug gugagcagcc agugcgugaa ccugaccacc     60
cggacccagc ugccaccagc cuacaccaac agcuucaccc ggggcgucua cuaccccgac    120
aagguguucc ggagcagcgu ccugcacagc acccaggacc uguuccugcc cuucuucagc    180
aacgugaccu gguuccacgc cauccacgug agcggcacca acggcaccaa gcgguucgac    240
aaccccgugc ugcccuucaa cgacggcgug uacuucgcca gcaccgagaa gagcaacauc    300
auccggggcu ggaucuucgg caccacccug gacagcaaga cccagagccu gcugaucgug    360
aauaacgcca ccaacguggu gaucaaggug ugcgaguucc aguucugcaa cgaccccuuc    420
cugggcgugu acuaccacaa gaacaacaag agcuggaugg agagcgaguu ccggguguac    480
agcagcgcca acaacugcac cuucgaguac gugagccagc ccuuccugau ggaccuggag    540
ggcaagcagg gcaacuucaa gaaccugcgg gaguucgugu ucaagaacau cgacggcuac    600
uucaagaucu acagcaagca caccccaauc aaccuggugc gggaucugcc ccagggcuuc    660
ucagcccugg agccccuggu ggaccugccc aucggcauca acaucacccg guuccagacc    720
cugcuggccc ugcaccggag cuaccugacc ccaggcgaca gcagcagcgg guggacagca    780
ggcgcggcug cuuacuacgu gggcuaccug cagccccgga ccuuccugcu gaaguacaac    840
gagaacggca ccaucaccga cgccguggac ugcgcccugg acccucugag cgagaccaag    900
ugcacccuga agagcuucac cguggagaag ggcaucuacc agaccagcaa cuuccgggug    960
cagcccaccg agagcaucgu gcgguucccc aacaucacca accugugccc cuucggcgag   1020
guguucaacg ccacccgguu cgccagcgug uacgccugga accggaagcg gaucagcaac   1080
ugcguggccg acuacagcgu gcuguacaac agcgccagcu ucagcaccuu caagugcuac   1140
ggcgugagcc ccaccaagcu gaacgaccug ugcuucacca acguguacgc cgacagcuuc   1200
gugauccgug gcgacgaggu gcggcagauc gcacccggcc agacaggcaa gaucgccgac   1260
uacaacuaca agcugcccga cgacuucacc ggcugcguga ucgccuggaa cagcaacaac   1320
cucgacagca aggugggcgg caacuacaac uaccuguacc ggcuguuccg gaagagcaac   1380
cugaagcccu ucgagcggga caucagcacc gagaucuacc aagccggcuc caccccuugc   1440
aacggcgugg agggcuucaa cugcuacuuc ccucugcaga gcuacggcuu ccagcccacc   1500
aacggcgugg gcuaccagcc cuaccgggug guggugcuga gcuucgagcu gcugcacgcc   1560
ccagccaccg uguguggccc caagaagagc accaaccugg ugaagaacaa gugcgugaac   1620
uucaacuuca acggccuuac cggcaccggc gugcugaccg agagcaacaa gaaauuccug   1680
cccuuucagc aguucggccg ggacaucgcc gacaccaccg acgcugugcg ggaucccag   1740
acccuggaga uccuggacau caccccuugc agcuucggcg gcgugagcgu gaucacccca   1800
ggcaccaaca ccagcaacca gguggccgug cuguaccagg acgugaacug caccgaggug   1860
cccguggcca uccacgccga ccagcugaca cccaccuggc gggucuacag caccggcagc   1920
aacguguucc agacccgggc cgguugccug aucggcgccg agcacgugaa caacagcuac   1980
gagugcgaca uccccaucgg cgccggcauc ugugccagcu accagaccca gaccaauuca   2040
ggaggaggcu ccggaggcgg uagcgcugag accggcaugc agaucuacga gggcaagcug   2100
accgcagagg gccugcgguu cggcaucgug gccagccgcg ccaaccacgc ucugguggac   2160
cggcuugugg agggcgcuau cgacgccauc gugagacacg gcggccggga agaggacauc   2220
acccuggugc gggugugcgg cagcugggag auucccgucg ccgccggaga acuggcccgg   2280
aaggaggaca ucgacgccgu gaucgccauc ggcgugcugu gcagaggcgc cacgcccagc   2340
uucgacuaca ucgccagcga ggugagcaag ggccuggccg accugagccu ggagcugcgg   2400
```

aagcccauca ccuucggcgu gaucaccgcc gacacccugg agcaggccau cgaggccgca 2460
ggcaccugcc acggcaacaa gggcugggaa gccgcccugu gcgccaucga gauggccaac 2520
cuguucaaga gccugcgg 2538

<210> SEQ ID NO 14
<211> LENGTH: 846
<212> TYPE: PRT
<213> ORGANISM: Artificial Sequence
<220> FEATURE:
<223> OTHER INFORMATION: Synthetic

<400> SEQUENCE: 14

```
Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335
```

-continued

```
Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Gly Gly Gly Ser Gly Gly Gly Ser
        675                 680                 685

Ala Glu Thr Gly Met Gln Ile Tyr Glu Gly Lys Leu Thr Ala Glu Gly
    690                 695                 700

Leu Arg Phe Gly Ile Val Ala Ser Arg Ala Asn His Ala Leu Val Asp
705                 710                 715                 720

Arg Leu Val Glu Gly Ala Ile Asp Ala Ile Val Arg His Gly Gly Arg
                725                 730                 735

Glu Glu Asp Ile Thr Leu Val Arg Val Cys Gly Ser Trp Glu Ile Pro
            740                 745                 750
```

```
Val Ala Ala Gly Glu Leu Ala Arg Lys Glu Asp Ile Asp Ala Val Ile
        755                 760                 765

Ala Ile Gly Val Leu Cys Arg Gly Ala Thr Pro Ser Phe Asp Tyr Ile
    770                 775                 780

Ala Ser Glu Val Ser Lys Gly Leu Ala Asp Leu Ser Leu Glu Leu Arg
785                 790                 795                 800

Lys Pro Ile Thr Phe Gly Val Ile Thr Ala Asp Thr Leu Glu Gln Ala
                805                 810                 815

Ile Glu Ala Ala Gly Thr Cys His Gly Asn Lys Gly Trp Glu Ala Ala
            820                 825                 830

Leu Cys Ala Ile Glu Met Ala Asn Leu Phe Lys Ser Leu Arg
        835                 840                 845


<210> SEQ ID NO 15
<211> LENGTH: 2300
<212> TYPE: RNA
<213> ORGANISM: Artificial Sequence
<220> FEATURE:
<223> OTHER INFORMATION: Synthetic

<400> SEQUENCE: 15

gggaaauaag agagaaaaga agaguaagaa gaaauauaag accccggcgc cgccaccaug      60

uucguguucc uggugcugcu gccccuggug agcagccagu gcgugaaccu gaccacccgg     120

acccagcugc caccagccua caccaacagc uucacccggg gcgucuacua ccccgacaag     180

guguuccgga gcagcguccu gcacagcacc caggaccugu uccugcccuu cuucagcaac     240

gugaccuggu uccacgccau ccacgugagc ggcaccaacg gcaccaagcg guucgacaac     300

cccgugcugc ccuucaacga cggcguguac uucgccagca ccgagaagag caacaucauc     360

cggggcugga ucuucggcac cacccuggac agcaagaccc agagccugcu gaucgugaau     420

aacgccacca acguggugau caaggugugc gaguuccagu ucugcaacga ccccuuccug     480

ggcguguacu accacaagaa caacaagagc uggauggaga gcgaguuccg gguguacagc     540

agcgccaaca acugcaccuu cgaguacgug agccagcccu uccugaugga ccuggagggc     600

aagcagggca acuucaagaa ccugcgggag uucguguuca agaacaucga cggcuacuuc     660

aagaucuaca gcaagcacac cccaaucaac cuggugcggg aucugcccca gggcuucuca     720

gcccuggagc cccugguggga ccugcccauc ggcaucaaca ucacccgguu ccagacccug     780

cuggcccugc accggagcua ccugacccca ggcgacagca gcagcgggug gacagcaggc     840

gcggcugcuu acuacguggg cuaccugcag ccccggaccu uccugcugaa guacaacgag     900

aacggcacca ucaccgacgc cguggacugc gcccuggacc cucugagcga gaccaagugc     960

acccugaaga gcuucaccgu ggagaagggc aucuaccaga ccagcaacuu ccgggugcag    1020

cccaccgaga gcaucgugcg guuccccaac aucaccaacc ugugccccuu cggcgaggug    1080

uucaacgcca cccgguucgc cagcguguac gccuggaacc ggaagcggau cagcaacugc    1140

guggccgacu acagcgugcu guacaacagc gccagcuuca gcaccuucaa gugcuacggc    1200

gugagcccca ccaagcugaa cgaccugugc uucaccaacg uguacgccga cagcuucgug    1260

auccguggcg acgaggugcg gcagaucgca cccggccaga caggcaagau cgccgacuac    1320

aacuacaagc ugcccgacga cuucaccggc ugcgugaucg ccuggaacag caacaaccuc    1380

gacagcaagg ugggcggcaa cuacaacuac cuguaccggc uguuccggaa gagcaaccug    1440

aagcccuucg agcgggacau cagcaccgag aucuaccaag ccggcuccac cccuugcaac    1500

ggcguggagg gcuucaacug cuacuucccu cugcagagcu acggcuucca gcccaccaac    1560
```

ggcgugggcu accagcccua ccgggguggug gugcugagcu ucgagcugcu gcacgcccca 1620
gccaccgugu guggccccaa gaagagcacc aaccugguga agaacaagug cgugaacuuc 1680
aacuucaacg gccuuaccgg caccggcgug cugaccgaga gcaacaagaa auuccugccc 1740
uuucagcagu ucggccggga caucgccgac accaccgacg cugugcggga uccccagacc 1800
cuggagaucc uggacaucac ccuugcagc uucggcggcg ugagcgugau caccccaggc 1860
accaacacca gcaaccaggu ggccgugcug uaccaggacg ugaacugcac cgaggugccc 1920
guggccaucc acgccgacca gcugacaccc accuggcggg ucuacagcac cggcagcaac 1980
guguuccaga cccgggccgg uugccugauc ggcgccgagc acgugaacaa cagcuacgag 2040
ugcgacaucc ccaucggcgc cggcaucugu gccagcuacc agacccagac caauucaucu 2100
ggcggaggca gcauccuggc caucuacagc accguggcca gcagccuggu gcugcuggug 2160
agccugggcg ccaucagcuu cugauaauag gcuggagccu cgguggccua gcuucuugcc 2220
ccuugggccu ccccccagcc ccuccucccc uuccugcacc cguacccccg uggucuuuga 2280
auaaagucug agugggcggc 2300

<210> SEQ ID NO 16
<211> LENGTH: 2124
<212> TYPE: RNA
<213> ORGANISM: Artificial Sequence
<220> FEATURE:
<223> OTHER INFORMATION: Synthetic

<400> SEQUENCE: 16
auguucgugu uccuggugcu gcugccccug gugagcagcc agugcgugaa ccugaccacc 60
cggacccagc ugccaccagc cuacaccaac agcuucaccc ggggcgucua cuaccccgac 120
aagguguucc ggagcagcgu ccugcacagc acccaggacc uguuccugcc cuucuucagc 180
aacgugaccu gguuccacgc cauccacgug agcggcacca acggcaccaa gcgguucgac 240
aaccccgugc ugcccuucaa cgacggcgug uacuucgcca gcaccgagaa gagcaacauc 300
auccggggcu ggaucuucgg caccacccug gacagcaaga cccagagccu gcugaucgug 360
aauaacgcca ccaacguggu gaucaaggug ugcgaguucc aguucugcaa cgaccccuuc 420
cugggcgugu acuaccacaa gaacaacaag agcuggaugg agagcgaguu ccggguguac 480
agcagcgcca acaacugcac cuucgaguac gugagccagc ccuuccugau ggaccuggag 540
ggcaagcagg gcaacuucaa gaaccugcgg gaguucgugu ucaagaacau cgacggcuac 600
uucaagaucu acagcaagca caccccaauc aaccuggugc gggaucugcc ccagggcuuc 660
ucagcccugg agccccuggu ggaccugccc aucggcauca acaucacccg guuccagacc 720
cugcuggccc ugcaccggag cuaccugacc ccaggcgaca gcagcagcgg gugggacagca 780 ggcgcggcug cuuacuacgu gggcuaccug cagccccgga ccuuccugcu gaaguacaac 840
gagaacggca ccaucaccga cgccguggac ugcgcccugg acccucugag cgagaccaag 900
ugcacccuga agagcuucac cguggagaag ggcaucuacc agaccagcaa cuuccgggug 960
cagcccaccg agagcaucgu gcgguucccc aacaucacca accugugccc cuucggcgag 1020
guguucaacg ccacccgguu cgccagcgug uacgccugga accggaagcg gaucagcaac 1080
ugcguggccg acuacagcgu gcuguacaac agcgccagcu ucagcaccuu caagugcuac 1140
ggcgugagcc ccaccaagcu gaacgaccug ugcuucacca acguguacgc cgacagcuuc 1200
gugauccgug gcgacgaggu gcggcagauc gcacccggcc agacaggcaa gaucgccgac 1260
uacaacuaca agcugcccga cgacuucacc ggcugcguga ucgccuggaa cagcaacaac 1320
cucgacagca aggugggcgg caacuacaac uaccuguacc ggcuguuccg gaagagcaac 1380
cugaagcccu ucgagcggga caucagcacc gagaucuacc aagccggcuc caccccuugc 1440
aacggcgugg agggcuucaa cugcuacuuc ccucugcaga gcuacggcuu ccagcccacc 1500
aacggcgugg gcuaccagcc cuaccgggug guggugcuga gcuucgagcu gcugcacgcc 1560
ccagccaccg uguguggccc caagaagagc accaaccugg ugaagaacaa gugcgugaac 1620
uucaacuuca acggccuuac cggcaccggc gugcugaccg agagcaacaa gaaauuccug 1680
cccuuucagc aguucggccg ggacaucgcc gacaccaccg acgcugugcg ggauccccag 1740
acccuggaga uccuggacau caccccuugc agcuucggcg gcgugagcgu gaucacccca 1800
ggcaccaaca ccagcaacca gguggccgug cuguaccagg acgugaacug caccgaggug 1860
cccguggcca uccacgccga ccagcugaca cccaccuggc gggucuacag caccggcagc 1920
aacguguucc agacccgggc cgguugccug aucggcgccg agcacgugaa caacagcuac 1980
gagugcgaca uccccaucgg cgccggcauc ugugccagcu accagaccca gaccaauuca 2040
ucuggcggag gcagcauccu ggccaucuac agcaccgugg ccagcagccu ggugcugcug 2100
gugagccugg gcgccaucag cuuc 2124

<210> SEQ ID NO 17
<211> LENGTH: 707
<212> TYPE: PRT
<213> ORGANISM: Artificial Sequence
<220> FEATURE:
<223> OTHER INFORMATION: Synthetic

<400> SEQUENCE: 17

Met Phe Val Phe Leu Val Leu Leu Pro Leu Val Ser Ser Gln Cys Val
1 5 10 15

Asn Leu Thr Thr Arg Thr Gln Leu Pro Pro Ala Tyr Thr Asn Ser Phe
20 25 30

Thr Arg Gly Val Tyr Tyr Pro Asp Lys Val Phe Arg Ser Ser Val Leu
35 40 45

His Ser Thr Gln Asp Leu Phe Leu Pro Phe Phe Ser Asn Val Thr Trp
50 55 60

Phe His Ala Ile His Val Ser Gly Thr Asn Gly Thr Lys Arg Phe Asp
65 70 75 80

Asn Pro Val Leu Pro Phe Asn Asp Gly Val Tyr Phe Ala Ser Thr Glu
85 90 95

Lys Ser Asn Ile Ile Arg Gly Trp Ile Phe Gly Thr Thr Leu Asp Ser
100 105 110

Lys Thr Gln Ser Leu Leu Ile Val Asn Asn Ala Thr Asn Val Val Ile
115 120 125

Lys Val Cys Glu Phe Gln Phe Cys Asn Asp Pro Phe Leu Gly Val Tyr
130 135 140

Tyr His Lys Asn Asn Lys Ser Trp Met Glu Ser Glu Phe Arg Val Tyr
145 150 155 160

Ser Ser Ala Asn Asn Cys Thr Phe Glu Tyr Val Ser Gln Pro Phe Leu
165 170 175

Met Asp Leu Glu Gly Lys Gln Gly Asn Phe Lys Asn Leu Arg Glu Phe
180 185 190

Val Phe Lys Asn Ile Asp Gly Tyr Phe Lys Ile Tyr Ser Lys His Thr
195 200 205

-continued

```
Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
```

-continued

```
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Gly Gly Gly Ser Ile Leu Ala Ile
        675                 680                 685

Tyr Ser Thr Val Ala Ser Ser Leu Val Leu Leu Val Ser Leu Gly Ala
    690                 695                 700

Ile Ser Phe
705


<210> SEQ ID NO 18
<211> LENGTH: 1853
<212> TYPE: RNA
<213> ORGANISM: Artificial Sequence
<220> FEATURE:
<223> OTHER INFORMATION: Synthetic

<400> SEQUENCE: 18

gggaaauaag agagaaaaga agaguaagaa gaaauauaag accccggcgc cgccaccaug      60

uucguguucc uggugcugcu gccccuggug agcagccagu gcgugaaccu gaccacccgg     120

acccagcugc caccagccua caccaacagc uucacccggg gcgucuacua ccccgacaag     180

guguuccgga gcagcguccu gcacagcacc caggaccugu uccugcccuu cuucagcaac     240

gugaccuggu uccacgccau ccacgugagc ggcaccaacg gcaccaagcg guucgacaac     300

cccgugcugc ccuucaacga cggcguguac uucgccagca ccgagaagag caacaucauc     360

cggggcugga ucuucggcac cacccuggac agcaagaccc agagccugcu gaucgugaau     420

aacgccacca acguggugau caaggugugc gaguuccagu ucugcaacga ccccuuccug     480

ggcguguacu accacaagaa caacaagagc uggauggaga gcgaguuccg gguguacagc     540

agcgccaaca acugcaccuu cgaguacgug agccagcccu uccugaugga ccuggagggc     600

aagcagggca acuucaagaa ccugcgggag uucguguuca agaacaucga cggcuacuuc     660

aagaucuaca gcaagcacac cccaaucaac cuggugcggg aucugcccca gggcuucuca     720

gcccuggagc cccuggugga ccugcccauc ggcaucaaca ucacccgguu ccagacccug     780

cuggcccugc accggagcua ccugacccca ggcgacagca gcagcgggug gacagcaggc     840

gcggcugcuu acuacguggg cuaccugcag ccccggaccu uccugcugaa guacaacgag     900

aacggcacca ucaccgacgc cguggacugc gcccuggacc cucugagcga gaccaagugc     960

acccugaaga gcuucaccgu ggagaagggc aucuaccaga ccagcaacuu ccgggugcag    1020

cccaccgaga gcaucgugcg guuccccaac aucaccaacc ugugccccuu cggcgaggug    1080

uucaacgcca cccgguucgc cagcguguac gccuggaacc ggaagcggau cagcaacugc    1140

guggccgacu acagcgugcu guacaacagc gccagcuuca gcaccuucaa gugcuacggc    1200

gugagcccca ccaagcugaa cgaccugugc uucaccaacg uguacgccga cagcuucgug    1260

auccguggcg acgaggugcg gcagaucgca ccccggccaga caggcaagau cgccgacuac    1320

aacuacaagc ugcccgacga cuucaccggc ugcgugaucg ccuggaacag caacaaccuc    1380

gacagcaagg ugggcggcaa cuacaacuac cuguaccggc uguuccggaa gagcaaccug    1440

aagcccuucg agcgggacau cagcaccgag aucuaccaag ccggcuccac ccccuugcaac    1500

ggcguggagg gcuucaacug cuacuucccu cugcagagcu acggcuucca gcccaccaac    1560
```

ggcgugggcu accagcccua ccggguggug gugcugagcu ucgagcugcu gcacgcccca 1620
gccaccgugu guggccccaa gaagagcacc ucuggcggag gcagcauccu ggccaucuac 1680
agcaccgugg ccagcagccu ggugcugcug gugagccugg gcgccaucag cuucugauaa 1740
uaggcuggag ccucgguggc cuagcuucuu gccccuuggg ccucccccca gccccuccuc 1800
cccuuccugc acccguaccc ccguggucuu ugaauaaagu cugagugggc ggc 1853

<210> SEQ ID NO 19
<211> LENGTH: 1677
<212> TYPE: RNA
<213> ORGANISM: Artificial Sequence
<220> FEATURE:
<223> OTHER INFORMATION: Synthetic

<400> SEQUENCE: 19
auguucgugu uccuggugcu gcugccccug gugagcagcc agugcgugaa ccugaccacc 60
cggacccagc ugccaccagc cuacaccaac agcuucaccc ggggcgucua cuaccccgac 120
aagguguucc ggagcagcgu ccugcacagc acccaggacc uguuccugcc cuucuucagc 180
aacgugaccu gguuccacgc cauccacgug agcggcacca acggcaccaa gcgguucgac 240
aaccccgugc ugcccuucaa cgacggcgug uacuucgcca gcaccgagaa gagcaacauc 300
auccggggcu ggaucuucgg caccacccug gacagcaaga cccagagccu gcugaucgug 360
aauaacgcca ccaacguggu gaucaaggug ugcgaguucc aguucugcaa cgaccccuuc 420
cugggcgugu acuaccacaa gaacaacaag agcuggaugg agagcgaguu ccggguguac 480
agcagcgcca acaacugcac cuucgaguac gugagccagc ccuuccugau ggaccuggag 540
ggcaagcagg gcaacuucaa gaaccugcgg gaguucgugu ucaagaacau cgacggcuac 600
uucaagaucu acagcaagca caccccaauc aaccuggugc gggaucugcc ccagggcuuc 660
ucagcccugg agccccuggu ggaccugccc aucggcauca acaucacccg guuccagacc 720
cugcuggccc ugcaccggag cuaccugacc ccaggcgaca gcagcagcgg guggacagca 780
ggcgcggcug cuuacuacgu gggcuaccug cagccccgga ccuuccugcu gaaguacaac 840
gagaacggca ccaucaccga cgccguggac ugcgcccugg acccucugag cgagaccaag 900
ugcacccuga agagcuucac cguggagaag ggcaucuacc agaccagcaa cuuccgggug 960
cagcccaccg agagcaucgu gcgguucccc aacaucacca accugugccc cuucggcgag 1020
guguucaacg ccacccgguu cgccagcgug uacgccugga accggaagcg gaucagcaac 1080
ugcguggccg acuacagcgu gcuguacaac agcgccagcu ucagcaccuu caagugcuac 1140
ggcgugagcc ccaccaagcu gaacgaccug ugcuucacca acguguacgc cgacagcuuc 1200
gugauccgug gcgacgaggu gcggcagauc gcacccggcc agacaggcaa gaucgccgac 1260
uacaacuaca agcugcccga cgacuucacc ggcugcguga ucgccuggaa cagcaacaac 1320
cucgacagca aggugggcgg caacuacaac uaccuguacc ggcuguuccg gaagagcaac 1380
cugaagcccu ucgagcggga caucagcacc gagaucuacc aagccggcuc caccccuugc 1440
aacggcgugg agggcuucaa cugcuacuuc ccucugcaga gcuacggcuu ccagcccacc 1500
aacggcgugg gcuaccagcc cuaccgggug guggugcuga gcuucgagcu gcugcacgcc 1560
ccagccaccg ugugugggccc caagaagagc accucuggcg gaggcagcau ccuggccauc 1620
uacagcaccg uggccagcag ccuggugcug cuggugagcc ugggcgccau cagcuuc 1677

<210> SEQ ID NO 20
<211> LENGTH: 559

-continued

```
<212> TYPE: PRT
<213> ORGANISM: Artificial Sequence
<220> FEATURE:
<223> OTHER INFORMATION: Synthetic

<400> SEQUENCE: 20

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380
```

-continued

```
Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Ser Gly Gly Gly Ser Ile Leu Ala Ile Tyr Ser Thr Val
    530                 535                 540

Ala Ser Ser Leu Val Leu Leu Val Ser Leu Gly Ala Ile Ser Phe
545                 550                 555
```

<210> SEQ ID NO 21
<211> LENGTH: 2042
<212> TYPE: RNA
<213> ORGANISM: Artificial Sequence
<220> FEATURE:
<223> OTHER INFORMATION: Synthetic

<400> SEQUENCE: 21

```
gggaaauaag agagaaaaga agaguaagaa gaaauauaag accccggcgc cgccaccaug     60

uucguguucc uggugcugcu gccccuggug agcagccagu gcgugaaccu gaccacccgg    120

acccagcugc caccagccua caccaacagc uucacccggg gcgucuacua ccccgacaag    180

guguuccgga gcagcguccu gcacagcacc caggaccugu uccugcccuu cuucagcaac    240

gugaccuggu uccacgccau ccacgugagc ggcaccaacg gcaccaagcg guucgacaac    300

cccgugcugc ccuucaacga cggcguguac uucgccagca ccgagaagag caacaucauc    360

cggggcugga ucuucggcac cacccuggac agcaagaccc agagccugcu gaucgugaau    420

aacgccacca acguggugau caaggugugc gaguuccagu ucugcaacga ccccuuccug    480

ggcguguacu accacaagaa caacaagagc uggauggaga gcgaguuccg gguguacagc    540

agcgccaaca acugcaccuu cgaguacgug agccagcccu uccugaugga ccuggagggc    600

aagcagggca acuucaagaa ccugcgggag uucguguuca agaacaucga cggcuacuuc    660

aagaucuaca gcaagcacac cccaaucaac cuggugcggg aucugcccca gggcuucuca    720

gcccuggagc cccuggugga ccugcccauc ggcaucaaca ucacccgguu ccagacccug    780

cuggcccugc accggagcua ccugacccca ggcgacagca gcagcgggug gacagcaggc    840

gcggcugcuu acuacguggg cuaccugcag ccccggaccu uccugcugaa guacaacgag    900

aacggcacca ucaccgacgc cguggacugc gcccuggacc cucugagcga gaccaagugc    960

acccugaaga gcuucaccgu ggagaagggc aucuaccaga ccagcaacuu ccgggugcag   1020

cccaccgaga gcaucgugcg guuccccaac aucaccaacc ugugccccuu cggcgaggug   1080
```

-continued uucaacgcca cccgguucgc cagcguguac gccuggaacc ggaagcggau cagcaacugc 1140
guggccgacu acagcgugcu guacaacagc gccagcuuca gcaccuucaa gugcuacggc 1200
gugagcccca ccaagcugaa cgaccugugc uucaccaacg uguacgccga cagcuucgug 1260
auccguggcg acgaggugcg gcagaucgca cccggccaga caggcaagau cgccgacuac 1320
aacuacaagc ugcccgacga cuucaccggc ugcgugaucg ccuggaacag caacaaccuc 1380
gacagcaagg ugggcggcaa cuacaacuac cuguaccggc uguuccggaa gagcaaccug 1440
aagcccuucg agcgggacau cagcaccgag aucuaccaag ccggcuccac cccuugcaac 1500
ggcguggagg gcuucaacug cuacuucccu cugcagagcu acggcuucca gcccaccaac 1560
ggcgugggcu accagcccua ccggguggug gugcugagcu ucgagcugcu gcacgcccca 1620
gccaccgugu guggccccaa gaagagcacc aaccugguga agaacaagug cgugaacuuc 1680
aacuucaacg gccuuaccgg caccggcgug cugaccgaga gcaacaagaa auuccugccc 1740
uuucagcagu ucggccggga caucgccgac accaccgacg cugugcggga uccccagacc 1800
cuggagaucc uggacaucac cccuugcagc uucggcggcu cuggcggagg cagcauccug 1860
gccaucuaca gcaccguggc cagcagccug gugcugcugg ugagccuggg cgccaucagc 1920
uucugauaau aggcuggagc cucgguggcc uagcuucuug ccccuugggc cuccccccag 1980
ccccuccucc ccuuccugca cccguacccc cguggucuuu gaauaaaguc ugagugggcg 2040
gc 2042

<210> SEQ ID NO 22
<211> LENGTH: 1866
<212> TYPE: RNA
<213> ORGANISM: Artificial Sequence
<220> FEATURE:
<223> OTHER INFORMATION: Synthetic

<400> SEQUENCE: 22
auguucgugu uccuggugcu gcugccccug gugagcagcc agugcgugaa ccugaccacc 60
cggacccagc ugccaccagc cuacaccaac agcuucaccc ggggcgucua cuaccccgac 120 aaggguguucc ggagcagcgu ccugcacagc acccaggacc uguuccugcc cuucuucagc 180
aacgugaccu gguuccacgc cauccacgug agcggcacca acggcaccaa gcgguucgac 240
aaccccgugc ugcccuucaa cgacggcgug uacuucgcca gcaccgagaa gagcaacauc 300
auccggggcu ggaucuucgg caccacccug gacagcaaga cccagagccu gcugaucgug 360
aauaacgcca ccaacguggu gaucaaggug ugcgaguucc aguucugcaa cgaccccuuc 420
cugggcgugu acuaccacaa gaacaacaag agcuggaugg agagcgaguu ccggguguac 480
agcagcgcca acaacugcac cuucgaguac gugagccagc ccuuccugau ggaccuggag 540
ggcaagcagg gcaacuucaa gaaccugcgg gaguucgugu ucaagaacau cgacggcuac 600
uucaagaucu acagcaagca caccccaauc aaccuggugc gggaucugcc ccagggcuuc 660
ucagcccugg agccccuggu ggaccugccc aucggcauca acaucacccg guuccagacc 720
cugcuggccc ugcaccggag cuaccugacc ccaggcgaca gcagcagcgg guggacagca 780
ggcgcggcug cuuacuacgu gggcuaccug cagccccgga ccuuccugcu gaaguacaac 840
gagaacggca ccaucaccga cgccguggac ugcgcccugg acccucugag cgagaccaag 900
ugcacccuga agagcuucac cguggagaag ggcaucuacc agaccagcaa cuuccgggug 960
cagcccaccg agagcaucgu gcgguucccc aacaucacca accugugccc cuucggcgag 1020
guguucaacg ccacccgguu cgccagcgug uacgccugga accggaagcg gaucagcaac 1080

```
ugcguggccg acuacagcgu gcuguacaac agcgccagcu ucagcaccuu caagugcuac   1140

ggcgugagcc ccaccaagcu gaacgaccug ugcuucacca acguguacgc cgacagcuuc   1200

gugauccgug gcgacgaggu gcggcagauc gcacccggcc agacaggcaa gaucgccgac   1260

uacaacuaca agcugcccga cgacuucacc ggcugcguga ucgccuggaa cagcaacaac   1320

cucgacagca aggugggcgg caacuacaac uaccuguacc ggcuguuccg gaagagcaac   1380

cugaagcccu ucgagcggga caucagcacc gagaucuacc aagccggcuc caccccuugc   1440

aacggcgugg agggcuucaa cugcuacuuc ccucugcaga gcuacggcuu ccagcccacc   1500

aacggcgugg gcuaccagcc cuaccgggug guggugcuga gcuucgagcu gcugcacgcc   1560

ccagccaccg uguguggccc caagaagagc accaaccugg ugaagaacaa gugcgugaac   1620

uucaacuuca acggccuuac cggcaccggc gugcugaccg agagcaacaa gaaauuccug   1680

cccuuucagc aguucggccg ggacaucgcc gacaccaccg acgcugugcg ggaucccccag   1740

acccuggaga uccuggacau caccccuugc agcuucggcg gcucuggcgg aggcagcauc   1800

cuggccaucu acagcaccgu ggccagcagc cuggugcugc uggugagccu gggcgccauc   1860

agcuuc                                                              1866
```

```
<210> SEQ ID NO 23
<211> LENGTH: 622
<212> TYPE: PRT
<213> ORGANISM: Artificial Sequence
<220> FEATURE:
<223> OTHER INFORMATION: Synthetic

<400> SEQUENCE: 23

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
```

```
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Ser Gly Gly Gly Ser Ile Leu Ala Ile Tyr Ser Thr Val Ala
        595                 600                 605

Ser Ser Leu Val Leu Leu Val Ser Leu Gly Ala Ile Ser Phe
    610                 615                 620
```

<210> SEQ ID NO 24

<211> LENGTH: 2066
<212> TYPE: RNA
<213> ORGANISM: Artificial Sequence
<220> FEATURE:
<223> OTHER INFORMATION: Synthetic

<400> SEQUENCE: 24
gggaaauaag agagaaaaga agaguaagaa gaaauauaag accccggcgc cgccaccaug 60
uucguguucc uggugcugcu gccccuggug agcagccagu gcgugaaccu gaccacccgg 120
acccagcugc caccagccua caccaacagc uucacccggg gcgucuacua ccccgacaag 180
guguuccgga gcagcguccu gcacagcacc caggaccugu uccugcccuu cuucagcaac 240
gugaccuggu uccacgccau ccacgugagc ggcaccaacg gcaccaagcg guucgacaac 300
cccgugcugc ccuucaacga cggcguguac uucgccagca ccgagaagag caacaucauc 360
cggggcugga ucuucggcac cacccuggac agcaagaccc agagccugcu gaucgugaau 420
aacgccacca acguggugau caaggugugc gaguuccagu ucugcaacga ccccuuccug 480
ggcguguacu accacaagaa caacaagagc uggauggaga gcgaguuccg gguguacagc 540
agcgccaaca acugcaccuu cgaguacgug agccagcccu uccugaugga ccuggagggc 600
aagcagggca acuucaagaa ccugcgggag uucguguuca agaacaucga cggcuacuuc 660
aagaucuaca gcaagcacac cccaaucaac cuggugcggg aucugcccca gggcuucuca 720
gcccuggagc cccuggugga ccugcccauc ggcaucaaca ucacccgguu ccagacccug 780
cuggcccugc accggagcua ccugacccca ggcgacagca gcagcgggug gacagcaggc 840
gcggcugcuu acuacguggg cuaccugcag ccccggaccu uccugcugaa guacaacgag 900
aacggcacca ucaccgacgc cguggacugc gcccuggacc cucugagcga gaccaagugc 960
acccugaaga gcuucaccgu gggcagcggc ggcggcagcg gcggaggcag cggaggaggc 1020
agcggcggag gcaguggagg ccagcccacc gagagcaucg ugcgguuccc caacaucacc 1080
aaccugugcc ccuucggcga gguguucaac gccacccggu ucgccagcgu guacgccugg 1140
aaccggaagc ggaucagcaa cugcguggcc gacuacagcg ugcuguacaa cagcgccagc 1200
uucagcaccu ucaagugcua cggcgugagc ccccaccaagc ugaacgaccu gugcuucacc 1260
aacguguacg ccgacagcuu cgugauccgu ggcgacgagg ugcggcagau cgcacccggc 1320
cagacaggca agaucgccga cuacaacuac aagcugcccg acgacuucac cggcugcgug 1380
aucgccugga acagcaacaa ccucgacagc aaggugggcg gcaacuacaa cuaccuguac 1440
cggcuguucc ggaagagcaa ccugaagccc uucgagcggg acaucagcac cgagaucuac 1500
caagccggcu ccaccccuug caacggcgug gagggcuuca acugcuacuu cccucugcag 1560
agcuacggcu uccagcccac caacggcgug ggcuaccagc ccuaccgggu gguggugcug 1620
agcuucgagc ugcugcacgc cccagccacc gugugguggcc ccaagaagag caccaaccug 1680
gugaagaaca agugcgugaa cuucaacuuc aacggccuua ccggcaccgg cgugcugacc 1740
gagagcaaca agaaauuccu gcccuuucag caguucggcc gggacaucgc cgacaccacc 1800
gacgcugugc gggaucccca gacccuggag auccuggaca ucaccccuug cagcuucggc 1860
ggcucuggcg gaggcagcau ccuggccauc uacagcaccg uggccagcag ccuggugcug 1920
cuggugagcc ugggcgccau cagcuucuga uaauaggcug gagccucggu ggccuagcuu 1980
cuugccccuu gggccucccc ccagccccuc cuccccuucc ugcacccgua cccccguggu 2040
cuuugaauaa agucugagug ggcggc 2066

<210> SEQ ID NO 25
<211> LENGTH: 1890
<212> TYPE: RNA
<213> ORGANISM: Artificial Sequence
<220> FEATURE:
<223> OTHER INFORMATION: Synthetic

<400> SEQUENCE: 25
auguucgugu uccuggugcu gcugccccug gugagcagcc agugcgugaa ccugaccacc 60
cggacccagc ugccaccagc cuacaccaac agcuucaccc ggggcgucua cuaccccgac 120
aagguguucc ggagcagcgu ccugcacagc acccaggacc uguuccugcc cuucuucagc 180
aacgugaccu gguuccacgc cauccacgug agcggcacca acggcaccaa gcgguucgac 240
aaccccgugc ugcccuucaa cgacggcgug uacuucgcca gcaccgagaa gagcaacauc 300
auccggggcu ggaucuucgg caccacccug gacagcaaga cccagagccu gcugaucgug 360
aauaacgcca ccaacguggu gaucaaggug ugcgaguucc aguucugcaa cgaccccuuc 420
cugggcgugu acuaccacaa gaacaacaag agcuggaugg agagcgaguu ccggguguac 480
agcagcgcca acaacugcac cuucgaguac gugagccagc ccuuccugau ggaccuggag 540
ggcaagcagg gcaacuucaa gaaccugcgg gaguucgugu ucaagaacau cgacggcuac 600
uucaagaucu acagcaagca caccccaauc aaccuggugc gggaucugcc ccagggcuuc 660
ucagcccugg agccccuggu ggaccugccc aucggcauca acaucacccg guuccagacc 720
cugcuggccc ugcaccggag cuaccugacc ccaggcgaca gcagcagcgg gguggacagca 780 ggcgcggcug cuuacuacgu gggcuaccug cagccccgga ccuuccugcu gaaguacaac 840
gagaacggca ccaucaccga cgccguggac ugcgcccugg acccucugag cgagaccaag 900
ugcacccuga agagcuucac cgugggcagc ggcggcggca gcggcggagg cagcggagga 960
ggcagcggcg gaggcagugg aggccagccc accgagagca ucgugcgguu ccccaacauc 1020
accaaccugu gccccuucgg cgagguguuc aacgccaccc gguucgccag cguguacgcc 1080
uggaaccgga agcggaucag caacugcgug gccgacuaca gcgugcugua caacagcgcc 1140
agcuucagca ccuucaagug cuacggcgug agccccacca agcugaacga ccugugcuuc 1200
accaacgugu acgccgacag cuucgugauc cguggcgacg aggugcggca gaucgcaccc 1260
ggccagacag gcaagaucgc cgacuacaac uacaagcugc ccgacgacuu caccggcugc 1320
gugaucgccu ggaacagcaa caaccucgac agcaaggugg gcggcaacua caacuaccug 1380
uaccggcugu uccggaagag caaccugaag cccuucgagc gggacaucag caccgagauc 1440
uaccaagccg gcuccacccc uugcaacggc guggagggcu ucaacugcua cuucccucug 1500
cagagcuacg gcuuccagcc caccaacggc gugggcuacc agcccuaccg gguggugcgug 1560 cugagcuucg agcugcugca cgccccagcc accgugugug gccccaagaa gagcaccaac 1620
cuggugaaga acaagugcgu gaacuucaac uucaacggcc uuaccggcac cggcgugcug 1680
accgagagca acaagaaauu ccugcccuuu cagcaguucg gccgggacau cgccgacacc 1740
accgacgcug ugcgggaucc ccagacccug gagauccugg acaucacccc uugcagcuuc 1800
ggcggcucug gcggaggcag cauccuggcc aucuacagca ccguggccag cagccuggug 1860
cugcugguga gccugggcgc caucagcuuc 1890

<210> SEQ ID NO 26
<211> LENGTH: 630
<212> TYPE: PRT
<213> ORGANISM: Artificial Sequence
<220> FEATURE:

<223> OTHER INFORMATION: Synthetic

<400> SEQUENCE: 26

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Gly Ser Gly Gly Gly Ser Gly Gly Gly Ser Gly Gly
305                 310                 315                 320

Gly Ser Gly Gly Gly Ser Gly Gly Gln Pro Thr Glu Ser Ile Val Arg
                325                 330                 335

Phe Pro Asn Ile Thr Asn Leu Cys Pro Phe Gly Glu Val Phe Asn Ala
            340                 345                 350

Thr Arg Phe Ala Ser Val Tyr Ala Trp Asn Arg Lys Arg Ile Ser Asn
        355                 360                 365

Cys Val Ala Asp Tyr Ser Val Leu Tyr Asn Ser Ala Ser Phe Ser Thr
    370                 375                 380

Phe Lys Cys Tyr Gly Val Ser Pro Thr Lys Leu Asn Asp Leu Cys Phe
385                 390                 395                 400

```
Thr Asn Val Tyr Ala Asp Ser Phe Val Ile Arg Gly Asp Glu Val Arg
                405                 410                 415

Gln Ile Ala Pro Gly Gln Thr Gly Lys Ile Ala Asp Tyr Asn Tyr Lys
            420                 425                 430

Leu Pro Asp Asp Phe Thr Gly Cys Val Ile Ala Trp Asn Ser Asn Asn
        435                 440                 445

Leu Asp Ser Lys Val Gly Gly Asn Tyr Asn Tyr Leu Tyr Arg Leu Phe
    450                 455                 460

Arg Lys Ser Asn Leu Lys Pro Phe Glu Arg Asp Ile Ser Thr Glu Ile
465                 470                 475                 480

Tyr Gln Ala Gly Ser Thr Pro Cys Asn Gly Val Glu Gly Phe Asn Cys
                485                 490                 495

Tyr Phe Pro Leu Gln Ser Tyr Gly Phe Gln Pro Thr Asn Gly Val Gly
            500                 505                 510

Tyr Gln Pro Tyr Arg Val Val Val Leu Ser Phe Glu Leu Leu His Ala
        515                 520                 525

Pro Ala Thr Val Cys Gly Pro Lys Lys Ser Thr Asn Leu Val Lys Asn
    530                 535                 540

Lys Cys Val Asn Phe Asn Phe Asn Gly Leu Thr Gly Thr Gly Val Leu
545                 550                 555                 560

Thr Glu Ser Asn Lys Lys Phe Leu Pro Phe Gln Gln Phe Gly Arg Asp
                565                 570                 575

Ile Ala Asp Thr Thr Asp Ala Val Arg Asp Pro Gln Thr Leu Glu Ile
            580                 585                 590

Leu Asp Ile Thr Pro Cys Ser Phe Gly Gly Ser Gly Gly Gly Ser Ile
        595                 600                 605

Leu Ala Ile Tyr Ser Thr Val Ala Ser Ser Leu Val Leu Leu Val Ser
    610                 615                 620

Leu Gly Ala Ile Ser Phe
625                 630
```

<210> SEQ ID NO 27
<211> LENGTH: 2066
<212> TYPE: RNA
<213> ORGANISM: Artificial Sequence
<220> FEATURE:
<223> OTHER INFORMATION: Synthetic

<400> SEQUENCE: 27

```
gggaaauaag agagaaaaga agaguaagaa gaaauauaag accccggcgc cgccaccaug      60

uucguguucc uggugcugcu gccccuggug agcagccagu gcgugaaccu gaccacccgg     120

acccagcugc caccagccua caccaacagc uucacccggg gcgucuacua ccccgacaag     180

gugugccgga gcagcguccu gcacagcacc caggaccugu uccugcccuu cuucagcaac     240

gugaccuggu uccacgccau ccacgugagc ggcaccaacg gcaccaagcg guucgacaac     300

cccgugcugc ccuucaacga cggcguguac uucgccagca ccgagaagag caacaucauc     360

cggggcugga ucuucggcac cacccuggac agcaagaccc agagccugcu gaucgugaau     420

aacgccacca acguggugau caaggugugc gaguuccagu ucugcaacga ccccuuccug     480

ggcguguacu accacaagaa caacaagagc uggauggaga gcgaguuccg ggugua cagc    540

agcgccaaca acugcaccuu cgaguacgug agccagcccu uccugaugga ccuggagggc     600

aagcagggca acuucaagaa ccugcgggag uucguguuca agaacaucga cggcuacuuc     660

aagaucuaca gcaagcacac cccaaucaac cuggugcggg aucugcccca gggcuucuca     720
```

gcccuggagc cccuggugga ccugcccauc ggcaucaaca ucacccgguu ccagacccug 780
cuggcccugc accggagcua ccugacccca ggcgacagca gcagcgggug gacagcaggc 840
gcggcugcuu acuacguggg cuaccugcag ccccggaccu uccugcugaa guacaacgag 900
aacggcacca ucaccgacgc cguggacugc gcccuggacc cucugagcga gaccaagugc 960
acccugaaga gcuucaccgu gggcagcggc ggcggcagcg gcggaggcag cggaggaggc 1020
agcggcggag gcaguggagg ccagcccacc gagagcaucg ugcgguuccc caacaucacc 1080
aaccugugcc ccuucggcga gguguucaac gccacccggu ucgccagcgu guacgccugg 1140
aaccggaagc ggaucagcaa cugcguggcc gacuacagcg ugcuguacaa cagcgccagc 1200
uucagcaccu ucaagugcua cggcgugagc cccaccaagc ugaacgaccu gugcuucacc 1260
aacguguacg ccgacagcuu cgugauccgu ggcgacgagg ugcggcagau cgcacccggc 1320
cagacaggca agaucgccga cuacaacuac aagcugcccg acgacuucac cggcugcgug 1380
aucgccugga acagcaacaa ccucgacagc aaggugggcg gcaacuacaa cuaccuguac 1440
cggcuguucc ggaagagcaa ccugaagccc uucgagcggg acaucagcac cgagaucuac 1500
caagccggcu ccaccccuug caacggcgug gagggcuuca acugcuacuu cccucugcag 1560
agcuacggcu uccagcccac caacggcgug ggcuaccagc ccuaccgggu gguggugcug 1620
agcuucgagc ugcugcacgc cccagccacc gugugugGcc ccaagaagag caccaaccug 1680
gugaagaaca agugcgugaa cuucaacuuc aacggccuua ccggcaccgg cgugcugacc 1740
gagagcaaca agaaauuccu gcccuuuugc caguucggcc gggacaucgc cgacaccacc 1800
gacgcugugc gggaucccca gacccuggag auccuggaca ucaccccuug cagcuucggc 1860
ggcucuggcg gaggcagcau ccuggccauc uacagcaccg uggccagcag ccuggugcug 1920
cuggugagcc ugggcgccau cagcuucuga uaauaggcug gagccucggu ggccuagcuu 1980
cuugccccuu gggccucccc ccagccccuc cuccccuucc ugcacccgua cccccguggu 2040
cuuugaauaa agucugagug ggcggc 2066

<210> SEQ ID NO 28
<211> LENGTH: 1890
<212> TYPE: RNA
<213> ORGANISM: Artificial Sequence
<220> FEATURE:
<223> OTHER INFORMATION: Synthetic

<400> SEQUENCE: 28
auguucgugu uccuggugcu gcugccccug gugagcagcc agugcgugaa ccugaccacc 60
cggacccagc ugccaccagc cuacaccaac agcuucaccc ggggcgucua cuaccccgac 120
aaggugugcc ggagcagcgu ccugcacagc acccaggacc uguuccugcc cuucuucagc 180
aacgugaccu gguuccacgc cauccacgug agcggcacca acggcaccaa gcgguucgac 240
aaccccgugc ugcccuucaa cgacggcgug uacuucgcca gcaccgagaa gagcaacauc 300
auccggggcu ggaucuucgg caccacccug gacagcaaga cccagagccu gcugaucgug 360
aauaacgcca ccaacguggu gaucaaggug ugcgaguucc aguucugcaa cgaccccuuc 420
cugggcgugu acuaccacaa gaacaacaag agcuggaugg agagcgaguu ccggguguac 480
agcagcgcca acaacugcac cuucgaguac gugagccagc ccuuccugau ggaccuggag 540
ggcaagcagg gcaacuucaa gaaccugcgg gaguucgugu ucaagaacau cgacggcuac 600
uucaagaucu acagcaagca caccccaauc aaccuggugc gggaucugcc ccagggcuuc 660
ucagcccugg agccccuggu ggaccugccc aucggcauca acaucacccg guuccagacc 720

```
cugcuggccc ugcaccggag cuaccugacc ccaggcgaca gcagcagcgg guggacagca    780

ggcgcggcug cuuacuacgu gggcuaccug cagccccgga ccuuccugcu gaaguacaac    840

gagaacggca ccaucaccga cgccguggac ugcgcccugg acccucugag cgagaccaag    900

ugcacccuga agagcuucac cgugggcagc ggcggcggca gcggcggagg cagcggagga    960

ggcagcggcg gaggcagugg aggccagccc accgagagca ucgugcgguu ccccaacauc   1020

accaaccugu gccccuucgg cgagguguuc aacgccaccc gguucgccag cguguacgcc   1080

uggaaccgga agcggaucag caacugcgug gccgacuaca gcgugcugua caacagcgcc   1140

agcuucagca ccuucaagug cuacggcgug agccccacca agcugaacga ccugugcuuc   1200

accaacgugu acgccgacag cuucgugauc cguggcgacg aggugcggca gaucgcaccc   1260

ggccagacag gcaagaucgc cgacuacaac uacaagcugc ccgacgacuu caccggcugc   1320

gugaucgccu ggaacagcaa caaccucgac agcaaggugg gcggcaacua caacuaccug   1380

uaccggcugu uccggaagag caaccugaag cccuucgagc gggacaucag caccgagauc   1440

uaccaagccg gcuccacccc uugcaacggc guggagggcu ucaacugcua cuucccucug   1500

cagagcuacg gcuuccagcc caccaacggc gugggcuacc agcccuaccg gguggguggug   1560

cugagcuucg agcugcugca cgccccagcc accgugugug gccccaagaa gagcaccaac   1620

cuggugaaga acaagugcgu gaacuucaac uucaacggcc uuaccggcac cggcgugcug   1680

accgagagca acaagaaauu ccugcccuuu ugccaguucg gccgggacau cgccgacacc   1740

accgacgcug ugcgggaucc ccagacccug gagauccugg acaucacccc uugcagcuuc   1800

ggcggcucug gcggaggcag cauccuggcc aucuacagca ccguggccag cagccuggug   1860

cugcugguga gccugggcgc caucagcuuc                                    1890
```

<210> SEQ ID NO 29
<211> LENGTH: 630
<212> TYPE: PRT
<213> ORGANISM: Artificial Sequence
<220> FEATURE:
<223> OTHER INFORMATION: Synthetic

<400> SEQUENCE: 29

```
Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Cys Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
```

-continued

```
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Gly Ser Gly Gly Gly Ser Gly Gly Gly Ser Gly Gly
305                 310                 315                 320

Gly Ser Gly Gly Gly Ser Gly Gly Gln Pro Thr Glu Ser Ile Val Arg
                325                 330                 335

Phe Pro Asn Ile Thr Asn Leu Cys Pro Phe Gly Glu Val Phe Asn Ala
            340                 345                 350

Thr Arg Phe Ala Ser Val Tyr Ala Trp Asn Arg Lys Arg Ile Ser Asn
        355                 360                 365

Cys Val Ala Asp Tyr Ser Val Leu Tyr Asn Ser Ala Ser Phe Ser Thr
    370                 375                 380

Phe Lys Cys Tyr Gly Val Ser Pro Thr Lys Leu Asn Asp Leu Cys Phe
385                 390                 395                 400

Thr Asn Val Tyr Ala Asp Ser Phe Val Ile Arg Gly Asp Glu Val Arg
                405                 410                 415

Gln Ile Ala Pro Gly Gln Thr Gly Lys Ile Ala Asp Tyr Asn Tyr Lys
            420                 425                 430

Leu Pro Asp Asp Phe Thr Gly Cys Val Ile Ala Trp Asn Ser Asn Asn
        435                 440                 445

Leu Asp Ser Lys Val Gly Gly Asn Tyr Asn Tyr Leu Tyr Arg Leu Phe
    450                 455                 460

Arg Lys Ser Asn Leu Lys Pro Phe Glu Arg Asp Ile Ser Thr Glu Ile
465                 470                 475                 480

Tyr Gln Ala Gly Ser Thr Pro Cys Asn Gly Val Glu Gly Phe Asn Cys
                485                 490                 495

Tyr Phe Pro Leu Gln Ser Tyr Gly Phe Gln Pro Thr Asn Gly Val Gly
            500                 505                 510

Tyr Gln Pro Tyr Arg Val Val Val Leu Ser Phe Glu Leu Leu His Ala
        515                 520                 525

Pro Ala Thr Val Cys Gly Pro Lys Lys Ser Thr Asn Leu Val Lys Asn
    530                 535                 540

Lys Cys Val Asn Phe Asn Phe Asn Gly Leu Thr Gly Thr Gly Val Leu
545                 550                 555                 560

Thr Glu Ser Asn Lys Lys Phe Leu Pro Phe Cys Gln Phe Gly Arg Asp
                565                 570                 575
```

```
Ile Ala Asp Thr Thr Asp Ala Val Arg Asp Pro Gln Thr Leu Glu Ile
            580                 585                 590

Leu Asp Ile Thr Pro Cys Ser Phe Gly Gly Ser Gly Gly Gly Ser Ile
        595                 600                 605

Leu Ala Ile Tyr Ser Thr Val Ala Ser Ser Leu Val Leu Leu Val Ser
    610                 615                 620

Leu Gly Ala Ile Ser Phe
625                 630
```

<210> SEQ ID NO 30
<211> LENGTH: 3182
<212> TYPE: RNA
<213> ORGANISM: Artificial Sequence
<220> FEATURE:
<223> OTHER INFORMATION: Synthetic

<400> SEQUENCE: 30

```
gggaaauaag agagaaaaga agaguaagaa gaaauauaag accccggcgc cgccaccaug     60

uucguguucc uggugcugcu gccccuggug agcagccagu gcgugaaccu gaccacccgg    120

acccagcugc caccagccua caccaacagc uucacccggg gcgucuacua ccccgacaag    180

guguuccgga gcagcguccu gcacagcacc caggaccugu uccugcccuu cuucagcaac    240

gugaccuggu uccacgccau ccacgugagc ggcaccaacg gcaccaagcg guucgacaac    300

cccgugcugc ccuucaacga cggcguguac uucgccagca ccgagaagag caacaucauc    360

cggggcugga ucuucggcac cacccuggac agcaagaccc agagccugcu gaucgugaau    420

aacgccacca acguggugau caaggugugc gaguuccagu ucugcaacga ccccuuccug    480

ggcguguacu accacaagaa caacaagagc uggauggaga gcgaguuccg gguguacagc    540

agcgccaaca acugcaccuu cgaguacgug agccagcccu uccugaugga ccuggagggc    600

aagcagggca acuucaagaa ccugcgggag uucguguuca agaacaucga cggcuacuuc    660

aagaucuaca gcaagcacac cccaaucaac cuggugcggg aucugcccca gggcuucuca    720

gcccuggagc cccuggugga ccugcccauc ggcaucaaca ucacccgguu ccagacccug    780

cuggcccugc accggagcua ccugacccca ggcgacagca gcagcgggug gacagcaggc    840

gcggcugcuu acuacguggg cuaccugcag ccccggaccu uccugcugaa guacaacgag    900

aacggcacca ucaccgacgc cguggacugc gcccuggacc cucugagcga gaccaagugc    960

acccugaaga gcuucaccgu ggagaagggc aucuaccaga ccagcaacuu cggcggcagc   1020

ggcggcguga gcgugaucac ccccaggcacc aacaccagca accagguggc cgugcuguac   1080

caggacguga acugcaccga ggugcccgug gccauccacg ccgaccagcu gacacccacc   1140

uggcgggucu acagcaccgg cagcaacgug uuccagaccc gggccgguug ccugaucggc   1200

gccgagcacg ugaacaacag cuacgagugc gacaucccca ucggcgccgg caucugugcc   1260

agcuaccaga cccagaccaa uucaccccgg agggcaagga gcguggccag ccagagcauc   1320

aucgccuaca ccaugagccu gggcgccgag aacagcgugg ccuacagcaa caacagcauc   1380

gccaucccca ccaacuucac caucagcgug accaccgaga uucugcccgu gagcaugacc   1440

aagaccagcg uggacugcac cauguacauc ugcggcgaca gcaccgagug cagcaaccug   1500

cugcugcagu acggcagcuu cugcacccag cugaaccggg cccugaccgg caucgccgug   1560

gagcaggaca agaacaccca ggagguguuc gcccagguga agcagaucua caagaccccu   1620

cccaucaagg acuucggcgg cuucaacuuc agccagaucc ugcccgaccc cagcaagccc   1680
```

agcaagcgga gcuucaucga ggaccugcug uucaacaagg ugacccuagc cgacgccggc 1740
uucaucaagc aguacggcga cugccucggc gacauagccg cccgggaccu gaucugcgcc 1800
cagaaguuca acggccugac cgugcugccu ccccugcuga ccgacgagau gaucgcccag 1860
uacaccagcg cccuguuagc cggaaccauc accagcggcu ggacuuucgg cgcuggagcc 1920
gcucugcaga uccccuucgc caugcagaug gccuaccggu ucaacggcau cggcgugacc 1980
cagaacgugc uguacgagaa ccagaagcug aucgccaacc aguucaacag cgccaucggc 2040
aagauccagg acagccugag cagcaccgcu agcgcccugg gcaagcugca ggacguggug 2100
aaccagaacg cccaggcccu gaacacccug gugaagcagc ugagcagcaa cuucggcgcc 2160
aucagcagcg ugcugaacga cauccugagc cggcuggacc cucccaacgc caccgugcag 2220
aucgaccggc ugaucacugg ccggcugcag agccugcaga ccuacgugac ccagcagcug 2280
auccgggccg ccgagauucg ggccagcgcc aaccuggccg ccaccaagau gagcgagugc 2340
gugcugggcc agagcaagcg gguggacuuc ugcggcaagg gcuaccaccu gaugagcuuu 2400
ccccagagcg caccccacgg aguggugguuc cugcacguga ccuacgugcc cgcccaggag 2460
aagaacuuca ccaccgcccc agccaucugc cacgacggca aggcccacuu uccccgggag 2520
ggcguguucg ugagcaacgg cacccacugg uucgugaccc agcggaacuu cuacgagccc 2580
cagaucauca ccaccgacaa caccuucgug agcggcaacu gcgacguggu gaucggcauc 2640
gugaacaaca ccguguacga uccccugcag cccgagcugg acagcuucaa ggaggagcug 2700
gacaaguacu ucaagaauca caccagcccc gacguggacc ugggcgacau cagcggcauc 2760
aacgccagcg uggugaacau ccagaaggag aucgaucggc ugaacgaggu ggccaagaac 2820
cugaacgaga gccugaucga ccugcaggag cugggcaagu acgagcagua caucaagugg 2880
cccugguaca ucuggcuggg cuucaucgcc ggccugaucg ccaucgugau ggugaccauc 2940
augcugugcu gcaugaccag cugcugcagc ugccugaagg gcuguugcag cugcggcagc 3000
ugcugcaagu ucgacgagga cgacagcgag cccgugcuga agggcgugaa gcugcacuac 3060
accugauaau aggcuggagc cucgguggcc uagcuucuug ccccuugggc cucccccag 3120 ccccuccucc ccuuccugca cccguacccc cguggucuuu gaauaaaguc ugagugggcg 3180
gc 3182

<210> SEQ ID NO 31
<211> LENGTH: 3006
<212> TYPE: RNA
<213> ORGANISM: Artificial Sequence
<220> FEATURE:
<223> OTHER INFORMATION: Synthetic

<400> SEQUENCE: 31
auguucgugu uccuggugcu gcugccccug gugagcagcc agugcgugaa ccugaccacc 60
cggacccagc ugccaccagc cuacaccaac agcuucaccc ggggcgucua cuaccccgac 120 aaggguguucc ggagcagcgu ccugcacagc acccaggacc uguuccugcc cuucuucagc 180
aacgugaccu gguuccacgc cauccacgug agcggcacca acggcaccaa gcgguucgac 240
aaccccgugc ugcccuucaa cgacggcgug uacuucgcca gcaccgagaa gagcaacauc 300
auccggggcu ggaucuucgg caccacccug gacagcaaga cccagagccu gcugaucgug 360
aauaacgcca ccaacguggu gaucaaggug ugcgaguucc aguucugcaa cgaccccuuc 420
cugggcgugu acuaccacaa gaacaacaag agcuggaugg agagcgaguu ccggguguac 480
agcagcgcca acaacugcac cuucgaguac gugagccagc ccuuccugau ggaccuggag 540

```
ggcaagcagg gcaacuucaa gaaccugcgg gaguucgugu ucaagaacau cgacggcuac    600
uucaagaucu acagcaagca caccccaauc aaccuggugc gggaucugcc ccagggcuuc    660
ucagcccugg agccccuggu ggaccugccc aucggcauca acaucacccg guuccagacc    720
cugcuggccc ugcaccggag cuaccugacc ccaggcgaca gcagcagcgg guggacagca    780
ggcgcggcug cuuacuacgu gggcuaccug cagccccgga ccuuccugcu gaaguacaac    840
gagaacggca ccaucaccga cgccguggac ugcgcccugg acccucugag cgagaccaag    900
ugcacccuga agagcuucac cguggagaag ggcaucuacc agaccagcaa cuucggcggc    960
agcggcggcg ugagcgugau caccccaggc accaacacca gcaaccaggu ggccgugcug   1020
uaccaggacg ugaacugcac cgaggugccc guggccaucc acgccgacca gcugacaccc   1080
accuggcggg ucuacagcac cggcagcaac guguuccaga cccgggccgg uugccugauc   1140
ggcgccgagc acgugaacaa cagcuacgag ugcgacaucc ccaucggcgc cggcaucugu   1200
gccagcuacc agacccagac caauucaccc cggagggcaa ggagcguggc cagccagagc   1260
aucaucgccu acaccaugag ccugggcgcc gagaacagcg uggccuacag caacaacagc   1320
aucgccaucc ccaccaacuu caccaucagc gugaccaccg agauucugcc cgugagcaug   1380
accaagacca gcguggacug caccauguac aucugcggcg acagcaccga gugcagcaac   1440
cugcugcugc aguacggcag cuucugcacc cagcugaacc gggcccugac cggcaucgcc   1500
guggagcagg acaagaacac ccaggaggug uucgcccagg ugaagcagau cuacaagacc   1560
ccucccauca aggacuucgg cggcuucaac uucagccaga uccugcccga ccccagcaag   1620
cccagcaagc ggagcuucau cgaggaccug cuguucaaca aggugacccu agccgacgcc   1680
ggcuucauca agcaguacgg cgacugccuc ggcgacauag ccgcccggga ccugaucugc   1740
gcccagaagu ucaacggccu gaccgugcug ccucccccugc ugaccgacga gaugaucgcc   1800
caguacacca gcgcccuguu agccggaacc aucaccagcg gcuggacuuu cggcgcugga   1860
gccgcucugc agaucccccuu cgccaugcag auggccuacc gguucaacgg caucggcgug   1920
acccagaacg ugcuguacga gaaccagaag cugaucgcca accaguucaa cagcgccauc   1980
ggcaagaucc aggacagccu gagcagcacc gcuagcgccc ugggcaagcu gcaggacgug   2040
gugaaccaga acgcccaggc ccugaacacc cuggugaagc agcugagcag caacuucggc   2100
gccaucagca gcgugcugaa cgacauccug agccggcugg acccucccaa cgccaccgug   2160
cagaucgacc ggcugaucac uggccggcug cagagccugc agaccuacgu gacccagcag   2220
cugauccggg ccgccgagau ucgggccagc gccaaccugg ccgccaccaa gaugagcgag   2280
ugcgugcugg gccagagcaa gcggguggac uucugcggca agggcuacca ccugaugagc   2340
uuuccccaga gcgcacccca cggaguggug uuccugcacg ugaccuacgu gcccgcccag   2400
gagaagaacu ucaccaccgc cccagccauc ugccacgacg gcaaggccca cuuuccccgg   2460
gagggcgugu ucgugagcaa cggcacccac ugguucguga cccagcggaa cuucuacgag   2520
ccccagauca ucaccaccga caacaccuuc gugagcggca acugcgacgu ggugaucggc   2580
aucgugaaca acaccgugua cgauccccug cagcccgagc uggacagcuu caaggaggag   2640
cuggacaagu acuucaagaa ucacaccagc cccgacgugg accugggcga caucagcggc   2700
aucaacgcca gcguggugaa cauccagaag gagaucgauc ggcugaacga gguggccaag   2760
aaccugaacg agagccugau cgaccugcag gagcugggca aguacgagca guacaucaag   2820
uggcccuggu acaucuggcu gggcuucauc gccggccuga ucgccaucgu gauggugacc   2880
```

aucaugcugu gcugcaugac cagcugcugc agcugccuga agggcuguug cagcugcggc 2940
agcugcugca aguucgacga ggacgacagc gagcccgugc ugaagggcgu gaagcugcac 3000
uacacc 3006

<210> SEQ ID NO 32
<211> LENGTH: 1002
<212> TYPE: PRT
<213> ORGANISM: Artificial Sequence
<220> FEATURE:
<223> OTHER INFORMATION: Synthetic

<400> SEQUENCE: 32

Met Phe Val Phe Leu Val Leu Leu Pro Leu Val Ser Ser Gln Cys Val
1 5 10 15

Asn Leu Thr Thr Arg Thr Gln Leu Pro Pro Ala Tyr Thr Asn Ser Phe
20 25 30

Thr Arg Gly Val Tyr Tyr Pro Asp Lys Val Phe Arg Ser Ser Val Leu
35 40 45

His Ser Thr Gln Asp Leu Phe Leu Pro Phe Phe Ser Asn Val Thr Trp
50 55 60

Phe His Ala Ile His Val Ser Gly Thr Asn Gly Thr Lys Arg Phe Asp
65 70 75 80

Asn Pro Val Leu Pro Phe Asn Asp Gly Val Tyr Phe Ala Ser Thr Glu
85 90 95

Lys Ser Asn Ile Ile Arg Gly Trp Ile Phe Gly Thr Thr Leu Asp Ser
100 105 110

Lys Thr Gln Ser Leu Leu Ile Val Asn Asn Ala Thr Asn Val Val Ile
115 120 125

Lys Val Cys Glu Phe Gln Phe Cys Asn Asp Pro Phe Leu Gly Val Tyr
130 135 140

Tyr His Lys Asn Asn Lys Ser Trp Met Glu Ser Glu Phe Arg Val Tyr
145 150 155 160

Ser Ser Ala Asn Asn Cys Thr Phe Glu Tyr Val Ser Gln Pro Phe Leu
165 170 175

Met Asp Leu Glu Gly Lys Gln Gly Asn Phe Lys Asn Leu Arg Glu Phe
180 185 190

Val Phe Lys Asn Ile Asp Gly Tyr Phe Lys Ile Tyr Ser Lys His Thr
195 200 205

Pro Ile Asn Leu Val Arg Asp Leu Pro Gln Gly Phe Ser Ala Leu Glu
210 215 220

Pro Leu Val Asp Leu Pro Ile Gly Ile Asn Ile Thr Arg Phe Gln Thr
225 230 235 240

Leu Leu Ala Leu His Arg Ser Tyr Leu Thr Pro Gly Asp Ser Ser Ser
245 250 255

Gly Trp Thr Ala Gly Ala Ala Ala Tyr Tyr Val Gly Tyr Leu Gln Pro
260 265 270

Arg Thr Phe Leu Leu Lys Tyr Asn Glu Asn Gly Thr Ile Thr Asp Ala
275 280 285

Val Asp Cys Ala Leu Asp Pro Leu Ser Glu Thr Lys Cys Thr Leu Lys
290 295 300

Ser Phe Thr Val Glu Lys Gly Ile Tyr Gln Thr Ser Asn Phe Gly Gly
305 310 315 320

Ser Gly Gly Val Ser Val Ile Thr Pro Gly Thr Asn Thr Ser Asn Gln
325 330 335

```
Val Ala Val Leu Tyr Gln Asp Val Asn Cys Thr Glu Val Pro Val Ala
            340                 345                 350

Ile His Ala Asp Gln Leu Thr Pro Thr Trp Arg Val Tyr Ser Thr Gly
        355                 360                 365

Ser Asn Val Phe Gln Thr Arg Ala Gly Cys Leu Ile Gly Ala Glu His
    370                 375                 380

Val Asn Asn Ser Tyr Glu Cys Asp Ile Pro Ile Gly Ala Gly Ile Cys
385                 390                 395                 400

Ala Ser Tyr Gln Thr Gln Thr Asn Ser Pro Arg Arg Ala Arg Ser Val
                405                 410                 415

Ala Ser Gln Ser Ile Ile Ala Tyr Thr Met Ser Leu Gly Ala Glu Asn
            420                 425                 430

Ser Val Ala Tyr Ser Asn Asn Ser Ile Ala Ile Pro Thr Asn Phe Thr
        435                 440                 445

Ile Ser Val Thr Thr Glu Ile Leu Pro Val Ser Met Thr Lys Thr Ser
    450                 455                 460

Val Asp Cys Thr Met Tyr Ile Cys Gly Asp Ser Thr Glu Cys Ser Asn
465                 470                 475                 480

Leu Leu Leu Gln Tyr Gly Ser Phe Cys Thr Gln Leu Asn Arg Ala Leu
                485                 490                 495

Thr Gly Ile Ala Val Glu Gln Asp Lys Asn Thr Gln Glu Val Phe Ala
            500                 505                 510

Gln Val Lys Gln Ile Tyr Lys Thr Pro Pro Ile Lys Asp Phe Gly Gly
        515                 520                 525

Phe Asn Phe Ser Gln Ile Leu Pro Asp Pro Ser Lys Pro Ser Lys Arg
    530                 535                 540

Ser Phe Ile Glu Asp Leu Leu Phe Asn Lys Val Thr Leu Ala Asp Ala
545                 550                 555                 560

Gly Phe Ile Lys Gln Tyr Gly Asp Cys Leu Gly Asp Ile Ala Ala Arg
                565                 570                 575

Asp Leu Ile Cys Ala Gln Lys Phe Asn Gly Leu Thr Val Leu Pro Pro
            580                 585                 590

Leu Leu Thr Asp Glu Met Ile Ala Gln Tyr Thr Ser Ala Leu Leu Ala
        595                 600                 605

Gly Thr Ile Thr Ser Gly Trp Thr Phe Gly Ala Gly Ala Ala Leu Gln
    610                 615                 620

Ile Pro Phe Ala Met Gln Met Ala Tyr Arg Phe Asn Gly Ile Gly Val
625                 630                 635                 640

Thr Gln Asn Val Leu Tyr Glu Asn Gln Lys Leu Ile Ala Asn Gln Phe
                645                 650                 655

Asn Ser Ala Ile Gly Lys Ile Gln Asp Ser Leu Ser Ser Thr Ala Ser
            660                 665                 670

Ala Leu Gly Lys Leu Gln Asp Val Val Asn Gln Asn Ala Gln Ala Leu
        675                 680                 685

Asn Thr Leu Val Lys Gln Leu Ser Ser Asn Phe Gly Ala Ile Ser Ser
    690                 695                 700

Val Leu Asn Asp Ile Leu Ser Arg Leu Asp Pro Pro Asn Ala Thr Val
705                 710                 715                 720

Gln Ile Asp Arg Leu Ile Thr Gly Arg Leu Gln Ser Leu Gln Thr Tyr
                725                 730                 735

Val Thr Gln Gln Leu Ile Arg Ala Ala Glu Ile Arg Ala Ser Ala Asn
            740                 745                 750

Leu Ala Ala Thr Lys Met Ser Glu Cys Val Leu Gly Gln Ser Lys Arg
```

```
        755                 760                 765

Val Asp Phe Cys Gly Lys Gly Tyr His Leu Met Ser Phe Pro Gln Ser
    770                 775                 780

Ala Pro His Gly Val Val Phe Leu His Val Thr Tyr Val Pro Ala Gln
785                 790                 795                 800

Glu Lys Asn Phe Thr Thr Ala Pro Ala Ile Cys His Asp Gly Lys Ala
                805                 810                 815

His Phe Pro Arg Glu Gly Val Phe Val Ser Asn Gly Thr His Trp Phe
            820                 825                 830

Val Thr Gln Arg Asn Phe Tyr Glu Pro Gln Ile Ile Thr Thr Asp Asn
        835                 840                 845

Thr Phe Val Ser Gly Asn Cys Asp Val Val Ile Gly Ile Val Asn Asn
    850                 855                 860

Thr Val Tyr Asp Pro Leu Gln Pro Glu Leu Asp Ser Phe Lys Glu Glu
865                 870                 875                 880

Leu Asp Lys Tyr Phe Lys Asn His Thr Ser Pro Asp Val Asp Leu Gly
                885                 890                 895

Asp Ile Ser Gly Ile Asn Ala Ser Val Val Asn Ile Gln Lys Glu Ile
            900                 905                 910

Asp Arg Leu Asn Glu Val Ala Lys Asn Leu Asn Glu Ser Leu Ile Asp
        915                 920                 925

Leu Gln Glu Leu Gly Lys Tyr Glu Gln Tyr Ile Lys Trp Pro Trp Tyr
    930                 935                 940

Ile Trp Leu Gly Phe Ile Ala Gly Leu Ile Ala Ile Val Met Val Thr
945                 950                 955                 960

Ile Met Leu Cys Cys Met Thr Ser Cys Cys Ser Cys Leu Lys Gly Cys
                965                 970                 975

Cys Ser Cys Gly Ser Cys Cys Lys Phe Asp Glu Asp Asp Ser Glu Pro
            980                 985                 990

Val Leu Lys Gly Val Lys Leu His  Tyr Thr
        995                 1000
```

<210> SEQ ID NO 33
<211> LENGTH: 2378
<212> TYPE: RNA
<213> ORGANISM: Artificial Sequence
<220> FEATURE:
<223> OTHER INFORMATION: Synthetic

<400> SEQUENCE: 33

```
gggaaauaag agagaaaaga agaguaagaa gaaauauaag accccggcgc cgccaccaug     60

uucguguucc uggugcugcu gccccuggug agcagccagg gcaccaucac cgacgccgug    120

gacugcgccc uggacccucu gagcgagacc aagugcaccc ugaagagcuu caccguggag    180

aagggcaucu accagaccag caacuucggc ggcagcggcg gcgugagcgu gaucacccca    240

ggcaccaaca ccagcaacca gguggccgug cuguaccagg acgugaacug caccgaggug    300

cccguggcca uccacgccga ccagcugaca cccaccuggc gggucuacag caccggcagc    360

aacguguucc agacccgggc cgguugccug aucggcgccg agcacgugaa caacagcuac    420

gagugcgaca uccccaucgg cgccggcauc ugugccagcu accagaccca gaccaauuca    480

ccccggaggg caaggagcgu ggccagccag agcaucaucg ccuacaccau gagccugggc    540

gccgagaaca gcguggccua cagcaacaac agcaucgcca uccccaccaa cuucaccauc    600

agcgugacca ccgagauucu gcccgugagc augaccaaga ccagcgugga cugcaccaug    660
```

```
uacaucugcg gcgacagcac cgagugcagc aaccugcugc ugaacuacac cagcuucugc    720

acccagcuga accgggcccu gaccggcauc gccguggagc aggacaagaa cacccaggag    780

guguucgccc aggugaagca gaucuacaag accccuccca ucaaggacuu cggcggcuuc    840

aacuucagcc agauccugcc cgaccccagc aagcccagca agcggagcuu caucgaggac    900

cugcuguuca acaaggugac ccuagccgac gccggcuuca ucaagcagua cggcgacugc    960

cucggcgaca uagccgcccg ggaccugauc ugcgcccaga aguucaacgg ccugaccgug   1020

cugccucccc ugcugaccga cgagaugauc gcccaguaca ccagcgcccu guuagccgga   1080

accaucacca gcggcuggac uuucggcgcu ggagccgcuc ugcagauccc cuucgccaug   1140

cagauggccu accgguucaa cggcaucggc gugacccaga acgugcugua cgagaaccag   1200

aagcugaucg ccaaccaguu caacagcgcc aucggcaaga uccaggacag ccugagcagc   1260

accgcuagcg cccugggcaa gcugcaggac gugguggaacc agaacgccca ggcccugaac   1320

acccugguga agcagcugag cagcaacuuc ggcgccauca gcagcgugcu gaacgacauc   1380

cugagccggc uggacccucc caacgccacc gugcagaucg accggcugau cacuggccgg   1440

cugcagagcc ugcagaccua cgugacccag cagcugaucc gggccgccga gauucgggcc   1500

agcgccaacc uggccgccac caagaugagc gagugcgugc ugggccagag caagcgggug   1560

gacuucugcg gcaagggcua ccaccugaug agcuuucccc agagcgcacc ccacggagug   1620

guguuccugc acgugaccua cgugcccgcc caggagaaga acuucaccac cgccccagcc   1680

aucugccacg acggcaaggc ccacuuuccc cgggagggcg uguucgugag caacggcacc   1740

cacugguucg ugacccagcg gaacuucuac gagccccaga ucaucaccac cgacaacacc   1800

uucgugagcg gcaacugcga cguggugauc ggcaucguga acaacaccgu guacgauccc   1860

cugcagcccg agcuggacag cuucaaggag gagcuggaca aguacuucaa gaaucacacc   1920

agccccgacg uggaccuggg cgacaucagc ggcaucaacg ccagcguggu gaacauccag   1980

aaggagaucg aucggcugaa cgagguggcc aagaaccuga acgagagccu gaucgaccug   2040

caggagcugg gcaaguacga gcaguacauc aaguggcccu gguacaucug gcugggcuuc   2100

aucgccggcc ugaucgccau cgugauggug accaucaugc ugugcugcau gaccagcugc   2160

ugcagcugcc ugaagggcug uugcagcugc ggcagcugcu gcaaguucga cgaggacgac   2220

agcgagcccg ugcugaaggg cgugaagcug cacuacaccu gauaauaggc uggagccucg   2280

guggccuagc uucuugcccc uugggccucc ccccagcccc uccuccccuu ccugcacccg   2340

uacccccgug gucuuugaau aaagucugag ugggcggc                          2378
```

<210> SEQ ID NO 34
<211> LENGTH: 2202
<212> TYPE: RNA
<213> ORGANISM: Artificial Sequence
<220> FEATURE:
<223> OTHER INFORMATION: Synthetic

<400> SEQUENCE: 34

```
auguucgugu uccuggugcu gcugccccug gugagcagcc agggcaccau caccgacgcc     60

guggacugcg cccuggaccc ucugagcgag accaagugca cccugaagag cuucaccgug    120

gagaagggca ucuaccagac cagcaacuuc ggcggcagcg gcggcgugag cgugaucacc    180

ccaggcacca acaccagcaa ccagguggcc gugcuguacc aggacgugaa cugcaccgag    240

gugcccgugg ccauccacgc cgaccagcug acacccaccu ggcgggucua cagcaccggc    300

agcaacgugu uccagacccg ggccgguugc cugaucggcg ccgagcacgu gaacaacagc    360
```

```
uacgagugcg acaucccau cggcgccggc aucugugcca gcuaccagac ccagaccaau    420

ucaccccgga gggcaaggag cguggccagc cagagcauca ucgccuacac caugagccug    480

ggcgccgaga acagcguggc cuacagcaac aacagcaucg ccaucccccac caacuucacc    540

aucagcguga ccaccgagau ucugcccgug agcaugacca agaccagcgu ggacugcacc    600

auguacaucu gcggcgacag caccgagugc agcaaccugc ugcugaacua caccagcuuc    660

ugcacccagc ugaaccgggc ccugaccggc aucgccgugg agcaggacaa gaacacccag    720

gagguguucg cccaggugaa gcagaucuac aagaccccuc ccaucaagga cuucggcggc    780

uucaacuuca gccagauccu gcccgacccc agcaagccca gcaagcggag cuucaucgag    840

gaccugcugu ucaacaaggu gacccuagcc gacgccggcu ucaucaagca guacggcgac    900

ugccucggcg acauagccgc ccgggaccug aucugcgccc agaaguucaa cggccugacc    960

gugcugccuc cccugcugac cgacgagaug aucgcccagu acaccagcgc ccuguuagcc   1020

ggaaccauca ccagcggcug gacuuucggc gcuggagccg cucugcagau ccccuucgcc   1080

augcagaugg ccuaccgguu caacggcauc ggcgugaccc agaacgugcu guacgagaac   1140

cagaagcuga ucgccaacca guucaacagc gccaucggca agauccagga cagccugagc   1200

agcaccgcua gcgcccuggg caagcugcag gacgugguga accagaacgc ccaggcccug   1260

aacacccugg ugaagcagcu gagcagcaac uucggcgcca ucagcagcgu gcugaacgac   1320

auccugagcc ggcuggaccc ucccaacgcc accgugcaga ucgaccggcu gaucacuggc   1380

cggcugcaga gccugcagac cuacgugacc cagcagcuga uccgggccgc cgagauucgg   1440

gccagcgcca accuggccgc caccaagaug agcgagugcg ugcugggcca gagcaagcgg   1500

guggacuucu gcggcaaggg cuaccaccug augagcuuuc cccagagcgc accccacgga   1560

guggguguucc ugcacgugac cuacgugccc gcccaggaga agaacuucac caccgcccca   1620

gccaucugcc acgacggcaa ggcccacuuu ccccgggagg gcguguucgu gagcaacggc   1680

acccacuggu ucgugaccca gcggaacuuc uacgagcccc agaucaucac caccgacaac   1740

accuucguga gcggcaacug cgacguggug aucggcaucg ugaacaacac cguguacgau   1800

ccccugcagc ccgagcugga cagcuucaag gaggagcugg acaaguacuu caagaaucac   1860

accagccccg acguggaccu gggcgacauc agcggcauca acgccagcgu ggugaacauc   1920

cagaaggaga ucgaucggcu gaacgaggug gccaagaacc ugaacgagag ccugaucgac   1980

cugcaggagc ugggcaagua cgagcaguac aucaaguggc ccugguacau cuggcugggc   2040

uucaucgccg gccugaucgc caucgugaug gugaccauca ugcugugcug caugaccagc   2100

ugcugcagcu gccugaaggg cuguugcagc ugcggcagcu gcugcaaguu cgacgaggac   2160

gacagcgagc ccgugcugaa gggcgugaag cugcacuaca cc                       2202
```

```
<210> SEQ ID NO 35
<211> LENGTH: 734
<212> TYPE: PRT
<213> ORGANISM: Artificial Sequence
<220> FEATURE:
<223> OTHER INFORMATION: Synthetic

<400> SEQUENCE: 35

Met Phe Val Phe Leu Val Leu Leu Pro Leu Val Ser Ser Gln Gly Thr
1               5                   10                  15

Ile Thr Asp Ala Val Asp Cys Ala Leu Asp Pro Leu Ser Glu Thr Lys
            20                  25                  30
```

```
Cys Thr Leu Lys Ser Phe Thr Val Glu Lys Gly Ile Tyr Gln Thr Ser
        35                  40                  45

Asn Phe Gly Gly Ser Gly Gly Val Ser Val Ile Thr Pro Gly Thr Asn
    50                  55                  60

Thr Ser Asn Gln Val Ala Val Leu Tyr Gln Asp Val Asn Cys Thr Glu
65                  70                  75                  80

Val Pro Val Ala Ile His Ala Asp Gln Leu Thr Pro Thr Trp Arg Val
                85                  90                  95

Tyr Ser Thr Gly Ser Asn Val Phe Gln Thr Arg Ala Gly Cys Leu Ile
            100                 105                 110

Gly Ala Glu His Val Asn Asn Ser Tyr Glu Cys Asp Ile Pro Ile Gly
        115                 120                 125

Ala Gly Ile Cys Ala Ser Tyr Gln Thr Gln Thr Asn Ser Pro Arg Arg
    130                 135                 140

Ala Arg Ser Val Ala Ser Gln Ser Ile Ile Ala Tyr Thr Met Ser Leu
145                 150                 155                 160

Gly Ala Glu Asn Ser Val Ala Tyr Ser Asn Asn Ser Ile Ala Ile Pro
                165                 170                 175

Thr Asn Phe Thr Ile Ser Val Thr Thr Glu Ile Leu Pro Val Ser Met
            180                 185                 190

Thr Lys Thr Ser Val Asp Cys Thr Met Tyr Ile Cys Gly Asp Ser Thr
        195                 200                 205

Glu Cys Ser Asn Leu Leu Leu Asn Tyr Thr Ser Phe Cys Thr Gln Leu
    210                 215                 220

Asn Arg Ala Leu Thr Gly Ile Ala Val Glu Gln Asp Lys Asn Thr Gln
225                 230                 235                 240

Glu Val Phe Ala Gln Val Lys Gln Ile Tyr Lys Thr Pro Pro Ile Lys
                245                 250                 255

Asp Phe Gly Gly Phe Asn Phe Ser Gln Ile Leu Pro Asp Pro Ser Lys
            260                 265                 270

Pro Ser Lys Arg Ser Phe Ile Glu Asp Leu Leu Phe Asn Lys Val Thr
        275                 280                 285

Leu Ala Asp Ala Gly Phe Ile Lys Gln Tyr Gly Asp Cys Leu Gly Asp
    290                 295                 300

Ile Ala Ala Arg Asp Leu Ile Cys Ala Gln Lys Phe Asn Gly Leu Thr
305                 310                 315                 320

Val Leu Pro Pro Leu Leu Thr Asp Glu Met Ile Ala Gln Tyr Thr Ser
                325                 330                 335

Ala Leu Leu Ala Gly Thr Ile Thr Ser Gly Trp Thr Phe Gly Ala Gly
            340                 345                 350

Ala Ala Leu Gln Ile Pro Phe Ala Met Gln Met Ala Tyr Arg Phe Asn
        355                 360                 365

Gly Ile Gly Val Thr Gln Asn Val Leu Tyr Glu Asn Gln Lys Leu Ile
    370                 375                 380

Ala Asn Gln Phe Asn Ser Ala Ile Gly Lys Ile Gln Asp Ser Leu Ser
385                 390                 395                 400

Ser Thr Ala Ser Ala Leu Gly Lys Leu Gln Asp Val Val Asn Gln Asn
                405                 410                 415

Ala Gln Ala Leu Asn Thr Leu Val Lys Gln Leu Ser Ser Asn Phe Gly
            420                 425                 430

Ala Ile Ser Ser Val Leu Asn Asp Ile Leu Ser Arg Leu Asp Pro Pro
        435                 440                 445

Asn Ala Thr Val Gln Ile Asp Arg Leu Ile Thr Gly Arg Leu Gln Ser
```

```
    450                 455                 460

Leu Gln Thr Tyr Val Thr Gln Gln Leu Ile Arg Ala Ala Glu Ile Arg
465                 470                 475                 480

Ala Ser Ala Asn Leu Ala Ala Thr Lys Met Ser Glu Cys Val Leu Gly
                485                 490                 495

Gln Ser Lys Arg Val Asp Phe Cys Gly Lys Gly Tyr His Leu Met Ser
            500                 505                 510

Phe Pro Gln Ser Ala Pro His Gly Val Val Phe Leu His Val Thr Tyr
        515                 520                 525

Val Pro Ala Gln Glu Lys Asn Phe Thr Thr Ala Pro Ala Ile Cys His
    530                 535                 540

Asp Gly Lys Ala His Phe Pro Arg Glu Gly Val Phe Val Ser Asn Gly
545                 550                 555                 560

Thr His Trp Phe Val Thr Gln Arg Asn Phe Tyr Glu Pro Gln Ile Ile
                565                 570                 575

Thr Thr Asp Asn Thr Phe Val Ser Gly Asn Cys Asp Val Val Ile Gly
            580                 585                 590

Ile Val Asn Asn Thr Val Tyr Asp Pro Leu Gln Pro Glu Leu Asp Ser
        595                 600                 605

Phe Lys Glu Glu Leu Asp Lys Tyr Phe Lys Asn His Thr Ser Pro Asp
    610                 615                 620

Val Asp Leu Gly Asp Ile Ser Gly Ile Asn Ala Ser Val Val Asn Ile
625                 630                 635                 640

Gln Lys Glu Ile Asp Arg Leu Asn Glu Val Ala Lys Asn Leu Asn Glu
                645                 650                 655

Ser Leu Ile Asp Leu Gln Glu Leu Gly Lys Tyr Glu Gln Tyr Ile Lys
            660                 665                 670

Trp Pro Trp Tyr Ile Trp Leu Gly Phe Ile Ala Gly Leu Ile Ala Ile
        675                 680                 685

Val Met Val Thr Ile Met Leu Cys Cys Met Thr Ser Cys Cys Ser Cys
    690                 695                 700

Leu Lys Gly Cys Cys Ser Cys Gly Ser Cys Cys Lys Phe Asp Glu Asp
705                 710                 715                 720

Asp Ser Glu Pro Val Leu Lys Gly Val Lys Leu His Tyr Thr
                725                 730
```

<210> SEQ ID NO 36
<211> LENGTH: 4241
<212> TYPE: RNA
<213> ORGANISM: Artificial Sequence
<220> FEATURE:
<223> OTHER INFORMATION: Synthetic

<400> SEQUENCE: 36

```
gggaaauaag agagaaaaga agaguaagaa gaaauauaag accccggcgc cgccaccaug      60

uuccugauca ucuucauccu gcccaccacc cuggccguga ucggcgacuu caacugcacc     120

aacagcuuca ucaacgacua caacaagacc aucccucgga ucagcgaaga cgugguggac     180

gugucccugg gccugggcac cuacuacgug cugaaccggg uguaccugaa caccacacug     240

cuguucaccg gcuacuuccc caagagcggc gccaacuucc gggaccuggc ccugaagggc     300

agcaucuacc ugagcaccuu gugguacaag ccucccuucc ugagcgacuu caauaacggc     360

aucuucucua aggugaagaa caccaagcug uacguaaaca acacccugua cagcgaguuc     420

agcaccaucg ugaucggcag cguguucguc aacaccagcu acaccaucgu ggugcagccc     480
```

-continued

```
cacaacggca uccuggagau caccgccugc caguacacca ugugcgagua cccucacacc    540
gugugcaaga gcaagggcuc cauccggaac gagagcuggc acaucgacag cagcgagccg    600
cugugccugu ucaagaagaa cuucaccuac aacgugagcg ccgacuggcu guacuuccac    660
uucuaccagg agcggggcgu guucuacgcc uacuacgccg acgugggcau gccaaccacc    720
uuccuguuca gccuguaccu gggcaccauc cugagccacu acuacgugau gccccugacc    780
ugcaacgcca ucagcucaaa caccgacaac gagacccugg aguacugggu gacuccacug    840
agccggcggc aguaccugcu gaacuucgac gagcacggcg ugaucaccaa cgccguggac    900
ugcgcccugg acccucugag cgagaccaag ugcacccuga agagcuucac cguggagaag    960
ggcaucuacc agaccagcgg cuucaccgug aagcccguag ccaccgugua ccggcggauc   1020
cccaaccugc ccgacugcga caucgacaac uggcugaaca acgucagcgu gcccagccca   1080
cugaacuggg agcggcggau cuucagcaac ugcaacuuca aucugagcac ccugcugcgg   1140
cuggugcacg uggacagcuu cagcugcaac aaccuggaca agagcaagau cuucgguagc   1200
ugcuucaaca gcaucaccgu ggacaaguuc gccaucccua accggcggcg ggacgaucug   1260
cagcugggca gcagcggcuu ccugcagagc agcaacuaca agaucgacau cagcagcuca   1320
agcugccagc uguacuacag ccugccccug gugaacguga ccaucaacaa cuucaacccc   1380
agcagcugga accggcggua cggcuucggc agcuucaacc ugagcagcua cgacguggug   1440
uacagcgacc acugcuucag cgugaacagc gacuucugcc ccugugccga cccuagcgug   1500
gugaacagcu gcgccaagag caagccuccc agcgccauuu gccccgccgg caccaaguac   1560
cggcacugcg accuggacac cacccuguac gugaagaacu ggugccggug cagcugccug   1620
cccgacccca ucagcaccua cagccccaac accugucccc agaagaaggu gguggugggu   1680
aucggcgagc acugucccgg ccugggcauc aacgaggaga agugcggcac ccagcugaac   1740
cacagcagcu gcuucuguag ccccgacgcc uuccugggcu ggagcuucga cagcugcauc   1800
agcaacaacc ggugcaacau cuuuagcaac uucaucuuca acggaaucaa cagcggcacc   1860
accugcagca acgaccugcu guauagcaac accgagauca gcaccggcgu gugcgugaac   1920
uacgaccugu acggcaucac cggccagggc aucuucaagg aggugagcgc cgccuacuac   1980
aacaacuggc agaaccugcu guacgacagc aacggcaaca ucaucggcuu caaggacuuu   2040
cugaccaaca agaccuacac cauccugccc ugcuacagcg gcggcgugag cgugaucacc   2100
ccaggcacca acaccagcaa ccagguggcc gugcuguacc aggacgugaa cugcaccgag   2160
gugcccgugg ccauccacgc cgaccagcug acacccaccu ggcgggucua cagcaccggc   2220
agcaacgugu uccagacccg ggccgguugc cugaucggcg ccgagcacgu gaacaacagc   2280
uacgagugcg acauccccau cggcgccggc aucugugcca gcuaccagac ccagaccaau   2340
ucaccccgga gggcaaggag cguggccagc cagagcauca ucgccuacac caugagccug   2400
ggcgccgaga acagcguggc cuacagcaac aacagcaucg ccaucccccac caacuucacc   2460
aucagcguga ccaccgagau ucugcccgug agcaugacca agaccagcgu ggacugcacc   2520
auguacaucu gcggcgacag caccgagugc agcaaccugc ugcugcagua cggcagcuuc   2580
ugcacccagc ugaaccgggc ccugaccggc aucgccgugg agcaggacaa gaacacccag   2640
gagguguucg cccaggugaa gcagaucuac aagaccccuc ccaucaagga cuucggcggc   2700
uucaacuuca gccagauccu gcccgacccc agcaagccca gcaagcggag cuucaucgag   2760
gaccugcugu ucaacaaggu gacccuagcc gacgccggcu ucaucaagca guacggcgac   2820
ugccucggcg acauagccgc ccgggaccug aucugcgccc agaaguucaa cggccugacc   2880
```

gugcugccuc cccugcugac cgacgagaug aucgcccagu acaccagcgc ccuguuagcc 2940
ggaaccauca ccagcggcug gacuuucggc gcuggagccg cucugcagau ccccuucgcc 3000
augcagaugg ccuaccgguu caacggcauc ggcgugaccc agaacgugcu guacgagaac 3060
cagaagcuga ucgccaacca guucaacagc gccaucggca agauccagga cagccugagc 3120
agcaccgcua gcgcccuggg caagcugcag gacguggug a accagaacgc ccaggcccug 3180
aacacccugg ugaagcagcu gagcagcaac uucggcgcca ucagcagcgu gcugaacgac 3240
auccugagcc ggcuggaccc ucccgaggcc gaggugcaga ucgaccggcu gaucacuggc 3300
cggcugcaga gccugcagac cuacgugacc cagcagcuga uccgggccgc cgagauucgg 3360
gccagcgcca accuggccgc caccaagaug agcgagugcg ugcugggcca gagcaagcgg 3420
guggacuucu gcggcaaggg cuaccaccug augagcuuuc cccagagcgc accccacgga 3480
gugguguucc ugcacgugac cuacgugccc gcccaggaga agaacuucac caccgcccca 3540
gccaucugcc acgacggcaa ggcccacuuu ccccgggagg gcguguucgu gagcaacggc 3600
acccacuggu ucgugaccca gcggaacuuc uacgagcccc agaucaucac caccgacaac 3660
accuucguga gcggcaacug cgacguggug aucggcaucg ugaacaacac cguguacgau 3720
ccccugcagc ccgagcugga cagcuucaag gaggagcugg acaaguacuu caagaaucac 3780
accagccccg acguggaccu gggcgacauc agcggcauca acgccagcgu ggugaacauc 3840
cagaaggaga ucgaucggcu gaacgaggug gccaagaacc ugaacgagag ccugaucgac 3900
cugcaggagc ugggcaagua cgagcaguac aucaaguggc ccugguacau cuggcugggc 3960
uucaucgccg gccugaucgc caucgugaug gugaccauca ugcugugcug caugaccagc 4020
ugcugcagcu gccugaaggg cuguugcagc ugcggcagcu gcugcaaguu cgacgaggac 4080
gacagcgagc ccgugcugaa gggcgugaag cugcacuaca ccugauaaua ggcuggagcc 4140
ucgguggccu agcuucuugc cccuugggcc ucccccccagc cccuccuccc cuuccugcac 4200
ccguaccccc guggucuuug aauaaagucu gagugggcgg c 4241

<210> SEQ ID NO 37
<211> LENGTH: 4065
<212> TYPE: RNA
<213> ORGANISM: Artificial Sequence
<220> FEATURE:
<223> OTHER INFORMATION: Synthetic

<400> SEQUENCE: 37
auguuccuga ucaucuucau ccugcccacc acccuggccg ugaucggcga cuucaacugc 60
accaacagcu ucaucaacga cuacaacaag accaucccuc ggaucagcga agacguggug 120
gacguguccc ugggccuggg caccuacuac gugcugaacc ggguguaccu gaacaccaca 180
cugcuguuca ccggcuacuu ccccaagagc ggcgccaacu uccgggaccu ggcccugaag 240
ggcagcaucu accugagcac cuuguggua c aagccucccu uccugagcga cuucaauaac 300
ggcaucuucu cuaaggugaa gaacaccaag cuguacguaa acaacacccu guacagcgag 360
uucagcacca ucgugaucgg cagcguguuc gucaacacca gcuacaccau cguggugcag 420
ccccacaacg gcauccugga gaucaccgcc ugccaguaca ccaugugcga guacccucac 480
accgugugca agagcaaggg cuccauccgg aacgagagcu ggcacaucga cagcagcgag 540
ccgcugugcc uguucaagaa gaacuucacc uacaacguga gcgccgacug gcuguacuuc 600
cacuucuacc aggagcgggg cguguucuac gccuacuacg ccgacguggg caugccaacc 660

-continued

```
accuuccugu ucagccugua ccugggcacc auccugagcc acuacuacgu gaugccccug    720
accugcaacg ccaucagcuc aaacaccgac aacgagaccc uggaguacug ggugacucca    780
cugagccggc ggcaguaccu gcugaacuuc gacgagcacg gcgugaucac caacgccgug    840
gacugcgccc uggacccucu gagcgagacc aagugcaccc ugaagagcuu caccguggag    900
aagggcaucu accagaccag cggcuucacc gugaagcccg uagccaccgu guaccggcgg    960
auccccaacc ugcccgacug cgacaucgac aacuggcuga acaacgucag cgugcccagc   1020
ccacugaacu gggagcggcg gaucuucagc aacugcaacu ucaaucugag cacccugcug   1080
cggcuggugc acguggacag cuucagcugc aacaaccugg acaagagcaa gaucuucggu   1140
agcugcuuca acagcaucac cguggacaag uucgccaucc cuaaccggcg gcgggacgau   1200
cugcagcugg gcagcagcgg cuuccugcag agcagcaacu acaagaucga caucagcagc   1260
ucaagcugcc agcuguacua cagccugccc cuggugaacg ugaccaucaa caacuucaac   1320
cccagcagcu ggaaccggcg guacggcuuc ggcagcuuca accugagcag cuacgacgug   1380
guguacagcg accacugcuu cagcgugaac agcgacuucu gccccugugc cgacccuagc   1440
gugguggaaca gcugcgccaa gagcaagccu cccagcgcca uuugccccgc cggcaccaag   1500
uaccggcacu gcgaccugga caccacccug uacgugaaga acuggugccg gugcagcugc   1560
cugcccgacc ccaucagcac cuacagcccc aacaccuguc cccagaagaa gguggguggug   1620
gguaucggcg agcacugucc cggccugggc aucaacgagg agaagugcgg cacccagcug   1680
aaccacagca gcugcuucug uagccccgac gccuuccugg gcuggagcuu cgacagcugc   1740
aucagcaaca accggugcaa caucuuuagc aacuucaucu ucaacggaau caacagcggc   1800
accaccugca gcaacgaccu gcuguauagc aacaccgaga ucagcaccgg cgugugcgug   1860
aacuacgacc uguacggcau caccggccag ggcaucuuca aggaggugag cgccgccuac   1920
uacaacaacu ggcagaaccu gcuguacgac agcaacggca acaucaucgg cuucaaggac   1980
uuucugacca acaagaccua caccauccug cccugcuaca gcggcggcgu gagcgugauc   2040
accccaggca ccaacaccag caaccaggug gccgugcugu accaggacgu gaacugcacc   2100
gaggugcccg uggccaucca cgccgaccag cugacaccca ccuggcgggu cuacagcacc   2160
ggcagcaacg uguuccagac ccgggccggu ugccugaucg gcgccgagca cgugaacaac   2220
agcuacgagu gcgacauccc caucggcgcc ggcaucugug ccagcuacca gacccagacc   2280
aauucacccc ggagggcaag gagcguggcc agccagagca ucaucgccua caccaugagc   2340
cugggcgccg agaacagcgu ggccuacagc aacaacagca ucgccauccc caccaacuuc   2400
accaucagcg ugaccaccga gauucugccc gugagcauga ccaagaccag cguggacugc   2460
accauguaca ucugcggcga cagcaccgag ugcagcaacc ugcugcugca guacggcagc   2520
uucugcaccc agcugaaccg ggcccugacc ggcaucgccg uggagcagga caagaacacc   2580
caggaggugu ucgcccaggu gaagcagauc uacaagaccc cucccaucaa ggacuucggc   2640
ggcuucaacu ucagccagau ccugcccgac cccagcaagc ccagcaagcg gagcuucauc   2700
gaggaccugc uguucaacaa ggugacccua gccgacgccg gcuucaucaa gcaguacggc   2760
gacugccucg gcgacauagc cgcccgggac cugaucugcg cccagaaguu caacggccug   2820
accgugcugc cuccccugcu gaccgacgag augaucgccc aguacaccag cgcccuguua   2880
gccggaacca ucaccagcgg cuggacuuuc ggcgcuggag ccgcucugca gauccccuuc   2940
gccaugcaga uggccuaccg guucaacggc aucggcguga cccagaacgu gcuguacgag   3000
aaccagaagc ugaucgccaa ccaguucaac agcgccaucg gcaagaucca ggacagccug   3060
```

```
agcagcaccg cuagcgcccu gggcaagcug caggacgugg ugaaccagaa cgcccaggcc   3120

cugaacaccc uggugaagca gcugagcagc aacuucggcg ccaucagcag cgugcugaac   3180

gacauccuga gccggcugga cccucccgag gccgaggugc agaucgaccg gcugaucacu   3240

ggccggcugc agagccugca gaccuacgug acccagcagc ugauccgggc cgccgagauu   3300

cgggccagcg ccaaccuggc cgccaccaag augagcgagu gcgugcuggg ccagagcaag   3360

cggguggacu ucugcggcaa gggcuaccac cugaugagcu uuccccagag cgcaccccac   3420

ggaguggugu uccugcacgu gaccuacgug cccgcccagg agaagaacuu caccaccgcc   3480

ccagccaucu gccacgacgg caaggcccac uuuccccggg agggcguguu cgugagcaac   3540

ggcacccacu gguucgugac ccagcggaac uucuacgagc cccagaucau caccaccgac   3600

aacaccuucg ugagcggcaa cugcgacgug gugaucggca ucgugaacaa caccguguac   3660

gauccccugc agcccgagcu ggacagcuuc aaggaggagc uggacaagua cuucaagaau   3720

cacaccagcc ccgacgugga ccugggcgac aucagcggca ucaacgccag cgugggugaac  3780

auccagaagg agaucgaucg gcugaacgag guggccaaga accugaacga gagccugauc   3840

gaccugcagg agcugggcaa guacgagcag uacaucaagu ggcccuggua caucuggcug   3900

ggcuucaucg ccggccugau cgccaucgug auggugacca ucaugcugug cugcaugacc   3960

agcugcugca gcugccugaa gggcuguugc agcugcggca gcugcugcaa guucgacgag   4020

gacgacagcg agcccgugcu gaagggcgug aagcugcacu acacc                   4065
```

<210> SEQ ID NO 38
<211> LENGTH: 1355
<212> TYPE: PRT
<213> ORGANISM: Artificial Sequence
<220> FEATURE:
<223> OTHER INFORMATION: Synthetic

<400> SEQUENCE: 38

```
Met Phe Leu Ile Ile Phe Ile Leu Pro Thr Thr Leu Ala Val Ile Gly
1               5                   10                  15

Asp Phe Asn Cys Thr Asn Ser Phe Ile Asn Asp Tyr Asn Lys Thr Ile
            20                  25                  30

Pro Arg Ile Ser Glu Asp Val Val Asp Val Ser Leu Gly Leu Gly Thr
        35                  40                  45

Tyr Tyr Val Leu Asn Arg Val Tyr Leu Asn Thr Thr Leu Leu Phe Thr
    50                  55                  60

Gly Tyr Phe Pro Lys Ser Gly Ala Asn Phe Arg Asp Leu Ala Leu Lys
65                  70                  75                  80

Gly Ser Ile Tyr Leu Ser Thr Leu Trp Tyr Lys Pro Pro Phe Leu Ser
                85                  90                  95

Asp Phe Asn Asn Gly Ile Phe Ser Lys Val Lys Asn Thr Lys Leu Tyr
            100                 105                 110

Val Asn Asn Thr Leu Tyr Ser Glu Phe Ser Thr Ile Val Ile Gly Ser
        115                 120                 125

Val Phe Val Asn Thr Ser Tyr Thr Ile Val Val Gln Pro His Asn Gly
    130                 135                 140

Ile Leu Glu Ile Thr Ala Cys Gln Tyr Thr Met Cys Glu Tyr Pro His
145                 150                 155                 160

Thr Val Cys Lys Ser Lys Gly Ser Ile Arg Asn Glu Ser Trp His Ile
                165                 170                 175

Asp Ser Ser Glu Pro Leu Cys Leu Phe Lys Lys Asn Phe Thr Tyr Asn
```

```
            180                 185                 190

Val Ser Ala Asp Trp Leu Tyr Phe His Phe Tyr Gln Glu Arg Gly Val
        195                 200                 205

Phe Tyr Ala Tyr Tyr Ala Asp Val Gly Met Pro Thr Thr Phe Leu Phe
    210                 215                 220

Ser Leu Tyr Leu Gly Thr Ile Leu Ser His Tyr Tyr Val Met Pro Leu
225                 230                 235                 240

Thr Cys Asn Ala Ile Ser Ser Asn Thr Asp Asn Glu Thr Leu Glu Tyr
                245                 250                 255

Trp Val Thr Pro Leu Ser Arg Arg Gln Tyr Leu Leu Asn Phe Asp Glu
            260                 265                 270

His Gly Val Ile Thr Asn Ala Val Asp Cys Ala Leu Asp Pro Leu Ser
        275                 280                 285

Glu Thr Lys Cys Thr Leu Lys Ser Phe Thr Val Glu Lys Gly Ile Tyr
    290                 295                 300

Gln Thr Ser Gly Phe Thr Val Lys Pro Val Ala Thr Val Tyr Arg Arg
305                 310                 315                 320

Ile Pro Asn Leu Pro Asp Cys Asp Ile Asp Asn Trp Leu Asn Asn Val
                325                 330                 335

Ser Val Pro Ser Pro Leu Asn Trp Glu Arg Arg Ile Phe Ser Asn Cys
            340                 345                 350

Asn Phe Asn Leu Ser Thr Leu Leu Arg Leu Val His Val Asp Ser Phe
        355                 360                 365

Ser Cys Asn Asn Leu Asp Lys Ser Lys Ile Phe Gly Ser Cys Phe Asn
    370                 375                 380

Ser Ile Thr Val Asp Lys Phe Ala Ile Pro Asn Arg Arg Arg Asp Asp
385                 390                 395                 400

Leu Gln Leu Gly Ser Ser Gly Phe Leu Gln Ser Ser Asn Tyr Lys Ile
                405                 410                 415

Asp Ile Ser Ser Ser Ser Cys Gln Leu Tyr Tyr Ser Leu Pro Leu Val
            420                 425                 430

Asn Val Thr Ile Asn Asn Phe Asn Pro Ser Ser Trp Asn Arg Arg Tyr
        435                 440                 445

Gly Phe Gly Ser Phe Asn Leu Ser Ser Tyr Asp Val Val Tyr Ser Asp
    450                 455                 460

His Cys Phe Ser Val Asn Ser Asp Phe Cys Pro Cys Ala Asp Pro Ser
465                 470                 475                 480

Val Val Asn Ser Cys Ala Lys Ser Lys Pro Pro Ser Ala Ile Cys Pro
                485                 490                 495

Ala Gly Thr Lys Tyr Arg His Cys Asp Leu Asp Thr Thr Leu Tyr Val
            500                 505                 510

Lys Asn Trp Cys Arg Cys Ser Cys Leu Pro Asp Pro Ile Ser Thr Tyr
        515                 520                 525

Ser Pro Asn Thr Cys Pro Gln Lys Lys Val Val Val Gly Ile Gly Glu
    530                 535                 540

His Cys Pro Gly Leu Gly Ile Asn Glu Glu Lys Cys Gly Thr Gln Leu
545                 550                 555                 560

Asn His Ser Ser Cys Phe Cys Ser Pro Asp Ala Phe Leu Gly Trp Ser
                565                 570                 575

Phe Asp Ser Cys Ile Ser Asn Asn Arg Cys Asn Ile Phe Ser Asn Phe
            580                 585                 590

Ile Phe Asn Gly Ile Asn Ser Gly Thr Thr Cys Ser Asn Asp Leu Leu
        595                 600                 605
```

-continued

```
Tyr Ser Asn Thr Glu Ile Ser Thr Gly Val Cys Val Asn Tyr Asp Leu
    610                 615                 620

Tyr Gly Ile Thr Gly Gln Gly Ile Phe Lys Glu Val Ser Ala Ala Tyr
625                 630                 635                 640

Tyr Asn Asn Trp Gln Asn Leu Leu Tyr Asp Ser Asn Gly Asn Ile Ile
                645                 650                 655

Gly Phe Lys Asp Phe Leu Thr Asn Lys Thr Tyr Thr Ile Leu Pro Cys
            660                 665                 670

Tyr Ser Gly Gly Val Ser Val Ile Thr Pro Gly Thr Asn Thr Ser Asn
        675                 680                 685

Gln Val Ala Val Leu Tyr Gln Asp Val Asn Cys Thr Glu Val Pro Val
    690                 695                 700

Ala Ile His Ala Asp Gln Leu Thr Pro Thr Trp Arg Val Tyr Ser Thr
705                 710                 715                 720

Gly Ser Asn Val Phe Gln Thr Arg Ala Gly Cys Leu Ile Gly Ala Glu
                725                 730                 735

His Val Asn Asn Ser Tyr Glu Cys Asp Ile Pro Ile Gly Ala Gly Ile
            740                 745                 750

Cys Ala Ser Tyr Gln Thr Gln Thr Asn Ser Pro Arg Arg Ala Arg Ser
        755                 760                 765

Val Ala Ser Gln Ser Ile Ile Ala Tyr Thr Met Ser Leu Gly Ala Glu
    770                 775                 780

Asn Ser Val Ala Tyr Ser Asn Asn Ser Ile Ala Ile Pro Thr Asn Phe
785                 790                 795                 800

Thr Ile Ser Val Thr Thr Glu Ile Leu Pro Val Ser Met Thr Lys Thr
                805                 810                 815

Ser Val Asp Cys Thr Met Tyr Ile Cys Gly Asp Ser Thr Glu Cys Ser
            820                 825                 830

Asn Leu Leu Leu Gln Tyr Gly Ser Phe Cys Thr Gln Leu Asn Arg Ala
        835                 840                 845

Leu Thr Gly Ile Ala Val Glu Gln Asp Lys Asn Thr Gln Glu Val Phe
    850                 855                 860

Ala Gln Val Lys Gln Ile Tyr Lys Thr Pro Pro Ile Lys Asp Phe Gly
865                 870                 875                 880

Gly Phe Asn Phe Ser Gln Ile Leu Pro Asp Pro Ser Lys Pro Ser Lys
                885                 890                 895

Arg Ser Phe Ile Glu Asp Leu Leu Phe Asn Lys Val Thr Leu Ala Asp
            900                 905                 910

Ala Gly Phe Ile Lys Gln Tyr Gly Asp Cys Leu Gly Asp Ile Ala Ala
        915                 920                 925

Arg Asp Leu Ile Cys Ala Gln Lys Phe Asn Gly Leu Thr Val Leu Pro
    930                 935                 940

Pro Leu Leu Thr Asp Glu Met Ile Ala Gln Tyr Thr Ser Ala Leu Leu
945                 950                 955                 960

Ala Gly Thr Ile Thr Ser Gly Trp Thr Phe Gly Ala Gly Ala Ala Leu
                965                 970                 975

Gln Ile Pro Phe Ala Met Gln Met Ala Tyr Arg Phe Asn Gly Ile Gly
            980                 985                 990

Val Thr Gln Asn Val Leu Tyr Glu  Asn Gln Lys Leu Ile  Ala Asn Gln
        995                 1000                1005

Phe Asn  Ser Ala Ile Gly Lys  Ile Gln Asp Ser Leu  Ser Ser Thr
    1010                1015                1020
```

```
Ala Ser  Ala Leu Gly Lys Leu  Gln Asp Val Val Asn  Gln Asn Ala
    1025                 1030                 1035

Gln Ala  Leu Asn Thr Leu Val  Lys Gln Leu Ser Ser  Asn Phe Gly
    1040                 1045                 1050

Ala Ile  Ser Ser Val Leu Asn  Asp Ile Leu Ser Arg  Leu Asp Pro
    1055                 1060                 1065

Pro Glu  Ala Glu Val Gln Ile  Asp Arg Leu Ile Thr  Gly Arg Leu
    1070                 1075                 1080

Gln Ser  Leu Gln Thr Tyr Val  Thr Gln Gln Leu Ile  Arg Ala Ala
    1085                 1090                 1095

Glu Ile  Arg Ala Ser Ala Asn  Leu Ala Ala Thr Lys  Met Ser Glu
    1100                 1105                 1110

Cys Val  Leu Gly Gln Ser Lys  Arg Val Asp Phe Cys  Gly Lys Gly
    1115                 1120                 1125

Tyr His  Leu Met Ser Phe Pro  Gln Ser Ala Pro His  Gly Val Val
    1130                 1135                 1140

Phe Leu  His Val Thr Tyr Val  Pro Ala Gln Glu Lys  Asn Phe Thr
    1145                 1150                 1155

Thr Ala  Pro Ala Ile Cys His  Asp Gly Lys Ala His  Phe Pro Arg
    1160                 1165                 1170

Glu Gly  Val Phe Val Ser Asn  Gly Thr His Trp Phe  Val Thr Gln
    1175                 1180                 1185

Arg Asn  Phe Tyr Glu Pro Gln  Ile Ile Thr Thr Asp  Asn Thr Phe
    1190                 1195                 1200

Val Ser  Gly Asn Cys Asp Val  Val Ile Gly Ile Val  Asn Asn Thr
    1205                 1210                 1215

Val Tyr  Asp Pro Leu Gln Pro  Glu Leu Asp Ser Phe  Lys Glu Glu
    1220                 1225                 1230

Leu Asp  Lys Tyr Phe Lys Asn  His Thr Ser Pro Asp  Val Asp Leu
    1235                 1240                 1245

Gly Asp  Ile Ser Gly Ile Asn  Ala Ser Val Val Asn  Ile Gln Lys
    1250                 1255                 1260

Glu Ile  Asp Arg Leu Asn Glu  Val Ala Lys Asn Leu  Asn Glu Ser
    1265                 1270                 1275

Leu Ile  Asp Leu Gln Glu Leu  Gly Lys Tyr Glu Gln  Tyr Ile Lys
    1280                 1285                 1290

Trp Pro  Trp Tyr Ile Trp Leu  Gly Phe Ile Ala Gly  Leu Ile Ala
    1295                 1300                 1305

Ile Val  Met Val Thr Ile Met  Leu Cys Cys Met Thr  Ser Cys Cys
    1310                 1315                 1320

Ser Cys  Leu Lys Gly Cys Cys  Ser Cys Gly Ser Cys  Cys Lys Phe
    1325                 1330                 1335

Asp Glu  Asp Asp Ser Glu Pro  Val Leu Lys Gly Val  Lys Leu His
    1340                 1345                 1350

Tyr Thr
    1355
```

<210> SEQ ID NO 39
<211> LENGTH: 4247
<212> TYPE: RNA
<213> ORGANISM: Artificial Sequence
<220> FEATURE:
<223> OTHER INFORMATION: Synthetic

<400> SEQUENCE: 39

-continued

```
gggaaauaag agagaaaaga agaguaagaa gaaauauaag accccggcgc cgccaccaug     60
uuccugaucc ugcugaucag ccugcccacc gccuucgccg ugaucggcga ccugaagugc    120
accagcgaca acaucaacga caaggacacc ggcccaccac ccaucagcac cgacaccgug    180
gacgugacca acggccuggg caccuacuac gugcuggacc ggguguaccu gaacaccacc    240
cuguuccuga acggcuacua ccccaccagc ggcagcaccu accggaauau ggcccugaag    300
ggcagcgugc ugcugagccg gcugugguuc aagccaccau uccugagcga cuucaucaac    360
ggaaucuucg ccaaggugaa gaacaccaag gugaucaagg accgggugau guacagcgag    420
uuccccgcca ucaccauugg caguaccuuc gugaacacca gcuacagcgu gguggugcag    480
ccccggacca ucaacagcac ccaggacggc gacaacaagc ugcagggccu gcuggaggug    540
agcgugugcc aguacaacau gugcgaguac ccucagacca ucugccaccc caaccugggc    600
aaccaccgga aggagcugug gcaccuggac accggcgugg ugagcugccu guacaagcgg    660
aacuucaccu acgacguaaa cgccgacuac cuguacuucc acuucuacca ggagggcggc    720
accuucuacg ccuacuucac cgacacgggc gugguggacca aguuccuguu caacguguac    780
cugggcaugg cccugagcca cuacuacgug augccccuga ccuguaacag caagcugacc    840
cuggaguacu gggugacccc ucugaccagc cggcaguacc ugcuggccuu caaccaggac    900
ggcaucaucu ucaacgccgu ggacugcgcc cuggacccuc ugagcgagac caagugcacc    960
cugaagagcu ucaccgugga gaagggcauc uaccagacca acggcuacac cgugcagccc   1020
aucgccgacg uguaccggcg gaagcccaac cugcccaacu gcaacaucga ggccuggcug   1080
aacgacaaga gcgugcccuc gccccugaac ugggagcgga agaccuucag caacugcaac   1140
uucaacauga gcagucugau gagcuucauc caggccgaca gcuucaccug caacaacauc   1200
gacgccgcca agaucuacgg caugugcuuc agcagcauca ccaucgacaa guuugccauc   1260
cccaacggcc ggaaggugga ccugcagcug ggcaaccugg gcuaccugca gagcuucaac   1320
uaccggaucg acaccaccgc caccucuugc cagcuguacu acaaccugcc cgccgccaac   1380
gugagcguga gccgguucaa ccccagcacc uggaacaagc gguucggcuu cauugaggac   1440
agcguguuca aaccccggcc cgcaggagua cugaccaacc acgacguggu guacgcccag   1500
cacugcuuca aggcacccaa gaacuucugc cccugcaagc ugaacggcag cuguguggc    1560
ucuggccccg guaagaacaa cggcauaggg acuugcccgg cagggaccaa cuaccugacc   1620
ugcgacaacc ugugcacacc cgaccccauc accuucaccg gcaccuacaa guguccccag   1680
accaagagcc ugguggggcau cggcgagcac ugcagcggcc uggccgugaa gagcgacuac   1740
ugcggcggca acagcugcac cugucggccc caggccuucc ugggcuggag cgccgacagc   1800
ugccugcagg gcgacaagug caacaucuuu gccaacuuca uccugcacga cgugaacagc   1860
ggccugaccu gcagcaccga ccugcagaag gccaacaccg acaucauccu gggcgugugc   1920
gugaacuacg acuuguacgg cauccugggc cagggcaucu ucguggaggu gaacgccacc   1980
uacuacaaca gcuggcagaa ccugcuguac gacagcaacg gcaaccugua cggcuuccgg   2040
gacuacauca ucaaccggac cuucaugauc cggagcugcu acagcggcgg cgugagcgug   2100
aucaccccag gcaccaacac cagcaaccag guggccgugc uguaccagga cgugaacugc   2160
accgaggugc ccguggccau ccacgccgac cagcugacac ccaccuggcg ggucuacagc   2220
accggcagca acguguucca gacccgggcc gguugccuga ucggcgccga gcacgugaac   2280
aacagcuacg agugcgacau ccccaucggc gccggcaucu gugccagcua ccagacccag   2340
accaauucac cccggagggc aaggagcgug gccagccaga gcaucaucgc cuacaccaug   2400
```

agccugggcg ccgagaacag cguggccuac agcaacaaca gcaucgccau ccccaccaac 2460
uucaccauca gcgugaccac cgagauucug cccgugagca ugaccaagac cagcguggac 2520
ugcaccaugu acaucugcgg cgacagcacc gagugcagca accugcugcu gcaguacggc 2580
agcuucugca cccagcugaa ccgggcccug accggcaucg ccguggagca ggacaagaac 2640
acccaggagg uguucgccca ggugaagcag aucuacaaga ccccucccau caaggacuuc 2700
ggcggcuuca acuucagcca gauccugccc gaccccagca agcccagcaa gcggagcuuc 2760
aucgaggacc ugcuguucaa caaggugacc cuagccgacg ccggcuucau caagcaguac 2820
ggcgacugcc ucggcgacau agccgcccgg gaccugaucu gcgcccagaa guucaacggc 2880
cugaccgugc ugccuccccu gcugaccgac gagaugaucg cccaguacac cagcgcccug 2940
uuagccggaa ccaucaccag cggcuggacu uucggcgcug gagccgcucu gcagaucccc 3000
uucgccaugc agauggccua ccgguucaac ggcaucggcg ugacccagaa cgugcuguac 3060
gagaaccaga agcugaucgc caaccaguuc aacagcgcca ucggcaagau ccaggacagc 3120
cugagcagca ccgcuagcgc ccugggcaag cugcaggacg uggugaacca gaacgcccag 3180
gcccugaaca cccuggugaa gcagcugagc agcaacuucg gcgccaucag cagcgugcug 3240
aacgacaucc ugagccggcu ggacccuccc gaggccgagg ugcagaucga ccggcugauc 3300
acuggccggc ugcagagccu gcagaccuac gugacccagc agcugauccg ggccgccgag 3360
auucgggcca gcgccaaccu ggccgccacc aagaugagcg agugcgugcu gggccagagc 3420
aagcgggugg acuucugcgg caagggcuac caccugauga gcuuucccca gagcgcaccc 3480
cacggagugg uguuccugca cgugaccuac gugcccgccc aggagaagaa cuucaccacc 3540
gccccagcca ucugccacga cggcaaggcc cacuuucccc gggagggcgu guucgugagc 3600
aacggcaccc acugguucgu gacccagcgg aacuucuacg agccccagau caucaccacc 3660
gacaacaccu ucgugagcgg caacugcgac guggugaucg gcaucgugaa caacaccgug 3720
uacgaucccc ugcagcccga gcuggacagc uucaaggagg agcuggacaa guacuucaag 3780
aaucacacca gccccgacgu ggaccugggc gacaucagcg gcaucaacgc cagcguggug 3840
aacauccaga aggagaucga ucggcugaac gagguggcca agaaccugaa cgagagccug 3900
aucgaccugc aggagcuggg caaguacgag caguacauca aguggcccug guacaucugg 3960
cugggcuuca ucgccggccu gaucgccauc gugaugguga ccaucaugcu gugcugcaug 4020
accagcugcu gcagcugccu gaagggcugu ugcagcugcg gcagcugcug caaguucgac 4080
gaggacgaca gcgagcccgu gcugaagggc gugaagcugc acuacaccug auaauaggcu 4140
ggagccucgg uggccuagcu ucuugccccu ugggccuccc cccagccccu ccuccccuuc 4200
cugcacccgu accccgugg ucuuugaaua aagucugagu gggcggc 4247

<210> SEQ ID NO 40
<211> LENGTH: 4071
<212> TYPE: RNA
<213> ORGANISM: Artificial Sequence
<220> FEATURE:
<223> OTHER INFORMATION: Synthetic

<400> SEQUENCE: 40
auguuccuga uccugcugau cagccugccc accgccuucg ccgugaucgg cgaccugaag 60
ugcaccagcg acaacaucaa cgacaaggac accggcccac cacccaucag caccgacacc 120
guggacguga ccaacggccu gggcaccuac uacgugcugg accgggugua ccugaacacc 180

-continued

```
acccuguucc ugaacggcua cuaccccacc agcggcagca ccuaccggaa uauggcccug    240
aagggcagcg ugcugcugag ccggcugugg uucaagccac cauuccugag cgacuucauc    300
aacggaaucu ucgccaaggu gaagaacacc aaggugauca aggaccgggu gauguacagc    360
gaguuccccg ccaucaccau uggcaguacc uucgugaaca ccagcuacag cgugguggug    420
cagccccgga ccaucaacag cacccaggac ggcgacaaca agcugcaggg ccugcuggag    480
gugagcgugu gccaguacaa caugugcgag uacccucaga ccaucugcca ccccaaccug    540
ggcaaccacc ggaaggagcu guggcaccug gacaccggcg uggugagcug ccuguacaag    600
cggaacuuca ccuacgacgu aaacgccgac uaccuguacu uccacuucua ccaggagggc    660
ggcaccuucu acgccuacuu caccgacacg ggcgugguga ccaaguuccu guucaacgug    720
uaccugggca uggcccugag ccacuacuac gugaugcccc ugaccuguaa cagcaagcug    780
acccuggagu acugggugac cccucugacc agccggcagu accugcuggc cuucaaccag    840
gacggcauca ucuucaacgc cguggacugc gcccuggacc cucugagcga gaccaagugc    900
acccugaaga gcuucaccgu ggagaagggc aucuaccaga ccaacggcua caccgugcag    960
cccaucgccg acguguaccg gcggaagccc aaccugccca acugcaacau cgaggccugg   1020
cugaacgaca agagcgugcc cucgccccug aacugggagc ggaagaccuu cagcaacugc   1080
aacuucaaca ugagcagucu gaugagcuuc auccaggccg acagcuucac cugcaacaac   1140
aucgacgccg ccaagaucua cggcaugugc uucagcagca ucaccaucga caaguuugcc   1200
auccccaacg gccggaaggu ggaccugcag cugggcaacc ugggcuaccu gcagagcuuc   1260
aacuaccgga ucgacaccac cgccaccucu ugccagcugu acuacaaccu gcccgccgcc   1320
aacgugagcg ugagccgguu caaccccagc accuggaaca agcgguucgg cuucauugag   1380
gacagcgugu ucaaaccccg gcccgcagga guacugacca accacgacgu ggugyacgcc   1440
cagcacugcu ucaaggcacc caagaacuuc ugccccugca agcugaacgg cagcugugug   1500
ggcucuggcc ccgguaagaa caacggcaua gggacuugcc cggcagggac caacuaccug   1560
accugcgaca accugugcac acccgacccc aucaccuuca ccggcaccua caagugucce   1620
cagaccaaga gccugguggg caucggcgag cacugcagcg gccuggccgu gaagagcgac   1680
uacugcggcg gcaacagcug caccugucgg ccccaggccu uccugggcug gagcgccgac   1740
agcugccugc agggcgacaa gugcaacauc uuugccaacu ucauccugca cgacgugaac   1800
agcggccuga ccugcagcac cgaccugcag aaggccaaca ccgacaucau ccugggcgug   1860
ugcgugaacu acgacuugua cggcauccug ggccagggca ucuucgugga ggugaacgcc   1920
accuacuaca acagcuggca gaaccugcug uacgacagca acggcaaccu guacggcuuc   1980
cgggacuaca ucaucaaccg gaccuucaug auccggagcu gcuacagcgg cggcgugagc   2040
gugaucaccc caggcaccaa caccagcaac cagguggccg ugcuguacca ggacgugaac   2100
ugcaccgagg ugcccguggc cauccacgcc gaccagcuga cacccaccug gcggguc uac   2160
agcaccggca gcaacguguu ccagacccgg gccgguugcc ugaucggcgc cgagcacgug   2220
aacaacagcu acgagugcga cauccccauc ggcgccggca ucugugccag cuaccagacc   2280
cagaccaauu caccccggag ggcaaggagc guggccagcc agagcaucau cgccuacacc   2340
augagccugg gcgccgagaa cagcguggcc uacagcaaca acagcaucgc cauccccacc   2400
aacuucacca ucagcgugac caccgagauu cugcccguga gcaugaccaa gaccagcgug   2460
gacugcacca uguacaucug cggcgacagc accgagugca gcaaccugcu gcugcaguac   2520
ggcagcuucu gcacccagcu gaaccgggcc cugaccggca ucgccgugga gcaggacaag   2580
```

```
aacacccagg agguguucgc ccaggugaag cagaucuaca agaccccucc caucaaggac   2640
uucggcggcu ucaacuucag ccagauccug cccgacccca gcaagcccag caagcggagc   2700
uucaucgagg accugcuguu caacaaggug acccuagccg acgccggcuu caucaagcag   2760
uacggcgacu gccucggcga cauagccgcc cgggaccuga ucugcgccca gaaguucaac   2820
ggccugaccg ugcugccucc ccugcugacc gacgagauga ucgcccagua caccagcgcc   2880
cuguuagccg gaaccaucac cagcggcugg acuuucggcg cuggagccgc ucugcagauc   2940
cccuucgcca ugcagauggc cuaccgguuc aacggcaucg gcgugaccca gaacgugcug   3000
uacgagaacc agaagcugau cgccaaccag uucaacagcg ccaucggcaa gauccaggac   3060
agccugagca gcaccgcuag cgcccugggc aagcugcagg acguggugaa ccagaacgcc   3120
caggcccuga acacccuggu gaagcagcug agcagcaacu ucggcgccau cagcagcgug   3180
cugaacgaca uccugagccg gcuggacccu cccgaggccg aggugcagau cgaccggcug   3240
aucacuggcc ggcugcagag ccugcagacc uacgugaccc agcagcugau ccgggccgcc   3300
gagauucggg ccagcgccaa ccuggccgcc accaagauga gcgagugcgu gcugggccag   3360
agcaagcggg uggacuucug cggcaagggc uaccaccuga ugagcuuucc ccagagcgca   3420
ccccacggag uggugguccu gcacgugacc uacgugcccg cccaggagaa gaacuucacc   3480
accgccccag ccaucugcca cgacggcaag gcccacuuuc cccgggaggg cguguucgug   3540
agcaacggca cccacugguu cgugacccag cggaacuucu acgagcccca gaucaucacc   3600
accgacaaca ccuucgugag cggcaacugc gacgugguga ucggcaucgu gaacaacacc   3660
guguacgauc cccugcagcc cgagcuggac agcuucaagg aggagcugga caaguacuuc   3720
aagaaucaca ccagccccga cguggaccug ggcgacauca gcggcaucaa cgccagcgug   3780
gugaacaucc agaaggagau cgaucggcug aacgaggugg ccaagaaccu gaacgagagc   3840
cugaucgacc ugcaggagcu gggcaaguac gagcaguaca ucaaguggcc cugguacauc   3900
uggcugggcu ucaucgccgg ccugaucgcc aucgugaugg ugaccaucau gcugugcugc   3960
augaccagcu gcugcagcug ccugaagggc uguugcagcu gcggcagcug cugcaaguuc   4020
gacgaggacg acagcgagcc cgugcugaag ggcgugaagc ugcacuacac c            4071
```

<210> SEQ ID NO 41
<211> LENGTH: 1357
<212> TYPE: PRT
<213> ORGANISM: Artificial Sequence
<220> FEATURE:
<223> OTHER INFORMATION: Synthetic

<400> SEQUENCE: 41

```
Met Phe Leu Ile Leu Leu Ile Ser Leu Pro Thr Ala Phe Ala Val Ile
1               5                   10                  15

Gly Asp Leu Lys Cys Thr Ser Asp Asn Ile Asn Asp Lys Asp Thr Gly
            20                  25                  30

Pro Pro Pro Ile Ser Thr Asp Thr Val Asp Val Thr Asn Gly Leu Gly
        35                  40                  45

Thr Tyr Tyr Val Leu Asp Arg Val Tyr Leu Asn Thr Thr Leu Phe Leu
    50                  55                  60

Asn Gly Tyr Tyr Pro Thr Ser Gly Ser Thr Tyr Arg Asn Met Ala Leu
65                  70                  75                  80

Lys Gly Ser Val Leu Leu Ser Arg Leu Trp Phe Lys Pro Pro Phe Leu
                85                  90                  95
```

-continued

```
Ser Asp Phe Ile Asn Gly Ile Phe Ala Lys Val Lys Asn Thr Lys Val
            100                 105                 110

Ile Lys Asp Arg Val Met Tyr Ser Glu Phe Pro Ala Ile Thr Ile Gly
        115                 120                 125

Ser Thr Phe Val Asn Thr Ser Tyr Ser Val Val Val Gln Pro Arg Thr
    130                 135                 140

Ile Asn Ser Thr Gln Asp Gly Asp Asn Lys Leu Gln Gly Leu Leu Glu
145                 150                 155                 160

Val Ser Val Cys Gln Tyr Asn Met Cys Glu Tyr Pro Gln Thr Ile Cys
                165                 170                 175

His Pro Asn Leu Gly Asn His Arg Lys Glu Leu Trp His Leu Asp Thr
            180                 185                 190

Gly Val Val Ser Cys Leu Tyr Lys Arg Asn Phe Thr Tyr Asp Val Asn
        195                 200                 205

Ala Asp Tyr Leu Tyr Phe His Phe Tyr Gln Glu Gly Gly Thr Phe Tyr
    210                 215                 220

Ala Tyr Phe Thr Asp Thr Gly Val Val Thr Lys Phe Leu Phe Asn Val
225                 230                 235                 240

Tyr Leu Gly Met Ala Leu Ser His Tyr Tyr Val Met Pro Leu Thr Cys
                245                 250                 255

Asn Ser Lys Leu Thr Leu Glu Tyr Trp Val Thr Pro Leu Thr Ser Arg
            260                 265                 270

Gln Tyr Leu Leu Ala Phe Asn Gln Asp Gly Ile Ile Phe Asn Ala Val
        275                 280                 285

Asp Cys Ala Leu Asp Pro Leu Ser Glu Thr Lys Cys Thr Leu Lys Ser
    290                 295                 300

Phe Thr Val Glu Lys Gly Ile Tyr Gln Thr Asn Gly Tyr Thr Val Gln
305                 310                 315                 320

Pro Ile Ala Asp Val Tyr Arg Arg Lys Pro Asn Leu Pro Asn Cys Asn
                325                 330                 335

Ile Glu Ala Trp Leu Asn Asp Lys Ser Val Pro Ser Pro Leu Asn Trp
            340                 345                 350

Glu Arg Lys Thr Phe Ser Asn Cys Asn Phe Asn Met Ser Ser Leu Met
        355                 360                 365

Ser Phe Ile Gln Ala Asp Ser Phe Thr Cys Asn Asn Ile Asp Ala Ala
    370                 375                 380

Lys Ile Tyr Gly Met Cys Phe Ser Ser Ile Thr Ile Asp Lys Phe Ala
385                 390                 395                 400

Ile Pro Asn Gly Arg Lys Val Asp Leu Gln Leu Gly Asn Leu Gly Tyr
                405                 410                 415

Leu Gln Ser Phe Asn Tyr Arg Ile Asp Thr Thr Ala Thr Ser Cys Gln
            420                 425                 430

Leu Tyr Tyr Asn Leu Pro Ala Ala Asn Val Ser Val Ser Arg Phe Asn
        435                 440                 445

Pro Ser Thr Trp Asn Lys Arg Phe Gly Phe Ile Glu Asp Ser Val Phe
    450                 455                 460

Lys Pro Arg Pro Ala Gly Val Leu Thr Asn His Asp Val Val Tyr Ala
465                 470                 475                 480

Gln His Cys Phe Lys Ala Pro Lys Asn Phe Cys Pro Cys Lys Leu Asn
                485                 490                 495

Gly Ser Cys Val Gly Ser Gly Pro Gly Lys Asn Asn Gly Ile Gly Thr
            500                 505                 510

Cys Pro Ala Gly Thr Asn Tyr Leu Thr Cys Asp Asn Leu Cys Thr Pro
```

```
        515                 520                 525

Asp Pro Ile Thr Phe Thr Gly Thr Tyr Lys Cys Pro Gln Thr Lys Ser
    530                 535                 540

Leu Val Gly Ile Gly Glu His Cys Ser Gly Leu Ala Val Lys Ser Asp
545                 550                 555                 560

Tyr Cys Gly Gly Asn Ser Cys Thr Cys Arg Pro Gln Ala Phe Leu Gly
                565                 570                 575

Trp Ser Ala Asp Ser Cys Leu Gln Gly Asp Lys Cys Asn Ile Phe Ala
            580                 585                 590

Asn Phe Ile Leu His Asp Val Asn Ser Gly Leu Thr Cys Ser Thr Asp
        595                 600                 605

Leu Gln Lys Ala Asn Thr Asp Ile Ile Leu Gly Val Cys Val Asn Tyr
    610                 615                 620

Asp Leu Tyr Gly Ile Leu Gly Gln Gly Ile Phe Val Glu Val Asn Ala
625                 630                 635                 640

Thr Tyr Tyr Asn Ser Trp Gln Asn Leu Leu Tyr Asp Ser Asn Gly Asn
                645                 650                 655

Leu Tyr Gly Phe Arg Asp Tyr Ile Ile Asn Arg Thr Phe Met Ile Arg
            660                 665                 670

Ser Cys Tyr Ser Gly Gly Val Ser Val Ile Thr Pro Gly Thr Asn Thr
        675                 680                 685

Ser Asn Gln Val Ala Val Leu Tyr Gln Asp Val Asn Cys Thr Glu Val
    690                 695                 700

Pro Val Ala Ile His Ala Asp Gln Leu Thr Pro Thr Trp Arg Val Tyr
705                 710                 715                 720

Ser Thr Gly Ser Asn Val Phe Gln Thr Arg Ala Gly Cys Leu Ile Gly
                725                 730                 735

Ala Glu His Val Asn Asn Ser Tyr Glu Cys Asp Ile Pro Ile Gly Ala
            740                 745                 750

Gly Ile Cys Ala Ser Tyr Gln Thr Gln Thr Asn Ser Pro Arg Arg Ala
        755                 760                 765

Arg Ser Val Ala Ser Gln Ser Ile Ile Ala Tyr Thr Met Ser Leu Gly
    770                 775                 780

Ala Glu Asn Ser Val Ala Tyr Ser Asn Asn Ser Ile Ala Ile Pro Thr
785                 790                 795                 800

Asn Phe Thr Ile Ser Val Thr Thr Glu Ile Leu Pro Val Ser Met Thr
                805                 810                 815

Lys Thr Ser Val Asp Cys Thr Met Tyr Ile Cys Gly Asp Ser Thr Glu
            820                 825                 830

Cys Ser Asn Leu Leu Leu Gln Tyr Gly Ser Phe Cys Thr Gln Leu Asn
        835                 840                 845

Arg Ala Leu Thr Gly Ile Ala Val Glu Gln Asp Lys Asn Thr Gln Glu
    850                 855                 860

Val Phe Ala Gln Val Lys Gln Ile Tyr Lys Thr Pro Pro Ile Lys Asp
865                 870                 875                 880

Phe Gly Gly Phe Asn Phe Ser Gln Ile Leu Pro Asp Pro Ser Lys Pro
                885                 890                 895

Ser Lys Arg Ser Phe Ile Glu Asp Leu Leu Phe Asn Lys Val Thr Leu
            900                 905                 910

Ala Asp Ala Gly Phe Ile Lys Gln Tyr Gly Asp Cys Leu Gly Asp Ile
        915                 920                 925

Ala Ala Arg Asp Leu Ile Cys Ala Gln Lys Phe Asn Gly Leu Thr Val
    930                 935                 940
```

```
Leu Pro Pro Leu Leu Thr Asp Glu Met Ile Ala Gln Tyr Thr Ser Ala
945                 950                 955                 960

Leu Leu Ala Gly Thr Ile Thr Ser Gly Trp Thr Phe Gly Ala Gly Ala
                965                 970                 975

Ala Leu Gln Ile Pro Phe Ala Met Gln Met Ala Tyr Arg Phe Asn Gly
            980                 985                 990

Ile Gly Val Thr Gln Asn Val Leu  Tyr Glu Asn Gln Lys  Leu Ile Ala
        995                 1000                 1005

Asn Gln  Phe Asn Ser Ala Ile  Gly Lys Ile Gln Asp  Ser Leu Ser
    1010                 1015                 1020

Ser Thr  Ala Ser Ala Leu Gly  Lys Leu Gln Asp Val  Val Asn Gln
    1025                 1030                 1035

Asn Ala  Gln Ala Leu Asn Thr  Leu Val Lys Gln Leu  Ser Ser Asn
    1040                 1045                 1050

Phe Gly  Ala Ile Ser Ser Val  Leu Asn Asp Ile Leu  Ser Arg Leu
    1055                 1060                 1065

Asp Pro  Pro Glu Ala Glu Val  Gln Ile Asp Arg Leu  Ile Thr Gly
    1070                 1075                 1080

Arg Leu  Gln Ser Leu Gln Thr  Tyr Val Thr Gln Gln  Leu Ile Arg
    1085                 1090                 1095

Ala Ala  Glu Ile Arg Ala Ser  Ala Asn Leu Ala Ala  Thr Lys Met
    1100                 1105                 1110

Ser Glu  Cys Val Leu Gly Gln  Ser Lys Arg Val Asp  Phe Cys Gly
    1115                 1120                 1125

Lys Gly  Tyr His Leu Met Ser  Phe Pro Gln Ser Ala  Pro His Gly
    1130                 1135                 1140

Val Val  Phe Leu His Val Thr  Tyr Val Pro Ala Gln  Glu Lys Asn
    1145                 1150                 1155

Phe Thr  Thr Ala Pro Ala Ile  Cys His Asp Gly Lys  Ala His Phe
    1160                 1165                 1170

Pro Arg  Glu Gly Val Phe Val  Ser Asn Gly Thr His  Trp Phe Val
    1175                 1180                 1185

Thr Gln  Arg Asn Phe Tyr Glu  Pro Gln Ile Ile Thr  Thr Asp Asn
    1190                 1195                 1200

Thr Phe  Val Ser Gly Asn Cys  Asp Val Val Ile Gly  Ile Val Asn
    1205                 1210                 1215

Asn Thr  Val Tyr Asp Pro Leu  Gln Pro Glu Leu Asp  Ser Phe Lys
    1220                 1225                 1230

Glu Glu  Leu Asp Lys Tyr Phe  Lys Asn His Thr Ser  Pro Asp Val
    1235                 1240                 1245

Asp Leu  Gly Asp Ile Ser Gly  Ile Asn Ala Ser Val  Val Asn Ile
    1250                 1255                 1260

Gln Lys  Glu Ile Asp Arg Leu  Asn Glu Val Ala Lys  Asn Leu Asn
    1265                 1270                 1275

Glu Ser  Leu Ile Asp Leu Gln  Glu Leu Gly Lys Tyr  Glu Gln Tyr
    1280                 1285                 1290

Ile Lys  Trp Pro Trp Tyr Ile  Trp Leu Gly Phe Ile  Ala Gly Leu
    1295                 1300                 1305

Ile Ala  Ile Val Met Val Thr  Ile Met Leu Cys Cys  Met Thr Ser
    1310                 1315                 1320

Cys Cys  Ser Cys Leu Lys Gly  Cys Cys Ser Cys Gly  Ser Cys Cys
    1325                 1330                 1335
```

Lys Phe Asp Glu Asp Asp Ser Glu Pro Val Leu Lys Gly Val Lys
1340 1345 1350

Leu His Tyr Thr
1355

<210> SEQ ID NO 42
<211> LENGTH: 1157
<212> TYPE: RNA
<213> ORGANISM: Artificial Sequence
<220> FEATURE:
<223> OTHER INFORMATION: Synthetic

<400> SEQUENCE: 42
gggaaauaag agagaaaaga agaguaagaa gaaauauaag accccggcgc cgccaccaug 60
uucguguucc uggugcugcu gccccuggug agcagccagu gcgugaaccu gaccacccgg 120
acccagcugc caccagccua caccaacagc uucacccggg gcgucuacua ccccgacaag 180
guguuccgga gcagcguccu gcacagcacc caggaccugu uccugcccuu cuucagcaac 240
gugaccuggu uccacgccau ccacgugagc ggcaccaacg gcaccaagcg guucgacaac 300
cccgugcugc ccuucaacga cggcguguac uucgccagca ccgagaagag caacaucauc 360
cggggcugga ucuucggcac cacccuggac agcaagaccc agagccugcu gaucgugaau 420
aacgccacca acguggugau caaggugugc gaguuccagu ucugcaacga ccccuuccug 480
ggcguguacu accacaagaa caacaagagc uggauggaga gcgaguuccg gguguacagc 540
agcgccaaca acugcaccuu cgaguacgug agccagcccu uccugaugga ccuggagggc 600
aagcagggca acuucaagaa ccugcgggag uucguguuca agaacaucga cggcuacuuc 660
aagaucuaca gcaagcacac cccaaucaac cuggugcggg aucugcccca gggcuucuca 720
gcccuggagc cccuggugga ccugcccauc ggcaucaaca ucacccgguu ccagacccug 780
cuggcccugc accggagcua ccugaccccca ggcgacagca gcagcgggug gacagcaggc 840
gcggcugcuu acuacguggg cuaccugcag ccccggaccu uccugcugaa guacaacgag 900
aacggcacca ucaccgacgc cguggacucu ggcggaggcg gcagcgccau cggcggcuac 960
auccccgagg ccccuagaga cggccaggcc uacgugcgga aggacggcga gugggugcug 1020
cugagcaccu uccugggcug auaauaggcu ggagccucgg uggccuagcu ucuugccccu 1080
ugggccuccc cccagccccu ccuccccuuc cugcacccgu acccccgugg ucuuugaaua 1140
aagucugagu gggcggc 1157

<210> SEQ ID NO 43
<211> LENGTH: 981
<212> TYPE: RNA
<213> ORGANISM: Artificial Sequence
<220> FEATURE:
<223> OTHER INFORMATION: Synthetic

<400> SEQUENCE: 43
auguucgugu uccuggugcu gcugccccug gugagcagcc agugcgugaa ccugaccacc 60
cggacccagc ugccaccagc cuacaccaac agcuucaccc ggggcgucua cuaccccgac 120
aagguguucc ggagcagcgu ccugcacagc acccaggacc uguuccugcc cuucuucagc 180
aacgugaccu gguuccacgc cauccacgug agcggcacca acggcaccaa gcgguucgac 240
aaccccgugc ugcccuucaa cgacggcgug uacuucgcca gcaccgagaa gagcaacauc 300
auccggggcu ggaucuucgg caccacccug gacagcaaga cccagagccu gcugaucgug 360
aauaacgcca ccaacguggu gaucaaggug ugcgaguucc aguucugcaa cgaccccuuc 420

```
cugggcgugu acuaccacaa gaacaacaag agcuggaugg agagcgaguu ccggguguac    480

agcagcgcca acaacugcac cuucgaguac gugagccagc ccuuccugau ggaccuggag    540

ggcaagcagg gcaacuucaa gaaccugcgg gaguucgugu ucaagaacau cgacggcuac    600

uucaagaucu acagcaagca caccccaauc aaccuggugc gggaucugcc ccagggcuuc    660

ucagcccugg agccccuggu ggaccugccc aucggcauca acaucacccg guuccagacc    720

cugcuggccc ugcaccggag cuaccugacc ccaggcgaca gcagcagcgg guggacagca    780

ggcgcggcug cuuacuacgu gggcuaccug cagccccgga ccuuccugcu gaaguacaac    840

gagaacggca ccaucaccga cgccguggac ucuggcggag gcggcagcgc caucggcggc    900

uacaucccccg aggccccuag agacggccag gccuacgugc ggaaggacgg cgagugggug    960

cugcugagca ccuuccuggg c                                              981
```

<210> SEQ ID NO 44
<211> LENGTH: 327
<212> TYPE: PRT
<213> ORGANISM: Artificial Sequence
<220> FEATURE:
<223> OTHER INFORMATION: Synthetic

<400> SEQUENCE: 44

```
Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255
```

-continued

```
Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Ser Gly Gly Gly Gly Ser Ala Ile Gly Gly Tyr Ile Pro Glu
    290                 295                 300

Ala Pro Arg Asp Gly Gln Ala Tyr Val Arg Lys Asp Gly Glu Trp Val
305                 310                 315                 320

Leu Leu Ser Thr Phe Leu Gly
                325


<210> SEQ ID NO 45
<211> LENGTH: 1130
<212> TYPE: RNA
<213> ORGANISM: Artificial Sequence
<220> FEATURE:
<223> OTHER INFORMATION: Synthetic

<400> SEQUENCE: 45

gggaaauaag agagaaaaga agaguaagaa gaaauauaag accccggcgc cgccaccaug     60

uucguguucc uggugcugcu gccccuggug agcagccagu gcgugaaccu gaccacccgg    120

acccagcugc caccagccua caccaacagc uucacccggg gcgucuacua ccccgacaag    180

guguuccgga gcagcguccu gcacagcacc caggaccugu uccugcccuu cuucagcaac    240

gugaccuggu uccacgccau ccacgugagc ggcaccaacg gcaccaagcg guucgacaac    300

cccgugcugc ccuucaacga cggcguguac uucgccagca ccgagaagag caacaucauc    360

cggggcugga ucuucggcac cacccuggac agcaagaccc agagccugcu gaucgugaau    420

aacgccacca acgugguggau caaggugugc gaguuccagu ucugcaacga ccccuuccug    480

ggcguguacu accacaagaa caacaagagc uggauggaga gcgaguuccg gguguacagc    540

agcgccaaca acugcaccuu cgaguacgug agccagcccu uccugaugga ccuggagggc    600

aagcagggca acuucaagaa ccugcgggag uucguguuca agaacaucga cggcuacuuc    660

aagaucuaca gcaagcacac cccaaucaac cuggugcggg aucugcccca gggcuucuca    720

gcccuggagc cccuggugga ccugcccauc ggcaucaaca ucacccgguu ccagacccug    780

cuggcccugc accggagcua ccugacccca ggcgacagca gcagcgggug gacagcaggc    840

gcggcugcuu acuacguggg cuaccugcag ccccggaccu uccugcugaa guacaacgag    900

aacggcacca ucaccgacgc cguggacucu ggcggaggca gcauccuggc caucuacagc    960

accguggcca gcagccuggu gcugcuggug agccugggcg ccaucagcuu cugauaauag   1020

gcuggagccu cgguggccua gcuucuugcc ccuugggccu ccccccagcc ccuccucccc   1080

uuccugcacc cguacccccg uggucuuuga auaaagucug agugggcggc              1130


<210> SEQ ID NO 46
<211> LENGTH: 954
<212> TYPE: RNA
<213> ORGANISM: Artificial Sequence
<220> FEATURE:
<223> OTHER INFORMATION: Synthetic

<400> SEQUENCE: 46

auguucgugu uccuggugcu gcugccccug gugagcagcc agugcgugaa ccugaccacc     60

cggacccagc ugccaccagc cuacaccaac agcuucaccc ggggcgucua cuaccccgac    120

aagguguucc ggagcagcgu ccugcacagc acccaggacc uguuccugcc cuucuucagc    180
```

```
aacgugaccu gguuccacgc cauccacgug agcggcacca acggcaccaa gcgguucgac    240

aaccccgugc ugcccuucaa cgacggcgug uacuucgcca gcaccgagaa gagcaacauc    300

auccggggcu ggaucuucgg caccacccug gacagcaaga cccagagccu gcugaucgug    360

aauaacgcca ccaacguggu gaucaaggug ugcgaguucc aguucugcaa cgaccccuuc    420

cugggcgugu acuaccacaa gaacaacaag agcuggaugg agagcgaguu ccggguguac    480

agcagcgcca acaacugcac cuucgaguac gugagccagc ccuuccugau ggaccuggag    540

ggcaagcagg gcaacuucaa gaaccugcgg gaguucgugu ucaagaacau cgacggcuac    600

uucaagaucu acagcaagca caccccaauc aaccuggugc gggaucugcc ccagggcuuc    660

ucagcccugg agccccuggu ggaccugccc aucggcauca acaucacccg guuccagacc    720

cugcuggccc ugcaccggag cuaccugacc ccaggcgaca gcagcagcgg guggacagca    780

ggcgcggcug cuuacuacgu gggcuaccug cagccccgga ccuuccugcu gaaguacaac    840

gagaacggca ccaucaccga cgccguggac ucuggcggag gcagcauccu ggccaucuac    900

agcaccgugg ccagcagccu ggugcugcug gugagccugg gcgccaucag cuuc          954
```

<210> SEQ ID NO 47
<211> LENGTH: 318
<212> TYPE: PRT
<213> ORGANISM: Artificial Sequence
<220> FEATURE:
<223> OTHER INFORMATION: Synthetic

<400> SEQUENCE: 47

```
Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
```

-continued

```
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Ser Gly Gly Gly Ser Ile Leu Ala Ile Tyr Ser Thr Val Ala
    290                 295                 300

Ser Ser Leu Val Leu Leu Val Ser Leu Gly Ala Ile Ser Phe
305                 310                 315
```

<210> SEQ ID NO 48
<211> LENGTH: 1238
<212> TYPE: RNA
<213> ORGANISM: Artificial Sequence
<220> FEATURE:
<223> OTHER INFORMATION: Synthetic

<400> SEQUENCE: 48

```
gggaaauaag agagaaaaga agaguaagaa gaaauauaag accccggcgc cgccaccaug      60
uucguguucc uggugcugcu gccccuggug agcagccagu gcgugaaccu gaccacccgg     120
acccagcugc caccagccua caccaacagc uucacccggg gcgucuacua ccccgacaag     180
guguuccgga gcagcguccu gcacagcacc caggaccugu uccugcccuu cuucagcaac     240
gugaccuggu uccacgccau ccacgugagc ggcaccaacg gcaccaagcg guucgacaac     300
cccgugcugc ccuucaacga cggcguguac uucgccagca ccgagaagag caacaucauc     360
cggggcugga ucuucggcac cacccuggac agcaagaccc agagccugcu gaucgugaau     420
aacgccacca acguggugau caaggugugc gaguuccagu ucugcaacga ccccuuccug     480
ggcguguacu accacaagaa caacaagagc uggauggaga gcgaguuccg gguguacagc     540
agcgccaaca acugcaccuu cgaguacgug agccagcccu uccugaugga ccuggagggc     600
aagcagggca acuucaagaa ccugcgggag uucguguuca agaacaucga cggcuacuuc     660
aagaucuaca gcaagcacac cccaaucaac cuggugcggg aucugcccca gggcuucuca     720
gcccuggagc cccuggugga ccugcccauc ggcaucaaca ucacccgguu ccagacccug     780
cuggcccugc accggagcua ccugacccca ggcgacagca gcagcgggug gacagcaggc     840
gcggcugcuu acuacguggg cuaccugcag ccccggaccu uccugcugaa guacaacgag     900
aacggcacca ucaccgacgc cguggacucu ggcggaggca gcauccuggc caucuacagc     960
accguggcca gcagccuggu gcugcuggug agccugggcg ccaucagcuu cggcggaggc    1020
agcgccaucg gcggcuacau ccccgaggcc ccuagagacg gccaggccua cgugcggaag    1080
gacggcgagu gggugcugcu gagcaccuuc cugggcaagu gauaauaggc uggagccucg    1140
guggccuagc uucuugcccc uugggccucc ccccagcccc uccuccccuu ccugcacccg    1200
uacccccgug gucuuugaau aaagucugag ugggcggc                           1238
```

<210> SEQ ID NO 49
<211> LENGTH: 1062
<212> TYPE: RNA
<213> ORGANISM: Artificial Sequence
<220> FEATURE:
<223> OTHER INFORMATION: Synthetic

<400> SEQUENCE: 49

```
auguucgugu uccuggugcu gcugccccug gugagcagcc agugcgugaa ccugaccacc     60

cggacccagc ugccaccagc cuacaccaac agcuucaccc ggggcgucua cuaccccgac    120

aagguguucc ggagcagcgu ccugcacagc acccaggacc uguuccugcc cuucuucagc    180

aacgugaccu gguuccacgc cauccacgug agcggcacca acggcaccaa gcgguucgac    240

aaccccgugc ugcccuucaa cgacggcgug uacuucgcca gcaccgagaa gagcaacauc    300

auccggggcu ggaucuucgg caccacccug gacagcaaga cccagagccu gcugaucgug    360

aauaacgcca ccaacguggu gaucaaggug ugcgaguucc aguucugcaa cgaccccuuc    420

cugggcgugu acuaccacaa gaacaacaag agcuggaugg agagcgaguu ccggguguac    480

agcagcgcca acaacugcac cuucgaguac gugagccagc ccuuccugau ggaccuggag    540

ggcaagcagg gcaacuucaa gaaccugcgg gaguucgugu ucaagaacau cgacggcuac    600

uucaagaucu acagcaagca caccccaauc aaccuggugc gggaucugcc ccagggcuuc    660

ucagcccugg agccccuggu ggaccugccc aucggcauca acaucacccg guuccagacc    720

cugcuggccc ugcaccggag cuaccugacc ccaggcgaca gcagcagcgg gugcacagca    780

ggcgcggcug cuuacuacgu gggcuaccug cagccccgga ccuuccugcu gaaguacaac    840

gagaacggca ccaucaccga cgccguggac ucuggcggag gcagcauccu ggccaucuac    900

agcaccgugg ccagcagccu ggugcugcug gugagccugg gcgccaucag cuucggcgga    960

ggcagcgcca ucggcggcua cauccccgag gccccuagag acggccaggc cuacgugcgg   1020

aaggacggcg agugggugcu gcugagcacc uuccugggca ag                      1062
```

<210> SEQ ID NO 50
<211> LENGTH: 354
<212> TYPE: PRT
<213> ORGANISM: Artificial Sequence
<220> FEATURE:
<223> OTHER INFORMATION: Synthetic

<400> SEQUENCE: 50

```
Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175
```

```
Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Ser Gly Gly Gly Ser Ile Leu Ala Ile Tyr Ser Thr Val Ala
    290                 295                 300

Ser Ser Leu Val Leu Leu Val Ser Leu Gly Ala Ile Ser Phe Gly Gly
305                 310                 315                 320

Gly Ser Ala Ile Gly Gly Tyr Ile Pro Glu Ala Pro Arg Asp Gly Gln
                325                 330                 335

Ala Tyr Val Arg Lys Asp Gly Glu Trp Val Leu Leu Ser Thr Phe Leu
            340                 345                 350

Gly Lys
```

<210> SEQ ID NO 51
<211> LENGTH: 1130
<212> TYPE: RNA
<213> ORGANISM: Artificial Sequence
<220> FEATURE:
<223> OTHER INFORMATION: Synthetic

<400> SEQUENCE: 51

```
gggaaauaag agagaaaaga agaguaagaa gaaauauaag accccggcgc cgccaccaug     60

uucguguucc uggugcugcu gccccuggug agcagccagu gcgugaaccu gaccaccccgg    120

acccagcugc caccagccua caccaacagc uucacccggg gcgucuacua ccccgacaag    180

gugugccgga gcagcguccu gcacagcacc caggaccugu uccugcccuu cuucagcaac    240

gugaccuggu uccacgccau ccacgugagc ggcaccaacg gcaccaagcg guucgacaac    300

cccgugcugc ccuucaacga cggcguguac uucgccagca ccgagaagag caacaucauc    360

cggggcugga ucuucggcac cacccuggac agcaagaccc agagccugcu gaucgugaau    420

aacgccacca acguggugau caaggugugc gaguuccagu ucugcaacga ccccuuccug    480

ggcguguacu accacaagaa caacaagagc uggauggaga gcgaguuccg gguguacagc    540

agcgccaaca acugcaccuu cgaguacgug agccagcccu uccugaugga ccuggagggc    600

aagcagggca acuucaagaa ccugcgggag uucgguguuca agaacaucga cggcuacuuc    660

aagaucuaca gcaagcacac cccaaucaac cuggugcggg aucugcccca gggcuucuca    720

gcccuggagc cccuggugga ccugcccauc ggcaucaaca ucacccgguu ccagacccug    780

cuggcccugc accggagcua ccugacccca ggcgacagca gcagcgggug gacagcaggc    840

gcggcugcuu acuacguggg cuaccugcag ccccggaccu uccugcugaa guacaacgag    900

aacggcacca ucaccgacgc cguggacucu ggcggaggca gcauccuggc caucuacagc    960

accguggcca gcagccuggu gcugcuggug agccugggcg ccaucagcuu cugauaauag   1020
```

gcuggagccu cgguggccua gcuucuugcc ccuugggccu ccccccagcc ccuccucccc 1080
uuccugcacc cguacccccg uggucuuuga auaaagucug agugggcggc 1130

<210> SEQ ID NO 52
<211> LENGTH: 954
<212> TYPE: RNA
<213> ORGANISM: Artificial Sequence
<220> FEATURE:
<223> OTHER INFORMATION: Synthetic

<400> SEQUENCE: 52
auguucgugu uccuggugcu gcugccccug gugagcagcc agugcgugaa ccugaccacc 60
cggacccagc ugccaccagc cuacaccaac agcuucaccc ggggcgucua cuaccccgac 120
aaggugugcc ggagcagcgu ccugcacagc acccaggacc uguuccugcc cuucuucagc 180
aacgugaccu gguuccacgc cauccacgug agcggcacca acggcaccaa gcgguucgac 240
aaccccgugc ugcccuucaa cgacggcgug uacuucgcca gcaccgagaa gagcaacauc 300
auccggggcu ggaucuucgg caccacccug gacagcaaga cccagagccu gcugaucgug 360
aauaacgcca ccaacguggu gaucaaggug ugcgaguucc aguucugcaa cgaccccuuc 420
cugggcgugu acuaccacaa gaacaacaag agcuggaugg agagcgaguu ccggguguac 480
agcagcgcca acaacugcac cuucgaguac gugagccagc ccuuccugau ggaccuggag 540
ggcaagcagg gcaacuucaa gaaccugcgg gaguucgugu ucaagaacau cgacggcuac 600
uucaagaucu acagcaagca caccccaauc aaccuggugc gggaucugcc ccagggcuuc 660
ucagcccugg agccccuggu ggaccugccc aucggcauca acaucacccg guuccagacc 720
cugcuggccc ugcaccggag cuaccugacc ccaggcgaca gcagcagcgg guggacagca 780
ggcgcggcug cuuacuacgu gggcuaccug cagccccgga ccuuccugcu gaaguacaac 840
gagaacggca ccaucaccga cgccguggac ucuggcggag gcagcauccu ggccaucuac 900
agcaccgugg ccagcagccu ggugcugcug gugagccugg gcgccaucag cuuc 954

<210> SEQ ID NO 53
<211> LENGTH: 318
<212> TYPE: PRT
<213> ORGANISM: Artificial Sequence
<220> FEATURE:
<223> OTHER INFORMATION: Synthetic

<400> SEQUENCE: 53

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Cys Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

-continued

```
Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Ser Gly Gly Gly Ser Ile Leu Ala Ile Tyr Ser Thr Val Ala
    290                 295                 300

Ser Ser Leu Val Leu Leu Val Ser Leu Gly Ala Ile Ser Phe
305                 310                 315
```

<210> SEQ ID NO 54
<211> LENGTH: 1181
<212> TYPE: RNA
<213> ORGANISM: Artificial Sequence
<220> FEATURE:
<223> OTHER INFORMATION: Synthetic

<400> SEQUENCE: 54

```
gggaaauaag agagaaaaga agaguaagaa gaaauauaag accccggcgc cgccaccaug      60

uucguguucc uggugcugcu gccccuggug agcagccagu gcgugaaccu gaccacccgg     120

acccagcugc caccagccua caccaacagc uucacccggg gcgucuacua ccccgacaag     180

gugugccgga gcagcguccu gcacagcacc caggaccugu uccugcccuu cuucagcaac     240

gugaccuggu uccacgccau ccacgugagc ggcaccaacg gcaccaagcg guucgacaac     300

cccgugcugc ccuucaacga cggcguguac uucgccagca ccgagaagag caacaucauc     360

cggggcugga ucuucggcac cacccuggac agcaagaccc agagccugcu gaucgugaau     420

aacgccacca acguggugau caaggugugc gaguuccagu ucugcaacga ccccuuccug     480

ggcguguacu accacaagaa caacaagagc uggauggaga gcgaguuccg gguguacagc     540

agcgccaaca acugcaccuu cgaguacgug agccagcccu uccugaugga ccuggagggc     600

aagcagggca acuucaagaa ccugcgggag uucguguuca agaacaucga cggcuacuuc     660

aagaucuaca gcaagcacac cccaaucaac cuggugcggg aucugcccca gggcuucuca     720

gcccuggagc cccuggugga ccugcccauc ggcaucaaca ucacccgguu ccagacccug     780

cuggcccugc accggagcua ccugacccca ggcgacagca gcagcgggug gacagcaggc     840

gcggcugcuu acuacguggg cuaccugcag ccccggaccu uccugcugaa guacaacgag     900

aacggcacca ucaccgacgc cguggacugc gcccuggacc cucugagcga gaccaagugc     960
```

-continued

```
acccugaaga gcuucaccuc uggcggaggc agcauccugg ccaucuacag caccguggcc   1020

agcagccugg ugcugcuggu gagccugggc gccaucagcu ucugauaaua ggcuggagcc   1080

ucgguggccu agcuucuugc cccuugggcc ucccccagc cccuccuccc cuuccugcac    1140

ccguaccccc guggucuuug aauaaagucu gagugggcgg c                       1181
```

<210> SEQ ID NO 55
<211> LENGTH: 1005
<212> TYPE: RNA
<213> ORGANISM: Artificial Sequence
<220> FEATURE:
<223> OTHER INFORMATION: Synthetic

<400> SEQUENCE: 55

```
auguucgugu uccuggugcu gcugccccug gugagcagcc agugcgugaa ccugaccacc     60

cggacccagc ugccaccagc cuacaccaac agcuucaccc ggggcgucua cuaccccgac    120

aaggugugcc ggagcagcgu ccugcacagc acccaggacc uguuccugcc cuucuucagc    180

aacgugaccu gguuccacgc cauccacgug agcggcacca acggcaccaa gcgguucgac    240

aaccccgugc ugcccuucaa cgacggcgug uacuucgcca gcaccgagaa gagcaacauc    300

auccggggcu ggaucuucgg caccacccug gacagcaaga cccagagccu gcugaucgug    360

aauaacgcca ccaacguggu gaucaaggug ugcgaguucc aguucugcaa cgaccccuuc    420

cugggcgugu acuaccacaa gaacaacaag agcuggaugg agagcgaguu ccggguguac    480

agcagcgcca acaacugcac cuucgaguac gugagccagc ccuuccugau ggaccuggag    540

ggcaagcagg gcaacuucaa gaaccugcgg gaguucgugu ucaagaacau cgacggcuac    600

uucaagaucu acagcaagca caccccaauc aaccuggugc gggaucugcc ccagggcuuc    660

ucagcccugg agccccuggu ggaccugccc aucggcauca acaucacccg guuccagacc    720

cugcuggccc ugcaccggag cuaccugacc ccaggcgaca gcagcagcgg guggacagca    780

ggcgcggcug cuuacuacgu gggcuaccug cagccccgga ccuuccugcu gaaguacaac    840

gagaacggca ccaucaccga cgccguggac ugcgcccugg acccucugag cgagaccaag    900

ugcacccuga agagcuucac cucuggcgga ggcagcaucc uggccaucua cagcaccgug    960

gccagcagcc uggugcugcu ggugagccug ggcgccauca gcuuc                    1005
```

<210> SEQ ID NO 56
<211> LENGTH: 335
<212> TYPE: PRT
<213> ORGANISM: Artificial Sequence
<220> FEATURE:
<223> OTHER INFORMATION: Synthetic

<400> SEQUENCE: 56

```
Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Cys Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95
```

-continued

```
Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Ser Gly Gly Gly Ser Ile Leu Ala Ile Tyr Ser Thr Val
305                 310                 315                 320

Ala Ser Ser Leu Val Leu Leu Val Ser Leu Gly Ala Ile Ser Phe
                325                 330                 335
```

<210> SEQ ID NO 57
<211> LENGTH: 1181
<212> TYPE: RNA
<213> ORGANISM: Artificial Sequence
<220> FEATURE:
<223> OTHER INFORMATION: Synthetic

<400> SEQUENCE: 57

```
gggaaauaag agagaaaaga agaguaagaa gaaauauaag accccggcgc cgccaccaug     60

uucguguucc uggugcugcu gccccuggug agcagccagu gcgugaaccu gaccacccgg    120

acccagcugc caccagccua caccaacagc uucacccggg gcgucuacua ccccgacaag    180

guguuccgga gcagcguccu gcacagcacc caggaccugu uccugcccuu cuucagcaac    240

gugaccuggu uccacgccau ccacgugagc ggcaccaacg gcaccaagcg guucgacaac    300

cccgugcugc ccuucaacga cggcguguac uucgccagca ccgagaagag caacaucauc    360

cggggcugga ucuucggcac cacccuggac agcaagaccc agagccugcu gaucgugaau    420

aacgccacca acguggugau caaggugugc gaguuccagu ucugcaacga ccccuuccug    480

ggcguguacu accacaagaa caacaagagc uggauggaga gcgaguuccg gguguacagc    540

agcgccaaca acugcaccuu cgaguacgug agccagcccu uccugaugga ccuggagggc    600

aagcagggca acuucaagaa ccugcgggag uucguguuca agaacaucga cggcuacuuc    660

aagaucuaca gcaagcacac cccaaucaac cuggugcggg aucugcccca gggcuucuca    720
```

gcccuggagc cccuggugga ccugcccauc ggcaucaaca ucacccgguu ccagacccug 780
cuggcccugc accggagcua ccugacccca ggcgacagca gcagcgggug gacagcaggc 840
gcggcugcuu acuacguggg cuaccugcag ccccggaccu uccugcugaa guacaacgag 900
aacggcacca ucaccgacgc cguggacugc gcccuggacc cucugagcga gaccaagugc 960
acccugaaga gcuucaccuc uggcggaggc agcauccugg ccaucuacag caccguggcc 1020
agcagccugg ugcugcuggu gagccugggc gccaucagcu ucugauaaua ggcuggagcc 1080
ucgguggccu agcuucuugc cccuugggcc ucccccagc cccuccuccc cuuccugcac 1140
ccguaccccc guggucuuug aauaaagucu gagugggcgg c 1181

<210> SEQ ID NO 58
<211> LENGTH: 1005
<212> TYPE: RNA
<213> ORGANISM: Artificial Sequence
<220> FEATURE:
<223> OTHER INFORMATION: Synthetic

<400> SEQUENCE: 58
auguucgugu uccuggugcu gcugccccug gugagcagcc agugcgugaa ccugaccacc 60
cggacccagc ugccaccagc cuacaccaac agcuucaccc ggggcgucua cuaccccgac 120
aagguguucc ggagcagcgu ccugcacagc acccaggacc uguuccugcc cuucuucagc 180
aacgugaccu gguuccacgc cauccacgug agcggcacca acggcaccaa gcgguucgac 240
aaccccgugc ugcccuucaa cgacggcgug uacuucgcca gcaccgagaa gagcaacauc 300
auccggggcu ggaucuucgg caccacccug gacagcaaga cccagagccu gcugaucgug 360
aauaacgcca ccaacguggu gaucaaggug ugcgaguucc aguucugcaa cgaccccuuc 420
cugggcgugu acuaccacaa gaacaacaag agcuggaugg agagcgaguu ccggguguac 480
agcagcgcca acaacugcac cuucgaguac gugagccagc ccuuccugau ggaccuggag 540
ggcaagcagg gcaacuucaa gaaccugcgg gaguucgugu ucaagaacau cgacggcuac 600
uucaagaucu acagcaagca caccccaauc aaccuggugc gggaucugcc ccagggcuuc 660
ucagcccugg agccccuggu ggaccugccc aucggcauca acaucacccg guuccagacc 720
cugcuggccc ugcaccggag cuaccugacc ccaggcgaca gcagcagcgg guggacagca 780
ggcgcggcug cuuacuacgu gggcuaccug cagccccgga ccuuccugcu gaaguacaac 840
gagaacggca ccaucaccga cgccguggac ugcgcccugg acccucugag cgagaccaag 900
ugcacccuga agagcuucac cucuggcgga ggcagcaucc uggccaucua cagcaccgug 960
gccagcagcc uggugcugcu ggugagccug ggcgccauca gcuuc 1005

<210> SEQ ID NO 59
<211> LENGTH: 335
<212> TYPE: PRT
<213> ORGANISM: Artificial Sequence
<220> FEATURE:
<223> OTHER INFORMATION: Synthetic

<400> SEQUENCE: 59

Met Phe Val Phe Leu Val Leu Leu Pro Leu Val Ser Ser Gln Cys Val
1 5 10 15

Asn Leu Thr Thr Arg Thr Gln Leu Pro Pro Ala Tyr Thr Asn Ser Phe
20 25 30

Thr Arg Gly Val Tyr Tyr Pro Asp Lys Val Phe Arg Ser Ser Val Leu
35 40 45

-continued

```
His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Ser Gly Gly Gly Ser Ile Leu Ala Ile Tyr Ser Thr Val
305                 310                 315                 320

Ala Ser Ser Leu Val Leu Leu Val Ser Leu Gly Ala Ile Ser Phe
                325                 330                 335


<210> SEQ ID NO 60
<211> LENGTH: 836
<212> TYPE: RNA
<213> ORGANISM: Artificial Sequence
<220> FEATURE:
<223> OTHER INFORMATION: Synthetic

<400> SEQUENCE: 60

gggaaauaag agagaaaaga agaguaagaa gaaauauaag accccggcgc cgccaccaug      60

uacagcaugc agcuggcuag cugcgugacc cugacccugg ugcugcuggu gaacagccag     120

cccaacauca ccaaccugug ccccuucggc gagguguuca acgccacccg guucgccagc     180

guguacgccu ggaaccggaa gcggaucagc aacugcgugg ccgacuacag cgugcuguac     240

aacagcgcca gcuucagcac cuucaagugc uacggcguga gccccaccaa gcugaacgac     300

cugugcuuca ccaacgugua cgccgacagc uucgugaucc guggcgacga ggugcggcag     360

aucgcacccg gccagacagg caagaucgcc gacuacaacu acaagcugcc cgacgacuuc     420
```

```
accggcugcg ugaucgccug gaacagcaac aaccucgaca gcaagguggg cggcaacuac    480

aacuaccugu accggcuguu ccggaagagc aaccugaagc ccuucgagcg ggacaucagc    540

accgagaucu accaagccgg cuccacccu ugcaacggcg uggagggcuu caacugcuac    600

uucccucugc agagcuacgg cuuccagccc accaacggcg ugggcuacca gcccuaccgg    660

gugguggugc ugagcuucga gcugcugcac gccccagcca ccgugugugg ccccaaguga    720

uaauaggcug gagccucggu ggccuagcuu cuugccccuu gggccucccc ccagccccuc    780

cucccccuucc ugcacccgua cccccguggu cuuugaauaa agucugagug ggcggc       836


<210> SEQ ID NO 61
<211> LENGTH: 660
<212> TYPE: RNA
<213> ORGANISM: Artificial Sequence
<220> FEATURE:
<223> OTHER INFORMATION: Synthetic

<400> SEQUENCE: 61

auguacagca ugcagcuggc uagcugcgug acccugaccc uggugcugcu ggugaacagc     60

cagcccaaca ucaccaaccu gugccccuuc ggcgaggugu ucaacgccac ccgguucgcc    120

agcguguacg ccuggaaccg gaagcggauc agcaacugcg uggccgacua cagcgugcug    180

uacaacagcg ccagcuucag caccuucaag ugcuacggcg ugagccccac caagcugaac    240

gaccugugcu ucaccaacgu guacgccgac agcuucguga uccguggcga cgaggugcgg    300

cagaucgcac ccggccagac aggcaagauc gccgacuaca acuacaagcu gcccgacgac    360

uucaccggcu gcgugaucgc cuggaacagc aacaaccucg acagcaaggu gggcggcaac    420

uacaacuacc uguaccggcu guuccggaag agcaaccuga agcccuucga gcgggacauc    480

agcaccgaga ucuaccaagc cggcuccacc ccuugcaacg gcguggaggg cuucaacugc    540

uacuucccuc ugcagagcua cggcuuccag cccaccaacg gcgugggcua ccagcccuac    600

cggguggugg ugcugagcuu cgagcugcug cacgccccag ccaccgugug uggccccaag    660


<210> SEQ ID NO 62
<211> LENGTH: 220
<212> TYPE: PRT
<213> ORGANISM: Artificial Sequence
<220> FEATURE:
<223> OTHER INFORMATION: Synthetic

<400> SEQUENCE: 62

Met Tyr Ser Met Gln Leu Ala Ser Cys Val Thr Leu Thr Leu Val Leu
1               5                   10                  15

Leu Val Asn Ser Gln Pro Asn Ile Thr Asn Leu Cys Pro Phe Gly Glu
            20                  25                  30

Val Phe Asn Ala Thr Arg Phe Ala Ser Val Tyr Ala Trp Asn Arg Lys
        35                  40                  45

Arg Ile Ser Asn Cys Val Ala Asp Tyr Ser Val Leu Tyr Asn Ser Ala
    50                  55                  60

Ser Phe Ser Thr Phe Lys Cys Tyr Gly Val Ser Pro Thr Lys Leu Asn
65                  70                  75                  80

Asp Leu Cys Phe Thr Asn Val Tyr Ala Asp Ser Phe Val Ile Arg Gly
                85                  90                  95

Asp Glu Val Arg Gln Ile Ala Pro Gly Gln Thr Gly Lys Ile Ala Asp
            100                 105                 110

Tyr Asn Tyr Lys Leu Pro Asp Asp Phe Thr Gly Cys Val Ile Ala Trp
        115                 120                 125
```

```
Asn Ser Asn Asn Leu Asp Ser Lys Val Gly Gly Asn Tyr Asn Tyr Leu
    130                 135                 140

Tyr Arg Leu Phe Arg Lys Ser Asn Leu Lys Pro Phe Glu Arg Asp Ile
145                 150                 155                 160

Ser Thr Glu Ile Tyr Gln Ala Gly Ser Thr Pro Cys Asn Gly Val Glu
                165                 170                 175

Gly Phe Asn Cys Tyr Phe Pro Leu Gln Ser Tyr Gly Phe Gln Pro Thr
            180                 185                 190

Asn Gly Val Gly Tyr Gln Pro Tyr Arg Val Val Val Leu Ser Phe Glu
        195                 200                 205

Leu Leu His Ala Pro Ala Thr Val Cys Gly Pro Lys
    210                 215                 220
```

<210> SEQ ID NO 63
<211> LENGTH: 1349
<212> TYPE: RNA
<213> ORGANISM: Artificial Sequence
<220> FEATURE:
<223> OTHER INFORMATION: Synthetic

<400> SEQUENCE: 63

```
gggaaauaag agagaaaaga agaguaagaa gaaauauaag accccggcgc cgccaccaug      60

uacagcaugc agcuggcuag cugcgugacc cugacccugg ugcugcuggu gaacagccag     120

cccaacauca ccaaccugug ccccuucggc gagguguuca acgccacccg guucgccagc     180

guguacgccu ggaaccggaa gcggaucagc aacugcgugg ccgacuacag cgugcuguac     240

aacagcgcca gcuucagcac cuucaagugc uacggcguga gccccaccaa gcugaacgac     300

cugugcuuca ccaacgugua cgccgacagc uucgugaucc guggcgacga ggugcggcag     360

aucgcacccg gccagacagg caagaucgcc gacuacaacu acaagcugcc cgacgacuuc     420

accggcugcg ugaucgccug gaacagcaac aaccucgaca gcaaggugggg cggcaacuac     480

aacuaccugu accggcuguu ccggaagagc aaccugaagc ccuucgagcg ggacaucagc     540

accgagaucu accaagccgg cuccaccccu ugcaacggcg uggagggcuu caacugcuac     600

uucccucugc agagcuacgg cuuccagccc accaacggcg ugggcuacca gcccuaccgg     660

gugguggugc ugagcuucga gcugcugcac gccccagcca ccgugugugg ccccaaggga     720

ggaggcagcg gcggcgauau caucaagcuu cugaacgagc aaguuaacaa ggaaaugcag     780

agcaguaauc ucuacaugag caugagcagc uggugcuaca cccacucccu ggacggagca     840

ggccucuucc uguucgacca cgcagccgag gaguacgagc acgcuaagaa guugaucauu     900

uucuugaacg agaacaacgu gcccgugcag cuaacgucaa ucagcgcacc ugagcacaag     960

uucgagggcc ugacccagau cuuccagaag gccuacgaac acgaacagca caucuccgag    1020

agcaucaaca auauugugga ucacgcuauc aaguccaagg accacgcuac cuucaacuuc    1080

cugcaguggu acguggccga gcaacaugag gaggaggugc uguucaagga cauccuggac    1140

aagaucgagc ugaucgguaa ugagaaucac ggccuguacc uggccgacca guacgugaag    1200

ggcaucgcca agagccggaa gucaggcuca ugauaaauagg cuggagccuc gguggccuag    1260

cuucuugccc cuugggccuc cccccagccc cuccuccccu uccugcaccc guacccccgu    1320

ggucuuugaa uaaagucuga gugggcggc                                     1349
```

<210> SEQ ID NO 64
<211> LENGTH: 1173
<212> TYPE: RNA

<213> ORGANISM: Artificial Sequence
<220> FEATURE:
<223> OTHER INFORMATION: Synthetic

<400> SEQUENCE: 64
auguacagca ugcagcuggc uagcugcgug acccugaccc uggugcugcu ggugaacagc 60
cagcccaaca ucaccaaccu gugccccuuc ggcgaggugu ucaacgccac ccgguucgcc 120
agcguguacg ccuggaaccg gaagcggauc agcaacugcg uggccgacua cagcgugcug 180
uacaacagcg ccagcuucag caccuucaag ugcuacggcg ugagccccac caagcugaac 240
gaccugugcu ucaccaacgu guacgccgac agcuucguga uccguggcga cgaggugcgg 300
cagaucgcac ccggccagac aggcaagauc gccgacuaca acuacaagcu gcccgacgac 360
uucaccggcu gcgugaucgc cuggaacagc aacaaccucg acagcaaggu gggcggcaac 420
uacaacuacc uguaccggcu guuccggaag agcaaccuga agcccuucga gcgggacauc 480
agcaccgaga ucuaccaagc cggcuccacc ccuugcaacg gcguggaggg cuucaacugc 540
uacuucccuc ugcagagcua cggcuuccag cccaccaacg gcgugggcua ccagcccuac 600
cggguggugg ugcugagcuu cgagcugcug cacgccccag ccaccgugug uggccccaag 660
ggaggaggca gcggcggcga uaucaucaag cuucugaacg agcaaguuaa caaggaaaug 720
cagagcagua aucucuacau gagcaugagc agcuggugcu acacccacuc ccuggacgga 780
gcaggccucu uccuguucga ccacgcagcc gaggaguacg agcacgcuaa gaaguugauc 840
auuuucuuga acgagaacaa cgugcccgug cagcuaacgu caaucagcgc accugagcac 900
aaguucgagg gccugaccca gaucuuccag aaggccuacg aacacgaaca gcacaucucc 960
gagagcauca acaauauugu ggaucacgcu aucaagucca aggaccacgc uaccuucaac 1020
uuccugcagu gguacguggc cgagcaacau gaggaggagg ugcuguucaa ggacauccug 1080
gacaagaucg agcugaucgg uaaugagaau cacggccugu accuggccga ccaguacgug 1140
aagggcaucg ccaagagccg gaagucaggc uca 1173

<210> SEQ ID NO 65
<211> LENGTH: 391
<212> TYPE: PRT
<213> ORGANISM: Artificial Sequence
<220> FEATURE:
<223> OTHER INFORMATION: Synthetic

<400> SEQUENCE: 65

Met Tyr Ser Met Gln Leu Ala Ser Cys Val Thr Leu Thr Leu Val Leu
1 5 10 15

Leu Val Asn Ser Gln Pro Asn Ile Thr Asn Leu Cys Pro Phe Gly Glu
20 25 30

Val Phe Asn Ala Thr Arg Phe Ala Ser Val Tyr Ala Trp Asn Arg Lys
35 40 45

Arg Ile Ser Asn Cys Val Ala Asp Tyr Ser Val Leu Tyr Asn Ser Ala
50 55 60

Ser Phe Ser Thr Phe Lys Cys Tyr Gly Val Ser Pro Thr Lys Leu Asn
65 70 75 80

Asp Leu Cys Phe Thr Asn Val Tyr Ala Asp Ser Phe Val Ile Arg Gly
85 90 95

Asp Glu Val Arg Gln Ile Ala Pro Gly Gln Thr Gly Lys Ile Ala Asp
100 105 110

Tyr Asn Tyr Lys Leu Pro Asp Asp Phe Thr Gly Cys Val Ile Ala Trp
115 120 125

```
Asn Ser Asn Asn Leu Asp Ser Lys Val Gly Gly Asn Tyr Asn Tyr Leu
    130                 135                 140

Tyr Arg Leu Phe Arg Lys Ser Asn Leu Lys Pro Phe Glu Arg Asp Ile
145                 150                 155                 160

Ser Thr Glu Ile Tyr Gln Ala Gly Ser Thr Pro Cys Asn Gly Val Glu
                165                 170                 175

Gly Phe Asn Cys Tyr Phe Pro Leu Gln Ser Tyr Gly Phe Gln Pro Thr
            180                 185                 190

Asn Gly Val Gly Tyr Gln Pro Tyr Arg Val Val Val Leu Ser Phe Glu
        195                 200                 205

Leu Leu His Ala Pro Ala Thr Val Cys Gly Pro Lys Gly Gly Gly Ser
    210                 215                 220

Gly Gly Asp Ile Ile Lys Leu Leu Asn Glu Gln Val Asn Lys Glu Met
225                 230                 235                 240

Gln Ser Ser Asn Leu Tyr Met Ser Met Ser Ser Trp Cys Tyr Thr His
                245                 250                 255

Ser Leu Asp Gly Ala Gly Leu Phe Leu Phe Asp His Ala Ala Glu Glu
            260                 265                 270

Tyr Glu His Ala Lys Lys Leu Ile Ile Phe Leu Asn Glu Asn Asn Val
        275                 280                 285

Pro Val Gln Leu Thr Ser Ile Ser Ala Pro Glu His Lys Phe Glu Gly
    290                 295                 300

Leu Thr Gln Ile Phe Gln Lys Ala Tyr Glu His Glu Gln His Ile Ser
305                 310                 315                 320

Glu Ser Ile Asn Asn Ile Val Asp His Ala Ile Lys Ser Lys Asp His
                325                 330                 335

Ala Thr Phe Asn Phe Leu Gln Trp Tyr Val Ala Glu Gln His Glu Glu
            340                 345                 350

Glu Val Leu Phe Lys Asp Ile Leu Asp Lys Ile Glu Leu Ile Gly Asn
        355                 360                 365

Glu Asn His Gly Leu Tyr Leu Ala Asp Gln Tyr Val Lys Gly Ile Ala
    370                 375                 380

Lys Ser Arg Lys Ser Gly Ser
385                 390
```

<210> SEQ ID NO 66
<211> LENGTH: 1376
<212> TYPE: RNA
<213> ORGANISM: Artificial Sequence
<220> FEATURE:
<223> OTHER INFORMATION: Synthetic

<400> SEQUENCE: 66

```
gggaaauaag agagaaaaga agaguaagaa gaaauauaag accccggcgc cgccaccaug      60

ggcauccugc ccagcccugg caugcccgcu cugcugagcc uggugagccu gcugagcgug     120

cugcugaugg gcugcguggc ugagaccggc augcagaucu acgagggcaa gcugaccgca     180

gagggccugc gguucggcau cguggccagc cgcgccaacc acgcucuggu ggaccggcuu     240

guggagggcg cuaucgacgc caucgugaga cacggcggcc gggaagagga caucacccug     300

gugcgggugu gcggcagcug ggagauuccc gucgccgccg gagaacuggc ccggaaggag     360

gacaucgacg ccgugaucgc caucggcgug cugugcagag gcgccacgcc cagcuucgac     420

uacaucgcca gcgaggugag caagggccug gccgaccuga gccuggagcu gcggaagccc     480

aucaccuucg gcgugaucac cgccgacacc cuggagcagg ccaucgaggc cgcaggcacc     540
```

ugccacggca acaagggcug ggaagccgcc cugugcgcca ucgagauggc caaccuguuc 600
aagagccugc ggggcggaag uggaggcucu gguggcagcg gaggaucugg cggcggccag 660
cccaacauca ccaaccugug ccccuucggc gagguguuca acgccacccg guucgccagc 720
guguacgccu ggaaccggaa gcggaucagc aacugcgugg ccgacuacag cgugcuguac 780
aacagcgcca gcuucagcac cuucaagugc uacggcguga gccccaccaa gcugaacgac 840
cugugcuuca ccaacgugua cgccgacagc uucgugaucc guggcgacga ggugcggcag 900
aucgcacccg gccagacagg caagaucgcc gacuacaacu acaagcugcc cgacgacuuc 960
accggcugcg ugaucgccug gaacagcaac aaccucgaca gcaagguggg cggcaacuac 1020
aacuaccugu accggcuguu ccggaagagc aaccugaagc ccuucgagcg ggacaucagc 1080
accgagaucu accaagccgg cuccaccccu ugcaacggcg uggagggcuu caacugcuac 1140
uucccucugc agagcuacgg cuuccagccc accaacggcg ugggcuacca gcccuaccgg 1200
gugguggugc ugagcuucga gcugcugcac gccccagcca ccgugugugg ccccaaguga 1260
uaauaggcug gagccucggu ggccuagcuu cuugccccuu gggccucccc ccagccccuc 1320
cuccccuucc ugcacccgua cccccguggu cuuugaauaa agucugagug ggcggc 1376

<210> SEQ ID NO 67
<211> LENGTH: 1200
<212> TYPE: RNA
<213> ORGANISM: Artificial Sequence
<220> FEATURE:
<223> OTHER INFORMATION: Synthetic

<400> SEQUENCE: 67
augggcaucc ugcccagccc uggcaugccc gcucugcuga gccuggugag ccugcugagc 60
gugcugcuga ugggcugcgu ggcugagacc ggcaugcaga ucuacgaggg caagcugacc 120
gcagagggcc ugcgguucgg caucguggcc agccgcgcca accacgcucu ggguggaccgg 180 cuuguggagg gcgcuaucga cgccaucgug agacacggcg gccgggaaga ggacaucacc 240
cuggugcggg ugugcggcag cugggagauu cccgucgccg ccggagaacu ggcccggaag 300
gaggacaucg acgccgugau cgccaucggc gugcugugca gaggcgccac gcccagcuuc 360
gacuacaucg ccagcgaggu gagcaagggc cuggccgacc ugagccugga gcugcggaag 420
cccaucaccu ucggcgugau caccgccgac acccuggagc aggccaucga ggccgcaggc 480
accugccacg gcaacaaggg cugggaagcc gcccugugcg ccaucgagau ggccaaccug 540
uucaagagcc ugcggggcgg aaguggaggc ucugguggca gcggaggauc uggcggcggc 600
cagcccaaca ucaccaaccu gugccccuuc ggcgaggugu ucaacgccac ccgguucgcc 660
agcguguacg ccuggaaccg gaagcggauc agcaacugcg uggccgacua cagcgugcug 720
uacaacagcg ccagcuucag caccuucaag ugcuacggcg ugagccccac caagcugaac 780
gaccugugcu ucaccaacgu guacgccgac agcuucguga uccguggcga cgaggugcgg 840
cagaucgcac ccggccagac aggcaagauc gccgacuaca acuacaagcu gcccgacgac 900
uucaccggcu gcgugaucgc cuggaacagc aacaaccucg acagcaaggu gggcggcaac 960
uacaacuacc uguaccggcu guuccggaag agcaaccuga agcccuucga gcgggacauc 1020
agcaccgaga ucuaccaagc cggcuccacc ccuugcaacg gcguggaggg cuucaacugc 1080
uacuucccuc ugcagagcua cggcuuccag cccaccaacg gcgugggcua ccagcccuac 1140
cggguggugg ugcugagcuu cgagcugcug cacgccccag ccaccgugug uggccccaag 1200

<210> SEQ ID NO 68
<211> LENGTH: 400
<212> TYPE: PRT
<213> ORGANISM: Artificial Sequence
<220> FEATURE:
<223> OTHER INFORMATION: Synthetic

<400> SEQUENCE: 68

```
Met Gly Ile Leu Pro Ser Pro Gly Met Pro Ala Leu Leu Ser Leu Val
1               5                   10                  15

Ser Leu Leu Ser Val Leu Leu Met Gly Cys Val Ala Glu Thr Gly Met
            20                  25                  30

Gln Ile Tyr Glu Gly Lys Leu Thr Ala Glu Gly Leu Arg Phe Gly Ile
        35                  40                  45

Val Ala Ser Arg Ala Asn His Ala Leu Val Asp Arg Leu Val Glu Gly
    50                  55                  60

Ala Ile Asp Ala Ile Val Arg His Gly Gly Arg Glu Glu Asp Ile Thr
65                  70                  75                  80

Leu Val Arg Val Cys Gly Ser Trp Glu Ile Pro Val Ala Ala Gly Glu
                85                  90                  95

Leu Ala Arg Lys Glu Asp Ile Asp Ala Val Ile Ala Ile Gly Val Leu
            100                 105                 110

Cys Arg Gly Ala Thr Pro Ser Phe Asp Tyr Ile Ala Ser Glu Val Ser
        115                 120                 125

Lys Gly Leu Ala Asp Leu Ser Leu Glu Leu Arg Lys Pro Ile Thr Phe
    130                 135                 140

Gly Val Ile Thr Ala Asp Thr Leu Glu Gln Ala Ile Glu Ala Ala Gly
145                 150                 155                 160

Thr Cys His Gly Asn Lys Gly Trp Glu Ala Ala Leu Cys Ala Ile Glu
                165                 170                 175

Met Ala Asn Leu Phe Lys Ser Leu Arg Gly Gly Ser Gly Gly Ser Gly
            180                 185                 190

Gly Ser Gly Gly Ser Gly Gly Gly Gln Pro Asn Ile Thr Asn Leu Cys
        195                 200                 205

Pro Phe Gly Glu Val Phe Asn Ala Thr Arg Phe Ala Ser Val Tyr Ala
    210                 215                 220

Trp Asn Arg Lys Arg Ile Ser Asn Cys Val Ala Asp Tyr Ser Val Leu
225                 230                 235                 240

Tyr Asn Ser Ala Ser Phe Ser Thr Phe Lys Cys Tyr Gly Val Ser Pro
                245                 250                 255

Thr Lys Leu Asn Asp Leu Cys Phe Thr Asn Val Tyr Ala Asp Ser Phe
            260                 265                 270

Val Ile Arg Gly Asp Glu Val Arg Gln Ile Ala Pro Gly Gln Thr Gly
        275                 280                 285

Lys Ile Ala Asp Tyr Asn Tyr Lys Leu Pro Asp Asp Phe Thr Gly Cys
    290                 295                 300

Val Ile Ala Trp Asn Ser Asn Asn Leu Asp Ser Lys Val Gly Gly Asn
305                 310                 315                 320

Tyr Asn Tyr Leu Tyr Arg Leu Phe Arg Lys Ser Asn Leu Lys Pro Phe
                325                 330                 335

Glu Arg Asp Ile Ser Thr Glu Ile Tyr Gln Ala Gly Ser Thr Pro Cys
            340                 345                 350

Asn Gly Val Glu Gly Phe Asn Cys Tyr Phe Pro Leu Gln Ser Tyr Gly
        355                 360                 365
```

```
Phe Gln Pro Thr Asn Gly Val Gly Tyr Gln Pro Tyr Arg Val Val Val
    370                 375                 380

Leu Ser Phe Glu Leu Leu His Ala Pro Ala Thr Val Cys Gly Pro Lys
385                 390                 395                 400


<210> SEQ ID NO 69
<211> LENGTH: 1334
<212> TYPE: RNA
<213> ORGANISM: Artificial Sequence
<220> FEATURE:
<223> OTHER INFORMATION: Synthetic

<400> SEQUENCE: 69

gggaaauaag agagaaaaga agaguaagaa gaaauauaag accccggcgc cgccaccaug      60

uacagcaugc agcuggcuag cugcgugacc cugacccugg ugcugcuggu gaacagccag     120

cccaacauca ccaaccugug ccccuucggc gagguguuca acgccacccg guucgccagc     180

guguacgccu ggaaccggaa gcggaucagc aacugcgugg ccgacuacag cgugcuguac     240

aacagcgcca gcuucagcac cuucaagugc uacggcguga gccccaccaa gcugaacgac     300

cugugcuuca ccaacgugua cgccgacagc uucgugaucc guggcgacga ggugcggcag     360

aucgcacccg gccagacagg caagaucgcc gacuacaacu acaagcugcc cgacgacuuc     420

accggcugcg ugaucgccug gaacagcaac aaccucgaca gcaaggugggg cggcaacuac     480

aacuaccugu accggcuguu ccggaagagc aaccugaagc ccuucgagcg ggacaucagc     540

accgagaucu accaagccgg cuccaccccu ugcaacggcg uggagggcuu caacugcuac     600

uucccucugc agagcuacgg cuuccagccc accaacggcg ugggcuacca gcccuaccgg     660

gugguggugc ugagcuucga gcugcugcac gccccagcca ccgugugugg ccccaaggga     720

ggaggcuccg gaggcgguag cgcugagacc ggcaugcaga ucuacgaggg caagcugacc     780

gcagagggcc ugcgguucgg caucguggcc agccgcgcca accacgcucu gguggaccgg     840

cuuguggagg gcgcuaucga cgccaucgug agacacggcg gccgggaaga ggacaucacc     900

cuggugcggg ugugcggcag cugggagauu cccgucgccg ccggagaacu ggcccggaag     960

gaggacaucg acgccgugau cgccaucggc gugcugugca gaggcgccac gcccagcuuc    1020

gacuacaucg ccagcgaggu gagcaagggc cuggccgacc ugagccugga gcugcggaag    1080

cccaucaccu ucggcgugau caccgccgac acccuggagc aggccaucga ggccgcaggc    1140

accugccacg gcaacaaggg cugggaagcc gcccugugcg ccaucgagau ggccaaccug    1200

uucaagagcc ugcggugaua auaggcugga gccucggugg ccuagcuucu ugccccuugg    1260

gccucccccc agccccuccu ccccuuccug cacccguacc cccguggucu uugaauaaag    1320

ucugaguggg cggc                                                      1334


<210> SEQ ID NO 70
<211> LENGTH: 1158
<212> TYPE: RNA
<213> ORGANISM: Artificial Sequence
<220> FEATURE:
<223> OTHER INFORMATION: Synthetic

<400> SEQUENCE: 70

auguacagca ugcagcuggc uagcugcgug acccugaccc uggugcugcu ggugaacagc      60

cagcccaaca ucaccaaccu gugccccuuc ggcgaggugu ucaacgccac ccgguucgcc     120

agcguguacg ccuggaaccg gaagcggauc agcaacugcg uggccgacua cagcgugcug     180

uacaacagcg ccagcuucag caccuucaag ugcuacggcg ugagccccac caagcugaac     240
```

```
gaccugugcu ucaccaacgu guacgccgac agcuucguga uccguggcga cgaggugcgg    300

cagaucgcac ccggccagac aggcaagauc gccgacuaca acuacaagcu gcccgacgac    360

uucaccggcu gcgugaucgc cuggaacagc aacaaccucg acagcaaggu gggcggcaac    420

uacaacuacc uguaccggcu guuccggaag agcaaccuga agcccuucga gcgggacauc    480

agcaccgaga ucuaccaagc cggcuccacc ccuugcaacg gcguggaggg cuucaacugc    540

uacuucccuc ugcagagcua cggcuuccag cccaccaacg gcgugggcua ccagcccuac    600

cggguggugg ugcugagcuu cgagcugcug cacgccccag ccaccgugug uggccccaag    660

ggaggaggcu ccggaggcgg uagcgcugag accggcaugc agaucuacga gggcaagcug    720

accgcagagg gccugcgguu cggcaucgug gccagccgcg ccaaccacgc ucugguggac    780

cggcuugugg agggcgcuau cgacgccauc gugagacacg gcggccggga agaggacauc    840

acccuggugc gggugugcgg cagcugggag auucccgucg ccgccggaga acuggcccgg    900

aaggaggaca ucgacgccgu gaucgccauc ggcgugcugu gcagaggcgc cacgcccagc    960

uucgacuaca ucgccagcga ggugagcaag ggccuggccg accugagccu ggagcugcgg   1020

aagcccauca ccuucggcgu gaucaccgcc gacacccugg agcaggccau cgaggccgca   1080

ggcaccugcc acggcaacaa gggcugggaa gccgcccugu gcgccaucga gauggccaac   1140

cuguucaaga gccugcgg                                                 1158
```

<210> SEQ ID NO 71
<211> LENGTH: 386
<212> TYPE: PRT
<213> ORGANISM: Artificial Sequence
<220> FEATURE:
<223> OTHER INFORMATION: Synthetic

<400> SEQUENCE: 71

```
Met Tyr Ser Met Gln Leu Ala Ser Cys Val Thr Leu Thr Leu Val Leu
1               5                   10                  15

Leu Val Asn Ser Gln Pro Asn Ile Thr Asn Leu Cys Pro Phe Gly Glu
            20                  25                  30

Val Phe Asn Ala Thr Arg Phe Ala Ser Val Tyr Ala Trp Asn Arg Lys
        35                  40                  45

Arg Ile Ser Asn Cys Val Ala Asp Tyr Ser Val Leu Tyr Asn Ser Ala
    50                  55                  60

Ser Phe Ser Thr Phe Lys Cys Tyr Gly Val Ser Pro Thr Lys Leu Asn
65                  70                  75                  80

Asp Leu Cys Phe Thr Asn Val Tyr Ala Asp Ser Phe Val Ile Arg Gly
                85                  90                  95

Asp Glu Val Arg Gln Ile Ala Pro Gly Gln Thr Gly Lys Ile Ala Asp
            100                 105                 110

Tyr Asn Tyr Lys Leu Pro Asp Asp Phe Thr Gly Cys Val Ile Ala Trp
        115                 120                 125

Asn Ser Asn Asn Leu Asp Ser Lys Val Gly Gly Asn Tyr Asn Tyr Leu
    130                 135                 140

Tyr Arg Leu Phe Arg Lys Ser Asn Leu Lys Pro Phe Glu Arg Asp Ile
145                 150                 155                 160

Ser Thr Glu Ile Tyr Gln Ala Gly Ser Thr Pro Cys Asn Gly Val Glu
                165                 170                 175

Gly Phe Asn Cys Tyr Phe Pro Leu Gln Ser Tyr Gly Phe Gln Pro Thr
            180                 185                 190
```

-continued

```
Asn Gly Val Gly Tyr Gln Pro Tyr Arg Val Val Val Leu Ser Phe Glu
        195                 200                 205

Leu Leu His Ala Pro Ala Thr Val Cys Gly Pro Lys Gly Gly Gly Ser
    210                 215                 220

Gly Gly Gly Ser Ala Glu Thr Gly Met Gln Ile Tyr Glu Gly Lys Leu
225                 230                 235                 240

Thr Ala Glu Gly Leu Arg Phe Gly Ile Val Ala Ser Arg Ala Asn His
                245                 250                 255

Ala Leu Val Asp Arg Leu Val Glu Gly Ala Ile Asp Ala Ile Val Arg
            260                 265                 270

His Gly Gly Arg Glu Glu Asp Ile Thr Leu Val Arg Val Cys Gly Ser
        275                 280                 285

Trp Glu Ile Pro Val Ala Ala Gly Glu Leu Ala Arg Lys Glu Asp Ile
    290                 295                 300

Asp Ala Val Ile Ala Ile Gly Val Leu Cys Arg Gly Ala Thr Pro Ser
305                 310                 315                 320

Phe Asp Tyr Ile Ala Ser Glu Val Ser Lys Gly Leu Ala Asp Leu Ser
                325                 330                 335

Leu Glu Leu Arg Lys Pro Ile Thr Phe Gly Val Ile Thr Ala Asp Thr
            340                 345                 350

Leu Glu Gln Ala Ile Glu Ala Ala Gly Thr Cys His Gly Asn Lys Gly
        355                 360                 365

Trp Glu Ala Ala Leu Cys Ala Ile Glu Met Ala Asn Leu Phe Lys Ser
    370                 375                 380

Leu Arg
385
```

<210> SEQ ID NO 72
<211> LENGTH: 947
<212> TYPE: RNA
<213> ORGANISM: Artificial Sequence
<220> FEATURE:
<223> OTHER INFORMATION: Synthetic

<400> SEQUENCE: 72

```
gggaaauaag agagaaaaga agaguaagaa gaaauauaag accccggcgc cgccaccaug      60

uacagcaugc agcuggcuag cugcgugacc cugacccugg ugcugcuggu gaacagccag     120

cccaacauca ccaaccugug ccccuucggc gagguguuca acgccacccg guucgccagc     180

guguacgccu ggaaccggaa gcggaucagc aacugcgugg ccgacuacag cgugcuguac     240

aacagcgcca gcuucagcac cuucaagugc uacggcguga gccccaccaa gcugaacgac     300

cugugcuuca ccaacgugua cgccgacagc uucgugaucc guggcgacga ggugcggcag     360

aucgcacccg gccagacagg caagaucgcc gacuacaacu acaagcugcc cgacgacuuc     420

accggcugcg ugaucgccug gaacagcaac aaccucgaca gcaaggugggg cggcaacuac     480

aacuaccugu accggcuguu ccggaagagc aaccugaagc ccuucgagcg ggacaucagc     540

accgagaucu accaagccgg cuccaccccu ugcaacggcg uggagggcuu caacugcuac     600

uucccucugc agagcuacgg cuuccagccc accaacggcg ugggcuacca gcccuaccgg     660

guggugguc ugagcuucga gcugcugcac gccccagcca ccgugugugg ccccaagucu     720

ggcggaggcg gcagcgccau cggcggcuac aucccccgagg ccccuagaga cggccaggcc     780

uacgugcgga aggacggcga gugggugcug cugagcaccu uccugggcug auaauaggcu     840

ggagccucgg uggccuagcu ucuugccccu ugggccuccc cccagccccu ccuccccuuc     900
```

cugcacccgu acccccgugg ucuuugaaua aagucugagu gggcggc 947

<210> SEQ ID NO 73
<211> LENGTH: 771
<212> TYPE: RNA
<213> ORGANISM: Artificial Sequence
<220> FEATURE:
<223> OTHER INFORMATION: Synthetic

<400> SEQUENCE: 73
auguacagca ugcagcuggc uagcugcgug acccugaccc uggugcugcu ggugaacagc 60
cagcccaaca ucaccaaccu gugcccccuuc ggcgaggugu ucaacgccac ccgguucgcc 120
agcguguacg ccuggaaccg gaagcggauc agcaacugcg uggccgacua cagcgugcug 180
uacaacagcg ccagcuucag caccuucaag ugcuacggcg ugagccccac caagcugaac 240
gaccugugcu ucaccaacgu guacgccgac agcuucguga uccguggcga cgaggugcgg 300
cagaucgcac ccggccagac aggcaagauc gccgacuaca acuacaagcu gcccgacgac 360
uucaccggcu gcgugaucgc cuggaacagc aacaaccucg acagcaaggu gggcggcaac 420
uacaacuacc uguaccggcu guuccggaag agcaaccuga agcccuucga gcgggacauc 480
agcaccgaga ucuaccaagc cggcuccacc ccuugcaacg gcguggaggg cuucaacugc 540
uacuucccuc ugcagagcua cggcuuccag cccaccaacg gcgugggcua ccagcccuac 600
cggguggugg ugcugagcuu cgagcugcug cacgccccag ccaccgugug uggccccaag 660
ucuggcggag gcggcagcgc caucggcggc uacaucccccg aggccccuag agacggccag 720
gccuacgugc ggaaggacgg cgagugggug cugcugagca ccuuccuggg c 771

<210> SEQ ID NO 74
<211> LENGTH: 257
<212> TYPE: PRT
<213> ORGANISM: Artificial Sequence
<220> FEATURE:
<223> OTHER INFORMATION: Synthetic

<400> SEQUENCE: 74

Met Tyr Ser Met Gln Leu Ala Ser Cys Val Thr Leu Thr Leu Val Leu
1               5                   10                  15

Leu Val Asn Ser Gln Pro Asn Ile Thr Asn Leu Cys Pro Phe Gly Glu
            20                  25                  30

Val Phe Asn Ala Thr Arg Phe Ala Ser Val Tyr Ala Trp Asn Arg Lys
        35                  40                  45

Arg Ile Ser Asn Cys Val Ala Asp Tyr Ser Val Leu Tyr Asn Ser Ala
    50                  55                  60

Ser Phe Ser Thr Phe Lys Cys Tyr Gly Val Ser Pro Thr Lys Leu Asn
65                  70                  75                  80

Asp Leu Cys Phe Thr Asn Val Tyr Ala Asp Ser Phe Val Ile Arg Gly
                85                  90                  95

Asp Glu Val Arg Gln Ile Ala Pro Gly Gln Thr Gly Lys Ile Ala Asp
            100                 105                 110

Tyr Asn Tyr Lys Leu Pro Asp Asp Phe Thr Gly Cys Val Ile Ala Trp
        115                 120                 125

Asn Ser Asn Asn Leu Asp Ser Lys Val Gly Gly Asn Tyr Asn Tyr Leu
    130                 135                 140

Tyr Arg Leu Phe Arg Lys Ser Asn Leu Lys Pro Phe Glu Arg Asp Ile
145                 150                 155                 160

Ser Thr Glu Ile Tyr Gln Ala Gly Ser Thr Pro Cys Asn Gly Val Glu

```
                165                 170                 175

Gly Phe Asn Cys Tyr Phe Pro Leu Gln Ser Tyr Gly Phe Gln Pro Thr
            180                 185                 190

Asn Gly Val Gly Tyr Gln Pro Tyr Arg Val Val Val Leu Ser Phe Glu
        195                 200                 205

Leu Leu His Ala Pro Ala Thr Val Cys Gly Pro Lys Ser Gly Gly Gly
    210                 215                 220

Gly Ser Ala Ile Gly Gly Tyr Ile Pro Glu Ala Pro Arg Asp Gly Gln
225                 230                 235                 240

Ala Tyr Val Arg Lys Asp Gly Glu Trp Val Leu Leu Ser Thr Phe Leu
                245                 250                 255

Gly


<210> SEQ ID NO 75
<211> LENGTH: 920
<212> TYPE: RNA
<213> ORGANISM: Artificial Sequence
<220> FEATURE:
<223> OTHER INFORMATION: Synthetic

<400> SEQUENCE: 75

gggaaauaag agagaaaaga agaguaagaa gaaauauaag accccggcgc cgccaccaug      60

uacagcaugc agcuggcuag cugcgugacc cugacccugg ugcugcuggu gaacagccag     120

cccaacauca ccaaccugug ccccuucggc gagguguuca acgccacccg guucgccagc     180

guguacgccu ggaaccggaa gcggaucagc aacugcgugg ccgacuacag cgugcuguac     240

aacagcgcca gcuucagcac cuucaagugc uacggcguga gccccaccaa gcugaacgac     300

cugugcuuca ccaacgugua cgccgacagc uucgugaucc guggcgacga ggugcggcag     360

aucgcacccg gccagacagg caagaucgcc gacuacaacu acaagcugcc cgacgacuuc     420

accggcugcg ugaucgccug gaacagcaac aaccucgaca gcaaggu ggg cggcaacuac     480

aacuaccugu accggcuguu ccggaagagc aaccugaagc ccuucgagcg ggacaucagc     540

accgagaucu accaagccgg cuccaccccu ugcaacggcg uggagggcuu caacugcuac     600

uucccucugc agagcuacgg cuuccagccc accaacggcg ugggcuacca gcccuaccgg     660

gugguggugc ugagcuucga gcugcugcac gccccagcca ccgugugugg ccccaagucu     720

ggcggaggca gcauccuggc caucuacagc accguggcca gcagccuggu gcugcuggug     780

agccugggcg ccaucagcuu cugauaauag gcuggagccu cgguggccua gcuucuugcc     840

ccuugggccu ccccccagcc ccuccucccc uuccugcacc cguacccccg uggucuuuga     900

auaaagucug agugggcggc                                                 920


<210> SEQ ID NO 76
<211> LENGTH: 744
<212> TYPE: RNA
<213> ORGANISM: Artificial Sequence
<220> FEATURE:
<223> OTHER INFORMATION: Synthetic

<400> SEQUENCE: 76

auguacagca ugcagcuggc uagcugcgug acccugaccc uggugcugcu ggugaacagc      60

cagcccaaca ucaccaaccu gugccccuuc ggcgaggugu ucaacgccac ccgguucgcc     120

agcguguacg ccuggaaccg gaagcggauc agcaacugcg uggccgacua cagcgugcug     180

uacaacagcg ccagcuucag caccuucaag ugcuacggcg ugagccccac caagcugaac     240
```

-continued

```
gaccugugcu ucaccaacgu guacgccgac agcuucguga uccguggcga cgaggugcgg    300

cagaucgcac ccggccagac aggcaagauc gccgacuaca acuacaagcu gcccgacgac    360

uucaccggcu gcgugaucgc cuggaacagc aacaaccucg acagcaaggu gggcggcaac    420

uacaacuacc uguaccggcu guuccggaag agcaaccuga agcccuucga gcgggacauc    480

agcaccgaga ucuaccaagc cggcuccacc ccuugcaacg gcguggaggg cuucaacugc    540

uacuucccuc ugcagagcua cggcuuccag cccaccaacg gcgugggcua ccagcccuac    600

cgggugugg ugcugagcuu cgagcugcug cacgccccag ccaccgugug uggccccaag    660

ucuggcggag gcagcauccu ggccaucuac agcaccgugg ccagcagccu ggugcugcug    720

gugagccugg gcgccaucag cuuc                                           744
```

```
<210> SEQ ID NO 77
<211> LENGTH: 248
<212> TYPE: PRT
<213> ORGANISM: Artificial Sequence
<220> FEATURE:
<223> OTHER INFORMATION: Synthetic

<400> SEQUENCE: 77

Met Tyr Ser Met Gln Leu Ala Ser Cys Val Thr Leu Thr Leu Val Leu
1               5                   10                  15

Leu Val Asn Ser Gln Pro Asn Ile Thr Asn Leu Cys Pro Phe Gly Glu
            20                  25                  30

Val Phe Asn Ala Thr Arg Phe Ala Ser Val Tyr Ala Trp Asn Arg Lys
        35                  40                  45

Arg Ile Ser Asn Cys Val Ala Asp Tyr Ser Val Leu Tyr Asn Ser Ala
    50                  55                  60

Ser Phe Ser Thr Phe Lys Cys Tyr Gly Val Ser Pro Thr Lys Leu Asn
65                  70                  75                  80

Asp Leu Cys Phe Thr Asn Val Tyr Ala Asp Ser Phe Val Ile Arg Gly
                85                  90                  95

Asp Glu Val Arg Gln Ile Ala Pro Gly Gln Thr Gly Lys Ile Ala Asp
            100                 105                 110

Tyr Asn Tyr Lys Leu Pro Asp Asp Phe Thr Gly Cys Val Ile Ala Trp
        115                 120                 125

Asn Ser Asn Asn Leu Asp Ser Lys Val Gly Gly Asn Tyr Asn Tyr Leu
    130                 135                 140

Tyr Arg Leu Phe Arg Lys Ser Asn Leu Lys Pro Phe Glu Arg Asp Ile
145                 150                 155                 160

Ser Thr Glu Ile Tyr Gln Ala Gly Ser Thr Pro Cys Asn Gly Val Glu
                165                 170                 175

Gly Phe Asn Cys Tyr Phe Pro Leu Gln Ser Tyr Gly Phe Gln Pro Thr
            180                 185                 190

Asn Gly Val Gly Tyr Gln Pro Tyr Arg Val Val Val Leu Ser Phe Glu
        195                 200                 205

Leu Leu His Ala Pro Ala Thr Val Cys Gly Pro Lys Ser Gly Gly Gly
    210                 215                 220

Ser Ile Leu Ala Ile Tyr Ser Thr Val Ala Ser Ser Leu Val Leu Leu
225                 230                 235                 240

Val Ser Leu Gly Ala Ile Ser Phe
                245

<210> SEQ ID NO 78
<211> LENGTH: 1025
```

<212> TYPE: RNA
<213> ORGANISM: Artificial Sequence
<220> FEATURE:
<223> OTHER INFORMATION: Synthetic

<400> SEQUENCE: 78
gggaaauaag agagaaaaga agaguaagaa gaaauauaag accccggcgc cgccaccaug 60
uacagcaugc agcuggcuag cugcgugacc cugacccugg ugcugcuggu gaacagccag 120
cccaacauca ccaaccugug ccccuucggc gagguguuca acgccacccg guucgccagc 180
guguacgccu ggaaccggaa gcggaucagc aacugcgugg ccgacuacag cgugcuguac 240
aacagcgcca gcuucagcac cuucaagugc uacggcguga gccccaccaa gcugaacgac 300
cugugcuuca ccaacgugua cgccgacagc uucgugaucc guggcgacga ggugcggcag 360
aucgcacccg gccagacagg caagaucgcc gacuacaacu acaagcugcc cgacgacuuc 420
accggcugcg ugaucgccug gaacagcaac aaccucgaca gcaagguggg cggcaacuac 480
aacuaccugu accggcuguu ccggaagagc aaccugaagc ccuucgagcg ggacaucagc 540
accgagaucu accaagccgg cuccaccccu ugcaacggcg uggagggcuu caacugcuac 600
uucccucugc agagcuacgg cuuccagccc accaacggcg ugggcuacca gcccuaccgg 660
gugguggugc ugagcuucga gcugcugcac gccccagcca ccgugugugg ccccaagucu 720
ggcggaggcg gcagcgccau cggcggcuac auccccgagg ccccuagaga cggccaggcc 780
uacgugcgga aggacggcga gugggugcug cugagcaccu uccugggcgg aggcagcauc 840
cuggccaucu acagcaccgu ggccagcagc cuggugcugc uggugagccu gggcgccauc 900
agcuucugau aauaggcugg agccucggug gccuagcuuc uugccccuug ggccuccccc 960
cagccccucc uccccuuccu gcacccguac ccccgugguc uuugaauaaa gucugagugg 1020
gcggc 1025

<210> SEQ ID NO 79
<211> LENGTH: 849
<212> TYPE: RNA
<213> ORGANISM: Artificial Sequence
<220> FEATURE:
<223> OTHER INFORMATION: Synthetic

<400> SEQUENCE: 79
auguacagca ugcagcuggc uagcugcgug acccugaccc uggugcugcu ggugaacagc 60
cagcccaaca ucaccaaccu gugccccuuc ggcgaggugu ucaacgccac ccgguucgcc 120
agcguguacg ccuggaaccg gaagcggauc agcaacugcg uggccgacua cagcgugcug 180
uacaacagcg ccagcuucag caccuucaag ugcuacggcg ugagccccac caagcugaac 240
gaccugugcu ucaccaacgu guacgccgac agcuucguga uccguggcga cgaggugcgg 300
cagaucgcac ccggccagac aggcaagauc gccgacuaca acuacaagcu gcccgacgac 360
uucaccggcu gcgugaucgc cuggaacagc aacaaccucg acagcaaggu gggcggcaac 420
uacaacuacc uguaccggcu guuccggaag agcaaccuga agcccuucga gcgggacauc 480
agcaccgaga ucuaccaagc cggcuccacc ccuugcaacg gcguggaggg cuucaacugc 540
uacuucccuc ugcagagcua cggcuuccag cccaccaacg gcgugggcua ccagcccuac 600
cggguggugg ugcugagcuu cgagcugcug cacgccccag ccaccgugug uggccccaag 660
ucuggcggag gcggcagcgc caucggcggc uacauccccg aggccccuag agacggccag 720
gccuacgugc ggaaggacgg cgagugggug cugcugagca ccuuccuggg cggaggcagc 780
auccuggcca ucuacagcac cguggccagc agccuggugc ugcuggugag ccugggcgcc 840
aucagcuuc 849

<210> SEQ ID NO 80
<211> LENGTH: 283
<212> TYPE: PRT
<213> ORGANISM: Artificial Sequence
<220> FEATURE:
<223> OTHER INFORMATION: Synthetic

<400> SEQUENCE: 80

Met Tyr Ser Met Gln Leu Ala Ser Cys Val Thr Leu Thr Leu Val Leu
1 5 10 15

Leu Val Asn Ser Gln Pro Asn Ile Thr Asn Leu Cys Pro Phe Gly Glu
20 25 30

Val Phe Asn Ala Thr Arg Phe Ala Ser Val Tyr Ala Trp Asn Arg Lys
35 40 45

Arg Ile Ser Asn Cys Val Ala Asp Tyr Ser Val Leu Tyr Asn Ser Ala
50 55 60

Ser Phe Ser Thr Phe Lys Cys Tyr Gly Val Ser Pro Thr Lys Leu Asn
65 70 75 80

Asp Leu Cys Phe Thr Asn Val Tyr Ala Asp Ser Phe Val Ile Arg Gly
85 90 95

Asp Glu Val Arg Gln Ile Ala Pro Gly Gln Thr Gly Lys Ile Ala Asp
100 105 110

Tyr Asn Tyr Lys Leu Pro Asp Asp Phe Thr Gly Cys Val Ile Ala Trp
115 120 125

Asn Ser Asn Asn Leu Asp Ser Lys Val Gly Gly Asn Tyr Asn Tyr Leu
130 135 140

Tyr Arg Leu Phe Arg Lys Ser Asn Leu Lys Pro Phe Glu Arg Asp Ile
145 150 155 160

Ser Thr Glu Ile Tyr Gln Ala Gly Ser Thr Pro Cys Asn Gly Val Glu
165 170 175

Gly Phe Asn Cys Tyr Phe Pro Leu Gln Ser Tyr Gly Phe Gln Pro Thr
180 185 190

Asn Gly Val Gly Tyr Gln Pro Tyr Arg Val Val Val Leu Ser Phe Glu
195 200 205

Leu Leu His Ala Pro Ala Thr Val Cys Gly Pro Lys Ser Gly Gly Gly
210 215 220

Gly Ser Ala Ile Gly Gly Tyr Ile Pro Glu Ala Pro Arg Asp Gly Gln
225 230 235 240

Ala Tyr Val Arg Lys Asp Gly Glu Trp Val Leu Leu Ser Thr Phe Leu
245 250 255

Gly Gly Gly Ser Ile Leu Ala Ile Tyr Ser Thr Val Ala Ser Ser Leu
260 265 270

Val Leu Leu Val Ser Leu Gly Ala Ile Ser Phe
275 280

<210> SEQ ID NO 81
<211> LENGTH: 1028
<212> TYPE: RNA
<213> ORGANISM: Artificial Sequence
<220> FEATURE:
<223> OTHER INFORMATION: Synthetic

<400> SEQUENCE: 81
gggaaauaag agagaaaaga agaguaagaa gaaauauaag accccggcgc cgccaccaug 60

```
uacagcaugc agcuggcuag cugcgugacc cugacccugg ugcugcuggu gaacagccag    120
cccaacauca ccaaccugug ccccuucggc gagguguuca acgccacccg guucgccagc    180
guguacgccu ggaaccggaa gcggaucagc aacugcgugg ccgacuacag cgugcuguac    240
aacagcgcca gcuucagcac cuucaagugc uacggcguga gccccaccaa gcugaacgac    300
cugugcuuca ccaacgugua cgccgacagc uucgugaucc guggcgacga ggugcggcag    360
aucgcacccg gccagacagg caagaucgcc gacuacaacu acaagcugcc cgacgacuuc    420
accggcugcg ugaucgccug gaacagcaac aaccucgaca gcaaggugggg cggcaacuac    480
aacuaccugu accggcuguu ccggaagagc aaccugaagc ccuucgagcg ggacaucagc    540
accgagaucu accaagccgg cuccaccccu ugcaacggcg uggagggcuu caacugcuac    600
uucccucugc agagcuacgg cuuccagccc accaacggcg ugggcuacca gcccuaccgg    660
guggguggugc ugagcuucga gcugcugcac gccccagcca ccgugugugg ccccaagucu    720
ggcggaggca gcauccuggc caucuacagc accguggcca gcagccuggu gcugcuggug    780
agccugggcg ccaucagcuu cggcggaggc agcgccaucg gcggcuacau ccccgaggcc    840
ccuagagacg gccaggccua cgugcggaag gacggcgagu gggugcugcu gagcaccuuc    900
cugggcaagu gauaauaggc uggagccucg guggccuagc uucuugcccc uuggggccucc    960
ccccagcccc uccuccccuu ccugcacccg uacccccgug gucuuugaau aaagucugag   1020
ugggcggc                                                            1028
```

<210> SEQ ID NO 82
<211> LENGTH: 852
<212> TYPE: RNA
<213> ORGANISM: Artificial Sequence
<220> FEATURE:
<223> OTHER INFORMATION: Synthetic

<400> SEQUENCE: 82

```
auguacagca ugcagcuggc uagcugcgug acccugaccc uggugcugcu ggugaacagc     60
cagcccaaca ucaccaaccu gugccccuuc ggcgaggugu ucaacgccac ccgguucgcc    120
agcguguacg ccuggaaccg gaagcggauc agcaacugcg uggccgacua cagcgugcug    180
uacaacagcg ccagcuucag caccuucaag ugcuacggcg ugagccccac caagcugaac    240
gaccugugcu ucaccaacgu guacgccgac agcuucguga uccguggcga cgaggugcgg    300
cagaucgcac ccggccagac aggcaagauc gccgacuaca acuacaagcu gcccgacgac    360
uucaccggcu gcgugaucgc cuggaacagc aacaaccucg acagcaaggu gggcggcaac    420
uacaacuacc uguaccggcu guuccggaag agcaaccuga agcccuucga gcgggacauc    480
agcaccgaga ucuaccaagc cggcuccacc ccuugcaacg gcguggaggg cuucaacugc    540
uacuucccuc ugcagagcua cggcuuccag cccaccaacg gcgugggcua ccagcccuac    600
cgggugggugg ugcugagcuu cgagcugcug cacgccccag ccaccgugug uggccccaag    660
ucuggcggag gcagcauccu ggccaucuac agcaccgugg ccagcagccu ggugcugcug    720
gugagccugg gcgccaucag cuucggcgga ggcagcgcca ucggcggcua cauccccgag    780
gccccuagag acggccaggc cuacgugcgg aaggacggcg agugggugcu gcugagcacc    840
uuccugggca ag                                                        852
```

<210> SEQ ID NO 83
<211> LENGTH: 284
<212> TYPE: PRT

<213> ORGANISM: Artificial Sequence
<220> FEATURE:
<223> OTHER INFORMATION: Synthetic

<400> SEQUENCE: 83

```
Met Tyr Ser Met Gln Leu Ala Ser Cys Val Thr Leu Thr Leu Val Leu
1               5                   10                  15

Leu Val Asn Ser Gln Pro Asn Ile Thr Asn Leu Cys Pro Phe Gly Glu
            20                  25                  30

Val Phe Asn Ala Thr Arg Phe Ala Ser Val Tyr Ala Trp Asn Arg Lys
        35                  40                  45

Arg Ile Ser Asn Cys Val Ala Asp Tyr Ser Val Leu Tyr Asn Ser Ala
    50                  55                  60

Ser Phe Ser Thr Phe Lys Cys Tyr Gly Val Ser Pro Thr Lys Leu Asn
65                  70                  75                  80

Asp Leu Cys Phe Thr Asn Val Tyr Ala Asp Ser Phe Val Ile Arg Gly
                85                  90                  95

Asp Glu Val Arg Gln Ile Ala Pro Gly Gln Thr Gly Lys Ile Ala Asp
            100                 105                 110

Tyr Asn Tyr Lys Leu Pro Asp Asp Phe Thr Gly Cys Val Ile Ala Trp
        115                 120                 125

Asn Ser Asn Asn Leu Asp Ser Lys Val Gly Gly Asn Tyr Asn Tyr Leu
    130                 135                 140

Tyr Arg Leu Phe Arg Lys Ser Asn Leu Lys Pro Phe Glu Arg Asp Ile
145                 150                 155                 160

Ser Thr Glu Ile Tyr Gln Ala Gly Ser Thr Pro Cys Asn Gly Val Glu
                165                 170                 175

Gly Phe Asn Cys Tyr Phe Pro Leu Gln Ser Tyr Gly Phe Gln Pro Thr
            180                 185                 190

Asn Gly Val Gly Tyr Gln Pro Tyr Arg Val Val Val Leu Ser Phe Glu
        195                 200                 205

Leu Leu His Ala Pro Ala Thr Val Cys Gly Pro Lys Ser Gly Gly Gly
    210                 215                 220

Ser Ile Leu Ala Ile Tyr Ser Thr Val Ala Ser Ser Leu Val Leu Leu
225                 230                 235                 240

Val Ser Leu Gly Ala Ile Ser Phe Gly Gly Gly Ser Ala Ile Gly Gly
                245                 250                 255

Tyr Ile Pro Glu Ala Pro Arg Asp Gly Gln Ala Tyr Val Arg Lys Asp
            260                 265                 270

Gly Glu Trp Val Leu Leu Ser Thr Phe Leu Gly Lys
        275                 280
```

<210> SEQ ID NO 84
<211> LENGTH: 1142
<212> TYPE: RNA
<213> ORGANISM: Artificial Sequence
<220> FEATURE:
<223> OTHER INFORMATION: Synthetic

<400> SEQUENCE: 84

```
gggaaauaag agagaaaaga agaguaagaa gaaauauaag accccggcgc cgccaccaug      60

uacagcaugc agcuggcuag cugcgugacc cugacccugg ugcugcuggu gaacagccag     120

cgggugcagc ccaccgagag caucgugcgg uuccccaaca ucaccaaccu gugccccuuc     180

ggcgaggugu ucaacgccac ccgguucgcc agcguguacg ccuggaaccg gaagcggauc     240

agcaacugcg uggccgacua cagcgugcug uacaacagcg ccagcuucag caccuucaag     300
```

ugcuacggcg ugagccccac caagcugaac gaccugugcu ucaccaacgu guacgccgac 360
agcuucguga uccguggcga cgaggugcgg cagaucgcac ccggccagac aggcaagauc 420
gccgacuaca acuacaagcu gcccgacgac uucaccggcu gcgugaucgc cuggaacagc 480
aacaaccucg acagcaaggu gggcggcaac uacaacuacc uguaccggcu guuccggaag 540
agcaaccuga agcccuucga gcgggacauc agcaccgaga ucuaccaagc cggcuccacc 600
ccuugcaacg gcguggaggg cuucaacugc uacuucccuc ugcagagcua cggcuuccag 660
cccaccaacg gcgugggcua ccagcccuac cgggugggg ugcugagcuu cgagcugcug 720
cacgccccag ccaccgugug uggccccaag aagagcacca accuggugaa gaacaagugc 780
gugaacuuca acuucaacgg ccuuaccggc accggcgugc ugaccgagag caacaagaaa 840
uuccugcccu uucagcaguu cggccgggac aucgccgaca ccaccgacgc ugugcgggau 900
ccccagaccc uggagauccu ggacaucacc ccuugcagcu cuggcggagg cagcauccug 960
gccaucuaca gcaccguggc cagcagccug gugcugcugg ugagccuggg cgccaucagc 1020
uucugauaau aggcuggagc cucgguggcc uagcuucuug ccccuugggc cuccccccag 1080
ccccuccucc ccuuccugca cccguacccc cguggucuuu gaauaaaguc ugagugggcg 1140
gc 1142

<210> SEQ ID NO 85
<211> LENGTH: 966
<212> TYPE: RNA
<213> ORGANISM: Artificial Sequence
<220> FEATURE:
<223> OTHER INFORMATION: Synthetic

<400> SEQUENCE: 85
auguacagca ugcagcuggc uagcugcgug acccugaccc uggugcugcu ggugaacagc 60
cagcgggugc agcccaccga gagcaucgug cgguucccca acaucaccaa ccugugcccc 120
uucggcgagg uguucaacgc cacccgguuc gccagcgugu acgccuggaa ccggaagcgg 180
aucagcaacu gcguggccga cuacagcgug cuguacaaca gcgccagcuu cagcaccuuc 240
aagugcuacg gcgugagccc caccaagcug aacgaccugu gcuucaccaa cguguacgcc 300
gacagcuucg ugauccgugg cgacgaggug cggcagaucg cacccggcca gacaggcaag 360
aucgccgacu acaacuacaa gcugcccgac gacuucaccg gcugcgugau cgccuggaac 420
agcaacaacc ucgacagcaa ggugggcggc aacuacaacu accuguaccg gcuguuccgg 480
aagagcaacc ugaagcccuu cgagcgggac aucagcaccg agaucuacca agccggcucc 540
accccuugca acggcgugga gggcuucaac ugcuacuucc cucugcagag cuacggcuuc 600
cagcccacca acggcguggg cuaccagccc uaccgggugg uggugcugag cuucgagcug 660
cugcacgccc cagccaccgu guguggcccc aagaagagca ccaaccuggu gaagaacaag 720
ugcgugaacu ucaacuucaa cggccuuacc ggcaccggcg ugcugaccga gagcaacaag 780
aaauuccugc ccuuucagca guucggccgg gacaucgccg acaccaccga cgcugugcgg 840
gauccccaga cccuggagau ccuggacauc accccuugca gcucuggcgg aggcagcauc 900
cuggccaucu acagcaccgu ggccagcagc cuggugcugc uggugagccu gggcgccauc 960
agcuuc 966

<210> SEQ ID NO 86
<211> LENGTH: 322
<212> TYPE: PRT

<213> ORGANISM: Artificial Sequence
<220> FEATURE:
<223> OTHER INFORMATION: Synthetic

<400> SEQUENCE: 86

```
Met Tyr Ser Met Gln Leu Ala Ser Cys Val Thr Leu Thr Leu Val Leu
1               5                   10                  15

Leu Val Asn Ser Gln Arg Val Gln Pro Thr Glu Ser Ile Val Arg Phe
            20                  25                  30

Pro Asn Ile Thr Asn Leu Cys Pro Phe Gly Glu Val Phe Asn Ala Thr
        35                  40                  45

Arg Phe Ala Ser Val Tyr Ala Trp Asn Arg Lys Arg Ile Ser Asn Cys
    50                  55                  60

Val Ala Asp Tyr Ser Val Leu Tyr Asn Ser Ala Ser Phe Ser Thr Phe
65                  70                  75                  80

Lys Cys Tyr Gly Val Ser Pro Thr Lys Leu Asn Asp Leu Cys Phe Thr
                85                  90                  95

Asn Val Tyr Ala Asp Ser Phe Val Ile Arg Gly Asp Glu Val Arg Gln
            100                 105                 110

Ile Ala Pro Gly Gln Thr Gly Lys Ile Ala Asp Tyr Asn Tyr Lys Leu
        115                 120                 125

Pro Asp Asp Phe Thr Gly Cys Val Ile Ala Trp Asn Ser Asn Asn Leu
    130                 135                 140

Asp Ser Lys Val Gly Gly Asn Tyr Asn Tyr Leu Tyr Arg Leu Phe Arg
145                 150                 155                 160

Lys Ser Asn Leu Lys Pro Phe Glu Arg Asp Ile Ser Thr Glu Ile Tyr
                165                 170                 175

Gln Ala Gly Ser Thr Pro Cys Asn Gly Val Glu Gly Phe Asn Cys Tyr
            180                 185                 190

Phe Pro Leu Gln Ser Tyr Gly Phe Gln Pro Thr Asn Gly Val Gly Tyr
        195                 200                 205

Gln Pro Tyr Arg Val Val Val Leu Ser Phe Glu Leu Leu His Ala Pro
    210                 215                 220

Ala Thr Val Cys Gly Pro Lys Lys Ser Thr Asn Leu Val Lys Asn Lys
225                 230                 235                 240

Cys Val Asn Phe Asn Phe Asn Gly Leu Thr Gly Thr Gly Val Leu Thr
                245                 250                 255

Glu Ser Asn Lys Lys Phe Leu Pro Phe Gln Gln Phe Gly Arg Asp Ile
            260                 265                 270

Ala Asp Thr Thr Asp Ala Val Arg Asp Pro Gln Thr Leu Glu Ile Leu
        275                 280                 285

Asp Ile Thr Pro Cys Ser Ser Gly Gly Gly Ser Ile Leu Ala Ile Tyr
    290                 295                 300

Ser Thr Val Ala Ser Ser Leu Val Leu Leu Val Ser Leu Gly Ala Ile
305                 310                 315                 320

Ser Phe
```

<210> SEQ ID NO 87
<211> LENGTH: 1142
<212> TYPE: RNA
<213> ORGANISM: Artificial Sequence
<220> FEATURE:
<223> OTHER INFORMATION: Synthetic

<400> SEQUENCE: 87

```
gggaaauaag agagaaaaga agaguaagaa gaaauauaag accccggcgc cgccaccaug     60
```

uacagcaugc agcuggcuag cugcgugacc cugacccugg ugcugcuggu gaacagccag 120
cgggugcagc ccaccgagag caucgugcgg uuccccaaca ucaccaaccu gugccccuuc 180
ggcgaggugu ucaacgccac ccgguucgcc agcguguacg ccuggaaccg gaagcggauc 240
agcaacugcg uggccgacua cagcgugcug uacaacagcg ccagcuucag caccuucaag 300
ugcuacggcg ugagccccac caagcugaac gaccugugcu ucaccaacgu guacgccgac 360
agcuucguga uccguggcga cgaggugcgg cagaucgcac ccggccagac aggcaagauc 420
gccgacuaca acuacaagcu gcccgacgac uucaccggcu gcgugaucgc cuggaacagc 480
aacaaccucg acagcaaggu gggcggcaac uacaacuacc uguaccggcu guuccggaag 540
agcaaccuga agcccuucga gcgggacauc agcaccgaga ucuaccaagc cggcuccacc 600
ccuugcaacg gcguggaggg cuucaacugc uacuucccuc ugcagagcua cggcuuccag 660
cccaccaacg gcgugggcua ccagcccuac cggguggugg ugcugagcuu cgagcugcug 720
cacgccccag ccaccgugug uggccccaag aagagcacca accuggugaa gaacaagugc 780
gugaacuuca acuucaacgg ccuuaccggc accggcgugc ugaccgagag caacaagaaa 840
uuccugcccu uuugccaguu cggccgggac aucgccgaca ccaccgacgc ugugcgggau 900
ccccagaccc uggagauccu ggacaucacc ccuugcagcu cuggcggagg cagcauccug 960
gccaucuaca gcaccguggc cagcagccug gugcugcugg ugagccuggg cgccaucagc 1020
uucugauaau aggcuggagc cucgguggcc uagcuucuug ccccuugggc cucccccag 1080 ccccuccucc ccuuccugca cccguacccc cguggucuuu gaauaaaguc ugagugggcg 1140
gc 1142

<210> SEQ ID NO 88
<211> LENGTH: 966
<212> TYPE: RNA
<213> ORGANISM: Artificial Sequence
<220> FEATURE:
<223> OTHER INFORMATION: Synthetic

<400> SEQUENCE: 88
auguacagca ugcagcuggc uagcugcgug acccugaccc uggugcugcu ggugaacagc 60
cagcgggugc agcccaccga gagcaucgug cgguucccca acaucaccaa ccugugcccc 120
uucggcgagg uguucaacgc cacccgguuc gccagcgugu acgccuggaa ccggaagcgg 180
aucagcaacu gcguggccga cuacagcgug cuguacaaca gcgccagcuu cagcaccuuc 240
aagugcuacg gcgugagccc caccaagcug aacgaccugu gcuucaccaa cguguacgcc 300
gacagcuucg ugauccgugg cgacgaggug cggcagaucg cacccggcca gacaggcaag 360
aucgccgacu acaacuacaa gcugcccgac gacuucaccg gcugcgugau cgccuggaac 420
agcaacaacc ucgacagcaa ggugggcggc aacuacaacu accuguaccg gcuguuccgg 480
aagagcaacc ugaagcccuu cgagcgggac aucagcaccg agaucuacca agccggcucc 540
accccuugca acggcgugga gggcuucaac ugcuacuucc cucugcagag cuacggcuuc 600
cagcccacca acggcguggg cuaccagccc uaccgguggu ggugcugag cuucgagcug 660 cugcacgccc cagccaccgu guguggcccc aagaagagca ccaaccuggu gaagaacaag 720
ugcgugaacu ucaacuucaa cggccuuacc ggcaccggcg ugcugaccga gagcaacaag 780
aaauuccugc ccuuuugcca guucggccgg gacaucgccg acaccaccga cgcugugcgg 840
gauccccaga cccuggagau ccuggacauc accccuugca gcucuggcgg aggcagcauc 900

-continued

```
cuggccaucu acagcaccgu ggccagcagc cuggugcugc uggugagccu gggcgccauc     960

agcuuc                                                                966


<210> SEQ ID NO 89
<211> LENGTH: 322
<212> TYPE: PRT
<213> ORGANISM: Artificial Sequence
<220> FEATURE:
<223> OTHER INFORMATION: Synthetic

<400> SEQUENCE: 89

Met Tyr Ser Met Gln Leu Ala Ser Cys Val Thr Leu Thr Leu Val Leu
1               5                   10                  15

Leu Val Asn Ser Gln Arg Val Gln Pro Thr Glu Ser Ile Val Arg Phe
            20                  25                  30

Pro Asn Ile Thr Asn Leu Cys Pro Phe Gly Glu Val Phe Asn Ala Thr
        35                  40                  45

Arg Phe Ala Ser Val Tyr Ala Trp Asn Arg Lys Arg Ile Ser Asn Cys
    50                  55                  60

Val Ala Asp Tyr Ser Val Leu Tyr Asn Ser Ala Ser Phe Ser Thr Phe
65                  70                  75                  80

Lys Cys Tyr Gly Val Ser Pro Thr Lys Leu Asn Asp Leu Cys Phe Thr
                85                  90                  95

Asn Val Tyr Ala Asp Ser Phe Val Ile Arg Gly Asp Glu Val Arg Gln
            100                 105                 110

Ile Ala Pro Gly Gln Thr Gly Lys Ile Ala Asp Tyr Asn Tyr Lys Leu
        115                 120                 125

Pro Asp Asp Phe Thr Gly Cys Val Ile Ala Trp Asn Ser Asn Asn Leu
    130                 135                 140

Asp Ser Lys Val Gly Gly Asn Tyr Asn Tyr Leu Tyr Arg Leu Phe Arg
145                 150                 155                 160

Lys Ser Asn Leu Lys Pro Phe Glu Arg Asp Ile Ser Thr Glu Ile Tyr
                165                 170                 175

Gln Ala Gly Ser Thr Pro Cys Asn Gly Val Glu Gly Phe Asn Cys Tyr
            180                 185                 190

Phe Pro Leu Gln Ser Tyr Gly Phe Gln Pro Thr Asn Gly Val Gly Tyr
        195                 200                 205

Gln Pro Tyr Arg Val Val Val Leu Ser Phe Glu Leu Leu His Ala Pro
    210                 215                 220

Ala Thr Val Cys Gly Pro Lys Lys Ser Thr Asn Leu Val Lys Asn Lys
225                 230                 235                 240

Cys Val Asn Phe Asn Phe Asn Gly Leu Thr Gly Thr Gly Val Leu Thr
                245                 250                 255

Glu Ser Asn Lys Lys Phe Leu Pro Phe Cys Gln Phe Gly Arg Asp Ile
            260                 265                 270

Ala Asp Thr Thr Asp Ala Val Arg Asp Pro Gln Thr Leu Glu Ile Leu
        275                 280                 285

Asp Ile Thr Pro Cys Ser Ser Gly Gly Gly Ser Ile Leu Ala Ile Tyr
    290                 295                 300

Ser Thr Val Ala Ser Ser Leu Val Leu Leu Val Ser Leu Gly Ala Ile
305                 310                 315                 320

Ser Phe


<210> SEQ ID NO 90
<211> LENGTH: 1748
```

<212> TYPE: RNA
<213> ORGANISM: Artificial Sequence
<220> FEATURE:
<223> OTHER INFORMATION: Synthetic

<400> SEQUENCE: 90
gggaaauaag agagaaaaga agaguaagaa gaaauauaag accccggcgc cgccaccaug 60
uucguguucc uggugcugcu gccccuggug agcagccagu gcgugaaccu gaccacccgg 120
acccagcugc caccagccua caccaacagc uucacccggg gcgucuacua ccccgacaag 180
guguuccgga gcagcguccu gcacagcacc caggaccugu uccugcccuu cuucagcaac 240
gugaccuggu uccacgccau ccacgugagc ggcaccaacg gcaccaagcg guucgacaac 300
cccgugcugc ccuucaacga cggcguguac uucgccagca ccgagaagag caacaucauc 360
cggggcugga ucuucggcac cacccuggac agcaagaccc agagccugcu gaucgugaau 420
aacgccacca acguggugau caaggugugc gaguuccagu ucugcaacga ccccuuccug 480
ggcguguacu accacaagaa caacaagagc uggauggaga gcgaguuccg gguguacagc 540
agcgccaaca acugcaccuu cgaguacgug agccagcccu uccugaugga ccuggagggc 600
aagcagggca acuucaagaa ccugcgggag uucguguuca agaacaucga cggcuacuuc 660
aagaucuaca gcaagcacac cccaaucaac cuggugcggg aucugcccca gggcuucuca 720
gcccuggagc cccuggugga ccugcccauc ggcaucaaca ucacccgguu ccagacccug 780
cuggcccugc accggagcua ccugacccca ggcgacagca gcagcgggug gacagcaggc 840
gcggcugcuu acuacguggg cuaccugcag ccccggaccu uccugcugaa guacaacgag 900
aacggcacca ucaccgacgc cguggacgga ggcggaucgg gaggcggacc caacaucacc 960
aaccugugcc ccuucggcga gguguucaac gccacccggu ucgccagcgu guacgccugg 1020
aaccggaagc ggaucagcaa cugcguggcc gacuacagcg ugcuguacaa cagcgccagc 1080
uucagcaccu ucaagugcua cggcgugagc cccaccaagc ugaacgaccu gugcuucacc 1140
aacguguacg ccgacagcuu cgugauccgu ggcgacgagg ugcggcagau cgcacccggc 1200
cagacaggca agaucgccga cuacaacuac aagcugcccg acgacuucac cggcugcgug 1260
aucgccugga acagcaacaa ccucgacagc aaggugggcg gcaacuacaa cuaccuguac 1320
cggcuguucc ggaagagcaa ccugaagccc uucgagcggg acaucagcac cgagaucuac 1380
caagccggcu ccaccccuug caacggcgug gagggcuuca acugcuacuu cccucugcag 1440
agcuacggcu uccagcccac caacggcgug ggcuaccagc ccuaccgggu gguggugcug 1500
agcuucgagc ugcugcacgc cccagccacc guguguggcc ccaagucugg cggaggcagc 1560
auccuggcca ucuacagcac cguggccagc agccuggugc ugcuggugag ccugggcgcc 1620
aucagcuucu gauaauaggc uggagccucg guggccuagc uucuugcccc uugggccucc 1680
ccccagcccc uccuccccuu ccugcacccg uacccccgug gucuuugaau aaagucugag 1740
ugggcggc 1748

<210> SEQ ID NO 91
<211> LENGTH: 1572
<212> TYPE: RNA
<213> ORGANISM: Artificial Sequence
<220> FEATURE:
<223> OTHER INFORMATION: Synthetic

<400> SEQUENCE: 91
auguucgugu uccuggugcu gcugccccug gugagcagcc agugcgugaa ccugaccacc 60

-continued

```
cggacccagc ugccaccagc cuacaccaac agcuucaccc ggggcgucua cuaccccgac    120

aagguguucc ggagcagcgu ccugcacagc acccaggacc uguuccugcc cuucuucagc    180

aacgugaccu gguuccacgc cauccacgug agcggcacca acggcaccaa gcgguucgac    240

aaccccgugc ugcccuucaa cgacggcgug uacuucgcca gcaccgagaa gagcaacauc    300

auccggggcu ggaucuucgg caccacccug gacagcaaga cccagagccu gcugaucgug    360

aauaacgcca ccaacguggu gaucaaggug ugcgaguucc aguucugcaa cgaccccuuc    420

cugggcgugu acuaccacaa gaacaacaag agcuggaugg agagcgaguu ccggguguac    480

agcagcgcca acaacugcac cuucgaguac gugagccagc ccuuccugau ggaccuggag    540

ggcaagcagg gcaacuucaa gaaccugcgg gaguucgugu ucaagaacau cgacggcuac    600

uucaagaucu acagcaagca caccccaauc aaccuggugc gggaucugcc ccagggcuuc    660

ucagcccugg agccccuggu ggaccugccc aucggcauca acaucacccg guuccagacc    720

cugcuggccc ugcaccggag cuaccugacc ccaggcgaca gcagcagcgg guggacagca    780

ggcgcggcug cuuacuacgu gggcuaccug cagccccgga ccuuccugcu gaaguacaac    840

gagaacggca ccaucaccga cgccguggac ggaggcggau cgggaggcgg acccaacauc    900

accaaccugu gccccuucgg cgaggugutc aacgccaccc gguucgccag cguguacgcc    960

uggaaccgga agcggaucag caacugcgug gccgacuaca gcgugcugua caacagcgcc   1020

agcuucagca ccuucaagug cuacggcgug agccccacca agcugaacga ccugugcuuc   1080

accaacgugu acgccgacag cuucgugauc cguggcgacg aggugcggca gaucgcaccc   1140

ggccagacag gcaagaucgc cgacuacaac uacaagcugc ccgacgacuu caccggcugc   1200

gugaucgccu ggaacagcaa caaccucgac agcaaggugg gcggcaacua caacuaccug   1260

uaccggcugu uccggaagag caaccugaag cccuucgagc gggacaucag caccgagauc   1320

uaccaagccg gcuccacccc uugcaacggc guggagggcu ucaacugcua cuuccccucug   1380

cagagcuacg gcuuccagcc caccaacggc gugggcuacc agcccuaccg gguggguggug   1440

cugagcuucg agcugcugca cgccccagcc accgugugug gccccaaguc uggcggaggc   1500

agcauccugg ccaucuacag caccguggcc agcagccugg ugcugcuggu gagccugggc   1560

gccaucagcu uc                                                        1572
```

<210> SEQ ID NO 92
<211> LENGTH: 524
<212> TYPE: PRT
<213> ORGANISM: Artificial Sequence
<220> FEATURE:
<223> OTHER INFORMATION: Synthetic

<400> SEQUENCE: 92

```
Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95
```

```
Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Gly Gly Gly Ser Gly Gly Gly Pro Asn Ile Thr Asn Leu Cys
    290                 295                 300

Pro Phe Gly Glu Val Phe Asn Ala Thr Arg Phe Ala Ser Val Tyr Ala
305                 310                 315                 320

Trp Asn Arg Lys Arg Ile Ser Asn Cys Val Ala Asp Tyr Ser Val Leu
                325                 330                 335

Tyr Asn Ser Ala Ser Phe Ser Thr Phe Lys Cys Tyr Gly Val Ser Pro
            340                 345                 350

Thr Lys Leu Asn Asp Leu Cys Phe Thr Asn Val Tyr Ala Asp Ser Phe
        355                 360                 365

Val Ile Arg Gly Asp Glu Val Arg Gln Ile Ala Pro Gly Gln Thr Gly
    370                 375                 380

Lys Ile Ala Asp Tyr Asn Tyr Lys Leu Pro Asp Asp Phe Thr Gly Cys
385                 390                 395                 400

Val Ile Ala Trp Asn Ser Asn Asn Leu Asp Ser Lys Val Gly Gly Asn
                405                 410                 415

Tyr Asn Tyr Leu Tyr Arg Leu Phe Arg Lys Ser Asn Leu Lys Pro Phe
            420                 425                 430

Glu Arg Asp Ile Ser Thr Glu Ile Tyr Gln Ala Gly Ser Thr Pro Cys
        435                 440                 445

Asn Gly Val Glu Gly Phe Asn Cys Tyr Phe Pro Leu Gln Ser Tyr Gly
    450                 455                 460

Phe Gln Pro Thr Asn Gly Val Gly Tyr Gln Pro Tyr Arg Val Val Val
465                 470                 475                 480

Leu Ser Phe Glu Leu Leu His Ala Pro Ala Thr Val Cys Gly Pro Lys
                485                 490                 495

Ser Gly Gly Gly Ser Ile Leu Ala Ile Tyr Ser Thr Val Ala Ser Ser
            500                 505                 510
```

```
Leu Val Leu Leu Val Ser Leu Gly Ala Ile Ser Phe
        515                 520


<210> SEQ ID NO 93
<211> LENGTH: 1925
<212> TYPE: RNA
<213> ORGANISM: Artificial Sequence
<220> FEATURE:
<223> OTHER INFORMATION: Synthetic

<400> SEQUENCE: 93

gggaaauaag agagaaaaga agaguaagaa gaaauauaag accccggcgc cgccaccaug     60

uucguguucc uggugcugcu gccccuggug agcagccagu gcgugaaccu gaccacccgg    120

acccagcugc caccagccua caccaacagc uucacccggg gcgucuacua ccccgacaag    180

guguuccgga gcagcguccu gcacagcacc caggaccugu uccugcccuu cuucagcaac    240

gugaccuggu uccacgccau ccacgugagc ggcaccaacg gcaccaagcg guucgacaac    300

cccgugcugc ccuucaacga cggcguguac uucgccagca ccgagaagag caacaucauc    360

cggggcugga ucuucggcac cacccuggac agcaagaccc agagccugcu gaucgugaau    420

aacgccacca acguggugau caaggugugc gaguuccagu ucugcaacga ccccuuccug    480

ggcguguacu accacaagaa caacaagagc uggauggaga gcgaguuccg gguguacagc    540

agcgccaaca acugcaccuu cgaguacgug agccagcccu uccugaugga ccuggagggc    600

aagcagggca acuucaagaa ccugcgggag uucguguuca agaacaucga cggcuacuuc    660

aagaucuaca gcaagcacac cccaaucaac cuggugcggg aucugcccca gggcuucuca    720

gcccuggagc cccuggugga ccugcccauc ggcaucaaca ucacccgguu ccagacccug    780

cuggcccugc accggagcua ccugacccca ggcgacagca gcagcgggug gacagcaggc    840

gcggcugcuu acuacguggg cuaccugcag ccccggaccu uccugcugaa guacaacgag    900

aacggcacca ucaccgacgc cguggacgga ggcggaucgg gaggcggacc caacaucacc    960

aaccugugcc ccuucggcga gguguucaac gccacccggu ucgccagcgu guacgccugg   1020

aaccggaagc ggaucagcaa cugcguggcc gacuacagcg ugcuguacaa cagcgccagc   1080

uucagcaccu ucaagugcua cggcgugagc ccccaccaagc ugaacgaccu gugcuucacc   1140

aacguguacg ccgacagcuu cgugauccgu ggcgacgagg ugcggcagau cgcacccggc   1200

cagacaggca agaucgccga cuacaacuac aagcugcccg acgacuucac cggcugcgug   1260

aucgccugga acagcaacaa ccucgacagc aaggugggcg gcaacuacaa cuaccuguac   1320

cggcuguucc ggaagagcaa ccugaagccc uucgagcggg acaucagcac cgagaucuac   1380

caagccggcu ccaccccuug caacggcgug gagggcuuca acugcuacuu cccucugcag   1440

agcuacggcu uccagcccac caacggcgug ggcuaccagc ccuaccgggu gguggugcug   1500

agcuucgagc ugcugcacgc cccagccacc gugugugggc ccaagucugg cggaggcagc   1560

auccuggcca ucuacagcac cguggccagc agccuggugc ugcuggugag ccugggcgcc   1620

aucagcuuca agaagaagaa gcggccacgg aacuccuaca agugcggcac caacaccaug   1680

gagcgggagg agagcgagca gaccaagaag cgggagaaga uccacauucc ugaacggucc   1740

gacgaagccc agcgggguguu caagagcagc aagaccagca gcugcgacaa gagcgacacc   1800

ugcuucugau aauaggcugg agccucggug gccuagcuuc uugccccuug ggccuccccc   1860

cagccccucc uccccuuccu gcacccguac cccguggguc uuugaauaaa gucugagugg   1920

gcggc                                                               1925
```

<210> SEQ ID NO 94
<211> LENGTH: 1749
<212> TYPE: RNA
<213> ORGANISM: Artificial Sequence
<220> FEATURE:
<223> OTHER INFORMATION: Synthetic

<400> SEQUENCE: 94
auguucgugu uccuggugcu gcugccccug gugagcagcc agugcgugaa ccugaccacc 60
cggacccagc ugccaccagc cuacaccaac agcuucaccc ggggcgucua cuaccccgac 120
aagguguucc ggagcagcgu ccugcacagc acccaggacc uguuccugcc cuucuucagc 180
aacgugaccu gguuccacgc cauccacgug agcggcacca acggcaccaa gcgguucgac 240
aaccccgugc ugcccuucaa cgacggcgug uacuucgcca gcaccgagaa gagcaacauc 300
auccggggcu ggaucuucgg caccacccug gacagcaaga cccagagccu gcugaucgug 360
aauaacgcca ccaacguggu gaucaaggug ugcgaguucc aguucugcaa cgaccccuuc 420
cugggcgugu acuaccacaa gaacaacaag agcuggaugg agagcgaguu ccggguguac 480
agcagcgcca acaacugcac cuucgaguac gugagccagc ccuuccugau ggaccuggag 540
ggcaagcagg gcaacuucaa gaaccugcgg gaguucgugu ucaagaacau cgacggcuac 600
uucaagaucu acagcaagca caccccaauc aaccuggugc gggaucugcc ccagggcuuc 660
ucagcccugg agccccuggu ggaccugccc aucggcauca acaucacccg guuccagacc 720
cugcuggccc ugcaccggag cuaccugacc ccaggcgaca gcagcagcgg guggacagca 780
ggcgcggcug cuuacuacgu gggcuaccug cagccccgga ccuuccugcu gaaguacaac 840
gagaacggca ccaucaccga cgccguggac ggaggcggau cgggaggcgg acccaacauc 900
accaaccugu gccccuucgg cgagguguuc aacgccaccc gguucgccag cguguacgcc 960
uggaaccgga agcggaucag caacugcgug gccgacuaca gcgugcugua caacagcgcc 1020
agcuucagca ccuucaagug cuacggcgug agccccacca agcugaacga ccugugcuuc 1080
accaacgugu acgccgacag cuucgugauc cguggcgacg aggugcggca gaucgcaccc 1140
ggccagacag gcaagaucgc cgacuacaac uacaagcugc ccgacgacuu caccggcugc 1200
gugaucgccu ggaacagcaa caaccucgac agcaaggugg gcggcaacua caacuaccug 1260
uaccggcugu uccggaagag caaccugaag cccuucgagc gggacaucag caccgagauc 1320
uaccaagccg gcuccacccc uugcaacggc guggagggcu ucaacugcua cuuccccucug 1380 cagagcuacg gcuuccagcc caccaacggc gugggcuacc agcccuaccg gguggguggug 1440 cugagcuucg agcugcugca cgccccagcc accgugugug gccccaaguc uggcggaggc 1500
agcauccugg ccaucuacag caccguggcc agcagccugg ugcugcuggu gagccugggc 1560
gccaucagcu ucaagaagaa gaagcggcca cggaacuccu acaagugcgg caccaacacc 1620
auggagcggg aggagagcga gcagaccaag aagcgggaga agauccacau uccugaacgg 1680
uccgacgaag cccagcgggu guucaagagc agcaagacca gcagcugcga caagagcgac 1740
accugcuuc 1749

<210> SEQ ID NO 95
<211> LENGTH: 583
<212> TYPE: PRT
<213> ORGANISM: Artificial Sequence
<220> FEATURE:
<223> OTHER INFORMATION: Synthetic

<400> SEQUENCE: 95

-continued

```
Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Gly Gly Gly Ser Gly Gly Gly Pro Asn Ile Thr Asn Leu Cys
    290                 295                 300

Pro Phe Gly Glu Val Phe Asn Ala Thr Arg Phe Ala Ser Val Tyr Ala
305                 310                 315                 320

Trp Asn Arg Lys Arg Ile Ser Asn Cys Val Ala Asp Tyr Ser Val Leu
                325                 330                 335

Tyr Asn Ser Ala Ser Phe Ser Thr Phe Lys Cys Tyr Gly Val Ser Pro
            340                 345                 350

Thr Lys Leu Asn Asp Leu Cys Phe Thr Asn Val Tyr Ala Asp Ser Phe
        355                 360                 365

Val Ile Arg Gly Asp Glu Val Arg Gln Ile Ala Pro Gly Gln Thr Gly
    370                 375                 380

Lys Ile Ala Asp Tyr Asn Tyr Lys Leu Pro Asp Asp Phe Thr Gly Cys
385                 390                 395                 400

Val Ile Ala Trp Asn Ser Asn Asn Leu Asp Ser Lys Val Gly Gly Asn
                405                 410                 415
```

-continued

```
Tyr Asn Tyr Leu Tyr Arg Leu Phe Arg Lys Ser Asn Leu Lys Pro Phe
            420                 425                 430

Glu Arg Asp Ile Ser Thr Glu Ile Tyr Gln Ala Gly Ser Thr Pro Cys
        435                 440                 445

Asn Gly Val Glu Gly Phe Asn Cys Tyr Phe Pro Leu Gln Ser Tyr Gly
    450                 455                 460

Phe Gln Pro Thr Asn Gly Val Gly Tyr Gln Pro Tyr Arg Val Val Val
465                 470                 475                 480

Leu Ser Phe Glu Leu Leu His Ala Pro Ala Thr Val Cys Gly Pro Lys
                485                 490                 495

Ser Gly Gly Gly Ser Ile Leu Ala Ile Tyr Ser Thr Val Ala Ser Ser
            500                 505                 510

Leu Val Leu Leu Val Ser Leu Gly Ala Ile Ser Phe Lys Lys Lys Lys
        515                 520                 525

Arg Pro Arg Asn Ser Tyr Lys Cys Gly Thr Asn Thr Met Glu Arg Glu
    530                 535                 540

Glu Ser Glu Gln Thr Lys Lys Arg Glu Lys Ile His Ile Pro Glu Arg
545                 550                 555                 560

Ser Asp Glu Ala Gln Arg Val Phe Lys Ser Ser Lys Thr Ser Ser Cys
                565                 570                 575

Asp Lys Ser Asp Thr Cys Phe
            580
```

<210> SEQ ID NO 96
<211> LENGTH: 1805
<212> TYPE: RNA
<213> ORGANISM: Artificial Sequence
<220> FEATURE:
<223> OTHER INFORMATION: Synthetic

<400> SEQUENCE: 96

```
gggaaauaag agagaaaaga agaguaagaa gaaauauaag accccggcgc cgccaccaug     60

uucguguucc uggugcugcu gccccuggug agcagccagu gcgugaaccu gaccacccgg    120

acccagcugc caccagccua caccaacagc uucacccggg gcgucuacua ccccgacaag    180

guguuccgga gcagcguccu gcacagcacc caggaccugu uccugcccuu cuucagcaac    240

gugaccuggu uccacgccau ccacgugagc ggcaccaacg gcaccaagcg guucgacaac    300

cccgugcugc ccuucaacga cggcguguac uucgccagca ccgagaagag caacaucauc    360

cggggcugga ucuucggcac cacccuggac agcaagaccc agagccugcu gaucgugaau    420

aacgccacca acgugguguau caaggugugc gaguuccagu ucugcaacga ccccuuccug    480

ggcguguacu accacaagaa caacaagagc uggauggaga gcgaguuccg gguguacagc    540

agcgccaaca acugcaccuu cgaguacgug agccagcccu uccugaugga ccuggagggc    600

aagcagggca acuucaagaa ccugcgggag uucguguuca agaacaucga cggcuacuuc    660

aagaucuaca gcaagcacac cccaaucaac cuggugcggg aucugcccca gggcuucuca    720

gcccuggagc cccuggugga ccugcccauc ggcaucaaca ucacccgguu ccagacccug    780

cuggcccugc accggagcua ccugacccca ggcgacagca gcagcgggug gacagcaggc    840

gcggcugcuu acuacguggg cuaccugcag ccccggaccu uccugcugaa guacaacgag    900

aacggcacca ucaccgacgc cguggacgga ggcggaucgg gaggcggacc caacaucacc    960

aaccugugcc ccuucggcga gguguucaac gccacccggu ucgccagcgu guacgccugg   1020

aaccggaagc ggaucagcaa cugcguggcc gacuacagcg ugcuguacaa cagcgccagc   1080
```

```
uucagcaccu ucaagugcua cggcgugagc cccaccaagc ugaacgaccu gugcuucacc   1140

aacguguacg ccgacagcuu cgugauccgu ggcgacgagg ugcggcagau cgcacccggc   1200

cagacaggca agaucgccga cuacaacuac aagcugcccg acgacuucac cggcugcgug   1260

aucgccugga acagcaacaa ccucgacagc aaggugggcg gcaacuacaa cuaccuguac   1320

cggcuguucc ggaagagcaa ccugaagccc uucgagcggg acaucagcac cgagaucuac   1380

caagccggcu ccaccccuug caacggcgug gagggcuuca acugcuacuu cccucugcag   1440

agcuacggcu uccagcccac caacggcgug ggcuaccagc ccuaccgggu gguggugcug   1500

agcuucgagc ugcugcacgc cccagccacc gugugugccc ccaagucugg cggaggcagc   1560

auccuggcca ucuacagcac cguggccagc agccuggugc ugcuggugag ccugggcgcc   1620

aucagcuuca agcggcagua caaggacaug augagcgagg gaggaccacc uggcgcugag   1680

ccacagugau aauaggcugg agccucggug gccuagcuuc uugccccuug ggccuccccc   1740

cagccccucc uccccuuccu gcacccguac cccguggguc uuugaauaaa gucugagugg   1800

gcggc                                                               1805
```

<210> SEQ ID NO 97
<211> LENGTH: 1629
<212> TYPE: RNA
<213> ORGANISM: Artificial Sequence
<220> FEATURE:
<223> OTHER INFORMATION: Synthetic

<400> SEQUENCE: 97

```
auguucgugu uccuggugcu gcugccccug gugagcagcc agugcgugaa ccugaccacc     60

cggacccagc ugccaccagc cuacaccaac agcuucaccc ggggcgucua cuaccccgac    120

aagguguucc ggagcagcgu ccugcacagc acccaggacc uguuccugcc cuucuucagc    180

aacgugaccu gguuccacgc cauccacgug agcggcacca acggcaccaa gcgguucgac    240

aaccccgugc ugcccuucaa cgacggcgug uacuucgcca gcaccgagaa gagcaacauc    300

auccggggcu ggaucuucgg caccacccug gacagcaaga cccagagccu gcugaucgug    360

aauaacgcca ccaacguggu gaucaaggug ugcgaguucc aguucugcaa cgaccccuuc    420

cugggcgugu acuaccacaa gaacaacaag agcuggaugg agagcgaguu ccggguguac    480

agcagcgcca acaacugcac cuucgaguac gugagccagc ccuuccugau ggaccuggag    540

ggcaagcagg gcaacuucaa gaaccugcgg gaguucgugu ucaagaacau cgacggcuac    600

uucaagaucu acagcaagca caccccaauc aaccuggugc gggaucugcc ccagggcuuc    660

ucagcccugg agccccuggu ggaccugccc aucggcauca acaucacccg guuccagacc    720

cugcuggccc ugcaccggag cuaccugacc ccaggcgaca gcagcagcgg guggacagca    780

ggcgcggcug cuuacuacgu gggcuaccug cagccccgga ccuuccugcu gaaguacaac    840

gagaacggca ccaucaccga cgccguggac ggaggcggau cgggaggcgg acccaacauc    900

accaaccugu gccccuucgg cgaggguguc aacgccaccc gguucgccag cguguacgcc    960

uggaaccgga agcggaucag caacugcgug gccgacuaca gcgugcugua caacagcgcc   1020

agcuucagca ccuucaagug cuacggcgug agccccacca agcugaacga ccugugcuuc   1080

accaacgugu acgccgacag cuucgugauc cguggcgacg aggugcggca gaucgcaccc   1140

ggccagacag gcaagaucgc cgacuacaac uacaagcugc ccgacgacuu caccggcugc   1200

gugaucgccu ggaacagcaa caaccucgac agcaaggugg gcggcaacua caacuaccug   1260

uaccggcugu uccggaagag caaccugaag cccuucgagc gggacaucag caccgagauc   1320
```

```
uaccaagccg gcuccacccc uugcaacggc guggagggcu ucaacugcua cuuccccucug   1380

cagagcuacg gcuuccagcc caccaacggc gugggcuacc agcccuaccg gguggguggug   1440

cugagcuucg agcugcugca cgccccagcc accgugugug gccccaaguc uggcggaggc   1500

agcauccugg ccaucuacag caccguggcc agcagccugg ugcugcuggu gagccugggc   1560

gccaucagcu ucaagcggca guacaaggac augaugagcg agggaggacc accuggcgcu   1620

gagccacag                                                            1629


<210> SEQ ID NO 98
<211> LENGTH: 543
<212> TYPE: PRT
<213> ORGANISM: Artificial Sequence
<220> FEATURE:
<223> OTHER INFORMATION: Synthetic

<400> SEQUENCE: 98

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Gly Gly Gly Ser Gly Gly Gly Pro Asn Ile Thr Asn Leu Cys
    290                 295                 300
```

```
Pro Phe Gly Glu Val Phe Asn Ala Thr Arg Phe Ala Ser Val Tyr Ala
305                 310                 315                 320

Trp Asn Arg Lys Arg Ile Ser Asn Cys Val Ala Asp Tyr Ser Val Leu
                325                 330                 335

Tyr Asn Ser Ala Ser Phe Ser Thr Phe Lys Cys Tyr Gly Val Ser Pro
            340                 345                 350

Thr Lys Leu Asn Asp Leu Cys Phe Thr Asn Val Tyr Ala Asp Ser Phe
        355                 360                 365

Val Ile Arg Gly Asp Glu Val Arg Gln Ile Ala Pro Gly Gln Thr Gly
    370                 375                 380

Lys Ile Ala Asp Tyr Asn Tyr Lys Leu Pro Asp Asp Phe Thr Gly Cys
385                 390                 395                 400

Val Ile Ala Trp Asn Ser Asn Asn Leu Asp Ser Lys Val Gly Gly Asn
                405                 410                 415

Tyr Asn Tyr Leu Tyr Arg Leu Phe Arg Lys Ser Asn Leu Lys Pro Phe
            420                 425                 430

Glu Arg Asp Ile Ser Thr Glu Ile Tyr Gln Ala Gly Ser Thr Pro Cys
        435                 440                 445

Asn Gly Val Glu Gly Phe Asn Cys Tyr Phe Pro Leu Gln Ser Tyr Gly
    450                 455                 460

Phe Gln Pro Thr Asn Gly Val Gly Tyr Gln Pro Tyr Arg Val Val Val
465                 470                 475                 480

Leu Ser Phe Glu Leu Leu His Ala Pro Ala Thr Val Cys Gly Pro Lys
                485                 490                 495

Ser Gly Gly Gly Ser Ile Leu Ala Ile Tyr Ser Thr Val Ala Ser Ser
            500                 505                 510

Leu Val Leu Leu Val Ser Leu Gly Ala Ile Ser Phe Lys Arg Gln Tyr
        515                 520                 525

Lys Asp Met Met Ser Glu Gly Gly Pro Pro Gly Ala Glu Pro Gln
    530                 535                 540
```

<210> SEQ ID NO 99
<211> LENGTH: 1853
<212> TYPE: RNA
<213> ORGANISM: Artificial Sequence
<220> FEATURE:
<223> OTHER INFORMATION: Synthetic

<400> SEQUENCE: 99

```
gggaaauaag agagaaaaga agaguaagaa gaaauauaag accccggcgc cgccaccaug     60

uucguguucc uggugcugcu gccccuggug agcagccagu gcgugaaccu gaccacccgg    120

acccagcugc caccagccua caccaacagc uucacccggg gcgucuacua ccccgacaag    180

guguuccgga gcagcguccu gcacagcacc caggaccugu uccugcccuu cuucagcaac    240

gugaccuggu uccacgccau ccacgugagc ggcaccaacg gcaccaagcg guucgacaac    300

cccgugcugc ccuucaacga cggcguguac uucgccagca ccgagaagag caacaucauc    360

cggggcugga ucuucggcac cacccuggac agcaagaccc agagccugcu gaucgugaau    420

aacgccacca acguggugau caaggugugc gaguuccagu ucugcaacga ccccuuccug    480

ggcguguacu accacaagaa caacaagagc uggauggaga gcgaguuccg gguguacagc    540

agcgccaaca acugcaccuu cgaguacgug agccagcccu uccugaugga ccuggagggc    600

aagcagggca acuucaagaa ccugcgggag uucguguuca agaacaucga cggcuacuuc    660

aagaucuaca gcaagcacac cccaaucaac cuggugcggg aucugcccca gggcuucuca    720
```

gcccuggagc cccuggugga ccugcccauc ggcaucaaca ucacccgguu ccagacccug 780
cuggcccugc accggagcua ccugacccca ggcgacagca gcagcgggug gacagcaggc 840
gcggcugcuu acuacguggg cuaccugcag ccccggaccu uccugcugaa guacaacgag 900
aacggcacca ucaccgacgc cguggacgga ggcggaucgg gaggcggacc caacaucacc 960
aaccugugcc ccuucggcga gguguucaac gccacccggu ucgccagcgu guacgccugg 1020
aaccggaagc ggaucagcaa cugcguggcc gacuacagcg ugcuguacaa cagcgccagc 1080
uucagcaccu ucaagugcua cggcgugagc cccaccaagc ugaacgaccu gugcuucacc 1140
aacguguacg ccgacagcuu cgugauccgu ggcgacgagg ugcggcagau cgcacccggc 1200
cagacaggca agaucgccga cuacaacuac aagcugcccg acgacuucac cggcugcgug 1260
aucgccugga acagcaacaa ccucgacagc aaggugggcg gcaacuacaa cuaccuguac 1320
cggcuguucc ggaagagcaa ccugaagccc uucgagcggg acaucagcac cgagaucuac 1380
caagccggcu ccaccccuug caacggcgug gagggcuuca acugcuacuu cccucugcag 1440
agcuacggcu uccagcccac caacggcgug ggcuaccagc ccuaccgggu gguggugcug 1500
agcuucgagc ugcugcacgc ccagccacc gugugugccc ccaagucugg cggaggcggc 1560
agcgccaucg gcggcuacau ccccgaggcc ccuagagacg gccaggccua cgugcggaag 1620
gacggcgagu gggugcugcu gagcaccuuc cugggcggag gcagcauccu ggccaucuac 1680
agcaccgugg ccagcagccu ggugcugcug gugagccugg gcgccaucag cuucugauaa 1740
uaggcuggag ccucgguggc cuagcuucuu gccccuuggg ccucccccca gccccuccuc 1800
cccuuccugc acccguaccc ccguggucuu ugaauaaagu cugagugggc ggc 1853

<210> SEQ ID NO 100
<211> LENGTH: 1677
<212> TYPE: RNA
<213> ORGANISM: Artificial Sequence
<220> FEATURE:
<223> OTHER INFORMATION: Synthetic

<400> SEQUENCE: 100
auguucgugu uccuggugcu gcugccccug gugagcagcc agugcgugaa ccugaccacc 60
cggacccagc ugccaccagc cuacaccaac agcuucaccc ggggcgucua cuaccccgac 120
aagguguucc ggagcagcgu ccugcacagc acccaggacc uguuccugcc cuucuucagc 180
aacgugaccu gguuccacgc cauccacgug agcggcacca acggcaccaa gcgguucgac 240
aaccccgugc ugcccuucaa cgacggcgug uacuucgcca gcaccgagaa gagcaacauc 300
auccggggcu ggaucuucgg caccacccug gacagcaaga cccagagccu gcugaucgug 360
aauaacgcca ccaacguggu gaucaaggug ugcgaguucc aguucugcaa cgaccccuuc 420
cugggcgugu acuaccacaa gaacaacaag agcuggaugg agagcgaguu ccggguguac 480
agcagcgcca acaacugcac cuucgaguac gugagccagc ccuuccugau ggaccuggag 540
ggcaagcagg gcaacuucaa gaaccugcgg gaguucgugu ucaagaacau cgacggcuac 600
uucaagaucu acagcaagca caccccaauc aaccuggugc gggaucugcc ccagggcuuc 660
ucagcccugg agccccuggu ggaccugccc aucggcauca acaucacccg guuccagacc 720
cugcuggccc ugcaccggag cuaccugacc ccaggcgaca gcagcagcgg guggacagca 780
ggcgcggcug cuuacuacgu gggcuaccug cagccccgga ccuuccugcu gaaguacaac 840
gagaacggca ccaucaccga cgccguggac ggaggcggau cgggaggcgg acccaacauc 900

```
accaaccugu gccccuucgg cgagguguuc aacgccaccc gguucgccag cguguacgcc    960

uggaaccgga agcggaucag caacugcgug gccgacuaca gcgugcugua caacagcgcc   1020

agcuucagca ccuucaagug cuacggcgug agccccacca agcugaacga ccugugcuuc   1080

accaacgugu acgccgacag cuucgugauc cguggcgacg aggugcggca gaucgcaccc   1140

ggccagacag gcaagaucgc cgacuacaac uacaagcugc ccgacgacuu caccggcugc   1200

gugaucgccu ggaacagcaa caaccucgac agcaaggugg gcggcaacua caacuaccug   1260

uaccggcugu uccggaagag caaccugaag cccuucgagc gggacaucag caccgagauc   1320

uaccaagccg gcuccacccc uugcaacggc guggagggcu ucaacugcua cuucccucug   1380

cagagcuacg gcuuccagcc caccaacggc gugggcuacc agcccuaccg gguggguggug   1440

cugagcuucg agcugcugca cgccccagcc accgugugug gccccaaguc uggcggaggc   1500

ggcagcgcca ucggcggcua caucccccgag gccccuagag acggccaggc cuacgugcgg   1560

aaggacggcg agugggugcu gcugagcacc uuccugggcg gaggcagcau ccuggccauc   1620

uacagcaccg uggccagcag ccuggugcug cuggugagcc ugggcgccau cagcuuc      1677
```

<210> SEQ ID NO 101
<211> LENGTH: 559
<212> TYPE: PRT
<213> ORGANISM: Artificial Sequence
<220> FEATURE:
<223> OTHER INFORMATION: Synthetic

<400> SEQUENCE: 101

```
Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
```

-continued

```
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Gly Gly Gly Ser Gly Gly Gly Pro Asn Ile Thr Asn Leu Cys
    290                 295                 300

Pro Phe Gly Glu Val Phe Asn Ala Thr Arg Phe Ala Ser Val Tyr Ala
305                 310                 315                 320

Trp Asn Arg Lys Arg Ile Ser Asn Cys Val Ala Asp Tyr Ser Val Leu
                325                 330                 335

Tyr Asn Ser Ala Ser Phe Ser Thr Phe Lys Cys Tyr Gly Val Ser Pro
            340                 345                 350

Thr Lys Leu Asn Asp Leu Cys Phe Thr Asn Val Tyr Ala Asp Ser Phe
        355                 360                 365

Val Ile Arg Gly Asp Glu Val Arg Gln Ile Ala Pro Gly Gln Thr Gly
    370                 375                 380

Lys Ile Ala Asp Tyr Asn Tyr Lys Leu Pro Asp Asp Phe Thr Gly Cys
385                 390                 395                 400

Val Ile Ala Trp Asn Ser Asn Asn Leu Asp Ser Lys Val Gly Gly Asn
                405                 410                 415

Tyr Asn Tyr Leu Tyr Arg Leu Phe Arg Lys Ser Asn Leu Lys Pro Phe
            420                 425                 430

Glu Arg Asp Ile Ser Thr Glu Ile Tyr Gln Ala Gly Ser Thr Pro Cys
        435                 440                 445

Asn Gly Val Glu Gly Phe Asn Cys Tyr Phe Pro Leu Gln Ser Tyr Gly
    450                 455                 460

Phe Gln Pro Thr Asn Gly Val Gly Tyr Gln Pro Tyr Arg Val Val Val
465                 470                 475                 480

Leu Ser Phe Glu Leu Leu His Ala Pro Ala Thr Val Cys Gly Pro Lys
                485                 490                 495

Ser Gly Gly Gly Gly Ser Ala Ile Gly Gly Tyr Ile Pro Glu Ala Pro
            500                 505                 510

Arg Asp Gly Gln Ala Tyr Val Arg Lys Asp Gly Glu Trp Val Leu Leu
        515                 520                 525

Ser Thr Phe Leu Gly Gly Gly Ser Ile Leu Ala Ile Tyr Ser Thr Val
    530                 535                 540

Ala Ser Ser Leu Val Leu Leu Val Ser Leu Gly Ala Ile Ser Phe
545                 550                 555
```

<210> SEQ ID NO 102
<211> LENGTH: 1856
<212> TYPE: RNA
<213> ORGANISM: Artificial Sequence
<220> FEATURE:
<223> OTHER INFORMATION: Synthetic

<400> SEQUENCE: 102

```
gggaaauaag agagaaaaga agaguaagaa gaaauauaag accccggcgc cgccaccaug      60

uucguguucc uggugcugcu gccccuggug agcagccagu gcgugaaccu gaccacccgg     120

acccagcugc caccagccua caccaacagc uucacccggg gcgucuacua ccccgacaag     180

guguuccgga gcagcguccu gcacagcacc caggaccugu uccugcccuu cuucagcaac     240
```

-continued gugaccuggu uccacgccau ccacgugagc ggcaccaacg gcaccaagcg guucgacaac 300
cccgugcugc ccuucaacga cggcguguac uucgccagca ccgagaagag caacaucauc 360
cggggcugga ucuucggcac cacccuggac agcaagaccc agagccugcu gaucgugaau 420
aacgccacca acguggugau caaggugugc gaguuccagu ucugcaacga ccccuuccug 480
ggcguguacu accacaagaa caacaagagc uggauggaga gcgaguuccg gguguacagc 540
agcgccaaca acugcaccuu cgaguacgug agccagcccu uccugaugga ccuggagggc 600
aagcagggca acuucaagaa ccugcgggag uucguguuca agaacaucga cggcuacuuc 660
aagaucuaca gcaagcacac cccaaucaac cuggugcggg aucugcccca gggcuucuca 720
gcccuggagc cccuggugga ccugcccauc ggcaucaaca ucacccgguu ccagacccug 780
cuggcccugc accggagcua ccugacccca ggcgacagca gcagcgggug gacagcaggc 840
gcggcugcuu acuacguggg cuaccugcag ccccggaccu uccugcugaa guacaacgag 900
aacggcacca ucaccgacgc cguggacgga ggcggaucgg gaggcggacc caacaucacc 960
aaccugugcc ccuucggcga gguguucaac gccacccggu ucgccagcgu guacgccugg 1020
aaccggaagc ggaucagcaa cugcguggcc gacuacagcg ugcuguacaa cagcgccagc 1080
uucagcaccu ucaagugcua cggcgugagc cccaccaagc ugaacgaccu gugcuucacc 1140
aacguguacg ccgacagcuu cgugauccgu ggcgacgagg ugcggcagau cgcacccggc 1200
cagacaggca agaucgccga cuacaacuac aagcugcccg acgacuucac cggcugcgug 1260
aucgccugga acagcaacaa ccucgacagc aagguggggcg gcaacuacaa cuaccuguac 1320
cggcuguucc ggaagagcaa ccugaagccc uucgagcggg acaucagcac cgagaucuac 1380
caagccggcu ccaccccuug caacggcgug gagggcuuca acugcuacuu cccucugcag 1440
agcuacggcu uccagcccac caacggcgug ggcuaccagc ccuaccgggu gguggugcug 1500
agcuucgagc ugcugcacgc cccagccacc gugugugggcc ccaagucugg cggaggcagc 1560
auccuggcca ucuacagcac cguggccagc agccuggugc ugcuggugag ccugggcgcc 1620
aucagcuucg gcggaggcag cgccaucggc ggcuacaucc ccgaggcccc uagagacggc 1680
caggccuacg ugcggaagga cggcgagugg gugcugcuga gcaccuuccu gggcaaguga 1740
uaauaggcug gagccucggu ggccuagcuu cuugccccuu gggccucccc ccagccccuc 1800
cuccccuucc ugcacccgua cccccguggu cuuugaauaa agucugagug ggcggc 1856

<210> SEQ ID NO 103
<211> LENGTH: 1680
<212> TYPE: RNA
<213> ORGANISM: Artificial Sequence
<220> FEATURE:
<223> OTHER INFORMATION: Synthetic

<400> SEQUENCE: 103
auguucgugu uccuggugcu gcugccccug gugagcagcc agugcgugaa ccugaccacc 60
cggacccagc ugccaccagc cuacaccaac agcuucaccc ggggcgucua cuaccccgac 120
aagguguucc ggagcagcgu ccugcacagc acccaggacc uguuccugcc cuucuucagc 180
aacgugaccu gguuccacgc cauccacgug agcggcacca acggcaccaa gcgguucgac 240
aaccccgugc ugcccuucaa cgacggcgug uacuucgcca gcaccgagaa gagcaacauc 300
auccggggcu ggaucuucgg caccacccug gacagcaaga cccagagccu gcugaucgug 360
aauaacgcca ccaacguggu gaucaaggug ugcgaguucc aguucugcaa cgaccccuuc 420

```
cugggcgugu acuaccacaa gaacaacaag agcuggaugg agagcgaguu ccggguguac    480

agcagcgcca acaacugcac cuucgaguac gugagccagc ccuuccugau ggaccuggag    540

ggcaagcagg gcaacuucaa gaaccugcgg gaguucgugu ucaagaacau cgacggcuac    600

uucaagaucu acagcaagca caccccaauc aaccuggugc gggaucugcc ccagggcuuc    660

ucagcccugg agccccuggu ggaccugccc aucggcauca acaucacccg guuccagacc    720

cugcuggccc ugcaccggag cuaccugacc ccaggcgaca gcagcagcgg guggacagca    780

ggcgcggcug cuuacuacgu gggcuaccug cagccccgga ccuuccugcu gaaguacaac    840

gagaacggca ccaucaccga cgccguggac ggaggcggau cgggaggcgg acccaacauc    900

accaaccugu gccccuucgg cgagguguuc aacgccaccc gguucgccag cguguacgcc    960

uggaaccgga agcggaucag caacugcgug gccgacuaca gcgugcugua caacagcgcc   1020

agcuucagca ccuucaagug cuacggcgug agccccacca agcugaacga ccugugcuuc   1080

accaacgugu acgccgacag cuucgugauc cguggcgacg aggugcggca gaucgcaccc   1140

ggccagacag gcaagaucgc cgacuacaac uacaagcugc ccgacgacuu caccggcugc   1200

gugaucgccu ggaacagcaa caaccucgac agcaaggugg gcggcaacua caacuaccug   1260

uaccggcugu uccggaagag caaccugaag cccuucgagc gggacaucag caccgagauc   1320

uaccaagccg gcuccacccc uugcaacggc guggagggcu ucaacugcua cuucccucug   1380

cagagcuacg gcuuccagcc caccaacggc gugggcuacc agcccuaccg ggugguggug   1440

cugagcuucg agcugcugca cgccccagcc accgugugug gccccaaguc uggcggaggc   1500

agcauccugg ccaucuacag caccguggcc agcagccugg ugcugcuggu gagccugggc   1560

gccaucagcu ucggcggagg cagcgccauc ggcggcuaca uccccgaggc cccuagagac   1620

ggccaggccu acgugcggaa ggacggcgag ugggugcugc ugagcaccuu ccugggcaag   1680
```

```
<210> SEQ ID NO 104
<211> LENGTH: 560
<212> TYPE: PRT
<213> ORGANISM: Artificial Sequence
<220> FEATURE:
<223> OTHER INFORMATION: Synthetic

<400> SEQUENCE: 104

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140
```

```
Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Gly Gly Gly Ser Gly Gly Gly Pro Asn Ile Thr Asn Leu Cys
    290                 295                 300

Pro Phe Gly Glu Val Phe Asn Ala Thr Arg Phe Ala Ser Val Tyr Ala
305                 310                 315                 320

Trp Asn Arg Lys Arg Ile Ser Asn Cys Val Ala Asp Tyr Ser Val Leu
                325                 330                 335

Tyr Asn Ser Ala Ser Phe Ser Thr Phe Lys Cys Tyr Gly Val Ser Pro
            340                 345                 350

Thr Lys Leu Asn Asp Leu Cys Phe Thr Asn Val Tyr Ala Asp Ser Phe
        355                 360                 365

Val Ile Arg Gly Asp Glu Val Arg Gln Ile Ala Pro Gly Gln Thr Gly
    370                 375                 380

Lys Ile Ala Asp Tyr Asn Tyr Lys Leu Pro Asp Asp Phe Thr Gly Cys
385                 390                 395                 400

Val Ile Ala Trp Asn Ser Asn Asn Leu Asp Ser Lys Val Gly Gly Asn
                405                 410                 415

Tyr Asn Tyr Leu Tyr Arg Leu Phe Arg Lys Ser Asn Leu Lys Pro Phe
            420                 425                 430

Glu Arg Asp Ile Ser Thr Glu Ile Tyr Gln Ala Gly Ser Thr Pro Cys
        435                 440                 445

Asn Gly Val Glu Gly Phe Asn Cys Tyr Phe Pro Leu Gln Ser Tyr Gly
    450                 455                 460

Phe Gln Pro Thr Asn Gly Val Gly Tyr Gln Pro Tyr Arg Val Val Val
465                 470                 475                 480

Leu Ser Phe Glu Leu Leu His Ala Pro Ala Thr Val Cys Gly Pro Lys
                485                 490                 495

Ser Gly Gly Gly Ser Ile Leu Ala Ile Tyr Ser Thr Val Ala Ser Ser
            500                 505                 510

Leu Val Leu Leu Val Ser Leu Gly Ala Ile Ser Phe Gly Gly Gly Ser
        515                 520                 525

Ala Ile Gly Gly Tyr Ile Pro Glu Ala Pro Arg Asp Gly Gln Ala Tyr
    530                 535                 540

Val Arg Lys Asp Gly Glu Trp Val Leu Leu Ser Thr Phe Leu Gly Lys
545                 550                 555                 560
```

<210> SEQ ID NO 105
<211> LENGTH: 1826
<212> TYPE: RNA
<213> ORGANISM: Artificial Sequence
<220> FEATURE:
<223> OTHER INFORMATION: Synthetic

<400> SEQUENCE: 105
gggaaauaag agagaaaaga agaguaagaa gaaauauaag accccggcgc cgccaccaug 60
uucguguucc uggugcugcu gccccuggug agcagccagu gcgugaaccu gaccacccgg 120
acccagcugc caccagccua caccaacagc uucacccggg gcgucuacua ccccgacaag 180
guguuccgga gcagcguccu gcacagcacc caggaccugu uccugcccuu cuucagcaac 240
gugaccuggu uccacgccau ccacgugagc ggcaccaacg gcaccaagcg guucgacaac 300
cccgugcugc ccuucaacga cggcguguac uucgccagca ccgagaagag caacaucauc 360
cggggcugga ucuucggcac cacccuggac agcaagaccc agagccugcu gaucgugaau 420
aacgccacca acguggugau caaggugugc gaguuccagu ucugcaacga ccccuuccug 480
ggcguguacu accacaagaa caacaagagc uggauggaga gcgaguuccg gguguacagc 540
agcgccaaca acugcaccuu cgaguacgug agccagcccu uccugaugga ccuggagggc 600
aagcagggca acuucaagaa ccugcgggag uucguguuca agaacaucga cggcuacuuc 660
aagaucuaca gcaagcacac cccaaucaac cuggugcggg aucugcccca gggcuucuca 720
gcccuggagc cccuggugga ccugcccauc ggcaucaaca ucacccgguu ccagacccug 780
cuggcccugc accggagcua ccugacccca ggcgacagca gcagcgggug gacagcaggc 840
gcggcugcuu acuacguggg cuaccugcag ccccggaccu uccugcugaa guacaacgag 900
aacggcacca ucaccgacgc cguggacgga ggcggaucgg gaggcggacc caacaucacc 960
aaccugugcc ccuucggcga gguguucaac gccacccggu ucgccagcgu guacgccugg 1020
aaccggaagc ggaucagcaa cugcguggcc gacuacagcg ugcuguacaa cagcgccagc 1080
uucagcaccu ucaagugcua cggcgugagc ccccaccaagc ugaacgaccu gugcuucacc 1140
aacguguacg ccgacagcuu cgugauccgu ggcgacgagg ugcggcagau cgcacccggc 1200
cagacaggca agaucgccga cuacaacuac aagcugcccg acgacuucac cggcugcgug 1260
aucgccugga acagcaacaa ccucgacagc aaggugggcg gcaacuacaa cuaccuguac 1320
cggcuguucc ggaagagcaa ccugaagccc uucgagcggg acaucagcac cgagaucuac 1380
caagccggcu ccaccccuug caacggcgug gagggcuuca acugcuacuu cccucugcag 1440
agcuacggcu uccagcccac caacggcgug ggcuaccagc ccuaccgggu gguggugcug 1500
agcuucgagc ugcugcacgc cccagccacc gugugugggcc ccaagucugg cggaggcagc 1560
auccuggcca ucuacagccu gggcuucauc gccggccuga ucgccaucgu gauggugacc 1620
aucaugcugu gcugcaugac cagcugcugc agcugccuga agggcuguug cagcugcggc 1680
agcugcugca aguucgacga ggacgacuga uaauaggcug gagccucggu ggccuagcuu 1740
cuugccccuu gggccucccc ccagccccuc cuccccuucc ugcacccgua cccccguggu 1800
cuuugaauaa agucugagug ggcggc 1826

<210> SEQ ID NO 106
<211> LENGTH: 1650
<212> TYPE: RNA
<213> ORGANISM: Artificial Sequence
<220> FEATURE:
<223> OTHER INFORMATION: Synthetic

<400> SEQUENCE: 106

```
auguucgugu uccuggugcu gcugccccug gugagcagcc agugcgugaa ccugaccacc      60
cggacccagc ugccaccagc cuacaccaac agcuucaccc ggggcgucua cuaccccgac     120
aagguguucc ggagcagcgu ccugcacagc acccaggacc uguuccugcc cuucuucagc     180
aacgugaccu gguuccacgc cauccacgug agcggcacca acggcaccaa gcgguucgac     240
aaccccgugc ugcccuucaa cgacggcgug uacuucgcca gcaccgagaa gagcaacauc     300
auccggggcu ggaucuucgg caccacccug gacagcaaga cccagagccu gcugaucgug     360
aauaacgcca ccaacguggu gaucaaggug ugcgaguucc aguucugcaa cgaccccuuc     420
cugggcgugu acuaccacaa gaacaacaag agcuggaugg agagcgaguu ccggguguac     480
agcagcgcca acaacugcac cuucgaguac gugagccagc ccuuccugau ggaccuggag     540
ggcaagcagg gcaacuucaa gaaccugcgg gaguucgugu ucaagaacau cgacggcuac     600
uucaagaucu acagcaagca caccccaauc aaccuggugc gggaucugcc ccagggcuuc     660
ucagcccugg agccccuggu ggaccugccc aucggcauca acaucacccg guuccagacc     720
cugcuggccc ugcaccggag cuaccugacc ccaggcgaca gcagcagcgg guggacagca     780
ggcgcggcug cuuacuacgu gggcuaccug cagccccgga ccuuccugcu gaaguacaac     840
gagaacggca ccaucaccga cgccguggac ggaggcggau cgggaggcgg acccaacauc     900
accaaccugu gccccuucgg cgagguguuc aacgccaccc gguucgccag cguguacgcc     960
uggaaccgga agcggaucag caacugcgug gccgacuaca gcgugcugua caacagcgcc    1020
agcuucagca ccuucaagug cuacggcgug agccccacca agcugaacga ccugugcuuc    1080
accaacgugu acgccgacag cuucgugauc cguggcgacg aggugcggca gaucgcaccc    1140
ggccagacag gcaagaucgc cgacuacaac uacaagcugc ccgacgacuu caccggcugc    1200
gugaucgccu ggaacagcaa caaccucgac agcaaggugg gcggcaacua caacuaccug    1260
uaccggcugu uccggaagag caaccugaag cccuucgagc gggacaucag caccgagauc    1320
uaccaagccg gcuccacccc uugcaacggc guggagggcu ucaacugcua cuuccccucug    1380
cagagcuacg gcuuccagcc caccaacggc gugggcuacc agcccuaccg gguggguggug   1440
cugagcuucg agcugcugca cgccccagcc accgugugug gccccaaguc uggcggaggc    1500
agcauccugg ccaucuacag ccugggcuuc aucgccggcc ugaucgccau cgugauggug    1560
accaucaugc ugugcugcau gaccagcugc ugcagcugcc ugaagggcug uugcagcugc    1620
ggcagcugcu gcaaguucga cgaggacgac                                    1650
```

<210> SEQ ID NO 107
<211> LENGTH: 550
<212> TYPE: PRT
<213> ORGANISM: Artificial Sequence
<220> FEATURE:
<223> OTHER INFORMATION: Synthetic

<400> SEQUENCE: 107

```
Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60
```

```
Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Gly Gly Gly Ser Gly Gly Gly Pro Asn Ile Thr Asn Leu Cys
    290                 295                 300

Pro Phe Gly Glu Val Phe Asn Ala Thr Arg Phe Ala Ser Val Tyr Ala
305                 310                 315                 320

Trp Asn Arg Lys Arg Ile Ser Asn Cys Val Ala Asp Tyr Ser Val Leu
                325                 330                 335

Tyr Asn Ser Ala Ser Phe Ser Thr Phe Lys Cys Tyr Gly Val Ser Pro
            340                 345                 350

Thr Lys Leu Asn Asp Leu Cys Phe Thr Asn Val Tyr Ala Asp Ser Phe
        355                 360                 365

Val Ile Arg Gly Asp Glu Val Arg Gln Ile Ala Pro Gly Gln Thr Gly
    370                 375                 380

Lys Ile Ala Asp Tyr Asn Tyr Lys Leu Pro Asp Asp Phe Thr Gly Cys
385                 390                 395                 400

Val Ile Ala Trp Asn Ser Asn Asn Leu Asp Ser Lys Val Gly Gly Asn
                405                 410                 415

Tyr Asn Tyr Leu Tyr Arg Leu Phe Arg Lys Ser Asn Leu Lys Pro Phe
            420                 425                 430

Glu Arg Asp Ile Ser Thr Glu Ile Tyr Gln Ala Gly Ser Thr Pro Cys
        435                 440                 445

Asn Gly Val Glu Gly Phe Asn Cys Tyr Phe Pro Leu Gln Ser Tyr Gly
    450                 455                 460

Phe Gln Pro Thr Asn Gly Val Gly Tyr Gln Pro Tyr Arg Val Val Val
465                 470                 475                 480
```

```
Leu Ser Phe Glu Leu Leu His Ala Pro Ala Thr Val Cys Gly Pro Lys
                485                 490                 495

Ser Gly Gly Gly Ser Ile Leu Ala Ile Tyr Ser Leu Gly Phe Ile Ala
            500                 505                 510

Gly Leu Ile Ala Ile Val Met Val Thr Ile Met Leu Cys Cys Met Thr
        515                 520                 525

Ser Cys Cys Ser Cys Leu Lys Gly Cys Cys Ser Cys Gly Ser Cys Cys
    530                 535                 540

Lys Phe Asp Glu Asp Asp
545                 550
```

<210> SEQ ID NO 108
<211> LENGTH: 1826
<212> TYPE: RNA
<213> ORGANISM: Artificial Sequence
<220> FEATURE:
<223> OTHER INFORMATION: Synthetic

<400> SEQUENCE: 108

```
gggaaauaag agagaaaaga agaguaagaa gaaauauaag accccggcgc cgccaccaug     60

uucguguucc uggugcugcu gccccuggug agcagccagu gcgugaaccu gaccacccgg    120

acccagcugc caccagccua caccaacagc uucacccggg gcgucuacua ccccgacaag    180

guguuccgga gcagcguccu gcacagcacc caggaccugu uccugcccuu cuucagcaac    240

gugaccuggu uccacgccau ccacgugagc ggcaccaacg gcaccaagcg guucgacaac    300

cccgugcugc ccuucaacga cggcguguac uucgccagca ccgagaagag caacaucauc    360

cggggcugga ucuucggcac cacccuggac agcaagaccc agagccugcu gaucgugaau    420

aacgccacca acguggugau caaggugugc gaguuccagu ucugcaacga ccccuuccug    480

ggcguguacu accacaagaa caacaagagc uggauggaga gcgaguuccg gguguacagc    540

agcgccaaca acugcaccuu cgaguacgug agccagcccu uccugaugga ccuggagggc    600

aagcagggca acuucaagaa ccugcgggag uucguguuca agaacaucga cggcuacuuc    660

aagaucuaca gcaagcacac cccaaucaac cuggugcggg aucugcccca gggcuucuca    720

gcccuggagc cccuggugga ccugcccauc ggcaucaaca ucacccgguu ccagacccug    780

cuggcccugc accggagcua ccugaccccca ggcgacagca gcagcgggug gacagcaggc    840

gcggcugcuu acuacguggg cuaccugcag ccccggaccu uccugcugaa guacaacgag    900

aacggcacca ucaccgacgc cguggacgga ggcggaucgg gaggcggacc caacaucacc    960

aaccugugcc ccuucggcga gguguucaac gccacccggu ucgccagcgu guacgccugg   1020

aaccggaagc ggaucagcaa cugcguggcc gacuacagcg ugcuguacaa cagcgccagc   1080

uucagcaccu ucaagugcua cggcgugagc ccccaccaagc ugaacgaccu gugcuucacc   1140

aacguguacg ccgacagcuu cgugauccgu ggcgacgagg ugcggcagau cgcacccggc   1200

cagacaggca agaucgccga cuacaacuac aagcugcccg acgacuucac cggcugcgug   1260

aucgccugga acagcaacaa ccucgacagc aaggugggcg gcaacuacaa cuaccuguac   1320

cggcuguucc ggaagagcaa ccugaagccc uucgagcggg acaucagcac cgagaucuac   1380

caagccggcu ccaccccuug caacggcgug gagggcuuca acugcuacuu cccucugcag   1440

agcuacggcu uccagcccac caacggcgug ggcuaccagc ccuaccgggu gguggugcug   1500

agcuucgagc ugcugcacgc cccagccacc guguguggcc ccaagucugg cggaggcagc   1560

agcagcaucg ccagcuucuu cuucaucauc gggcugauca ucggccucuu ccuggugcug   1620
```

cgggugggca uccaccugug caucaagcug aagcacacca agaagagaca gaucuacacc 1680
gacaucgaga ugaaccggcu gggcaaguga uaauaggcug gagccucggu ggccuagcuu 1740
cuugccccuu gggccucccc ccagccccuc cuccccuucc ugcacccgua cccccguggu 1800
cuuugaauaa agucugagug ggcggc 1826

<210> SEQ ID NO 109
<211> LENGTH: 1650
<212> TYPE: RNA
<213> ORGANISM: Artificial Sequence
<220> FEATURE:
<223> OTHER INFORMATION: Synthetic

<400> SEQUENCE: 109
auguucgugu uccuggugcu gcugccccug gugagcagcc agugcgugaa ccugaccacc 60
cggacccagc ugccaccagc cuacaccaac agcuucaccc ggggcgucua cuaccccgac 120
aagguguucc ggagcagcgu ccugcacagc acccaggacc uguuccugcc cuucuucagc 180
aacgugaccu gguuccacgc cauccacgug agcggcacca acggcaccaa gcgguucgac 240
aaccccgugc ugcccuucaa cgacggcgug uacuucgcca gcaccgagaa gagcaacauc 300
auccggggcu ggaucuucgg caccacccug gacagcaaga cccagagccu gcugaucgug 360
aauaacgcca ccaacguggu gaucaaggug ugcgaguucc aguucugcaa cgaccccuuc 420
cugggcgugu acuaccacaa gaacaacaag agcuggaugg agagcgaguu ccggguguac 480
agcagcgcca acaacugcac cuucgaguac gugagccagc ccuuccugau ggaccuggag 540
ggcaagcagg gcaacuucaa gaaccugcgg gaguucgugu ucaagaacau cgacggcuac 600
uucaagaucu acagcaagca caccccaauc aaccuggugc gggaucugcc ccagggcuuc 660
ucagcccugg agccccuggu ggaccugccc aucggcauca acaucacccg guuccagacc 720
cugcuggccc ugcaccggag cuaccugacc ccaggcgaca gcagcagcgg gugggacagca 780 ggcgcggcug cuuacuacgu gggcuaccug cagccccgga ccuuccugcu gaaguacaac 840
gagaacggca ccaucaccga cgccguggac ggaggcggau cgggaggcgg acccaacauc 900
accaaccugu gccccuucgg cgagguguuc aacgccaccc gguucgccag cguguacgcc 960
uggaaccgga agcggaucag caacugcgug gccgacuaca gcgugcugua caacagcgcc 1020
agcuucagca ccuucaagug cuacggcgug agccccacca agcugaacga ccugugcuuc 1080
accaacgugu acgccgacag cuucgugauc cguggcgacg aggugcggca gaucgcaccc 1140
ggccagacag gcaagaucgc cgacuacaac uacaagcugc ccgacgacuu caccggcugc 1200
gugaucgccu ggaacagcaa caaccucgac agcaaggugg gcggcaacua caacuaccug 1260
uaccggcugu uccggaagag caaccugaag cccuucgagc gggacaucag caccgagauc 1320
uaccaagccg gcuccacccc uugcaacggc guggagggcu ucaacugcua cuuccccucug 1380 cagagcuacg gcuuccagcc caccaacggc gugggcuacc agcccuaccg ggugguggug 1440
cugagcuucg agcugcugca cgccccagcc accgugugug gccccaaguc uggcggaggc 1500
agcagcagca ucgccagcuu cuucuucauc aucgggcuga ucaucggccu cuuccuggug 1560
cugcgggugg gcauccaccu gugcaucaag cugaagcaca ccaagaagag acagaucuac 1620
accgacaucg agaugaaccg gcugggcaag 1650

<210> SEQ ID NO 110
<211> LENGTH: 550
<212> TYPE: PRT
<213> ORGANISM: Artificial Sequence
<220> FEATURE:
<223> OTHER INFORMATION: Synthetic

<400> SEQUENCE: 110

```
Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Gly Gly Gly Ser Gly Gly Gly Pro Asn Ile Thr Asn Leu Cys
    290                 295                 300

Pro Phe Gly Glu Val Phe Asn Ala Thr Arg Phe Ala Ser Val Tyr Ala
305                 310                 315                 320

Trp Asn Arg Lys Arg Ile Ser Asn Cys Val Ala Asp Tyr Ser Val Leu
                325                 330                 335

Tyr Asn Ser Ala Ser Phe Ser Thr Phe Lys Cys Tyr Gly Val Ser Pro
            340                 345                 350

Thr Lys Leu Asn Asp Leu Cys Phe Thr Asn Val Tyr Ala Asp Ser Phe
        355                 360                 365

Val Ile Arg Gly Asp Glu Val Arg Gln Ile Ala Pro Gly Gln Thr Gly
    370                 375                 380

Lys Ile Ala Asp Tyr Asn Tyr Lys Leu Pro Asp Asp Phe Thr Gly Cys
385                 390                 395                 400
```

Val Ile Ala Trp Asn Ser Asn Asn Leu Asp Ser Lys Val Gly Gly Asn
405 410 415

Tyr Asn Tyr Leu Tyr Arg Leu Phe Arg Lys Ser Asn Leu Lys Pro Phe
420 425 430

Glu Arg Asp Ile Ser Thr Glu Ile Tyr Gln Ala Gly Ser Thr Pro Cys
435 440 445

Asn Gly Val Glu Gly Phe Asn Cys Tyr Phe Pro Leu Gln Ser Tyr Gly
450 455 460

Phe Gln Pro Thr Asn Gly Val Gly Tyr Gln Pro Tyr Arg Val Val Val
465 470 475 480

Leu Ser Phe Glu Leu Leu His Ala Pro Ala Thr Val Cys Gly Pro Lys
485 490 495

Ser Gly Gly Gly Ser Ser Ser Ile Ala Ser Phe Phe Phe Ile Ile Gly
500 505 510

Leu Ile Ile Gly Leu Phe Leu Val Leu Arg Val Gly Ile His Leu Cys
515 520 525

Ile Lys Leu Lys His Thr Lys Lys Arg Gln Ile Tyr Thr Asp Ile Glu
530 535 540

Met Asn Arg Leu Gly Lys
545 550

<210> SEQ ID NO 111
<211> LENGTH: 1775
<212> TYPE: RNA
<213> ORGANISM: Artificial Sequence
<220> FEATURE:
<223> OTHER INFORMATION: Synthetic

<400> SEQUENCE: 111
gggaaauaag agagaaaaga agaguaagaa gaaauauaag accccggcgc cgccaccaug 60
uucguguucc uggugcugcu gccccuggug agcagccagu gcgugaaccu gaccacccgg 120
acccagcugc caccagccua caccaacagc uucacccggg gcgucuacua ccccgacaag 180
guguuccgga gcagcguccu gcacagcacc caggaccugu uccugcccuu cuucagcaac 240
gugaccuggu uccacgccau ccacgugagc ggcaccaacg gcaccaagcg guucgacaac 300
cccgugcugc ccuucaacga cggcguguac uucgccagca ccgagaagag caacaucauc 360
cggggcugga ucuucggcac cacccuggac agcaagaccc agagccugcu gaucgugaau 420
aacgccacca acguggugau caaggugugc gaguuccagu ucugcaacga ccccuuccug 480
ggcguguacu accacaagaa caacaagagc uggauggaga gcgaguuccg gguguacagc 540
agcgccaaca acugcaccuu cgaguacgug agccagcccu uccugaugga ccuggagggc 600
aagcagggca acuucaagaa ccugcgggag uucguguuca agaacaucga cggcuacuuc 660
aagaucuaca gcaagcacac cccaaucaac cuggugcggg aucugcccca gggcuucuca 720
gcccuggagc cccuggugga ccugcccauc ggcaucaaca ucacccgguu ccagacccug 780
cuggcccugc accggagcua ccugacccca ggcgacagca gcagcgggug gacagcaggc 840
gcggcugcuu acuacguggg cuaccugcag ccccggaccu uccugcugaa guacaacgag 900
aacggcacca ucaccgacgc cguggacgga ggcggaucgg gaggcggacc caacaucacc 960
aaccugugcc ccuucggcga gguguucaac gccacccggu ucgccagcgu guacgccugg 1020
aaccggaagc ggaucagcaa cugcguggcc gacuacagcg ugcuguacaa cagcgccagc 1080
uucagcaccu ucaagugcua cggcgugagc ccccaccaagc ugaacgaccu gugcuucacc 1140
aacguguacg ccgacagcuu cgugauccgu ggcgacgagg ugcggcagau cgcacccggc 1200
cagacaggca agaucgccga cuacaacuac aagcugcccg acgacuucac cggcugcgug 1260
aucgccugga acagcaacaa ccucgacagc aaggugggcg gcaacuacaa cuaccuguac 1320
cggcuguucc ggaagagcaa ccugaagccc uucgagcggg acaucagcac cgagaucuac 1380
caagccggcu ccaccccuug caacggcgug gagggcuuca acugcuacuu cccucugcag 1440
agcuacggcu uccagcccac caacggcgug ggcuaccagc ccuaccgggu gguggugcug 1500
agcuucgagc ugcugcacgc cccagccacc guguguggcc ccaagucugg cggaggcggc 1560
agcgccaucg gcggcuacau ccccgaggcc ccuagagacg gccaggccua cgugcggaag 1620
gacggcgagu gggugcugcu gagcaccuuc cugggcugau aauaggcugg agccucggug 1680
gccuagcuuc uugccccuug ggccuccccc cagccccucc uccccuuccu gcacccguac 1740
ccccgugguc uuugaauaaa gucugagugg gcggc 1775

<210> SEQ ID NO 112
<211> LENGTH: 1599
<212> TYPE: RNA
<213> ORGANISM: Artificial Sequence
<220> FEATURE:
<223> OTHER INFORMATION: Synthetic

<400> SEQUENCE: 112
auguucgugu uccuggugcu gcugccccug gugagcagcc agugcgugaa ccugaccacc 60
cggacccagc ugccaccagc cuacaccaac agcuucaccc ggggcgucua cuaccccgac 120
aagguguucc ggagcagcgu ccugcacagc acccaggacc uguuccugcc cuucuucagc 180
aacgugaccu gguuccacgc cauccacgug agcggcacca acggcaccaa gcgguucgac 240
aaccccgugc ugcccuucaa cgacggcgug uacuucgcca gcaccgagaa gagcaacauc 300
auccggggcu ggaucuucgg caccacccug gacagcaaga cccagagccu gcugaucgug 360
aauaacgcca ccaacguggu gaucaaggug ugcgaguucc aguucugcaa cgaccccuuc 420
cugggcgugu acuaccacaa gaacaacaag agcuggaugg agagcgaguu ccggguguac 480
agcagcgcca acaacugcac cuucgaguac gugagccagc ccuuccugau ggaccuggag 540
ggcaagcagg gcaacuucaa gaaccugcgg gaguucgugu ucaagaacau cgacggcuac 600
uucaagaucu acagcaagca caccccaauc aaccuggugc gggaucugcc ccagggcuuc 660
ucagcccugg agccccuggu ggaccugccc aucggcauca acaucacccg guuccagacc 720
cugcuggccc ugcaccggag cuaccugacc ccaggcgaca gcagcagcgg guggacagca 780
ggcgcggcug cuuacuacgu gggcuaccug cagccccgga ccuuccugcu gaaguacaac 840
gagaacggca ccaucaccga cgccguggac ggaggcggau cgggaggcgg acccaacauc 900
accaaccugu gccccuucgg cgagguguuc aacgccaccc gguucgccag cguguacgcc 960
uggaaccgga agcggaucag caacugcgug gccgacuaca gcgugcugua caacagcgcc 1020
agcuucagca ccuucaagug cuacggcgug agccccacca agcugaacga ccugugcuuc 1080
accaacgugu acgccgacag cuucgugauc cguggcgacg aggugcggca gaucgcaccc 1140
ggccagacag gcaagaucgc cgacuacaac uacaagcugc ccgacgacuu caccggcugc 1200
gugaucgccu ggaacagcaa caaccucgac agcaaggugg gcggcaacua caacuaccug 1260
uaccggcugu uccggaagag caaccugaag cccuucgagc gggacaucag caccgagauc 1320
uaccaagccg gcuccacccc uugcaacggc guggagggcu ucaacugcua cuucccucug 1380
cagagcuacg gcuuccagcc caccaacggc gugggcuacc agcccuaccg gguggugg ug 1440 cugagcuucg agcugcugca cgccccagcc accgugugug gccccaaguc uggcggaggc 1500
ggcagcgcca ucggcggcua cauccccgag gccccuagag acggccaggc cuacgugcgg 1560
aaggacggcg agugggugcu gcugagcacc uuccugggc 1599

<210> SEQ ID NO 113
<211> LENGTH: 533
<212> TYPE: PRT
<213> ORGANISM: Artificial Sequence
<220> FEATURE:
<223> OTHER INFORMATION: Synthetic

<400> SEQUENCE: 113

Met Phe Val Phe Leu Val Leu Leu Pro Leu Val Ser Ser Gln Cys Val
1 5 10 15

Asn Leu Thr Thr Arg Thr Gln Leu Pro Pro Ala Tyr Thr Asn Ser Phe
20 25 30

Thr Arg Gly Val Tyr Tyr Pro Asp Lys Val Phe Arg Ser Ser Val Leu
35 40 45

His Ser Thr Gln Asp Leu Phe Leu Pro Phe Phe Ser Asn Val Thr Trp
50 55 60

Phe His Ala Ile His Val Ser Gly Thr Asn Gly Thr Lys Arg Phe Asp
65 70 75 80

Asn Pro Val Leu Pro Phe Asn Asp Gly Val Tyr Phe Ala Ser Thr Glu
85 90 95

Lys Ser Asn Ile Ile Arg Gly Trp Ile Phe Gly Thr Thr Leu Asp Ser
100 105 110

Lys Thr Gln Ser Leu Leu Ile Val Asn Asn Ala Thr Asn Val Val Ile
115 120 125

Lys Val Cys Glu Phe Gln Phe Cys Asn Asp Pro Phe Leu Gly Val Tyr
130 135 140

Tyr His Lys Asn Asn Lys Ser Trp Met Glu Ser Glu Phe Arg Val Tyr
145 150 155 160

Ser Ser Ala Asn Asn Cys Thr Phe Glu Tyr Val Ser Gln Pro Phe Leu
165 170 175

Met Asp Leu Glu Gly Lys Gln Gly Asn Phe Lys Asn Leu Arg Glu Phe
180 185 190

Val Phe Lys Asn Ile Asp Gly Tyr Phe Lys Ile Tyr Ser Lys His Thr
195 200 205

Pro Ile Asn Leu Val Arg Asp Leu Pro Gln Gly Phe Ser Ala Leu Glu
210 215 220

Pro Leu Val Asp Leu Pro Ile Gly Ile Asn Ile Thr Arg Phe Gln Thr
225 230 235 240

Leu Leu Ala Leu His Arg Ser Tyr Leu Thr Pro Gly Asp Ser Ser Ser
245 250 255

Gly Trp Thr Ala Gly Ala Ala Ala Tyr Tyr Val Gly Tyr Leu Gln Pro
260 265 270

Arg Thr Phe Leu Leu Lys Tyr Asn Glu Asn Gly Thr Ile Thr Asp Ala
275 280 285

Val Asp Gly Gly Gly Ser Gly Gly Gly Pro Asn Ile Thr Asn Leu Cys
290 295 300

Pro Phe Gly Glu Val Phe Asn Ala Thr Arg Phe Ala Ser Val Tyr Ala
305 310 315 320

Trp Asn Arg Lys Arg Ile Ser Asn Cys Val Ala Asp Tyr Ser Val Leu
325 330 335

```
Tyr Asn Ser Ala Ser Phe Ser Thr Phe Lys Cys Tyr Gly Val Ser Pro
            340                 345                 350

Thr Lys Leu Asn Asp Leu Cys Phe Thr Asn Val Tyr Ala Asp Ser Phe
        355                 360                 365

Val Ile Arg Gly Asp Glu Val Arg Gln Ile Ala Pro Gly Gln Thr Gly
    370                 375                 380

Lys Ile Ala Asp Tyr Asn Tyr Lys Leu Pro Asp Asp Phe Thr Gly Cys
385                 390                 395                 400

Val Ile Ala Trp Asn Ser Asn Asn Leu Asp Ser Lys Val Gly Gly Asn
                405                 410                 415

Tyr Asn Tyr Leu Tyr Arg Leu Phe Arg Lys Ser Asn Leu Lys Pro Phe
            420                 425                 430

Glu Arg Asp Ile Ser Thr Glu Ile Tyr Gln Ala Gly Ser Thr Pro Cys
        435                 440                 445

Asn Gly Val Glu Gly Phe Asn Cys Tyr Phe Pro Leu Gln Ser Tyr Gly
    450                 455                 460

Phe Gln Pro Thr Asn Gly Val Gly Tyr Gln Pro Tyr Arg Val Val Val
465                 470                 475                 480

Leu Ser Phe Glu Leu Leu His Ala Pro Ala Thr Val Cys Gly Pro Lys
                485                 490                 495

Ser Gly Gly Gly Gly Ser Ala Ile Gly Gly Tyr Ile Pro Glu Ala Pro
            500                 505                 510

Arg Asp Gly Gln Ala Tyr Val Arg Lys Asp Gly Glu Trp Val Leu Leu
        515                 520                 525

Ser Thr Phe Leu Gly
    530
```

<210> SEQ ID NO 114
<211> LENGTH: 1973
<212> TYPE: RNA
<213> ORGANISM: Artificial Sequence
<220> FEATURE:
<223> OTHER INFORMATION: Synthetic

<400> SEQUENCE: 114

```
gggaaauaag agagaaaaga agaguaagaa gaaauauaag accccggcgc cgccaccaug     60

uucguguucc uggugcugcu gccccuggug agcagccagu gcgugaaccu gaccaccccgg    120

acccagcugc caccagccua caccaacagc uucacccggg gcgucuacua ccccgacaag    180

guguuccgga gcagcguccu gcacagcacc caggaccugu uccugcccuu cuucagcaac    240

gugaccuggu uccacgccau ccacgugagc ggcaccaacg gcaccaagcg guucgacaac    300

cccgugcugc ccuucaacga cggcguguac uucgccagca ccgagaagag caacaucauc    360

cggggcugga ucuucggcac cacccuggac agcaagaccc agagccugcu gaucgugaau    420

aacgccacca acguggugau caaggugugc gaguuccagu ucugcaacga ccccuuccug    480

ggcguguacu accacaagaa caacaagagc uggauggaga gcgaguuccg gguguacagc    540

agcgccaaca acugcaccuu cgaguacgug agccagcccu uccugaugga ccuggagggc    600

aagcagggca acuucaagaa ccugcgggag uucguguuca agaacaucga cggcuacuuc    660

aagaucuaca gcaagcacac cccaaucaac cuggugcggg aucugcccca gggcuucuca    720

gcccuggagc cccuggugga ccugcccauc ggcaucaaca ucacccgguu ccagacccug    780

cuggcccugc accggagcua ccugacccca ggcgacagca gcagcgggug gacagcaggc    840

gcggcugcuu acuacguggg cuaccugcag ccccggaccu uccugcugaa guacaacgag    900
```

aacggcacca ucaccgacgc cguggacgga ggcggaucgg gaggcggaca gcgggugcag 960
cccaccgaga gcaucgugcg guuccccaac aucaccaacc ugugccccuu cggcgaggug 1020
uucaacgcca cccgguucgc cagcguguac gccuggaacc ggaagcggau cagcaacugc 1080
guggccgacu acagcgugcu guacaacagc gccagcuuca gcaccuucaa gugcuacggc 1140
gugagcccca ccaagcugaa cgaccugugc uucaccaacg uguacgccga cagcuucgug 1200
auccguggcg acgaggugcg gcagaucgca cccggccaga caggcaagau cgccgacuac 1260
aacuacaagc ugcccgacga cuucaccggc ugcgugaucg ccuggaacag caacaaccuc 1320
gacagcaagg ugggcggcaa cuacaacuac cuguaccggc uguuccggaa gagcaaccug 1380
aagcccuucg agcgggacau cagcaccgag aucuaccaag ccggcuccac cccuugcaac 1440
ggcguggagg gcuucaacug cuacuucccu cugcagagcu acggcuucca gcccaccaac 1500
ggcgugggcu accagcccua ccgggguggug gugcugagcu ucgagcugcu gcacgcccca 1560
gccaccgugu guggccccaa gaagagcacc aaccugguga agaacaagug cgugaacuuc 1620
aacuucaacg gccuuaccgg caccggcgug cugaccgaga gcaacaagaa auuccugccc 1680
uuucagcagu ucggccggga caucgccgac accaccgacg cugugcggga uccccagacc 1740
cuggagaucc uggacaucac cccuugcagc ucuggcggag gcagcauccu ggccaucuac 1800
agcaccgugg ccagcagccu ggugcugcug gugagccugg gcgccaucag cuucugauaa 1860
uaggcuggag ccucggugge cuagcuucuu gccccuuggg ccucccccca gccccuccuc 1920
cccuuccugc acccguaccc ccguggucuu ugaauaaagu cugagugggc ggc 1973

<210> SEQ ID NO 115
<211> LENGTH: 1797
<212> TYPE: RNA
<213> ORGANISM: Artificial Sequence
<220> FEATURE:
<223> OTHER INFORMATION: Synthetic

<400> SEQUENCE: 115
auguucgugu uccuggugcu gcugccccug gugagcagcc agugcgugaa ccugaccacc 60
cggacccagc ugccaccagc cuacaccaac agcuucaccc ggggcgucua cuaccccgac 120
aagguguucc ggagcagcgu ccugcacagc acccaggacc uguuccugcc cuucuucagc 180
aacgugaccu gguuccacgc cauccacgug agcggcacca acggcaccaa gcgguucgac 240
aaccccgugc ugcccuucaa cgacggcgug uacuucgcca gcaccgagaa gagcaacauc 300
auccggggcu ggaucuucgg caccacccug gacagcaaga cccagagccu gcugaucgug 360
aauaacgcca ccaacguggu gaucaaggug ugcgaguucc aguucugcaa cgaccccuuc 420
cugggcgugu acuaccacaa gaacaacaag agcuggaugg agagcgaguu ccgggugguac 480 agcagcgcca acaacugcac cuucgaguac gugagccagc ccuuccugau ggaccuggag 540
ggcaagcagg gcaacuucaa gaaccugcgg gaguucgugu ucaagaacau cgacggcuac 600
uucaagaucu acagcaagca caccccaauc aaccuggugc gggaucugcc ccagggcuuc 660
ucagcccugg agccccuggu ggaccugccc aucggcauca acaucacccg guuccagacc 720
cugcuggccc ugcaccggag cuaccugacc ccaggcgaca gcagcagcgg guggacagca 780
ggcgcggcug cuuacuacgu gggcuaccug cagccccgga ccuuccugcu gaaguacaac 840
gagaacggca ccaucaccga cgccguggac ggaggcggau cgggaggcgg acagcgggug 900
cagcccaccg agagcaucgu gcgguucccc aacaucacca accugugccc cuucggcgag 960

```
guguucaacg ccacccgguu cgccagcgug uacgccugga accggaagcg gaucagcaac   1020

ugcguggccg acuacagcgu gcuguacaac agcgccagcu ucagcaccuu caagugcuac   1080

ggcgugagcc ccaccaagcu gaacgaccug ugcuucacca acguguacgc cgacagcuuc   1140

gugauccgug gcgacgaggu gcggcagauc gcacccggcc agacaggcaa gaucgccgac   1200

uacaacuaca agcugcccga cgacuucacc ggcugcguga ucgccuggaa cagcaacaac   1260

cucgacagca aggugggcgg caacuacaac uaccuguacc ggcuguuccg gaagagcaac   1320

cugaagcccu ucgagcggga caucagcacc gagaucuacc aagccggcuc caccccuugc   1380

aacggcgugg agggcuucaa cugcuacuuc ccucugcaga gcuacggcuu ccagcccacc   1440

aacggcgugg gcuaccagcc cuaccgggug gugguguga gcuucgagcu gcugcacgcc   1500

ccagccaccg uguguggccc caagaagagc accaaccugg ugaagaacaa gugcgugaac   1560

uucaacuuca acggccuuac cggcaccggc gugcugaccg agagcaacaa gaaauuccug   1620

cccuuucagc aguucggccg ggacaucgcc gacaccaccg acgcugugcg ggaucccag   1680

acccuggaga uccuggacau caccccuugc agcucuggcg gaggcagcau ccuggccauc   1740

uacagcaccg uggccagcag ccuggugcug cuggugagcc ugggcgccau cagcuuc      1797
```

```
<210> SEQ ID NO 116
<211> LENGTH: 599
<212> TYPE: PRT
<213> ORGANISM: Artificial Sequence
<220> FEATURE:
<223> OTHER INFORMATION: Synthetic

<400> SEQUENCE: 116

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220
```

```
Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Gly Gly Gly Ser Gly Gly Gly Gln Arg Val Gln Pro Thr Glu
    290                 295                 300

Ser Ile Val Arg Phe Pro Asn Ile Thr Asn Leu Cys Pro Phe Gly Glu
305                 310                 315                 320

Val Phe Asn Ala Thr Arg Phe Ala Ser Val Tyr Ala Trp Asn Arg Lys
                325                 330                 335

Arg Ile Ser Asn Cys Val Ala Asp Tyr Ser Val Leu Tyr Asn Ser Ala
            340                 345                 350

Ser Phe Ser Thr Phe Lys Cys Tyr Gly Val Ser Pro Thr Lys Leu Asn
        355                 360                 365

Asp Leu Cys Phe Thr Asn Val Tyr Ala Asp Ser Phe Val Ile Arg Gly
    370                 375                 380

Asp Glu Val Arg Gln Ile Ala Pro Gly Gln Thr Gly Lys Ile Ala Asp
385                 390                 395                 400

Tyr Asn Tyr Lys Leu Pro Asp Asp Phe Thr Gly Cys Val Ile Ala Trp
                405                 410                 415

Asn Ser Asn Asn Leu Asp Ser Lys Val Gly Gly Asn Tyr Asn Tyr Leu
            420                 425                 430

Tyr Arg Leu Phe Arg Lys Ser Asn Leu Lys Pro Phe Glu Arg Asp Ile
        435                 440                 445

Ser Thr Glu Ile Tyr Gln Ala Gly Ser Thr Pro Cys Asn Gly Val Glu
    450                 455                 460

Gly Phe Asn Cys Tyr Phe Pro Leu Gln Ser Tyr Gly Phe Gln Pro Thr
465                 470                 475                 480

Asn Gly Val Gly Tyr Gln Pro Tyr Arg Val Val Val Leu Ser Phe Glu
                485                 490                 495

Leu Leu His Ala Pro Ala Thr Val Cys Gly Pro Lys Lys Ser Thr Asn
            500                 505                 510

Leu Val Lys Asn Lys Cys Val Asn Phe Asn Phe Asn Gly Leu Thr Gly
        515                 520                 525

Thr Gly Val Leu Thr Glu Ser Asn Lys Lys Phe Leu Pro Phe Gln Gln
    530                 535                 540

Phe Gly Arg Asp Ile Ala Asp Thr Thr Asp Ala Val Arg Asp Pro Gln
545                 550                 555                 560

Thr Leu Glu Ile Leu Asp Ile Thr Pro Cys Ser Ser Gly Gly Gly Ser
                565                 570                 575

Ile Leu Ala Ile Tyr Ser Thr Val Ala Ser Ser Leu Val Leu Leu Val
            580                 585                 590

Ser Leu Gly Ala Ile Ser Phe
        595
```

<210> SEQ ID NO 117
<211> LENGTH: 1799
<212> TYPE: RNA
<213> ORGANISM: Artificial Sequence
<220> FEATURE:

<223> OTHER INFORMATION: Synthetic

<400> SEQUENCE: 117

```
gggaaauaag agagaaaaga agaguaagaa gaaauauaag accccggcgc cgccaccaug      60
uucguguucc uggugcugcu gccccuggug agcagccagu gcgugaaccu gaccacccgg     120
acccagcugc caccagccua caccaacagc uucacccggg gcgucuacua ccccgacaag     180
guguuccgga gcagcguccu gcacagcacc caggaccugu uccugcccuu cuucagcaac     240
gugaccuggu uccacgccau ccacgugagc ggcaccaacg gcaccaagcg guucgacaac     300
cccgugcugc ccuucaacga cggcguguac uucgccagca ccgagaagag caacaucauc     360
cggggcugga ucuucggcac cacccuggac agcaagaccc agagccugcu gaucgugaau     420
aacgccacca acguggugau caaggugugc gaguuccagu ucugcaacga ccccuuccug     480
ggcguguacu accacaagaa caacaagagc uggauggaga gcgaguuccg gguguacagc     540
agcgccaaca acugcaccuu cgaguacgug agccagcccu uccugaugga ccuggagggc     600
aagcagggca acuucaagaa ccugcgggag uucguguuca agaacaucga cggcuacuuc     660
aagaucuaca gcaagcacac cccaaucaac cuggugcggg aucugcccca gggcuucuca     720
gcccuggagc cccuggugga ccugcccauc ggcaucaaca ucacccgguu ccagacccug     780
cuggcccugc accggagcua ccugacccca ggcgacagca gcagcgggug gacagcaggc     840
gcggcugcuu acuacguggg cuaccugcag ccccggaccu uccugcugaa guacaacgag     900
aacggcacca ucaccgacgc cguggacugc gcccuggacc cucugagcga gaccaagugc     960
acccugaaga gcuucaccgg aggcggaucg ggaggcggac ccaacaucac caaccugugc    1020
cccuucggcg agguguucaa cgccacccgg uucgccagcg uguacgccug gaaccggaag    1080
cggaucagca acugcguggc cgacuacagc gugcuguaca acagcgccag cuucagcacc    1140
uucaagugcu acggcgugag ccccaccaag cugaacgacc ugugcuucac caacguguac    1200
gccgacagcu ucgugauccg uggcgacgag gugcggcaga ucgcacccgg ccagacaggc    1260
aagaucgccg acuacaacua caagcugccc gacgacuuca ccggcugcgu gaucgccugg    1320
aacagcaaca accucgacag caaggugggc ggcaacuaca acuaccugua ccggcuguuc    1380
cggaagagca accugaagcc cuucgagcgg gacaucagca ccgagaucua ccaagccggc    1440
uccacccuu gcaacggcgu ggagggcuuc aacugcuacu ucccucugca gagcuacggc    1500
uuccagccca ccaacggcgu gggcuaccag ccccuaccggg ugguggugcu gagcuucgag    1560
cugcugcacg ccccagccac cgugugugggc cccaagucug gcggaggcag cauccuggcc    1620
aucuacagca ccguggccag cagccuggug cugcugguga gccugggcgc caucagcuuc    1680
ugauaauagg cuggagccuc gguggccuag cuucuugccc cuugggccuc cccccagccc    1740
cuccuccccu uccugcaccc guacccccgu ggucuuugaa uaaagucuga gugggcggc     1799
```

<210> SEQ ID NO 118
<211> LENGTH: 1623
<212> TYPE: RNA
<213> ORGANISM: Artificial Sequence
<220> FEATURE:
<223> OTHER INFORMATION: Synthetic

<400> SEQUENCE: 118

```
auguucgugu uccuggugcu gcugccccug gugagcagcc agugcgugaa ccugaccacc      60
cggacccagc ugccaccagc cuacaccaac agcuucaccc ggggcgucua cuaccccgac     120
aagguguucc ggagcagcgu ccugcacagc acccaggacc uguuccugcc cuucuucagc     180
```

```
aacgugaccu gguuccacgc cauccacgug agcggcacca acggcaccaa gcgguucgac    240

aaccccgugc ugcccuucaa cgacggcgug uacuucgcca gcaccgagaa gagcaacauc    300

auccggggcu ggaucuucgg caccacccug gacagcaaga cccagagccu gcugaucgug    360

aauaacgcca ccaacguggu gaucaaggug ugcgaguucc aguucugcaa cgaccccuuc    420

cugggcgugu acuaccacaa gaacaacaag agcuggaugg agagcgaguu ccggguguac    480

agcagcgcca acaacugcac cuucgaguac gugagccagc ccuuccugau ggaccuggag    540

ggcaagcagg gcaacuucaa gaaccugcgg gaguucgugu ucaagaacau cgacggcuac    600

uucaagaucu acagcaagca caccccaauc aaccuggugc gggaucugcc ccagggcuuc    660

ucagcccugg agccccuggu ggaccugccc aucggcauca acaucacccg guuccagacc    720

cugcuggccc ugcaccggag cuaccugacc ccaggcgaca gcagcagcgg guggacagca    780

ggcgcggcug cuuacuacgu gggcuaccug cagccccgga ccuuccugcu gaaguacaac    840

gagaacggca ccaucaccga cgccguggac ugcgcccugg acccucugag cgagaccaag    900

ugcacccuga agagcuucac cggaggcgga ucgggaggcg gacccaacau caccaaccug    960

ugccccuucg gcgagguguu caacgccacc cgguucgcca gcguguacgc cuggaaccgg   1020

aagcggauca gcaacugcgu ggccgacuac agcgugcugu acaacagcgc cagcuucagc   1080

accuucaagu gcuacggcgu gagccccacc aagcugaacg accugugcuu caccaacgug   1140

uacgccgaca gcuucgugau ccguggcgac gaggugcggc agaucgcacc cggccagaca   1200

ggcaagaucg ccgacuacaa cuacaagcug cccgacgacu ucaccggcug cgugaucgcc   1260

uggaacagca acaaccucga cagcaaggug ggcggcaacu acaacuaccu guaccggcug   1320

uuccggaaga gcaaccugaa gcccuucgag cgggacauca gcaccgagau cuaccaagcc   1380

ggcuccaccc cuugcaacgg cguggagggc uucaacugcu acuucccucu gcagagcuac   1440

ggcuuccagc ccaccaacgg cgugggcuac cagcccuacc gggugguggu gcugagcuuc   1500

gagcugcugc acgccccagc caccgugugu ggccccaagu cuggcggagg cagcauccug   1560

gccaucuaca gcaccguggc cagcagccug gugcugcugg ugagccuggg cgccaucagc   1620

uuc                                                                 1623
```

<210> SEQ ID NO 119
<211> LENGTH: 541
<212> TYPE: PRT
<213> ORGANISM: Artificial Sequence
<220> FEATURE:
<223> OTHER INFORMATION: Synthetic

<400> SEQUENCE: 119

```
Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95
```

-continued

```
Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Gly Gly Gly Ser Gly Gly Gly Pro Asn Ile Thr Asn Leu
305                 310                 315                 320

Cys Pro Phe Gly Glu Val Phe Asn Ala Thr Arg Phe Ala Ser Val Tyr
                325                 330                 335

Ala Trp Asn Arg Lys Arg Ile Ser Asn Cys Val Ala Asp Tyr Ser Val
            340                 345                 350

Leu Tyr Asn Ser Ala Ser Phe Ser Thr Phe Lys Cys Tyr Gly Val Ser
        355                 360                 365

Pro Thr Lys Leu Asn Asp Leu Cys Phe Thr Asn Val Tyr Ala Asp Ser
    370                 375                 380

Phe Val Ile Arg Gly Asp Glu Val Arg Gln Ile Ala Pro Gly Gln Thr
385                 390                 395                 400

Gly Lys Ile Ala Asp Tyr Asn Tyr Lys Leu Pro Asp Asp Phe Thr Gly
                405                 410                 415

Cys Val Ile Ala Trp Asn Ser Asn Asn Leu Asp Ser Lys Val Gly Gly
            420                 425                 430

Asn Tyr Asn Tyr Leu Tyr Arg Leu Phe Arg Lys Ser Asn Leu Lys Pro
        435                 440                 445

Phe Glu Arg Asp Ile Ser Thr Glu Ile Tyr Gln Ala Gly Ser Thr Pro
    450                 455                 460

Cys Asn Gly Val Glu Gly Phe Asn Cys Tyr Phe Pro Leu Gln Ser Tyr
465                 470                 475                 480

Gly Phe Gln Pro Thr Asn Gly Val Gly Tyr Gln Pro Tyr Arg Val Val
                485                 490                 495

Val Leu Ser Phe Glu Leu Leu His Ala Pro Ala Thr Val Cys Gly Pro
            500                 505                 510

Lys Ser Gly Gly Gly Ser Ile Leu Ala Ile Tyr Ser Thr Val Ala Ser
```

```
        515                 520                 525

Ser Leu Val Leu Leu Val Ser Leu Gly Ala Ile Ser Phe
    530                 535                 540
```

<210> SEQ ID NO 120
<211> LENGTH: 2024
<212> TYPE: RNA
<213> ORGANISM: Artificial Sequence
<220> FEATURE:
<223> OTHER INFORMATION: Synthetic

<400> SEQUENCE: 120

```
gggaaauaag agagaaaaga agaguaagaa gaaauauaag accccggcgc cgccaccaug     60

uucguguucc uggugcugcu gccccuggug agcagccagu gcgugaaccu gaccacccgg    120

acccagcugc caccagccua caccaacagc uucacccggg gcgucuacua ccccgacaag    180

guguuccgga gcagcguccu gcacagcacc caggaccugu uccugcccuu cuucagcaac    240

gugaccuggu uccacgccau ccacgugagc ggcaccaacg gcaccaagcg guucgacaac    300

cccgugcugc ccuucaacga cggcguguac uucgccagca ccgagaagag caacaucauc    360

cggggcugga ucuucggcac cacccuggac agcaagaccc agagccugcu gaucgugaau    420

aacgccacca acgugguguau caaggugugc gaguuccagu ucugcaacga ccccuuccug    480

ggcguguacu accacaagaa caacaagagc uggauggaga gcgaguuccg gguguacagc    540

agcgccaaca acugcaccuu cgaguacgug agccagcccu uccugaugga ccuggagggc    600

aagcagggca acuucaagaa ccugcgggag uucguguuca agaacaucga cggcuacuuc    660

aagaucuaca gcaagcacac cccaaucaac cuggugcggg aucugcccca gggcuucuca    720

gcccuggagc cccuggugga ccugcccauc ggcaucaaca ucacccgguu ccagacccug    780

cuggcccugc accggagcua ccugacccca ggcgacagca gcagcgggug gacagcaggc    840

gcggcugcuu acuacguggg cuaccugcag ccccggaccu uccugcugaa guacaacgag    900

aacggcacca ucaccgacgc cguggacugc gcccuggacc cucugagcga gaccaagugc    960

acccugaaga gcuucaccgg aggcggaucg ggaggcggac agcgggugca gcccaccgag   1020

agcaucgugc gguuccccaa caucaccaac cugugcccu ucggcgaggu guucaacgcc   1080

acccgguucg ccagcgugua cgccuggaac cggaagcgga ucagcaacug cguggccgac   1140

uacagcgugc uguacaacag cgccagcuuc agcaccuuca agugcuacgg cgugagcccc   1200

accaagcuga acgaccugug cuucaccaac guguacgccg acagcuucgu gauccguggc   1260

gacgaggugc ggcagaucgc acccggccag acaggcaaga ucgccgacua caacuacaag   1320

cugcccgacg acuucaccgg cugcgugauc gccuggaaca gcaacaaccu cgacagcaag   1380

gugggcggca acuacaacua ccuguaccgg cuguuccgga agagcaaccu gaagcccuuc   1440

gagcgggaca ucagcaccga gaucuaccaa gccggcucca ccccuugcaa cggcguggag   1500

ggcuucaacu gcuacuuccc ucugcagagc uacggcuucc agcccaccaa cggcgugggc   1560

uaccagcccu accggguggu ggugcugagc uucgagcugc ugcacgcccc agccaccgug   1620

uguggcccca agaagagcac caaccuggug aagaacaagu gcgugaacuu caacuucaac   1680

ggccuuaccg gcaccggcgu gcugaccgag agcaacaaga aauuccugcc cuuucagcag   1740

uucggccggg acaucgccga caccaccgac gcugugcggg auccccagac ccuggagauc   1800

cuggacauca ccccuugcag cucuggcgga ggcagcaucc uggccaucua cagcaccgug   1860

gccagcagcc uggugcugcu ggugagccug ggcgccauca gcuucugaua auaggcugga   1920
```

gccucggugg ccuagcuucu ugccccuugg gccuccccc agccccuccu ccccuuccug 1980
cacccguacc cccguggucu uugaauaaag ucugaguggg cggc 2024

<210> SEQ ID NO 121
<211> LENGTH: 1848
<212> TYPE: RNA
<213> ORGANISM: Artificial Sequence
<220> FEATURE:
<223> OTHER INFORMATION: Synthetic

<400> SEQUENCE: 121
auguucgugu uccuggugcu gcugccccug gugagcagcc agugcgugaa ccugaccacc 60
cggacccagc ugccaccagc cuacaccaac agcuucaccc ggggcgucua cuaccccgac 120
aagguguucc ggagcagcgu ccugcacagc acccaggacc uguuccugcc cuucuucagc 180
aacgugaccu gguuccacgc cauccacgug agcggcacca acggcaccaa gcgguucgac 240
aaccccgugc ugcccuucaa cgacggcgug uacuucgcca gcaccgagaa gagcaacauc 300
auccggggcu ggaucuucgg caccacccug gacagcaaga cccagagccu gcugaucgug 360
aauaacgcca ccaacguggu gaucaaggug ugcgaguucc aguucugcaa cgaccccuuc 420
cugggcgugu acuaccacaa gaacaacaag agcuggaugg agagcgaguu ccggguguac 480
agcagcgcca acaacugcac cuucgaguac gugagccagc ccuuccugau ggaccuggag 540
ggcaagcagg gcaacuucaa gaaccugcgg gaguucgugu ucaagaacau cgacggcuac 600
uucaagaucu acagcaagca caccccaauc aaccuggugc gggaucugcc ccagggcuuc 660
ucagcccugg agccccuggu ggaccugccc aucggcauca acaucacccg guuccagacc 720
cugcuggccc ugcaccggag cuaccugacc ccaggcgaca gcagcagcgg gugggacagca 780 ggcgcggcug cuuacuacgu gggcuaccug cagccccgga ccuuccugcu gaaguacaac 840
gagaacggca ccaucaccga cgccguggac ugcgcccugg acccucugag cgagaccaag 900
ugcacccuga agagcuucac cggaggcgga ucgggaggcg gacagcgggu gcagcccacc 960
gagagcaucg ugcgguuccc caacaucacc aaccugugcc ccuucggcga gguguucaac 1020
gccacccggu ucgccagcgu guacgccugg aaccggaagc ggaucagcaa cugcguggcc 1080
gacuacagcg ugcuguacaa cagcgccagc uucagcaccu ucaagugcua cggcgugagc 1140
cccaccaagc ugaacgaccu gugcuucacc aacguguacg ccgacagcuu cgugauccgu 1200
ggcgacgagg ugcggcagau cgcacccggc cagacaggca agaucgccga cuacaacuac 1260
aagcugcccg acgacuucac cggcugcgug aucgccugga acagcaacaa ccucgacagc 1320
aaggugggcg gcaacuacaa cuaccuguac cggcuguucc ggaagagcaa ccugaagccc 1380
uucgagcggg acaucagcac cgagaucuac caagccggcu ccaccccuug caacggcgug 1440
gagggcuuca acugcuacuu cccucugcag agcuacggcu uccagcccac caacggcgug 1500
ggcuaccagc ccuaccgggu gguggugcug agcuucgagc ugcugcacgc cccagccacc 1560 gugugu ggcc ccaagaagag caccaaccug gugaagaaca agugcgugaa cuucaacuuc 1620
aacggccuua ccggcaccgg cgugcugacc gagagcaaca agaaauuccu gcccuuucag 1680
caguucggcc gggacaucgc cgacaccacc gacgcugugc gggaucccca gacccuggag 1740
auccuggaca ucaccccuug cagcucuggc ggaggcagca uccuggccau cuacagcacc 1800
guggccagca gccuggugcu gcuggugagc cugggcgcca ucagcuuc 1848

<210> SEQ ID NO 122
<211> LENGTH: 616

<212> TYPE: PRT
<213> ORGANISM: Artificial Sequence
<220> FEATURE:
<223> OTHER INFORMATION: Synthetic

<400> SEQUENCE: 122

```
Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Gly Gly Gly Ser Gly Gly Gly Gln Arg Val Gln Pro Thr
305                 310                 315                 320

Glu Ser Ile Val Arg Phe Pro Asn Ile Thr Asn Leu Cys Pro Phe Gly
                325                 330                 335

Glu Val Phe Asn Ala Thr Arg Phe Ala Ser Val Tyr Ala Trp Asn Arg
            340                 345                 350

Lys Arg Ile Ser Asn Cys Val Ala Asp Tyr Ser Val Leu Tyr Asn Ser
        355                 360                 365

Ala Ser Phe Ser Thr Phe Lys Cys Tyr Gly Val Ser Pro Thr Lys Leu
    370                 375                 380
```

```
Asn Asp Leu Cys Phe Thr Asn Val Tyr Ala Asp Ser Phe Val Ile Arg
385                 390                 395                 400

Gly Asp Glu Val Arg Gln Ile Ala Pro Gly Gln Thr Gly Lys Ile Ala
                405                 410                 415

Asp Tyr Asn Tyr Lys Leu Pro Asp Asp Phe Thr Gly Cys Val Ile Ala
            420                 425                 430

Trp Asn Ser Asn Asn Leu Asp Ser Lys Val Gly Gly Asn Tyr Asn Tyr
        435                 440                 445

Leu Tyr Arg Leu Phe Arg Lys Ser Asn Leu Lys Pro Phe Glu Arg Asp
    450                 455                 460

Ile Ser Thr Glu Ile Tyr Gln Ala Gly Ser Thr Pro Cys Asn Gly Val
465                 470                 475                 480

Glu Gly Phe Asn Cys Tyr Phe Pro Leu Gln Ser Tyr Gly Phe Gln Pro
                485                 490                 495

Thr Asn Gly Val Gly Tyr Gln Pro Tyr Arg Val Val Val Leu Ser Phe
            500                 505                 510

Glu Leu Leu His Ala Pro Ala Thr Val Cys Gly Pro Lys Lys Ser Thr
        515                 520                 525

Asn Leu Val Lys Asn Lys Cys Val Asn Phe Asn Phe Asn Gly Leu Thr
    530                 535                 540

Gly Thr Gly Val Leu Thr Glu Ser Asn Lys Lys Phe Leu Pro Phe Gln
545                 550                 555                 560

Gln Phe Gly Arg Asp Ile Ala Asp Thr Thr Asp Ala Val Arg Asp Pro
                565                 570                 575

Gln Thr Leu Glu Ile Leu Asp Ile Thr Pro Cys Ser Ser Gly Gly Gly
            580                 585                 590

Ser Ile Leu Ala Ile Tyr Ser Thr Val Ala Ser Ser Leu Val Leu Leu
        595                 600                 605

Val Ser Leu Gly Ala Ile Ser Phe
    610                 615
```

<210> SEQ ID NO 123
<211> LENGTH: 3995
<212> TYPE: RNA
<213> ORGANISM: Artificial Sequence
<220> FEATURE:
<223> OTHER INFORMATION: Synthetic

<400> SEQUENCE: 123

```
gggaaauaag agagaaaaga agaguaagaa gaaauauaag accccggcgc cgccaccaug     60

uucguguucc uggugcugcu gccccuggug agcagccagu gcgugaaccu gaccacccgg    120

acccagcugc caccagccua caccaacagc uucacccggg gcgucuacua ccccgacaag    180

guguuccgga gcagcguccu gcacagcacc caggaccugu uccugcccuu cuucagcaac    240

gugaccuggu uccacgccau ccacgugagc ggcaccaacg gcaccaagcg guucgacaac    300

cccgugcugc ccuucaacga cggcguguac uucgccagca ccgagaagag caacaucauc    360

cggggcugga ucuucggcac cacccuggac agcaagaccc agagccugcu gaucgugaau    420

aacgccacca acguggugau caaggugugc gaguuccagu ucugcaacga ccccuuccug    480

ggcguguacu accacaagaa caacaagagc uggauggaga gcgaguuccg gguguacagc    540

agcgccaaca acugcaccuu cgaguacgug agccagcccu uccugaugga ccuggagggc    600

aagcagggca acuucaagaa ccugcgggag uucguguuca agaacaucga cggcuacuuc    660

aagaucuaca gcaagcacac cccaaucaac cuggugcggg aucugcccca gggcuucuca    720
```

-continued

```
gcccuggagc cccuggugga ccugcccauc ggcaucaaca ucacccgguu ccagacccug    780
cuggcccugc accggagcua ccugacccca ggcgacagca gcagcgggug gacagcaggc    840
gcggcugcuu acuacguggg cuaccugcag ccccggaccu uccugcugaa guacaacgag    900
aacggcacca ucaccgacgc cguggacugc gcccuggacc cucugagcga gaccaagugc    960
acccugaaga gcuucaccgu ggagaagggc aucuaccaga ccagcaacuu ccgggugcag   1020
cccaccgaga gcaucgugcg guuccccaac aucaccaacc ugugccccuu cggcgaggug   1080
uucaacgcca cccgguucgc cagcguguac gccuggaacc ggaagcggau cagcaacugc   1140
guggccgacu acagcgugcu guacaacagc gccagcuuca gcaccuucaa gugcuacggc   1200
gugagcccca ccaagcugaa cgaccugugc uucaccaacg uguacgccga cagcuucgug   1260
auccguggcg acgaggugcg gcagaucgca cccggccaga caggcaagau cgccgacuac   1320
aacuacaagc ugcccgacga cuucaccggc ugcgugaucg ccuggaacag caacaaccuc   1380
gacagcaagg uggcggcaa cuacaacuac cuguaccggc uguuccggaa gagcaaccug    1440
aagcccuucg agcgggacau cagcaccgag aucuaccaag ccggcuccac cccuugcaac   1500
ggcguggagg gcuucaacug cuacuucccu cugcagagcu acggcuucca gcccaccaac   1560
ggcgugggcu accagcccua ccggguggug gugcugagcu ucgagcugcu gcacgcccca   1620
gccaccgugu guggccccaa gaagagcacc aaccugguga agaacaagug cgugaacuuc   1680
aacuucaacg gccuuaccgg caccggcgug cugaccgaga gcaacaagaa auuccugccc   1740
uuucagcagu ucggccggga caucgccgac accaccgacg cugugcggga uccccagacc   1800
cuggagaucc uggacaucac cccuugcagc uucggcggcg ugagcgugau caccccaggc   1860
accaacacca gcaaccaggu ggccgugcug uaccaggacg ugaacugcac cgaggugccc   1920
guggccaucc acgccgacca gcugacaccc accuggcggg ucuacagcac cggcagcaac   1980
guguuccaga cccgggccgg uugccugauc ggcgccgagc acgugaacaa cagcuacgag   2040
ugcgacaucc ccaucggcgc cggcaucugu gccagcuacc agacccagac caauucaccc   2100
cggagggcaa ggagcguggc cagccagagc aucaucgccu acaccaugag ccugggcgcc   2160
gagaacagcg uggccuacag caacaacagc aucgccaucc ccaccaacuu caccaucagc   2220
gugaccaccg agauucugcc cgugagcaug accaagacca gcguggacug caccauguac   2280
aucugcggcg acagcaccga gugcagcaac cugcugcugc aguacggcag cuucugcacc   2340
cagcugaacc gggcccugac cggcaucgcc guggagcagg acaagaacac ccaggaggug   2400
uucgcccagg ugaagcagau cuacaagacc ccucccauca aggacuucgg cggcuucaac   2460
uucagccaga uccugcccga ccccagcaag cccagcaagc ggagcuucau cgaggaccug   2520
cuguucaaca aggugacccu agccgacgcc ggcuucauca agcaguacgg cgacugccuc   2580
ggcgacauag ccgcccggga ccugaucugc gcccagaagu ucaacggccu gaccgugcug   2640
ccuccccugc ugaccgacga gaugaucgcc caguacacca gcgcccuguu agccggaacc   2700
aucaccagcg gcuggacuuu cggcgcugga gccgcucugc agauccccuu cgccaugcag   2760
auggccuacc gguucaacgg caucggcgug acccagaacg ugcuguacga gaaccagaag   2820
cugaucgcca accaguucaa cagcgccauc ggcaagaucc aggacagccu gagcagcacc   2880
gcuagcgccc ugggcaagcu gcaggacgug gugaaccaga acgcccaggc ccugaacacc   2940
cuggugaagc agcugagcag caacuucggc gccaucagca gcgugcugaa cgacauccug   3000
agccggcugg acaaggugga ggccgaggug cagaucgacc ggcugaucac uggccggcug   3060
cagagccugc agaccuacgu gacccagcag cugauccggg ccgccgagau ucgggccagc   3120
```

gccaaccugg ccgccaccaa gaugagcgag ugcgugcugg gccagagcaa gcggguggac 3180
uucugcggca agggcuacca ccugaugagc uuuccccaga gcgcaccccca cggaguggug 3240 uuccugcacg ugaccuacgu gcccgcccag gagaagaacu ucaccaccgc cccagccauc 3300
ugccacgacg gcaaggccca cuuuccccgg gagggcgugu ucgugagcaa cggcacccac 3360
ugguucguga cccagcggaa cuucuacgag ccccagauca ucaccaccga caacaccuuc 3420
gugagcggca acugcgacgu ggugaucggc aucgugaaca acaccgugua cgauccccug 3480
cagcccgagc uggacagcuu caaggaggag cuggacaagu acuucaagaa ucacaccagc 3540
cccgacgugg accugggcga caucagcggc aucaacgcca gcguggugaa cauccagaag 3600
gagaucgauc ggcugaacga gguggccaag aaccugaacg agagccugau cgaccugcag 3660
gagcugggca aguacgagca guacaucaag uggcccuggu acaucuggcu gggcuucauc 3720
gccggccuga ucgccaucgu gauggugacc aucaugcugu gcugcaugac cagcugcugc 3780
agcugccuga agggcuguug cagcugcggc agcugcugca aguucgacga ggacgacagc 3840
gagcccgugc ugaagggcgu gaagcugcac uacaccugau aauaggcugg agccucggug 3900
gccuagcuuc uugccccuug ggccuccccc cagccccucc uccccuuccu gcacccguac 3960
ccccgugguc uuugaauaaa gucugagugg gcggc 3995

<210> SEQ ID NO 124
<211> LENGTH: 3819
<212> TYPE: RNA
<213> ORGANISM: Artificial Sequence
<220> FEATURE:
<223> OTHER INFORMATION: Synthetic

<400> SEQUENCE: 124
auguucgugu uccuggugcu gcugccccug gugagcagcc agugcgugaa ccugaccacc 60
cggacccagc ugccaccagc cuacaccaac agcuucaccc ggggcgucua cuaccccgac 120
aagguguucc ggagcagcgu ccugcacagc acccaggacc uguuccugcc cuucuucagc 180
aacgugaccu gguuccacgc cauccacgug agcggcacca acggcaccaa gcgguucgac 240
aaccccgugc ugcccuucaa cgacggcgug uacuucgcca gcaccgagaa gagcaacauc 300
auccggggcu ggaucuucgg caccacccug gacagcaaga cccagagccu gcugaucgug 360
aauaacgcca ccaacguggu gaucaaggug ugcgaguucc aguucugcaa cgaccccuuc 420
cugggcgugu acuaccacaa gaacaacaag agcuggaugg agagcgaguu ccggguguac 480
agcagcgcca acaacugcac cuucgaguac gugagccagc ccuuccugau ggaccuggag 540
ggcaagcagg gcaacuucaa gaaccugcgg gaguucgugu ucaagaacau cgacggcuac 600
uucaagaucu acagcaagca caccccaauc aaccuggugc gggaucugcc ccagggcuuc 660
ucagcccugg agccccuggu ggaccugccc aucggcauca acaucacccg guuccagacc 720
cugcuggccc ugcaccggag cuaccugacc ccaggcgaca gcagcagcgg guggacagca 780
ggcgcggcug cuuacuacgu gggcuaccug cagccccgga ccuuccugcu gaaguacaac 840
gagaacggca ccaucaccga cgccguggac ugcgcccugg acccucugag cgagaccaag 900
ugcacccuga agagcuucac cguggagaag ggcaucuacc agaccagcaa cuuccgggug 960
cagcccaccg agagcaucgu gcgguucccc aacaucacca accugugccc cuucggcgag 1020
guguucaacg ccacccgguu cgccagcgug uacgccugga accggaagcg gaucagcaac 1080
ugcguggccg acuacagcgu gcuguacaac agcgccagcu ucagcaccuu caagugcuac 1140

-continued

```
ggcgugagcc ccaccaagcu gaacgaccug ugcuucacca acguguacgc cgacagcuuc   1200
gugauccgug gcgacgaggu gcggcagauc gcacccggcc agacaggcaa gaucgccgac   1260
uacaacuaca agcugcccga cgacuucacc ggcugcguga ucgccuggaa cagcaacaac   1320
cucgacagca aggugggcgg caacuacaac uaccuguacc ggcuguuccg gaagagcaac   1380
cugaagcccu ucgagcggga caucagcacc gagaucuacc aagccggcuc caccccuugc   1440
aacggcgugg agggcuucaa cugcuacuuc ccucugcaga gcuacggcuu ccagcccacc   1500
aacggcgugg gcuaccagcc cuaccgggug guggugcuga gcuucgagcu gcugcacgcc   1560
ccagccaccg uguguggccc caagaagagc accaaccugg ugaagaacaa gugcgugaac   1620
uucaacuuca acggccuuac cggcaccggc gugcugaccg agagcaacaa gaaauuccug   1680
cccuuucagc aguucggccg ggacaucgcc gacaccaccg acgcugugcg ggaucccccag   1740
acccuggaga uccuggacau caccccuugc agcuucggcg gcgugagcgu gaucacccca   1800
ggcaccaaca ccagcaacca gguggccgug cuguaccagg acgugaacug caccgaggug   1860
cccguggcca uccacgccga ccagcugaca cccaccuggc gggucuacag caccggcagc   1920
aacguguucc agacccgggc cgguugccug aucggcgccg agcacgugaa caacagcuac   1980
gagugcgaca uccccaucgg cgccggcauc ugugccagcu accagaccca gaccaauuca   2040
ccccggaggg caaggagcgu ggccagccag agcaucaucg ccuacaccau gagccugggc   2100
gccgagaaca gcguggccua cagcaacaac agcaucgcca uccccaccaa cuucaccauc   2160
agcgugacca ccgagauucu gcccgugagc augaccaaga ccagcgugga cugcaccaug   2220
uacaucugcg gcgacagcac cgagugcagc aaccugcugc ugcaguacgg cagcuucugc   2280
acccagcuga accgggcccu gaccggcauc gccguggagc aggacaagaa cacccaggag   2340
guguucgccc aggugaagca gaucuacaag accccuccca ucaaggacuu cggcggcuuc   2400
aacuucagcc agauccugcc cgaccccagc aagcccagca agcggagcuu caucgaggac   2460
cugcuguuca acaaggugac ccuagccgac gccggcuuca ucaagcagua cggcgacugc   2520
cucggcgaca uagccgcccg ggaccugauc ugcgcccaga aguucaacgg ccugaccgug   2580
cugccucccc ugcugaccga cgagaugauc gcccaguaca ccagcgcccu guuagccgga   2640
accaucacca gcggcuggac uuucggcgcu ggagccgcuc ugcagauccc cuucgccaug   2700
cagauggccu accgguucaa cggcaucggc gugacccaga acgugcugua cgagaaccag   2760
aagcugaucg ccaaccaguu caacagcgcc aucggcaaga uccaggacag ccugagcagc   2820
accgcuagcg cccugggcaa gcugcaggac gugguugaacc agaacgccca ggcccugaac   2880
acccugguga agcagcugag cagcaacuuc ggcgccauca gcagcgugcu gaacgacauc   2940
cugagccggc uggacaaggu ggaggccgag gugcagaucg accggcugau cacuggccgg   3000
cugcagagcc ugcagaccua cgugacccag cagcugaucc gggccgccga gauucgggcc   3060
agcgccaacc uggccgccac caagaugagc gagugcgugc ugggccagag caagcgggug   3120
gacuucugcg gcaagggcua ccaccugaug agcuuucccc agagcgcacc ccacggagug   3180
guguuccugc acgugaccua cgugcccgcc caggagaaga acuucaccac cgccccagcc   3240
aucugccacg acggcaaggc ccacuuuccc cgggagggcg uguucgugag caacggcacc   3300
cacugguucg ugacccagcg gaacuucuac gagccccaga ucaucaccac cgacaacacc   3360
uucgugagcg gcaacugcga cgugguggauc ggcaucguga acaacaccgu guacgauccc   3420
cugcagcccg agcuggacag cuucaaggag gagcuggaca aguacuucaa gaaucacacc   3480
agccccgacg uggaccuggg cgacaucagc ggcaucaacg ccagcguggu gaacauccag   3540
```

```
aaggagaucg aucggcugaa cgagguggcc aagaaccuga acgagagccu gaucgaccug   3600

caggagcugg gcaaguacga gcaguacauc aaguggcccu gguacaucug gcugggcuuc   3660

aucgccggcc ugaucgccau cgugauggug accaucaugc ugugcugcau gaccagcugc   3720

ugcagcugcc ugaagggcug uugcagcugc ggcagcugcu gcaaguucga cgaggacgac   3780

agcgagcccg ugcugaaggg cgugaagcug cacuacacc                          3819


<210> SEQ ID NO 125
<211> LENGTH: 1273
<212> TYPE: PRT
<213> ORGANISM: Artificial Sequence
<220> FEATURE:
<223> OTHER INFORMATION: Synthetic

<400> SEQUENCE: 125

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
```

```
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735
```

-continued

```
Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
            980                 985                 990

Ile Asp Arg Leu Ile Thr Gly Arg  Leu Gln Ser Leu Gln  Thr Tyr Val
        995                 1000                1005

Thr Gln  Gln Leu Ile Arg Ala  Ala Glu Ile Arg Ala  Ser Ala Asn
    1010                 1015                 1020

Leu Ala  Ala Thr Lys Met Ser  Glu Cys Val Leu Gly  Gln Ser Lys
    1025                 1030                 1035

Arg Val  Asp Phe Cys Gly Lys  Gly Tyr His Leu Met  Ser Phe Pro
    1040                 1045                 1050

Gln Ser  Ala Pro His Gly Val  Val Phe Leu His Val  Thr Tyr Val
    1055                 1060                 1065

Pro Ala  Gln Glu Lys Asn Phe  Thr Thr Ala Pro Ala  Ile Cys His
    1070                 1075                 1080

Asp Gly  Lys Ala His Phe Pro  Arg Glu Gly Val Phe  Val Ser Asn
    1085                 1090                 1095

Gly Thr  His Trp Phe Val Thr  Gln Arg Asn Phe Tyr  Glu Pro Gln
    1100                 1105                 1110

Ile Ile  Thr Thr Asp Asn Thr  Phe Val Ser Gly Asn  Cys Asp Val
    1115                 1120                 1125

Val Ile  Gly Ile Val Asn Asn  Thr Val Tyr Asp Pro  Leu Gln Pro
    1130                 1135                 1140
```

```
Glu Leu  Asp Ser Phe Lys Glu  Glu Leu Asp Lys Tyr  Phe Lys Asn
    1145                 1150                 1155

His Thr  Ser Pro Asp Val Asp  Leu Gly Asp Ile Ser  Gly Ile Asn
    1160                 1165                 1170

Ala Ser  Val Val Asn Ile Gln  Lys Glu Ile Asp Arg  Leu Asn Glu
    1175                 1180                 1185

Val Ala  Lys Asn Leu Asn Glu  Ser Leu Ile Asp Leu  Gln Glu Leu
    1190                 1195                 1200

Gly Lys  Tyr Glu Gln Tyr Ile  Lys Trp Pro Trp Tyr  Ile Trp Leu
    1205                 1210                 1215

Gly Phe  Ile Ala Gly Leu Ile  Ala Ile Val Met Val  Thr Ile Met
    1220                 1225                 1230

Leu Cys  Cys Met Thr Ser Cys  Cys Ser Cys Leu Lys  Gly Cys Cys
    1235                 1240                 1245

Ser Cys  Gly Ser Cys Cys Lys  Phe Asp Glu Asp Asp  Ser Glu Pro
    1250                 1255                 1260

Val Leu  Lys Gly Val Lys Leu  His Tyr Thr
    1265                 1270


<210> SEQ ID NO 126
<211> LENGTH: 8
<212> TYPE: PRT
<213> ORGANISM: Artificial Sequence
<220> FEATURE:
<223> OTHER INFORMATION: Synthetic

<400> SEQUENCE: 126

Lys Pro Ser Lys Arg Ser Phe Ile
1               5


<210> SEQ ID NO 127
<211> LENGTH: 13
<212> TYPE: PRT
<213> ORGANISM: Artificial Sequence
<220> FEATURE:
<223> OTHER INFORMATION: Synthetic

<400> SEQUENCE: 127

Thr Gln Thr Asn Ser Pro Arg Arg Ala Arg Ser Val Ala
1               5                   10


<210> SEQ ID NO 128
<211> LENGTH: 9
<212> TYPE: RNA
<213> ORGANISM: Artificial Sequence
<220> FEATURE:
<223> OTHER INFORMATION: Synthetic

<400> SEQUENCE: 128

ccrccaugg                                                               9


<210> SEQ ID NO 129
<211> LENGTH: 11
<212> TYPE: RNA
<213> ORGANISM: Artificial Sequence
<220> FEATURE:
<223> OTHER INFORMATION: Synthetic

<400> SEQUENCE: 129

gggauccuac c                                                           11


<210> SEQ ID NO 130
```

<211> LENGTH: 9
<212> TYPE: RNA
<213> ORGANISM: Artificial Sequence
<220> FEATURE:
<223> OTHER INFORMATION: Synthetic

<400> SEQUENCE: 130 uuauuuaww 9

<210> SEQ ID NO 131
<211> LENGTH: 47
<212> TYPE: RNA
<213> ORGANISM: Artificial Sequence
<220> FEATURE:
<223> OTHER INFORMATION: Synthetic

<400> SEQUENCE: 131
gggaaauaag agagaaaaga agaguaagaa gaaauauaag agccacc 47

<210> SEQ ID NO 132
<211> LENGTH: 119
<212> TYPE: RNA
<213> ORGANISM: Artificial Sequence
<220> FEATURE:
<223> OTHER INFORMATION: Synthetic

<400> SEQUENCE: 132
ugauaauagg cuggagccuc gguggccaug cuucuugccc cuugggccuc cccccagccc 60
cuccuccccu uccugcaccc guacccccgu ggucuuugaa uaaagucuga gugggcggc 119

<210> SEQ ID NO 133
<211> LENGTH: 15
<212> TYPE: PRT
<213> ORGANISM: Artificial Sequence
<220> FEATURE:
<223> OTHER INFORMATION: Synthetic

<400> SEQUENCE: 133

Gly Gly Ser Gly Gly Ser Gly Gly Ser Gly Gly Ser Gly Gly Gly
1 5 10 15

<210> SEQ ID NO 134
<211> LENGTH: 8
<212> TYPE: PRT
<213> ORGANISM: Artificial Sequence
<220> FEATURE:
<223> OTHER INFORMATION: Synthetic

<400> SEQUENCE: 134

Gly Gly Gly Ser Gly Gly Gly Ser
1 5

<210> SEQ ID NO 135
<211> LENGTH: 7
<212> TYPE: PRT
<213> ORGANISM: Artificial Sequence
<220> FEATURE:
<223> OTHER INFORMATION: Synthetic

<400> SEQUENCE: 135

Gly Gly Gly Ser Gly Gly Gly
1 5

<210> SEQ ID NO 136
<211> LENGTH: 4
<212> TYPE: PRT

<213> ORGANISM: Artificial Sequence
<220> FEATURE:
<223> OTHER INFORMATION: Synthetic

<400> SEQUENCE: 136

Gly Gly Gly Ser
1

<210> SEQ ID NO 137
<211> LENGTH: 4
<212> TYPE: PRT
<213> ORGANISM: Artificial Sequence
<220> FEATURE:
<223> OTHER INFORMATION: Synthetic

<400> SEQUENCE: 137

Ser Gly Gly Ser
1

<210> SEQ ID NO 138
<211> LENGTH: 5
<212> TYPE: PRT
<213> ORGANISM: Artificial Sequence
<220> FEATURE:
<223> OTHER INFORMATION: Synthetic

<400> SEQUENCE: 138

Ser Gly Gly Gly Ser
1 5

<210> SEQ ID NO 139
<211> LENGTH: 1602
<212> TYPE: RNA
<213> ORGANISM: Artificial Sequence
<220> FEATURE:
<223> OTHER INFORMATION: Synthetic

<400> SEQUENCE: 139
auguacagca ugcagcuggc uagcugcgug acccugaccc uggugcugcu ggugaacagc 60
cagcccaaca ucaccaaccu gugccccuuc ggcgaggugu ucaacgccac ccgguucgcc 120
agcguguacg ccuggaaccg gaagcggauc agcaacugcg uggccgacua cagcgugcug 180
uacaacagcg ccagcuucag caccuucaag ugcuacggcg ugagccccac caagcugaac 240
gaccugugcu ucaccaacgu guacgccgac agcuucguga uccguggcga cgaggugcgg 300
cagaucgcac ccggccagac aggcaagauc gccgacuaca acuacaagcu gcccgacgac 360
uucaccggcu gcgugaucgc cuggaacagc aacaaccucg acagcaaggu gggcggcaac 420
uacaacuacc uguaccggcu guuccggaag agcaaccuga agcccuucga gcgggacauc 480
agcaccgaga ucuaccaagc cggcuccacc ccuugcaacg gcguggaggg cuucaacugc 540
uacuucccuc ugcagagcua cggcuuccag cccaccaacg gcgugggcua ccagcccuac 600
cggguggugg ugcugagcuu cgagcugcug cacgccccag ccaccgugug uggccccaag 660
ucuggcggag gcagcggagg cggaagccag ugcgugaacc ugaccacccg gacccagcug 720
ccaccagccu acaccaacag cuucacccgg ggcgucuacu accccgacaa ggguguuccgg 780 agcagcgucc ugcacagcac ccaggaccug uuccugcccu ucuucagcaa cgugaccugg 840
uuccacgcca uccacgugag cggcaccaac ggcaccaagc gguucgacaa ccccgugcug 900
cccuucaacg acggcgugua cuucgccagc accgagaaga gcaacaucau ccggggcugg 960
aucuucggca ccacccugga cagcaagacc cagagccugc ugaucgugaa uaacgccacc 1020

```
aacgugguga ucaaggugug cgaguuccag uucugcaacg accccuuccu gggcguguac   1080

uaccacaaga acaacaagag cuggauggag agcgaguucc ggguguacag cagcgccaac   1140

aacugcaccu ucgaguacgu gagccagccc uuccugaugg accuggaggg caagcagggc   1200

aacuucaaga accugcggga guucguguuc aagaacaucg acggcuacuu caagaucuac   1260

agcaagcaca ccccaaucaa ccuggugcgg gaucugcccc agggcuucuc agcccuggag   1320

ccccuggugg accugcccau cggcaucaac aucacccggu uccagacccu gcuggcccug   1380

caccggagcu accugacccc aggcgacagc agcagcgggu ggacagcagg cgcggcugcu   1440

uacuacgugg gcuaccugca gccccggacc uuccugcuga aguacaacga gaacggcacc   1500

aucaccgacg ccguggacuc uggcggaggc agcauccugg ccaucuacag caccguggcc   1560

agcagccugg ugcugcuggu gagccugggc gccaucagcu uc                      1602
```

<210> SEQ ID NO 140
<211> LENGTH: 534
<212> TYPE: PRT
<213> ORGANISM: Artificial Sequence
<220> FEATURE:
<223> OTHER INFORMATION: Synthetic

<400> SEQUENCE: 140

```
Met Tyr Ser Met Gln Leu Ala Ser Cys Val Thr Leu Thr Leu Val Leu
1               5                   10                  15

Leu Val Asn Ser Gln Pro Asn Ile Thr Asn Leu Cys Pro Phe Gly Glu
            20                  25                  30

Val Phe Asn Ala Thr Arg Phe Ala Ser Val Tyr Ala Trp Asn Arg Lys
        35                  40                  45

Arg Ile Ser Asn Cys Val Ala Asp Tyr Ser Val Leu Tyr Asn Ser Ala
    50                  55                  60

Ser Phe Ser Thr Phe Lys Cys Tyr Gly Val Ser Pro Thr Lys Leu Asn
65                  70                  75                  80

Asp Leu Cys Phe Thr Asn Val Tyr Ala Asp Ser Phe Val Ile Arg Gly
                85                  90                  95

Asp Glu Val Arg Gln Ile Ala Pro Gly Gln Thr Gly Lys Ile Ala Asp
            100                 105                 110

Tyr Asn Tyr Lys Leu Pro Asp Asp Phe Thr Gly Cys Val Ile Ala Trp
        115                 120                 125

Asn Ser Asn Asn Leu Asp Ser Lys Val Gly Gly Asn Tyr Asn Tyr Leu
    130                 135                 140

Tyr Arg Leu Phe Arg Lys Ser Asn Leu Lys Pro Phe Glu Arg Asp Ile
145                 150                 155                 160

Ser Thr Glu Ile Tyr Gln Ala Gly Ser Thr Pro Cys Asn Gly Val Glu
                165                 170                 175

Gly Phe Asn Cys Tyr Phe Pro Leu Gln Ser Tyr Gly Phe Gln Pro Thr
            180                 185                 190

Asn Gly Val Gly Tyr Gln Pro Tyr Arg Val Val Val Leu Ser Phe Glu
        195                 200                 205

Leu Leu His Ala Pro Ala Thr Val Cys Gly Pro Lys Ser Gly Gly Gly
    210                 215                 220

Ser Gly Gly Gly Ser Gln Cys Val Asn Leu Thr Thr Arg Thr Gln Leu
225                 230                 235                 240

Pro Pro Ala Tyr Thr Asn Ser Phe Thr Arg Gly Val Tyr Tyr Pro Asp
                245                 250                 255

Lys Val Phe Arg Ser Ser Val Leu His Ser Thr Gln Asp Leu Phe Leu
```

```
            260                 265                 270

Pro Phe Phe Ser Asn Val Thr Trp Phe His Ala Ile His Val Ser Gly
        275                 280                 285

Thr Asn Gly Thr Lys Arg Phe Asp Asn Pro Val Leu Pro Phe Asn Asp
    290                 295                 300

Gly Val Tyr Phe Ala Ser Thr Glu Lys Ser Asn Ile Ile Arg Gly Trp
305                 310                 315                 320

Ile Phe Gly Thr Thr Leu Asp Ser Lys Thr Gln Ser Leu Leu Ile Val
                325                 330                 335

Asn Asn Ala Thr Asn Val Val Ile Lys Val Cys Glu Phe Gln Phe Cys
            340                 345                 350

Asn Asp Pro Phe Leu Gly Val Tyr Tyr His Lys Asn Asn Lys Ser Trp
        355                 360                 365

Met Glu Ser Glu Phe Arg Val Tyr Ser Ser Ala Asn Asn Cys Thr Phe
    370                 375                 380

Glu Tyr Val Ser Gln Pro Phe Leu Met Asp Leu Glu Gly Lys Gln Gly
385                 390                 395                 400

Asn Phe Lys Asn Leu Arg Glu Phe Val Phe Lys Asn Ile Asp Gly Tyr
                405                 410                 415

Phe Lys Ile Tyr Ser Lys His Thr Pro Ile Asn Leu Val Arg Asp Leu
            420                 425                 430

Pro Gln Gly Phe Ser Ala Leu Glu Pro Leu Val Asp Leu Pro Ile Gly
        435                 440                 445

Ile Asn Ile Thr Arg Phe Gln Thr Leu Leu Ala Leu His Arg Ser Tyr
    450                 455                 460

Leu Thr Pro Gly Asp Ser Ser Ser Gly Trp Thr Ala Gly Ala Ala Ala
465                 470                 475                 480

Tyr Tyr Val Gly Tyr Leu Gln Pro Arg Thr Phe Leu Leu Lys Tyr Asn
                485                 490                 495

Glu Asn Gly Thr Ile Thr Asp Ala Val Asp Ser Gly Gly Gly Ser Ile
            500                 505                 510

Leu Ala Ile Tyr Ser Thr Val Ala Ser Ser Leu Val Leu Leu Val Ser
        515                 520                 525

Leu Gly Ala Ile Ser Phe
    530


<210> SEQ ID NO 141
<211> LENGTH: 1778
<212> TYPE: RNA
<213> ORGANISM: Artificial Sequence
<220> FEATURE:
<223> OTHER INFORMATION: Synthetic

<400> SEQUENCE: 141

gggaaauaag agagaaaaga agaguaagaa gaaauauaag accccggcgc cgccaccaug      60

uacagcaugc agcuggcuag cugcgugacc cugacccugg ugcugcuggu gaacagccag     120

cccaacauca ccaaccugug ccccuucggc gagguguuca acgccacccg guucgccagc     180

guguacgccu ggaaccggaa gcggaucagc aacugcgugg ccgacuacag cgugcuguac     240

aacagcgcca gcuucagcac cuucaagugc uacggcguga gccccaccaa gcugaacgac     300

cugugcuuca ccaacgugua cgccgacagc uucgugaucc guggcgacga ggugcggcag     360

aucgcacccg gccagacagg caagaucgcc gacuacaacu acaagcugcc cgacgacuuc     420

accggcugcg ugaucgccug gaacagcaac aaccucgaca gcaagguggg cggcaacuac     480
```

aacuaccugu accggcuguu ccggaagagc aaccugaagc ccuucgagcg ggacaucagc 540
accgagaucu accaagccgg cuccaccccu ugcaacggcg uggagggcuu caacugcuac 600
uucccucugc agagcuacgg cuuccagccc accaacggcg ugggcuacca gcccuaccgg 660
gugguggugc ugagcuucga gcugcugcac gccccagcca ccgugugugg ccccaagucu 720
ggcggaggca gcggaggcgg aagccagugc gugaaccuga ccacccggac ccagcugcca 780
ccagccuaca ccaacagcuu cacccggggc gucuacuacc ccgacaaggu guuccggagc 840
agcguccugc acagcaccca ggaccuguuc cugcccuucu ucagcaacgu gaccugguuc 900
cacgccaucc acgugagcgg caccaacggc accaagcggu ucgacaaccc cgugcugccc 960
uucaacgacg gcguguacuu cgccagcacc gagaagagca acaucauccg ggcuggauc 1020 uucggcacca cccuggacag caagacccag agccugcuga ucgugaauaa cgccaccaac 1080
guggugauca aggugugcga guuccaguuc ugcaacgacc ccuuccuggg cguguacuac 1140
cacaagaaca acaagagcug gauggagagc gaguuccggg uguacagcag cgccaacaac 1200
ugcaccuucg aguacgugag ccagcccuuc cugauggacc uggagggcaa gcagggcaac 1260
uucaagaacc ugcgggaguu cguguucaag aacaucgacg gcuacuucaa gaucuacagc 1320
aagcacaccc caaucaaccu ggugcgggau cugccccagg gcuucucagc ccuggagccc 1380
cugguggacc ugcccaucgg caucaacauc acccgguucc agacccugcu ggcccugcac 1440
cggagcuacc ugaccccagg cgacagcagc agcgggugga cagcaggcgc ggcugcuuac 1500
uacgugggcu accugcagcc ccggaccuuc cugcugaagu acaacgagaa cggcaccauc 1560
accgacgccg uggacucugg cggaggcagc auccuggcca ucuacagcac cguggccagc 1620
agccuggugc ugcuggugag ccugggcgcc aucagcuucu gauaauaggc uggagccucg 1680
guggccuagc uucuugcccc uugggccucc ccccagcccc uccuccccuu ccugcacccg 1740
uacccccgug gucuuugaau aaagucugag ugggcggc 1778

<210> SEQ ID NO 142
<211> LENGTH: 1602
<212> TYPE: RNA
<213> ORGANISM: Artificial Sequence
<220> FEATURE:
<223> OTHER INFORMATION: Synthetic

<400> SEQUENCE: 142
auguucgugu uccuggugcu gcugccccug gugagcagcc agugcgugaa ccugaccacc 60
cggacccagc ugccaccagc cuacaccaac agcuucaccc ggggcgucua cuaccccgac 120
aagguguucc ggagcagcgu ccugcacagc acccaggacc uguuccugcc cuucuucagc 180
aacgugaccu gguuccacgc cauccacgug agcggcacca acggcaccaa gcgguucgac 240
aaccccgugc ugcccuucaa cgacggcgug uacuucgcca gcaccgagaa gagcaacauc 300
auccggggcu ggaucuucgg caccacccug gacagcaaga cccagagccu gcugaucgug 360
aauaacgcca ccaacguggu gaucaaggug ugcgaguucc aguucugcaa cgaccccuuc 420
cugggcgugu acuaccacaa gaacaacaag agcuggaugg agagcgaguu ccggguguac 480
agcagcgcca acaacugcac cuucgaguac gugagccagc ccuuccugau ggaccuggag 540
ggcaagcagg gcaacuucaa gaaccugcgg gaguucgugu ucaagaacau cgacggcuac 600
uucaagaucu acagcaagca caccccaauc aaccuggugc gggaucugcc ccagggcuuc 660
ucagcccugg agccccuggu ggaccugccc aucggcauca acaucacccg guuccagacc 720
cugcuggccc ugcaccggag cuaccugacc ccaggcgaca gcagcagcgg guggacagca 780

```
ggcgcggcug cuuacuacgu gggcuaccug cagccccgga ccuuccugcu gaaguacaac    840

gagaacggca ccaucaccga cgccguggac ggaggcgcca aguucguggc cgccuggacu    900

cugaaggccg cagccggcgg acccaacauc accaaccugu gccccuucgg cgagguguuc    960

aacgccaccc gguucgccag cguguacgcc uggaaccgga agcggaucag caacugcgug   1020

gccgacuaca gcgugcugua caacagcgcc agcuucagca ccuucaagug cuacggcgug   1080

agccccacca agcugaacga ccugugcuuc accaacgugu acgccgacag cuucgugauc   1140

cguggcgacg aggugcggca gaucgcaccc ggccagacag gcaagaucgc cgacuacaac   1200

uacaagcugc ccgacgacuu caccggcugc gugaucgccu ggaacagcaa caaccucgac   1260

agcaaggugg gcggcaacua caacuaccug uaccggcugu uccggaagag caaccugaag   1320

cccuucgagc gggacaucag caccgagauc uaccaagccg gcuccacccc uugcaacggc   1380

guggagggcu ucaacugcua cuucccucug cagagcuacg gcuuccagcc caccaacggc   1440

gugggcuacc agcccuaccg gguggugug cugagcuucg agcugcugca cgccccagcc   1500

accgugugug gccccaaguc uggcggaggc agcauccugg ccaucuacag caccguggcc   1560

agcagccugg ugcugcuggu gagccugggc gccaucagcu uc                      1602
```

```
<210> SEQ ID NO 143
<211> LENGTH: 534
<212> TYPE: PRT
<213> ORGANISM: Artificial Sequence
<220> FEATURE:
<223> OTHER INFORMATION: Synthetic

<400> SEQUENCE: 143

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
```

-continued

```
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Gly Gly Ala Lys Phe Val Ala Ala Trp Thr Leu Lys Ala Ala
    290                 295                 300

Ala Gly Gly Pro Asn Ile Thr Asn Leu Cys Pro Phe Gly Glu Val Phe
305                 310                 315                 320

Asn Ala Thr Arg Phe Ala Ser Val Tyr Ala Trp Asn Arg Lys Arg Ile
                325                 330                 335

Ser Asn Cys Val Ala Asp Tyr Ser Val Leu Tyr Asn Ser Ala Ser Phe
            340                 345                 350

Ser Thr Phe Lys Cys Tyr Gly Val Ser Pro Thr Lys Leu Asn Asp Leu
        355                 360                 365

Cys Phe Thr Asn Val Tyr Ala Asp Ser Phe Val Ile Arg Gly Asp Glu
    370                 375                 380

Val Arg Gln Ile Ala Pro Gly Gln Thr Gly Lys Ile Ala Asp Tyr Asn
385                 390                 395                 400

Tyr Lys Leu Pro Asp Asp Phe Thr Gly Cys Val Ile Ala Trp Asn Ser
                405                 410                 415

Asn Asn Leu Asp Ser Lys Val Gly Gly Asn Tyr Asn Tyr Leu Tyr Arg
            420                 425                 430

Leu Phe Arg Lys Ser Asn Leu Lys Pro Phe Glu Arg Asp Ile Ser Thr
        435                 440                 445

Glu Ile Tyr Gln Ala Gly Ser Thr Pro Cys Asn Gly Val Glu Gly Phe
    450                 455                 460

Asn Cys Tyr Phe Pro Leu Gln Ser Tyr Gly Phe Gln Pro Thr Asn Gly
465                 470                 475                 480

Val Gly Tyr Gln Pro Tyr Arg Val Val Val Leu Ser Phe Glu Leu Leu
                485                 490                 495

His Ala Pro Ala Thr Val Cys Gly Pro Lys Ser Gly Gly Gly Ser Ile
            500                 505                 510

Leu Ala Ile Tyr Ser Thr Val Ala Ser Ser Leu Val Leu Leu Val Ser
        515                 520                 525

Leu Gly Ala Ile Ser Phe
    530


<210> SEQ ID NO 144
<211> LENGTH: 1778
<212> TYPE: RNA
<213> ORGANISM: Artificial Sequence
<220> FEATURE:
<223> OTHER INFORMATION: Synthetic

<400> SEQUENCE: 144

gggaaauaag agagaaaaga agaguaagaa gaaauauaag accccggcgc cgccaccaug      60

uucguguucc uggugcugcu gccccuggug agcagccagu gcgugaaccu gaccacccgg     120

acccagcugc caccagccua caccaacagc uucacccggg gcgucuacua ccccgacaag     180

guguuccgga gcagcguccu gcacagcacc caggaccugu uccugcccuu cuucagcaac     240
```

gugaccuggu uccacgccau ccacgugagc ggcaccaacg gcaccaagcg guucgacaac 300
cccgugcugc ccuucaacga cggcguguac uucgccagca ccgagaagag caacaucauc 360
cggggcugga ucuucggcac cacccuggac agcaagaccc agagccugcu gaucgugaau 420
aacgccacca acguggugau caaggugugc gaguuccagu ucugcaacga ccccuuccug 480
ggcguguacu accacaagaa caacaagagc uggauggaga gcgaguuccg gguguacagc 540
agcgccaaca acugcaccuu cgaguacgug agccagcccu uccugaugga ccuggagggc 600
aagcagggca acuucaagaa ccugcgggag uucguguuca agaacaucga cggcuacuuc 660
aagaucuaca gcaagcacac cccaaucaac cuggugcggg aucugcccca gggcuucuca 720
gcccuggagc cccuggugga ccugcccauc ggcaucaaca ucacccgguu ccagacccug 780 cuggccccugc accggagcua ccugacccca ggcgacagca gcagcgggug gacagcaggc 840
gcggcugcuu acuacguggg cuaccugcag ccccggaccu uccugcugaa guacaacgag 900
aacggcacca ucaccgacgc cguggacgga ggcgccaagu ucguggccgc cuggacucug 960
aaggccgcag ccggcggacc caacaucacc aaccugugcc ccuucggcga gguguucaac 1020
gccacccggu ucgccagcgu guacgccugg aaccggaagc ggaucagcaa cugcguggcc 1080
gacuacagcg ugcuguacaa cagcgccagc uucagcaccu ucaagugcua cggcgugagc 1140
cccaccaagc ugaacgaccu gugcuucacc aacguguacg ccgacagcuu cgugauccgu 1200
ggcgacgagg ugcggcagau cgcacccggc cagacaggca agaucgccga cuacaacuac 1260
aagcugcccg acgacuucac cggcugcgug aucgccugga acagcaacaa ccucgacagc 1320 aagguggggcg gcaacuacaa cuaccuguac cggcuguucc ggaagagcaa ccugaagccc 1380
uucgagcggg acaucagcac cgagaucuac caagccggcu ccacccccuug caacggcgug 1440 gagggcuuca acugcuacuu cccucugcag agcuacggcu uccagcccac caacggcgug 1500
ggcuaccagc ccuaccgggu gguggugcug agcuucgagc ugcugcacgc cccagccacc 1560 gugugguggcc ccaagucugg cggaggcagc auccuggcca ucuacagcac cguggccagc 1620
agccuggugc ugcuggugag ccugggcgcc aucagcuucu gauaauaggc uggagccucg 1680
guggccuagc uucuugcccc uugggccucc ccccagcccc uccuccccuu ccugcacccg 1740
uacccccgug gucuuugaau aaagucugag ugggcggc 1778

<210> SEQ ID NO 145
<211> LENGTH: 1785
<212> TYPE: RNA
<213> ORGANISM: Artificial Sequence
<220> FEATURE:
<223> OTHER INFORMATION: Synthetic

<400> SEQUENCE: 145
auguacagca ugcagcuggc uagcugcgug acccugaccc uggugcugcu ggugaacagc 60
cagggcgccg agaacagcgu ggccuacagc aacaacagca ucgccauccc caccaacuuc 120
accaucagcg ugaccaccga gauucugccc gugagcauga ccaagaccag cguggacugc 180
accauguaca ucugcggcga cagcaccgag ugcagcaacc ugcugcugca guacggcagc 240
uucugcaccc agcugaaccg ggcccugacc ggcaucgccg uggagcagga caagaacacc 300
caggaggugu ucgcccaggu gaagcagauc uacaagaccc cucccaucaa ggacuucggc 360
ggcuucaacu ucagccagau ccugcccgac ccccagcaagc ccagcaagcg gagcuucauc 420
gaggaccugc uguucaacaa ggugacccua gccgacgccg gcuucaucaa gcaguacggc 480
gacugccucg gcgacauagc cgcccgggac cugaucugcg cccagaaguu caacggccug 540
accgugcugc cuccccugcu gaccgacgag augaucgccc aguacaccag cgcccuguua 600
gccggaacca ucaccagcgg cuggacuuuc ggcgcuggag ccgcucugca gauccccuuc 660
gccaugcaga uggccuaccg guucaacggc aucggcguga cccagaacgu gcuguacgag 720
aaccagaagc ugaucgccaa ccaguucaac agcgccaucg gcaagaucca ggacagccug 780
agcagcaccg cuagcgcccu gggcaagcug caggacgugg ugaaccagaa cgcccaggcc 840
cugaacaccc uggugaagca gcugagcagc aacuucggcg ccaucagcag cgugcugaac 900
gacauccuga gccggcugga cccucccgag gccgaggugc agaucgaccg gcugaucacu 960
ggccggcugc agagccugca gaccuacgug acccagcagc ugauccgggc cgccgagauu 1020
cgggccagcg ccaaccuggc cgccaccaag augagcgagu gcgugcuggg ccagagcaag 1080
cggguggacu ucugcggcaa gggcuaccac cugaugagcu uuccccagag cgcaccccac 1140
ggaguggugu uccugcacgu gaccuacgug cccgcccagg agaagaacuu caccaccgcc 1200
ccagccaucu gccacgacgg caaggcccac uuuccccggg agggcguguu cgugagcaac 1260
ggcacccacu gguucgugac ccagcggaac uucuacgagc cccagaucau caccaccgac 1320
aacaccuucg ugagcggcaa cugcgacgug gugaucggca ucgugaacaa caccguguac 1380
gauccccugc agcccgagcu ggacagcuuc aaggaggagc uggacaagua cuucaagaau 1440
cacaccagcc ccgacgugga ccugggcgac aucagcggca ucaacgccag cgugguguaac 1500 auccagaagg agaucgaucg gcugaacgag guggccaaga accugaacga gagccugauc 1560
gaccugcagg agcugggcaa guacgagcag uacaucaagu ggcccuggua caucuggcug 1620
ggcuucaucg ccggccugau cgccaucgug auggugacca ucaugcugug cugcaugacc 1680
agcugcugca gcugccugaa gggcuguugc agcugcggca gcugcugcaa guucgacgag 1740
gacgacagcg agcccgugcu gaagggcgug aagcugcacu acacc 1785

<210> SEQ ID NO 146
<211> LENGTH: 595
<212> TYPE: PRT
<213> ORGANISM: Artificial Sequence
<220> FEATURE:
<223> OTHER INFORMATION: Synthetic

<400> SEQUENCE: 146

Met Tyr Ser Met Gln Leu Ala Ser Cys Val Thr Leu Thr Leu Val Leu
1 5 10 15

Leu Val Asn Ser Gln Gly Ala Glu Asn Ser Val Ala Tyr Ser Asn Asn
20 25 30

Ser Ile Ala Ile Pro Thr Asn Phe Thr Ile Ser Val Thr Thr Glu Ile
35 40 45

Leu Pro Val Ser Met Thr Lys Thr Ser Val Asp Cys Thr Met Tyr Ile
50 55 60

Cys Gly Asp Ser Thr Glu Cys Ser Asn Leu Leu Leu Gln Tyr Gly Ser
65 70 75 80

Phe Cys Thr Gln Leu Asn Arg Ala Leu Thr Gly Ile Ala Val Glu Gln
85 90 95

Asp Lys Asn Thr Gln Glu Val Phe Ala Gln Val Lys Gln Ile Tyr Lys
100 105 110

Thr Pro Pro Ile Lys Asp Phe Gly Gly Phe Asn Phe Ser Gln Ile Leu
115 120 125

Pro Asp Pro Ser Lys Pro Ser Lys Arg Ser Phe Ile Glu Asp Leu Leu

-continued

```
    130                 135                 140

Phe Asn Lys Val Thr Leu Ala Asp Ala Gly Phe Ile Lys Gln Tyr Gly
145                 150                 155                 160

Asp Cys Leu Gly Asp Ile Ala Ala Arg Asp Leu Ile Cys Ala Gln Lys
                165                 170                 175

Phe Asn Gly Leu Thr Val Leu Pro Pro Leu Leu Thr Asp Glu Met Ile
            180                 185                 190

Ala Gln Tyr Thr Ser Ala Leu Leu Ala Gly Thr Ile Thr Ser Gly Trp
        195                 200                 205

Thr Phe Gly Ala Gly Ala Ala Leu Gln Ile Pro Phe Ala Met Gln Met
    210                 215                 220

Ala Tyr Arg Phe Asn Gly Ile Gly Val Thr Gln Asn Val Leu Tyr Glu
225                 230                 235                 240

Asn Gln Lys Leu Ile Ala Asn Gln Phe Asn Ser Ala Ile Gly Lys Ile
                245                 250                 255

Gln Asp Ser Leu Ser Ser Thr Ala Ser Ala Leu Gly Lys Leu Gln Asp
            260                 265                 270

Val Val Asn Gln Asn Ala Gln Ala Leu Asn Thr Leu Val Lys Gln Leu
        275                 280                 285

Ser Ser Asn Phe Gly Ala Ile Ser Ser Val Leu Asn Asp Ile Leu Ser
    290                 295                 300

Arg Leu Asp Pro Pro Glu Ala Glu Val Gln Ile Asp Arg Leu Ile Thr
305                 310                 315                 320

Gly Arg Leu Gln Ser Leu Gln Thr Tyr Val Thr Gln Gln Leu Ile Arg
                325                 330                 335

Ala Ala Glu Ile Arg Ala Ser Ala Asn Leu Ala Ala Thr Lys Met Ser
            340                 345                 350

Glu Cys Val Leu Gly Gln Ser Lys Arg Val Asp Phe Cys Gly Lys Gly
        355                 360                 365

Tyr His Leu Met Ser Phe Pro Gln Ser Ala Pro His Gly Val Val Phe
    370                 375                 380

Leu His Val Thr Tyr Val Pro Ala Gln Glu Lys Asn Phe Thr Thr Ala
385                 390                 395                 400

Pro Ala Ile Cys His Asp Gly Lys Ala His Phe Pro Arg Glu Gly Val
                405                 410                 415

Phe Val Ser Asn Gly Thr His Trp Phe Val Thr Gln Arg Asn Phe Tyr
            420                 425                 430

Glu Pro Gln Ile Ile Thr Thr Asp Asn Thr Phe Val Ser Gly Asn Cys
        435                 440                 445

Asp Val Val Ile Gly Ile Val Asn Asn Thr Val Tyr Asp Pro Leu Gln
    450                 455                 460

Pro Glu Leu Asp Ser Phe Lys Glu Glu Leu Asp Lys Tyr Phe Lys Asn
465                 470                 475                 480

His Thr Ser Pro Asp Val Asp Leu Gly Asp Ile Ser Gly Ile Asn Ala
                485                 490                 495

Ser Val Val Asn Ile Gln Lys Glu Ile Asp Arg Leu Asn Glu Val Ala
            500                 505                 510

Lys Asn Leu Asn Glu Ser Leu Ile Asp Leu Gln Glu Leu Gly Lys Tyr
        515                 520                 525

Glu Gln Tyr Ile Lys Trp Pro Trp Tyr Ile Trp Leu Gly Phe Ile Ala
    530                 535                 540

Gly Leu Ile Ala Ile Val Met Val Thr Ile Met Leu Cys Cys Met Thr
545                 550                 555                 560
```

```
Ser Cys Cys Ser Cys Leu Lys Gly Cys Cys Ser Cys Gly Ser Cys Cys
                565                 570                 575

Lys Phe Asp Glu Asp Asp Ser Glu Pro Val Leu Lys Gly Val Lys Leu
            580                 585                 590

His Tyr Thr
        595


<210> SEQ ID NO 147
<211> LENGTH: 1961
<212> TYPE: RNA
<213> ORGANISM: Artificial Sequence
<220> FEATURE:
<223> OTHER INFORMATION: Synthetic

<400> SEQUENCE: 147

gggaaauaag agagaaaaga agaguaagaa gaaauauaag accccggcgc cgccaccaug     60

uacagcaugc agcuggcuag cugcgugacc cugacccugg ugcugcuggu gaacagccag    120

ggcgccgaga acagcguggc cuacagcaac aacagcaucg ccaucccccac caacuucacc    180

aucagcguga ccaccgagau ucugcccgug agcaugacca agaccagcgu ggacugcacc    240

auguacaucu gcggcgacag caccgagugc agcaaccugc ugcugcagua cggcagcuuc    300

ugcacccagc ugaaccgggc ccugaccggc aucgccgugg agcaggacaa gaacacccag    360

gagguguucg cccaggugaa gcagaucuac aagaccccuc ccaucaagga cuucggcggc    420

uucaacuuca gccagauccu gcccgacccc agcaagccca gcaagcggag cuucaucgag    480

gaccugcugu ucaacaaggu gacccuagcc gacgccggcu ucaucaagca guacggcgac    540

ugccucggcg acauagccgc ccgggaccug aucugcgccc agaaguucaa cggccugacc    600

gugcugccuc cccugcugac cgacgagaug aucgcccagu acaccagcgc ccuguuagcc    660

ggaaccauca ccagcggcug gacuuucggc gcuggagccg cucugcagau ccccuucgcc    720

augcagaugg ccuaccgguu caacggcauc ggcgugaccc agaacgugcu guacgagaac    780

cagaagcuga ucgccaacca guucaacagc gccaucggca agauccagga cagccugagc    840

agcaccgcua gcgcccuggg caagcugcag gacguggug a accagaacgc ccaggcccug    900

aacacccugg ugaagcagcu gagcagcaac uucggcgcca ucagcagcgu gcugaacgac    960

auccugagcc ggcuggaccc ucccgaggcc gaggugcaga ucgaccggcu gaucacuggc   1020

cggcugcaga gccugcagac cuacgugacc cagcagcuga uccgggccgc cgagauucgg   1080

gccagcgcca accuggccgc caccaagaug agcgagugcg ugcugggcca gagcaagcgg   1140

guggacuucu gcggcaaggg cuaccaccug augagcuuuc cccagagcgc accccacgga   1200

gugguguucc ugcacgugac cuacgugccc gcccaggaga agaacuucac caccgcccca   1260

gccaucugcc acgacggcaa ggcccacuuu ccccgggagg gcguguucgu gagcaacggc   1320

acccacuggu ucgugaccca gcggaacuuc uacgagcccc agaucaucac caccgacaac   1380

accuucguga gcggcaacug cgacguggug aucggcaucg ugaacaacac cguguacgau   1440

ccccugcagc ccgagcugga cagcuucaag gaggagcugg acaaguacuu caagaaucac   1500

accagccccg acguggaccu gggcgacauc agcggcauca acgccagcgu ggugaacauc   1560

cagaaggaga ucgaucggcu gaacgaggug gccaagaacc ugaacgagag ccugaucgac   1620

cugcaggagc ugggcaagua cgagcaguac aucaaguggc ccugguacau cuggcugggc   1680

uucaucgccg gccugaucgc caucgugaug gugaccauca ugcugugcug caugaccagc   1740

ugcugcagcu gccugaaggg cuguugcagc ugcggcagcu gcugcaaguu cgacgaggac   1800
```

gacagcgagc ccgugcugaa gggcgugaag cugcacuaca ccugauaaua ggcuggagcc 1860
ucgguggccu agcuucuugc cccuugggcc uccccccagc cccuccuccc cuuccugcac 1920
ccguaccccc guggucuuug aauaaagucu gagugggcgg c 1961

<210> SEQ ID NO 148
<211> LENGTH: 13
<212> TYPE: PRT
<213> ORGANISM: Artificial Sequence
<220> FEATURE:
<223> OTHER INFORMATION: Synthetic

<400> SEQUENCE: 148

Ala Lys Phe Val Ala Ala Trp Thr Leu Lys Ala Ala Ala
1 5 10

<210> SEQ ID NO 149
<211> LENGTH: 2216
<212> TYPE: RNA
<213> ORGANISM: Artificial Sequence
<220> FEATURE:
<223> OTHER INFORMATION: Synthetic

<400> SEQUENCE: 149
gggaaauaag agagaaaaga agaguaagaa gaaauauaag accccggcgc cgccaccaug 60
uucguguucc uggugcugcu gccccuggug agcagccagu gcgugaaccu gaccacccgg 120
acccagcugc caccagccua caccaacagc uucacccggg gcgucuacua ccccgacaag 180
guguuccgga gcagcguccu gcacagcacc caggaccugu uccugcccuu cuucagcaac 240
gugaccuggu uccacgccau ccacgugagc ggcaccaacg gcaccaagcg guucgacaac 300
cccgugcugc ccuucaacga cggcguguac uucgccagca ccgagaagag caacaucauc 360
cggggcugga ucuucggcac cacccuggac agcaagaccc agagccugcu gaucgugaau 420
aacgccacca acguggugau caaggugugc gaguuccagu ucugcaacga ccccuuccug 480
ggcguguacu accacaagaa caacaagagc uggauggaga gcgaguuccg gguguacagc 540
agcgccaaca acugcaccuu cgaguacgug agccagcccu uccugaugga ccuggagggc 600
aagcagggca acuucaagaa ccugcgggag uucguguuca agaacaucga cggcuacuuc 660
aagaucuaca gcaagcacac ccccaaucaac cuggugcggg aucugcccca gggcuucuca 720
gcccuggagc cccuggugga ccugcccauc ggcaucaaca ucacccgguu ccagacccug 780 cuggccccugc accggagcua ccugacccca ggcgacagca gcagcgggug gacagcaggc 840
gcggcugcuu acuacguggg cuaccugcag ccccggaccu uccugcugaa guacaacgag 900
aacggcacca ucaccgacgc cguggacugc gcccuggacc cucugagcga gaccaagugc 960
acccugaaga gcuucaccgu ggagaagggc aucuaccaga ccagcaacuu ccgggugcag 1020
cccaccgaga gcaucgugcg guuccccaac aucaccaacc ugugccccuu cggcgaggug 1080
uucaacgcca cccgguucgc cagcguguac gccuggaacc ggaagcggau cagcaacugc 1140
guggccgacu acagcgugcu guacaacagc gccagcuuca gcaccuucaa gugcuacggc 1200
gugagcccca ccaagcugaa cgaccugugc uucaccaacg uguacgccga cagcuucgug 1260
auccguggcg acgaggugcg gcagaucgca cccggccaga caggcaagau cgccgacuac 1320
aacuacaagc ugcccgacga cuucaccggc ugcgugaucg ccuggaacag caacaaccuc 1380
gacagcaagg ugggcggcaa cuacaacuac cuguaccggc uguuccggaa gagcaaccug 1440
aagcccuucg agcgggacau cagcaccgag aucuaccaag ccggcuccac cccuugcaac 1500
ggcguggagg gcuucaacug cuacuucccu cugcagagcu acggcuucca gcccaccaac 1560
ggcgugggcu accagcccua ccgggguggug gugcugagcu ucgagcugcu gcacgcccca 1620
gccaccgugu guggccccaa gaagagcacc aaccugguga agaacaagug cgugaacuuc 1680
aacuucaacg gccuuaccgg caccggcgug cugaccgaga gcaacaagaa auuccugccc 1740
uuucagcagu ucggccggga caucgccgac accaccgacg cugugcggga uccccagacc 1800
cuggagaucc uggacaucac cccuugcagc uucggcggcg ugagcgugau caccccaggc 1860
accaacacca gcaaccaggu ggccgugcug uaccaggacg ugaacugcac cgaggugccc 1920
guggccaucc acgccgacca gcugacaccc accuggcggg ucuacagcac cggcagcaac 1980
guguuccaga cccgggccgg uugccugauc ggcgccgagc acgugaacaa cagcuacgag 2040
ugcgacaucc ccaucggcgc cggcaucugu gccagcuacc agacccagac caauucauga 2100
uaauaggcug gagccucggu ggccuagcuu cuugccccuu gggccucccc ccagccccuc 2160
cuccccuucc ugcacccgua cccccguggu cuuugaauaa agucugagug ggcggc 2216

<210> SEQ ID NO 150
<211> LENGTH: 2040
<212> TYPE: RNA
<213> ORGANISM: Artificial Sequence
<220> FEATURE:
<223> OTHER INFORMATION: Synthetic

<400> SEQUENCE: 150
auguucgugu uccuggugcu gcugccccug gugagcagcc agugcgugaa ccugaccacc 60
cggacccagc ugccaccagc cuacaccaac agcuucaccc ggggcgucua cuaccccgac 120
aagguguucc ggagcagcgu ccugcacagc acccaggacc uguuccugcc cuucuucagc 180
aacgugaccu gguuccacgc cauccacgug agcggcacca acggcaccaa gcgguucgac 240
aaccccgugc ugcccuucaa cgacggcgug uacuucgcca gcaccgagaa gagcaacauc 300
auccggggcu ggaucuucgg caccacccug gacagcaaga cccagagccu gcugaucgug 360
aauaacgcca ccaacguggu gaucaaggug ugcgaguucc aguucugcaa cgaccccuuc 420
cugggcgugu acuaccacaa gaacaacaag agcuggaugg agagcgaguu ccggguguac 480
agcagcgcca acaacugcac cuucgaguac gugagccagc ccuuccugau ggaccuggag 540
ggcaagcagg gcaacuucaa gaaccugcgg gaguucgugu ucaagaacau cgacggcuac 600
uucaagaucu acagcaagca caccccaauc aaccuggugc gggaucugcc ccagggcuuc 660
ucagcccugg agccccuggu ggaccugccc aucggcauca acaucacccg guuccagacc 720
cugcuggccc ugcaccggag cuaccugacc ccaggcgaca gcagcagcgg guggacagca 780
ggcgcggcug cuuacuacgu gggcuaccug cagccccgga ccuuccugcu gaaguacaac 840
gagaacggca ccaucaccga cgccguggac ugcgcccugg acccucugag cgagaccaag 900
ugcacccuga agagcuucac cguggagaag ggcaucuacc agaccagcaa cuuccgggug 960
cagcccaccg agagcaucgu gcgguucccc aacaucacca accugugccc cuucggcgag 1020
guguucaacg ccacccgguu cgccagcgug uacgccugga accggaagcg gaucagcaac 1080
ugcguggccg acuacagcgu gcuguacaac agcgccagcu ucagcaccuu caagugcuac 1140
ggcgugagcc ccaccaagcu gaacgaccug ugcuucacca acguguacgc cgacagcuuc 1200
gugauccgug gcgacgaggu gcggcagauc gcacccggcc agacaggcaa gaucgccgac 1260
uacaacuaca agcugcccga cgacuucacc ggcugcguga ucgccuggaa cagcaacaac 1320

-continued

```
cucgacagca aggugggcgg caacuacaac uaccuguacc ggcuguuccg gaagagcaac   1380

cugaagcccu ucgagcggga caucagcacc gagaucuacc aagccggcuc caccccuugc   1440

aacggcgugg agggcuucaa cugcuacuuc ccucugcaga gcuacggcuu ccagcccacc   1500

aacggcgugg gcuaccagcc cuaccgggug guggugcuga gcuucgagcu gcugcacgcc   1560

ccagccaccg ugugguggccc caagaagagc accaaccugg ugaagaacaa gugcgugaac   1620

uucaacuuca acggccuuac cggcaccggc gugcugaccg agagcaacaa gaaauuccug   1680

cccuuucagc aguucggccg ggacaucgcc gacaccaccg acgcugugcg ggauccccag   1740

acccuggaga uccuggacau caccccuugc agcuucggcg gcgugagcgu gaucacccca   1800

ggcaccaaca ccagcaacca gguggccgug cuguaccagg acgugaacug caccgaggug   1860

cccguggcca uccacgccga ccagcugaca cccaccuggc gggucuacag caccggcagc   1920

aacguguucc agacccgggc cgguugccug aucggcgccg agcacgugaa caacagcuac   1980

gagugcgaca uccccaucgg cgccggcauc ugugccagcu accagaccca gaccaauuca   2040
```

```
<210> SEQ ID NO 151
<211> LENGTH: 680
<212> TYPE: PRT
<213> ORGANISM: Artificial Sequence
<220> FEATURE:
<223> OTHER INFORMATION: Synthetic

<400> SEQUENCE: 151

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240
```

-continued

```
Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
```

-continued

```
          660                 665                 670

Ser Tyr Gln Thr Gln Thr Asn Ser
        675                 680


<210> SEQ ID NO 152
<211> LENGTH: 4
<212> TYPE: PRT
<213> ORGANISM: Artificial Sequence
<220> FEATURE:
<223> OTHER INFORMATION: Synthetic

<400> SEQUENCE: 152

Gly Ser Gly Gly
1
```

SARS-CoV-2 mRNA DOMAIN VACCINES

RELATED APPLICATIONS

This application is a national stage filing under 35 U.S.C. § 371 of International Patent Application Serial No. PCT/US2021/016979, filed Feb. 6, 2021, entitled "SARS-CoV-2 MRNA DOMAIN VACCINES" which claims the benefit under 35 U.S.C. § 119 (e) of U.S. provisional application No. 62/971,825, filed Feb. 7, 2020, U.S. provisional application No. 63/016,175, filed Apr. 27, 2020, U.S. provisional application No. 63/044,330, filed Jun. 25, 2020, and U.S. provisional application No. 63/063,137, filed Aug. 7, 2020, the entire contents of each of which are incorporated by reference herein in its entirety.

REFERENCE TO A SEQUENCE LISTING SUBMITTED AS A TEXT FILE VIA EFS-WEB

This application contains a Sequence Listing which has been submitted in ASCII format via EFS-Web and is hereby incorporated by reference in its entirety. Said ASCII copy, created on Aug. 1, 2022, is named M137870157US03-SEQ-JXV and is 451,145 bytes in size.

BACKGROUND

Human coronaviruses are highly contagious enveloped, positive single-stranded RNA viruses of the Coronaviridae family. Two sub-families of Coronaviridae are known to cause human disease. The most important being the β-coronaviruses (betacoronaviruses). The β-coronaviruses are common etiological agents of mild to moderate upper respiratory tract infections. Outbreaks of novel coronavirus infections such as the infections caused by a coronavirus initially identified from the Chinese city of Wuhan in December 2019, however, have been associated with a high mortality rate death toll. This recently identified coronavirus, referred to as Severe Acute Respiratory Syndrome Coronavirus 2 (SARS-CoV-2) (formerly referred to as a "2019 novel coronavirus," or a "2019-nCoV") has rapidly infected hundreds of thousands of people. The pandemic disease that the SARS-CoV-2 virus causes has been named by World Health Organization (WHO) as COVID-19 (Coronavirus Disease 2019). The first genome sequence of a SARS-CoV-2 isolate (Wuhan-Hu-1) was released by investigators from the Chinese CDC in Beijing on Jan. 10, 2020 at Virological, a UK-based discussion forum for analysis and interpretation of virus molecular evolution and epidemiology. The sequence was then deposited in GenBank on Jan. 12, 2020, having Genbank Accession number MN908947.1.

Currently, there is no specific treatment for COVID-19 or vaccine for SARS-CoV-2 infection. The continuing health problems and mortality associated with coronavirus infections, particularly the SARS-CoV-2 pandemic, are of tremendous concern internationally. The public health crisis caused by SARS-CoV-2 reinforces the importance of rapidly developing effective and safe vaccine candidates against these viruses.

SUMMARY

Provided herein, in some embodiments, are compositions (e.g., vaccines) that comprise one or more messenger ribonucleic acid (mRNA) molecules that encode(s) highly immunogenic antigen(s) capable of eliciting potent neutralizing antibody responses against SARS-CoV-2 antigens. The mRNA molecules described herein are used to express key neutralizing domains of the SARS-CoV-2 coronavirus spike (S) protein that are efficient at inducing protective immunity when used individually or in combination as an immunogenic composition or vaccine to protect people from infection by the natural virus and/or to reduce symptoms if infected.

The envelope S proteins of known betacoronaviruses determine the virus host tropism and entry into host cells and are critical for SARS-CoV-2 infection. The organization of the S protein is similar among betacoronaviruses, such as SARS-CoV-2, SARS-CoV, MERS-CoV, HKU1-CoV, MHV-CoV and NL63-CoV, including two subunits, S1 and S2, which mediate attachment and membrane fusion, respectively. The S1 subunit includes an N terminal domain (NTD) and a receptor binding domain (RBD).

The expression of subunit antigens focuses the immune response to specific subunits with minimal stimulation of memory B and T cells specific to other domains of the antigen that are shared with other related viruses. Data provided herein demonstrates that administration of mRNA encoding membrane bound or soluble SARS-CoV-2 S1 subunit antigen generated antibody titers to each of SARS-CoV-2 RBD antigen, NTD antigen, wildtype full-length S protein, and S protein having double proline mutations to stabilize the prefusion conformation. As shown herein, at all doses tested, a two-dose regimen (i.e., including a booster dose) was effective at inducing antibodies that could recognize and bind to SARS-CoV-2 WT S protein. Surprisingly, the induced titers were highest when measured against the double proline stabilized version of the S protein even though the double proline mutation is not found in the S1 subunit (the double proline mutation occurs in S2, and S2 was not present in the immunogen tested).

Additionally, both the NTD and RBD are known to be sites for binding of antibodies that neutralize virus activity. RBD in the case of SARS-CoV-2 is the receptor binding site of the spike protein which binds the angiotensin-converting enzyme 2 (ACE2). The NTD, the function of which is not thoroughly understood, seems to have a role in binding sugar moieties and in facilitating the conformational transition of the spike protein from prefusion to a post fusion conformation. Regardless, both the NTD and RBD domains induce high binding antibody and neutralizing antibody titers as shown herein.

For example, quite surprisingly, the data provided in some embodiments herein show that while sera from the administration of mRNA encoding a membrane bound RBD antigen (RBD-TM) or a membrane bound NTD antigen (NTD-TM) showed immunogenicity to the SARS-CoV-2 S1/S2 spike protein, the 50:50 combination of the two mRNAs (and thus the two antigens) generated unexpectedly high, synergistic, neutralizing antibody titers to the SARS-CoV-2 S1/S2 spike protein.

Thus, some aspects of the present disclosure provide compositions comprising an mRNA encoding a functional domain of a SARS-CoV-2 S protein capable of inducing an immune response, such as a neutralizing antibody response, to a SARS-CoV-2. In some embodiments, the mRNA is formulated in a lipid nanoparticle.

In some aspects an mRNA comprising an open reading frame (ORF) that encodes at least two domains of a SARS-CoV-2 Spike protein, and less than the full length spike protein is provided. A spike protein that is less than the full length spike protein is one or more domains and/or subunits of the spike protein having at least one amino acid less than the full length spike protein or a fusion protein having one or more domains linked together in an non-natural order or sequence. In some embodiments one of the two domains is an N-terminal domain (NTD) of a SARS-CoV-2 Spike protein. In some embodiments one of the two domains is a receptor binding domain (RBD) of a SARS-CoV-2 Spike protein. In some embodiments the ORF encodes a transmembrane domain (TD) linked to the NTD and/or RBD. In some embodiments the TD is an influenza hemagglutinin transmembrane domain. In some embodiments the ORF comprises NTD—RBD—TM. In some embodiments the at least two domains are linked through a cleavable or non-cleavable linker. In some embodiments the non-cleavable linker is a glycine-serine (GS) linker. In some embodiments the GS linker 4-15 amino acids. In some embodiments the linker is a pan HLA DR-binding epitope (PADRE). In some embodiments the ORF encodes a signal peptide. In some embodiments the signal peptide is linked to the NTD. In some embodiments the signal peptide is linked to the RBD. In some embodiments the signal peptide is heterologous to SARS-CoV-2. In some embodiments the at least two domains are soluble. In some embodiments the ORF encodes a trafficking signal domain. In some embodiments the trafficking signal domain is a macrophage marker. In some embodiments the macrophage marker CD86 and/or CD11b. In some embodiments the trafficking signal domain is a VSV-G cytosolic tail (VSVGct). In some embodiments one of the two domains is a first repetitive heptapeptide: HPPHCPC (HR1) of a SARS-CoV-2 Spike protein. In some embodiments one of the two domains is a second repetitive heptapeptide: HPPHCPC (HR2) of a SARS-CoV-2 Spike protein. In some embodiments the ORF encodes a transmembrane domain (TD) linked to the HR1 and/or HR2. In some embodiments the TD is an influenza hemagglutinin transmembrane domain. In some embodiments the ORF encodes a fusion peptide (FP). In some embodiments the ORF encodes a CT tail.

In some aspects an mRNA comprising an open reading frame (ORF) that encodes a receptor binding domain (RBD) of a SARS-CoV-2 Spike protein is provided. In some embodiments the RBD is soluble. In some embodiments the RBD is linked to a transmembrane domain, optionally an influenza hemagglutinin transmembrane domain.

The details of one or more embodiments of the invention are set forth in the description below. Other features or advantages of the present invention will be apparent from the following drawings and detailed description of several embodiments, and also from the appended claims.

BRIEF DESCRIPTION OF THE DRAWINGS

FIG. 3 shows sequence alignments of the antigens depicted in FIG. 2.

FIG. 5 shows sequence alignments of various S1 subunit antigens described herein.

DETAILED DESCRIPTION

Figure 1:
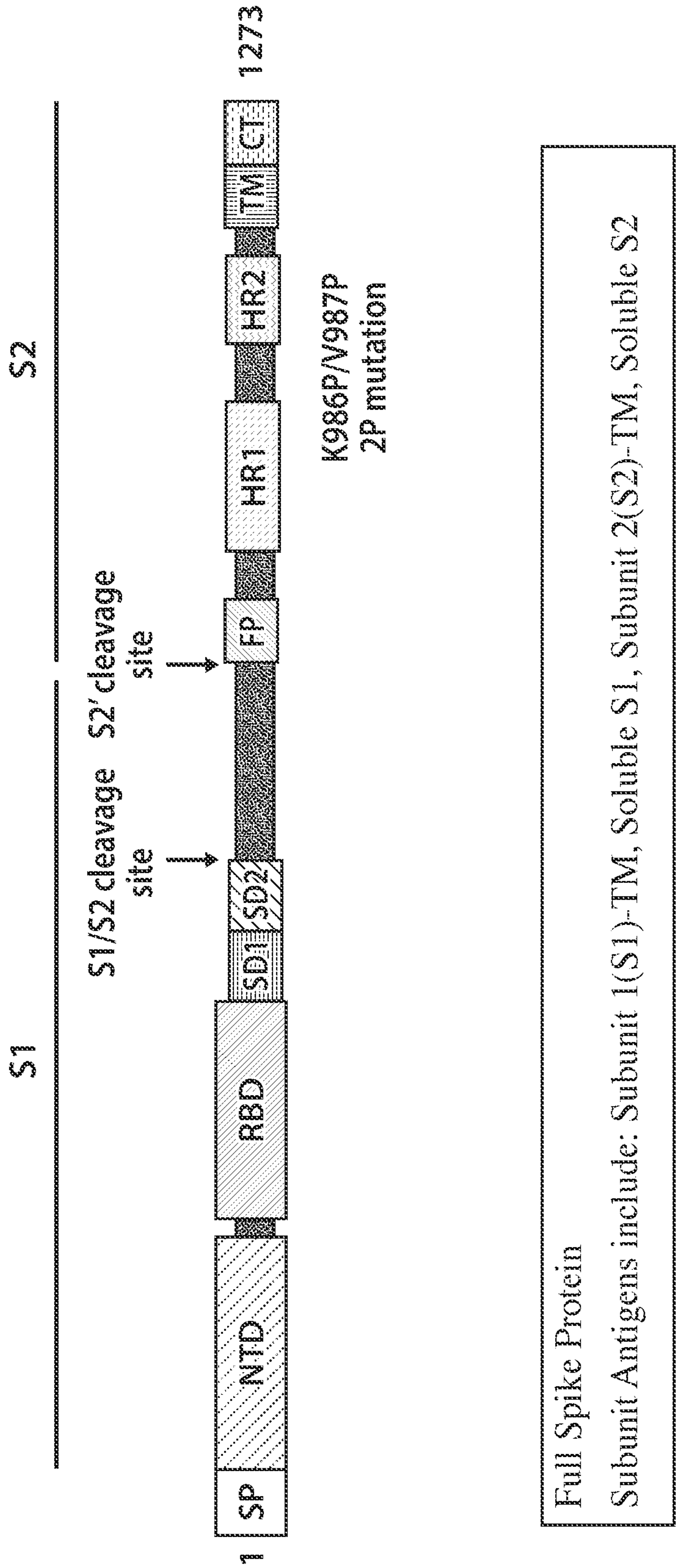
FIG. 1 Schematic representation of wild-type and 2P spike protein antigens encoded by mRNAs of the invention; signal peptide (SP), no fill, N-terminal domain (NTD), dotted; receptor-binding domain (RBD), downward diagonal stripes; subdomain 1 (SD1), horizontal stripes; subdomain 2 (SD2), wave; fusion peptide (FP), upward diagonal stripes; heptad repeat 1 (HR1) weave; heptad repeat 2 (HR2) diagonal brick; (TM), vertical stripes; and cytoplasmic tail (CT), brick.

Severe acute respiratory syndrome coronavirus 2 (SARS-CoV-2) is a newly emerging respiratory virus with high morbidity and mortality. SARS-CoV-2 has rapidly spread around the world compared with SARS-CoV, which appeared in 2002, and Middle East respiratory syndrome coronavirus (MERS-CoV), which emerged in 2012. The World Health Organization (WHO) reports that, as of Jul. 6, 2020, the current outbreak of COVID-19 has almost 11.5 million confirmed cases worldwide with more than 530,000 deaths. New cases of COVID-19 infection are on the rise and are still increasing rapidly. It is thus crucial that a variety of safe and effective vaccines and drugs be developed to prevent and treat COVID-19 and reduce the serious impact that COVID-19 is having across the world. Vaccines and drugs made using a variety of modalities, and vaccines having improved safety and efficacy, are imperative. Their remains a need to accelerate the advanced design and development of vaccines and therapeutic drugs against coronavirus disease 2019 (COVID-19).

On Jan. 7, 2020, severe acute respiratory syndrome coronavirus 2 (SARS-CoV-2) was identified as the etiological agent of a novel pneumonia that emerged in December 2019, in Wuhan City, Hubei province in China (Lu H. et al. (2020) J Med Virol. April; 92(4):401-402.). Soon after, the virus caused an outbreak in China and has spread to the world. According to the analysis of genomic structure of SARS-CoV-2, it belongs to β-coronaviruses (CoVs) (Chan et al. 2020 Emerg Microbes Infect.; 9(1):221-236).

A key protein on the surface of coronavirus is the Spike protein. A large variety of mRNA constructs have been designed and are disclosed herein. When formulated in appropriate delivery vehicles mRNA encoding Spike antigen, subunits and domains thereof are capable of inducing a strong immune response against SARS-CoV-2, thus producing effective and potent mRNA vaccines. Administration of the mRNA encoding various Spike protein antigens, in particular, Spike protein subunit and domain antigens, results in delivery of the mRNA to immune tissues and cells of the immune system where it is rapidly translated into proteins antigens. Other immune cells, for example, B cells and T cells, are then able to recognize and mount and immune response develop an immune response against the encoded protein and ultimately create a long-lasting protective response against the coronavirus. Low immunogenicity, a drawback in protein vaccine development due to poor presentation to the immune system or incorrect folding of the antigens, is avoided through the use of the highly effective mRNA vaccines encoding spike protein, subunits and domains thereof disclosed herein.

The present disclosure provides compositions (e.g., mRNA vaccines) that elicit potent neutralizing antibodies against coronavirus antigens. In some embodiments, a composition includes mRNA encoding at least one (e.g., one, two, or more) coronavirus antigen, such as a SARS-CoV-2 antigen. In some embodiments, the mRNA encodes a spike protein domain, such as a receptor binding domain (RBD), an N-terminal domain (NTD), or a combination of an RBD and NTD.

Some aspects of the present disclosure provide a messenger ribonucleic acid (mRNA) comprising an open reading frame encoding a fusion protein comprising a receptor binding domain (RBD) of a SARS-CoV-2 Spike protein and a protein transmembrane domain, e.g., a naturally occurring or heterologous transmembrane domain.

In some embodiments, the protein transmembrane domain is an influenza hemagglutinin transmembrane domain.

In some embodiments, the fusion protein comprises an amino acid sequence having at least 80% identity to the amino acid sequence of SEQ ID NO: 77.

In some embodiments, the fusion protein comprises an amino acid sequence having at least 85%, at least 90%, at least 95%, at least 96%, at least 97%, at least 98%, or at least 99% identity to the amino acid sequence of SEQ ID NO: 77.

In some embodiments, the fusion protein comprises the amino acid sequence of SEQ ID NO: 77.

In some embodiments, the open reading frame comprises a nucleotide sequence having at least 70% identity to the nucleotide sequence of SEQ ID NO: 76.

In some embodiments, the wherein the open reading frame comprises a nucleotide sequence having at least 75%, at least 80%, at least 90%, at least 95%, at least 96%, at least 97%, at least 98%, or at least 99% identity to the nucleotide sequence of SEQ ID NO: 76.

In some embodiments, the open reading frame comprises the nucleotide sequence of SEQ ID NO: 76.

Other aspects of the present disclosure provide a messenger ribonucleic acid (mRNA) comprising an open reading frame encoding a fusion protein comprising an amino (N)-terminal domain of a SARS-CoV-2 Spike protein and a transmembrane domain.

In some embodiments, the transmembrane domain is an influenza hemagglutinin transmembrane domain.

In some embodiments, the fusion protein comprises an amino acid sequence having at least 80% identity to the amino acid sequence of SEQ ID NO: 47.

In some embodiments, the fusion protein comprises an amino acid sequence having at least 85%, at least 90%, at least 95%, at least 96%, at least 97%, at least 98%, or at least 99% identity to the amino acid sequence of SEQ ID NO: 47.

In some embodiments, the fusion protein comprises the amino acid sequence of SEQ ID NO: 47.

In some embodiments, the open reading frame comprises a nucleotide sequence having at least 70% identity to the nucleotide sequence of SEQ ID NO: 46.

In some embodiments, the open reading frame comprises a nucleotide sequence having at least 75%, at least 80%, at least 90%, at least 95%, at least 96%, at least 97%, at least 98%, or at least 99% identity to the nucleotide sequence of SEQ ID NO: 46.

In some embodiments, the open reading frame comprises the nucleotide sequence of SEQ ID NO: 46.

Yet other aspects of the present disclosure provide a messenger ribonucleic acid (mRNA) comprising an open reading frame encoding a fusion protein comprising a receptor binding domain of a SARS-CoV-2 Spike protein linked to an amino (N)-terminal domain of a SARS-CoV-2 Spike protein, optionally via a linker.

In some embodiments, the fusion protein further comprises a transmembrane domain.

In some embodiments, the fusion protein comprises an amino acid sequence having at least 80% identity to the amino acid sequence of SEQ ID NO: 92.

In some embodiments, the fusion protein comprises an amino acid sequence having at least 85%, at least 90%, at least 95%, at least 96%, at least 97%, at least 98%, or at least 99% identity to the amino acid sequence of SEQ ID NO: 92.

In some embodiments, the fusion protein comprises the amino acid sequence of SEQ ID NO: 92.

In some embodiments, the open reading frame comprises a nucleotide sequence having at least 70% identity to the nucleotide sequence of SEQ ID NO: 91.

In some embodiments, the open reading frame comprises a nucleotide sequence having at least 75%, at least 80%, at least 90%, at least 95%, at least 96%, at least 97%, at least 98%, or at least 99% identity to the nucleotide sequence of SEQ ID NO: 91.

In some embodiments, the open reading frame comprises the nucleotide sequence of SEQ ID NO: 91.

In some embodiments, the mRNA further comprises a 5' untranslated region (UTR), optionally comprising the nucleotide sequence of SEQ ID NO: 131 or 2.

In some embodiments, the mRNA further comprises a 3' untranslated region (UTR), optionally comprising the nucleotide sequence of SEQ ID NO: 132 or 4.

In some embodiments, the mRNA further comprises a 5' cap, optionally 7mG(5')ppp(5')NlmpNp.

In some embodiments, the mRNA further comprises a polyA tail, optionally having a length of about 100 nucleotides.

In some embodiments, the mRNA comprises a chemical modification, optionally 1-methylpseudouridine.

Some aspects of the present disclosure provide a composition comprising the mRNA of any one of the preceding paragraphs.

Other aspects of the present disclosure provide a composition comprising at least two of the mRNA of any one of the preceding paragraphs.

Other aspects of the present disclosure provide a composition comprising: (a) a messenger ribonucleic acid (mRNA) comprising an open reading frame encoding a fusion protein comprising a receptor binding domain (RBD) of a SARS-CoV-2 Spike protein and a protein transmembrane domain; and (b) an mRNA comprising an open reading frame encoding a fusion protein comprising an amino (N)-terminal domain of a SARS-CoV-2 Spike protein and a transmembrane domain. In some embodiments, the ratio of the mRNA of (a) to the mRNA of (b) is about 1:1, e.g., 1:2, 1:3, 21, or 3:1. In some embodiments, at least 50% of the mRNA of a composition is the mRNA of (a). For example, at least 55%, 60%, 65%, 70%, 75%, 80%, 85%, 90%, or 95% of the mRNA of a composition is the mRNA of (a). In some embodiments, at least 50% of the mRNA of a composition is the mRNA of (b). For example, at least 55%, 60%, 65%, 70%, 75%, 80%, 85%, 90%, or 95% of the mRNA of a composition is the mRNA of (b).

In some embodiments, the protein transmembrane domain is an influenza hemagglutinin transmembrane domain.

In some embodiments, the fusion protein of (a) comprises an amino acid sequence having at least 80% identity to the amino acid sequence of SEQ ID NO: 77.

In some embodiments, the fusion protein of (a) comprises an amino acid sequence having at least 85%, at least 90%, at least 95%, at least 96%, at least 97%, at least 98%, or at least 99% identity to the amino acid sequence of SEQ ID NO: 77.

In some embodiments, the fusion protein of (a) comprises the amino acid sequence of SEQ ID NO: 77.

In some embodiments, the open reading frame of (a) comprises a nucleotide sequence having at least 70% identity to the nucleotide sequence of SEQ ID NO: 76.

In some embodiments, the open reading frame of (a) comprises a nucleotide sequence having at least 75%, at least 80%, at least 90%, at least 95%, at least 96%, at least 97%, at least 98%, or at least 99% identity to the nucleotide sequence of SEQ ID NO: 76.

In some embodiments, the open reading frame of (a) comprises the nucleotide sequence of SEQ ID NO: 76.

In some embodiments, the fusion protein of (b) comprises an amino acid sequence having at least 80% identity to the amino acid sequence of SEQ ID NO: 47.

In some embodiments, the fusion protein of (b) comprises an amino acid sequence having at least 85%, at least 90%, at least 95%, at least 96%, at least 97%, at least 98%, or at least 99% identity to the amino acid sequence of SEQ ID NO: 47.

In some embodiments, the fusion protein of (b) comprises the amino acid sequence of SEQ ID NO: 47.

In some embodiments, the open reading frame of (b) comprises a nucleotide sequence having at least 70% identity to the nucleotide sequence of SEQ ID NO: 46.

In some embodiments, the open reading frame of (b) comprises a nucleotide sequence having at least 75%, at least 80%, at least 90%, at least 95%, at least 96%, at least 97%, at least 98%, or at least 99% identity to the nucleotide sequence of SEQ ID NO: 46.

In some embodiments, the open reading frame of (b) comprises the nucleotide sequence of SEQ ID NO: 46.

In some embodiments, the mRNA is formulated in a lipid nanoparticle.

In some embodiments, the composition further comprises a lipid nanoparticle.

In some embodiments, the mRNA of (a) is formulated in a lipid nanoparticle, and the mRNA of (b) is formulated in a lipid nanoparticle.

In some embodiments, the lipid nanoparticle comprises a cationic lipid.

In some embodiments, the lipid nanoparticle further comprises a neutral lipid.

In some embodiments, the lipid nanoparticle further comprises a sterol.

In some embodiments, the lipid nanoparticle further comprises a polyethylene glycol (PEG)-modified lipid.

In some embodiments, the lipid nanoparticle comprises an ionizable cationic lipid, a neutral lipid, a sterol, and a PEG-modified lipid.

In some embodiments, the ionizable cationic lipid is heptadecan-9-yl 8 ((2 hydroxyethyl)(6 oxo 6-(undecyloxy) hexyl)amino)octanoate (Compound 1).

In some embodiments, the neutral lipid is 1,2 distearoyl-sn-glycero-3-phosphocholine (DSPC).

In some embodiments, the sterol is cholesterol.

In some embodiments, the PEG-modified lipid is 1,2 dimyristoyl-sn-glycerol, methoxypolyethyleneglycol (PEG2000 DMG).

In some embodiments, the lipid nanoparticle comprises 20-60 mol % ionizable cationic lipid, 5-25 mol % neutral lipid, 25-55 mol % sterol, and 0.5-15 mol % PEG-modified lipid.

In some embodiments, the lipid nanoparticle comprises: 47 mol % ionizable cationic lipid; 11.5 mol % neutral lipid; 38.5 mol % sterol; and 3.0 mol % PEG-modified lipid; 48 mol % ionizable cationic lipid; 11 mol % neutral lipid; 38.5 mol % sterol; and 2.5 mol % PEG-modified lipid; 49 mol % ionizable cationic lipid; 10.5 mol % neutral lipid; 38.5 mol % sterol; and 2.0 mol % PEG-modified lipid; 50 mol % ionizable cationic lipid; 10 mol % neutral lipid; 38.5 mol % sterol; and 1.5 mol % PEG-modified lipid; or 51 mol % ionizable cationic lipid; 9.5 mol % neutral lipid; 38.5 mol % sterol; and 1.0 mol % PEG-modified lipid.

In some embodiments, the lipid nanoparticle comprises: 47 mol % Compound 1; 11.5 mol % DSPC; 38.5 mol % cholesterol; and 3.0 mol % PEG2000 DMG; 48 mol % Compound 1; 11 mol % DSPC; 38.5 mol % cholesterol; and 2.5 mol % PEG2000 DMG; 49 mol % Compound 1; 10.5 mol % DSPC; 38.5 mol % cholesterol; and 2.0 mol % PEG2000 DMG; 50 mol % Compound 1; 10 mol % DSPC; 38.5 mol % cholesterol; and 1.5 mol % PEG2000 DMG; or 51 mol % Compound 1; 9.5 mol % DSPC; 38.5 mol % cholesterol; and 1.0 mol % PEG2000 DMG.

Further aspects of the present disclosure provide a method comprising administering to a subject the mRNA or the composition of any one of the preceding claims in an amount effective to induce in the subject a neutralizing antibody response against SARS-CoV-2.

Other aspects of the present disclosure provide a method comprising administering to a subject the mRNA or the composition of any one of the preceding claims in an amount effective to induce in the subject and a T cell immune response against SARS-CoV-2.

Some aspects of the present disclosure provide a messenger ribonucleic acid (mRNA) comprising an open reading frame (ORF) that encodes a coronavirus antigen capable of inducing an immune response, such as a neutralizing antibody response, to a SARS-CoV-2, wherein the antigen comprises a protein fragment or a functional protein domain of a SARS-CoV-2, optionally wherein the RNA is formulated in a lipid nanoparticle.

In some embodiments, the antigen is a functional protein domain.

In some embodiments, the protein domain is an N-terminal domain (NTD) of a SARS-CoV-2 Spike protein.

In some embodiments, the NTD is linked to a transmembrane domain, optionally an influenza hemagglutinin transmembrane domain.

In some embodiments, the antigen comprises an amino acid sequence having at least 80%, at least 85%, at least 90%, at least 95%, at least 96%, at least 97%, at least 98%, or at least 99% identity to the amino acid sequence of SEQ ID NO: 47, optionally wherein the antigen comprises the amino acid sequence of SEQ ID NO: 47.

In some embodiments, the open reading frame comprises a nucleotide sequence having at least 70%, least 75%, at least 80%, at least 90%, at least 95%, at least 96%, at least 97%, at least 98%, or at least 99% identity to the nucleotide sequence of SEQ ID NO: 46, optionally wherein the open reading frame comprises the nucleotide sequence of SEQ ID NO: 46.

In some embodiments, the protein domain is a receptor binding domain (RBD) of a SARS-CoV-2 Spike protein.

In some embodiments, the RBD is soluble.

In some embodiments, the antigen comprises an amino acid sequence having at least 80%, at least 85%, at least 90%, at least 95%, at least 96%, at least 97%, at least 98%, or at least 99% identity to the amino acid sequence of SEQ ID NO: 62, optionally wherein the antigen comprises the amino acid sequence of SEQ ID NO: 62.

In some embodiments, the open reading frame comprises a nucleotide sequence having at least 70%, least 75%, at least 80%, at least 90%, at least 95%, at least 96%, at least 97%, at least 98%, or at least 99% identity to the nucleotide sequence of SEQ ID NO: 61, optionally wherein the open reading frame comprises the nucleotide sequence of SEQ ID NO: 61.

In some embodiments, the RBD is linked to a transmembrane domain, optionally an influenza hemagglutinin transmembrane domain.

In some embodiments, the antigen comprises an amino acid sequence having at least 80%, at least 85%, at least 90%, at least 95%, at least 96%, at least 97%, at least 98%, or at least 99% identity to the amino acid sequence of SEQ ID NO: 77, optionally wherein the antigen comprises the amino acid sequence of SEQ ID NO: 77.

In some embodiments, the open reading frame comprises a nucleotide sequence having at least 70%, least 75%, at least 80%, at least 90%, at least 95%, at least 96%, at least 97%, at least 98%, or at least 99% identity to the nucleotide sequence of SEQ ID NO: 76, optionally wherein the open reading frame comprises the nucleotide sequence of SEQ ID NOs: 76.

In some embodiments, the NTD is linked to an RBD of a SARS-CoV-2 Spike protein to form an NTD-RBD fusion protein.

In some embodiments, the NTD-RBD fusion is linked to a transmembrane domain (TM), optionally an influenza hemagglutinin transmembrane domain, to form an NTD-RBD-TM protein.

In some embodiments, the antigen comprises an amino acid sequence having at least 80%, at least 85%, at least 90%, at least 95%, at least 96%, at least 97%, at least 98%, or at least 99% identity to the amino acid sequence of SEQ ID NO: 92, optionally wherein the antigen comprises the amino acid sequence of SEQ ID NO: 92.

In some embodiments, the open reading frame comprises a nucleotide sequence having at least 70%, least 75%, at least 80%, at least 90%, at least 95%, at least 96%, at least 97%, at least 98%, or at least 99% identity to the nucleotide sequence of SEQ ID NO: 91, optionally wherein the open reading frame comprises the nucleotide sequence of SEQ ID NO: 91.

In some embodiments, the NTD-RBD fusion comprises a C-terminal truncation.

In some embodiments, the antigen comprises an amino acid sequence having at least 80%, at least 85%, at least 90%, at least 95%, at least 96%, at least 97%, at least 98%, or at least 99% identity to the amino acid sequence of SEQ ID NO: 107, optionally wherein the antigen comprises the amino acid sequence of SEQ ID NO: 107.

In some embodiments, the open reading frame comprises a nucleotide sequence having at least 70%, least 75%, at least 80%, at least 90%, at least 95%, at least 96%, at least 97%, at least 98%, or at least 99% identity to the nucleotide sequence of SEQ ID NO: 106, optionally wherein the open reading frame comprises the nucleotide sequence of SEQ ID NO: 106.

In some embodiments, the NTD and/or RBD includes an extended region.

In some embodiments, the antigen comprises an amino acid sequence having at least 80%, at least 85%, at least 90%, at least 95%, at least 96%, at least 97%, at least 98%, or at least 99% identity to the amino acid sequence of any one of SEQ ID NOs: 59, 86, 89, 116, 119, or 122, optionally wherein the antigen comprises the amino acid sequence of any one of SEQ ID NOs: 59, 86, 89, 116, 119, or 122.

In some embodiments, the open reading frame comprises a nucleotide sequence having at least 70%, least 75%, at least 80%, at least 90%, at least 95%, at least 96%, at least 97%, at least 98%, or at least 99% identity to the nucleotide sequence of any one of SEQ ID NOs: 58, 85, 88, 115, 118, or 121, optionally wherein the open reading frame comprises the nucleotide sequence of any one of SEQ ID NOs: 58, 85, 88, 115, 118, or 121.

In some embodiments, the protein domain is an S1 subunit domain of a SARS-CoV-2 Spike protein.

In some embodiments, the S1 subunit is soluble.

In some embodiments, the antigen comprises an amino acid sequence having at least 80%, at least 85%, at least 90%, at least 95%, at least 96%, at least 97%, at least 98%, or at least 99% identity to the amino acid sequence of SEQ ID NO: 5, optionally wherein the antigen comprises the amino acid sequence of SEQ ID NO: 5.

In some embodiments, the open reading frame comprises a nucleotide sequence having at least 70%, least 75%, at least 80%, at least 90%, at least 95%, at least 96%, at least 97%, at least 98%, or at least 99% identity to the nucleotide sequence of SEQ ID NO: 3, optionally wherein the open reading frame comprises the nucleotide sequence of SEQ ID NO: 3.

In some embodiments, the S1 subunit is linked to a transmembrane domain, optionally an influenza hemagglutinin transmembrane domain.

In some embodiments, the antigen comprises an amino acid sequence having at least 80%, at least 85%, at least 90%, at least 95%, at least 96%, at least 97%, at least 98%, or at least 99% identity to the amino acid sequence of SEQ ID NO: 17, optionally wherein the antigen comprises the amino acid sequence of SEQ ID NO: 17.

In some embodiments, the open reading frame comprises a nucleotide sequence having at least 70%, least 75%, at least 80%, at least 90%, at least 95%, at least 96%, at least 97%, at least 98%, or at least 99% identity to the nucleotide sequence of SEQ ID NO: 16, optionally wherein the open reading frame comprises the nucleotide sequence of SEQ ID NO: 16.

In some embodiments, the S1 subunit has been modified to remove an RBD or a portion of an RBD of S protein.

In some embodiments, the antigen comprises an amino acid sequence having at least 80%, at least 85%, at least 90%, at least 95%, at least 96%, at least 97%, at least 98%, or at least 99% identity to the amino acid sequence of any one of SEQ ID NOs: 20, 23, 26, 29, 32 or 35, optionally wherein the antigen comprises the amino acid sequence of any one of SEQ ID NOs: 20, 23, 26, 29, 32, or 35.

In some embodiments, the open reading frame comprises a nucleotide sequence having at least 70%, least 75%, at least 80%, at least 90%, at least 95%, at least 96%, at least 97%, at least 98%, or at least 99% identity to the nucleotide sequence of any one of SEQ ID NOs: 19, 22, 25, 28, 41, or 34, optionally wherein the open reading frame comprises the nucleotide sequence of any one of SEQ ID NOs: 19, 22, 25, 28, 31, or 34.

In some embodiments, the S1 subunit is linked to an S2 subunit of an S protein.

In some embodiments, the S2 subunit is from a SARS-CoV-2 S protein.

In some embodiments, the S1 subunit is from an HKU1 S protein.

In some embodiments, the antigen comprises an amino acid sequence having at least 80%, at least 85%, at least 90%, at least 95%, at least 96%, at least 97%, at least 98%, or at least 99% identity to the amino acid sequence of SEQ ID NO: 38, optionally wherein the antigen comprises the amino acid sequence of SEQ ID NO: 38.

In some embodiments, the open reading frame comprises a nucleotide sequence having at least 70%, least 75%, at least 80%, at least 90%, at least 95%, at least 96%, at least 97%, at least 98%, or at least 99% identity to the nucleotide sequence of SEQ ID NO: 37, optionally wherein the open reading frame comprises the nucleotide sequence of SEQ ID NO: 37.

In some embodiments, the S1 subunit is from an OC43 S protein.

In some embodiments, the antigen comprises an amino acid sequence having at least 80%, at least 85%, at least 90%, at least 95%, at least 96%, at least 97%, at least 98%, or at least 99% identity to the amino acid sequence of SEQ ID NO: 41, optionally wherein the antigen comprises the amino acid sequence of SEQ ID NO: 41.

In some embodiments, the open reading frame comprises a nucleotide sequence having at least 70%, least 75%, at least 80%, at least 90%, at least 95%, at least 96%, at least 97%, at least 98%, or at least 99% identity to the nucleotide sequence of SEQ ID NO: 40, optionally wherein the open reading frame comprises the nucleotide sequence of SEQ ID NO: 40.

In some embodiments, the antigen further comprises a scaffold domain, optionally selected from ferritin, lumazine synthetase and a foldon.

In some embodiments, the scaffold domain is ferritin.

In some embodiments, the antigen comprises an amino acid sequence having at least 80%, at least 85%, at least 90%, at least 95%, at least 96%, at least 97%, at least 98%, or at least 99% identity to the amino acid sequence of SEQ ID NO: 8 or 65, optionally wherein the antigen comprises the amino acid sequence of SEQ ID NO: 8 or 65.

In some embodiments, the open reading frame comprises a nucleotide sequence having at least 70%, least 75%, at least 80%, at least 90%, at least 95%, at least 96%, at least 97%, at least 98%, or at least 99% identity to the nucleotide sequence of SEQ ID NO: 7 or 64, optionally wherein the open reading frame comprises the nucleotide sequence of SEQ ID NO: 7 or 64.

In some embodiments, the scaffold domain is lumazine synthetase.

In some embodiments, the antigen comprises an amino acid sequence having at least 80%, at least 85%, at least 90%, at least 95%, at least 96%, at least 97%, at least 98%, or at least 99% identity to the amino acid sequence of any one of SEQ ID NOs: 11, 14, 68, or 71, optionally wherein the antigen comprises the amino acid sequence of any one of SEQ ID NOs: 11, 14, 68, or 71.

In some embodiments, the open reading frame comprises a nucleotide sequence having at least 70%, least 75%, at least 80%, at least 90%, at least 95%, at least 96%, at least 97%, at least 98%, or at least 99% identity to the nucleotide sequence of any one of SEQ ID NOs: 10, 13, 67, or 70, optionally wherein the open reading frame comprises the nucleotide sequence of any one of SEQ ID NOs: 10, 13, 67, or 70.

In some embodiments, the scaffold domain is a foldon.

In some embodiments, the antigen comprises an amino acid sequence having at least 80%, at least 85%, at least 90%, at least 95%, at least 96%, at least 97%, at least 98%, or at least 99% identity to the amino acid sequence of any one of SEQ ID NOs: 44, 50, 74, 80, 83, 101, 104 or 113, optionally wherein the antigen comprises the amino acid sequence of any one of SEQ ID NOs: 44, 50, 74, 80, 83, 101, 104 or 113.

In some embodiments, the open reading frame comprises a nucleotide sequence having at least 70%, least 75%, at least 80%, at least 90%, at least 95%, at least 96%, at least 97%, at least 98%, or at least 99% identity to the nucleotide sequence of any one of SEQ ID NOs: 43, 49, 73, 79, 82, 100, 103, or 112, optionally wherein the open reading frame comprises the nucleotide sequence of any one of SEQ ID NOs: 43, 49, 73, 79, 82, 100, 103, or 112.

In some embodiments, the antigen further comprises a trafficking signal, optionally selected from macrophage markers, optionally CD86, CD11B and/or VSVGct.

In some embodiments, the antigen comprises an amino acid sequence having at least 80%, at least 85%, at least 90%, at least 95%, at least 96%, at least 97%, at least 98%, or at least 99% identity to the amino acid sequence of any one of SEQ ID NOs: 95, 98, or 110, optionally wherein the antigen comprises the amino acid sequence of any one of SEQ ID NOs: 95, 98, or 110.

In some embodiments, the open reading frame comprises a nucleotide sequence having at least 70%, least 75%, at least 80%, at least 90%, at least 95%, at least 96%, at least 97%, at least 98%, or at least 99% identity to the nucleotide sequence of any one of SEQ ID NOs: 94, 97, or 109, optionally wherein the open reading frame comprises the nucleotide sequence of any one of SEQ ID NOs: 94, 97, or 109.

In some embodiments, the mRNA is formulated in a lipid nanoparticle.

In some embodiments, the lipid nanoparticle comprises a cationic lipid, optionally an ionizable cationic lipid, a neutral lipid, a sterol, and/or a polyethylene glycol (PEG)-modified lipid. An ionizable cationic lipid is used interchangeably herein with ionizable lipid and cationic lipid to refer to an ionizable lipid. In some embodiments, the lipid nanoparticle comprises 40-50 mol % ionizable lipid, optionally 45-50 mol %, for example, 45-46 mol %, 46-47 mol %, 47-48 mol %, 48-49 mol %, or 49-50 mol % for example about 45 mol %, 45.5 mol %, 46 mol %, 46.5 mol %, 47 mol %, 47.5 mol %, 48 mol %, 48.5 mol %, 49 mol %, or 49.5 mol %. In some embodiments, the lipid nanoparticle comprises 30-45 mol % sterol, optionally 35-40 mol %, for example, 30-31 mol %, 31-32 mol %, 32-33 mol %, 33-34 mol %, 35-35 mol %, 35-36 mol %, 36-37 mol %, 38-38 mol %, 38-39 mol %, or 39-40 mol %. In some embodiments, the lipid nanoparticle comprises 5-15 mol % helper lipid, optionally 10-12 mol %, for example, 5-6 mol %, 6-7 mol %, 7-8 mol %, 8-9 mol %, 9-10 mol %, 10-11 mol %, 11-12 mol %, 12-13 mol %, 13-14 mol %, or 14-15 mol %. In some embodiments, the lipid nanoparticle comprises 1-5% PEG lipid, optionally 1-3 mol %, for example 1.5 to 2.5 mol %, 1-2 mol %, 2-3 mol %, 3-4 mol %, or 4-5 mol %.

In some embodiments, the ionizable cationic lipid is heptadecan-9-yl 8 ((2 hydroxyethyl)(6 oxo 6-(undecyloxy) hexyl)amino)octanoate (Compound 1), the neutral lipid is 1,2 distearoyl-sn-glycero-3-phosphocholine (DSPC), the sterol is cholesterol, and/or the PEG-modified lipid is 1,2 dimyristoyl-sn-glycerol, methoxypolyethyleneglycol (PEG2000 DMG).

In some embodiments, the lipid nanoparticle comprises 20-60 mol % ionizable cationic lipid, 5-25 mol % neutral lipid, 25-55 mol % sterol, and 0.5-15 mol % PEG-modified lipid.

In some embodiments, the lipid nanoparticle comprises: 47 mol % ionizable cationic lipid; 11.5 mol % neutral lipid; 38.5 mol % sterol; and 3.0 mol % PEG-modified lipid; 48 mol % ionizable cationic lipid; 11 mol % neutral lipid; 38.5 mol % sterol; and 2.5 mol % PEG-modified lipid; 49 mol % ionizable cationic lipid; 10.5 mol % neutral lipid; 38.5 mol % sterol; and 2.0 mol % PEG-modified lipid; 50 mol % ionizable cationic lipid; 10 mol % neutral lipid; 38.5 mol % sterol; and 1.5 mol % PEG-modified lipid; or 51 mol % ionizable cationic lipid; 9.5 mol % neutral lipid; 38.5 mol % sterol; and 1.0 mol % PEG-modified lipid.

In some embodiments, the lipid nanoparticle comprises: 47 mol % Compound 1; 11.5 mol % DSPC; 38.5 mol % cholesterol; and 3.0 mol % PEG2000 DMG; 48 mol % Compound 1; 11 mol % DSPC; 38.5 mol % cholesterol; and 2.5 mol % PEG2000 DMG; 49 mol % Compound 1; 10.5 mol % DSPC; 38.5 mol % cholesterol; and 2.0 mol % PEG2000 DMG; 50 mol % Compound 1; 10 mol % DSPC; 38.5 mol % cholesterol; and 1.5 mol % PEG2000 DMG; or 51 mol % Compound 1; 9.5 mol % DSPC; 38.5 mol % cholesterol; and 1.0 mol % PEG2000 DMG.

The entire contents of International Application No. PCT/US2016/058327 (Publication No. WO2017/070626) and International Application No. PCT/US2018/022777 (Publication No. WO2018/170347) are incorporated herein by reference.

SARS-Cov-2

The genome of SARS-CoV-2 is a single-stranded positive-sense RNA (+ssRNA) with the size of 29.8-30 kb encoding about 9860 amino acids (Chan et al. 2000, supra; Kim et al. 2020 Cell, May 14; 181(4):914-921.e10.). SARS-CoV-2 is a polycistronic mRNA with 5'-cap and 3'-poly-A tail. The SARS-CoV-2 genome is organized into specific genes encoding structural proteins and nonstructural proteins (Nsps). The order of the structural proteins in the genome is 5'-replicase (open reading frame (ORF)1/ab)-structural proteins [Spike (S)-Envelope (E)-Membrane (M)-Nucleocapsid (N)]-3'. The genome of coronaviruses includes a variable number of open reading frames that encode accessory proteins, nonstructural proteins, and structural proteins (Song et al. 2019 Viruses; 11(1):p. 59). Most of the antigenic peptides are located in the structural proteins (Cui et al. 2019 Nat. Rev. Microbiol.;

17(3):181-192). Spike surface glycoprotein (S), a small envelope protein (E), matrix protein (M), and nucleocapsid protein (N) are four main structural proteins. Since S-protein contributes to cell tropism it is capable of inducing neutralizing antibodies (NAb) and protective immunity, it can be considered one of the most important targets in coronavirus vaccine development among all other structural proteins. Moreover, amino acid sequence analysis has shown that S-protein contains conserved regions among the coronaviruses, which may be the basis for universal vaccine development Antigens The compositions of the invention, e.g., vaccine compositions, feature nucleic acids, in particular, mRNAs, designed to encode an antigen of interest, e.g., an antigen derived from a betacoronavirus structural protein, in particular, antigens derived from SARS-CoV-2 Spike protein. The compositions of the invention, e.g., vaccine compositions, do not comprise antigens per se, but rather comprise nucleic acids, in particular, mRNA(s) that encode antigens or antigenic sequences once delivered to a cell, tissue or subject. Delivery of nucleic acid molecules, in particular mRNA(s) is achieved by formulating said nucleic acid molecules in appropriate carriers or delivery vehicles (e.g., lipid nanoparticles) such that upon administration to cells, tissues or subjects, nucleic acid is taken up by cells which, in turn, express protein(s) encoded by the nucleic acids, e.g., mRNAs. The term "antigen" as used herein refers to a substance such as a protein (e.g., glycoprotein), polypeptide, peptide, or the like, which elicits an immune response, e.g., elicits an immune response when present in a subject (for example, when present in a human or mammalian subject). The instant invention is based at least in part on the understanding that mRNA-encoded antigens, when expressed from mRNA administered to a cell or subject, can cause the immune system to produce an immune response to the expressed antigen, for example can trigger the production of antibodies against the expresses antigen, e.g., binding and/or neutralizing antibodies, can trigger B and or T cell responses specific to the expressed antigen, and ultimately can cause protective or prophylactic response against subsequent encounter with the antigen or with a pathogen with which the antigen is associated. Preferred mRNA-encoded antigens are "viral antigens". As used herein, the term "viral antigen" refers to an antigen derived from a virus, for example from a pathogenic virus. The term antigen as used herein can refer to a full-length protein, for example, a full-length viral protein, or can refer to a fragment (e.g., a polypeptide or peptide fragment), subunit or domain of a protein, e.g., a viral protein subunit or domain.

Many proteins have a quaternary or three-dimensional structure, which consists of more than one polypeptide or several polypeptide chains that associate into an oligomeric molecule. As used herein the term "subunit" refers to a single protein molecule, for example, a polypeptide or polypeptide chain resulting from processing of a nascent protein molecule, which subunit assembles (or "coassembles") with other protein molecules (e.g., subunits or chains) to form a protein complex. Proteins can have a relatively small number of subunits and therefore be described as "oligomeric" or can consist of a large number of subunits and therefore be described as "multimeric". The subunits of an oligomeric or multimeric protein may be identical, homologous or totally dissimilar and dedicated to disparate tasks.

Proteins or protein subunits can further comprise domains. As used herein, the term "domain" refers to a distinct functional and/or structural unit within a protein. Typically, a "domain" is responsible for a particular function or interaction, contributing to the overall role of a protein. Domains can exist in a variety of biological contexts. Similar domains (i.e., domains sharing structural, functional and/or sequence homology) can exist within a single protein or can exist within distinct proteins having similar or different functions. A protein domain is often a conserved part of a given protein tertiary structure or sequence that can function and exist independently of the rest of the protein or subunit thereof.

In structural and molecular biology, identical, homologous or similar subunits or domains can help to classify newly identified or novel proteins, as was done immediately upon publication of the SARS-CoV-2 viral genomic sequence.

As used herein, the term antigen is distinct from the term "epitope" which is a substructure of an antigen, e.g., a polypeptide or carbohydrate structure, which may be recognized by an antigen binding site but is insufficient to induce an immune response. The art describes protein antigens that are delivered to subjects or immune cells in isolated form, e.g., isolated protein, polypeptide or peptide antigens, however, the design, testing, validation, and production of protein antigens can be costly and time-consuming, especially when producing proteins at large scale. By contrast, mRNA technology is amenable to rapid design and testing of mRNA constructs encoding a variety of antigens. Moreover, rapid production of mRNA coupled with formulation in appropriate delivery vehicles (e.g., lipid nanoparticles), can proceed quickly and can rapidly produce mRNA vaccines at large scale. Potential benefit also arises from the fact that antigens encoded by the mRNAs of the invention are expressed by the cells of the subject, e.g., are expressed by the human body, and thus the subject, e.g., the human body, serves as the "factory" to produce the antigens which, in turn, elicits the desired immune response.

In preferred aspects, antigens are proteins capable of inducing an immune response (e.g., causing an immune system to produce antibodies against the antigens). Herein, use of the term "antigen" encompasses immunogenic proteins, as well as polypeptides or peptides derived from immunogenic proteins, for example immunogenic fragments (an immunogenic fragment that induces (or is capable of inducing) an immune response to an antigen, unless otherwise stated. It should be understood that the term "protein" encompasses polypeptides and peptides and the term "antigen" encompasses antigenic fragments. Other molecules may be antigenic such as bacterial polysaccharides or combinations of protein and polysaccharide structures, but for the viral vaccines included herein, viral proteins, fragments of viral proteins and designed and or mutated proteins derived from the betacoronavirus SARS-CoV-2 are the antigens featured herein.

Nucleic Acids/mRNA

The vaccine technology described herein features nucleic acids, particularly messenger RNA (mRNA) designed to encode an antigen of interest, e.g., a betacoronavirus spike protein antigen, subunit, domain or fragments (e.g., antigenic fragments) thereof. The nucleic acids, for example mRNAs, of the invention are preferably formulated in appropriate carriers or delivery vehicles (e.g., lipid nanoparticles), such that the nucleic acids, e.g., mRNAs are suitable for use in vivo. When appropriately formulated, nucleic acids, e.g., mRNAs, are capable of being delivered to cells and/or tissues within a subject, e.g., a human subject, to effectuate translation of protein encoded by these nucleic acids.

Nucleic acid molecules are macromolecules comprised of linked nucleotides that carry that carry genetic information and by directing the process of protein synthesis, direct most if not all cellular functions. Nucleic acids comprise a polymer of nucleotides (nucleotide monomers). Thus, nucleic acids are also referred to as polynucleotides (also referred to as polynucleotide chains). The two main classes of nucleic acids are deoxyribonucleic acid (DNA) and ribonucleic acid (RNA). DNA constitutes the genetic material in all free-living organisms and most viruses. RNA is the genetic material of certain viruses, but it is also found in all living cells, where it plays an important role cellular processes, most notably the making of proteins.

Nucleosides are the structural subunit of nucleic acids such as DNA and RNA. A nucleoside is composed of a nitrogenous base (a nucleobase), usually either a pyrimidine (cytosine, thymine or uracil) or a purine (adenine or guanine), covalently attached to a five-carbon carbohydrate ribose or "sugar" which is either ribose or deoxyribose. Nucleotides consist of a nitrogenous base, a sugar (ribose or deoxyribose) and one to three phosphate groups. In essence, a nucleotide is simply a nucleoside with an additional phosphate group or groups.

The nucleic acid molecules, DNA and RNA, are composed of nucleotides that are linked to one another in a chain by chemical bonds, called ester bonds, between the sugar base of one nucleotide and the phosphate group of the adjacent nucleotide. The sugar is the 3' end, and the phosphate is the 5' end of each nucleotide. The phosphate group attached to the 5' carbon of the sugar on one nucleotide forms an ester bond with the free hydroxyl on the 3' carbon of the next nucleotide. These bonds are called phosphodiester bonds, and the sugar-phosphate backbone is described as extending, or growing, in the 5' to 3' direction when the molecule is synthesized.

The nucleobase portion of nucleic acids features purine bases, adenine (A) and guanine (G), and pyrimidine bases, cytosine (C), thymine (T) in DNA, and uracil (U) in RNA. The sugar portion of nucleic acids features deoxyribose in DNA, ribose in RNA. The five nucleosides are commonly abbreviated to their one-letter codes A, G, C, T and U, respectively. However, thymidine is more commonly written as "dT" ("d" represents "deoxy") as it contains a 2'-deoxyribofuranose moiety rather than the ribofuranose ring found in uridine. This is because thymidine is found in deoxyribonucleic acid (DNA) and not ribonucleic acid (RNA). Conversely, uridine is found in RNA and not DNA. The remaining three nucleosides may be found in both RNA and DNA. In RNA, they would be represented as A, C and G whereas in DNA they would be represented as dA, dC and dG.

The skilled artisan will appreciate that, except where otherwise noted, nucleic acid sequences set forth in the instant application may recite "T"s in a representative DNA sequence but where the sequence represents mRNA, the "T"s would be substituted for "U"s. Thus, any of the DNAs disclosed and identified by a particular sequence identification number herein also disclose the corresponding mRNA sequence complementary to the DNA, where each "T" of the DNA sequence is substituted with "U."

Nucleic acids may be or may include, for example, deoxyribonucleic acids (DNAs), ribonucleic acids (RNAs), e.g. mRNAs, threose nucleic acids (TNAs), glycol nucleic acids (GNAs), peptide nucleic acids (PNAs), locked nucleic acids (LNAs, including LNA having a p-D-ribo configuration, α-LNA having an α-L-ribo configuration (a diastereomer of LNA), 2'-amino-LNA having a 2'-amino functionalization, and 2'-amino-α-LNA having a 2'-amino functionalization), ethylene nucleic acids (ENA), cyclohexenyl nucleic acids (CeNA) and/or chimeras and/or combinations thereof.

Featured in the instant invention are messenger RNAs (mRNAs), particularly mRNAs designed to encode an antigen of interest, e.g., a betacoronavirus spike protein antigen, subunit, domain or fragments (e.g., antigenic fragments) thereof. Messenger RNA (mRNA), a subtype of RNA, is a single-stranded molecule of RNA that corresponds to the genetic sequence of a gene. mRNA is created during the process of transcription wherein a single strand of DNA is decoded by RNA polymerase, and mRNA is synthesized, i.e., transcribed. mRNA is read by a ribosome in the process of synthesizing a protein, i.e., translation. Accordingly, messenger RNA (mRNA) is an RNA that encodes a (at least one) protein (a naturally-occurring, non-naturally-occurring, or modified polymer of amino acids) and can be translated to produce the encoded protein in vitro, in vivo, in situ, or ex vivo.

The compositions of the present disclosure comprise a (at least one) mRNA having an open reading frame (ORF) encoding a coronavirus antigen. In some embodiments, the mRNA further comprises a 5' UTR, 3' UTR, a poly(A) tail and/or a 5' cap or cap analog. An open reading frame (ORF) is a continuous stretch of DNA or RNA beginning with a start codon (e.g., methionine (ATG or AUG)) and ending with a stop codon (e.g., TAA, TAG or TGA, or UAA, UAG or UGA). An ORF typically encodes a protein. It will be understood that the sequences disclosed herein may further comprise additional elements, e.g., 5' and 3' UTRs, but that those elements, unlike the ORF, need not necessarily be present in an mRNA of the present disclosure. It should also be understood that the mRNAs if the invention, e.g., mRNAs featured in the betacoronavirus vaccines of the present disclosure, may include any 5' untranslated region (UTR) and/or any 3' UTR. Exemplary UTR sequences are provided in the Sequence Listing (e.g., SEQ ID NOs: 2, 4, 131, and 132); however, other UTR sequences may be used or exchanged for any of the UTR sequences described herein. UTRs may also be omitted from the mRNAs provided herein.

In some embodiments, a composition comprises an mRNA that comprises a nucleotide sequence having at least 70%, at least 75%, at least 80%, at least 85%, at least 90%, at least 95%, at least 96%, at least 97%, at least 98%, at least 99%, or 100% identity to the nucleotide sequence of any one of SEQ ID NOs: 45, 75, or 90. In some embodiments, a composition comprises an mRNA that comprises a nucleotide sequence having at least 70%, at least 75%, at least 80%, at least 85%, at least 90%, at least 95%, at least 96%, at least 97%, at least 98%, at least 99%, or 100% identity to the nucleotide sequence of any one of the sequences in Tables 1-15.

In some embodiments, a composition comprises an mRNA that comprises an ORF having at least 70%, at least 75%, at least 80%, at least 85%, at least 90%, at least 95%, at least 96%, at least 97%, at least 98%, at least 99%, or 100% identity to the nucleotide sequence of any one of SEQ ID NOs: 46, 76, or 91. In some embodiments, a composition comprises an mRNA that comprises an ORF having at least 70%, at least 75%, at least 80%, at least 85%, at least 90%, at least 95%, at least 96%, at least 97%, at least 98%, at least 99%, or 100% identity to the nucleotide sequence of any one of the sequences in Table 1-15.

Exemplary sequences of the coronavirus antigens and the mRNA encoding the coronavirus antigens of the compositions of the present disclosure are provided in Tables 1-15.

It should be understood that any one of the antigens encoded by the mRNA described herein may or may not comprise a signal sequence.

Encoded Coronavirus Spike (S) Protein Antigens

The envelope spike (S) proteins of known betacoronaviruses determine the virus host tropism and entry into host cells. Coronavirus spike (S) protein is a choice antigen for the vaccine design as it can induce neutralizing antibodies and protective immunity. S protein is critical for SARS-CoV-2 infection. The organization of the S protein is similar among betacoronaviruses, such as SARS-CoV-2, SARS-CoV, MERS-CoV, HKU1-CoV, MHV-CoV and NL63-CoV.

As used herein, the term "Spike protein" refers to a glycoprotein that that forms homotrimers protruding from the envelope (viral surface) of viruses including betacoronaviruses. Trimerized Spike protein facilitates entry of the virion into a host cell by binding to a receptor on the surface of a host cell followed by fusion of the viral and host cell membranes. The S protein is a highly glycosylated and large type I transmembrane fusion protein that is made up of 1,160 to 1,400 amino acids, depending upon the type of virus. Betacoronavirus Spike proteins comprise between about 1100 to 1500 amino acids and comprise the structure (i.e., the domain composition and organization) as set forth in FIG. 1. SARS-CoV-2 spike (S) protein is a choice antigen for the vaccine design as it can induce neutralizing antibodies and protective immunity. mRNAs of the invention are designed to produce SARS-CoV-2 Spike proteins (i.e., encode Spike proteins such that Spike protein is expressed when the mRNA is delivered to a cell or tissue, for example a cell or tissue in a subject), as well as antigenic variants thereof. The skilled artisan will understand that, while an essentially full length or complete Spike protein may be necessary for a virus, e.g., a betacoronavirus, to perform its intended function of facilitating virus entry into a host cell, a certain amount of variation in Spike protein structure and/or sequence is tolerated when seeking primarily to elicit an immune response against Spike protein. For example, minor truncation, e.g., of one to a few, possibly up to 5 or up to 10 amino acids from the N- or C-terminus of the encoded Spike protein, e.g., encoded Spike protein antigen, may be tolerated without changing the antigenic properties of the protein. Likewise, variation (e.g., conservative substitution) of one to a few, possibly up to 5 or up to 10 amino acids (or more) of the encoded Spike protein, e.g., encoded Spike protein antigen, may be tolerated without changing the antigenic properties of the protein. In exemplary embodiments, a Spike protein, e.g., an encoded Spike protein antigen, has the amino acid sequence set forth in any one of the sequences of Tables 1-15 (e.g., derived from the amino acid sequence set forth as SEQ ID NO: 125). In other embodiments, a Spike protein, e.g., an encoded Spike protein antigen, has no greater than 100, no greater than 90, no greater than 80, no greater than 70, no greater than 60, no greater than 50, no greater than 40, no greater than 30, no greater than 20, no greater than 10, or no greater than 5 amino acid substitutions and/or deletions as compared to (when aligned with) a Spike protein having the amino acid sequence as set forth in any one of the sequences of Tables 1-15 (e.g., derived from the amino acid sequence set forth as SEQ ID NO: 125). Where minor variations are made in encoded Spike protein sequences, the variant preferably has the same activity as the reference Spike protein sequence and/or has the same immune specificity as the reference Spike protein, as determined for example, in immunoassays (e.g., enzyme-linked immunosorbent assays (ELISA assays).

S proteins of coronaviruses can be divided into two important functional subunits, of which include the N-terminal S1 subunit, which forms of the globular head of the S protein, and the C-terminal S2 region that forms the stalk of the protein and is directly embedded into the viral envelope. Upon interaction with a potential host cell, the S1 subunit will recognize and bind to receptors on the host cell, specifically angiotensin-converting enzyme 2 (ACE2) receptors, whereas the S2 subunit, which is the most conserved component of the S protein, will be responsible for fusing the envelope of the virus with the host cell membrane. (See e.g., Shang et al., PLoS Pathog. 2020 March; 16(3): e1008392.). Each monomer of trimeric S protein trimer contains the two subunits, S1 and S2, mediating attachment and membrane fusion, respectively. See, e.g., FIG. 1. As part of the infection process in vivo, the two subunits are separated from each other by an enzymatic cleavage process. S protein is first cleaved by furin-mediated cleavage at the S1/S2 site in infected cells, In vivo, a subsequent serine protease-mediated cleavage event occurs at the S2' site within S1. In SARS-CoV2, the S1/S2 cleavage site is at amino acids 676—TQTNSPRRAR/SVA—688 (referencing SEQ ID NO: 127). The S2' cleavage site is at amino acids 811—KPSKR/SFI—818 (referencing SEQ ID NO: 126).

As used herein, for example in the context of designing SARS-CoV-2 S protein antigens encoded by the nucleic acids, e.g., mRNAs, of the invention, the term "S1 subunit" (e.g., S1 subunit antigen) refers to the N-terminal subunit of the Spike protein beginning at the S protein N-terminus and ending at the S1/S2 cleavage site whereas the term "S2 subunit" (e.g., S2 subunit antigen) refers to the C-terminal subunit of the Spike protein beginning at the S1/S2 cleavage site and ending at the C-terminus of the Spike protein. As described supra, the skilled artisan will understand that, while an essentially full length or complete Spike protein S1 or S2 subunit may be necessary for receptor binding or membrane fusion, respectively, a certain amount of variation in S1 or S2 structure and/or sequence is tolerated when seeking primarily to elicit an immune response against Spike protein subunits. For example, minor truncation, e.g., of one to a few, possibly up to 4, 5, 6, 7, 8, 9 or 10 amino acids from the N- or C-terminus of the encoded subunit, e.g., encoded S1 or S2 protein antigens, may be tolerated without changing the antigenic properties of the protein. Likewise, variation (e.g., conservative substitution) of one to a few, possibly up to 4, 5, 6, 7, 8, 9 or 10 amino acids (or more) of the encoded Spike protein subunits, e.g., encoded S1 or S2 protein antigen, may be tolerated without changing the antigenic properties of the protein(s). In exemplary embodiments, a Spike protein, e.g., an encoded Spike protein antigen, has the amino acid sequence set forth in any one of the sequences of Tables 1-15 (e.g., derived from the amino acid sequence set forth as SEQ ID NO: 125). In other embodiments, a Spike protein subunit, e.g., an encoded S1 or S2 protein antigen, has no greater than 50, no greater than 40, no greater than 30, no greater than 20, no greater than 10, or no greater than 5 amino acid substitutions and/or deletions as compared to (when aligned with) a Spike protein S1 subunit comprising or consisting of amino acids 1-685 or a Spike protein S2 subunit comprising or consisting of amino acids 686-1273 of the Spike protein having the amino acid sequence as set forth as SEQ ID NO: 125. Where minor variations are made in encoded Spike protein subunit sequences, the variant preferably has the same activity as the reference Spike protein subunit sequence and/or has the same immune specificity as the reference Spike protein subunit, as determined for example, in immunoassays (e.g., enzyme-linked immunosorbent assays (ELISA assays).

The S1 and S2 subunits of the SARS-CoV-2 Spike protein further include domains readily discernable by structure and function, which in turn can be featured in designing antigens to be encoded by the nucleic acid vaccines, in particular, mRNA vaccines of the invention. Within the S1 subunit, domains include the N-terminal domain (NTD) and the receptor-binding domain (RBD), said RBD domain further including a receptor-binding motif (RBM). The wild type S1 subunit also includes a signal peptide (SD), N-terminal to the NTD domain and a first subdomain (SD1) and second subdomain (SD2). Within the S2 subunit, domains include fusion peptide (FP), heptad repeat 1 (HR1), heptad repeat 2 (HR2), transmembrane domain (TM), and cytoplasm domain, also known as cytoplasmic tail (CT) (Lu R. et al., supra; Wan et al., J. Virol. March 2020, 94 (7) e00127-20). The HR1 and HR2 domains can be referred to as the "fusion core region" of SARS-CoV-2 (Xia et al., 2020 Cell Mol Immunol. January; 17(1):1-12.). FIG. 1 depicts the domain architecture in the SARS-CoV-2 Spike protein. The S1 subunit includes an N terminal domain (NTD), a linker region, a receptor binding domain (RBD), a first subdomain (SD1), and a second subdomain (SD2). An S1 subunit may be modified to add a C-terminal transmembrane domain (TM) or it may be soluble. The S2 subunit includes, inter alia, a first heptad repeat (HR1), a second heptad repeat (HR2), a transmembrane domain (TM), and a cytoplasmic tail. A soluble S2 subunit may be generated without a TM domain.

The NTD and RBD of S1 are good antigens for the vaccine design approach of the invention as these domains have been shown to be the targets of neutralizing antibodies in betacoronavirus-infected individuals. As used herein, for example, in the context of an antigen design (said antigen encoded by an mRNA of the invention and to be expressed, for example, from and mRNA vaccine of the invention), the term "N-terminal domain" or "NTD" refers to a domain within the SARS-CoV-2 S1 subunit comprising approximately 290 amino acids in length, having identity to amino acids 1-290 of the S1 subunit of the Spike protein having the amino acid sequence set forth as SEQ ID NO: 125. As used herein, for example, in the context of an antigen design (said antigen encoded by an mRNA of the invention and to be expressed, for example, from and mRNA vaccine of the invention), the term "receptor binding domain" or "RBD" refers to a domain within the S1 subunit of SARS-CoV-2 comprising approximately 175-225 amino acids in length, having identity to amino acids 316-517 of the S1 subunit of the Spike protein having the amino acid sequence set forth as SEQ ID NO: 125. As used herein, the term "receptor binding motif" refers to the portion of the RBD that directly contacts the ACE2 receptor. Expressed RBDs are predicted to specifically bind to angiotensin-converting enzyme 2 (ACE2) as its receptor and/or specifically react with RBD-binding and/or neutralizing antibodies, e.g., CR3022.

The compositions provided herein include mRNA that may encode any one or more full-length or partial (truncated or other deletion of sequence) S protein subunit (e.g., S1 or S2 subunit), one or more domain or combination of domains of an S protein subunit (e.g., NTD, RBD, or NTD-RBD fusions, with or without an SD1 and/or SD2), or chimeras of full-length or partial and S2 protein subunits. Other S protein subunit and/or domain configurations are contemplated herein.

Figure 2:
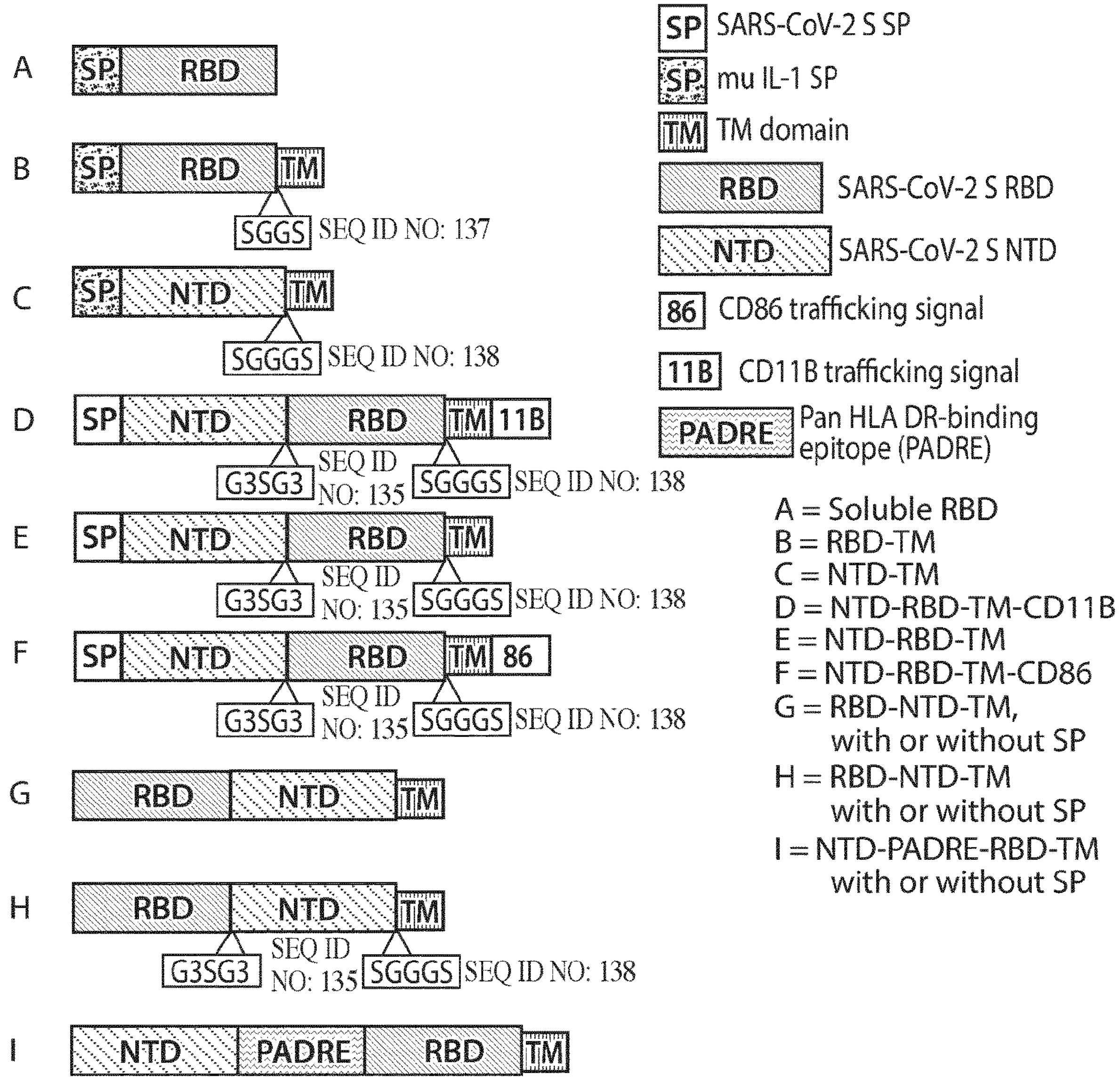
FIG. 2 shows exemplary linear designs of the antigens encoded by the mRNAs described in Examples 1-3.
Figure 6:
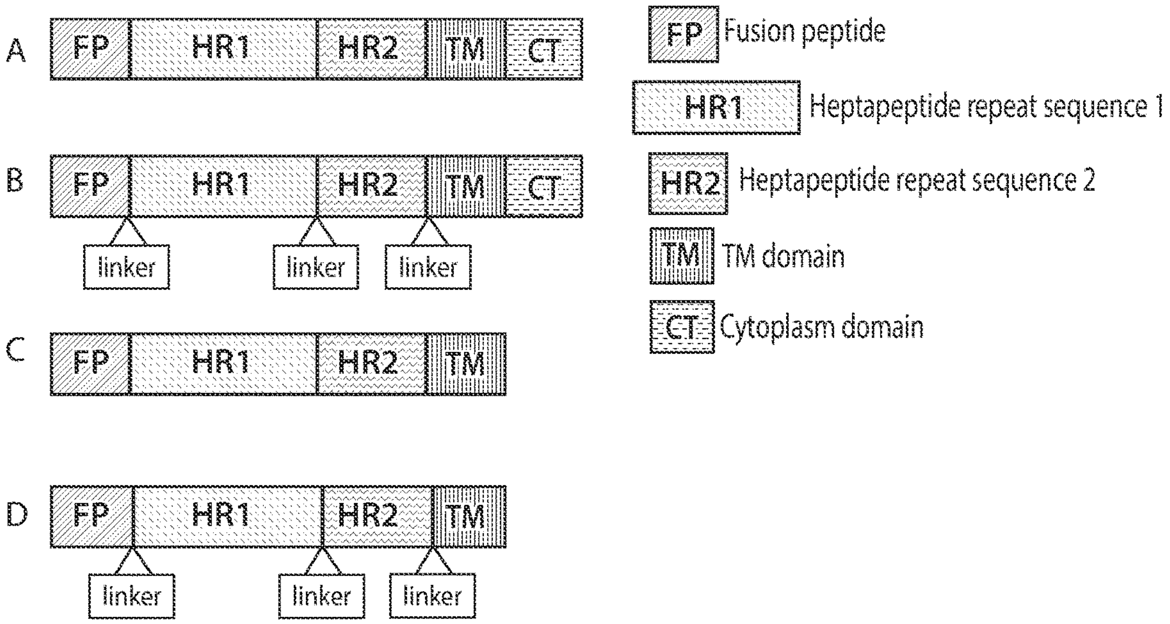
FIG. 6 shows exemplary linear designs of the antigens encoded by the mRNAs described in Examples 7 and 8.

FIG. 2 and FIG. 6 depict exemplary domain and subunit antigens derived from the SARS-CoV-2 Spike protein. FIGS. 2A and 2B depict soluble and transmembrane RBD antigens respectively. A transmembrane NTD antigen is shown in FIG. 2C. The domain antigens shown in FIGS. 2D-2F and 2I represent exemplary fusion proteins of NTD and RBD, each with a SP and TM domain. Two of the constructs also have a terminal trafficking domain (CD86 and/or CD11b). The domains are linked through linkers, in particular GS linkers or a PADRE linker (FIG. 2I). Domain constructs having an RBD domain N-terminal to an NTD domain are depicted in FIGS. 2G and 2H. Each construct may also include a SP and/or TM domain.

Encoded Subunit Antigens

Some aspects of the present disclosure provide compositions comprising an mRNA that encodes a (at least one) subunit of a SARS-CoV-2 S protein. In some embodiments, the mRNA encodes an S1 subunit (e.g., full length or partial). In other embodiments, the mRNA encodes an S2 subunit (e.g., full length or partial). In yet other embodiments, the mRNA encodes a chimeric S1-S2 protein, wherein one of the subunits is from a SARS-CoV-2 S protein, and the other subunit is from another organism, e.g., a virus, such influenza virus. The SARS-CoV-2 subunits (S1 and/or S2) encoded by the mRNA of the present disclosure may be soluble or membrane bound (e.g., linked to a transmembrane domain). Exemplary antigen designs based on S2 are shown in FIG. 6. FIG. 6A depicts a full length S2, including the FP, HR1, HR2, TM and CT domains. A version of S2 comprised of linkers between subunits is shown in FIG. 6B. Domain antigens without the CT domain are shown in FIGS. 6C and 6D.

Soluble Subunit Antigens

A soluble protein is present in the cytoplasm of a cell or is secreted from a cell (e.g., not membrane bound). Soluble antigens secreted by cells may be opsonized by complement and captured by follicular dendritic cells in lymph nodes, where they may be recognized by B cells specific to epitopes present on the expressed protein. The expression of subunit antigens further allows focusing of the immune response to specific subunits and with minimal stimulation of memory B and T cells specific to other domains of the antigen that are shared with other related viruses. Without being bound by theory, it is thought that presentation of the SARS-CoV-2 S1 subunit, including the NTD, the RBD, and, in some instances, the intervening polypeptides of the SARS-CoV-2 S1 subunit, in soluble form, generates an S1 subunit-specific immune response. Thus, in some embodiments, an mRNA provided herein encodes a soluble SARS-CoV-2 S1 subunit antigen and/or a soluble SARS-CoV-2 S2 subunit antigen. A non-limiting example of a soluble SARS-CoV-2 S1 subunit antigen and the mRNA encoding it is provided in Tables 1A and 1B below. Other examples of soluble SARS-CoV-2 subunit antigens are provided herein.

TABLE 1A

| Soluble Subunit Antigen | | |
|---|---|---|
| | SEQ ID NO: | |
| Name | mRNA ORF | Protein |
| SARS-CoV-2 Soluble S1 Subunit | 3 | 5 |

TABLE 1B

| Soluble Subunit Antigen | | |
|---|---|---|
| SARS-CoV-2 Soluble S1 Subunit | | |
| SEQ ID NO: 1 consists of from 5' end to 3' end: 5' UTR SEQ ID NO: 2, mRNA ORF SEQ ID NO: 3 and 3' UTR SEQ ID NO: 4. | | 1 |
| Chemistry | 1-methylpseudouridine | |
| Cap | 7mG(5')ppp(5')N1mpNp | |
| 5' UTR | GGGAAAUAAGAGAGAAAAGAAGAGUAAGAAGAAAUAUAAGACCCCG<br>GCGCCGCCACC | 2 |
| ORF of mRNA Construct (excluding the stop codon) | AUGUUCGUGUUCCUGGUGCUGCUGCCCCUGGUGAGCAGCCAGUGCG<br>UGAACCUGACCACCCGGACCCAGCUGCCACCAGCCUACACCAACAG<br>CUUCACCCGGGGCGUCUACUACCCCGACAAGGUGUUCCGGAGCAGC<br>GUCCUGCACAGCACCCAGGACCUGUUCCUGCCCUUCUUCAGCAACG<br>UGACCUGGUUCCACGCCAUCCACGUGAGCGGCACCAACGGCACCAA<br>GCGGUUCGACAACCCCGUGCUGCCCUUCAACGACGGCGUGUACUUC<br>GCCAGCACCGAGAAGAGCAACAUCAUCCGGGGCUGGAUCUUCGGCA<br>CCACCCUGGACAGCAAGACCCAGAGCCUGCUGAUCGUGAAUAACGC<br>CACCAACGUGGUGAUCAAGGUGUGCGAGUUCCAGUUCUGCAACGAC<br>CCCUUCCUGGGCGUGUACUACCACAAGAACAACAAGAGCUGGAUGG<br>AGAGCGAGUUCCGGGUGUACAGCAGCGCCAACAACUGCACCUUCGA<br>GUACGUGAGCCAGCCCUUCCUGAUGGACCUGGAGGGCAAGCAGGGC<br>AACUUCAAGAACCUGCGGGAGUUCGUGUUCAAGAACAUCGACGGCU<br>ACUUCAAGAUCUACAGCAAGCACACCCCAAUCAACCUGGUGCGGGA<br>UCUGCCCCAGGGCUUCUCAGCCCUGGAGCCCCUGGUGGACCUGCCC<br>AUCGGCAUCAACAUCACCCGGUUCCAGACCCUGCUGGCCCUGCACC<br>GGAGCUACCUGACCCCAGGCGACAGCAGCAGCGGGUGGACAGCAGG<br>CGCGGCUGCUUACUACGUGGGCUACCUGCAGCCCCGGACCUUCCUG<br>CUGAAGUACAACGAGAACGGCACCAUCACCGACGCCGUGGACUGCG<br>CCCUGGACCCUCUGAGCGAGACCAAGUGCACCCUGAAGAGCUUCAC<br>CGUGGAGAAGGGCAUCUACCAGACCAGCAACUUCCGGGUGCAGCCC<br>ACCGAGAGCAUCGUGCGGUUCCCCAACAUCACCAACCUGUGCCCCU<br>UCGGCGAGGUGUUCAACGCCACCCGGUUCGCCAGCGUGUACGCCUG<br>GAACCGGAAGCGGAUCAGCAACUGCGUGGCCGACUACAGCGUGCUG<br>UACAACAGCGCCAGCUUCAGCACCUUCAAGUGCUACGGCGUGAGCC<br>CCACCAAGCUGAACGACCUGUGCUUCACCAACGUGUACGCCGACAG<br>CUUCGUGAUCCGUGGCGACGAGGUGCGGCAGAUCGCACCCGGCCAG<br>ACAGGCAAGAUCGCCGACUACAACUACAAGCUGCCCGACGACUUCA<br>CCGGCUGCGUGAUCGCCUGGAACAGCAACAACCUCGACAGCAAGGU<br>GGGCGGCAACUACAACUACCUGUACCGGCUGUUCCGGAAGAGCAAC<br>CUGAAGCCCUUCGAGCGGGACAUCAGCACCGAGAUCUACCAAGCCG<br>GCUCCACCCCUUGCAACGGCGUGGAGGGCUUCAACUGCUACUUCCC<br>UCUGCAGAGCUACGGCUUCCAGCCCACCAACGGCGUGGGCUACCAG<br>CCCUACCGGGUGGUGGUGCUGAGCUUCGAGCUGCUGCACGCCCCAG<br>CCACCGUGUGUGGCCCCAAGAAGAGCACCAACCUGGUGAAGAACAA<br>GUGCGUGAACUUCAACUUCAACGGCCUUACCGGCACCGGCGUGCUG<br>ACCGAGAGCAACAAGAAAUUCCUGCCCUUUCAGCAGUUCGGCCGGG<br>ACAUCGCCGACACCACCGACGCUGUGCGGGAUCCCCAGACCCUGGA<br>GAUCCUGGACAUCACCCCUUGCAGCUUCGGCGGCGUGAGCGUGAUC<br>ACCCCAGGCACCAACACCAGCAACCAGGUGGCCGUGCUGUACCAGG<br>ACGUGAACUGCACCGAGGUGCCCGUGGCCAUCCACGCCGACCAGCU<br>GACACCCACCUGGCGGGUCUACAGCACCGGCAGCAACGUGUUCCAG<br>ACCCGGGCCGGUUGCCUGAUCGGCGCCGAGCACGUGAACAACAGCU<br>ACGAGUGCGACAUCCCCAUCGGCGCCGGCAUCUGUGCCAGCUACCA<br>GACCCAGACCAAUUCA | 3 |

TABLE 1B-continued

| Soluble Subunit Antigen | | |
|---|---|---|
| 3' UTR | UGAUAAUAGGCUGGAGCCUCGGUGGCCUAGCUUCUUGCCCCUUGGG<br>CCUCCCCCCAGCCCCUCCUCCCCUUCCUGCACCCGUACCCCCGUGG<br>UCUUUGAAUAAAGUCUGAGUGGGCGGC | 4 |
| Corresponding amino acid sequence | MFVFLVLLPLVSSQCVNLTTRTQLPPAYTNSFTRGVYYPDKVFRSS<br>VLHSTQDLFLPFFSNVTWFHAIHVSGTNGTKRFDNPVLPFNDGVYF<br>ASTEKSNIIRGWIFGTTLDSKTQSLLIVNNATNVVIKVCEFQFCND<br>PFLGVYYHKNNKSWMESEFRVYSSANNCTFEYVSQPFLMDLEGKQG<br>NFKNLREFVFKNIDGYFKIYSKHTPINLVRDLPQGFSALEPLVDLP<br>IGINITRFQTLLALHRSYLTPGDSSSGWTAGAAAYYVGYLQPRTFL<br>LKYNENGTITDAVDCALDPLSETKCTLKSFTVEKGIYQTSNFRVQP<br>TESIVRFPNITNLCPFGEVFNATRFASVYAWNRKRISNCVADYSVL<br>YNSASFSTFKCYGVSPTKLNDLCFTNVYADSFVIRGDEVRQIAPGQ<br>TGKIADYNYKLPDDFTGCVIAWNSNNLDSKVGGNYNYLYRLFRKSN<br>LKPFERDISTEIYQAGSTPCNGVEGFNCYFPLQSYGFQPTNGVGYQ<br>PYRVVVLSFELLHAPATVCGPKKSTNLVKNKCVNFNFNGLTGTGVL<br>TESNKKFLPFQQFGRDIADTTDAVRDPQTLEILDITPCSFGGVSVI<br>TPGTNTSNQVAVLYQDVNCTEVPVAIHADQLTPTWRVYSTGSNVFQ<br>TRAGCLIGAEHVNNSYECDIPIGAGICASYQTQTNS | 5 |
| PolyA tail | 100 nt | |

Membrane Bound Subunit Antigens

A membrane bound protein is anchored in a cell membrane (not soluble). Without being bound by theory, it is thought that antigen presenting cells will carry the embedded antigen to the draining lymph nodes to generate a strong immune response. The germinal center reaction that occurs in the draining lymph node involves prolonged contact between CD4$^+$ $T_{FH}$ cells and B cells, allowing co-stimulation and local cytokine signals such as IL-4 and IL-21 that favor replication of B cells specific to the presented antigen and class switching to the production of IgG1, each of which may promote the generation of long-lived plasma cells and memory B cells. Thus, in some embodiments, an mRNA encodes a membrane bound SARS-CoV-2 S1 subunit antigen and/or a membrane bound SARS-CoV-2 S2 subunit antigen. In some embodiments, a membrane bound antigen (e.g., S1 subunit, S2 subunit, NTD, RBD, or any combination thereof) is linked to a transmembrane domain, e.g., a naturally occurring transmembrane domain or a heterologous transmembrane domain (derived from a heterologous protein), which is responsible for anchoring the protein in the cell membrane. A non-limiting example of a membrane bound SARS-CoV-2 S1 subunit antigen and a SARS-CoV-2 S2 subunit antigen and the mRNA encoding them are provided in Tables 2A and 2B below. Other membrane bound SARS-CoV-2 S1 subunit antigens are contemplated herein.

TABLE 2A

| Membrane Bound Subunit Antigen | | |
|---|---|---|
| | SEQ ID NO: | |
| Name | mRNA ORF | Protein |
| SARS-CoV-2 S1 Subunit Linked to Transmembrane Domain (S1-666-TM) | 16 | 17 |
| SARS-CoV-2 S2 Subunit Linked to Transmembrane Domain (S2-TM) | 145 | 146 |

TABLE 2B

| Membrane Bound Subunit Antigen | | |
|---|---|---|
| SARS-CoV-2 S1 Subunit Linked to Transmembrane Domain (S1-666-TM) | | |
| SEQ ID NO: 15 consists of from 5' end to 3' end: 5' UTR SEQ ID NO: 2, mRNA ORF SEQ ID NO: 16 and 3' UTR SEQ ID NO: 4. | | 15 |
| Chemistry | 1-methylpseudouridine | |
| Cap | 7mG(5')ppp(5')NlmpNp | |
| 5' UTR | GGGAAAUAAGAGAGAAAAGAAGAGUAAGAAGAAAUAUAAGACCCCG<br>GCGCCGCCACC | 2 |
| ORF of mRNA Construct (excluding the stop codon) | AUGUUCGUGUUCCUGGUGCUGCUGCCCCUGGUGAGCAGCCAGUGCG<br>UGAACCUGACCACCCGGACCCAGCUGCCACCAGCCUACACCAACAG<br>CUUCACCCGGGGCGUCUACUACCCCGACAAGGUGUUCCGGAGCAGC<br>GUCCUGCACAGCACCCAGGACCUGUUCCUGCCCUUCUUCAGCAACG<br>UGACCUGGUUCCACGCCAUCCACGUGAGCGGCACCAACGGCACCAA<br>GCGGUUCGACAACCCCGUGCUGCCCUUCAACGACGGCGUGUACUUC<br>GCCAGCACCGAGAAGAGCAACAUCAUCCGGGGCUGGAUCUUCGGCA<br>CCACCCUGGACAGCAAGACCCAGAGCCUGCUGAUCGUGAAUAACGC<br>CACCAACGUGGUGAUCAAGGUGUGCGAGUUCCAGUUCUGCAACGAC<br>CCCUUCCUGGGCGUGUACUACCACAAGAACAACAAGAGCUGGAUGG<br>AGAGCGAGUUCCGGGUGUACAGCAGCGCCAACAACUGCACCUUCGA | 16 |

TABLE 2B-continued

| Membrane Bound Subunit Antigen | | |
|---|---|---|
| | GUACGUGAGCCAGCCCUUCCUGAUGGACCUGGAGGGCAAGCAGGGC AACUUCAAGAACCUGCGGGAGUUCGUGUUCAAGAACAUCGACGGCU ACUUCAAGAUCUACAGCAAGCACACCCCAAUCAACCUGGUGCGGGA UCUGCCCCAGGGCUUCUCAGCCCUGGAGCCCCUGGUGGACCUGCCC AUCGGCAUCAACAUCACCCGGUUCCAGACCCUGCUGGCCCUGCACC GGAGCUACCUGACCCCAGGCGACAGCAGCAGCGGGUGGACAGCAGG CGCGGCUGCUUACUACGUGGGCUACCUGCAGCCCCGGACCUUCCUG CUGAAGUACAACGAGAACGGCACCAUCACCGACGCCGUGGACUGCG CCCUGGACCCUCUGAGCGAGACCAAGUGCACCCUGAAGAGCUUCAC CGUGGAGAAGGGCAUCUACCAGACCAGCAACUUCCGGGUGCAGCCC ACCGAGAGCAUCGUGCGGUUCCCCAACAUCACCAACCUGUGCCCCU UCGGCGAGGUGUUCAACGCCACCCGGUUCGCCAGCGUGUACGCCUG GAACCGGAAGCGGAUCAGCAACUGCGUGGCCGACUACAGCGUGCUG UACAACAGCGCCAGCUUCAGCACCUUCAAGUGCUACGGCGUGAGCC CCACCAAGCUGAACGACCUGUGCUUCACCAACGUGUACGCCGACAG CUUCGUGAUCCGUGGCGACGAGGUGCGGCAGAUCGCACCCGGCCAG ACAGGCAAGAUCGCCGACUACAACUACAAGCUGCCCGACGACUUCA CCGGCUGCGUGAUCGCCUGGAACAGCAACAACCUCGACAGCAAGGU GGGCGGCAACUACAACUACCUGUACCGGCUGUUCCGGAAGAGCAAC CUGAAGCCCUUCGAGCGGGACAUCAGCACCGAGAUCUACCAAGCCG GCUCCACCCCUUGCAACGGCGUGGAGGGCUUCAACUGCUACUUCCC UCUGCAGAGCUACGGCUUCCAGCCCACCAACGGCGUGGGCUACCAG CCCUACCGGGUGGUGGUGCUGAGCUUCGAGCUGCUGCACGCCCCAG CCACCGUGUGUGGCCCCAAGAAGAGCACCAACCUGGUGAAGAACAA GUGCGUGAACUUCAACUUCAACGGCCUUACCGGCACCGGCGUGCUG ACCGAGAGCAACAAGAAAUUCCUGCCCUUUCAGCAGUUCGGCCGGG ACAUCGCCGACACCACCGACGCUGUGCGGGAUCCCCAGACCCUGGA GAUCCUGGACAUCACCCCUUGCAGCUUCGGCGGCGUGAGCGUGAUC ACCCCAGGCACCAACACCAGCAACCAGGUGGCCGUGCUGUACCAGG ACGUGAACUGCACCGAGGUGCCCGUGGCCAUCCACGCCGACCAGCU GACACCCACCUGGCGGGUCUACAGCACCGGCAGCAACGUGUUCCAG ACCCGGGCCGGUUGCCUGAUCGGCGCCGAGCACGUGAACAACAGCU ACGAGUGCGACAUCCCCAUCGGCGCCGGCAUCUGUGCCAGCUACCA GACCCAGACCAAUUCAUCUGGCGGAGGCAGCAUCCUGGCCAUCUAC AGCACCGUGGCCAGCAGCCUGGUGCUGCUGGUGAGCCUGGGCGCCA UCAGCUUC | |
| 3' UTR | UGAUAAUAGGCUGGAGCCUCGGUGGCCUAGCUUCUUGCCCCUUGGG CCUCCCCCCAGCCCCUCCUCCCCUUCCUGCACCCGUACCCCCGUGG UCUUUGAAUAAAGUCUGAGUGGGCGGC | 4 |
| Corresponding amino acid sequence | MFVFLVLLPLVSSQCVNLTTRTQLPPAYTNSFTRGVYYPDKVFRSS VLHSTQDLFLPFFSNVTWFHAIHVSGTNGTKRFDNPVLPFNDGVYF ASTEKSNIIRGWIFGTTLDSKTQSLLIVNNATNVVIKVCEFQFCND PFLGVYYHKNNKSWMESEFRVYSSANNCTFEYVSQPFLMDLEGKQG NFKNLREFVFKNIDGYFKIYSKHTPINLVRDLPQGFSALEPLVDLP IGINITRFQTLLALHRSYLTPGDSSSGWTAGAAAYYVGYLQPRTFL LKYNENGTITDAVDCALDPLSETKCTLKSFTVEKGIYQTSNFRVQP TESIVRFPNITNLCPFGEVFNATRFASVYAWNRKRISNCVADYSVL YNSASFSTFKCYGVSPTKLNDLCFTNVYADSFVIRGDEVRQIAPGQ TGKIADYNYKLPDDFTGCVIAWNSNNLDSKVGGNYNYLYRLFRKSN LKPFERDISTEIYQAGSTPCNGVEGFNCYFPLQSYGFQPTNGVGYQ PYRVVVLSFELLHAPATVCGPKKSTNLVKNKCVNFNFNGLTGTGVL TESNKKFLPFQQFGRDIADTTDAVRDPQTLEILDITPCSFGGVSVI TPGTNTSNQVAVLYQDVNCTEVPVAIHADQLTPTWRVYSTGSNVFQ TRAGCLIGAEHVNNSYECDIPIGAGICASYQTQTNSGGGSILAIYS TVASSLVLLVSLGAISF | 17 |
| PolyA tail | 100 nt | |

| SARS-CoV-2 S2 Subunit comprising a Transmembrane Domain (S2-TM) | | |
|---|---|---|
| SEQ ID NO: 147 consists of from 5' end to 3' end: 5' UTR SEQ ID NO: 2, mRNA ORF SEQ ID NO: 145 and 3' UTR SEQ ID NO: 4. | | 147 |
| Chemistry | 1-methylpseudouridine | |
| Cap | 7mG(5')ppp(5')NlmpNp | |
| 5' UTR | GGGAAAUAAGAGAGAAAAGAAGAGUAAGAAGAAAUAUAAGACCCCG GCGCCGCCACC | 2 |
| ORF of mRNA Construct (excluding the stop codon) | AUGUACAGCAUGCAGCUGGCUAGCUGCGUGACCCUGACCCUGGUGC UGCUGGUGAACAGCCAGGGCGCCGAGAACAGCGUGGCCUACAGCAA CAACAGCAUCGCCAUCCCCACCAACUUCACCAUCAGCGUGACCACC GAGAUUCUGCCCGUGAGCAUGACCAAGACCAGCGUGGACUGCACCA UGUACAUCUGCGGCGACAGCACCGAGUGCAGCAACCUGCUGCUGCA GUACGGCAGCUUCUGCACCCAGCUGAACCGGGCCCUGACCGGCAUC | 145 |

TABLE 2B-continued

| | Membrane Bound Subunit Antigen | |
|---|---|---|
| | GCCGUGGAGCAGGACAAGAACACCCAGGAGGUGUUCGCCCAGGUGA<br>AGCAGAUCUACAAGACCCCUCCCAUCAAGGACUUCGGCGGCUUCAA<br>CUUCAGCCAGAUCCUGCCCGACCCCAGCAAGCCCAGCAAGCGGAGC<br>UUCAUCGAGGACCUGCUGUUCAACAAGGUGACCCUAGCCGACGCCG<br>GCUUCAUCAAGCAGUACGGCGACUGCCUCGGCGACAUAGCCGCCCG<br>GGACCUGAUCUGCGCCCAGAAGUUCAACGGCCUGACCGUGCUGCCU<br>CCCCUGCUGACCGACGAGAUGAUCGCCCAGUACACCAGCGCCCUGU<br>UAGCCGGAACCAUCACCAGCGGCUGGACUUUCGGCGCUGGAGCCGC<br>UCUGCAGAUCCCCUUCGCCAUGCAGAUGGCCUACCGGUUCAACGGC<br>AUCGGCGUGACCCAGAACGUGCUGUACGAGAACCAGAAGCUGAUCG<br>CCAACCAGUUCAACAGCGCCAUCGGCAAGAUCCAGGACAGCCUGAG<br>CAGCACCGCUAGCGCCCUGGGCAAGCUGCAGGACGUGGUGAACCAG<br>AACGCCCAGGCCCUGAACACCCUGGUGAAGCAGCUGAGCAGCAACU<br>UCGGCGCCAUCAGCAGCGUGCUGAACGACAUCCUGAGCCGGCUGGA<br>CCCUCCCGAGGCCGAGGUGCAGAUCGACCGGCUGAUCACUGGCCGG<br>CUGCAGAGCCUGCAGACCUACGUGACCCAGCAGCUGAUCCGGGCCG<br>CCGAGAUUCGGGCCAGCGCCAACCUGGCCGCCACCAAGAUGAGCGA<br>GUGCGUGCUGGGCCAGAGCAAGCGGGUGGACUUCUGCGGCAAGGGC<br>UACCACCUGAUGAGCUUUCCCCAGAGCGCACCCCACGGAGUGGUGU<br>UCCUGCACGUGACCUACGUGCCCGCCCAGGAGAAGAACUUCACCAC<br>CGCCCCAGCCAUCUGCCACGACGGCAAGGCCCACUUUCCCCGGGAG<br>GGCGUGUUCGUGAGCAACGGCACCCACUGGUUCGUGACCCAGCGGA<br>ACUUCUACGAGCCCCAGAUCAUCACCACCGACAACACCUUCGUGAG<br>CGGCAACUGCGACGUGGUGAUCGGCAUCGUGAACAACACCGUGUAC<br>GAUCCCCUGCAGCCCGAGCUGGACAGCUUCAAGGAGGAGCUGGACA<br>AGUACUUCAAGAAUCACACCAGCCCCGACGUGGACCUGGGCGACAU<br>CAGCGGCAUCAACGCCAGCGUGGUGAACAUCCAGAAGGAGAUCGAU<br>CGGCUGAACGAGGUGGCCAAGAACCUGAACGAGAGCCUGAUCGACC<br>UGCAGGAGCUGGGCAAGUACGAGCAGUACAUCAAGUGGCCCUGGUA<br>CAUCUGGCUGGGCUUCAUCGCCGGCCUGAUCGCCAUCGUGAUGGUG<br>ACCAUCAUGCUGUGCUGCAUGACCAGCUGCUGCAGCUGCCUGAAGG<br>GCUGUUGCAGCUGCGGCAGCUGCUGCAAGUUCGACGAGGACGACAG<br>CGAGCCCGUGCUGAAGGGCGUGAAGCUGCACUACACC | |
| 3' UTR | UGAUAAUAGGCUGGAGCCUCGGUGGCCUAGCUUCUUGCCCCUUGGG<br>CCUCCCCCCAGCCCCUCCUCCCCUUCCUGCACCCGUACCCCCGUGG<br>UCUUUGAAUAAAGUCUGAGUGGGCGGC | 4 |
| Corresponding amino acid sequence | MYSMQLASCVTLTLVLLVNSQGAENSVAYSNNSIAIPTNFTISVTT<br>EILPVSMTKTSVDCTMYICGDSTECSNLLLQYGSFCTQLNRALTGI<br>AVEQDKNTQEVFAQVKQTYKTPPIKDFGGFNFSQILPDPSKPSKRS<br>FIEDLLFNKVTLADAGFIKQYGDCLGDIAARDLICAQKFNGLTVLP<br>PLLTDEMIAQYTSALLAGTITSGWTFGAGAALQIPFAMQMAYRFNG<br>IGVTQNVLYENQKLIANQFNSAIGKIQDSLSSTASALGKLQDVVNQ<br>NAQALNTLVKQLSSNFGAISSVLNDILSRLDPPEAEVQIDRLITGR<br>LQSLQTYVTQQLIRAAEIRASANLAATKMSECVLGQSKRVDFCGKG<br>YHLMSFPQSAPHGVVFLHVTYVPAQEKNFTTAPAICHDGKAHFPRE<br>GVFVSNGTHWFVTQRNFYEPQIITTDNTFVSGNCDVVIGIVNNTVY<br>DPLQPELDSFKEELDKYFKNHTSPDVDLGDISGINASVVNIQKEID<br>RLNEVAKNLNESLIDLQELGKYEQYIKWPWYIWLGFIAGLIAIVMV<br>TIMLCCMTSCCSCLKGCCSCGSCCKFDEDDSEPVLKGVKLHYT | 146 |
| PolyA tail | 100 nt | |

Subunit Antigen Truncations and RBD Deletions

In some embodiments, a composition comprises an miRNA that encodes an S1 subunit that has been modified to remove the RBD or a portion of the RBD. Truncation of the S1 subunit provides fewer epitopes for the immune system to recognize, thereby biasing the immune response to the remaining epitopes, which may select for antibodies to specific epitopes that are important for virus neutralization. Truncation or partial deletion of the RBD may prevent the expressed protein or cells carrying it from interacting with receptor ACE2, making it more likely to reach the lymph node and stimulate a desired immune response. Furthermore, removing the RBD may prevent epitope masking by cross-reactive antibodies previously raised against related viruses, and thus focus the elicited immune response toward the desired antigen specifically. Additionally, removal of the RBD may alter the conformation of the expressed subunit, allowing B cells specific to these alternative conformational epitopes to uptake and present linear peptides to T cells, thereby indirectly enhancing the $CD4^+$ T cell response to those epitopes, which are still present in the native conformation.

In some embodiments, a composition comprises an miRNA that encodes an S1 subunit that has been modified to remove the RBD or a portion of the RBD, wherein the S2 subunit contains a glycan. Glycans are attached to proteins by N-linked glycosylation via asparagine residues or O-linked glycosylation on serine or threonine residues. The presence of a glycan shield on some components of a protein may mask peptide epitopes, thereby focusing the antibody response towards other exposed peptide epitopes. Furthermore, glycosylated proteins also elicit antibodies that recognize the coating glycans. B cells that recognize the glycan epitope will intake and present linear peptide epitopes to $CD4^+$ T cells, thereby boosting the $CD4^+$ T cell response to linear epitopes found throughout the protein.

Non-limiting examples of truncated SARS-CoV-2 S subunit antigens and the mRNA encoding them are provided in Tables 3A and 3B below.

Non-limiting examples of SARS-CoV-2 S1 subunits having an RBD deletion and the mRNA encoding them are provided in Tables 4A and 4B below.

TABLE 3A

| Subunit Antigen Truncations | SEQ ID NO: | |
|---|---|---|
| Name | mRNA ORF | Protein |
| SARS-CoV-2 S1 Subunit Truncated and Linked to Transmembrane Domain (S1-531-TM) | 19 | 20 |
| SARS-CoV-2 S1 Subunit Truncated and Linked to Transmembrane Domain (S1-594-TM) | 22 | 23 |

TABLE 3A-continued

| Subunit Antigen Truncations | SEQ ID NO: | |
|---|---|---|
| Name | mRNA ORF | Protein |
| SARS-CoV-2 S1 Subunit Truncated with PolyG and Linked to Transmembrane Domain (S1-594-PolyG-TM) | 25 | 26 |
| SARS-CoV-2 S1 Subunit Truncated with PolyG/DS and Linked to Transmembrane Domain (S1-594-PolyG-DS-TM) | 28 | 29 |
| SARS-CoV-2 S1 Subunit Truncated and Linked to Transmembrane Domain (S1-666-TM) | 150 | 151 |

TABLE 3B

Subunit Antigen Truncations

SARS-CoV-2 S1 Subunit Truncated and Linked to Transmembrane Domain (S1-531-TM)

| | | |
|---|---|---|
| SEQ ID NO: 18 consists of from 5' end to 3' end: 5' UTR SEQ ID NO: 2, mRNA ORF SEQ ID NO: 19 and 3' UTR SEQ ID NO: 4. | | 18 |
| Chemistry | 1-methylpseudouridine | |
| Cap | 7mG(5')ppp(5')NlmpNp | |
| 5' UTR | GGGAAAUAAGAGAGAAAAGAAGAGUAAGAAGAAAUAUAAGACCCCG<br>GCGCCGCCACC | 2 |
| ORF of mRNA Construct (excluding the stop codon) | AUGUUCGUGUUCCUGGUGCUGCUGCCCCUGGUGAGCAGCCAGUGCG<br>UGAACCUGACCACCCGGACCCAGCUGCCACCAGCCUACACCAACAG<br>CUUCACCCGGGGCGUCUACUACCCCGACAAGGUGUUCCGGAGCAGC<br>GUCCUGCACAGCACCCAGGACCUGUUCCUGCCCUUCUUCAGCAACG<br>UGACCUGGUUCCACGCCAUCCACGUGAGCGGCACCAACGGCACCAA<br>GCGGUUCGACAACCCCGUGCUGCCCUUCAACGACGGCGUGUACUUC<br>GCCAGCACCGAGAAGAGCAACAUCAUCCGGGGCUGGAUCUUCGGCA<br>CCACCCUGGACAGCAAGACCCAGAGCCUGCUGAUCGUGAAUAACGC<br>CACCAACGUGGUGAUCAAGGUGUGCGAGUUCCAGUUCUGCAACGAC<br>CCCUUCCUGGGCGUGUACUACCACAAGAACAACAAGAGCUGGAUGG<br>AGAGCGAGUUCCGGGUGUACAGCAGCGCCAACAACUGCACCUUCGA<br>GUACGUGAGCCAGCCCUUCCUGAUGGACCUGGAGGGCAAGCAGGGC<br>AACUUCAAGAACCUGCGGGAGUUCGUGUUCAAGAACAUCGACGGCU<br>ACUUCAAGAUCUACAGCAAGCACACCCCAAUCAACCUGGUGCGGGA<br>UCUGCCCCAGGGCUUCUCAGCCCUGGAGCCCCUGGUGGACCUGCCC<br>AUCGGCAUCAACAUCACCCGGUUCCAGACCCUGCUGGCCCUGCACC<br>GGAGCUACCUGACCCCAGGCGACAGCAGCAGCGGGUGGACAGCAGG<br>CGCGGCUGCUUACUACGUGGGCUACCUGCAGCCCCGGACCUUCCUG<br>CUGAAGUACAACGAGAACGGCACCAUCACCGACGCCGUGGACUGCG<br>CCCUGGACCCUCUGAGCGAGACCAAGUGCACCCUGAAGAGCUUCAC<br>CGUGGAGAAGGGCAUCUACCAGACCAGCAACUUCCGGGUGCAGCCC<br>ACCGAGAGCAUCGUGCGGUUCCCCAACAUCACCAACCUGUGCCCCU<br>UCGGCGAGGUGUUCAACGCCACCCGGUUCGCCAGCGUGUACGCCUG<br>GAACCGGAAGCGGAUCAGCAACUGCGUGGCCGACUACAGCGUGCUG<br>UACAACAGCGCCAGCUUCAGCACCUUCAAGUGCUACGGCGUGAGCC<br>CCACCAAGCUGAACGACCUGUGCUUCACCAACGUGUACGCCGACAG<br>CUUCGUGAUCCGUGGCGACGAGGUGCGGCAGAUCGCACCCGGCCAG<br>ACAGGCAAGAUCGCCGACUACAACUACAAGCUGCCCGACGACUUCA<br>CCGGCUGCGUGAUCGCCUGGAACAGCAACAACCUCGACAGCAAGGU<br>GGGCGGCAACUACAACUACCUGUACCGGCUGUUCCGGAAGAGCAAC<br>CUGAAGCCCUUCGAGCGGGACAUCAGCACCGAGAUCUACCAAGCCG<br>GCUCCACCCCUUGCAACGGCGUGGAGGGCUUCAACUGCUACUUCCC<br>UCUGCAGAGCUACGGCUUCCAGCCCACCAACGGCGUGGGCUACCAG<br>CCCUACCGGGUGGUGGUGCUGAGCUUCGAGCUGCUGCACGCCCCAG<br>CCACCGUGUGUGGCCCCAAGAAGAGCACCUCUGGCGGAGGCAGCAU<br>CCUGGCCAUCUACAGCACCGUGGCCAGCAGCCUGGUGCUGCUGGUG<br>AGCCUGGGCGCCAUCAGCUUC | 19 |
| 3' UTR | UGAUAAUAGGCUGGAGCCUCGGUGGCCUAGCUUCUUGCCCCUUGGG<br>CCUCCCCCCAGCCCCUCCUCCCCUUCCUGCACCCGUACCCCCGUGG<br>UCUUUGAAUAAAGUCUGAGUGGGCGGC | 4 |

TABLE 3B-continued

| Subunit Antigen Truncations | | |
|---|---|---|
| Corresponding amino acid sequence | MFVFLVLLPLVSSQCVNLTTRTQLPPAYTNSFTRGVYYPDKVFRSS<br>VLHSTQDLFLPFFSNVTWFHAIHVSGTNGTKRFDNPVLPFNDGVYF<br>ASTEKSNIIRGWIFGTTLDSKTQSLLIVNNATNVVIKVCEFQFCND<br>PFLGVYYHKNNKSWMESEFRVYSSANNCTFEYVSQPFLMDLEGKQG<br>NFKNLREFVFKNIDGYFKIYSKHTPINLVRDLPQGFSALEPLVDLP<br>IGINITRFQTLLALHRSYLTPGDSSSGWTAGAAAYYVGYLQPRTFL<br>LKYNENGTITDAVDCALDPLSETKCTLKSFTVEKGIYQTSNFRVQP<br>TESIVRFPNITNLCPFGEVFNATRFASVYAWNRKRISNCVADYSVL<br>YNSASFSTFKCYGVSPTKLNDLCFTNVYADSFVIRGDEVRQIAPGQ<br>TGKIADYNYKLPDDFTGCVIAWNSNNLDSKVGGNYNYLYRLFRKSN<br>LKPFERDISTEIYQAGSTPCNGVEGFNCYFPLQSYGFQPTNGVGYQ<br>PYRVVVLSFELLHAPATVCGPKKSTsgggsilaiystvasslvllv<br>slgaisf | 20 |
| PolyA tail | 100 nt | |
| SARS-CoV-2 S1 Subunit Truncated and Linked to Transmembrane Domain (S1-594-TM) | | |
| SEQ ID NO: 21 consists of from 5' end to 3' end: 5' UTR SEQ ID NO: 2, mRNA ORF SEQ ID NO: 22 and 3' UTR SEQ ID NO: 4. | | 21 |
| Chemistry | 1-methylpseudouridine | |
| Cap | 7mG(5')ppp(5')N1mpNp | |
| 5' UTR | GGGAAAUAAGAGAGAAAAGAAGAGUAAGAAGAAAUAUAAGACCCCG<br>GCGCCGCCACC | 2 |
| ORF of mRNA Construct (excluding the stop codon) | AUGUUCGUGUUCCUGGUGCUGCUGCCCCUGGUGAGCAGCCAGUGCG<br>UGAACCUGACCACCCGGACCCAGCUGCCACCAGCCUACACCAACAG<br>CUUCACCCGGGGCGUCUACUACCCCGACAAGGUGUUCCGGAGCAGC<br>GUCCUGCACAGCACCCAGGACCUGUUCCUGCCCUUCUUCAGCAACG<br>UGACCUGGUUCCACGCCAUCCACGUGAGCGGCACCAACGGCACCAA<br>GCGGUUCGACAACCCCGUGCUGCCCUUCAACGACGGCGUGUACUUC<br>GCCAGCACCGAGAAGAGCAACAUCAUCCGGGGCUGGAUCUUCGGCA<br>CCACCCUGGACAGCAAGACCCAGAGCCUGCUGAUCGUGAAUAACGC<br>CACCAACGUGGUGAUCAAGGUGUGCGAGUUCCAGUUCUGCAACGAC<br>CCCUUCCUGGGCGUGUACUACCACAAGAACAACAAGAGCUGGAUGG<br>AGAGCGAGUUCCGGGUGUACAGCAGCGCCAACAACUGCACCUUCGA<br>GUACGUGAGCCAGCCCUUCCUGAUGGACCUGGAGGGCAAGCAGGGC<br>AACUUCAAGAACCUGCGGGAGUUCGUGUUCAAGAACAUCGACGGCU<br>ACUUCAAGAUCUACAGCAAGCACACCCCAAUCAACCUGGUGCGGGA<br>UCUGCCCCAGGGCUUCUCAGCCCUGGAGCCCCUGGUGGACCUGCCC<br>AUCGGCAUCAACAUCACCCGGUUCCAGACCCUGCUGGCCCUGCACC<br>GGAGCUACCUGACCCCAGGCGACAGCAGCAGCGGGUGGACAGCAGG<br>CGCGGCUGCUUACUACGUGGGCUACCUGCAGCCCCGGACCUUCCUG<br>CUGAAGUACAACGAGAACGGCACCAUCACCGACGCCGUGGACUGCG<br>CCCUGGACCCUCUGAGCGAGACCAAGUGCACCCUGAAGAGCUUCAC<br>CGUGGAGAAGGGCAUCUACCAGACCAGCAACUUCCGGGUGCAGCCC<br>ACCGAGAGCAUCGUGCGGUUCCCCAACAUCACCAACCUGUGCCCCU<br>UCGGCGAGGUGUUCAACGCCACCCGGUUCGCCAGCGUGUACGCCUG<br>GAACCGGAAGCGGAUCAGCAACUGCGUGGCCGACUACAGCGUGCUG<br>UACAACAGCGCCAGCUUCAGCACCUUCAAGUGCUACGGCGUGAGCC<br>CCACCAAGCUGAACGACCUGUGCUUCACCAACGUGUACGCCGACAG<br>CUUCGUGAUCCGUGGCGACGAGGUGCGGCAGAUCGCACCCGGCCAG<br>ACAGGCAAGAUCGCCGACUACAACUACAAGCUGCCCGACGACUUCA<br>CCGGCUGCGUGAUCGCCUGGAACAGCAACAACCUCGACAGCAAGGU<br>GGGCGGCAACUACAACUACCUGUACCGGCUGUUCCGGAAGAGCAAC<br>CUGAAGCCCUUCGAGCGGGACAUCAGCACCGAGAUCUACCAAGCCG<br>GCUCCACCCCUUGCAACGGCGUGGAGGGCUUCAACUGCUACUUCCC<br>UCUGCAGAGCUACGGCUUCCAGCCCACCAACGGCGUGGGCUACCAG<br>CCCUACCGGGUGGUGGUGCUGAGCUUCGAGCUGCUGCACGCCCCAG<br>CCACCGUGUGUGGCCCCAAGAAGAGCACCAACCUGGUGAAGAACAA<br>GUGCGUGAACUUCAACUUCAACGGCCUUACCGGCACCGGCGUGCUG<br>ACCGAGAGCAACAAGAAAUUCCUGCCCUUUCAGCAGUUCGGCCGGG<br>ACAUCGCCGACACCACCGACGCUGUGCGGGAUCCCCAGACCCUGGA<br>GAUCCUGGACAUCACCCCUUGCAGCUUCGGCGGCUCUGGCGGAGGC<br>AGCAUCCUGGCCAUCUACAGCACCGUGGCCAGCAGCCUGGUGCUGC<br>UGGUGAGCCUGGGCGCCAUCAGCUUC | 22 |
| 3' UTR | UGAUAAUAGGCUGGAGCCUCGGUGGCCUAGCUUCUUGCCCCUUGGG<br>CCUCCCCCCAGCCCCUCCUCCCCUUCCUGCACCCGUACCCCCGUGG<br>UCUUUGAAUAAAGUCUGAGUGGGCGGC | 4 |
| Corresponding amino acid sequence | MFVFLVLLPLVSSQCVNLTTRTQLPPAYTNSFTRGVYYPDKVFRSS<br>VLHSTQDLFLPFFSNVTWFHAIHVSGTNGTKRFDNPVLPFNDGVYF<br>ASTEKSNIIRGWIFGTTLDSKTQSLLIVNNATNVVIKVCEFQFCND<br>PFLGVYYHKNNKSWMESEFRVYSSANNCTFEYVSQPFLMDLEGKQG | 23 |

TABLE 3B-continued

| Subunit Antigen Truncations | | |
|---|---|---|
| | NFKNLREFVFKNIDGYFKIYSKHTPINLVRDLPQGFSALEPLVDLP<br>IGINITRFQTLLALHRSYLTPGDSSSGWTAGAAAYYVGYLQPRTFL<br>LKYNENGTITDAVDCALDPLSETKCTLKSFTVEKGIYQTSNFRVQP<br>TESIVRFPNITNLCPFGEVFNATRFASVYAWNRKRISNCVADYSVL<br>YNSASFSTFKCYGVSPTKLNDLCFTNVYADSFVIRGDEVRQIAPGQ<br>TGKIADYNYKLPDDFTGCVIAWNSNNLDSKVGGNYNYLYRLFRKSN<br>LKPFERDISTEIYQAGSTPCNGVEGFNCYFPLQSYGFQPTNGVGYQ<br>PYRVVVLSFELLHAPATVCGPKKSTNLVKNKCVNFNFNGLTGTGVL<br>TESNKKFLPFQQFGRDIADTTDAVRDPQTLEILDITPCSFGGsggg<br>silaiystvasslvllvslgaisf | |
| PolyA tail | 100 nt | |

SARS-CoV-2 S1 Subunit Truncated with PolyG and Linked to Transmembrane Domain (S1-594-PolyG-TM)

| | | |
|---|---|---|
| SEQ ID NO: 24 consists of from 5' end to 3' end: 5' UTR SEQ ID NO: 2, mRNA ORF SEQ ID NO: 25 and 3' UTR SEQ ID NO: 4. | | 24 |
| Chemistry | 1-methylpseudouridine | |
| Cap | 7mG(5')ppp(5')NlmpNp | |
| 5' UTR | GGGAAAUAAGAGAGAAAAGAAGAGUAAGAAGAAAUAUAAGACCCCG<br>GCGCCGCCACC | 2 |
| ORF of mRNA Construct (excluding the stop codon) | AUGUUCGUGUUCCUGGUGCUGCUGCCCCUGGUGAGCAGCCAGUGCG<br>UGAACCUGACCACCCGGACCCAGCUGCCACCAGCCUACACCAACAG<br>CUUCACCCGGGGCGUCUACUACCCCGACAAGGUGUUCCGGAGCAGC<br>GUCCUGCACAGCACCCAGGACCUGUUCCUGCCCUUCUUCAGCAACG<br>UGACCUGGUUCCACGCCAUCCACGUGAGCGGCACCAACGGCACCAA<br>GCGGUUCGACAACCCCGUGCUGCCCUUCAACGACGGCGUGUACUUC<br>GCCAGCACCGAGAAGAGCAACAUCAUCCGGGGCUGGAUCUUCGGCA<br>CCACCCUGGACAGCAAGACCCAGAGCCUGCUGAUCGUGAAUAACGC<br>CACCAACGUGGUGAUCAAGGUGUGCGAGUUCCAGUUCUGCAACGAC<br>CCCUUCCUGGGCGUGUACUACCACAAGAACAACAAGAGCUGGAUGG<br>AGAGCGAGUUCCGGGUGUACAGCAGCGCCAACAACUGCACCUUCGA<br>GUACGUGAGCCAGCCCUUCCUGAUGGACCUGGAGGGCAAGCAGGGC<br>AACUUCAAGAACCUGCGGGAGUUCGUGUUCAAGAACAUCGACGGCU<br>ACUUCAAGAUCUACAGCAAGCACACCCCAAUCAACCUGGUGCGGGA<br>UCUGCCCCAGGGCUUCUCAGCCCUGGAGCCCCUGGUGGACCUGCCC<br>AUCGGCAUCAACAUCACCCGGUUCCAGACCCUGCUGGCCCUGCACC<br>GGAGCUACCUGACCCCAGGCGACAGCAGCAGCGGGUGGACAGCAGG<br>CGCGGCUGCUUACUACGUGGGCUACCUGCAGCCCCGGACCUUCCUG<br>CUGAAGUACAACGAGAACGGCACCAUCACCGACGCCGUGGACUGCG<br>CCCUGGACCCUCUGAGCGAGACCAAGUGCACCCUGAAGAGCUUCAC<br>CGUGGGCAGCGGCGGCGGCAGCGGCGGAGGCAGCGGAGGAGGCAGC<br>GGCGGAGGCAGUGGAGGCCAGCCCACCGAGAGCAUCGUGCGGUUCC<br>CCAACAUCACCAACCUGUGCCCCUUCGGCGAGGUGUUCAACGCCAC<br>CCGGUUCGCCAGCGUGUACGCCUGGAACCGGAAGCGGAUCAGCAAC<br>UGCGUGGCCGACUACAGCGUGCUGUACAACAGCGCCAGCUUCAGCA<br>CCUUCAAGUGCUACGGCGUGAGCCCCACCAAGCUGAACGACCUGUG<br>CUUCACCAACGUGUACGCCGACAGCUUCGUGAUCCGUGGCGACGAG<br>GUGCGGCAGAUCGCACCCGGCCAGACAGGCAAGAUCGCCGACUACA<br>ACUACAAGCUGCCCGACGACUUCACCGGCUGCGUGAUCGCCUGGAA<br>CAGCAACAACCUCGACAGCAAGGUGGGCGGCAACUACAACUACCUG<br>UACCGGCUGUUCCGGAAGAGCAACCUGAAGCCCUUCGAGCGGGACA<br>UCAGCACCGAGAUCUACCAAGCCGGCUCCACCCCUUGCAACGGCGU<br>GGAGGGCUUCAACUGCUACUUCCCUCUGCAGAGCUACGGCUUCCAG<br>CCCACCAACGGCGUGGGCUACCAGCCCUACCGGGUGGUGGUGCUGA<br>GCUUCGAGCUGCUGCACGCCCCAGCCACCGUGUGUGGCCCCAAGAA<br>GAGCACCAACCUGGUGAAGAACAAGUGCGUGAACUUCAACUUCAAC<br>GGCCUUACCGGCACCGGCGUGCUGACCGAGAGCAACAAGAAAUUCC<br>UGCCCUUUCAGCAGUUCGGCCGGGACAUCGCCGACACCACCGACGC<br>UGUGCGGGAUCCCCAGACCCUGGAGAUCCUGGACAUCACCCCUUGC<br>AGCUUCGGCGGCUCUGGCGGAGGCAGCAUCCUGGCCAUCUACAGCA<br>CCGUGGCCAGCAGCCUGGUGCUGCUGGUGAGCCUGGGCGCCAUCAG<br>CUUC | 25 |
| 3' UTR | UGAUAAUAGGCUGGAGCCUCGGUGGCCUAGCUUCUUGCCCCUUGGG<br>CCUCCCCCCAGCCCCUCCUCCCCUUCCUGCACCCGUACCCCCGUGG<br>UCUUUGAAUAAAGUCUGAGUGGGCGGC | 4 |
| Corresponding amino acid sequence | MFVFLVLLPLVSSQCVNLTTRTQLPPAYTNSFTRGVYYPDKVFRSS<br>VLHSTQDLFLPFFSNVTWFHAIHVSGTNGTKRFDNPVLPFNDGVYF<br>ASTEKSNIIRGWIFGTTLDSKTQSLLIVNNATNVVIKVCEFQFCND<br>PFLGVYYHKNNKSWMESEFRVYSSANNCTFEYVSQPFLMDLEGKQG<br>NFKNLREFVFKNIDGYFKIYSKHTPINLVRDLPQGFSALEPLVDLP | 26 |

TABLE 3B-continued

| Subunit Antigen Truncations | | |
|---|---|---|
| | IGINITRFQTLLALHRSYLTPGDSSSGWTAGAAAYYVGYLQPRTFL<br>LKYNENGTITDAVDCALDPLSETKCTLKSFTVGSGGGSGGGSGGGS<br>GGGSGGQPTESIVRFPNITNLCPFGEVFNATRFASVYAWNRKRISN<br>CVADYSVLYNSASFSTFKCYGVSPTKLNDLCFTNVYADSFVIRGDE<br>VRQIAPGQTGKIADYNYKLPDDFTGCVIAWNSNNLDSKVGGNYNYL<br>YRLFRKSNLKPFERDISTEIYQAGSTPCNGVEGFNCYFPLQSYGFQ<br>PTNGVGYQPYRVVVLSFELLHAPATVCGPKKSTNLVKNKCVNFNFN<br>GLTGTGVLTESNKKFLPFQQFGRDIADTTDAVRDPQTLEILDITPC<br>SFGGsgggsilaiystvasslvllvslgaisf | |
| PolyA tail | 100 nt | |
| **SARS-CoV-2 S1 Subunit Truncated with PolyG/DS and Linked to Transmembrane Domain (S1-594-PolyG-DS-TM)** | | |
| SEQ ID NO: 27 consists of from 5' end to 3' end: 5' UTR SEQ ID NO: 2, mRNA ORF SEQ ID NO: 28 and 3' UTR SEQ ID NO: 4. | | 27 |
| Chemistry | 1-methylpseudouridine | |
| Cap | 7mG(5')ppp(5')NlmpNp | |
| 5' UTR | GGGAAAUAAGAGAGAAAAGAAGAGUAAGAAGAAAUAUAAGACCCCG<br>GCGCCGCCACC | 2 |
| ORF of mRNA Construct (excluding the stop codon) | AUGUUCGUGUUCCUGGUGCUGCUGCCCCUGGUGAGCAGCCAGUGCG<br>UGAACCUGACCACCCGGACCCAGCUGCCACCAGCCUACACCAACAG<br>CUUCACCCGGGGCGUCUACUACCCCGACAAGGUGUGCCGGAGCAGC<br>GUCCUGCACAGCACCCAGGACCUGUUCCUGCCCUUCUUCAGCAACG<br>UGACCUGGUUCCACGCCAUCCACGUGAGCGGCACCAACGGCACCAA<br>GCGGUUCGACAACCCCGUGCUGCCCUUCAACGACGGCGUGUACUUC<br>GCCAGCACCGAGAAGAGCAACAUCAUCCGGGGCUGGAUCUUCGGCA<br>CCACCCUGGACAGCAAGACCCAGAGCCUGCUGAUCGUGAAUAACGC<br>CACCAACGUGGUGAUCAAGGUGUGCGAGUUCCAGUUCUGCAACGAC<br>CCCUUCCUGGGCGUGUACUACCACAAGAACAACAAGAGCUGGAUGG<br>AGAGCGAGUUCCGGGUGUACAGCAGCGCCAACAACUGCACCUUCGA<br>GUACGUGAGCCAGCCCUUCCUGAUGGACCUGGAGGGCAAGCAGGGC<br>AACUUCAAGAACCUGCGGGAGUUCGUGUUCAAGAACAUCGACGGCU<br>ACUUCAAGAUCUACAGCAAGCACACCCCAAUCAACCUGGUGCGGGA<br>UCUGCCCCAGGGCUUCUCAGCCCUGGAGCCCCUGGUGGACCUGCCC<br>AUCGGCAUCAACAUCACCCGGUUCCAGACCCUGCUGGCCCUGCACC<br>GGAGCUACCUGACCCCAGGCGACAGCAGCAGCGGGUGGACAGCAGG<br>CGCGGCUGCUUACUACGUGGGCUACCUGCAGCCCCGGACCUUCCUG<br>CUGAAGUACAACGAGAACGGCACCAUCACCGACGCCGUGGACUGCG<br>CCCUGGACCCUCUGAGCGAGACCAAGUGCACCCUGAAGAGCUUCAC<br>CGUGGGCAGCGGCGGCGGCAGCGGCGGAGGCAGCGGAGGAGGCAGC<br>GGCGGAGGCAGUGGAGGCCAGCCCACCGAGAGCAUCGUGCGGUUCC<br>CCAACAUCACCAACCUGUGCCCCUUCGGCGAGGUGUUCAACGCCAC<br>CCGGUUCGCCAGCGUGUACGCCUGGAACCGGAAGCGGAUCAGCAAC<br>UGCGUGGCCGACUACAGCGUGCUGUACAACAGCGCCAGCUUCAGCA<br>CCUUCAAGUGCUACGGCGUGAGCCCCACCAAGCUGAACGACCUGUG<br>CUUCACCAACGUGUACGCCGACAGCUUCGUGAUCCGUGGCGACGAG<br>GUGCGGCAGAUCGCACCCGGCCAGACAGGCAAGAUCGCCGACUACA<br>ACUACAAGCUGCCCGACGACUUCACCGGCUGCGUGAUCGCCUGGAA<br>CAGCAACAACCUCGACAGCAAGGUGGGCGGCAACUACAACUACCUG<br>UACCGGCUGUUCCGGAAGAGCAACCUGAAGCCCUUCGAGCGGGACA<br>UCAGCACCGAGAUCUACCAAGCCGGCUCCACCCCUUGCAACGGCGU<br>GGAGGGCUUCAACUGCUACUUCCCUCUGCAGAGCUACGGCUUCCAG<br>CCCACCAACGGCGUGGGCUACCAGCCCUACCGGGUGGUGGUGCUGA<br>GCUUCGAGCUGCUGCACGCCCCAGCCACCGUGUGUGGCCCCAAGAA<br>GAGCACCAACCUGGUGAAGAACAAGUGCGUGAACUUCAACUUCAAC<br>GGCCUUACCGGCACCGGCGUGCUGACCGAGAGCAACAAGAAAUUCC<br>UGCCCUUUUGCCAGUUCGGCCGGGACAUCGCCGACACCACCGACGC<br>UGUGCGGGAUCCCCAGACCCUGGAGAUCCUGGACAUCACCCCUUGC<br>AGCUUCGGCGGCUCUGGCGGAGGCAGCAUCCUGGCCAUCUACAGCA<br>CCGUGGCCAGCAGCCUGGUGCUGCUGGUGAGCCUGGGCGCCAUCAG<br>CUUC | 28 |
| 3' UTR | UGAUAAUAGGCUGGAGCCUCGGUGGCCUAGCUUCUUGCCCCUUGGG<br>CCUCCCCCCAGCCCCUCCUCCCCUUCCUGCACCCGUACCCCCGUGG<br>UCUUUGAAUAAAGUCUGAGUGGGCGGC | 4 |
| Corresponding amino acid sequence | MFVFLVLLPLVSSQCVNLTTRTQLPPAYTNSFTRGVYYPDKVCRSS<br>VLHSTQDLFLPFFSNVTWFHAIHVSGTNGTKRFDNPVLPFNDGVYF<br>ASTEKSNIIRGWIFGTTLDSKTQSLLIVNNATNVVIKVCEFQFCND<br>PFLGVYYHKNNKSWMESEFRVYSSANNCTFEYVSQPFLMDLEGKQG<br>NFKNLREFVFKNIDGYFKIYSKHTPINLVRDLPQGFSALEPLVDLP<br>IGINITRFQTLLALHRSYLTPGDSSSGWTAGAAAYYVGYLQPRTFL | 29 |

TABLE 3B-continued

| Subunit Antigen Truncations | | |
|---|---|---|
| | LKYNENGTITDAVDCALDPLSETKCTLKSFTVGSGGGSGGGSGGGS<br>GGGSGGQPTESIVRFPNITNLCPFGEVFNATRFASVYAWNRKRISN<br>CVADYSVLYNSASFSTFKCYGVSPTKLNDLCFTNVYADSEVIRGDE<br>VRQIAPGQTGKIADYNYKLPDDFTGCVIAWNSNNLDSKVGGNYNYL<br>YRLFRKSNLKPFERDISTEIYQAGSTPCNGVEGFNCYFPLQSYGFQ<br>PTNGVGYQPYRVVVLSFELLHAPATVCGPKKSTNLVKNKCVNFNFN<br>GLTGTGVLTESNKKFLPFCQFGRDIADTTDAVRDPQTLEILDITPC<br>SFGGsgggsilaiystvasslvllvslgaisf | |
| PolyA tail | 100 nt | |
| **SARS-COV-2 S1 Subunit Truncated and Linked to Transmembrane Domain (S1-666-TM)** | | |
| SEQ ID NO: 149 consists of from 5' end to 3' end: 5' UTR SEQ ID NO: 2, mRNA ORF SEQ ID NO: 150 and 3' UTR SEQ ID NO: 4. | | 149 |
| Chemistry | 1-methylpseudouridine | |
| Cap | 7mG(5')ppp(5')NlmpNp | |
| 5' UTR | GGGAAAUAAGAGAGAAAAGAAGAGUAAGAAGAAAUAUAAGACCCCG<br>GCGCCGCCACC | 2 |
| ORF of mRNA Construct (excluding the stop codon) | AUGUUCGUGUUCCUGGUGCUGCUGCCCCUGGUGAGCAGCCAGUGCGU<br>GAACCUGACCACCCGGACCCAGCUGCCACCAGCCUACACCAACAGCU<br>UCACCCGGGGCGUCUACUACCCCGACAAGGUGUUCCGGAGCAGCGUC<br>CUGCACAGCACCCAGGACCUGUUCCUGCCCUUCUUCAGCAACGUGAC<br>CUGGUUCCACGCCAUCCACGUGAGCGGCACCAACGGCACCAAGCGGU<br>UCGACAACCCCGUGCUGCCCUUCAACGACGGCGUGUACUUCGCCAGC<br>ACCGAGAAGAGCAACAUCAUCCGGGGCUGGAUCUUCGGCACCACCCU<br>GGACAGCAAGACCCAGAGCCUGCUGAUCGUGAAUAACGCCACCAACG<br>UGGUGAUCAAGGUGUGCGAGUUCCAGUUCUGCAACGACCCCUUCCUG<br>GGCGUGUACUACCACAAGAACAACAAGAGCUGGAUGGAGAGCGAGUU<br>CCGGGUGUACAGCAGCGCCAACAACUGCACCUUCGAGUACGUGAGCC<br>AGCCCUUCCUGAUGGACCUGGAGGGCAAGCAGGGCAACUUCAAGAAC<br>CUGCGGGAGUUCGUGUUCAAGAACAUCGACGGCUACUUCAAGAUCUA<br>CAGCAAGCACACCCCAAUCAACCUGGUGCGGGAUCUGCCCCAGGGCU<br>UCUCAGCCCUGGAGCCCCUGGUGGACCUGCCCAUCGGCAUCAACAUC<br>ACCCGGUUCCAGACCCUGCUGGCCCUGCACCGGAGCUACCUGACCCC<br>AGGCGACAGCAGCAGCGGGUGGACAGCAGGCGCGGCUGCUUACUACG<br>UGGGCUACCUGCAGCCCCGGACCUUCCUGCUGAAGUACAACGAGAAC<br>GGCACCAUCACCGACGCCGUGGACUGCGCCCUGGACCCUCUGAGCGA<br>GACCAAGUGCACCCUGAAGAGCUUCACCGUGGAGAAGGGCAUCUACC<br>AGACCAGCAACUUCCGGGUGCAGCCCACCGAGAGCAUCGUGCGGUUC<br>CCCAACAUCACCAACCUGUGCCCCUUCGGCGAGGUGUUCAACGCCAC<br>CCGGUUCGCCAGCGUGUACGCCUGGAACCGGAAGCGGAUCAGCAACU<br>GCGUGGCCGACUACAGCGUGCUGUACAACAGCGCCAGCUUCAGCACC<br>UUCAAGUGCUACGGCGUGAGCCCCACCAAGCUGAACGACCUGUGCUU<br>CACCAACGUGUACGCCGACAGCUUCGUGAUCCGUGGCGACGAGGUGC<br>GGCAGAUCGCACCCGGCCAGACAGGCAAGAUCGCCGACUACAACUAC<br>AAGCUGCCCGACGACUUCACCGGCUGCGUGAUCGCCUGGAACAGCAA<br>CAACCUCGACAGCAAGGUGGGCGGCAACUACAACUACCUGUACCGGC<br>UGUUCCGGAAGAGCAACCUGAAGCCCUUCGAGCGGGACAUCAGCACC<br>GAGAUCUACCAAGCCGGCUCCACCCCUUGCAACGGCGUGGAGGGCUU<br>CAACUGCUACUUCCCUCUGCAGAGCUACGGCUUCCAGCCCACCAACG<br>GCGUGGGCUACCAGCCCUACCGGGUGGUGGUGCUGAGCUUCGAGCUG<br>CUGCACGCCCCAGCCACCGUGUGUGGCCCCAAGAAGAGCACCAACCU<br>GGUGAAGAACAAGUGCGUGAACUUCAACUUCAACGGCCUUACCGGCA<br>CCGGCGUGCUGACCGAGAGCAACAAGAAAUUCCUGCCCUUUCAGCAG<br>UUCGGCCGGGACAUCGCCGACACCACCGACGCUGUGCGGGAUCCCCA<br>GACCCUGGAGAUCCUGGACAUCACCCCUUGCAGCUUCGGCGGCGUGA<br>GCGUGAUCACCCCAGGCACCAACACCAGCAACCAGGUGGCCGUGCUG<br>UACCAGGACGUGAACUGCACCGAGGUGCCCGUGGCCAUCCACGCCGA<br>CCAGCUGACACCCACCUGGCGGGUCUACAGCACCGGCAGCAACGUGU<br>UCCAGACCCGGGCCGGUUGCCUGAUCGGCGCCGAGCACGUGAACAAC<br>AGCUACGAGUGCGACAUCCCCAUCGGCGCCGGCAUCUGUGCCAGCUA<br>CCAGACCCAGACCAAUUCA | 150 |
| 3' UTR | UGAUAAUAGGCUGGAGCCUCGGUGGCCUAGCUUCUUGCCCCUUGGG<br>CCUCCCCCCAGCCCCUCCUCCCCUUCCUGCACCCGUACCCCCGUGG<br>UCUUUGAAUAAAGUCUGAGUGGGCGGC | 4 |
| Corresponding amino acid sequence | MFVFLVLLPLVSSQCVNLTTRTQLPPAYTNSFTRGVYYPDKVFRSSV<br>LHSTQDLFLPFFSNVTWFHAIHVSGTNGTKRFDNPVLPFNDGVYFAS<br>TEKSNIIRGWIFGTTLDSKTQSLLIVNNATNVVIKVCEFQFCNDPFL<br>GVYYHKNNKSWMESEFRVYSSANNCTFEYVSQPFLMDLEGKQGNFKN<br>LREFVFKNIDGYFKIYSKHTPINLVRDLPQGFSALEPLVDLPIGINI<br>TRFQTLLALHRSYLTPGDSSSGWTAGAAAYYVGYLQPRTFLLKYNEN | 151 |

TABLE 3B-continued

| Subunit Antigen Truncations | |
|---|---|
| | GTITDAVDCALDPLSETKCTLKSFTVEKGIYQTSNFRVQPTESIVRF<br>PNITNLCPFGEVFNATRFASVYAWNRKRISNCVADYSVLYNSASFST<br>FKCYGVSPTKLNDLCFTNVYADSFVIRGDEVRQIAPGQTGKIADYNY<br>KLPDDFTGCVIAWNSNNLDSKVGGNYNYLYRLFRKSNLKPFERDIST<br>ETYQAGSTPCNGVEGFNCYFPLQSYGFQPTNGVGYQPYRVVVLSFEL<br>LHAPATVCGPKKSTNLVKNKCVNFNFNGLTGTGVLTESNKKFLPFQQ<br>FGRDIADTTDAVRDPQTLEILDITPCSFGGVSVITPGTNTSNQVAVL<br>YQDVNCTEVPVAIHADQLTPTWRVYSTGSNVFQTRAGCLIGAEHVNN<br>SYECDIPIGAGICASYQTQTNS |
| PolyA tail | 100 nt |

TABLE 4A

| Subunit Antigen RBD Deletions | | |
|---|---|---|
| | SEQ ID NO: | |
| Name | mRNA ORF | Protein |
| SARS-CoV-2 S1 Subunit with Deletion of RBD and Glycan Added to S2 Subunit | 31 | 32 |

TABLE 4A-continued

| Subunit Antigen RBD Deletions | | |
|---|---|---|
| | SEQ ID NO: | |
| Name | mRNA ORF | Protein |
| SARS-CoV-2 S1 Subunit with Deletion of RBD and NTD and Glycan Added to S2 Subunit | 34 | 35 |

TABLE 4B

| Subunit Antigen RBD Deletions | | |
|---|---|---|
| SARS-COV-2 S1 Subunit with Deletion of RBD and Glycan Added to S2 Subunit | | |
| SEQ ID NO: 30 consists of from 5' end to 3' end: 5' UTR SEQ ID NO: 2, mRNA ORF SEQ ID NO: 31 and 3' UTR SEQ ID NO: 4. | | 30 |
| Chemistry | 1-methylpseudouridine | |
| Cap | 7mG(5')ppp(5')NImpNp | |
| 5' UTR | GGGAAAUAAGAGAGAAAAGAAGAGUAAGAAGAAAUAUAAGACCCCG<br>GCGCCGCCACC | 2 |
| ORF of mRNA Construct (excluding the stop codon) | AUGUUCGUGUUCCUGGUGCUGCUGCCCCUGGUGAGCAGCCAGUGCG<br>UGAACCUGACCACCCGGACCCAGCUGCCACCAGCCUACACCAACAG<br>CUUCACCCGGGGCGUCUACUACCCCGACAAGGUGUUCCGGAGCAGC<br>GUCCUGCACAGCACCCAGGACCUGUUCCUGCCCUUCUUCAGCAACG<br>UGACCUGGUUCCACGCCAUCCACGUGAGCGGCACCAACGGCACCAA<br>GCGGUUCGACAACCCCGUGCUGCCCUUCAACGACGGCGUGUACUUC<br>GCCAGCACCGAGAAGAGCAACAUCAUCCGGGGCUGGAUCUUCGGCA<br>CCACCCUGGACAGCAAGACCCAGAGCCUGCUGAUCGUGAAUAACGC<br>CACCAACGUGGUGAUCAAGGUGUGCGAGUUCCAGUUCUGCAACGAC<br>CCCUUCCUGGGCGUGUACUACCACAAGAACAACAAGAGCUGGAUGG<br>AGAGCGAGUUCCGGGUGUACAGCAGCGCCAACAACUGCACCUUCGA<br>GUACGUGAGCCAGCCCUUCCUGAUGGACCUGGAGGGCAAGCAGGGC<br>AACUUCAAGAACCUGCGGGAGUUCGUGUUCAAGAACAUCGACGGCU<br>ACUUCAAGAUCUACAGCAAGCACACCCCAAUCAACCUGGUGCGGGA<br>UCUGCCCCAGGGCUUCUCAGCCCUGGAGCCCCUGGUGGACCUGCCC<br>AUCGGCAUCAACAUCACCCGGUUCCAGACCCUGCUGGCCCUGCACC<br>GGAGCUACCUGACCCCAGGCGACAGCAGCAGCGGGUGGACAGCAGG<br>CGCGGCUGCUUACUACGUGGGCUACCUGCAGCCCCGGACCUUCCUG<br>CUGAAGUACAACGAGAACGGCACCAUCACCGACGCCGUGGACUGCG<br>CCCUGGACCCUCUGAGCGAGACCAAGUGCACCCUGAAGAGCUUCAC<br>CGUGGAGAAGGGCAUCUACCAGACCAGCAACUUCGGCGGCAGCGGC<br>GGCGUGAGCGUGAUCACCCCAGGCACCAACACCAGCAACCAGGUGG<br>CCGUGCUGUACCAGGACGUGAACUGCACCGAGGUGCCCGUGGCCAU<br>CCACGCCGACCAGCUGACACCCACCUGGCGGGUCUACAGCACCGGC<br>AGCAACGUGUUCCAGACCCGGGCCGGUUGCCUGAUCGGCGCCGAGC<br>ACGUGAACAACAGCUACGAGUGCGACAUCCCCAUCGGCGCCGGCAU<br>CUGUGCCAGCUACCAGACCCAGACCAAUUCACCCCGGAGGGCAAGG<br>AGCGUGGCCAGCCAGAGCAUCAUCGCCUACACCAUGAGCCUGGGCG<br>CCGAGAACAGCGUGGCCUACAGCAACAACAGCAUCGCCAUCCCCAC<br>CAACUUCACCAUCAGCGUGACCACCGAGAUUCUGCCCGUGAGCAUG<br>ACCAAGACCAGCGUGGACUGCACCAUGUACAUCUGCGGCGACAGCA<br>CCGAGUGCAGCAACCUGCUGCUGCAGUACGGCAGCUUCUGCACCCA | 31 |

TABLE 4B-continued

| Subunit Antigen RBD Deletions | | |
|---|---|---|
| | GCUGAACCGGGCCCUGACCGGCAUCGCCGUGGAGCAGGACAAGAAC<br>ACCCAGGAGGUGUUCGCCCAGGUGAAGCAGAUCUACAAGACCCCUC<br>CCAUCAAGGACUUCGGCGGCUUCAACUUCAGCCAGAUCCUGCCCGA<br>CCCCAGCAAGCCCAGCAAGCGGAGCUUCAUCGAGGACCUGCUGUUC<br>AACAAGGUGACCCUAGCCGACGCCGGCUUCAUCAAGCAGUACGGCG<br>ACUGCCUCGGCGACAUAGCCGCCCGGGACCUGAUCUGCGCCCAGAA<br>GUUCAACGGCCUGACCGUGCUGCCUCCCCUGCUGACCGACGAGAUG<br>AUCGCCCAGUACACCAGCGCCCUGUUAGCCGGAACCAUCACCAGCG<br>GCUGGACUUUCGGCGCUGGAGCCGCUCUGCAGAUCCCCUUCGCCAU<br>GCAGAUGGCCUACCGGUUCAACGGCAUCGGCGUGACCCAGAACGUG<br>CUGUACGAGAACCAGAAGCUGAUCGCCAACCAGUUCAACAGCGCCA<br>UCGGCAAGAUCCAGGACAGCCUGAGCAGCACCGCUAGCGCCCUGGG<br>CAAGCUGCAGGACGUGGUGAACCAGAACGCCCAGGCCCUGAACACC<br>CUGGUGAAGCAGCUGAGCAGCAACUUCGGCGCCAUCAGCAGCGUGC<br>UGAACGACAUCCUGAGCCGGCUGGACCCUCCCAACGCCACCGUGCA<br>GAUCGACCGGCUGAUCACUGGCCGGCUGCAGAGCCUGCAGACCUAC<br>GUGACCCAGCAGCUGAUCCGGGCCGCCGAGAUUCGGGCCAGCGCCA<br>ACCUGGCCGCCACCAAGAUGAGCGAGUGCGUGCUGGGCCAGAGCAA<br>GCGGGUGGACUUCUGCGGCAAGGGCUACCACCUGAUGAGCUUUCCC<br>CAGAGCGCACCCCACGGAGUGGUGUUCCUGCACGUGACCUACGUGC<br>CCGCCCAGGAGAAGAACUUCACCACCGCCCCAGCCAUCUGCCACGA<br>CGGCAAGGCCCACUUUCCCCGGGAGGGCGUGUUCGUGAGCAACGGC<br>ACCCACUGGUUCGUGACCCAGCGGAACUUCUACGAGCCCCAGAUCA<br>UCACCACCGACAACACCUUCGUGAGCGGCAACUGCGACGUGGUGAU<br>CGGCAUCGUGAACAACACCGUGUACGAUCCCCUGCAGCCCGAGCUG<br>GACAGCUUCAAGGAGGAGCUGGACAAGUACUUCAAGAAUCACACCA<br>GCCCCGACGUGGACCUGGGCGACAUCAGCGGCAUCAACGCCAGCGU<br>GGUGAACAUCCAGAAGGAGAUCGAUCGGCUGAACGAGGUGGCCAAG<br>AACCUGAACGAGAGCCUGAUCGACCUGCAGGAGCUGGGCAAGUACG<br>AGCAGUACAUCAAGUGGCCCUGGUACAUCUGGCUGGGCUUCAUCGC<br>CGGCCUGAUCGCCAUCGUGAUGGUGACCAUCAUGCUGUGCUGCAUG<br>ACCAGCUGCUGCAGCUGCCUGAAGGGCUGUUGCAGCUGCGGCAGCU<br>GCUGCAAGUUCGACGAGGACGACAGCGAGCCCGUGCUGAAGGGCGU<br>GAAGCUGCACUACACC | |
| 3' UTR | UGAUAAUAGGCUGGAGCCUCGGUGGCCUAGCUUCUUGCCCCUUGGG<br>CCUCCCCCCAGCCCCUCCUCCCCUUCCUGCACCCGUACCCCCGUGG<br>UCUUUGAAUAAAGUCUGAGUGGGCGGC | 4 |
| Corresponding amino acid sequence | MFVFLVLLPLVSSQCVNLTTRTQLPPAYTNSFTRGVYYPDKVFRSS<br>VLHSTQDLFLPFFSNVTWFHAIHVSGTNGTKRFDNPVLPFNDGVYF<br>ASTEKSNIIRGWIFGTTLDSKTQSLLIVNNATNVVIKVCEFQFCND<br>PFLGVYYHKNNKSWMESEFRVYSSANNCTFEYVSQPFLMDLEGKQG<br>NFKNLREFVFKNIDGYFKIYSKHTPINLVRDLPQGFSALEPLVDLP<br>IGINITRFQTLLALHRSYLTPGDSSSGWTAGAAAYYVGYLQPRTFL<br>LKYNENGTITDAVDCALDPLSETKCTLKSFTVEKGIYQTSNFGGSG<br>GVSVITPGTNTSNQVAVLYQDVNCTEVPVAIHADQLTPTWRVYSTG<br>SNVFQTRAGCLIGAEHVNNSYECDIPIGAGICASYQTQTNSPRRAR<br>SVASQSIIAYTMSLGAENSVAYSNNSIAIPTNFTISVTTEILPVSM<br>TKTSVDCTMYICGDSTECSNLLLQYGSFCTQLNRALTGIAVEQDKN<br>TQEVFAQVKQTYKTPPIKDFGGFNFSQILPDPSKPSKRSFIEDLLF<br>NKVTLADAGFIKQYGDCLGDIAARDLICAQKFNGLTVLPPLLTDEM<br>IAQYTSALLAGTITSGWTFGAGAALQIPFAMQMAYRFNGIGVTQNV<br>LYENQKLIANQFNSAIGKIQDSLSSTASALGKLQDVVNQNAQALNT<br>LVKQLSSNFGAISSVLNDILSRLDPPNATVQIDRLITGRLQSLQTY<br>VTQQLIRAAEIRASANLAATKMSECVLGQSKRVDFCGKGYHLMSFP<br>QSAPHGVVFLHVTYVPAQEKNFTTAPAICHDGKAHFPREGVFVSNG<br>THWFVTQRNFYEPQIITTDNTFVSGNCDVVIGIVNNTVYDPLQPEL<br>DSFKEELDKYFKNHTSPDVDLGDISGINASVVNIQKEIDRLNEVAK<br>NLNESLIDLQELGKYEQYIKWPWYIWLGFIAGLIAIVMVTIMLCCM<br>TSCCSCLKGCCSCGSCCKFDEDDSEPVLKGVKLHYT | 32 |
| PolyA tail | 100 nt | |
| SARS-COV-2 S1 Subunit with Deletion of RBD and NTD and Glycan Added to S2 Subunit | | |
| SEQ ID NO: 33 consists of from 5' end to 3' end: 5' UTR SEQ ID NO: 2, mRNA ORF SEQ ID NO: 34 and 3' UTR SEQ ID NO: 4. | | 33 |
| Chemistry | 1-methylpseudouridine | |
| Cap | 7mG(5')ppp(5')NlmpNp | |
| 5' UTR | GGGAAAUAAGAGAGAAAAGAAGAGUAAGAAGAAAUAUAAGACCCCG<br>GCGCCGCCACC | 2 |

TABLE 4B-continued

| Subunit Antigen RBD Deletions | | |
|---|---|---|
| ORF of mRNA Construct (excluding the stop codon) | AUGUUCGUGUUCCUGGUGCUGCUGCCCCUGGUGAGCAGCCAGGGCA<br>CCAUCACCGACGCCGUGGACUGCGCCCUGGACCCUCUGAGCGAGAC<br>CAAGUGCACCCUGAAGAGCUUCACCGUGGAGAAGGGCAUCUACCAG<br>ACCAGCAACUUCGGCGGCAGCGGCGGCGUGAGCGUGAUCACCCCAG<br>GCACCAACACCAGCAACCAGGUGGCCGUGCUGUACCAGGACGUGAA<br>CUGCACCGAGGUGCCCGUGGCCAUCCACGCCGACCAGCUGACACCC<br>ACCUGGCGGGUCUACAGCACCGGCAGCAACGUGUUCCAGACCCGGG<br>CCGGUUGCCUGAUCGGCGCCGAGCACGUGAACAACAGCUACGAGUG<br>CGACAUCCCCAUCGGCGCCGGCAUCUGUGCCAGCUACCAGACCCAG<br>ACCAAUUCACCCCGGAGGGCAAGGAGCGUGGCCAGCCAGAGCAUCA<br>UCGCCUACACCAUGAGCCUGGGCGCCGAGAACAGCGUGGCCUACAG<br>CAACAACAGCAUCGCCAUCCCCACCAACUUCACCAUCAGCGUGACC<br>ACCGAGAUUCUGCCCGUGAGCAUGACCAAGACCAGCGUGGACUGCA<br>CCAUGUACAUCUGCGGCGACAGCACCGAGUGCAGCAACCUGCUGCU<br>GAACUACACCAGCUUCUGCACCCAGCUGAACCGGGCCCUGACCGGC<br>AUCGCCGUGGAGCAGGACAAGAACACCCAGGAGGUGUUCGCCCAGG<br>UGAAGCAGAUCUACAAGACCCCUCCCAUCAAGGACUUCGGCGGCUU<br>CAACUUCAGCCAGAUCCUGCCCGACCCCAGCAAGCCCAGCAAGCGG<br>AGCUUCAUCGAGGACCUGCUGUUCAACAAGGUGACCCUAGCCGACG<br>CCGGCUUCAUCAAGCAGUACGGCGACUGCCUCGGCGACAUAGCCGC<br>CCGGGACCUGAUCUGCGCCCAGAAGUUCAACGGCCUGACCGUGCUG<br>CCUCCCCUGCUGACCGACGAGAUGAUCGCCCAGUACACCAGCGCCC<br>UGUUAGCCGGAACCAUCACCAGCGGCUGGACUUUCGGCGCUGGAGC<br>CGCUCUGCAGAUCCCCUUCGCCAUGCAGAUGGCCUACCGGUUCAAC<br>GGCAUCGGCGUGACCCAGAACGUGCUGUACGAGAACCAGAAGCUGA<br>UCGCCAACCAGUUCAACAGCGCCAUCGGCAAGAUCCAGGACAGCCU<br>GAGCAGCACCGCUAGCGCCCUGGGCAAGCUGCAGGACGUGGUGAAC<br>CAGAACGCCCAGGCCCUGAACACCCUGGUGAAGCAGCUGAGCAGCA<br>ACUUCGGCGCCAUCAGCAGCGUGCUGAACGACAUCCUGAGCCGGCU<br>GGACCCUCCCAACGCCACCGUGCAGAUCGACCGGCUGAUCACUGGC<br>CGGCUGCAGAGCCUGCAGACCUACGUGACCCAGCAGCUGAUCCGGG<br>CCGCCGAGAUUCGGGCCAGCGCCAACCUGGCCGCCACCAAGAUGAG<br>CGAGUGCGUGCUGGGCCAGAGCAAGCGGGUGGACUUCUGCGGCAAG<br>GGCUACCACCUGAUGAGCUUUCCCCAGAGCGCACCCCACGGAGUGG<br>UGUUCCUGCACGUGACCUACGUGCCCGCCCAGGAGAAGAACUUCAC<br>CACCGCCCCAGCCAUCUGCCACGACGGCAAGGCCCACUUUCCCCGG<br>GAGGGCGUGUUCGUGAGCAACGGCACCCACUGGUUCGUGACCCAGC<br>GGAACUUCUACGAGCCCCAGAUCAUCACCACCGACAACACCUUCGU<br>GAGCGGCAACUGCGACGUGGUGAUCGGCAUCGUGAACAACACCGUG<br>UACGAUCCCCUGCAGCCCGAGCUGGACAGCUUCAAGGAGGAGCUGG<br>ACAAGUACUUCAAGAAUCACACCAGCCCCGACGUGGACCUGGGCGA<br>CAUCAGCGGCAUCAACGCCAGCGUGGUGAACAUCCAGAAGGAGAUC<br>GAUCGGCUGAACGAGGUGGCCAAGAACCUGAACGAGAGCCUGAUCG<br>ACCUGCAGGAGCUGGGCAAGUACGAGCAGUACAUCAAGUGGCCCUG<br>GUACAUCUGGCUGGGCUUCAUCGCCGGCCUGAUCGCCAUCGUGAUG<br>GUGACCAUCAUGCUGUGCUGCAUGACCAGCUGCUGCAGCUGCCUGA<br>AGGGCUGUUGCAGCUGCGGCAGCUGCUGCAAGUUCGACGAGGACGA<br>CAGCGAGCCCGUGCUGAAGGGCGUGAAGCUGCACUACACC | 34 |
| 3' UTR | UGAUAAUAGGCUGGAGCCUCGGUGGCCUAGCUUCUUGCCCCUUGGG<br>CCUCCCCCCAGCCCCUCCUCCCCUUCCUGCACCCGUACCCCCGUGG<br>UCUUUGAAUAAAGUCUGAGUGGGCGGC | 4 |
| Corresponding amino acid sequence | MFVFLVLLPLVSSQGTITDAVDCALDPLSETKCTLKSFTVEKGIYQ<br>TSNFGGSGGVSVITPGTNTSNQVAVLYQDVNCTEVPVAIHADQLTP<br>TWRVYSTGSNVFQTRAGCLIGAEHVNNSYECDIPIGAGICASYQTQ<br>TNSPRRARSVASQSIIAYTMSLGAENSVAYSNNSIAIPTNFTISVT<br>TEILPVSMTKTSVDCTMYICGDSTECSNLLLNYTSFCTQLNRALTG<br>IAVEQDKNTQEVFAQVKQTYKTPPIKDFGGFNFSQILPDPSKPSKR<br>SFIEDLLFNKVTLADAGFIKQYGDCLGDIAARDLICAQKFNGLTVL<br>PPLLTDEMIAQYTSALLAGTITSGWTFGAGAALQIPFAMQMAYRFN<br>GIGVTONVLYENQKLIANQFNSAIGKIQDSLSSTASALGKLQDVVN<br>QNAQALNTLVKQLSSNFGAISSVLNDILSRLDPPNATVQIDRLITG<br>RLQSLQTYVTQQLIRAAEIRASANLAATKMSECVLGQSKRVDFCGK<br>GYHLMSFPQSAPHGVVFLHVTYVPAQEKNFTTAPAICHDGKAHFPR<br>EGVFVSNGTHWFVTQRNFYEPQIITTDNTFVSGNCDVVIGIVNNTV<br>YDPLQPELDSFKEELDKYFKNHTSPDVDLGDISGINASVVNIQKEI<br>DRLNEVAKNLNESLIDLQELGKYEQYIKWPWYIWLGFIAGLIAIVM<br>VTIMLCCMTSCCSCLKGCCSCGSCCKFDEDDSEPVLKGVKLHYT | 35 |
| PolyA tail | 100 nt | |

Chimeric S1-S2 Subunit Antigens

In some embodiments, a composition comprises an miRNA that encodes a chimeric protein, for example a chimeric S1-S2 protein with an S1 subunit from an S protein of one virus and an S2 subunit from an S protein of another, different virus. For example, an P2 subunit may be from SARS-CoV-2, while the S1 subunit may be from HKU1. As another example, an 2 subunit may be from SARS-CoV-2, while the S1 subunit may be from OC43. These chimeric proteins are likely to be opsonized by circulating antibodies specific to the S1 subunit of HKU1 or OC43 generated by previous exposures, promoting efficient uptake and cross-presentation of SARS-CoV-2 S2 subunit peptides to $CD4^+$ T cells by macrophages and dendritic cells. Opsonization by circulating antibodies also promotes capture by follicular dendritic cells for presentation to B cells with receptors specific to SARS-CoV-2 S2 subunit epitopes. Non-limiting examples of chimeric S1/S2 subunit constructs and the mRNA encoding them are provided in Tables 5A and 5B below.

TABLE 5A

| Chimeric S1 Subunit-S2 Subunit Antigens | | |
|---|---|---|
| | SEQ ID NO: | |
| Name | mRNA ORF | Protein |
| SARS-CoV-2 S2 Subunit Linked to HKU1 S1 Subunit | 37 | 38 |
| SARS-CoV-2 S2 Subunit Linked to OC43 S1 Subunit | 40 | 41 |

TABLE 5B

| Chimeric S1 Subunit-S2 Subunit Antigens | | |
|---|---|---|
| SARS-COV-2 S2 Subunit Linked to HKU1 S1 Subunit | | |
| | SEQ ID NO: 36 consists of from 5' end to 3' end: 5' UTR SEQ ID NO: 2, mRNA ORF SEQ ID NO: 37 and 3' UTR SEQ ID NO: 4. | 36 |
| Chemistry | 1-methylpseudouridine | |
| Cap | 7mG(5')ppp(5')NlmpNp | |
| 5' UTR | GGGAAAUAAGAGAGAAAAGAAGAGUAAGAAGAAAUAUAAGACCCCG<br>GCGCCGCCACC | 2 |
| ORF of mRNA Construct (excluding the stop codon) | AUGUUCCUGAUCAUCUUCAUCCUGCCCACCACCCUGGCCGUGAUCG<br>GCGACUUCAACUGCACCAACAGCUUCAUCAACGACUACAACAAGAC<br>CAUCCCUCGGAUCAGCGAAGACGUGGUGGACGUGUCCCUGGGCCUG<br>GGCACCUACUACGUGCUGAACCGGGUGUACCUGAACACCACACUGC<br>UGUUCACCGGCUACUUCCCCAAGAGCGGCGCCAACUUCCGGGACCU<br>GGCCCUGAAGGGCAGCAUCUACCUGAGCACCUUGUGGUACAAGCCU<br>CCCUUCCUGAGCGACUUCAAUAACGGCAUCUUCUCUAAGGUGAAGA<br>ACACCAAGCUGUACGUAAACAACACCCUGUACAGCGAGUUCAGCAC<br>CAUCGUGAUCGGCAGCGUGUUCGUCAACACCAGCUACACCAUCGUG<br>GUGCAGCCCCACAACGGCAUCCUGGAGAUCACCGCCUGCCAGUACA<br>CCAUGUGCGAGUACCCUCACACCGUGUGCAAGAGCAAGGGCUCCAU<br>CCGGAACGAGAGCUGGCACAUCGACAGCAGCGAGCCGCUGUGCCUG<br>UUCAAGAAGAACUUCACCUACAACGUGAGCGCCGACUGGCUGUACU<br>UCCACUUCUACCAGGAGCGGGGCGUGUUCUACGCCUACUACGCCGA<br>CGUGGGCAUGCCAACCACCUUCCUGUUCAGCCUGUACCUGGGCACC<br>AUCCUGAGCCACUACUACGUGAUGCCCCUGACCUGCAACGCCAUCA<br>GCUCAAACACCGACAACGAGACCCUGGAGUACUGGGUGACUCCACU<br>GAGCCGGCGGCAGUACCUGCUGAACUUCGACGAGCACGGCGUGAUC<br>ACCAACGCCGUGGACUGCGCCCUGGACCCUCUGAGCGAGACCAAGU<br>GCACCCUGAAGAGCUUCACCGUGGAGAAGGGCAUCUACCAGACCAG<br>CGGCUUCACCGUGAAGCCCGUAGCCACCGUGUACCGGCGGAUCCCC<br>AACCUGCCCGACUGCGACAUCGACAACUGGCUGAACAACGUCAGCG<br>UGCCCAGCCCACUGAACUGGGAGCGGCGGAUCUUCAGCAACUGCAA<br>CUUCAAUCUGAGCACCCUGCUGCGGCUGGUGCACGUGGACAGCUUC<br>AGCUGCAACAACCUGGACAAGAGCAAGAUCUUCGGUAGCUGCUUCA<br>ACAGCAUCACCGUGGACAAGUUCGCCAUCCCUAACCGGCGGCGGGA<br>CGAUCUGCAGCUGGGCAGCAGCGGCUUCCUGCAGAGCAGCAACUAC<br>AAGAUCGACAUCAGCAGCUCAAGCUGCCAGCUGUACUACAGCCUGC<br>CCCUGGUGAACGUGACCAUCAACAACUUCAACCCCAGCAGCUGGAA<br>CCGGCGGUACGGCUUCGGCAGCUUCAACCUGAGCAGCUACGACGUG<br>GUGUACAGCGACCACUGCUUCAGCGUGAACAGCGACUUCUGCCCCU<br>GUGCCGACCCUAGCGUGGUGAACAGCUGCGCCAAGAGCAAGCCUCC<br>CAGCGCCAUUUGCCCCGCCGGCACCAAGUACCGGCACUGCGACCUG<br>GACACCACCCUGUACGUGAAGAACUGGUGCCGGUGCAGCUGCCUGC<br>CCGACCCCAUCAGCACCUACAGCCCCAACACCUGUCCCCAGAAGAA<br>GGUGGUGGUGGGUAUCGGCGAGCACUGUCCCGGCCUGGGCAUCAAC<br>GAGGAGAAGUGCGGCACCCAGCUGAACCACAGCAGCUGCUUCUGUA<br>GCCCCGACGCCUUCCUGGGCUGGAGCUUCGACAGCUGCAUCAGCAA<br>CAACCGGUGCAACAUCUUUAGCAACUUCAUCUUCAACGGAAUCAAC<br>AGCGGCACCACCUGCAGCAACGACCUGCUGUAUAGCAACACCGAGA<br>UCAGCACCGGCGUGUGCGUGAACUACGACCUGUACGGCAUCACCGG<br>CCAGGGCAUCUUCAAGGAGGUGAGCGCCGCCUACUACAACAACUGG<br>CAGAACCUGCUGUACGACAGCAACGGCAACAUCAUCGGCUUCAAGG<br>ACUUUCUGACCAACAAGACCUACACCAUCCUGCCCUGCUACAGCGG<br>CGGCGUGAGCGUGAUCACCCCAGGCACCAACACCAGCAACCAGGUG<br>GCCGUGCUGUACCAGGACGUGAACUGCACCGAGGUGCCCGUGGCCA<br>UCCACGCCGACCAGCUGACACCCACCUGGCGGGUCUACAGCACCGG<br>CAGCAACGUGUUCCAGACCCGGGCCGGUUGCCUGAUCGGCGCCGAG<br>CACGUGAACAACAGCUACGAGUGCGACAUCCCCAUCGGCGCCGGCA | 37 |

TABLE 5B-continued

| Chimeric S1 Subunit-S2 Subunit Antigens | | |
|---|---|---|
| | UCUGUGCCAGCUACCAGACCCAGACCAAUUCACCCCGGAGGGCAAG<br>GAGCGUGGCCAGCCAGAGCAUCAUCGCCUACACCAUGAGCCUGGGC<br>GCCGAGAACAGCGUGGCCUACAGCAACAACAGCAUCGCCAUCCCCA<br>CCAACUUCACCAUCAGCGUGACCACCGAGAUUCUGCCCGUGAGCAU<br>GACCAAGACCAGCGUGGACUGCACCAUGUACAUCUGCGGCGACAGC<br>ACCGAGUGCAGCAACCUGCUGCUGCAGUACGGCAGCUUCUGCACCC<br>AGCUGAACCGGGCCCUGACCGGCAUCGCCGUGGAGCAGGACAAGAA<br>CACCCAGGAGGUGUUCGCCCAGGUGAAGCAGAUCUACAAGACCCCU<br>CCCAUCAAGGACUUCGGCGGCUUCAACUUCAGCCAGAUCCUGCCCG<br>ACCCCAGCAAGCCCAGCAAGCGGAGCUUCAUCGAGGACCUGCUGUU<br>CAACAAGGUGACCCUAGCCGACGCCGGCUUCAUCAAGCAGUACGGC<br>GACUGCCUCGGCGACAUAGCCGCCCGGGACCUGAUCUGCGCCCAGA<br>AGUUCAACGGCCUGACCGUGCUGCCUCCCCUGCUGACCGACGAGAU<br>GAUCGCCCAGUACACCAGCGCCCUGUUAGCCGGAACCAUCACCAGC<br>GGCUGGACUUUCGGCGCUGGAGCCGCUCUGCAGAUCCCCUUCGCCA<br>UGCAGAUGGCCUACCGGUUCAACGGCAUCGGCGUGACCCAGAACGU<br>GCUGUACGAGAACCAGAAGCUGAUCGCCAACCAGUUCAACAGCGCC<br>AUCGGCAAGAUCCAGGACAGCCUGAGCAGCACCGCUAGCGCCCUGG<br>GCAAGCUGCAGGACGUGGUGAACCAGAACGCCCAGGCCCUGAACAC<br>CCUGGUGAAGCAGCUGAGCAGCAACUUCGGCGCCAUCAGCAGCGUG<br>CUGAACGACAUCCUGAGCCGGCUGGACCCUCCCGAGGCCGAGGUGC<br>AGAUCGACCGGCUGAUCACUGGCCGGCUGCAGAGCCUGCAGACCUA<br>CGUGACCCAGCAGCUGAUCCGGGCCGCCGAGAUUCGGGCCAGCGCC<br>AACCUGGCCGCCACCAAGAUGAGCGAGUGCGUGCUGGGCCAGAGCA<br>AGCGGGUGGACUUCUGCGGCAAGGGCUACCACCUGAUGAGCUUUCC<br>CCAGAGCGCACCCCACGGAGUGGUGUUCCUGCACGUGACCUACGUG<br>CCCGCCCAGGAGAAGAACUUCACCACCGCCCCAGCCAUCUGCCACG<br>ACGGCAAGGCCCACUUUCCCCGGGAGGGCGUGUUCGUGAGCAACGG<br>CACCCACUGGUUCGUGACCCAGCGGAACUUCUACGAGCCCCAGAUC<br>AUCACCACCGACAACACCUUCGUGAGCGGCAACUGCGACGUGGUGA<br>UCGGCAUCGUGAACAACACCGUGUACGAUCCCCUGCAGCCCGAGCU<br>GGACAGCUUCAAGGAGGAGCUGGACAAGUACUUCAAGAAUCACACC<br>AGCCCCGACGUGGACCUGGGCGACAUCAGCGGCAUCAACGCCAGCG<br>UGGUGAACAUCCAGAAGGAGAUCGAUCGGCUGAACGAGGUGGCCAA<br>GAACCUGAACGAGAGCCUGAUCGACCUGCAGGAGCUGGGCAAGUAC<br>GAGCAGUACAUCAAGUGGCCCUGGUACAUCUGGCUGGGCUUCAUCG<br>CCGGCCUGAUCGCCAUCGUGAUGGUGACCAUCAUGCUGUGCUGCAU<br>GACCAGCUGCUGCAGCUGCCUGAAGGGCUGUUGCAGCUGCGGCAGC<br>UGCUGCAAGUUCGACGAGGACGACAGCGAGCCCGUGCUGAAGGGCG<br>UGAAGCUGCACUACACC | |
| 3' UTR | UGAUAAUAGGCUGGAGCCUCGGUGGCCUAGCUUCUUGCCCCUUGGG<br>CCUCCCCCCAGCCCCUCCUCCCCUUCCUGCACCCGUACCCCCGUGG<br>UCUUUGAAUAAAGUCUGAGUGGGCGGC | 4 |
| Corresponding amino acid sequence | MFLIIFILPTTLAVIGDFNCTNSFINDYNKTIPRISEDVVDVSLGL<br>GTYYVLNRVYLNTTLLFTGYFPKSGANFRDLALKGSIYLSTLWYKP<br>PFLSDFNNGIFSKVKNTKLYVNNTLYSEFSTIVIGSVFVNTSYTIV<br>VQPHNGILEITACQYTMCEYPHTVCKSKGSIRNESWHIDSSEPLCL<br>FKKNFTYNVSADWLYFHFYQERGVFYAYYADVGMPTTFLFSLYLGT<br>ILSHYYVMPLTCNAISSNTDNETLEYWVTPLSRRQYLLNFDEHGVI<br>TNAVDCALDPLSETKCTLKSFTVEKGIYQTSGFTVKPVATVYRRIP<br>NLPDCDIDNWLNNVSVPSPLNWERRIFSNCNFNLSTLLRLVHVDSF<br>SCNNLDKSKIFGSCFNSITVDKFAIPNRRRDDLQLGSSGFLQSSNY<br>KIDISSSSCQLYYSLPLVNVTINNFNPSSWNRRYGFGSFNLSSYDV<br>VYSDHCFSVNSDFCPCADPSVVNSCAKSKPPSAICPAGTKYRHCDL<br>DTTLYVKNWCRCSCLPDPISTYSPNTCPQKKVVVGIGEHCPGLGIN<br>EEKCGTQLNHSSCFCSPDAFLGWSFDSCISNNRCNIFSNFIFNGIN<br>SGTTCSNDLLYSNTEISTGVCVNYDLYGITGQGIFKEVSAAYYNNW<br>QNLLYDSNGNIIGFKDFLTNKTYTILPCYSGGVSVITPGTNTSNQV<br>AVLYQDVNCTEVPVAIHADQLTPTWRVYSTGSNVFQTRAGCLIGAE<br>HVNNSYECDIPIGAGICASYQTQTNSPRRARSVASQSIIAYTMSLG<br>AENSVAYSNNSIAIPTNFTISVTTEILPVSMTKTSVDCTMYICGDS<br>TECSNLLLQYGSFCTQLNRALTGIAVEQDKNTQEVFAQVKQIYKTP<br>PIKDFGGFNFSQILPDPSKPSKRSFIEDLLFNKVTLADAGFIKQYG<br>DCLGDIAARDLICAQKFNGLTVLPPLLTDEMIAQYTSALLAGTITS<br>GWTFGAGAALQIPFAMQMAYRFNGIGVTQNVLYENQKLIANQFNSA<br>IGKIQDSLSSTASALGKLQDVVNQNAQALNTLVKQLSSNFGAISSV<br>LNDILSRLDPPEAEVQIDRLITGRLQSLQTYVTQQLIRAAEIRASA<br>NLAATKMSECVLGQSKRVDFCGKGYHLMSFPQSAPHGVVFLHVTYV<br>PAQEKNFTTAPAICHDGKAHFPREGVFVSNGTHWFVTQRNFYEPQI | 38 |

TABLE 5B-continued

| Chimeric S1 Subunit-S2 Subunit Antigens | | |
|---|---|---|
| | ITTDNTFVSGNCDVVIGIVNNTVYDPLQPELDSFKEELDKYFKNHT<br>SPDVDLGDISGINASVVNIQKEIDRLNEVAKNLNESLIDLQELGKY<br>EQYIKWPWYIWLGFIAGLIAIVMVTIMLCCMTSCCSCLKGCCSCGS<br>CCKFDEDDSEPVLKGVKLHYT | |
| PolyA tail | 100 nt | |
| **SARS-COV-2 S2 Subunit Linked to OC43 S1 Subunit** | | |
| SEQ ID NO: 39 consists of from 5' end to 3' end: 5' UTR SEQ ID NO: 2, mRNA ORF SEQ ID NO: 40 and 3' UTR SEQ ID NO: 4. | | 39 |
| Chemistry | 1-methylpseudouridine | |
| Cap | 7mG(5')ppp(5')NImpNp | |
| 5' UTR | GGGAAAUAAGAGAGAAAAGAAGAGUAAGAAGAAAUAUAAGACCCCG<br>GCGCCGCCACC | 2 |
| ORF of mRNA Construct (excluding the stop codon) | AUGUUCCUGAUCCUGCUGAUCAGCCUGCCCACCGCCUUCGCCGUGA<br>UCGGCGACCUGAAGUGCACCAGCGACAACAUCAACGACAAGGACAC<br>CGGCCCACCACCCAUCAGCACCGACACCGUGGACGUGACCAACGGC<br>CUGGGCACCUACUACGUGCUGGACCGGGUGUACCUGAACACCACCC<br>UGUUCCUGAACGGCUACUACCCCACCAGCGGCAGCACCUACCGGAA<br>UAUGGCCCUGAAGGGCAGCGUGCUGCUGAGCCGGCUGUGGUUCAAG<br>CCACCAUUCCUGAGCGACUUCAUCAACGGAAUCUUCGCCAAGGUGA<br>AGAACACCAAGGUGAUCAAGGACCGGGUGAUGUACAGCGAGUUCCC<br>CGCCAUCACCAUUGGCAGUACCUUCGUGAACACCAGCUACAGCGUG<br>GUGGUGCAGCCCCGGACCAUCAACAGCACCCAGGACGGCGACAACA<br>AGCUGCAGGGCCUGCUGGAGGUGAGCGUGUGCCAGUACAACAUGUG<br>CGAGUACCCUCAGACCAUCUGCCACCCCAACCUGGGCAACCACCGG<br>AAGGAGCUGUGGCACCUGGACACCGGCGUGGUGAGCUGCCUGUACA<br>AGCGGAACUUCACCUACGACGUAAACGCCGACUACCUGUACUUCCA<br>CUUCUACCAGGAGGGCGGCACCUUCUACGCCUACUUCACCGACACG<br>GGCGUGGUGACCAAGUUCCUGUUCAACGUGUACCUGGGCAUGGCCC<br>UGAGCCACUACUACGUGAUGCCCCUGACCUGUAACAGCAAGCUGAC<br>CCUGGAGUACUGGGUGACCCCUCUGACCAGCCGGCAGUACCUGCUG<br>GCCUUCAACCAGGACGGCAUCAUCUUCAACGCCGUGGACUGCGCCC<br>UGGACCCUCUGAGCGAGACCAAGUGCACCCUGAAGAGCUUCACCGU<br>GGAGAAGGGCAUCUACCAGACCAACGGCUACACCGUGCAGCCCAUC<br>GCCGACGUGUACCGGCGGAAGCCCAACCUGCCCAACUGCAACAUCG<br>AGGCCUGGCUGAACGACAAGAGCGUGCCCUCGCCCCUGAACUGGGA<br>GCGGAAGACCUUCAGCAACUGCAACUUCAACAUGAGCAGUCUGAUG<br>AGCUUCAUCCAGGCCGACAGCUUCACCUGCAACAACAUCGACGCCG<br>CCAAGAUCUACGGCAUGUGCUUCAGCAGCAUCACCAUCGACAAGUU<br>UGCCAUCCCCAACGGCCGGAAGGUGGACCUGCAGCUGGGCAACCUG<br>GGCUACCUGCAGAGCUUCAACUACCGGAUCGACACCACCGCCACCU<br>CUUGCCAGCUGUACUACAACCUGCCCGCCGCCAACGUGAGCGUGAG<br>CCGGUUCAACCCCAGCACCUGGAACAAGCGGUUCGGCUUCAUUGAG<br>GACAGCGUGUUCAAACCCCGGCCCGCAGGAGUACUGACCAACCACG<br>ACGUGGUGUACGCCCAGCACUGCUUCAAGGCACCCAAGAACUUCUG<br>CCCCUGCAAGCUGAACGGCAGCUGUGUGGGCUCUGGCCCCGGUAAG<br>AACAACGGCAUAGGGACUUGCCCGGCAGGGACCAACUACCUGACCU<br>GCGACAACCUGUGCACACCCGACCCCAUCACCUUCACCGGCACCUA<br>CAAGUGUCCCCAGACCAAGAGCCUGGUGGGCAUCGGCGAGCACUGC<br>AGCGGCCUGGCCGUGAAGAGCGACUACUGCGGCGGCAACAGCUGCA<br>CCUGUCGGCCCCAGGCCUUCCUGGGCUGGAGCGCCGACAGCUGCCU<br>GCAGGGCGACAAGUGCAACAUCUUUGCCAACUUCAUCCUGCACGAC<br>GUGAACAGCGGCCUGACCUGCAGCACCGACCUGCAGAAGGCCAACA<br>CCGACAUCAUCCUGGGCGUGUGCGUGAACUACGACUUGUACGGCAU<br>CCUGGGCCAGGGCAUCUUCGUGGAGGUGAACGCCACCUACUACAAC<br>AGCUGGCAGAACCUGCUGUACGACAGCAACGGCAACCUGUACGGCU<br>UCCGGGACUACAUCAUCAACCGGACCUUCAUGAUCCGGAGCUGCUA<br>CAGCGGCGGCGUGAGCGUGAUCACCCCAGGCACCAACACCAGCAAC<br>CAGGUGGCCGUGCUGUACCAGGACGUGAACUGCACCGAGGUGCCCG<br>UGGCCAUCCACGCCGACCAGCUGACACCCACCUGGCGGGUCUACAG<br>CACCGGCAGCAACGUGUUCCAGACCCGGGCCGGUUGCCUGAUCGGC<br>GCCGAGCACGUGAACAACAGCUACGAGUGCGACAUCCCCAUCGGCG<br>CCGGCAUCUGUGCCAGCUACCAGACCCAGACCAAUUCACCCCGGAG<br>GGCAAGGAGCGUGGCCAGCCAGAGCAUCAUCGCCUACACCAUGAGC<br>CUGGGCGCCGAGAACAGCGUGGCCUACAGCAACAACAGCAUCGCCA<br>UCCCCACCAACUUCACCAUCAGCGUGACCACCGAGAUUCUGCCCGU<br>GAGCAUGACCAAGACCAGCGUGGACUGCACCAUGUACAUCUGCGGC<br>GACAGCACCGAGUGCAGCAACCUGCUGCUGCAGUACGGCAGCUUCU<br>GCACCCAGCUGAACCGGGCCCUGACCGGCAUCGCCGUGGAGCAGGA<br>CAAGAACACCCAGGAGGUGUUCGCCCAGGUGAAGCAGAUCUACAAG<br>ACCCCUCCCAUCAAGGACUUCGGCGGCUUCAACUUCAGCCAGAUCC | 40 |

TABLE 5B-continued

| Chimeric S1 Subunit-S2 Subunit Antigens | | |
|---|---|---|
| | UGCCCGACCCCAGCAAGCCCAGCAAGCGGAGCUUCAUCGAGGACCU<br>GCUGUUCAACAAGGUGACCCUAGCCGACGCCGGCUUCAUCAAGCAG<br>UACGGCGACUGCCUCGGCGACAUAGCCGCCCGGGACCUGAUCUGCG<br>CCCAGAAGUUCAACGGCCUGACCGUGCUGCCUCCCCUGCUGACCGA<br>CGAGAUGAUCGCCCAGUACACCAGCGCCCUGUUAGCCGGAACCAUC<br>ACCAGCGGCUGGACUUUCGGCGCUGGAGCCGCUCUGCAGAUCCCCU<br>UCGCCAUGCAGAUGGCCUACCGGUUCAACGGCAUCGGCGUGACCCA<br>GAACGUGCUGUACGAGAACCAGAAGCUGAUCGCCAACCAGUUCAAC<br>AGCGCCAUCGGCAAGAUCCAGGACAGCCUGAGCAGCACCGCUAGCG<br>CCCUGGGCAAGCUGCAGGACGUGGUGAACCAGAACGCCCAGGCCCU<br>GAACACCCUGGUGAAGCAGCUGAGCAGCAACUUCGGCGCCAUCAGC<br>AGCGUGCUGAACGACAUCCUGAGCCGGCUGGACCCUCCCGAGGCCG<br>AGGUGCAGAUCGACCGGCUGAUCACUGGCCGGCUGCAGAGCCUGCA<br>GACCUACGUGACCCAGCAGCUGAUCCGGGCCGCCGAGAUUCGGGCC<br>AGCGCCAACCUGGCCGCCACCAAGAUGAGCGAGUGCGUGCUGGGCC<br>AGAGCAAGCGGGUGGACUUCUGCGGCAAGGGCUACCACCUGAUGAG<br>CUUUCCCCAGAGCGCACCCCACGGAGUGGUGUUCCUGCACGUGACC<br>UACGUGCCCGCCCAGGAGAAGAACUUCACCACCGCCCCAGCCAUCU<br>GCCACGACGGCAAGGCCCACUUUCCCCGGGAGGGCGUGUUCGUGAG<br>CAACGGCACCCACUGGUUCGUGACCCAGCGGAACUUCUACGAGCCC<br>CAGAUCAUCACCACCGACAACACCUUCGUGAGCGGCAACUGCGACG<br>UGGUGAUCGGCAUCGUGAACAACACCGUGUACGAUCCCCUGCAGCC<br>CGAGCUGGACAGCUUCAAGGAGGAGCUGGACAAGUACUUCAAGAAU<br>CACACCAGCCCCGACGUGGACCUGGGCGACAUCAGCGGCAUCAACG<br>CCAGCGUGGUGAACAUCCAGAAGGAGAUCGAUCGGCUGAACGAGGU<br>GGCCAAGAACCUGAACGAGAGCCUGAUCGACCUGCAGGAGCUGGGC<br>AAGUACGAGCAGUACAUCAAGUGGCCCUGGUACAUCUGGCUGGGCU<br>UCAUCGCCGGCCUGAUCGCCAUCGUGAUGGUGACCAUCAUGCUGUG<br>CUGCAUGACCAGCUGCUGCAGCUGCCUGAAGGGCUGUUGCAGCUGC<br>GGCAGCUGCUGCAAGUUCGACGAGGACGACAGCGAGCCCGUGCUGA<br>AGGGCGUGAAGCUGCACUACACC | |
| 3' UTR | UGAUAAUAGGCUGGAGCCUCGGUGGCCUAGCUUCUUGCCCCUUGGG<br>CCUCCCCCCAGCCCCUCCUCCCCUUCCUGCACCCGUACCCCCGUGG<br>UCUUUGAAUAAAGUCUGAGUGGGCGGC | 4 |
| Corresponding amino acid sequence | MFLILLISLPTAFAVIGDLKCTSDNINDKDTGPPPISTDTVDVTNG<br>LGTYYVLDRVYLNTTLFLNGYYPTSGSTYRNMALKGSVLLSRLWFK<br>PPFLSDFINGIFAKVKNTKVIKDRVMYSEFPAITIGSTFVNTSYSV<br>VVQPRTINSTODGDNKLQGLLEVSVCQYNMCEYPQTICHPNLGNHR<br>KELWHLDTGVVSCLYKRNFTYDVNADYLYFHFYQEGGTFYAYFTDT<br>GVVTKFLFNVYLGMALSHYYVMPLTCNSKLTLEYWVTPLTSRQYLL<br>AFNQDGIIFNAVDCALDPLSETKCTLKSFTVEKGIYQTNGYTVQPI<br>ADVYRRKPNLPNCNIEAWLNDKSVPSPLNWERKTFSNCNFNMSSLM<br>SFIQADSFTCNNIDAAKIYGMCFSSITIDKFAIPNGRKVDLQLGNL<br>GYLQSFNYRIDTTATSCQLYYNLPAANVSVSRFNPSTWNKRFGFIE<br>DSVFKPRPAGVLTNHDVVYAQHCFKAPKNFCPCKLNGSCVGSGPGK<br>NNGIGTCPAGTNYLTCDNLCTPDPITFTGTYKCPQTKSLVGIGEHC<br>SGLAVKSDYCGGNSCTCRPQAFLGWSADSCLQGDKCNIFANFILHD<br>VNSGLTCSTDLQKANTDIILGVCVNYDLYGILGQGIFVEVNATYYN<br>SWQNLLYDSNGNLYGFRDYIINRTFMIRSCYSGGVSVITPGTNTSN<br>QVAVLYQDVNCTEVPVAIHADQLTPTWRVYSTGSNVFQTRAGCLIG<br>AEHVNNSYECDIPIGAGICASYQTQTNSPRRARSVASQSIIAYTMS<br>LGAENSVAYSNNSIAIPTNFTISVTTEILPVSMTKTSVDCTMYICG<br>DSTECSNLLLQYGSFCTQLNRALTGIAVEQDKNTQEVFAQVKQIYK<br>TPPIKDFGGFNFSQILPDPSKPSKRSFIEDLLFNKVTLADAGFIKQ<br>YGDCLGDIAARDLICAQKFNGLTVLPPLLTDEMIAQYTSALLAGTI<br>TSGWTFGAGAALQIPFAMQMAYRENGIGVTQNVLYENQKLIANQFN<br>SAIGKIQDSLSSTASALGKLQDVVNQNAQALNTLVKQLSSNFGAIS<br>SVLNDILSRLDPPEAEVQIDRLITGRLQSLQTYVTQQLIRAAEIRA<br>SANLAATKMSECVLGQSKRVDFCGKGYHLMSFPQSAPHGVVFLHVT<br>YVPAQEKNFTTAPAICHDGKAHFPREGVFVSNGTHWFVTQRNFYEP<br>QIITTDNTFVSGNCDVVIGIVNNTVYDPLQPELDSFKEELDKYFKN<br>HTSPDVDLGDISGINASVVNIQKEIDRLNEVAKNLNESLIDLQELG<br>KYEQYIKWPWYIWLGFIAGLIAIVMVTIMLCCMTSCCSCLKGCCSC<br>GSCCKFDEDDSEPVLKGVKLHYT | 41 |
| PolyA tail | 100 nt | |

Encoded Domain Antigens

Other aspects of the present disclosure provide compositions comprising an mRNA that encodes a (at least one) subdomain of the SARS-CoV-2 S1 subunit of the S protein. The subdomain may be an N-terminal domain (NTD) or a receptor binding domain (RBD) (with or without the SD1 and/or SD2). In some embodiments, an mRNA encodes a combination (e.g., a non-natural combination) of an NTD and an RBD (with or without the SD1 and/or SD2). In some embodiments, the NTD and/or RBD is linked to a transmembrane domain (with or without the SD1 and/or SD2). In some embodiments, the mRNA encodes two subdomains of the SARS-CoV-2 S1 subunit of the S protein (NTD and RBD) that have been mutated to comprise cysteine residues.

Such mutations, in some embodiments, result in the formation of a disulfide bond. As an example, an mRNA may encode an NTD comprising an F43C mutation and an RBD comprising a Q563C mutation, ultimately resulting in a an NTD linked to an RBD via disulfide bond.

N Terminal Domain (NTD) Constructs

In some embodiments, an mRNA provided herein encodes an NTD of an S1 subunit of a SARS-CoV-2 S protein. The NTD of certain betacoronaviruses elicits protective levels of antibodies. Antibodies specific to the NTD of other betacoronaviruses such as MERS act by preventing membrane fusion and viral entry (Zhou H et al. Nat Commun. 2019; 3068), providing a second mechanism of neutralization that is distinct from preventing viral attachment to ACE2. The SARS-CoV-2 NTDs encoded by an mRNA of the present disclosure may be soluble or membrane bound. A non-limiting example of a membrane bound SARS-CoV-2 NTD antigen and the mRNA encoding it is provided in Tables 6A and 6B below.

TABLE 6A

Membrane Bound NTD Antigens

| | SEQ ID NO: | |
|---|---|---|
| Name | mRNA ORF | Protein |
| SARS-CoV-2 NTD Linked to Transmembrane Domain (NTD-TM) | 46 | 47 |

TABLE 6B

Membrane Bound NTD Antigens<br>SARS-COV-2 NTD Linked to Transmembrane Domain (NTD-TM)

| | | |
|---|---|---|
| | SEQ ID NO: 45 consists of from 5' end to 3' end: 5' UTR SEQ ID NO: 2, mRNA ORF SEQ ID NO: 46 and 3' UTR SEQ ID NO: 4. | 45 |
| Chemistry | 1-methylpseudouridine | |
| Cap | 7mG(5')ppp(5')NImpNp | |
| 5' UTR | GGGAAAUAAGAGAGAAAAGAAGAGUAAGAAGAAAUAUAAGACCCCG<br>GCGCCGCCACC | 2 |
| ORF of mRNA Construct (excluding the stop codon) | AUGUUCGUGUUCCUGGUGCUGCUGCCCCUGGUGAGCAGCCAGUGCG<br>UGAACCUGACCACCCGGACCCAGCUGCCACCAGCCUACACCAACAG<br>CUUCACCCGGGGCGUCUACUACCCCGACAAGGUGUUCCGGAGCAGC<br>GUCCUGCACAGCACCCAGGACCUGUUCCUGCCCUUCUUCAGCAACG<br>UGACCUGGUUCCACGCCAUCCACGUGAGCGGCACCAACGGCACCAA<br>GCGGUUCGACAACCCCGUGCUGCCCUUCAACGACGGCGUGUACUUC<br>GCCAGCACCGAGAAGAGCAACAUCAUCCGGGGCUGGAUCUUCGGCA<br>CCACCCUGGACAGCAAGACCCAGAGCCUGCUGAUCGUGAAUAACGC<br>CACCAACGUGGUGAUCAAGGUGUGCGAGUUCCAGUUCUGCAACGAC<br>CCCUUCCUGGGCGUGUACUACCACAAGAACAACAAGAGCUGGAUGG<br>AGAGCGAGUUCCGGGUGUACAGCAGCGCCAACAACUGCACCUUCGA<br>GUACGUGAGCCAGCCCUUCCUGAUGGACCUGGAGGGCAAGCAGGGC<br>AACUUCAAGAACCUGCGGGAGUUCGUGUUCAAGAACAUCGACGGCU<br>ACUUCAAGAUCUACAGCAAGCACACCCCAAUCAACCUGGUGCGGGA<br>UCUGCCCCAGGGCUUCUCAGCCCUGGAGCCCCUGGUGGACCUGCCC<br>AUCGGCAUCAACAUCACCCGGUUCCAGACCCUGCUGGCCCUGCACC<br>GGAGCUACCUGACCCCAGGCGACAGCAGCAGCGGGUGGACAGCAGG<br>CGCGGCUGCUUACUACGUGGGCUACCUGCAGCCCCGGACCUUCCUG<br>CUGAAGUACAACGAGAACGGCACCAUCACCGACGCCGUGGACUCUG<br>GCGGAGGCAGCAUCCUGGCCAUCUACAGCACCGUGGCCAGCAGCCU<br>GGUGCUGCUGGUGAGCCUGGGCGCCAUCAGCUUC | 46 |
| 3' UTR | UGAUAAUAGGCUGGAGCCUCGGUGGCCUAGCUUCUUGCCCCUUGGG<br>CCUCCCCCCAGCCCCUCCUCCCCUUCCUGCACCCGUACCCCCGUGG<br>UCUUUGAAUAAAGUCUGAGUGGGCGGC | 4 |
| Corresponding amino acid sequence | MFVFLVLLPLVSSQCVNLTTRTQLPPAYTNSFTRGVYYPDKVFRSS<br>VLHSTQDLFLPFFSNVTWFHAIHVSGTNGTKRFDNPVLPFNDGVYF<br>ASTEKSNIIRGWIFGTTLDSKTQSLLIVNNATNVVIKVCEFQFCND<br>PFLGVYYHKNNKSWMESEFRVYSSANNCTFEYVSQPFLMDLEGKQG<br>NFKNLREFVFKNIDGYFKIYSKHTPINLVRDLPQGFSALEPLVDLP<br>IGINITRFQTLLALHRSYLTPGDSSSGWTAGAAAYYVGYLQPRTFL<br>LKYNENGTITDAVDSGGGSILAIYSTVASSLVLLVSLGAISF | 47 |
| PolyA tail | 100 nt | |

Receptor Binding Domain (RBD) Constructs

In other embodiments, an mRNA provided herein encodes an RBD of an S1 subunit of a SARS-CoV-2 S protein. The RBD binds ACE2 receptors on host cells, which mediate virus attachment to cells. Attachment is necessary for the virus to enter cells and replicate. Thus, RBD targeted antibody responses, which block virus attachment into the cell, effectively neutralize extracellular virus particles, preventing proliferation and promoting further immune responses to other components of the neutralized virus particles. The SARS-CoV-2 RBDs encoded by an mRNA of the present disclosure may be soluble or membrane bound (e.g., linked to a transmembrane domain).

Soluble RBD Antigens

In some embodiments, an mRNA encodes a soluble SARS-CoV-2 RBD. Dendritic cells sample soluble proteins by pinocytosis and, upon migrating to the draining lymph node, present linear peptides that comprise the sampled protein to $CD4^+$ T cells. These $CD4^+$ T cells provide proliferation signals to B cells that have recognized, taken up, and presented an epitope from the RBD, so administration of specifically RBD without other components of the SARS-CoV-2 spike protein expected to focus the immune response towards the epitopes present in the RBD. Non-limiting examples of soluble SARS-CoV-2 RBDs and the mRNA encoding them are provided in the Tables 7A and 7B below.

TABLE 7

Soluble RBD Antigens

| Name | SEQ ID NO: mRNA ORF | SEQ ID NO: Protein |
|---|---|---|
| SARS-CoV-2 Soluble RBD | 61 | 62 |

TABLE 7B

Soluble RBD Antigens
SARS-COV-2 Soluble RBD

| | | |
|---|---|---|
| SEQ ID NO: 60 consists of from 5' end to 3' end: 5' UTR SEQ ID NO: 2, mRNA ORF SEQ ID NO: 61 and 3' UTR SEQ ID NO: 4. | | 60 |
| Chemistry | 1-methylpseudouridine | |
| Cap | 7mG(5')ppp(5')NImpNp | |
| 5' UTR | GGGAAAUAAGAGAGAAAAGAAGAGUAAGAAGAAAUAUAAGACCCCG GCGCCGCCACC | 2 |
| ORF of mRNA Construct (excluding the stop codon) | AUGUACAGCAUGCAGCUGGCUAGCUGCGUGACCCUGACCCUGGUGC UGCUGGUGAACAGCCAGCCCAACAUCACCAACCUGUGCCCCUUCGG CGAGGUGUUCAACGCCACCCGGUUCGCCAGCGUGUACGCCUGGAAC CGGAAGCGGAUCAGCAACUGCGUGGCCGACUACAGCGUGCUGUACA ACAGCGCCAGCUUCAGCACCUUCAAGUGCUACGGCGUGAGCCCCAC CAAGCUGAACGACCUGUGCUUCACCAACGUGUACGCCGACAGCUUC GUGAUCCGUGGCGACGAGGUGCGGCAGAUCGCACCCGGCCAGACAG GCAAGAUCGCCGACUACAACUACAAGCUGCCCGACGACUUCACCGG CUGCGUGAUCGCCUGGAACAGCAACAACCUCGACAGCAAGGUGGGC GGCAACUACAACUACCUGUACCGGCUGUUCCGGAAGAGCAACCUGA AGCCCUUCGAGCGGGACAUCAGCACCGAGAUCUACCAAGCCGGCUC CACCCCUUGCAACGGCGUGGAGGGCUUCAACUGCUACUUCCCUCUG CAGAGCUACGGCUUCCAGCCCACCAACGGCGUGGGCUACCAGCCCU ACCGGGUGGUGGUGCUGAGCUUCGAGCUGCUGCACGCCCCAGCCAC CGUGUGUGGCCCCAAG | 61 |
| 3' UTR | UGAUAAUAGGCUGGAGCCUCGGUGGCCUAGCUUCUUGCCCCUUGGG CCUCCCCCCAGCCCCUCCUCCCCUUCCUGCACCCGUACCCCCGUGG UCUUUGAAUAAAGUCUGAGUGGGCGGC | 4 |
| Corresponding amino acid sequence | MYSMQLASCVTLTLVLLVNSQPNITNLCPFGEVFNATRFASVYAWN RKRISNCVADYSVLYNSASFSTFKCYGVSPTKLNDLCFTNVYADSF VIRGDEVRQIAPGQTGKIADYNYKLPDDFTGCVIAWNSNNLDSKVG GNYNYLYRLFRKSNLKPFERDISTEIYQAGSTPCNGVEGFNCYFPL QSYGFQPTNGVGYQPYRVVVLSFELLHAPATVCGPK | 62 |
| PolyA tail | 100 nt | |

Membrane Bound RBD Antigens

In some embodiments, an mRNA encodes a membrane bound SARS-CoV-2 RBD. Cells expressing membrane bound RBD are expected to carry these membrane-bound antigens to the draining lymph node and promote efficient recognition of epitopes by RBD-specific B cells. Because the B cell surface contains many surface bound antibodies and the expressing cell contains many copies of the membrane bound RBD, it is expected that initial recognition of antigen by a B cell will be followed by cross-linking of B cell receptors, stimulating a strong response through an avidity effect. Non-limiting examples of membrane bound SARS-CoV-2 RBDs and the mRNA encoding them are provided in Tables 8A and 8B below.

TABLE 8A

| Membrane Bound RBD Antigens | | |
|---|---|---|
| | SEQ ID NO: | |
| Name | mRNA ORF | Protein |
| SARS-CoV-2 RBD Linked to Transmembrane Domain (RBD-TM) | 76 | 77 |

TABLE 8B

| Membrane Bound RBD Antigens<br>SARS-COV-2 RBD Linked to Transmembrane Domain (RBD-TM) | | |
|---|---|---|
| SEQ ID NO: 75 consists of from 5' end to 3' end: 5' UTR SEQ ID NO: 2, mRNA ORF SEQ ID NO: 76 and 3' UTR SEQ ID NO: 4. | | 75 |
| Chemistry | 1-methylpseudouridine | |
| Cap | 7mG(5')ppp(5')NImpNp | |
| 5' UTR | GGGAAAUAAGAGAGAAAAGAAGAGUAAGAAGAAAUAUAAGACCCCG<br>GCGCCGCCACC | 2 |
| ORF of mRNA Construct (excluding the stop codon) | AUGUACAGCAUGCAGCUGGCUAGCUGCGUGACCCUGACCCUGGUGC<br>UGCUGGUGAACAGCCAGCCCAACAUCACCAACCUGUGCCCCUUCGG<br>CGAGGUGUUCAACGCCACCCGGUUCGCCAGCGUGUACGCCUGGAAC<br>CGGAAGCGGAUCAGCAACUGCGUGGCCGACUACAGCGUGCUGUACA<br>ACAGCGCCAGCUUCAGCACCUUCAAGUGCUACGGCGUGAGCCCCAC<br>CAAGCUGAACGACCUGUGCUUCACCAACGUGUACGCCGACAGCUUC<br>GUGAUCCGUGGCGACGAGGUGCGGCAGAUCGCACCCGGCCAGACAG<br>GCAAGAUCGCCGACUACAACUACAAGCUGCCCGACGACUUCACCGG<br>CUGCGUGAUCGCCUGGAACAGCAACAACCUCGACAGCAAGGUGGGC<br>GGCAACUACAACUACCUGUACCGGCUGUUCCGGAAGAGCAACCUGA<br>AGCCCUUCGAGCGGGACAUCAGCACCGAGAUCUACCAAGCCGGCUC<br>CACCCCUUGCAACGGCGUGGAGGGCUUCAACUGCUACUUCCCUCUG<br>CAGAGCUACGGCUUCCAGCCCACCAACGGCGUGGGCUACCAGCCCU<br>ACCGGGUGGUGGUGCUGAGCUUCGAGCUGCUGCACGCCCCAGCCAC<br>CGUGUGUGGCCCCAAGUCUGGCGGAGGCAGCAUCCUGGCCAUCUAC<br>AGCACCGUGGCCAGCAGCCUGGUGCUGCUGGUGAGCCUGGGCGCCA<br>UCAGCUUC | 76 |
| 3' UTR | UGAUAAUAGGCUGGAGCCUCGGUGGCCUAGCUUCUUGCCCCUUGGG<br>CCUCCCCCCAGCCCCUCCUCCCCUUCCUGCACCCGUACCCCCGUGG<br>UCUUUGAAUAAAGUCUGAGUGGGCGGC | 4 |
| Corresponding amino acid sequence | MYSMQLASCVTLTLVLLVNSQPNITNLCPFGEVFNATRFASVYAWN<br>RKRISNCVADYSVLYNSASFSTFKCYGVSPTKLNDLCFTNVYADSF<br>VIRGDEVRQIAPGQTGKIADYNYKLPDDFTGCVIAWNSNNLDSKVG<br>GNYNYLYRLFRKSNLKPFERDISTEIYQAGSTPCNGVEGFNCYFPL<br>QSYGFQPTNGVGYQPYRVVVLSFELLHAPATVCGPKSGGGSILAIY<br>STVASSLVLLVSLGAISF | 77 |
| PolyA tail | 100 nt | |

Domain Fusion Antigens

In yet other embodiments, an mRNA provided herein encodes a SARS-CoV-2 NTD-RBD fusion protein. For example, the NTD and the RBD of a SARS-CoV-2 S1 subunit of an S protein may be linked to each other through a linker, such as a short amino acid (e.g., glycine-serine) linker to allow flexibility/hinging and space between the domains. In another embodiment, a linker comprising an antigenic epitope, e.g., a Class II universal T cell epitope such as PADRE, can be used. In some embodiments, a transmembrane region is linked to the NTD-RBD fusion, for example, through another short amino acid (e.g., glycine-serine or PADRE) linker for flexibility and to permit a reasonable distance between the membrane and the antigen. Without being bound by theory, it is thought that this membrane bound, tandem configuration presents most, if not all, known neutralizing and protective epitopes in one open reading frame. Administration of this fusion protein should then focus the immune response towards known protective epitopes and reduce the unnecessary generation of antibodies and T cells specific to non-protective epitopes. Furthermore, antibodies to different domains may neutralize virus particles through different mechanisms, such as by blocking attachment to host cells or preventing bound virus from undergoing membrane fusion and entering host cells. The broad response elicited by a fusion protein comprising different domains may thus be more evolutionarily robust, requiring multiple distinct mutations to escape vaccine-induced immunity. Non-limiting examples of SARS-CoV-2 NTD-RBD fusion proteins and the mRNA encoding them are provided in Tables 9A and 9B below.

Linkers

A variety of linkers may be used in accordance with the present disclosure. Linkers, as provide herein, are simply amino acid sequences that artificially link together two other amino acid sequences. Linkers used herein may be cleavable or non-cleavable. Cleavable linkers allow an mRNA to be translated into a polypeptide, after which cleavage of the linker allows each individual component to be released independently. Non-cleavable linkers keep one or more protein subunits connected, allowing the whole protein to perform a function that requires close proximity of the component subunits. Non-limiting examples of such linkers include glycine-serine (GS) linkers (non-cleavable); and F2A linker, P2A linker, T2A linker, and E2Alinker (cleavable). Other links may be used herein.

In some embodiments, the linker is a GS linker. GS linkers are polypeptide linkers that include glycine and serine amino acids repeats. They comprise flexible and hydrophilic residues and can be used to perform fusion of protein subunits without interfering in the folding and function of the protein domains, and without formation of secondary structures. In some embodiments, an mRNA encodes a fusion protein that comprises a GS linker that is 3 to 20 amino acids long. For example, the GS linker may have a length of (or have a length of at least) 3, 4, 5, 6, 7, 8, 9, 10, 11, 12, 13, 14, 15, 16, 17, 18, 19, or 20 amino acids. In some embodiments, a GS linker is (or is at least) 15 amino acids long (e.g., GGSGGSGGSGGSGGG (SEQ ID NO: 133)). In some embodiments, a GS linker is (or is at least) 8 amino acids long (e.g., GGGSGGGS (SEQ ID NO: 134)). In some embodiments, a GS linker is (or is at least) 7 amino acids long (e.g., GGGSGGG (SEQ ID NO: 135)). In some embodiments, a GS linker is (or is at least) 4 amino acid long (e.g., GGGS (SEQ ID NO: 136)). In some embodiments, the GS linker comprises (GGGS)n (SEQ ID NO: 136), where n is any integer from 1-5. In some embodiments, a GS linker is (or is at least) 4 amino acid long (e.g., GSGG (SEQ ID NO: 152)). In some embodiments, the GS linker comprises (GSGG)n (SEQ ID NO: 152), where n is any integer from 1-5.

In some embodiments, a linker is a glycine linker, for example having a length of (or a length of at least) 3 amino acids (e.g., GGG).

In some embodiments, a protein encoded by an mRNA vaccine includes more than one linker, which may be the same or different from each other (e.g., GGGSGGG (SEQ ID NO: 135) and GGGS (SEQ ID NO: 136) in the same S protein construct).

In some embodiments, a linker comprises mRNA encoding a pan HLA DR-binding epitope (PADRE) (e.g., AKFVAAWTLKAAA (SEQ ID NO: 148)). PADRE is an immunodominant helper CD4 T cell epitope and a potent immunogen (See, e.g., Alexander J. et al. J of Immuno. 164(3): 1625-33, incorporated herein by reference).

TABLE 9A

| Domain Fusion Antigen | | |
|---|---|---|
| | SEQ ID NO: | |
| Name | mRNA ORF | Protein |
| SARS-CoV-2 NTD-RBD Linked to Transmembrane Domain (NTD-RBD-TM) | 91 | 92 |
| SARS-CoV-2 RBD-NTD Linked to Transmembrane Domain (RBD-NTD-TM) | 139 | 140 |
| SARS-CoV-2 NTD-PADRE-RBD Linked to Transmembrane Domain (NTD-PADRE-RBD-TM) | 142 | 143 |

TABLE 9B

| Domain Fusion Antigen | | |
|---|---|---|
| SARS-COV-2 NTD-RBD Linked to Transmembrane Domain (NTD-RBD-TM) | | |
| | SEQ ID NO: 90 consists of from 5' end to 3' end: 5' UTR SEQ ID NO: 2, mRNA ORF SEQ ID NO: 91 and 3' UTR SEQ ID NO: 4. | 90 |
| Chemistry | 1-methylpseudouridine | |
| Cap | 7mG(5')ppp(5')NImpNp | |
| 5' UTR | GGGAAAUAAGAGAGAAAAGAAGAGUAAGAAGAAAUAUAAGACCCCG<br>GCGCCGCCACC | 2 |
| ORF of mRNA Construct (excluding the stop codon) | AUGUUCGUGUUCCUGGUGCUGCUGCCCCUGGUGAGCAGCCAGUGCG<br>UGAACCUGACCACCCGGACCCAGCUGCCACCAGCCUACACCAACAG<br>CUUCACCCGGGGCGUCUACUACCCCGACAAGGUGUUCCGGAGCAGC<br>GUCCUGCACAGCACCCAGGACCUGUUCCUGCCCUUCUUCAGCAACG<br>UGACCUGGUUCCACGCCAUCCACGUGAGCGGCACCAACGGCACCAA<br>GCGGUUCGACAACCCCGUGCUGCCCUUCAACGACGGCGUGUACUUC<br>GCCAGCACCGAGAAGAGCAACAUCAUCCGGGGCUGGAUCUUCGGCA<br>CCACCCUGGACAGCAAGACCCAGAGCCUGCUGAUCGUGAAUAACGC<br>CACCAACGUGGUGAUCAAGGUGUGCGAGUUCCAGUUCUGCAACGAC<br>CCCUUCCUGGGCGUGUACUACCACAAGAACAACAAGAGCUGGAUGG<br>AGAGCGAGUUCCGGGUGUACAGCAGCGCCAACAACUGCACCUUCGA<br>GUACGUGAGCCAGCCCUUCCUGAUGGACCUGGAGGGCAAGCAGGGC<br>AACUUCAAGAACCUGCGGGAGUUCGUGUUCAAGAACAUCGACGGCU<br>ACUUCAAGAUCUACAGCAAGCACACCCCAAUCAACCUGGUGCGGGA<br>UCUGCCCCAGGGCUUCUCAGCCCUGGAGCCCCUGGUGGACCUGCCC<br>AUCGGCAUCAACAUCACCCGGUUCCAGACCCUGCUGGCCCUGCACC<br>GGAGCUACCUGACCCCAGGCGACAGCAGCAGCGGGUGGACAGCAGG<br>CGCGGCUGCUUACUACGUGGGCUACCUGCAGCCCCGGACCUUCCUG<br>CUGAAGUACAACGAGAACGGCACCAUCACCGACGCCGUGGACGGAG<br>GCGGAUCGGGAGGCGGACCCAACAUCACCAACCUGUGCCCCUUCGG<br>CGAGGUGUUCAACGCCACCCGGUUCGCCAGCGUGUACGCCUGGAAC<br>CGGAAGCGGAUCAGCAACUGCGUGGCCGACUACAGCGUGCUGUACA<br>ACAGCGCCAGCUUCAGCACCUUCAAGUGCUACGGCGUGAGCCCCAC<br>CAAGCUGAACGACCUGUGCUUCACCAACGUGUACGCCGACAGCUUC<br>GUGAUCCGUGGCGACGAGGUGCGGCAGAUCGCACCCGGCCAGACAG<br>GCAAGAUCGCCGACUACAACUACAAGCUGCCCGACGACUUCACCGG<br>CUGCGUGAUCGCCUGGAACAGCAACAACCUCGACAGCAAGGUGGGC<br>GGCAACUACAACUACCUGUACCGGCUGUUCCGGAAGAGCAACCUGA | 91 |

TABLE 9B-continued

| Domain Fusion Antigen | | |
|---|---|---|
| | AGCCCUUCGAGCGGGACAUCAGCACCGAGAUCUACCAAGCCGGCUC<br>CACCCCUUGCAACGGCGUGGAGGGCUUCAACUGCUACUUCCCUCUG<br>CAGAGCUACGGCUUCCAGCCCACCAACGGCGUGGGCUACCAGCCCU<br>ACCGGGUGGUGGUGCUGAGCUUCGAGCUGCUGCACGCCCCAGCCAC<br>CGUGUGUGGCCCCAAGUCUGGCGGAGGCAGCAUCCUGGCCAUCUAC<br>AGCACCGUGGCCAGCAGCCUGGUGCUGCUGGUGAGCCUGGGCGCCA<br>UCAGCUUC | |
| 3' UTR | UGAUAAUAGGCUGGAGCCUCGGUGGCCUAGCUUCUUGCCCCUUGGG<br>CCUCCCCCCAGCCCCUCCUCCCCUUCCUGCACCCGUACCCCCGUGG<br>UCUUUGAAUAAAGUCUGAGUGGGCGGC | 4 |
| Corresponding amino acid sequence | MFVFLVLLPLVSSQCVNLTTRTQLPPAYTNSFTRGVYYPDKVFRSS<br>VLHSTQDLFLPFFSNVTWFHAIHVSGTNGTKRFDNPVLPFNDGVYF<br>ASTEKSNIIRGWIFGTTLDSKTQSLLIVNNATNVVIKVCEFQFCND<br>PFLGVYYHKNNKSWMESEFRVYSSANNCTFEYVSQPFLMDLEGKQG<br>NFKNLREFVFKNIDGYFKIYSKHTPINLVRDLPQGFSALEPLVDLP<br>IGINITRFQTLLALHRSYLTPGDSSSGWTAGAAAYYVGYLQPRTFL<br>LKYNENGTITDAVDgggsgggPNITNLCPFGEVFNATRFASVYAWN<br>RKRISNCVADYSVLYNSASFSTFKCYGVSPTKLNDLCFTNVYADSF<br>VIRGDEVRQIAPGQTGKIADYNYKLPDDFTGCVIAWNSNNLDSKVG<br>GNYNYLYRLFRKSNLKPFERDISTEIYQAGSTPCNGVEGFNCYFPL<br>QSYGFQPTNGVGYQPYRVVVLSFELLHAPATVCGPKsgggsilaiy<br>stvasslvllvslgaisf | 92 |
| PolyA tail | 100 nt | |
| SARS-COV-2 RBD-NTD Linked to Transmembrane Domain (RBD-NTD-TM) | | |
| SEQ ID NO: 141 consists of from 5' end to 3' end: 5' UTR SEQ ID NO: 2, mRNA ORF SEQ ID NO: 139 and 3' UTR SEQ ID NO: 4. | | 141 |
| Chemistry | 1-methylpseudouridine | |
| Cap | 7mG(5')ppp(5')NImpNp | |
| 5' UTR | GGGAAAUAAGAGAGAAAAGAAGAGUAAGAAGAAAUAUAAGACCCCG<br>GCGCCGCCACC | 2 |
| ORF of mRNA Construct (excluding the stop codon) | AUGUACAGCAUGCAGCUGGCUAGCUGCGUGACCCUGACCCUGGUGC<br>UGCUGGUGAACAGCCAGCCCAACAUCACCAACCUGUGCCCCUUCGG<br>CGAGGUGUUCAACGCCACCCGGUUCGCCAGCGUGUACGCCUGGAAC<br>CGGAAGCGGAUCAGCAACUGCGUGGCCGACUACAGCGUGCUGUACA<br>ACAGCGCCAGCUUCAGCACCUUCAAGUGCUACGGCGUGAGCCCCAC<br>CAAGCUGAACGACCUGUGCUUCACCAACGUGUACGCCGACAGCUUC<br>GUGAUCCGUGGCGACGAGGUGCGGCAGAUCGCACCCGGCCAGACAG<br>GCAAGAUCGCCGACUACAACUACAAGCUGCCCGACGACUUCACCGG<br>CUGCGUGAUCGCCUGGAACAGCAACAACCUCGACAGCAAGGUGGGC<br>GGCAACUACAACUACCUGUACCGGCUGUUCCGGAAGAGCAACCUGA<br>AGCCCUUCGAGCGGGACAUCAGCACCGAGAUCUACCAAGCCGGCUC<br>CACCCCUUGCAACGGCGUGGAGGGCUUCAACUGCUACUUCCCUCUG<br>CAGAGCUACGGCUUCCAGCCCACCAACGGCGUGGGCUACCAGCCCU<br>ACCGGGUGGUGGUGCUGAGCUUCGAGCUGCUGCACGCCCCAGCCAC<br>CGUGUGUGGCCCCAAGUCUGGCGGAGGCAGCGGAGGCGGAAGCCAG<br>UGCGUGAACCUGACCACCCGGACCCAGCUGCCACCAGCCUACACCA<br>ACAGCUUCACCCGGGGCGUCUACUACCCCGACAAGGUGUUCCGGAG<br>CAGCGUCCUGCACAGCACCCAGGACCUGUUCCUGCCCUUCUUCAGC<br>AACGUGACCUGGUUCCACGCCAUCCACGUGAGCGGCACCAACGGCA<br>CCAAGCGGUUCGACAACCCCGUGCUGCCCUUCAACGACGGCGUGUA<br>CUUCGCCAGCACCGAGAAGAGCAACAUCAUCCGGGGCUGGAUCUUC<br>GGCACCACCCUGGACAGCAAGACCCAGAGCCUGCUGAUCGUGAAUA<br>ACGCCACCAACGUGGUGAUCAAGGUGUGCGAGUUCCAGUUCUGCAA<br>CGACCCCUUCCUGGGCGUGUACUACCACAAGAACAACAAGAGCUGG<br>AUGGAGAGCGAGUUCCGGGUGUACAGCAGCGCCAACAACUGCACCU<br>UCGAGUACGUGAGCCAGCCCUUCCUGAUGGACCUGGAGGGCAAGCA<br>GGGCAACUUCAAGAACCUGCGGGAGUUCGUGUUCAAGAACAUCGAC<br>GGCUACUUCAAGAUCUACAGCAAGCACACCCCAAUCAACCUGGUGC<br>GGGAUCUGCCCCAGGGCUUCUCAGCCCUGGAGCCCCUGGUGGACCU<br>GCCCAUCGGCAUCAACAUCACCCGGUUCCAGACCCUGCUGGCCCUG<br>CACCGGAGCUACCUGACCCCAGGCGACAGCAGCAGCGGGUGGACAG<br>CAGGCGCGGCUGCUUACUACGUGGGCUACCUGCAGCCCCGGACCUU<br>CCUGCUGAAGUACAACGAGAACGGCACCAUCACCGACGCCGUGGAC<br>UCUGGCGGAGGCAGCAUCCUGGCCAUCUACAGCACCGUGGCCAGCA<br>GCCUGGUGCUGCUGGUGAGCCUGGGCGCCAUCAGCUUC | 139 |

TABLE 9B-continued

| Domain Fusion Antigen | | |
|---|---|---|
| 3' UTR | UGAUAAUAGGCUGGAGCCUCGGUGGCCUAGCUUCUUGCCCCUUGGG<br>CCUCCCCCCAGCCCCUCCUCCCCUUCCUGCACCCGUACCCCCGUGG<br>UCUUUGAAUAAAGUCUGAGUGGGCGGC | 4 |
| Corresponding amino acid sequence | MYSMQLASCVTLTLVLLVNSQPNITNLCPFGEVFNATRFASVYAWN<br>RKRISNCVADYSVLYNSASFSTFKCYGVSPTKLNDLCFTNVYADSF<br>VIRGDEVRQIAPGQTGKIADYNYKLPDDFTGCVIAWNSNNLDSKVG<br>GNYNYLYRLFRKSNLKPFERDISTEIYQAGSTPCNGVEGFNCYFPL<br>QSYGFQPTNGVGYQPYRVVVLSFELLHAPATVCGPKSGGGSGGGSQ<br>CVNLTTRTQLPPAYTNSFTRGVYYPDKVFRSSVLHSTQDLFLPFFS<br>NVTWFHAIHVSGTNGTKRFDNPVLPFNDGVYFASTEKSNIIRGWIF<br>GTTLDSKTQSLLIVNNATNVVIKVCEFQFCNDPFLGVYYHKNNKSW<br>MESEFRVYSSANNCTFEYVSQPFLMDLEGKQGNFKNLREFVFKNID<br>GYFKIYSKHTPINLVRDLPQGFSALEPLVDLPIGINITRFQTLLAL<br>HRSYLTPGDSSSGWTAGAAAYYVGYLQPRTFLLKYNENGTITDAVD<br>SGGGSILAIYSTVASSLVLLVSLGAISF | 140 |
| PolyA tail | 100 nt | |

| SARS-COV-2 NTD-PADRE-RBD Linked to Transmembrane Domain (NTD-PADRE-RBD-TM) | | |
|---|---|---|
| SEQ ID NO: 144 consists of from 5' end to 3' end: 5' UTR SEQ ID NO: 2, mRNA ORF SEQ ID NO: 142 and 3' UTR SEQ ID NO: 4. | | 144 |
| Chemistry | 1-methylpseudouridine | |
| Cap | 7mG(5')ppp(5')NlmpNp | |
| 5' UTR | GGGAAAUAAGAGAGAAAAGAAGAGUAAGAAGAAAUAUAAGACCCCG<br>GCGCCGCCACC | 2 |
| ORF of mRNA Construct (excluding the stop codon) | AUGUUCGUGUUCCUGGUGCUGCUGCCCCUGGUGAGCAGCCAGUGCG<br>UGAACCUGACCACCCGGACCCAGCUGCCACCAGCCUACACCAACAG<br>CUUCACCCGGGGCGUCUACUACCCCGACAAGGUGUUCCGGAGCAGC<br>GUCCUGCACAGCACCCAGGACCUGUUCCUGCCCUUCUUCAGCAACG<br>UGACCUGGUUCCACGCCAUCCACGUGAGCGGCACCAACGGCACCAA<br>GCGGUUCGACAACCCCGUGCUGCCCUUCAACGACGGCGUGUACUUC<br>GCCAGCACCGAGAAGAGCAACAUCAUCCGGGGCUGGAUCUUCGGCA<br>CCACCCUGGACAGCAAGACCCAGAGCCUGCUGAUCGUGAAUAACGC<br>CACCAACGUGGUGAUCAAGGUGUGCGAGUUCCAGUUCUGCAACGAC<br>CCCUUCCUGGGCGUGUACUACCACAAGAACAACAAGAGCUGGAUGG<br>AGAGCGAGUUCCGGGUGUACAGCAGCGCCAACAACUGCACCUUCGA<br>GUACGUGAGCCAGCCCUUCCUGAUGGACCUGGAGGGCAAGCAGGGC<br>AACUUCAAGAACCUGCGGGAGUUCGUGUUCAAGAACAUCGACGGCU<br>ACUUCAAGAUCUACAGCAAGCACACCCCAAUCAACCUGGUGCGGGA<br>UCUGCCCCAGGGCUUCUCAGCCCUGGAGCCCCUGGUGGACCUGCCC<br>AUCGGCAUCAACAUCACCCGGUUCCAGACCCUGCUGGCCCUGCACC<br>GGAGCUACCUGACCCCAGGCGACAGCAGCAGCGGGUGGACAGCAGG<br>CGCGGCUGCUUACUACGUGGGCUACCUGCAGCCCCGGACCUUCCUG<br>CUGAAGUACAACGAGAACGGCACCAUCACCGACGCCGUGGACGGAG<br>GCGCCAAGUUCGUGGCCGCCUGGACUCUGAAGGCCGCAGCCGGCGG<br>ACCCAACAUCACCAACCUGUGCCCCUUCGGCGAGGUGUUCAACGCC<br>ACCCGGUUCGCCAGCGUGUACGCCUGGAACCGGAAGCGGAUCAGCA<br>ACUGCGUGGCCGACUACAGCGUGCUGUACAACAGCGCCAGCUUCAG<br>CACCUUCAAGUGCUACGGCGUGAGCCCCACCAAGCUGAACGACCUG<br>UGCUUCACCAACGUGUACGCCGACAGCUUCGUGAUCCGUGGCGACG<br>AGGUGCGGCAGAUCGCACCCGGCCAGACAGGCAAGAUCGCCGACUA<br>CAACUACAAGCUGCCCGACGACUUCACCGGCUGCGUGAUCGCCUGG<br>AACAGCAACAACCUCGACAGCAAGGUGGGCGGCAACUACAACUACC<br>UGUACCGGCUGUUCCGGAAGAGCAACCUGAAGCCCUUCGAGCGGGA<br>CAUCAGCACCGAGAUCUACCAAGCCGGCUCCACCCCUUGCAACGGC<br>GUGGAGGGCUUCAACUGCUACUUCCCUCUGCAGAGCUACGGCUUCC<br>AGCCCACCAACGGCGUGGGCUACCAGCCCUACCGGGUGGUGGUGCU<br>GAGCUUCGAGCUGCUGCACGCCCCAGCCACCGUGUGUGGCCCCAAG<br>UCUGGCGGAGGCAGCAUCCUGGCCAUCUACAGCACCGUGGCCAGCA<br>GCCUGGUGCUGCUGGUGAGCCUGGGCGCCAUCAGCUUC | 142 |
| 3' UTR | UGAUAAUAGGCUGGAGCCUCGGUGGCCUAGCUUCUUGCCCCUUGGG<br>CCUCCCCCCAGCCCCUCCUCCCCUUCCUGCACCCGUACCCCCGUGG<br>UCUUUGAAUAAAGUCUGAGUGGGCGGC | 4 |

TABLE 9B-continued

| Domain Fusion Antigen | | |
|---|---|---|
| Corresponding amino acid sequence | MFVFLVLLPLVSSQCVNLTTRTQLPPAYTNSFTRGVYYPDKVFRSS<br>VLHSTQDLFLPFFSNVTWFHAIHVSGTNGTKRFDNPVLPFNDGVYF<br>ASTEKSNIIRGWIFGTTLDSKTQSLLIVNNATNVVIKVCEFQFCND<br>PFLGVYYHKNNKSWMESEFRVYSSANNCTFEYVSQPFLMDLEGKQG<br>NFKNLREFVFKNIDGYFKIYSKHTPINLVRDLPQGFSALEPLVDLP<br>IGINITRFQTLLALHRSYLTPGDSSSGWTAGAAAYYVGYLQPRTFL<br>LKYNENGTITDAVDGGAKFVAAWTLKAAAGGPNITNLCPFGEVFNA<br>TRFASVYAWNRKRISNCVADYSVLYNSASFSTFKCYGVSPTKLNDL<br>CFTNVYADSFVIRGDEVRQIAPGQTGKIADYNYKLPDDFTGCVIAW<br>NSNNLDSKVGGNYNYLYRLFRKSNLKPFERDISTEIYQAGSTPCNG<br>VEGFNCYFPLQSYGFQPTNGVGYQPYRVVVLSFELLHAPATVCGPK<br>SGGGSILAIYSTVASSLVLLVSLGAISF | 143 |
| PolyA tail | 100 nt | |

Trafficking Signals

In some embodiments, an mRNA encodes a SARS-CoV-2 S protein domain (e.g., NTD, RBD, or NTD-RBD fusion) linked to a Golgi trafficking signal. Non-limiting examples of such signals include macrophage markers, such as CD6 and/or CD11b, which are highly expressed and the intracellular region may control efficient export from the Golgi apparatus to the cell surface. Other cell trafficking signals (sequences) may be used herein, for example, the VSV-G cytosolic tail (VSVGct). More efficient trafficking of encoded proteins to the cell surface is expected to increase antigen availability for B cell recognition and therefore promote the generation of antibodies to the encoded SARS-CoV-2 S protein domains. Non-limiting examples of SARS-CoV-2 antigens linked to a trafficking signal and the mRNA encoding them are provided in Tables 10A and 10B below.

TABLE 10A

Domain Fusion Antigens Linked to a Trafficking Signal

| Name | SEQ ID NO: mRNA ORF | SEQ ID NO: Protein |
|---|---|---|
| SARS-CoV-2 NTD-RBD Linked to Transmembrane Domain and huCD86 (NTD-RBD-TM-CD86) | 94 | 95 |
| SARS-CoV-2 NTD-RBD Linked to Transmembrane Domain and huCD11B (NTD-RBD-TM-CD11B) | 97 | 98 |
| SARS-CoV-2 NTD-RBD Linked to VSVGct (NTD-RBD-VSVGct) | 109 | 110 |

TABLE 10B

Domain Fusion Antigens Linked to a Trafficking Signal

SARS-COV-2 NTD-RBD Linked to Transmembrane Domain and huCD86 (NTD-RBD-TM-CD86)

| | | |
|---|---|---|
| SEQ ID NO: 93 consists of from 5' end to 3' end: 5' UTR SEQ ID NO: 2, mRNA ORF SEQ ID NO: 94 and 3' UTR SEQ ID NO: 4. | | 93 |
| Chemistry | 1-methylpseudouridine | |
| Cap | 7mG(5')ppp(5')NImpNp | |
| 5' UTR | GGGAAAUAAGAGAGAAAAGAAGAGUAAGAAGAAAUAUAAGACCCCG<br>GCGCCGCCACC | 2 |
| ORF of mRNA Construct (excluding the stop codon) | AUGUUCGUGUUCCUGGUGCUGCUGCCCCUGGUGAGCAGCCAGUGCG<br>UGAACCUGACCACCCGGACCCAGCUGCCACCAGCCUACACCAACAG<br>CUUCACCCGGGGCGUCUACUACCCCGACAAGGUGUUCCGGAGCAGC<br>GUCCUGCACAGCACCCAGGACCUGUUCCUGCCCUUCUUCAGCAACG<br>UGACCUGGUUCCACGCCAUCCACGUGAGCGGCACCAACGGCACCAA<br>GCGGUUCGACAACCCCGUGCUGCCCUUCAACGACGGCGUGUACUUC<br>GCCAGCACCGAGAAGAGCAACAUCAUCCGGGGCUGGAUCUUCGGCA<br>CCACCCUGGACAGCAAGACCCAGAGCCUGCUGAUCGUGAAUAACGC<br>CACCAACGUGGUGAUCAAGGUGUGCGAGUUCCAGUUCUGCAACGAC<br>CCCUUCCUGGGCGUGUACUACCACAAGAACAACAAGAGCUGGAUGG<br>AGAGCGAGUUCCGGGUGUACAGCAGCGCCAACAACUGCACCUUCGA<br>GUACGUGAGCCAGCCCUUCCUGAUGGACCUGGAGGGCAAGCAGGGC<br>AACUUCAAGAACCUGCGGGAGUUCGUGUUCAAGAACAUCGACGGCU<br>ACUUCAAGAUCUACAGCAAGCACACCCCAAUCAACCUGGUGCGGGA<br>UCUGCCCCAGGGCUUCUCAGCCCUGGAGCCCCUGGUGGACCUGCCC<br>AUCGGCAUCAACAUCACCCGGUUCCAGACCCUGCUGGCCCUGCACC<br>GGAGCUACCUGACCCCAGGCGACAGCAGCAGCGGGUGGACAGCAGG<br>CGCGGCUGCUUACUACGUGGGCUACCUGCAGCCCCGGACCUUCCUG<br>CUGAAGUACAACGAGAACGGCACCAUCACCGACGCCGUGGACGGAG<br>GCGGAUCGGGAGGCGGACCCAACAUCACCAACCUGUGCCCCUUCGG<br>CGAGGUGUUCAACGCCACCCGGUUCGCCAGCGUGUACGCCUGGAAC | 94 |

TABLE 10B-continued

| Domain Fusion Antigens Linked to a Trafficking Signal | | |
|---|---|---|
| | CGGAAGCGGAUCAGCAACUGCGUGGCCGACUACAGCGUGCUGUACA<br>ACAGCGCCAGCUUCAGCACCUUCAAGUGCUACGGCGUGAGCCCCAC<br>CAAGCUGAACGACCUGUGCUUCACCAACGUGUACGCCGACAGCUUC<br>GUGAUCCGUGGCGACGAGGUGCGGCAGAUCGCACCCGGCCAGACAG<br>GCAAGAUCGCCGACUACAACUACAAGCUGCCCGACGACUUCACCGG<br>CUGCGUGAUCGCCUGGAACAGCAACAACCUCGACAGCAAGGUGGGC<br>GGCAACUACAACUACCUGUACCGGCUGUUCCGGAAGAGCAACCUGA<br>AGCCCUUCGAGCGGGACAUCAGCACCGAGAUCUACCAAGCCGGCUC<br>CACCCCUUGCAACGGCGUGGAGGGCUUCAACUGCUACUUCCCUCUG<br>CAGAGCUACGGCUUCCAGCCCACCAACGGCGUGGGCUACCAGCCCU<br>ACCGGGUGGUGGUGCUGAGCUUCGAGCUGCUGCACGCCCCAGCCAC<br>CGUGUGUGGCCCCAAGUCUGGCGGAGGCAGCAUCCUGGCCAUCUAC<br>AGCACCGUGGCCAGCAGCCUGGUGCUGCUGGUGAGCCUGGGCGCCA<br>UCAGCUUCAAGAAGAAGAAGCGGCCACGGAACUCCUACAAGUGCGG<br>CACCAACACCAUGGAGCGGGAGGAGAGCGAGCAGACCAAGAAGCGG<br>GAGAAGAUCCACAUUCCUGAACGGUCCGACGAAGCCCAGCGGGUGU<br>UCAAGAGCAGCAAGACCAGCAGCUGCGACAAGAGCGACACCUGCUU<br>C | |
| 3' UTR | UGAUAAUAGGCUGGAGCCUCGGUGGCCUAGCUUCUUGCCCCUUGGG<br>CCUCCCCCCAGCCCCUCCUCCCCUUCCUGCACCCGUACCCCCGUGG<br>UCUUUGAAUAAAGUCUGAGUGGGCGGC | 4 |
| Corresponding amino acid sequence | MFVFLVLLPLVSSQCVNLTTRTQLPPAYTNSFTRGVYYPDKVFRSS<br>VLHSTQDLFLPFFSNVTWFHAIHVSGTNGTKRFDNPVLPFNDGVYF<br>ASTEKSNIIRGWIFGTTLDSKTQSLLIVNNATNVVIKVCEFQFCND<br>PFLGVYYHKNNKSWMESEFRVYSSANNCTFEYVSQPFLMDLEGKQG<br>NFKNLREFVFKNIDGYFKIYSKHTPINLVRDLPQGFSALEPLVDLP<br>IGINITRFQTLLALHRSYLTPGDSSSGWTAGAAAYYVGYLQPRTFL<br>LKYNENGTITDAVDgggsgggPNITNLCPFGEVFNATRFASVYAWN<br>RKRISNCVADYSVLYNSASFSTFKCYGVSPTKLNDLCFTNVYADSF<br>VIRGDEVRQIAPGQTGKIADYNYKLPDDFTGCVIAWNSNNLDSKVG<br>GNYNYLYRLFRKSNLKPFERDISTEIYQAGSTPCNGVEGFNCYFPL<br>QSYGFQPTNGVGYQPYRVVVLSFELLHAPATVCGPKsgggsilaiy<br>stvasslvllvslgaisfKKKKRPRNSYKCGTNTMEREESEQTKKR<br>EKIHIPERSDEAQRVFKSSKTSSCDKSDTCF | 95 |
| PolyA tail | 100 nt | |
| SARS-COV-2 NTD-RBD Linked to Transmembrane Domain and huCD11B (NTD-RBD-TM-CD11B) | | |
| SEQ ID NO: 96 consists of from 5' end to 3' end: 5' UTR SEQ ID NO: 2, mRNA ORF SEQ ID NO: 97 and 3' UTR SEQ ID NO: 4. | | 96 |
| Chemistry | 1-methylpseudouridine | |
| Cap | 7mG(5')ppp(5')NImpNp | |
| 5' UTR | GGGAAAUAAGAGAGAAAAGAAGAGUAAGAAGAAAUAUAAGACCCCG<br>GCGCCGCCACC | 2 |
| ORF of mRNA Construct (excluding the stop codon) | AUGUUCGUGUUCCUGGUGCUGCUGCCCCUGGUGAGCAGCCAGUGCG<br>UGAACCUGACCACCCGGACCCAGCUGCCACCAGCCUACACCAACAG<br>CUUCACCCGGGGCGUCUACUACCCCGACAAGGUGUUCCGGAGCAGC<br>GUCCUGCACAGCACCCAGGACCUGUUCCUGCCCUUCUUCAGCAACG<br>UGACCUGGUUCCACGCCAUCCACGUGAGCGGCACCAACGGCACCAA<br>GCGGUUCGACAACCCCGUGCUGCCCUUCAACGACGGCGUGUACUUC<br>GCCAGCACCGAGAAGAGCAACAUCAUCCGGGGCUGGAUCUUCGGCA<br>CCACCCUGGACAGCAAGACCCAGAGCCUGCUGAUCGUGAAUAACGC<br>CACCAACGUGGUGAUCAAGGUGUGCGAGUUCCAGUUCUGCAACGAC<br>CCCUUCCUGGGCGUGUACUACCACAAGAACAACAAGAGCUGGAUGG<br>AGAGCGAGUUCCGGGUGUACAGCAGCGCCAACAACUGCACCUUCGA<br>GUACGUGAGCCAGCCCUUCCUGAUGGACCUGGAGGGCAAGCAGGGC<br>AACUUCAAGAACCUGCGGGAGUUCGUGUUCAAGAACAUCGACGGCU<br>ACUUCAAGAUCUACAGCAAGCACACCCCAAUCAACCUGGUGCGGGA<br>UCUGCCCCAGGGCUUCUCAGCCCUGGAGCCCCUGGUGGACCUGCCC<br>AUCGGCAUCAACAUCACCCGGUUCCAGACCCUGCUGGCCCUGCACC<br>GGAGCUACCUGACCCCAGGCGACAGCAGCAGCGGGUGGACAGCAGG<br>CGCGGCUGCUUACUACGUGGGCUACCUGCAGCCCCGGACCUUCCUG<br>CUGAAGUACAACGAGAACGGCACCAUCACCGACGCCGUGGACGGAG<br>GCGGAUCGGGAGGCGGACCCAACAUCACCAACCUGUGCCCCUUCGG<br>CGAGGUGUUCAACGCCACCCGGUUCGCCAGCGUGUACGCCUGGAAC<br>CGGAAGCGGAUCAGCAACUGCGUGGCCGACUACAGCGUGCUGUACA<br>ACAGCGCCAGCUUCAGCACCUUCAAGUGCUACGGCGUGAGCCCCAC<br>CAAGCUGAACGACCUGUGCUUCACCAACGUGUACGCCGACAGCUUC<br>GUGAUCCGUGGCGACGAGGUGCGGCAGAUCGCACCCGGCCAGACAG | 97 |

TABLE 10B-continued

| Domain Fusion Antigens Linked to a Trafficking Signal | | |
|---|---|---|
| | GCAAGAUCGCCGACUACAACUACAAGCUGCCCGACGACUUCACCGG<br>CUGCGUGAUCGCCUGGAACAGCAACAACCUCGACAGCAAGGUGGGC<br>GGCAACUACAACUACCUGUACCGGCUGUUCCGGAAGAGCAACCUGA<br>AGCCCUUCGAGCGGGACAUCAGCACCGAGAUCUACCAAGCCGGCUC<br>CACCCCUUGCAACGGCGUGGAGGGCUUCAACUGCUACUUCCCUCUG<br>CAGAGCUACGGCUUCCAGCCCACCAACGGCGUGGGCUACCAGCCCU<br>ACCGGGUGGUGGUGCUGAGCUUCGAGCUGCUGCACGCCCCAGCCAC<br>CGUGUGUGGCCCCAAGUCUGGCGGAGGCAGCAUCCUGGCCAUCUAC<br>AGCACCGUGGCCAGCAGCCUGGUGCUGCUGGUGAGCCUGGGCGCCA<br>UCAGCUUCAAGCGGCAGUACAAGGACAUGAUGAGCGAGGGAGGACC<br>ACCUGGCGCUGAGCCACAG | |
| 3' UTR | UGAUAAUAGGCUGGAGCCUCGGUGGCCUAGCUUCUUGCCCCUUGGG<br>CCUCCCCCCAGCCCCUCCUCCCCUUCCUGCACCCGUACCCCCGUGG<br>UCUUUGAAUAAAGUCUGAGUGGGCGGC | 4 |
| Corresponding amino acid sequence | MFVFLVLLPLVSSQCVNLTTRTQLPPAYTNSFTRGVYYPDKVFRSS<br>VLHSTQDLFLPFFSNVTWFHAIHVSGTNGTKRFDNPVLPFNDGVYF<br>ASTEKSNIIRGWIFGTTLDSKTQSLLIVNNATNVVIKVCEFQFCND<br>PFLGVYYHKNNKSWMESEFRVYSSANNCTFEYVSQPFLMDLEGKQG<br>NFKNLREFVFKNIDGYFKIYSKHTPINLVRDLPQGFSALEPLVDLP<br>IGINITRFQTLLALHRSYLTPGDSSSGWTAGAAAYYVGYLQPRTFL<br>LKYNENGTITDAVDgggsgggPNITNLCPFGEVFNATRFASVYAWN<br>RKRISNCVADYSVLYNSASFSTFKCYGVSPTKLNDLCFTNVYADSF<br>VIRGDEVRQIAPGQTGKIADYNYKLPDDFTGCVIAWNSNNLDSKVG<br>GNYNYLYRLFRKSNLKPFERDISTEIYQAGSTPCNGVEGFNCYFPL<br>QSYGFQPTNGVGYQPYRVVVLSFELLHAPATVCGPKsgggsilaiy<br>stvasslvllvslgaisfKRQYKDMMSEGGPPGAEPQ | 98 |
| PolyA tail | 100 nt | |
| SARS-COV-2 NTD-RBD Linked to VSVGct (NTD-RBD-VSVGct) | | |
| SEQ ID NO: 108 consists of from 5' end to 3' end: 5' UTR SEQ ID NO: 2, mRNA ORF SEQ ID NO: 109 and 3' UTR SEQ ID NO: 4. | | 108 |
| Chemistry | 1-methylpseudouridine | |
| Cap | 7mG(5')ppp(5')NImpNp | |
| 5' UTR | GGGAAAUAAGAGAGAAAAGAAGAGUAAGAAGAAAUAUAAGACCCCG<br>GCGCCGCCACC | 2 |
| ORF of mRNA Construct (excluding the stop codon) | AUGUUCGUGUUCCUGGUGCUGCUGCCCCUGGUGAGCAGCCAGUGCG<br>UGAACCUGACCACCCGGACCCAGCUGCCACCAGCCUACACCAACAG<br>CUUCACCCGGGGCGUCUACUACCCCGACAAGGUGUUCCGGAGCAGC<br>GUCCUGCACAGCACCCAGGACCUGUUCCUGCCCUUCUUCAGCAACG<br>UGACCUGGUUCCACGCCAUCCACGUGAGCGGCACCAACGGCACCAA<br>GCGGUUCGACAACCCCGUGCUGCCCUUCAACGACGGCGUGUACUUC<br>GCCAGCACCGAGAAGAGCAACAUCAUCCGGGGCUGGAUCUUCGGCA<br>CCACCCUGGACAGCAAGACCCAGAGCCUGCUGAUCGUGAAUAACGC<br>CACCAACGUGGUGAUCAAGGUGUGCGAGUUCCAGUUCUGCAACGAC<br>CCCUUCCUGGGCGUGUACUACCACAAGAACAACAAGAGCUGGAUGG<br>AGAGCGAGUUCCGGGUGUACAGCAGCGCCAACAACUGCACCUUCGA<br>GUACGUGAGCCAGCCCUUCCUGAUGGACCUGGAGGGCAAGCAGGGC<br>AACUUCAAGAACCUGCGGGAGUUCGUGUUCAAGAACAUCGACGGCU<br>ACUUCAAGAUCUACAGCAAGCACACCCCAAUCAACCUGGUGCGGGA<br>UCUGCCCCAGGGCUUCUCAGCCCUGGAGCCCCUGGUGGACCUGCCC<br>AUCGGCAUCAACAUCACCCGGUUCCAGACCCUGCUGGCCCUGCACC<br>GGAGCUACCUGACCCCAGGCGACAGCAGCAGCGGGUGGACAGCAGG<br>CGCGGCUGCUUACUACGUGGGCUACCUGCAGCCCCGGACCUUCCUG<br>CUGAAGUACAACGAGAACGGCACCAUCACCGACGCCGUGGACGGAG<br>GCGGAUCGGGAGGCGGACCCAACAUCACCAACCUGUGCCCCUUCGG<br>CGAGGUGUUCAACGCCACCCGGUUCGCCAGCGUGUACGCCUGGAAC<br>CGGAAGCGGAUCAGCAACUGCGUGGCCGACUACAGCGUGCUGUACA<br>ACAGCGCCAGCUUCAGCACCUUCAAGUGCUACGGCGUGAGCCCCAC<br>CAAGCUGAACGACCUGUGCUUCACCAACGUGUACGCCGACAGCUUC<br>GUGAUCCGUGGCGACGAGGUGCGGCAGAUCGCACCCGGCCAGACAG<br>GCAAGAUCGCCGACUACAACUACAAGCUGCCCGACGACUUCACCGG<br>CUGCGUGAUCGCCUGGAACAGCAACAACCUCGACAGCAAGGUGGGC<br>GGCAACUACAACUACCUGUACCGGCUGUUCCGGAAGAGCAACCUGA<br>AGCCCUUCGAGCGGGACAUCAGCACCGAGAUCUACCAAGCCGGCUC<br>CACCCCUUGCAACGGCGUGGAGGGCUUCAACUGCUACUUCCCUCUG<br>CAGAGCUACGGCUUCCAGCCCACCAACGGCGUGGGCUACCAGCCCU<br>ACCGGGUGGUGGUGCUGAGCUUCGAGCUGCUGCACGCCCCAGCCAC<br>CGUGUGUGGCCCCAAGUCUGGCGGAGGCAGCAGCAGCAUCGCCAGC<br>UUCUUCUUCAUCAUCGGGCUGAUCAUCGGCCUCUUCCUGGUGCUGC | 109 |

TABLE 10B-continued

| Domain Fusion Antigens Linked to a Trafficking Signal | | |
|---|---|---|
| | GGGUGGGCAUCCACCUGUGCAUCAAGCUGAAGCACACCAAGAAGAG<br>ACAGAUCUACACCGACAUCGAGAUGAACCGGCUGGGCAAG | |
| 3' UTR | UGAUAAUAGGCUGGAGCCUCGGUGGCCUAGCUUCUUGCCCCUUGGG<br>CCUCCCCCCAGCCCCUCCUCCCCUUCCUGCACCCGUACCCCCGUGG<br>UCUUUGAAUAAAGUCUGAGUGGGCGGC | 4 |
| Corresponding amino acid sequence | MFVFLVLLPLVSSQCVNLTTRTQLPPAYTNSFTRGVYYPDKVFRSS<br>VLHSTQDLFLPFFSNVTWFHAIHVSGTNGTKRFDNPVLPFNDGVYF<br>ASTEKSNIIRGWIFGTTLDSKTQSLLIVNNATNVVIKVCEFQFCND<br>PFLGVYYHKNNKSWMESEFRVYSSANNCTFEYVSQPFLMDLEGKQG<br>NFKNLREFVFKNIDGYFKIYSKHTPINLVRDLPQGFSALEPLVDLP<br>IGINITRFQTLLALHRSYLTPGDSSSGWTAGAAAYYVGYLQPRTFL<br>LKYNENGTITDAVDgggsgggPNITNLCPFGEVFNATRFASVYAWN<br>RKRISNCVADYSVLYNSASFSTFKCYGVSPTKLNDLCFTNVYADSF<br>VIRGDEVRQIAPGQTGKIADYNYKLPDDFTGCVIAWNSNNLDSKVG<br>GNYNYLYRLFRKSNLKPFERDISTEIYQAGSTPCNGVEGFNCYFPL<br>QSYGFQPTNGVGYQPYRVVVLSFELLHAPATVCGPKsgggsSSIAS<br>FFFIIGLIIGLFLVLRVGIHLCIKLKHTKKRQIYTDIEMNRLGK | 110 |
| PolyA tail | 100 nt | |

Domain Fusion C-Terminal Truncations

In other embodiments, an mRNA provided herein encodes a SARS-CoV-2 NTD-RBD fusion protein in which some portion of the C-terminal domain has been truncated/deleted. In one embodiment, 13 (or at least 13) amino acids have been deleted from the C-terminal domain of the NTD-RBD fusion protein. Deletion of these amino acids is expected to increase exposure of epitopes to antibodies, thereby stimulating a more robust immune response to protective epitopes present on the NTD and RBD domains.

A non-limiting example of SARS-CoV-2 domain fusion antigen having a C-terminal truncation and the mRNA encoding it is provided in Tables 1A and 11B below.

TABLE 11A

| Domain Fusion C-Terminal Truncation | | |
|---|---|---|
| | SEQ ID NO: | |
| Name | mRNA ORF | Protein |
| SARS-CoV-2 NTD-RBD with C-terminal Truncation of 13 Amino Acids (NTD-RBD-Δ13) | 106 | 107 |

TABLE 11B

| Domain Fusion C-Terminal Truncation SARS-COV-2 NTD-RBD with C-terminal Truncation of 13 Amino Acids (NTD-RBD-Δ13) | | |
|---|---|---|
| | SEQ ID NO: 105 consists of from 5' end to 3' end: 5' UTR SEQ ID NO: 2, mRNA ORF SEQ ID NO: 106 and 3' UTR SEQ ID NO: 4. | 105 |
| Chemistry | 1-methylpseudouridine | |
| Cap | 7mG(5')ppp(5')NImpNp | |
| 5' UTR | GGGAAAUAAGAGAGAAAAGAAGAGUAAGAAGAAAUAUAAGACCCCG<br>GCGCCGCCACC | 2 |
| ORF of mRNA Construct (excluding the stop codon) | AUGUUCGUGUUCCUGGUGCUGCUGCCCCUGGUGAGCAGCCAGUGCG<br>UGAACCUGACCACCCGGACCCAGCUGCCACCAGCCUACACCAACAG<br>CUUCACCCGGGGCGUCUACUACCCCGACAAGGUGUUCCGGAGCAGC<br>GUCCUGCACAGCACCCAGGACCUGUUCCUGCCCUUCUUCAGCAACG<br>UGACCUGGUUCCACGCCAUCCACGUGAGCGGCACCAACGGCACCAA<br>GCGGUUCGACAACCCCGUGCUGCCCUUCAACGACGGCGUGUACUUC<br>GCCAGCACCGAGAAGAGCAACAUCAUCCGGGGCUGGAUCUUCGGCA<br>CCACCCUGGACAGCAAGACCCAGAGCCUGCUGAUCGUGAAUAACGC<br>CACCAACGUGGUGAUCAAGGUGUGCGAGUUCCAGUUCUGCAACGAC<br>CCCUUCCUGGGCGUGUACUACCACAAGAACAACAAGAGCUGGAUGG<br>AGAGCGAGUUCCGGGUGUACAGCAGCGCCAACAACUGCACCUUCGA<br>GUACGUGAGCCAGCCCUUCCUGAUGGACCUGGAGGGCAAGCAGGGC<br>AACUUCAAGAACCUGCGGGAGUUCGUGUUCAAGAACAUCGACGGCU<br>ACUUCAAGAUCUACAGCAAGCACACCCCAAUCAACCUGGUGCGGGA<br>UCUGCCCCAGGGCUUCUCAGCCCUGGAGCCCCUGGUGGACCUGCCC<br>AUCGGCAUCAACAUCACCCGGUUCCAGACCCUGCUGGCCCUGCACC<br>GGAGCUACCUGACCCCAGGCGACAGCAGCAGCGGGUGGACAGCAGG<br>CGCGGCUGCUUACUACGUGGGCUACCUGCAGCCCCGGACCUUCCUG<br>CUGAAGUACAACGAGAACGGCACCAUCACCGACGCCGUGGACGGAG<br>GCGGAUCGGGAGGCGGACCCAACAUCACCAACCUGUGCCCCUUCGG | 106 |

TABLE 11B-continued

| Domain Fusion C-Terminal Truncation<br>SARS-COV-2 NTD-RBD with C-terminal Truncation<br>of 13 Amino Acids (NTD-RBD-Δ13) | | |
|---|---|---|
| | CGAGGUGUUCAACGCCACCCGGUUCGCCAGCGUGUACGCCUGGAAC<br>CGGAAGCGGAUCAGCAACUGCGUGGCCGACUACAGCGUGCUGUACA<br>ACAGCGCCAGCUUCAGCACCUUCAAGUGCUACGGCGUGAGCCCCAC<br>CAAGCUGAACGACCUGUGCUUCACCAACGUGUACGCCGACAGCUUC<br>GUGAUCCGUGGCGACGAGGUGCGGCAGAUCGCACCCGGCCAGACAG<br>GCAAGAUCGCCGACUACAACUACAAGCUGCCCGACGACUUCACCGG<br>CUGCGUGAUCGCCUGGAACAGCAACAACCUCGACAGCAAGGUGGGC<br>GGCAACUACAACUACCUGUACCGGCUGUUCCGGAAGAGCAACCUGA<br>AGCCCUUCGAGCGGGACAUCAGCACCGAGAUCUACCAAGCCGGCUC<br>CACCCCUUGCAACGGCGUGGAGGGCUUCAACUGCUACUUCCCUCUG<br>CAGAGCUACGGCUUCCAGCCCACCAACGGCGUGGGCUACCAGCCCU<br>ACCGGGUGGUGGUGCUGAGCUUCGAGCUGCUGCACGCCCCAGCCAC<br>CGUGUGUGGCCCCAAGUCUGGCGGAGGCAGCAUCCUGGCCAUCUAC<br>AGCCUGGGCUUCAUCGCCGGCCUGAUCGCCAUCGUGAUGGUGACCA<br>UCAUGCUGUGCUGCAUGACCAGCUGCUGCAGCUGCCUGAAGGGCUG<br>UUGCAGCUGCGGCAGCUGCUGCAAGUUCGACGAGGACGAC | |
| 3' UTR | UGAUAAUAGGCUGGAGCCUCGGUGGCCUAGCUUCUUGCCCCUUGGG<br>CCUCCCCCCAGCCCCUCCUCCCCUUCCUGCACCCGUACCCCCGUGG<br>UCUUUGAAUAAAGUCUGAGUGGGCGGC | 4 |
| Corresponding<br>amino acid<br>sequence | MFVFLVLLPLVSSQCVNLTTRTQLPPAYTNSFTRGVYYPDKVFRSS<br>VLHSTQDLFLPFFSNVTWFHAIHVSGTNGTKRFDNPVLPFNDGVYF<br>ASTEKSNIIRGWIFGTTLDSKTQSLLIVNNATNVVIKVCEFQFCND<br>PFLGVYYHKNNKSWMESEFRVYSSANNCTFEYVSQPFLMDLEGKQG<br>NFKNLREFVFKNIDGYFKIYSKHTPINLVRDLPQGFSALEPLVDLP<br>IGINITRFOTLLALHRSYLTPGDSSSGWTAGAAAYYVGYLQPRTFL<br>LKYNENGTITDAVDgggsgggPNITNLCPFGEVFNATRFASVYAWN<br>RKRISNCVADYSVLYNSASFSTFKCYGVSPTKLNDLCFTNVYADSF<br>VIRGDEVRQIAPGQTGKIADYNYKLPDDFTGCVIAWNSNNLDSKVG<br>GNYNYLYRLFRKSNLKPFERDISTEIYQAGSTPCNGVEGFNCYFPL<br>QSYGFQPTNGVGYQPYRVVVLSFELLHAPATVCGPKsgggsilaiy<br>SLGFIAGLIAIVMVTIMLCCMTSCCSCLKGCCSCGSCCKFDEDD | 107 |
| PolyA tail | 100 nt | |

Domain Extensions

SARS-CoV-2 S protein domain antigens, in some embodiments, include "extended" regions that include sequences adjacent to and/or flanking what is understood in the art to be the NTD domain or the RBD domain. The RBD_EXT series encompasses the SD1 (subdomain 1). The NTD_EXT series encompasses a C-terminal helix in the NTD. Some B cells and antibodies recognize conformational epitopes found only in properly folded, but not denatured, forms of the SARS-CoV-2 S protein NTD and RBD. Inclusion of sequences adjacent to and/or flanking the NTD and RBD domains not only can provide additional B-cell epitopes to the antigen, but may potentially result in more optimal folding of those domains and stimulate B cells with antibodies specific to epitopes that may be found on the edge of either domain. Furthermore, the inclusion of these extension sequences may thus increase the distance between the NTD or RBD and the expressing cell membrane, increasing exposure of both domains to antibodies that may bind less efficiently if the expressed protein was too close to the cell surface. Finally, the inclusion of extension sequences increases the pool of peptides that could potentially be presented to $CD4^+$ T cells by B cells that have recognized an NTD or RBD epitope, then processed the entire protein for antigen presentation, thereby increasing the chance that an NTD or RBD-specific B cell receives sufficient T cell help. Non-limiting example of SARS-CoV-2 domain extensions and the mRNA encoding them are provided in Tables 12A and 12B below.

TABLE 12

| Domain Extensions | | |
|---|---|---|
| | SEQ ID NO: | |
| Name | mRNA ORF | Protein |
| SARS-CoV-2 NTD DS Extended Linked to Transmembrane Domain (NTD-EXT-F43C-TM) | 52 | 53 |
| SARS-CoV-2 NTD DS Extended Linked to Transmembrane Domain (NTD-F43C-EXT-TM) | 55 | 56 |
| SARS-CoV-2 NTD Extended Linked to Transmembrane Domain (NTD-EXT-TM) | 58 | 59 |
| SARS-CoV-2 RBD Extended Linked to Transmembrane Domain (RBD-EXT-TM) | 85 | 86 |
| SARS-CoV-2 RBD DS Extended Linked to Transmembrane Domain (RBD-Q563D-EXT-TM) | 88 | 89 |
| SARS-CoV-2 NTD-RBD Extended Linked to Transmembrane Domain (NTD-RBD-EXT-TM) | 115 | 116 |
| SARS-CoV-2 NTD Extended-RBD Linked to Transmembrane Domain (NTD-EXT-RBD-TM) | 118 | 119 |
| SARS-CoV-2 NTD Extended-RBD-Extended Linked to Transmembrane Domain (NTD-EXT-RBD-EXT-TM) | 121 | 122 |

TABLE 12B

| Domain Extensions | | |
|---|---|---|
| SARS-CoV-2 NTD DS Extended Linked to Transmembrane Domain (NTD-EXT-F43C-TM) | | |
| SEQ ID NO: 51 consists of from 5' end to 3' end: 5' UTR SEQ ID NO: 2, mRNA ORF SEQ ID NO: 52 and 3' UTR SEQ ID NO: 4. | | 51 |
| Chemistry | 1-methylpseudouridine | |
| Cap | 7mG(5')ppp(5')NlmpNp | |
| 5' UTR | GGGAAAUAAGAGAGAAAAGAAGAGUAAGAAGAAAUAUAAGACCCCG GCGCCGCCACC | 2 |
| ORF of mRNA Construct (excluding the stop codon) | AUGUUCGUGUUCCUGGUGCUGCUGCCCCUGGUGAGCAGCCAGUGCG UGAACCUGACCACCCGGACCCAGCUGCCACCAGCCUACACCAACAG CUUCACCCGGGGCGUCUACUACCCCGACAAGGUGUGCCGGAGCAGC GUCCUGCACAGCACCCAGGACCUGUUCCUGCCCUUCUUCAGCAACG UGACCUGGUUCCACGCCAUCCACGUGAGCGGCACCAACGGCACCAA GCGGUUCGACAACCCCGUGCUGCCCUUCAACGACGGCGUGUACUUC GCCAGCACCGAGAAGAGCAACAUCAUCCGGGGCUGGAUCUUCGGCA CCACCCUGGACAGCAAGACCCAGAGCCUGCUGAUCGUGAAUAACGC CACCAACGUGGUGAUCAAGGUGUGCGAGUUCCAGUUCUGCAACGAC CCCUUCCUGGGCGUGUACUACCACAAGAACAACAAGAGCUGGAUGG AGAGCGAGUUCCGGGUGUACAGCAGCGCCAACAACUGCACCUUCGA GUACGUGAGCCAGCCCUUCCUGAUGGACCUGGAGGGCAAGCAGGGC AACUUCAAGAACCUGCGGGAGUUCGUGUUCAAGAACAUCGACGGCU ACUUCAAGAUCUACAGCAAGCACACCCCAAUCAACCUGGUGCGGGA UCUGCCCCAGGGCUUCUCAGCCCUGGAGCCCCUGGUGGACCUGCCC AUCGGCAUCAACAUCACCCGGUUCCAGACCCUGCUGGCCCUGCACC GGAGCUACCUGACCCCAGGCGACAGCAGCAGCGGGUGGACAGCAGG CGCGGCUGCUUACUACGUGGGCUACCUGCAGCCCCGGACCUUCCUG CUGAAGUACAACGAGAACGGCACCAUCACCGACGCCGUGGACUCUG GCGGAGGCAGCAUCCUGGCCAUCUACAGCACCGUGGCCAGCAGCCU GGUGCUGCUGGUGAGCCUGGGCGCCAUCAGCUUC | 52 |
| 3' UTR | UGAUAAUAGGCUGGAGCCUCGGUGGCCUAGCUUCUUGCCCCUUGGG CCUCCCCCCAGCCCCUCCUCCCCUUCCUGCACCCGUACCCCCGUGG UCUUUGAAUAAAGUCUGAGUGGGCGGC | 4 |
| Corresponding amino acid sequence | MFVFLVLLPLVSSQCVNLTTRTQLPPAYTNSFTRGVYYPDKVCRSS VLHSTQDLFLPFFSNVTWFHAIHVSGTNGTKRFDNPVLPFNDGVYF ASTEKSNIIRGWIFGTTLDSKTQSLLIVNNATNVVIKVCEFQFCND PFLGVYYHKNNKSWMESEFRVYSSANNCTFEYVSQPFLMDLEGKQG NFKNLREFVFKNIDGYFKIYSKHTPINLVRDLPQGFSALEPLVDLP IGINITRFQTLLALHRSYLTPGDSSSGWTAGAAAYYVGYLQPRTFL LKYNENGTITDAVDsgggsilaiystvasslvllvslgaisf | 53 |
| PolyA tail | 100 nt | |
| SARS-CoV-2 NTD DS Extended Linked to Transmembrane Domain (NTD-F43C-EXT-TM) | | |
| SEQ ID NO: 54 consists of from 5' end to 3' end: 5' UTR SEQ ID NO: 2, mRNA ORF SEQ ID NO: 55 and 3' UTR SEQ ID NO: 4. | | 54 |
| Chemistry | 1-methylpseudouridine | |
| Cap | 7mG(5')ppp(5')NlmpNp | |
| 5' UTR | GGGAAAUAAGAGAGAAAAGAAGAGUAAGAAGAAAUAUAAGACCCCG GCGCCGCCACC | 2 |
| ORF of mRNA Construct (excluding the stop codon) | AUGUUCGUGUUCCUGGUGCUGCUGCCCCUGGUGAGCAGCCAGUGCG UGAACCUGACCACCCGGACCCAGCUGCCACCAGCCUACACCAACAG CUUCACCCGGGGCGUCUACUACCCCGACAAGGUGUGCCGGAGCAGC GUCCUGCACAGCACCCAGGACCUGUUCCUGCCCUUCUUCAGCAACG UGACCUGGUUCCACGCCAUCCACGUGAGCGGCACCAACGGCACCAA GCGGUUCGACAACCCCGUGCUGCCCUUCAACGACGGCGUGUACUUC GCCAGCACCGAGAAGAGCAACAUCAUCCGGGGCUGGAUCUUCGGCA CCACCCUGGACAGCAAGACCCAGAGCCUGCUGAUCGUGAAUAACGC CACCAACGUGGUGAUCAAGGUGUGCGAGUUCCAGUUCUGCAACGAC CCCUUCCUGGGCGUGUACUACCACAAGAACAACAAGAGCUGGAUGG AGAGCGAGUUCCGGGUGUACAGCAGCGCCAACAACUGCACCUUCGA GUACGUGAGCCAGCCCUUCCUGAUGGACCUGGAGGGCAAGCAGGGC AACUUCAAGAACCUGCGGGAGUUCGUGUUCAAGAACAUCGACGGCU ACUUCAAGAUCUACAGCAAGCACACCCCAAUCAACCUGGUGCGGGA UCUGCCCCAGGGCUUCUCAGCCCUGGAGCCCCUGGUGGACCUGCCC AUCGGCAUCAACAUCACCCGGUUCCAGACCCUGCUGGCCCUGCACC GGAGCUACCUGACCCCAGGCGACAGCAGCAGCGGGUGGACAGCAGG CGCGGCUGCUUACUACGUGGGCUACCUGCAGCCCCGGACCUUCCUG | 55 |

TABLE 12B-continued

| Domain Extensions | | |
|---|---|---|
| | CUGAAGUACAACGAGAACGGCACCAUCACCGACGCCGUGGACUGCG<br>CCCUGGACCCUCUGAGCGAGACCAAGUGCACCCUGAAGAGCUUCAC<br>CUCUGGCGGAGGCAGCAUCCUGGCCAUCUACAGCACCGUGGCCAGC<br>AGCCUGGUGCUGCUGGUGAGCCUGGGCGCCAUCAGCUUC | |
| 3' UTR | UGAUAAUAGGCUGGAGCCUCGGUGGCCUAGCUUCUUGCCCCUUGGG<br>CCUCCCCCCAGCCCCUCCUCCCCUUCCUGCACCCGUACCCCCGUGG<br>UCUUUGAAUAAAGUCUGAGUGGGCGGC | 4 |
| Corresponding amino acid sequence | MFVFLVLLPLVSSQCVNLTTRTQLPPAYTNSFTRGVYYPDKVCRSS<br>VLHSTQDLFLPFFSNVTWFHAIHVSGTNGTKRFDNPVLPFNDGVYF<br>ASTEKSNIIRGWIFGTTLDSKTQSLLIVNNATNVVIKVCEFQFCND<br>PFLGVYYHKNNKSWMESEFRVYSSANNCTFEYVSQPFLMDLEGKQG<br>NFKNLREFVFKNIDGYFKIYSKHTPINLVRDLPQGFSALEPLVDLP<br>IGINITRFQTLLALHRSYLTPGDSSSGWTAGAAAYYVGYLQPRTFL<br>LKYNENGTITDAVDCALDPLSETKCTLKSFTsgggsilaiystvas<br>slvllvslgaisf | 56 |
| PolyA tail | 100 nt | |
| SARS-CoV-2 NTD Extended Linked to Transmembrane Domain (NTD-EXT-TM) | | |
| SEQ ID NO: 57 consists of from 5' end to 3' end: 5' UTR SEQ ID NO: 2, mRNA ORF SEQ ID NO: 58 and 3' UTR SEQ ID NO: 4. | | 57 |
| Chemistry | 1-methylpseudouridine | |
| Cap | 7mG(5')ppp(5')NlmpNp | |
| 5' UTR | GGGAAAUAAGAGAGAAAAGAAGAGUAAGAAGAAAUAUAAGACCCCG<br>GCGCCGCCACC | 2 |
| ORF of mRNA Construct (excluding the stop codon) | AUGUUCGUGUUCCUGGUGCUGCUGCCCCUGGUGAGCAGCCAGUGCG<br>UGAACCUGACCACCCGGACCCAGCUGCCACCAGCCUACACCAACAG<br>CUUCACCCGGGGCGUCUACUACCCCGACAAGGUGUUCCGGAGCAGC<br>GUCCUGCACAGCACCCAGGACCUGUUCCUGCCCUUCUUCAGCAACG<br>UGACCUGGUUCCACGCCAUCCACGUGAGCGGCACCAACGGCACCAA<br>GCGGUUCGACAACCCCGUGCUGCCCUUCAACGACGGCGUGUACUUC<br>GCCAGCACCGAGAAGAGCAACAUCAUCCGGGGCUGGAUCUUCGGCA<br>CCACCCUGGACAGCAAGACCCAGAGCCUGCUGAUCGUGAAUAACGC<br>CACCAACGUGGUGAUCAAGGUGUGCGAGUUCCAGUUCUGCAACGAC<br>CCCUUCCUGGGCGUGUACUACCACAAGAACAACAAGAGCUGGAUGG<br>AGAGCGAGUUCCGGGUGUACAGCAGCGCCAACAACUGCACCUUCGA<br>GUACGUGAGCCAGCCCUUCCUGAUGGACCUGGAGGGCAAGCAGGGC<br>AACUUCAAGAACCUGCGGGAGUUCGUGUUCAAGAACAUCGACGGCU<br>ACUUCAAGAUCUACAGCAAGCACACCCCAAUCAACCUGGUGCGGGA<br>UCUGCCCCAGGGCUUCUCAGCCCUGGAGCCCCUGGUGGACCUGCCC<br>AUCGGCAUCAACAUCACCCGGUUCCAGACCCUGCUGGCCCUGCACC<br>GGAGCUACCUGACCCCAGGCGACAGCAGCAGCGGGUGGACAGCAGG<br>CGCGGCUGCUUACUACGUGGGCUACCUGCAGCCCCGGACCUUCCUG<br>CUGAAGUACAACGAGAACGGCACCAUCACCGACGCCGUGGACUGCG<br>CCCUGGACCCUCUGAGCGAGACCAAGUGCACCCUGAAGAGCUUCAC<br>CUCUGGCGGAGGCAGCAUCCUGGCCAUCUACAGCACCGUGGCCAGC<br>AGCCUGGUGCUGCUGGUGAGCCUGGGCGCCAUCAGCUUC | 58 |
| 3' UTR | UGAUAAUAGGCUGGAGCCUCGGUGGCCUAGCUUCUUGCCCCUUGGG<br>CCUCCCCCCAGCCCCUCCUCCCCUUCCUGCACCCGUACCCCCGUGG<br>UCUUUGAAUAAAGUCUGAGUGGGCGGC | 4 |
| Corresponding amino acid sequence | MFVFLVLLPLVSSQCVNLTTRTQLPPAYTNSFTRGVYYPDKVFRSS<br>VLHSTQDLFLPFFSNVTWFHAIHVSGTNGTKRFDNPVLPFNDGVYF<br>ASTEKSNIIRGWIFGTTLDSKTQSLLIVNNATNVVIKVCEFQFCND<br>PFLGVYYHKNNKSWMESEFRVYSSANNCTFEYVSQPFLMDLEGKQG<br>NFKNLREFVFKNIDGYFKIYSKHTPINLVRDLPQGFSALEPLVDLP<br>IGINITRFQTLLALHRSYLTPGDSSSGWTAGAAAYYVGYLQPRTFL<br>LKYNENGTITDAVDCALDPLSETKCTLKSFTsgggsilaiystvas<br>slvllvslgaisf | 59 |
| PolyA tail | 100 nt | |
| SARS-COV-2 RBD Extended Linked to Transmembrane Domain (RBD-EXT-TM) | | |
| SEQ ID NO: 84 consists of from 5' end to 3' end: 5' UTR SEQ ID NO: 2, mRNA ORF SEQ ID NO: 85 and 3' UTR SEQ ID NO: 4. | | 84 |
| Chemistry | 1-methylpseudouridine | |
| Cap | 7mG(5')ppp(5')NlmpNp | |

TABLE 12B-continued

| Domain Extensions | | |
|---|---|---|
| 5' UTR | GGGAAAUAAGAGAGAAAAGAAGAGUAAGAAGAAAUAUAAGACCCCG<br>GCGCCGCCACC | 2 |
| ORF of mRNA Construct (excluding the stop codon) | AUGUACAGCAUGCAGCUGGCUAGCUGCGUGACCCUGACCCUGGUGC<br>UGCUGGUGAACAGCCAGCGGGUGCAGCCCACCGAGAGCAUCGUGCG<br>GUUCCCCAACAUCACCAACCUGUGCCCCUUCGGCGAGGUGUUCAAC<br>GCCACCCGGUUCGCCAGCGUGUACGCCUGGAACCGGAAGCGGAUCA<br>GCAACUGCGUGGCCGACUACAGCGUGCUGUACAACAGCGCCAGCUU<br>CAGCACCUUCAAGUGCUACGGCGUGAGCCCCACCAAGCUGAACGAC<br>CUGUGCUUCACCAACGUGUACGCCGACAGCUUCGUGAUCCGUGGCG<br>ACGAGGUGCGGCAGAUCGCACCCGGCCAGACAGGCAAGAUCGCCGA<br>CUACAACUACAAGCUGCCCGACGACUUCACCGGCUGCGUGAUCGCC<br>UGGAACAGCAACAACCUCGACAGCAAGGUGGGCGGCAACUACAACU<br>ACCUGUACCGGCUGUUCCGGAAGAGCAACCUGAAGCCCUUCGAGCG<br>GGACAUCAGCACCGAGAUCUACCAAGCCGGCUCCACCCCUUGCAAC<br>GGCGUGGAGGGCUUCAACUGCUACUUCCCUCUGCAGAGCUACGGCU<br>UCCAGCCCACCAACGGCGUGGGCUACCAGCCCUACCGGGUGGUGGU<br>GCUGAGCUUCGAGCUGCUGCACGCCCCAGCCACCGUGUGUGGCCCC<br>AAGAAGAGCACCAACCUGGUGAAGAACAAGUGCGUGAACUUCAACU<br>UCAACGGCCUUACCGGCACCGGCGUGCUGACCGAGAGCAACAAGAA<br>AUUCCUGCCCUUUCAGCAGUUCGGCCGGGACAUCGCCGACACCACC<br>GACGCUGUGCGGGAUCCCCAGACCCUGGAGAUCCUGGACAUCACCC<br>CUUGCAGCUCUGGCGGAGGCAGCAUCCUGGCCAUCUACAGCACCGU<br>GGCCAGCAGCCUGGUGCUGCUGGUGAGCCUGGGCGCCAUCAGCUUC | 85 |
| 3' UTR | UGAUAAUAGGCUGGAGCCUCGGUGGCCUAGCUUCUUGCCCCUUGGG<br>CCUCCCCCCAGCCCCUCCUCCCCUUCCUGCACCCGUACCCCCGUGG<br>UCUUUGAAUAAAGUCUGAGUGGGCGGC | 4 |
| Corresponding amino acid sequence | mysmqlascvtltlvllvnsQRVQPTESIVRFPNITNLCPFGEVFN<br>ATRFASVYAWNRKRISNCVADYSVLYNSASFSTFKCYGVSPTKLND<br>LCFTNVYADSFVIRGDEVRQIAPGQTGKIADYNYKLPDDFTGCVIA<br>WNSNNLDSKVGGNYNYLYRLFRKSNLKPFERDISTEIYQAGSTPCN<br>GVEGFNCYFPLQSYGFQPTNGVGYQPYRVVVLSFELLHAPATVCGP<br>KKSTNLVKNKCVNFNFNGLTGTGVLTESNKKFLPFQQFGRDIADTT<br>DAVRDPQTLEILDITPCSsgggsilaiystvasslvllvslgaisf | 86 |
| PolyA tail | 100 nt | |
| SARS-CoV-2 RBD DS Extended Linked to Transmembrane Domain (RBD-Q563D-EXT-TM) | | |
| SEQ ID NO: 87 consists of from 5' end to 3' end: 5' UTR SEQ ID NO: 2, mRNA ORF SEQ ID NO: 88 and 3' UTR SEQ ID NO: 4. | | 87 |
| Chemistry | 1-methylpseudouridine | |
| Cap | 7mG(5')ppp(5')NlmpNp | |
| 5' UTR | GGGAAAUAAGAGAGAAAAGAAGAGUAAGAAGAAAUAUAAGACCCCG<br>GCGCCGCCACC | 2 |
| ORF of mRNA Construct (excluding the stop codon) | AUGUACAGCAUGCAGCUGGCUAGCUGCGUGACCCUGACCCUGGUGC<br>UGCUGGUGAACAGCCAGCGGGUGCAGCCCACCGAGAGCAUCGUGCG<br>GUUCCCCAACAUCACCAACCUGUGCCCCUUCGGCGAGGUGUUCAAC<br>GCCACCCGGUUCGCCAGCGUGUACGCCUGGAACCGGAAGCGGAUCA<br>GCAACUGCGUGGCCGACUACAGCGUGCUGUACAACAGCGCCAGCUU<br>CAGCACCUUCAAGUGCUACGGCGUGAGCCCCACCAAGCUGAACGAC<br>CUGUGCUUCACCAACGUGUACGCCGACAGCUUCGUGAUCCGUGGCG<br>ACGAGGUGCGGCAGAUCGCACCCGGCCAGACAGGCAAGAUCGCCGA<br>CUACAACUACAAGCUGCCCGACGACUUCACCGGCUGCGUGAUCGCC<br>UGGAACAGCAACAACCUCGACAGCAAGGUGGGCGGCAACUACAACU<br>ACCUGUACCGGCUGUUCCGGAAGAGCAACCUGAAGCCCUUCGAGCG<br>GGACAUCAGCACCGAGAUCUACCAAGCCGGCUCCACCCCUUGCAAC<br>GGCGUGGAGGGCUUCAACUGCUACUUCCCUCUGCAGAGCUACGGCU<br>UCCAGCCCACCAACGGCGUGGGCUACCAGCCCUACCGGGUGGUGGU<br>GCUGAGCUUCGAGCUGCUGCACGCCCCAGCCACCGUGUGUGGCCCC<br>AAGAAGAGCACCAACCUGGUGAAGAACAAGUGCGUGAACUUCAACU<br>UCAACGGCCUUACCGGCACCGGCGUGCUGACCGAGAGCAACAAGAA<br>AUUCCUGCCCUUUUGCCAGUUCGGCCGGGACAUCGCCGACACCACC<br>GACGCUGUGCGGGAUCCCCAGACCCUGGAGAUCCUGGACAUCACCC<br>CUUGCAGCUCUGGCGGAGGCAGCAUCCUGGCCAUCUACAGCACCGU<br>GGCCAGCAGCCUGGUGCUGCUGGUGAGCCUGGGCGCCAUCAGCUUC | 88 |
| 3' UTR | UGAUAAUAGGCUGGAGCCUCGGUGGCCUAGCUUCUUGCCCCUUGGG<br>CCUCCCCCCAGCCCCUCCUCCCCUUCCUGCACCCGUACCCCCGUGG<br>UCUUUGAAUAAAGUCUGAGUGGGCGGC | 4 |

TABLE 12B-continued

| Domain Extensions | | |
|---|---|---|
| Corresponding amino acid sequence | mysmqlascvtltlvllvnsQRVQPTESIVRFPNITNLCPFGEVEN<br>ATRFASVYAWNRKRISNCVADYSVLYNSASFSTFKCYGVSPTKLND<br>LCFTNVYADSFVIRGDEVRQIAPGQTGKIADYNYKLPDDFTGCVIA<br>WNSNNLDSKVGGNYNYLYRLFRKSNLKPFERDISTEIYQAGSTPCN<br>GVEGFNCYFPLQSYGFQPTNGVGYQPYRVVVLSFELLHAPATVCGP<br>KKSTNLVKNKCVNFNFNGLTGTGVLTESNKKFLPFCQFGRDIADTT<br>DAVRDPQTLEILDITPCSsgggsilaiystvasslvllvslgaisf | 89 |
| PolyA tail | 100 nt | |
| SARS-CoV-2 NTD-RBD Extended Linked to Transmembrane Domain (NTD-RBD-EXT-TM) | | |
| SEQ ID NO: 114 consists of from 5' end to 3' end: 5' UTR SEQ ID NO: 2, mRNA ORF SEQ ID NO: 115 and 3' UTR SEQ ID NO: 4. | | 114 |
| Chemistry | 1-methylpseudouridine | |
| Cap | 7mG(5')ppp(5')NlmpNp | |
| 5' UTR | GGGAAAUAAGAGAGAAAAGAAGAGUAAGAAGAAAUAUAAGACCCCG<br>GCGCCGCCACC | 2 |
| ORF of mRNA Construct (excluding the stop codon) | AUGUUCGUGUUCCUGGUGCUGCUGCCCCUGGUGAGCAGCCAGUGCG<br>UGAACCUGACCACCCGGACCCAGCUGCCACCAGCCUACACCAACAG<br>CUUCACCCGGGGCGUCUACUACCCCGACAAGGUGUUCCGGAGCAGC<br>GUCCUGCACAGCACCCAGGACCUGUUCCUGCCCUUCUUCAGCAACG<br>UGACCUGGUUCCACGCCAUCCACGUGAGCGGCACCAACGGCACCAA<br>GCGGUUCGACAACCCCGUGCUGCCCUUCAACGACGGCGUGUACUUC<br>GCCAGCACCGAGAAGAGCAACAUCAUCCGGGGCUGGAUCUUCGGCA<br>CCACCCUGGACAGCAAGACCCAGAGCCUGCUGAUCGUGAAUAACGC<br>CACCAACGUGGUGAUCAAGGUGUGCGAGUUCCAGUUCUGCAACGAC<br>CCCUUCCUGGGCGUGUACUACCACAAGAACAACAAGAGCUGGAUGG<br>AGAGCGAGUUCCGGGUGUACAGCAGCGCCAACAACUGCACCUUCGA<br>GUACGUGAGCCAGCCCUUCCUGAUGGACCUGGAGGGCAAGCAGGGC<br>AACUUCAAGAACCUGCGGGAGUUCGUGUUCAAGAACAUCGACGGCU<br>ACUUCAAGAUCUACAGCAAGCACACCCCAAUCAACCUGGUGCGGGA<br>UCUGCCCCAGGGCUUCUCAGCCCUGGAGCCCCUGGUGGACCUGCCC<br>AUCGGCAUCAACAUCACCCGGUUCCAGACCCUGCUGGCCCUGCACC<br>GGAGCUACCUGACCCCAGGCGACAGCAGCAGCGGGUGGACAGCAGG<br>CGCGGCUGCUUACUACGUGGGCUACCUGCAGCCCCGGACCUUCCUG<br>CUGAAGUACAACGAGAACGGCACCAUCACCGACGCCGUGGACGGAG<br>GCGGAUCGGGAGGCGGACAGCGGGUGCAGCCCACCGAGAGCAUCGU<br>GCGGUUCCCCAACAUCACCAACCUGUGCCCCUUCGGCGAGGUGUUC<br>AACGCCACCCGGUUCGCCAGCGUGUACGCCUGGAACCGGAAGCGGA<br>UCAGCAACUGCGUGGCCGACUACAGCGUGCUGUACAACAGCGCCAG<br>CUUCAGCACCUUCAAGUGCUACGGCGUGAGCCCCACCAAGCUGAAC<br>GACCUGUGCUUCACCAACGUGUACGCCGACAGCUUCGUGAUCCGUG<br>GCGACGAGGUGCGGCAGAUCGCACCCGGCCAGACAGGCAAGAUCGC<br>CGACUACAACUACAAGCUGCCCGACGACUUCACCGGCUGCGUGAUC<br>GCCUGGAACAGCAACAACCUCGACAGCAAGGUGGGCGGCAACUACA<br>ACUACCUGUACCGGCUGUUCCGGAAGAGCAACCUGAAGCCCUUCGA<br>GCGGGACAUCAGCACCGAGAUCUACCAAGCCGGCUCCACCCCUUGC<br>AACGGCGUGGAGGGCUUCAACUGCUACUUCCCUCUGCAGAGCUACG<br>GCUUCCAGCCCACCAACGGCGUGGGCUACCAGCCCUACCGGGUGGU<br>GGUGCUGAGCUUCGAGCUGCUGCACGCCCCAGCCACCGUGUGUGGC<br>CCCAAGAAGAGCACCAACCUGGUGAAGAACAAGUGCGUGAACUUCA<br>ACUUCAACGGCCUUACCGGCACCGGCGUGCUGACCGAGAGCAACAA<br>GAAAUUCCUGCCCUUUCAGCAGUUCGGCCGGGACAUCGCCGACACC<br>ACCGACGCUGUGCGGGAUCCCCAGACCCUGGAGAUCCUGGACAUCA<br>CCCCUUGCAGCUCUGGCGGAGGCAGCAUCCUGGCCAUCUACAGCAC<br>CGUGGCCAGCAGCCUGGUGCUGCUGGUGAGCCUGGGCGCCAUCAGC<br>UUC | 115 |
| 3' UTR | UGAUAAUAGGCUGGAGCCUCGGUGGCCUAGCUUCUUGCCCCUUGGG<br>CCUCCCCCCAGCCCCUCCUCCCCUUCCUGCACCCGUACCCCCGUGG<br>UCUUUGAAUAAAGUCUGAGUGGGCGGC | 4 |
| Corresponding amino acid sequence | MFVFLVLLPLVSSQCVNLTTRTQLPPAYTNSFTRGVYYPDKVFRSS<br>VLHSTQDLFLPFFSNVTWFHAIHVSGTNGTKRFDNPVLPFNDGVYF<br>ASTEKSNIIRGWIFGTTLDSKTQSLLIVNNATNVVIKVCEFQFCND<br>PFLGVYYHKNNKSWMESEFRVYSSANNCTFEYVSQPFLMDLEGKQG<br>NFKNLREFVFKNIDGYFKIYSKHTPINLVRDLPQGFSALEPLVDLP<br>IGINITRFQTLLALHRSYLTPGDSSSGWTAGAAAYYVGYLQPRTFL<br>LKYNENGTITDAVDgggsgggQRVQPTESIVRFPNITNLCPFGEVF<br>NATRFASVYAWNRKRISNCVADYSVLYNSASFSTFKCYGVSPTKLN<br>DLCFTNVYADSFVIRGDEVRQIAPGQTGKIADYNYKLPDDFTGCVI<br>AWNSNNLDSKVGGNYNYLYRLFRKSNLKPFERDISTEIYQAGSTPC<br>NGVEGFNCYFPLQSYGFQPTNGVGYQPYRVVVLSFELLHAPATVCG | 116 |

TABLE 12B-continued

| Domain Extensions | | |
|---|---|---|
| | PKKSTNLVKNKCVNFNFNGLTGTGVLTESNKKFLPFQQFGRDIADT<br>TDAVRDPQTLEILDITPCSsgggsilaiystvasslvllvslgais<br>f | |
| PolyA tail | 100 nt | |

SARS-CoV-2 NTD Extended-RBD Linked to Transmembrane Domain (NTD-EXT-RBD-TM)

| | | |
|---|---|---|
| SEQ ID NO: 117 consists of from 5' end to 3' end: 5' UTR SEQ ID NO: 2, mRNA ORF SEQ ID NO: 118 and 3' UTR SEQ ID No: 4. | | 117 |
| Chemistry | 1-methylpseudouridine | |
| Cap | 7mG(5')ppp(5')NlmpNp | |
| 5' UTR | GGGAAAUAAGAGAGAAAAGAAGAGUAAGAAGAAAUAUAAGACCCCG<br>GCGCCGCCACC | 2 |
| ORF of mRNA Construct (excluding the stop codon) | AUGUUCGUGUUCCUGGUGCUGCUGCCCCUGGUGAGCAGCCAGUGCG<br>UGAACCUGACCACCCGGACCCAGCUGCCACCAGCCUACACCAACAG<br>CUUCACCCGGGGCGUCUACUACCCCGACAAGGUGUUCCGGAGCAGC<br>GUCCUGCACAGCACCCAGGACCUGUUCCUGCCCUUCUUCAGCAACG<br>UGACCUGGUUCCACGCCAUCCACGUGAGCGGCACCAACGGCACCAA<br>GCGGUUCGACAACCCCGUGCUGCCCUUCAACGACGGCGUGUACUUC<br>GCCAGCACCGAGAAGAGCAACAUCAUCCGGGGCUGGAUCUUCGGCA<br>CCACCCUGGACAGCAAGACCCAGAGCCUGCUGAUCGUGAAUAACGC<br>CACCAACGUGGUGAUCAAGGUGUGCGAGUUCCAGUUCUGCAACGAC<br>CCCUUCCUGGGCGUGUACUACCACAAGAACAACAAGAGCUGGAUGG<br>AGAGCGAGUUCCGGGUGUACAGCAGCGCCAACAACUGCACCUUCGA<br>GUACGUGAGCCAGCCCUUCCUGAUGGACCUGGAGGGCAAGCAGGGC<br>AACUUCAAGAACCUGCGGGAGUUCGUGUUCAAGAACAUCGACGGCU<br>ACUUCAAGAUCUACAGCAAGCACACCCCAAUCAACCUGGUGCGGGA<br>UCUGCCCCAGGGCUUCUCAGCCCUGGAGCCCCUGGUGGACCUGCCC<br>AUCGGCAUCAACAUCACCCGGUUCCAGACCCUGCUGGCCCUGCACC<br>GGAGCUACCUGACCCCAGGCGACAGCAGCAGCGGGUGGACAGCAGG<br>CGCGGCUGCUUACUACGUGGGCUACCUGCAGCCCCGGACCUUCCUG<br>CUGAAGUACAACGAGAACGGCACCAUCACCGACGCCGUGGACUGCG<br>CCCUGGACCCUCUGAGCGAGACCAAGUGCACCCUGAAGAGCUUCAC<br>CGGAGGCGGAUCGGGAGGCGGACCCAACAUCACCAACCUGUGCCCC<br>UUCGGCGAGGUGUUCAACGCCACCCGGUUCGCCAGCGUGUACGCCU<br>GGAACCGGAAGCGGAUCAGCAACUGCGUGGCCGACUACAGCGUGCU<br>GUACAACAGCGCCAGCUUCAGCACCUUCAAGUGCUACGGCGUGAGC<br>CCCACCAAGCUGAACGACCUGUGCUUCACCAACGUGUACGCCGACA<br>GCUUCGUGAUCCGUGGCGACGAGGUGCGGCAGAUCGCACCCGGCCA<br>GACAGGCAAGAUCGCCGACUACAACUACAAGCUGCCCGACGACUUC<br>ACCGGCUGCGUGAUCGCCUGGAACAGCAACAACCUCGACAGCAAGG<br>UGGGCGGCAACUACAACUACCUGUACCGGCUGUUCCGGAAGAGCAA<br>CCUGAAGCCCUUCGAGCGGGACAUCAGCACCGAGAUCUACCAAGCC<br>GGCUCCACCCCUUGCAACGGCGUGGAGGGCUUCAACUGCUACUUCC<br>CUCUGCAGAGCUACGGCUUCCAGCCCACCAACGGCGUGGGCUACCA<br>GCCCUACCGGGUGGUGGUGCUGAGCUUCGAGCUGCUGCACGCCCCA<br>GCCACCGUGUGUGGCCCCAAGUCUGGCGGAGGCAGCAUCCUGGCCA<br>UCUACAGCACCGUGGCCAGCAGCCUGGUGCUGCUGGUGAGCCUGGG<br>CGCCAUCAGCUUC | 118 |
| 3' UTR | UGAUAAUAGGCUGGAGCCUCGGUGGCCUAGCUUCUUGCCCCUUGGG<br>CCUCCCCCCAGCCCCUCCUCCCCUUCCUGCACCCGUACCCCCGUGG<br>UCUUUGAAUAAAGUCUGAGUGGGCGGC | 4 |
| Corresponding amino acid sequence | MFVFLVLLPLVSSQCVNLTTRTQLPPAYTNSFTRGVYYPDKVFRSS<br>VLHSTQDLFLPFFSNVTWFHAIHVSGTNGTKRFDNPVLPFNDGVYF<br>ASTEKSNIIRGWIFGTTLDSKTQSLLIVNNATNVVIKVCEFQFCND<br>PFLGVYYHKNNKSWMESEFRVYSSANNCTFEYVSQPFLMDLEGKQG<br>NFKNLREFVFKNIDGYFKIYSKHTPINLVRDLPQGFSALEPLVDLP<br>IGINITRFQTLLALHRSYLTPGDSSSGWTAGAAAYYVGYLQPRTFL<br>LKYNENGTITDAVDCALDPLSETKCTLKSFTgggsgggPNITNLCP<br>FGEVFNATRFASVYAWNRKRISNCVADYSVLYNSASFSTFKCYGVS<br>PTKLNDLCFTNVYADSFVIRGDEVRQIAPGQTGKIADYNYKLPDDF<br>TGCVIAWNSNNLDSKVGGNYNYLYRLFRKSNLKPFERDISTEIYQA<br>GSTPCNGVEGFNCYFPLQSYGFQPTNGVGYQPYRVVVLSFELLHAP<br>ATVCGPKsgggsilaiystvasslvllvslgaisf | 119 |
| PolyA tail | 100 nt | |

TABLE 12B-continued

| Domain Extensions | | |
|---|---|---|
| SARS-CoV-2 NTD Extended-RBD-Extended Linked to Transmembrane Domain (NTD-EXT-RBD-EXT-TM) | | |
| SEQ ID NO: 120 consists of from 5' end to 3' end: 5' UTR SEQ ID NO: 2, mRNA ORF SEQ ID NO: 121 and 3' UTR SEQ ID NO: 4 | | 120 |
| Chemistry | 1-methylpseudouridine | |
| Cap | 7mG(5')ppp(5')NlmpNp | |
| 5' UTR | GGGAAAUAAGAGAGAAAAGAAGAGUAAGAAGAAAUAUAAGACCCCG<br>GCGCCGCCACC | 2 |
| ORF of mRNA Construct (excluding the stop codon) | AUGUUCGUGUUCCUGGUGCUGCUGCCCCUGGUGAGCAGCCAGUGCG<br>UGAACCUGACCACCCGGACCCAGCUGCCACCAGCCUACACCAACAG<br>CUUCACCCGGGGCGUCUACUACCCCGACAAGGUGUUCCGGAGCAGC<br>GUCCUGCACAGCACCCAGGACCUGUUCCUGCCCUUCUUCAGCAACG<br>UGACCUGGUUCCACGCCAUCCACGUGAGCGGCACCAACGGCACCAA<br>GCGGUUCGACAACCCCGUGCUGCCCUUCAACGACGGCGUGUACUUC<br>GCCAGCACCGAGAAGAGCAACAUCAUCCGGGGCUGGAUCUUCGGCA<br>CCACCCUGGACAGCAAGACCCAGAGCCUGCUGAUCGUGAAUAACGC<br>CACCAACGUGGUGAUCAAGGUGUGCGAGUUCCAGUUCUGCAACGAC<br>CCCUUCCUGGGCGUGUACUACCACAAGAACAACAAGAGCUGGAUGG<br>AGAGCGAGUUCCGGGUGUACAGCAGCGCCAACAACUGCACCUUCGA<br>GUACGUGAGCCAGCCCUUCCUGAUGGACCUGGAGGGCAAGCAGGGC<br>AACUUCAAGAACCUGCGGGAGUUCGUGUUCAAGAACAUCGACGGCU<br>ACUUCAAGAUCUACAGCAAGCACACCCCAAUCAACCUGGUGCGGGA<br>UCUGCCCCAGGGCUUCUCAGCCCUGGAGCCCCUGGUGGACCUGCCC<br>AUCGGCAUCAACAUCACCCGGUUCCAGACCCUGCUGGCCCUGCACC<br>GGAGCUACCUGACCCCAGGCGACAGCAGCAGCGGGUGGACAGCAGG<br>CGCGGCUGCUUACUACGUGGGCUACCUGCAGCCCCGGACCUUCCUG<br>CUGAAGUACAACGAGAACGGCACCAUCACCGACGCCGUGGACUGCG<br>CCCUGGACCCUCUGAGCGAGACCAAGUGCACCCUGAAGAGCUUCAC<br>CGGAGGCGGAUCGGGAGGCGGACAGCGGGUGCAGCCCACCGAGAGC<br>AUCGUGCGGUUCCCCAACAUCACCAACCUGUGCCCCUUCGGCGAGG<br>UGUUCAACGCCACCCGGUUCGCCAGCGUGUACGCCUGGAACCGGAA<br>GCGGAUCAGCAACUGCGUGGCCGACUACAGCGUGCUGUACAACAGC<br>GCCAGCUUCAGCACCUUCAAGUGCUACGGCGUGAGCCCCACCAAGC<br>UGAACGACCUGUGCUUCACCAACGUGUACGCCGACAGCUUCGUGAU<br>CCGUGGCGACGAGGUGCGGCAGAUCGCACCCGGCCAGACAGGCAAG<br>AUCGCCGACUACAACUACAAGCUGCCCGACGACUUCACCGGCUGCG<br>UGAUCGCCUGGAACAGCAACAACCUCGACAGCAAGGUGGGCGGCAA<br>CUACAACUACCUGUACCGGCUGUUCCGGAAGAGCAACCUGAAGCCC<br>UUCGAGCGGGACAUCAGCACCGAGAUCUACCAAGCCGGCUCCACCC<br>CUUGCAACGGCGUGGAGGGCUUCAACUGCUACUUCCCUCUGCAGAG<br>CUACGGCUUCCAGCCCACCAACGGCGUGGGCUACCAGCCCUACCGG<br>GUGGUGGUGCUGAGCUUCGAGCUGCUGCACGCCCCAGCCACCGUGU<br>GUGGCCCCAAGAAGAGCACCAACCUGGUGAAGAACAAGUGCGUGAA<br>CUUCAACUUCAACGGCCUUACCGGCACCGGCGUGCUGACCGAGAGC<br>AACAAGAAAUUCCUGCCCUUUCAGCAGUUCGGCCGGGACAUCGCCG<br>ACACCACCGACGCUGUGCGGGAUCCCCAGACCCUGGAGAUCCUGGA<br>CAUCACCCCUUGCAGCUCUGGCGGAGGCAGCAUCCUGGCCAUCUAC<br>AGCACCGUGGCCAGCAGCCUGGUGCUGCUGGUGAGCCUGGGCGCCA<br>UCAGCUUC | 121 |
| 3' UTR | UGAUAAUAGGCUGGAGCCUCGGUGGCCUAGCUUCUUGCCCCUUGGG<br>CCUCCCCCCAGCCCCUCCUCCCCUUCCUGCACCCGUACCCCCGUGG<br>UCUUUGAAUAAAGUCUGAGUGGGCGGC | 4 |
| Corresponding amino acid sequence | MFVFLVLLPLVSSQCVNLTTRTQLPPAYTNSFTRGVYYPDKVFRSS<br>VLHSTQDLFLPFFSNVTWFHAIHVSGTNGTKRFDNPVLPFNDGVYF<br>ASTEKSNIIRGWIFGTTLDSKTQSLLIVNNATNVVIKVCEFQFCND<br>PFLGVYYHKNNKSWMESEFRVYSSANNCTFEYVSQPFLMDLEGKQG<br>NFKNLREFVFKNIDGYFKIYSKHTPINLVRDLPQGFSALEPLVDLP<br>IGINITRFQTLLALHRSYLTPGDSSSGWTAGAAAYYVGYLQPRTFL<br>LKYNENGTITDAVDCALDPLSETKCTLKSFTgggsgggQRVQPTES<br>IVRFPNITNLCPFGEVFNATRFASVYAWNRKRISNCVADYSVLYNS<br>ASFSTFKCYGVSPTKLNDLCFTNVYADSFVIRGDEVRQIAPGQTGK<br>IADYNYKLPDDFTGCVIAWNSNNLDSKVGGNYNYLYRLFRKSNLKP<br>FERDISTEIYQAGSTPCNGVEGFNCYFPLQSYGFQPTNGVGYQPYR<br>VVVLSFELLHAPATVCGPKKSTNLVKNKCVNFNFNGLTGTGVLTES<br>NKKFLPFQQFGRDIADTTDAVRDPQTLEILDITPCSsgggsilaiy<br>stvasslvllvslgaisf | 122 |
| PolyA tail | 100 nt | |

Domain Mixtures

The present disclosure provides, in some aspects, compositions that comprise a mixture of mRNAs encoding SARS-CoV-2 S protein subdomains. In one example, a composition comprises a mixture of an mRNA encoding an NTD (with or without SD1, SD2, and/or a transmembrane domain) and an mRNA encoding an RBD (with or without SD1, SD2, and/or a transmembrane domain). In some embodiments, a composition comprises an mRNA (e.g., SEQ ID NO: 45 or 46) encoding an NTD linked to a transmembrane domain (e.g., SEQ ID NO: 47) and an mRNA (e.g., SEQ ID NO: 75 or 76 encoding an RBD linked to a transmembrane domain (e.g., SEQ ID NO: 77).

The ratio of the concentration of one mRNA to another in a composition may be 1:1 (50:50), 1:2, 1:3, 1:4, or 1:5. In some embodiments, the ratio is 1:1. For example, a composition may comprise a 1:1 ratio of an mRNA (e.g., SEQ ID NO: 45 or 46) encoding an NTD linked to a transmembrane domain (e.g., SEQ ID NO: 47) to an mRNA (e.g., SEQ ID NO: 75 or 76 encoding an RBD linked to a transmembrane domain (e.g., SEQ ID NO: 77). In some embodiments, the ratio is 1:2. For example, a composition may comprise a 1:2 ratio of an mRNA (e.g., SEQ ID NO: 45 or 46) encoding an NTD linked to a transmembrane domain (e.g., SEQ ID NO: 47) to an mRNA (e.g., SEQ ID NO: 75 or 76) encoding an RBD linked to a transmembrane domain (e.g., SEQ ID NO: 77). Another example, a composition may comprise a 1:2 ratio of an mRNA (e.g., SEQ ID NO: 75 or 76) encoding an RBD linked to a transmembrane domain (e.g., SEQ ID NO: 77) to an mRNA (e.g., SEQ ID NO: 45 or 46) encoding an NTD linked to a transmembrane domain (e.g., SEQ ID NO: 47). Different mRNAs encoding different antigens may stimulate immune responses of varying strength (Magini D et al. PLoS ONE. 2016; 11:e0161193), and administration of an equimolar ratio of two mRNAs encoding two different antigens may result in an immune response to one but not the other (John S et al. Vaccine. 2018; 36:1689-1699). Manipulation of the ratio of co-delivered mRNAs may be useful for eliciting broad immune responses that target desired antigens with equal potency.

Encoded Nanoparticle Antigens

The mRNA vaccines provided herein, in some embodiments, encode fusion proteins that comprise coronavirus antigens linked to a scaffold domain. In some embodiments, a scaffold domain imparts desired properties to an antigen encoded by an mRNA of the disclosure. For example, scaffold domain may improve the immunogenicity of an antigen, e.g., by altering the structure of the antigen, altering the uptake and processing of the antigen, and/or causing the antigen to bind to another molecule. In some embodiments, a scaffold domain linked to antigen facilitates self-assembly of the antigen into a viral nanoparticle or a larger protein-folded immunogen. Non-limiting examples of scaffold domains that may be used as provide herein include, ferritin domains, lumazine synthetase domains, foldon domains, and encapsulin domains. Other scaffold domains may be used.

Ferritin

In some embodiments, a ferritin domain is used as a scaffold domain. Ferritin is a protein, the main function of which is intracellular iron storage. Ferritin is comprised of twenty-four (24) subunits, each composed of a four-alpha-helix bundle that self-assemble into a quaternary structure with octahedral symmetry (Cho K. J. et al. J Mol Biol. 2009; 390: 83-98; (Granier T. et al. J Biol Inorg Chem. 2003; 8: 105-111; and Lawson D. M. et al. Nature. 1991; 349: 541-544). Ferritin self-assembles into nanoparticles with robust thermal and chemical stability. Enclosing antigens within ferritin nanoparticles in this manner is expected to both delay degradation of the antigen and aggregate individual antigens, with each nanoparticle containing twenty-four (24) antigen subunits. Aggregation of multiple copies of the same antigen enhances both antigen uptake and migration by dendritic cells, as well as more robust $CD4^+$ and $CD8^+$ T cell responses (Kastenmiller K et al. J Clin Invest. 2011; 121(5):1782-96). Thus, the ferritin nanoparticle is a well-suited platform for antigen presentation and vaccine development.

An mRNA provided herein, in some embodiments, encodes an RBD linked to a ferritin domain, for example, through a glycine (e.g., GGG) linker domain. Other linkers may be used.

In other embodiments, an mRNA provided herein encodes an S1 domain of an S protein linked to a ferritin domain, for example, through a glycine (e.g., GGG) linker. As indicated elsewhere herein, other linkers may be used.

Non-limiting examples of SARS-CoV-2 antigens linked to a ferritin domain and the mRNA encoding them are provided in Tables 13A and 13B below.

TABLE 13A

Antigens Linked to a Ferritin Domain

| Name | SEQ ID NO: mRNA ORF | SEQ ID NO: Protein |
|---|---|---|
| SARS-CoV-2 S1 Subunit Linked to Ferritin (S1-Ferritin) | 7 | 8 |
| SARS-CoV-2 RBD Linked to Ferritin (RBD-Ferritin) | 64 | 65 |

TABLE 13B

| Antigens Linked to a Ferritin Domain | | |
|---|---|---|
| SARS-CoV-2 S1 Subunit Linked to Ferritin (S1-Ferritin) | | |
| SEQ ID NO: 6 consists of from 5' end to 3' end: 5' UTR SEQ ID NO: 2, mRNA ORF SEQ ID No: 7 3' UTR SEQ ID NO: 4. | | 6 |
| Chemistry | 1-methylpseudouridine | |
| Cap | 7mG(5')ppp(5')N1mpNp | |
| 5' UTR | GGGAAAUAAGAGAGAAAAGAAGAGUAAGAAGAAAUAUAAGACCCCG GCGCCGCCACC | 2 |

TABLE 13B-continued

| Antigens Linked to a Ferritin Domain | | |
|---|---|---|
| ORF of mRNA Construct (excluding the stop codon) | AUGUUCGUGUUCCUGGUGCUGCUGCCCCUGGUGAGCAGCCAGUGCG<br>UGAACCUGACCACCCGGACCCAGCUGCCACCAGCCUACACCAACAG<br>CUUCACCCGGGGCGUCUACUACCCCGACAAGGUGUUCCGGAGCAGC<br>GUCCUGCACAGCACCCAGGACCUGUUCCUGCCCUUCUUCAGCAACG<br>UGACCUGGUUCCACGCCAUCCACGUGAGCGGCACCAACGGCACCAA<br>GCGGUUCGACAACCCCGUGCUGCCCUUCAACGACGGCGUGUACUUC<br>GCCAGCACCGAGAAGAGCAACAUCAUCCGGGGCUGGAUCUUCGGCA<br>CCACCCUGGACAGCAAGACCCAGAGCCUGCUGAUCGUGAAUAACGC<br>CACCAACGUGGUGAUCAAGGUGUGCGAGUUCCAGUUCUGCAACGAC<br>CCCUUCCUGGGCGUGUACUACCACAAGAACAACAAGAGCUGGAUGG<br>AGAGCGAGUUCCGGGUGUACAGCAGCGCCAACAACUGCACCUUCGA<br>GUACGUGAGCCAGCCCUUCCUGAUGGACCUGGAGGGCAAGCAGGGC<br>AACUUCAAGAACCUGCGGGAGUUCGUGUUCAAGAACAUCGACGGCU<br>ACUUCAAGAUCUACAGCAAGCACACCCCAAUCAACCUGGUGCGGGA<br>UCUGCCCCAGGGCUUCUCAGCCCUGGAGCCCCUGGUGGACCUGCCC<br>AUCGGCAUCAACAUCACCCGGUUCCAGACCCUGCUGGCCCUGCACC<br>GGAGCUACCUGACCCCAGGCGACAGCAGCAGCGGGUGGACAGCAGG<br>CGCGGCUGCUUACUACGUGGGCUACCUGCAGCCCCGGACCUUCCUG<br>CUGAAGUACAACGAGAACGGCACCAUCACCGACGCCGUGGACUGCG<br>CCCUGGACCCUCUGAGCGAGACCAAGUGCACCCUGAAGAGCUUCAC<br>CGUGGAGAAGGGCAUCUACCAGACCAGCAACUUCCGGGUGCAGCCC<br>ACCGAGAGCAUCGUGCGGUUCCCCAACAUCACCAACCUGUGCCCCU<br>UCGGCGAGGUGUUCAACGCCACCCGGUUCGCCAGCGUGUACGCCUG<br>GAACCGGAAGCGGAUCAGCAACUGCGUGGCCGACUACAGCGUGCUG<br>UACAACAGCGCCAGCUUCAGCACCUUCAAGUGCUACGGCGUGAGCC<br>CCACCAAGCUGAACGACCUGUGCUUCACCAACGUGUACGCCGACAG<br>CUUCGUGAUCCGUGGCGACGAGGUGCGGCAGAUCGCACCCGGCCAG<br>ACAGGCAAGAUCGCCGACUACAACUACAAGCUGCCCGACGACUUCA<br>CCGGCUGCGUGAUCGCCUGGAACAGCAACAACCUCGACAGCAAGGU<br>GGGCGGCAACUACAACUACCUGUACCGGCUGUUCCGGAAGAGCAAC<br>CUGAAGCCCUUCGAGCGGGACAUCAGCACCGAGAUCUACCAAGCCG<br>GCUCCACCCCUUGCAACGGCGUGGAGGGCUUCAACUGCUACUUCCC<br>UCUGCAGAGCUACGGCUUCCAGCCCACCAACGGCGUGGGCUACCAG<br>CCCUACCGGGUGGUGGUGCUGAGCUUCGAGCUGCUGCACGCCCCAG<br>CCACCGUGUGUGGCCCCAAGAAGAGCACCAACCUGGUGAAGAACAA<br>GUGCGUGAACUUCAACUUCAACGGCCUUACCGGCACCGGCGUGCUG<br>ACCGAGAGCAACAAGAAAUUCCUGCCCUUUCAGCAGUUCGGCCGGG<br>ACAUCGCCGACACCACCGACGCUGUGCGGGAUCCCCAGACCCUGGA<br>GAUCCUGGACAUCACCCCUUGCAGCUUCGGCGGCGUGAGCGUGAUC<br>ACCCCAGGCACCAACACCAGCAACCAGGUGGCCGUGCUGUACCAGG<br>ACGUGAACUGCACCGAGGUGCCCGUGGCCAUCCACGCCGACCAGCU<br>GACACCCACCUGGCGGGUCUACAGCACCGGCAGCAACGUGUUCCAG<br>ACCCGGGCCGGUUGCCUGAUCGGCGCCGAGCACGUGAACAACAGCU<br>ACGAGUGCGACAUCCCCAUCGGCGCCGGCAUCUGUGCCAGCUACCA<br>GACCCAGACCAAUUCAGGAGGAGGCAGCGGCGGCGAUAUCAUCAAG<br>CUUCUGAACGAGCAAGUUAACAAGGAAAUGCAGAGCAGUAAUCUCU<br>ACAUGAGCAUGAGCAGCUGGUGCUACACCCACUCCCUGGACGGAGC<br>AGGCCUCUUCCUGUUCGACCACGCAGCCGAGGAGUACGAGCACGCU<br>AAGAAGUUGAUCAUUUUCUUGAACGAGAACAACGUGCCCGUGCAGC<br>UAACGUCAAUCAGCGCACCUGAGCACAAGUUCGAGGGCCUGACCCA<br>GAUCUUCCAGAAGGCCUACGAACACGAACAGCACAUCUCCGAGAGC<br>AUCAACAAUAUUGUGGAUCACGCUAUCAAGUCCAAGGACCACGCUA<br>CCUUCAACUUCCUGCAGUGGUACGUGGCCGAGCAACAUGAGGAGGA<br>GGUGCUGUUCAAGGACAUCCUGGACAAGAUCGAGCUGAUCGGUAAU<br>GAGAAUCACGGCCUGUACCUGGCCGACCAGUACGUGAAGGGCAUCG<br>CCAAGAGCCGGAAGUCAGGCUCA | 7 |
| 3' UTR | UGAUAAUAGGCUGGAGCCUCGGUGGCCUAGCUUCUUGCCCCUUGGG<br>CCUCCCCCCAGCCCCUCCUCCCCUUCCUGCACCCGUACCCCCGUGG<br>UCUUUGAAUAAAGUCUGAGUGGGCGGC | 4 |
| Corresponding amino acid sequence | MFVFLVLLPLVSSQCVNLTTRTQLPPAYTNSFTRGVYYPDKVFRSS<br>VLHSTQDLFLPFFSNVTWFHAIHVSGTNGTKRFDNPVLPFNDGVYF<br>ASTEKSNIIRGWIFGTTLDSKTQSLLIVNNATNVVIKVCEFQFCND<br>PFLGVYYHKNNKSWMESEFRVYSSANNCTFEYVSQPFLMDLEGKQG<br>NFKNLREFVFKNIDGYFKIYSKHTPINLVRDLPQGFSALEPLVDLP<br>IGINITRFQTLLALHRSYLTPGDSSSGWTAGAAAYYVGYLQPRTFL<br>LKYNENGTITDAVDCALDPLSETKCTLKSFTVEKGIYQTSNFRVQP<br>TESIVRFPNITNLCPFGEVFNATRFASVYAWNRKRISNCVADYSVL<br>YNSASFSTFKCYGVSPTKLNDLCFTNVYADSFVIRGDEVRQIAPGQ<br>TGKIADYNYKLPDDFTGCVIAWNSNNLDSKVGGNYNYLYRLFRKSN<br>LKPFERDISTEIYQAGSTPCNGVEGFNCYFPLQSYGFQPTNGVGYQ<br>PYRVVVLSFELLHAPATVCGPKKSTNLVKNKCVNFNFNGLTGTGVL<br>TESNKKFLPFQQFGRDIADTTDAVRDPQTLEILDITPCSFGGVSVI<br>TPGTNTSNQVAVLYQDVNCTEVPVAIHADQLTPTWRVYSTGSNVFQ<br>TRAGCLIGAEHVNNSYECDIPIGAGICASYQTQTNSgggSGGDIIK<br>LLNEQVNKEMQSSNLYMSMSSWCYTHSLDGAGLFLFDHAAEEYEHA | 8 |

TABLE 13B-continued

| Antigens Linked to a Ferritin Domain | | |
|---|---|---|
| | KKLIIFLNENNVPVqLTSISAPEHKFEGLTQIFQKAYEHEQHISES<br>INNIVDHAIKSKDHATFNFLQWYVAEQHEEEVLFKDILDKIELIGN<br>ENHGLYLADQYVKGIAKSRKSGS | |
| PolyA tail | 100 nt | |
| SARS-CoV-2 RBD Linked to Ferritin (RBD-Ferritin) | | |
| SEQ ID NO: 63 consists of from 5' end to 3' end: 5' UTR SEQ ID NO: 2, mRNA ORF SEQ ID NO: 64 and 3' UTR SEQ ID NO: 4. | | 63 |
| Chemistry | 1-methylpseudouridine | |
| Cap | 7mG(5')ppp(5')NlmpNp | |
| 5' UTR | GGGAAAUAAGAGAGAAAAGAAGAGUAAGAAGAAAUAUAAGACCCCG<br>GCGCCGCCACC | 2 |
| ORF of mRNA Construct (excluding the stop codon) | AUGUACAGCAUGCAGCUGGCUAGCUGCGUGACCCUGACCCUGGUGC<br>UGCUGGUGAACAGCCAGCCCAACAUCACCAACCUGUGCCCCUUCGG<br>CGAGGUGUUCAACGCCACCCGGUUCGCCAGCGUGUACGCCUGGAAC<br>CGGAAGCGGAUCAGCAACUGCGUGGCCGACUACAGCGUGCUGUACA<br>ACAGCGCCAGCUUCAGCACCUUCAAGUGCUACGGCGUGAGCCCCAC<br>CAAGCUGAACGACCUGUGCUUCACCAACGUGUACGCCGACAGCUUC<br>GUGAUCCGUGGCGACGAGGUGCGGCAGAUCGCACCCGGCCAGACAG<br>GCAAGAUCGCCGACUACAACUACAAGCUGCCCGACGACUUCACCGG<br>CUGCGUGAUCGCCUGGAACAGCAACAACCUCGACAGCAAGGUGGGC<br>GGCAACUACAACUACCUGUACCGGCUGUUCCGGAAGAGCAACCUGA<br>AGCCCUUCGAGCGGGACAUCAGCACCGAGAUCUACCAAGCCGGCUC<br>CACCCCUUGCAACGGCGUGGAGGGCUUCAACUGCUACUUCCCUCUG<br>CAGAGCUACGGCUUCCAGCCCACCAACGGCGUGGGCUACCAGCCCU<br>ACCGGGUGGUGGUGCUGAGCUUCGAGCUGCUGCACGCCCCAGCCAC<br>CGUGUGUGGCCCCAAGGGAGGAGGCAGCGGCGGCGAUAUCAUCAAG<br>CUUCUGAACGAGCAAGUUAACAAGGAAAUGCAGAGCAGUAAUCUCU<br>ACAUGAGCAUGAGCAGCUGGUGCUACACCCACUCCCUGGACGGAGC<br>AGGCCUCUUCCUGUUCGACCACGCAGCCGAGGAGUACGAGCACGCU<br>AAGAAGUUGAUCAUUUUCUUGAACGAGAACAACGUGCCCGUGCAGC<br>UAACGUCAAUCAGCGCACCUGAGCACAAGUUCGAGGGCCUGACCCA<br>GAUCUUCCAGAAGGCCUACGAACACGAACAGCACAUCUCCGAGAGC<br>AUCAACAAUAUUGUGGAUCACGCUAUCAAGUCCAAGGACCACGCUA<br>CCUUCAACUUCCUGCAGUGGUACGUGGCCGAGCAACAUGAGGAGGA<br>GGUGCUGUUCAAGGACAUCCUGGACAAGAUCGAGCUGAUCGGUAAU<br>GAGAAUCACGGCCUGUACCUGGCCGACCAGUACGUGAAGGGCAUCG<br>CCAAGAGCCGGAAGUCAGGCUCA | 64 |
| 3' UTR | UGAUAAUAGGCUGGAGCCUCGGUGGCCUAGCUUCUUGCCCCUUGGG<br>CCUCCCCCCAGCCCCUCCUCCCCUUCCUGCACCCGUACCCCCGUGG<br>UCUUUGAAUAAAGUCUGAGUGGGCGGC | 4 |
| Corresponding amino acid sequence | MYSMQLASCVTLTLVLLVNSQPNITNLCPFGEVFNATRFASVYAWN<br>RKRISNCVADYSVLYNSASFSTFKCYGVSPTKLNDLCFTNVYADSF<br>VIRGDEVRQIAPGQTGKIADYNYKLPDDFTGCVIAWNSNNLDSKVG<br>GNYNYLYRLFRKSNLKPFERDISTEIYQAGSTPCNGVEGFNCYFPL<br>QSYGFQPTNGVGYQPYRVVVLSFELLHAPATVCGPKGGGSGGDIIK<br>LLNEQVNKEMQSSNLYMSMSSWCYTHSLDGAGLFLFDHAAEEYEHA<br>KKLIIFLNENNVPVqLTSISAPEHKFEGLTQIFQKAYEHEQHISES<br>INNIVDHAIKSKDHATFNFLQWYVAEQHEEEVLFKDILDKIELIGN<br>ENHGLYLADQYVKGIAKSRKSGS | 65 |
| PolyA tail | 100 nt | |

Lumazine Synthetase

In some embodiments, a lumazine synthetase domain is used as a scaffold domain. Lumazine synthetase is an enzyme responsible for the penultimate catalytic step in the biosynthesis of riboflavin in a variety of organisms, including archaea, bacteria, fungi, plants, and eubacteria. Lumazine synthetase is composed of homooligomers, which vary in size and subunit number, including pentamers, decamers, and icosahedral sixty-mers, depending on its species of origin. The lumazine synthetase monomer is 150 amino acids long and includes beta-sheets with flanking, tandem alpha-helices. Different quaternary structures have been reported for lumazine synthetase, illustrating its morphological versatility: from homopentamers up to symmetrical assemblies of twelve (12) pentamers forming capsids of 150 Å diameter. Presentation of antigens on the surface of lumazine synthetase results in a high local concentration of antigens displayed in an ordered array. Such repetitive structures enable the cross-linking of B-cell receptors and result in strong immune responses through an avidity effect.

An mRNA provided herein, in some embodiments, encodes an RBD linked to a lumazine synthetase domain, for example, through a glycine-serine (e.g., GGS). Other linkers may be used.

In other embodiments, an mRNA provided herein encodes an S1 domain of an S protein linked to a lumazine synthetase domain, for example, through a glycine-serine (e.g., GGS) linker. As indicated elsewhere herein, other linkers may be used.

Non-limiting examples of SARS-CoV-2 antigens linked to a foldon domain and the mRNA encoding them are provided in Tables 14A and 14B below.

TABLE 14A

| Antigens Linked to a Lumazine Synthetase Domain | | |
|---|---|---|
| Name | SEQ ID NO: | |
| SARS-CoV-2 Soluble S1 Linked to Lumazine Synthetase C-terminus (LS-S1) | 10 | 11 |
| SARS-CoV-2 Soluble S1 Linked to Lumazine Synthetase N-Terminus (S1-LS) | 13 | 14 |
| SARS-CoV-2 RBD Linked to Lumazine Synthetase C Terminus (LS-RBD) | 67 | 68 |
| SARS-CoV-2 RBD Linked to Lumazine Synthetase N Terminus (RBD-LS) | 70 | 71 |

TABLE 14B

| Antigens Linked to a Lumazine Synthetase Domain | | |
|---|---|---|
| SARS-CoV-2 Soluble S1 Linked to Lumazine Synthetase C-terminus (LS-S1) | | |
| SEQ ID NO: 9 consists of from 5' end to 3' end: 5' UTR SEQ ID NO: 2, mRNA ORF SEQ ID NO: 10 and 3' UTR SEQ ID NO: 4. | | 9 |
| Chemistry | 1-methylpseudouridine | |
| Cap | 7mG(5')ppp(5')NlmpNp | |
| 5' UTR | GGGAAAUAAGAGAGAAAAGAAGAGUAAGAAGAAAUAUAAGACCCCG<br>GCGCCGCCACC | 2 |
| ORF of mRNA Construct (excluding the stop codon) | AUGGGCAUCCUGCCCAGCCCUGGCAUGCCCGCUCUGCUGAGCCUGG<br>UGAGCCUGCUGAGCGUGCUGCUGAUGGGCUGCGUGGCUGAGACCGG<br>CAUGCAGAUCUACGAGGGCAAGCUGACCGCAGAGGGCCUGCGGUUC<br>GGCAUCGUGGCCAGCCGCGCCAACCACGCUCUGGUGGACCGGCUUG<br>UGGAGGGCGCUAUCGACGCCAUCGUGAGACACGGCGGCCGGGAAGA<br>GGACAUCACCCUGGUGCGGGUGUGCGGCAGCUGGGAGAUUCCCGUC<br>GCCGCCGGAGAACUGGCCCGGAAGGAGGACAUCGACGCCGUGAUCG<br>CCAUCGGCGUGCUGUGCAGAGGCGCCACGCCCAGCUUCGACUACAU<br>CGCCAGCGAGGUGAGCAAGGGCCUGGCCGACCUGAGCCUGGAGCUG<br>CGGAAGCCCAUCACCUUCGGCGUGAUCACCGCCGACACCCUGGAGC<br>AGGCCAUCGAGGCCGCAGGCACCUGCCACGGCAACAAGGGCUGGGA<br>AGCCGCCCUGUGCGCCAUCGAGAUGGCCAACCUGUUCAAGAGCCUG<br>CGGGGCGGAAGUGGAGGCUCUGGUGGCAGCGGAGGAUCUGGCGGCG<br>GCACCACCCGGACCCAGCUGCCACCAGCCUACACCAACAGCUUCAC<br>CCGGGGCGUCUACUACCCCGACAAGGUGUUCCGGAGCAGCGUCCUG<br>CACAGCACCCAGGACCUGUUCCUGCCCUUCUUCAGCAACGUGACCU<br>GGUUCCACGCCAUCCACGUGAGCGGCACCAACGGCACCAAGCGGUU<br>CGACAACCCCGUGCUGCCCUUCAACGACGGCGUGUACUUCGCCAGC<br>ACCGAGAAGAGCAACAUCAUCCGGGGCUGGAUCUUCGGCACCACCC<br>UGGACAGCAAGACCCAGAGCCUGCUGAUCGUGAAUAACGCCACCAA<br>CGUGGUGAUCAAGGUGUGCGAGUUCCAGUUCUGCAACGACCCCUUC<br>CUGGGCGUGUACUACCACAAGAACAACAAGAGCUGGAUGGAGAGCG<br>AGUUCCGGGUGUACAGCAGCGCCAACAACUGCACCUUCGAGUACGU<br>GAGCCAGCCCUUCCUGAUGGACCUGGAGGGCAAGCAGGGCAACUUC<br>AAGAACCUGCGGGAGUUCGUGUUCAAGAACAUCGACGGCUACUUCA<br>AGAUCUACAGCAAGCACACCCCAAUCAACCUGGUGCGGGAUCUGCC<br>CCAGGGCUUCUCAGCCCUGGAGCCCCUGGUGGACCUGCCCAUCGGC<br>AUCAACAUCACCCGGUUCCAGACCCUGCUGGCCCUGCACCGGAGCU<br>ACCUGACCCCAGGCGACAGCAGCAGCGGGUGGACAGCAGGCGCGGC<br>UGCUUACUACGUGGGCUACCUGCAGCCCCGGACCUUCCUGCUGAAG<br>UACAACGAGAACGGCACCAUCACCGACGCCGUGGACUGCGCCCUGG<br>ACCCUCUGAGCGAGACCAAGUGCACCCUGAAGAGCUUCACCGUGGA<br>GAAGGGCAUCUACCAGACCAGCAACUUCCGGGUGCAGCCCACCGAG<br>AGCAUCGUGCGGUUCCCCAACAUCACCAACCUGUGCCCCUUCGGCG<br>AGGUGUUCAACGCCACCCGGUUCGCCAGCGUGUACGCCUGGAACCG<br>GAAGCGGAUCAGCAACUGCGUGGCCGACUACAGCGUGCUGUACAAC<br>AGCGCCAGCUUCAGCACCUUCAAGUGCUACGGCGUGAGCCCCACCA<br>AGCUGAACGACCUGUGCUUCACCAACGUGUACGCCGACAGCUUCGU<br>GAUCCGUGGCGACGAGGUGCGGCAGAUCGCACCCGGCCAGACAGGC<br>AAGAUCGCCGACUACAACUACAAGCUGCCCGACGACUUCACCGGCU<br>GCGUGAUCGCCUGGAACAGCAACAACCUCGACAGCAAGGUGGGCGG<br>CAACUACAACUACCUGUACCGGCUGUUCCGGAAGAGCAACCUGAAG<br>CCCUUCGAGCGGGACAUCAGCACCGAGAUCUACCAAGCCGGCUCCA<br>CCCCUUGCAACGGCGUGGAGGGCUUCAACUGCUACUUCCCUCUGCA<br>GAGCUACGGCUUCCAGCCCACCAACGGCGUGGGCUACCAGCCCUAC<br>CGGGUGGUGGUGCUGAGCUUCGAGCUGCUGCACGCCCCAGCCACCG<br>UGUGUGGCCCCAAGAAGAGCACCAACCUGGUGAAGAACAAGUGCGU | 10 |

TABLE 14B-continued

| Antigens Linked to a Lumazine Synthetase Domain | | |
|---|---|---|
| | GAACUUCAACUUCAACGGCCUUACCGGCACCGGCGUGCUGACCGAG<br>AGCAACAAGAAAUUCCUGCCCUUUCAGCAGUUCGGCCGGGACAUCG<br>CCGACACCACCGACGCUGUGCGGGAUCCCCAGACCCUGGAGAUCCU<br>GGACAUCACCCCUUGCAGCUUCGGCGGCGUGAGCGUGAUCACCCCA<br>GGCACCAACACCAGCAACCAGGUGGCCGUGCUGUACCAGGACGUGA<br>ACUGCACCGAGGUGCCCGUGGCCAUCCACGCCGACCAGCUGACACC<br>CACCUGGCGGGUCUACAGCACCGGCAGCAACGUGUUCCAGACCCGG<br>GCCGGUUGCCUGAUCGGCGCCGAGCACGUGAACAACAGCUACGAGU<br>GCGACAUCCCCAUCGGCGCCGGCAUCUGUGCCAGCUACCAGACCCA<br>GACCAAUUCA | |
| 3' UTR | UGAUAAUAGGCUGGAGCCUCGGUGGCCUAGCUUCUUGCCCCUUGGG<br>CCUCCCCCCAGCCCCUCCUCCCCUUCCUGCACCCGUACCCCCGUGG<br>UCUUUGAAUAAAGUCUGAGUGGGCGGC | 4 |
| Corresponding amino acid sequence | MGILPSPGMPALLSLVSLLSVLLMGCVAETGMQIYEGKLTAEGLRF<br>GIVASRANHALVDRLVEGAIDAIVRHGGREEDITLVRVCGSWEIPV<br>AAGELARKEDIDAVIAIGVLCRGATPSFDYIASEVSKGLADLSLEL<br>RKPITFGVITADTLEQAIEAAGTCHGNKGWEAALCAIEMANLFKSL<br>RGGSGGSGGSGGSGGGTTRTQLPPAYTNSFTRGVYYPDKVFRSSVL<br>HSTQDLFLPFFSNVTWFHAIHVSGTNGTKRFDNPVLPFNDGVYFAS<br>TEKSNIIRGWIFGTTLDSKTQSLLIVNNATNVVIKVCEFQFCNDPF<br>LGVYYHKNNKSWMESEFRVYSSANNCTFEYVSQPFLMDLEGKQGNF<br>KNLREFVFKNIDGYFKIYSKHTPINLVRDLPQGFSALEPLVDLPIG<br>INITRFQTLLALHRSYLTPGDSSSGWTAGAAAYYVGYLQPRTFLLK<br>YNENGTITDAVDCALDPLSETKCTLKSFTVEKGIYQTSNFRVQPTE<br>SIVRFPNITNLCPFGEVFNATRFASVYAWNRKRISNCVADYSVLYN<br>SASFSTFKCYGVSPTKLNDLCFTNVYADSFVIRGDEVRQIAPGQTG<br>KIADYNYKLPDDFTGCVIAWNSNNLDSKVGGNYNYLYRLFRKSNLK<br>PFERDISTEIYQAGSTPCNGVEGFNCYFPLQSYGFQPTNGVGYQPY<br>RVVVLSFELLHAPATVCGPKKSTNLVKNKCVNFNFNGLTGTGVLTE<br>SNKKFLPFQQFGRDIADTTDAVRDPQTLEILDITPCSFGGVSVITP<br>GTNTSNQVAVLYQDVNCTEVPVAIHADQLTPTWRVYSTGSNVFQTR<br>AGCLIGAEHVNNSYECDIPIGAGICASYQTQTNS | 11 |
| PolyA tail | 100 nt | |
| SARS-CoV-2 Soluble S1 Linked to Lumazine Synthetase N-Terminus (S1-LS) | | |
| SEQ ID NO: 12 consists of from 5' end to 3' end: 5' UTR SEQ ID NO: 2, mRNA ORF SEQ ID NO: 13 and 3' UTR SEQ ID NO: 4. | | 12 |
| Chemistry | 1-methylpseudouridine | |
| Cap | 7mG(5')ppp(5')NlmpNp | |
| 5' UTR | GGGAAAUAAGAGAGAAAAGAAGAGUAAGAAGAAAUAUAAGACCCCG<br>GCGCCGCCACC | 2 |
| ORF of mRNA Construct (excluding the stop codon) | AUGUUCGUGUUCCUGGUGCUGCUGCCCCUGGUGAGCAGCCAGUGCG<br>UGAACCUGACCACCCGGACCCAGCUGCCACCAGCCUACACCAACAG<br>CUUCACCCGGGGCGUCUACUACCCCGACAAGGUGUUCCGGAGCAGC<br>GUCCUGCACAGCACCCAGGACCUGUUCCUGCCCUUCUUCAGCAACG<br>UGACCUGGUUCCACGCCAUCCACGUGAGCGGCACCAACGGCACCAA<br>GCGGUUCGACAACCCCGUGCUGCCCUUCAACGACGGCGUGUACUUC<br>GCCAGCACCGAGAAGAGCAACAUCAUCCGGGGCUGGAUCUUCGGCA<br>CCACCCUGGACAGCAAGACCCAGAGCCUGCUGAUCGUGAAUAACGC<br>CACCAACGUGGUGAUCAAGGUGUGCGAGUUCCAGUUCUGCAACGAC<br>CCCUUCCUGGGCGUGUACUACCACAAGAACAACAAGAGCUGGAUGG<br>AGAGCGAGUUCCGGGUGUACAGCAGCGCCAACAACUGCACCUUCGA<br>GUACGUGAGCCAGCCCUUCCUGAUGGACCUGGAGGGCAAGCAGGGC<br>AACUUCAAGAACCUGCGGGAGUUCGUGUUCAAGAACAUCGACGGCU<br>ACUUCAAGAUCUACAGCAAGCACACCCCAAUCAACCUGGUGCGGGA<br>UCUGCCCCAGGGCUUCUCAGCCCUGGAGCCCCUGGUGGACCUGCCC<br>AUCGGCAUCAACAUCACCCGGUUCCAGACCCUGCUGGCCCUGCACC<br>GGAGCUACCUGACCCCAGGCGACAGCAGCAGCGGGUGGACAGCAGG<br>CGCGGCUGCUUACUACGUGGGCUACCUGCAGCCCCGGACCUUCCUG<br>CUGAAGUACAACGAGAACGGCACCAUCACCGACGCCGUGGACUGCG<br>CCCUGGACCCUCUGAGCGAGACCAAGUGCACCCUGAAGAGCUUCAC<br>CGUGGAGAAGGGCAUCUACCAGACCAGCAACUUCCGGGUGCAGCCC<br>ACCGAGAGCAUCGUGCGGUUCCCCAACAUCACCAACCUGUGCCCCU<br>UCGGCGAGGUGUUCAACGCCACCCGGUUCGCCAGCGUGUACGCCUG<br>GAACCGGAAGCGGAUCAGCAACUGCGUGGCCGACUACAGCGUGCUG<br>UACAACAGCGCCAGCUUCAGCACCUUCAAGUGCUACGGCGUGAGCC<br>CCACCAAGCUGAACGACCUGUGCUUCACCAACGUGUACGCCGACAG<br>CUUCGUGAUCCGUGGCGACGAGGUGCGGCAGAUCGCACCCGGCCAG<br>ACAGGCAAGAUCGCCGACUACAACUACAAGCUGCCCGACGACUUCA<br>CCGGCUGCGUGAUCGCCUGGAACAGCAACAACCUCGACAGCAAGGU | 13 |

TABLE 14B-continued

| Antigens Linked to a Lumazine Synthetase Domain | | |
|---|---|---|
| | GGGCGGCAACUACAACUACCUGUACCGGCUGUUCCGGAAGAGCAAC<br>CUGAAGCCCUUCGAGCGGGACAUCAGCACCGAGAUCUACCAAGCCG<br>GCUCCACCCCUUGCAACGGCGUGGAGGGCUUCAACUGCUACUUCCC<br>UCUGCAGAGCUACGGCUUCCAGCCCACCAACGGCGUGGGCUACCAG<br>CCCUACCGGGUGGUGGUGCUGAGCUUCGAGCUGCUGCACGCCCCAG<br>CCACCGUGUGUGGCCCCAAGAAGAGCACCAACCUGGUGAAGAACAA<br>GUGCGUGAACUUCAACUUCAACGGCCUUACCGGCACCGGCGUGCUG<br>ACCGAGAGCAACAAGAAAUUCCUGCCCUUUCAGCAGUUCGGCCGGG<br>ACAUCGCCGACACCACCGACGCUGUGCGGGAUCCCCAGACCCUGGA<br>GAUCCUGGACAUCACCCCUUGCAGCUUCGGCGGCGUGAGCGUGAUC<br>ACCCCAGGCACCAACACCAGCAACCAGGUGGCCGUGCUGUACCAGG<br>ACGUGAACUGCACCGAGGUGCCCGUGGCCAUCCACGCCGACCAGCU<br>GACACCCACCUGGCGGGUCUACAGCACCGGCAGCAACGUGUUCCAG<br>ACCCGGGCCGGUUGCCUGAUCGGCGCCGAGCACGUGAACAACAGCU<br>ACGAGUGCGACAUCCCCAUCGGCGCCGGCAUCUGUGCCAGCUACCA<br>GACCCAGACCAAUUCAGGAGGAGGCUCCGGAGGCGGUAGCGCUGAG<br>ACCGGCAUGCAGAUCUACGAGGGCAAGCUGACCGCAGAGGGCCUGC<br>GGUUCGGCAUCGUGGCCAGCCGCGCCAACCACGCUCUGGUGGACCG<br>GCUUGUGGAGGGCGCUAUCGACGCCAUCGUGAGACACGGCGGCCGG<br>GAAGAGGACAUCACCCUGGUGCGGGUGUGCGGCAGCUGGGAGAUUC<br>CCGUCGCCGCCGGAGAACUGGCCCGGAAGGAGGACAUCGACGCCGU<br>GAUCGCCAUCGGCGUGCUGUGCAGAGGCGCCACGCCCAGCUUCGAC<br>UACAUCGCCAGCGAGGUGAGCAAGGGCCUGGCCGACCUGAGCCUGG<br>AGCUGCGGAAGCCCAUCACCUUCGGCGUGAUCACCGCCGACACCCU<br>GGAGCAGGCCAUCGAGGCCGCAGGCACCUGCCACGGCAACAAGGGC<br>UGGGAAGCCGCCCUGUGCGCCAUCGAGAUGGCCAACCUGUUCAAGA<br>GCCUGCGG | |
| 3' UTR | UGAUAAUAGGCUGGAGCCUCGGUGGCCUAGCUUCUUGCCCCUUGGG<br>CCUCCCCCCAGCCCCUCCUCCCCUUCCUGCACCCGUACCCCCGUGG<br>UCUUUGAAUAAAGUCUGAGUGGGCGGC | 4 |
| Corresponding amino acid sequence | MFVFLVLLPLVSSQCVNLTTRTQLPPAYTNSFTRGVYYPDKVFRSS<br>VLHSTQDLFLPFFSNVTWFHAIHVSGTNGTKRFDNPVLPFNDGVYF<br>ASTEKSNIIRGWIFGTTLDSKTQSLLIVNNATNVVIKVCEFQFCND<br>PFLGVYYHKNNKSWMESEFRVYSSANNCTFEYVSQPFLMDLEGKQG<br>NFKNLREFVFKNIDGYFKIYSKHTPINLVRDLPQGFSALEPLVDLP<br>IGINITRFQTLLALHRSYLTPGDSSSGWTAGAAAYYVGYLQPRTFL<br>LKYNENGTITDAVDCALDPLSETKCTLKSFTVEKGIYQTSNFRVQP<br>TESIVRFPNITNLCPFGEVENATRFASVYAWNRKRISNCVADYSVL<br>YNSASFSTFKCYGVSPTKLNDLCFTNVYADSFVIRGDEVRQIAPGQ<br>TGKIADYNYKLPDDFTGCVIAWNSNNLDSKVGGNYNYLYRLFRKSN<br>LKPFERDISTEIYQAGSTPCNGVEGFNCYFPLQSYGFQPTNGVGYQ<br>PYRVVVLSFELLHAPATVCGPKKSTNLVKNKCVNFNFNGLTGTGVL<br>TESNKKFLPFQQFGRDIADTTDAVRDPQTLEILDITPCSFGGVSVI<br>TPGTNTSNQVAVLYQDVNCTEVPVAIHADQLTPTWRVYSTGSNVFQ<br>TRAGCLIGAEHVNNSYECDIPIGAGICASYQTQTNSgggsgggsAE<br>TGMQIYEGKLTAEGLRFGIVASRANHALVDRLVEGAIDAIVRHGGR<br>EEDITLVRVCGSWEIPVAAGELARKEDIDAVIAIGVLCRGATPSFD<br>YIASEVSKGLADLSLELRKPITFGVITADTLEQAIEAAGTCHGNKG<br>WEAALCAIEMANLFKSLR | 14 |
| PolyA tail | 100 nt | |
| SARS-CoV-2 RBD Linked to Lumazine Synthetase C Terminus (LS-RBD) | | |
| SEQ ID NO: 66 consists of from 5' end to 3' end: 5' UTR SEQ ID NO: 2, mRNA ORF SEQ ID NO: 67 and 3' UTR SEQ ID NO: 4. | | 66 |
| Chemistry | 1-methylpseudouridine | |
| Cap | 7mG(5')ppp(5')NlmpNp | |
| 5' UTR | GGGAAAUAAGAGAGAAAAGAAGAGUAAGAAGAAAUAUAAGACCCCG<br>GCGCCGCCACC | 2 |
| ORF of mRNA Construct (excluding the stop codon) | AUGGGCAUCCUGCCCAGCCCUGGCAUGCCCGCUCUGCUGAGCCUGG<br>UGAGCCUGCUGAGCGUGCUGCUGAUGGGCUGCGUGGCUGAGACCGG<br>CAUGCAGAUCUACGAGGGCAAGCUGACCGCAGAGGGCCUGCGGUUC<br>GGCAUCGUGGCCAGCCGCGCCAACCACGCUCUGGUGGACCGGCUUG<br>UGGAGGGCGCUAUCGACGCCAUCGUGAGACACGGCGGCCGGGAAGA<br>GGACAUCACCCUGGUGCGGGUGUGCGGCAGCUGGGAGAUUCCCGUC<br>GCCGCCGGAGAACUGGCCCGGAAGGAGGACAUCGACGCCGUGAUCG<br>CCAUCGGCGUGCUGUGCAGAGGCGCCACGCCCAGCUUCGACUACAU<br>CGCCAGCGAGGUGAGCAAGGGCCUGGCCGACCUGAGCCUGGAGCUG<br>CGGAAGCCCAUCACCUUCGGCGUGAUCACCGCCGACACCCUGGAGC<br>AGGCCAUCGAGGCCGCAGGCACCUGCCACGGCAACAAGGGCUGGGA<br>AGCCGCCCUGUGCGCCAUCGAGAUGGCCAACCUGUUCAAGAGCCUG | 67 |

TABLE 14B-continued

| Antigens Linked to a Lumazine Synthetase Domain | | |
|---|---|---|
| | CGGGGCGGAAGUGGAGGCUCUGGUGGCAGCGGAGGAUCUGGCGGCG GCCAGCCCAACAUCACCAACCUGUGCCCCUUCGGCGAGGUGUUCAA CGCCACCCGGUUCGCCAGCGUGUACGCCUGGAACCGGAAGCGGAUC AGCAACUGCGUGGCCGACUACAGCGUGCUGUACAACAGCGCCAGCU UCAGCACCUUCAAGUGCUACGGCGUGAGCCCCACCAAGCUGAACGA CCUGUGCUUCACCAACGUGUACGCCGACAGCUUCGUGAUCCGUGGC GACGAGGUGCGGCAGAUCGCACCCGGCCAGACAGGCAAGAUCGCCG ACUACAACUACAAGCUGCCCGACGACUUCACCGGCUGCGUGAUCGC CUGGAACAGCAACAACCUCGACAGCAAGGUGGGCGGCAACUACAAC UACCUGUACCGGCUGUUCCGGAAGAGCAACCUGAAGCCCUUCGAGC GGGACAUCAGCACCGAGAUCUACCAAGCCGGCUCCACCCCUUGCAA CGGCGUGGAGGGCUUCAACUGCUACUUCCCUCUGCAGAGCUACGGC UUCCAGCCCACCAACGGCGUGGGCUACCAGCCCUACCGGGUGGUGG UGCUGAGCUUCGAGCUGCUGCACGCCCCAGCCACCGUGUGUGGCCC CAAG | |
| 3' UTR | UGAUAAUAGGCUGGAGCCUCGGUGGCCUAGCUUCUUGCCCCUUGGG CCUCCCCCCAGCCCCUCCUCCCCUUCCUGCACCCGUACCCCCGUGG UCUUUGAAUAAAGUCUGAGUGGGCGGC | 4 |
| Corresponding amino acid sequence | MGILPSPGMPALLSLVSLLSVLLMGCVAETGMQIYEGKLTAEGLRF GIVASRANHALVDRLVEGAIDAIVRHGGREEDITLVRVCGSWEIPV AAGELARKEDIDAVIAIGVLCRGATPSFDYIASEVSKGLADLSLEL RKPITFGVITADTLEQAIEAAGTCHGNKGWEAALCAIEMANLFKSL RGGSGGSGGSGGSGGGQPNITNLCPFGEVFNATRFASVYAWNRKRI SNCVADYSVLYNSASFSTFKCYGVSPTKLNDLCFTNVYADSFVIRG DEVRQIAPGQTGKIADYNYKLPDDFTGCVIAWNSNNLDSKVGGNYN YLYRLFRKSNLKPFERDISTEIYQAGSTPCNGVEGFNCYFPLQSYG FQPTNGVGYQPYRVVVLSFELLHAPATVCGPK | 68 |
| PolyA tail | 100 nt | |
| SARS-CoV-2 RBD Linked to Lumazine Synthetase N Terminus (RBD-LS) | | |
| SEQ ID NO: 69 consists of from 5' end to 3' end: 5' UTR SEQ ID NO: 2, mRNA ORF SEQ ID NO: 70 and 3' UTR SEQ ID NO: 4. | | 69 |
| Chemistry | 1-methylpseudouridine | |
| Cap | 7mG(5')ppp(5')NlmpNp | |
| 5' UTR | GGGAAAUAAGAGAGAAAAGAAGAGUAAGAAGAAAUAUAAGACCCCG GCGCCGCCACC | 2 |
| ORF of mRNA Construct (excluding the stop codon) | AUGUACAGCAUGCAGCUGGCUAGCUGCGUGACCCUGACCCUGGUGC UGCUGGUGAACAGCCAGCCCAACAUCACCAACCUGUGCCCCUUCGG CGAGGUGUUCAACGCCACCCGGUUCGCCAGCGUGUACGCCUGGAAC CGGAAGCGGAUCAGCAACUGCGUGGCCGACUACAGCGUGCUGUACA ACAGCGCCAGCUUCAGCACCUUCAAGUGCUACGGCGUGAGCCCCAC CAAGCUGAACGACCUGUGCUUCACCAACGUGUACGCCGACAGCUUC GUGAUCCGUGGCGACGAGGUGCGGCAGAUCGCACCCGGCCAGACAG GCAAGAUCGCCGACUACAACUACAAGCUGCCCGACGACUUCACCGG CUGCGUGAUCGCCUGGAACAGCAACAACCUCGACAGCAAGGUGGGC GGCAACUACAACUACCUGUACCGGCUGUUCCGGAAGAGCAACCUGA AGCCCUUCGAGCGGGACAUCAGCACCGAGAUCUACCAAGCCGGCUC CACCCCUUGCAACGGCGUGGAGGGCUUCAACUGCUACUUCCCUCUG CAGAGCUACGGCUUCCAGCCCACCAACGGCGUGGGCUACCAGCCCU ACCGGGUGGUGGUGCUGAGCUUCGAGCUGCUGCACGCCCCAGCCAC CGUGUGUGGCCCCAAGGGAGGAGGCUCCGGAGGCGGUAGCGCUGAG ACCGGCAUGCAGAUCUACGAGGGCAAGCUGACCGCAGAGGGCCUGC GGUUCGGCAUCGUGGCCAGCCGCGCCAACCACGCUCUGGUGGACCG GCUUGUGGAGGGCGCUAUCGACGCCAUCGUGAGACACGGCGGCCGG GAAGAGGACAUCACCCUGGUGCGGGUGUGCGGCAGCUGGGAGAUUC CCGUCGCCGCCGGAGAACUGGCCCGGAAGGAGGACAUCGACGCCGU GAUCGCCAUCGGCGUGCUGUGCAGAGGCGCCACGCCCAGCUUCGAC UACAUCGCCAGCGAGGUGAGCAAGGGCCUGGCCGACCUGAGCCUGG AGCUGCGGAAGCCCAUCACCUUCGGCGUGAUCACCGCCGACACCCU GGAGCAGGCCAUCGAGGCCGCAGGCACCUGCCACGGCAACAAGGGC UGGGAAGCCGCCCUGUGCGCCAUCGAGAUGGCCAACCUGUUCAAGA GCCUGCGG | 70 |
| 3' UTR | UGAUAAUAGGCUGGAGCCUCGGUGGCCUAGCUUCUUGCCCCUUGGG CCUCCCCCCAGCCCCUCCUCCCCUUCCUGCACCCGUACCCCCGUGG UCUUUGAAUAAAGUCUGAGUGGGCGGC | 4 |

TABLE 14B-continued

| Antigens Linked to a Lumazine Synthetase Domain | | |
|---|---|---|
| Corresponding amino acid sequence | MYSMQLASCVTLTLVLLVNSQPNITNLCPFGEVENATRFASVYAWN RKRISNCVADYSVLYNSASFSTFKCYGVSPTKLNDLCFTNVYADSF VIRGDEVRQIAPGQTGKIADYNYKLPDDFTGCVIAWNSNNLDSKVG GNYNYLYRLFRKSNLKPFERDISTEIYQAGSTPCNGVEGFNCYFPL QSYGFQPTNGVGYQPYRVVVLSFELLHAPATVCGPKgggsgggsAE TGMQIYEGKLTAEGLRFGIVASRANHALVDRLVEGAIDAIVRHGGR EEDITLVRVCGSWEIPVAAGELARKEDIDAVIAIGVLCRGATPSFD YIASEVSKGLADLSLELRKPITFGVITADTLEQAIEAAGTCHGNKG WEAALCAIEMANLFKSLR | 71 |
| PolyA tail | 100 nt | |

Foldon

In some embodiments, a foldon domain is used as a scaffold domain. The C-terminal domain of T4 fibritin (foldon) is obligatory for the formation of the fibritin trimer structure and can be used as an artificial trimerization domain (see, e.g., Meier S. et al. Journal of Molecular Biology 2004 Dec. 3; 344(4): 1051-1069; Tao Y et al. Structure 1997 Jun. 15; 5(6):789-98). When fused to the S protein ectodomain, a foldon domain promotes correct trimerization of the S protein, thus avoiding misfolding of the protein. Such a process resulting in production of the prefusion conformation of the S protein results in increased expression, conformational homogeneity, and elicitation of potent neutralizing antibody responses.

Without being bound by theory, it is thought that this configuration would result in the foldon being largely immunogenically silent on the intracellular region of the protein. Non-limiting examples of SARS-CoV-2 antigens linked to a foldon domain and the mRNA encoding them are provided in Tables 15A and 15B below.

TABLE 15A

| Antigens Linked to a Foldon Domain | | |
|---|---|---|
| | SEQ ID NO: | |
| Name | mRNA ORF | Protein |
| SARS-CoV-2 NTD Linked to Foldon Domain | 43 | 44 |
| SARS-CoV-2 NTD Linked to Transmembrane Domain and Foldon Domain | 49 | 50 |
| SARS-CoV-2 RBD Linked to Foldon Domain | 73 | 74 |
| SARS-CoV-2 RBD Linked to Foldon Domain and Transmembrane Domain (RBD-FD-TM) | 79 | 80 |
| SARS-CoV-2 RBD Linked to Transmembrane Domain and Foldon Domain (RBD-TM-FD) | 82 | 83 |
| SARS-CoV-2 NTD-RBD Linked to Foldon Domain and Transmembrane Domain (NTD-RBD-FD-TM) | 100 | 101 |
| SARS-CoV-2 NTD-RBD Linked to Transmembrane Domain and Foldon Domain (NTD-RBD-TM-FD) | 103 | 104 |
| SARS-CoV-2 NTD-RBD Linked to Foldon Domain | 112 | 113 |

TABLE 15B

| Antigens Linked to a Foldon Domain | | |
|---|---|---|
| SARS-CoV-2 NTD Linked to Foldon Domain | | |
| SEQ ID NO: 42 consists of from 5' end to 3' end: 5' UTR SEQ ID NO: 2, mRNA ORF SEQ ID NO: 43 3' UTR SEQ ID NO: 4. | | 42 |
| Chemistry | 1-methylpseudouridine | |
| Cap | 7mG(5')ppp(5')NlmpNp | |
| 5' UTR | GGGAAAUAAGAGAGAAAAGAAGAGUAAGAAGAAAUAUAAGACCCCG GCGCCGCCACC | 2 |
| ORF of mRNA Construct (excluding the stop codon) | AUGUUCGUGUUCCUGGUGCUGCUGCCCCUGGUGAGCAGCCAGUGCG UGAACCUGACCACCCGGACCCAGCUGCCACCAGCCUACACCAACAG CUUCACCCGGGGCGUCUACUACCCCGACAAGGUGUUCCGGAGCAGC GUCCUGCACAGCACCCAGGACCUGUUCCUGCCCUUCUUCAGCAACG UGACCUGGUUCCACGCCAUCCACGUGAGCGGCACCAACGGCACCAA GCGGUUCGACAACCCCGUGCUGCCCUUCAACGACGGCGUGUACUUC GCCAGCACCGAGAAGAGCAACAUCAUCCGGGGCUGGAUCUUCGGCA CCACCCUGGACAGCAAGACCCAGAGCCUGCUGAUCGUGAAUAACGC CACCAACGUGGUGAUCAAGGUGUGCGAGUUCCAGUUCUGCAACGAC CCCUUCCUGGGCGUGUACUACCACAAGAACAACAAGAGCUGGAUGG AGAGCGAGUUCCGGGUGUACAGCAGCGCCAACAACUGCACCUUCGA GUACGUGAGCCAGCCCUUCCUGAUGGACCUGGAGGGCAAGCAGGGC AACUUCAAGAACCUGCGGGAGUUCGUGUUCAAGAACAUCGACGGCU ACUUCAAGAUCUACAGCAAGCACACCCCAAUCAACCUGGUGCGGGA UCUGCCCCAGGGCUUCUCAGCCCUGGAGCCCCUGGUGGACCUGCCC AUCGGCAUCAACAUCACCCGGUUCCAGACCCUGCUGGCCCUGCACC GGAGCUACCUGACCCCAGGCGACAGCAGCAGCGGGUGGACAGCAGG CGCGGCUGCUUACUACGUGGGCUACCUGCAGCCCCGGACCUUCCUG CUGAAGUACAACGAGAACGGCACCAUCACCGACGCCGUGGACUCUG GCGGAGGCGGCAGCGCCAUCGGCGGCUACAUCCCCGAGGCCCCUAG | 43 |

TABLE 15B-continued

| Antigens Linked to a Foldon Domain | | |
|---|---|---|
| | AGACGGCCAGGCCUACGUGCGGAAGGACGGCGAGUGGGUGCUGCUG AGCACCUUCCUGGGC | |
| 3' UTR | UGAUAAUAGGCUGGAGCCUCGGUGGCCUAGCUUCUUGCCCCUUGGG CCUCCCCCCAGCCCCUCCUCCCCUUCCUGCACCCGUACCCCCGUGG UCUUUGAAUAAAGUCUGAGUGGGCGGC | 4 |
| Corresponding amino acid sequence | MFVFLVLLPLVSSQCVNLTTRTQLPPAYTNSFTRGVYYPDKVFRSS VLHSTQDLFLPFFSNVTWFHAIHVSGTNGTKRFDNPVLPFNDGVYF ASTEKSNIIRGWIFGTTLDSKTQSLLIVNNATNVVIKVCEFQFCND PFLGVYYHKNNKSWMESEFRVYSSANNCTFEYVSQPFLMDLEGKQG NFKNLREFVFKNIDGYFKIYSKHTPINLVRDLPQGFSALEPLVDLP IGINITRFQTLLALHRSYLTPGDSSSGWTAGAAAYYVGYLQPRTFL LKYNENGTITDAVDsggggSAIGGYIPEAPRDGQAYVRKDGEWVLL STFLG | 44 |
| PolyA tail | 100 nt | |
| SARS-CoV-2 NTD Linked to Transmembrane Domain and Foldon Domain | | |
| SEQ ID NO: 48 consists of from 5' end to 3' end: 5' UTR SEQ ID NO: 2, mRNA ORF SEQ ID NO: 49 and 3' UTR SEQ ID NO: 4. | | 48 |
| Chemistry | 1-methylpseudouridine | |
| Cap | 7mG(5')ppp(5')NlmpNp | |
| 5' UTR | GGGAAAUAAGAGAGAAAAGAAGAGUAAGAAGAAAUAUAAGACCCCG GCGCCGCCACC | 2 |
| ORF of mRNA Construct (excluding the stop codon) | AUGUUCGUGUUCCUGGUGCUGCUGCCCCUGGUGAGCAGCCAGUGCG UGAACCUGACCACCCGGACCCAGCUGCCACCAGCCUACACCAACAG CUUCACCCGGGGCGUCUACUACCCCGACAAGGUGUUCCGGAGCAGC GUCCUGCACAGCACCCAGGACCUGUUCCUGCCCUUCUUCAGCAACG UGACCUGGUUCCACGCCAUCCACGUGAGCGGCACCAACGGCACCAA GCGGUUCGACAACCCCGUGCUGCCCUUCAACGACGGCGUGUACUUC GCCAGCACCGAGAAGAGCAACAUCAUCCGGGGCUGGAUCUUCGGCA CCACCCUGGACAGCAAGACCCAGAGCCUGCUGAUCGUGAAUAACGC CACCAACGUGGUGAUCAAGGUGUGCGAGUUCCAGUUCUGCAACGAC CCCUUCCUGGGCGUGUACUACCACAAGAACAACAAGAGCUGGAUGG AGAGCGAGUUCCGGGUGUACAGCAGCGCCAACAACUGCACCUUCGA GUACGUGAGCCAGCCCUUCCUGAUGGACCUGGAGGGCAAGCAGGGC AACUUCAAGAACCUGCGGGAGUUCGUGUUCAAGAACAUCGACGGCU ACUUCAAGAUCUACAGCAAGCACACCCCAAUCAACCUGGUGCGGGA UCUGCCCCAGGGCUUCUCAGCCCUGGAGCCCCUGGUGGACCUGCCC AUCGGCAUCAACAUCACCCGGUUCCAGACCCUGCUGGCCCUGCACC GGAGCUACCUGACCCCAGGCGACAGCAGCAGCGGGUGGACAGCAGG CGCGGCUGCUUACUACGUGGGCUACCUGCAGCCCCGGACCUUCCUG CUGAAGUACAACGAGAACGGCACCAUCACCGACGCCGUGGACUCUG GCGGAGGCAGCAUCCUGGCCAUCUACAGCACCGUGGCCAGCAGCCU GGUGCUGCUGGUGAGCCUGGGCGCCAUCAGCUUCGGCGGAGGCAGC GCCAUCGGCGGCUACAUCCCCGAGGCCCCUAGAGACGGCCAGGCCU ACGUGCGGAAGGACGGCGAGUGGGUGCUGCUGAGCACCUUCCUGGG CAAG | 49 |
| 3' UTR | UGAUAAUAGGCUGGAGCCUCGGUGGCCUAGCUUCUUGCCCCUUGGG CCUCCCCCCAGCCCCUCCUCCCCUUCCUGCACCCGUACCCCCGUGG UCUUUGAAUAAAGUCUGAGUGGGCGGC | 4 |
| Corresponding amino acid sequence | MFVFLVLLPLVSSQCVNLTTRTQLPPAYTNSFTRGVYYPDKVFRSS VLHSTQDLFLPFFSNVTWFHAIHVSGTNGTKRFDNPVLPFNDGVYF ASTEKSNIIRGWIFGTTLDSKTQSLLIVNNATNVVIKVCEFQFCND PFLGVYYHKNNKSWMESEFRVYSSANNCTFEYVSQPFLMDLEGKQG NFKNLREFVFKNIDGYFKIYSKHTPINLVRDLPQGFSALEPLVDLP IGINITRFQTLLALHRSYLTPGDSSSGWTAGAAAYYVGYLQPRTFL LKYNENGTITDAVDsgggsilaiystvasslvllvslgaisfgggS AIGGYIPEAPRDGQAYVRKDGEWVLLSTFLGk | 50 |
| PolyA tail | 100 nt | |
| SARS-CoV-2 RBD Linked to Foldon Domain | | |
| SEQ ID NO: 72 consists of from 5' end to 3' end: 5' UTR SEQ ID NO: 2, mRNA ORF SEQ ID NO: 73 and 3' UTR SEQ ID NO: 4. | | 72 |
| Chemistry | 1-methylpseudouridine | |
| Cap | 7mG(5')ppp(5')NlmpNp | |

TABLE 15B-continued

| Antigens Linked to a Foldon Domain | | |
|---|---|---|
| 5' UTR | GGGAAAUAAGAGAGAAAAGAAGAGUAAGAAGAAAUAUAAGACCCCG GCGCCGCCACC | 2 |
| ORF of mRNA Construct (excluding the stop codon) | AUGUACAGCAUGCAGCUGGCUAGCUGCGUGACCCUGACCCUGGUGC UGCUGGUGAACAGCCAGCCCAACAUCACCAACCUGUGCCCCUUCGG CGAGGUGUUCAACGCCACCCGGUUCGCCAGCGUGUACGCCUGGAAC CGGAAGCGGAUCAGCAACUGCGUGGCCGACUACAGCGUGCUGUACA ACAGCGCCAGCUUCAGCACCUUCAAGUGCUACGGCGUGAGCCCCAC CAAGCUGAACGACCUGUGCUUCACCAACGUGUACGCCGACAGCUUC GUGAUCCGUGGCGACGAGGUGCGGCAGAUCGCACCCGGCCAGACAG GCAAGAUCGCCGACUACAACUACAAGCUGCCCGACGACUUCACCGG CUGCGUGAUCGCCUGGAACAGCAACAACCUCGACAGCAAGGUGGGC GGCAACUACAACUACCUGUACCGGCUGUUCCGGAAGAGCAACCUGA AGCCCUUCGAGCGGGACAUCAGCACCGAGAUCUACCAAGCCGGCUC CACCCCUUGCAACGGCGUGGAGGGCUUCAACUGCUACUUCCCUCUG CAGAGCUACGGCUUCCAGCCCACCAACGGCGUGGGCUACCAGCCCU ACCGGGUGGUGGUGCUGAGCUUCGAGCUGCUGCACGCCCCAGCCAC CGUGUGUGGCCCCAAGUCUGGCGGAGGCGGCAGCGCCAUCGGCGGC UACAUCCCCGAGGCCCCUAGAGACGGCCAGGCCUACGUGCGGAAGG ACGGCGAGUGGGUGCUGCUGAGCACCUUCCUGGGC | 73 |
| 3' UTR | UGAUAAUAGGCUGGAGCCUCGGUGGCCUAGCUUCUUGCCCCUUGGG CCUCCCCCCAGCCCCUCCUCCCCUUCCUGCACCCGUACCCCCGUGG UCUUUGAAUAAAGUCUGAGUGGGCGGC | 4 |
| Corresponding amino acid sequence | mysmqlascvtltlvllvnsQPNITNLCPFGEVFNATRFASVYAWN RKRISNCVADYSVLYNSASFSTFKCYGVSPTKLNDLCFTNVYADSF VIRGDEVRQIAPGQTGKIADYNYKLPDDFTGCVIAWNSNNLDSKVG GNYNYLYRLFRKSNLKPFERDISTEIYQAGSTPCNGVEGFNCYFPL QSYGFQPTNGVGYQPYRVVVLSFELLHAPATVCGPKsggggSAIGG YIPEAPRDGQAYVRKDGEWVLLSTFLG | 74 |
| PolyA tail | 100 nt | |
| SARS-CoV-2 RBD Linked to Foldon Domain and Transmembrane Domain (RBD-FD-TM) | | |
| SEQ ID NO: 78 consists of from 5' end to 3' end: 5' UTR SEQ ID NO: 2, mRNA ORF SEQ ID NO: 79 and 3' UTR SEQ ID NO: 4. | | 78 |
| Chemistry | 1-methylpseudouridine | |
| Cap | 7mG(5')ppp(5')NlmpNp | |
| 5' UTR | GGGAAAUAAGAGAGAAAAGAAGAGUAAGAAGAAAUAUAAGACCCCG GCGCCGCCACC | 2 |
| ORF of mRNA Construct (excluding the stop codon) | AUGUACAGCAUGCAGCUGGCUAGCUGCGUGACCCUGACCCUGGUGC UGCUGGUGAACAGCCAGCCCAACAUCACCAACCUGUGCCCCUUCGG CGAGGUGUUCAACGCCACCCGGUUCGCCAGCGUGUACGCCUGGAAC CGGAAGCGGAUCAGCAACUGCGUGGCCGACUACAGCGUGCUGUACA ACAGCGCCAGCUUCAGCACCUUCAAGUGCUACGGCGUGAGCCCCAC CAAGCUGAACGACCUGUGCUUCACCAACGUGUACGCCGACAGCUUC GUGAUCCGUGGCGACGAGGUGCGGCAGAUCGCACCCGGCCAGACAG GCAAGAUCGCCGACUACAACUACAAGCUGCCCGACGACUUCACCGG CUGCGUGAUCGCCUGGAACAGCAACAACCUCGACAGCAAGGUGGGC GGCAACUACAACUACCUGUACCGGCUGUUCCGGAAGAGCAACCUGA AGCCCUUCGAGCGGGACAUCAGCACCGAGAUCUACCAAGCCGGCUC CACCCCUUGCAACGGCGUGGAGGGCUUCAACUGCUACUUCCCUCUG CAGAGCUACGGCUUCCAGCCCACCAACGGCGUGGGCUACCAGCCCU ACCGGGUGGUGGUGCUGAGCUUCGAGCUGCUGCACGCCCCAGCCAC CGUGUGUGGCCCCAAGUCUGGCGGAGGCGGCAGCGCCAUCGGCGGC UACAUCCCCGAGGCCCCUAGAGACGGCCAGGCCUACGUGCGGAAGG ACGGCGAGUGGGUGCUGCUGAGCACCUUCCUGGGCGGAGGCAGCAU CCUGGCCAUCUACAGCACCGUGGCCAGCAGCCUGGUGCUGCUGGUG AGCCUGGGCGCCAUCAGCUUC | 79 |
| 3' UTR | UGAUAAUAGGCUGGAGCCUCGGUGGCCUAGCUUCUUGCCCCUUGGG CCUCCCCCCAGCCCCUCCUCCCCUUCCUGCACCCGUACCCCCGUGG UCUUUGAAUAAAGUCUGAGUGGGCGGC | 4 |

TABLE 15B-continued

| Antigens Linked to a Foldon Domain | | |
|---|---|---|
| Corresponding amino acid sequence | mysmqlascvtltlvllvnsQPNITNLCPFGEVFNATRFASVYAWN RKRISNCVADYSVLYNSASFSTFKCYGVSPTKLNDLCFTNVYADSF VIRGDEVRQIAPGQTGKIADYNYKLPDDFTGCVIAWNSNNLDSKVG GNYNYLYRLFRKSNLKPFERDISTEIYQAGSTPCNGVEGFNCYFPL QSYGFQPTNGVGYQPYRVVVLSFELLHAPATVCGPKsggggSAIGG YIPEAPRDGQAYVRKDGEWVLLSTFLGggsilaiystvasslvllv slgaisf | 80 |
| PolyA tail | 100 nt | |
| SARS-COV-2 RBD Linked to Transmembrane Domain and Foldon Domain (RBD-TM-FD) | | |
| SEQ ID NO: 81 consists of from 5' end to 3' end: 5' UTR SEQ ID NO: 2, mRNA ORF SEQ ID NO: 82 and 3' UTR SEQ ID NO: 4. | | 81 |
| Chemistry | 1-methylpseudouridine | |
| Cap | 7mG(5')ppp(5')NlmpNp | |
| 5' UTR | GGGAAAUAAGAGAGAAAAGAAGAGUAAGAAGAAAUAUAAGACCCCG GCGCCGCCACC | 2 |
| ORF of mRNA Construct (excluding the stop codon) | AUGUACAGCAUGCAGCUGGCUAGCUGCGUGACCCUGACCCUGGUGC UGCUGGUGAACAGCCAGCCCAACAUCACCAACCUGUGCCCCUUCGG CGAGGUGUUCAACGCCACCCGGUUCGCCAGCGUGUACGCCUGGAAC CGGAAGCGGAUCAGCAACUGCGUGGCCGACUACAGCGUGCUGUACA ACAGCGCCAGCUUCAGCACCUUCAAGUGCUACGGCGUGAGCCCCAC CAAGCUGAACGACCUGUGCUUCACCAACGUGUACGCCGACAGCUUC GUGAUCCGUGGCGACGAGGUGCGGCAGAUCGCACCCGGCCAGACAG GCAAGAUCGCCGACUACAACUACAAGCUGCCCGACGACUUCACCGG CUGCGUGAUCGCCUGGAACAGCAACAACCUCGACAGCAAGGUGGGC GGCAACUACAACUACCUGUACCGGCUGUUCCGGAAGAGCAACCUGA AGCCCUUCGAGCGGGACAUCAGCACCGAGAUCUACCAAGCCGGCUC CACCCCUUGCAACGGCGUGGAGGGCUUCAACUGCUACUUCCCUCUG CAGAGCUACGGCUUCCAGCCCACCAACGGCGUGGGCUACCAGCCCU ACCGGGUGGUGGUGCUGAGCUUCGAGCUGCUGCACGCCCCAGCCAC CGUGUGUGGCCCCAAGUCUGGCGGAGGCAGCAUCCUGGCCAUCUAC AGCACCGUGGCCAGCAGCCUGGUGCUGCUGGUGAGCCUGGGCGCCA UCAGCUUCGGCGGAGGCAGCGCCAUCGGCGGCUACAUCCCCGAGGC CCCUAGAGACGGCCAGGCCUACGUGCGGAAGGACGGCGAGUGGGUG CUGCUGAGCACCUUCCUGGGCAAG | 82 |
| 3' UTR | UGAUAAUAGGCUGGAGCCUCGGUGGCCUAGCUUCUUGCCCCUUGGG CCUCCCCCCAGCCCCUCCUCCCCUUCCUGCACCCGUACCCCCGUGG UCUUUGAAUAAAGUCUGAGUGGGCGGC | 4 |
| Corresponding amino acid sequence | mysmqlascvtltlvllvnsQPNITNLCPFGEVFNATRFASVYAWN RKRISNCVADYSVLYNSASFSTFKCYGVSPTKLNDLCFTNVYADSF VIRGDEVRQIAPGQTGKIADYNYKLPDDFTGCVIAWNSNNLDSKVG GNYNYLYRLFRKSNLKPFERDISTEIYQAGSTPCNGVEGFNCYFPL QSYGFQPTNGVGYQPYRVVVLSFELLHAPATVCGPKsgggsilaiy stvasslvllvslgaisfgggSAIGGYIPEAPRDGQAYVRKDGEWV LLSTFLGK | 83 |
| PolyA tail | 100 nt | |
| SARS-CoV-2 NTD-RBD Linked to Foldon Domain and Transmembrane Domain (NTD-RBD-FD-TM) | | |
| SEQ ID NO: 99 consists of from 5' end to 3' end: 5' UTR SEQ ID NO: 2, mRNA ORF SEQ ID NO: 100 and 3' UTR SEQ ID NO: 4. | | 99 |
| Chemistry | 1-methylpseudouridine | |
| Cap | 7mG(5')ppp(5')NlmpNp | |
| 5' UTR | GGGAAAUAAGAGAGAAAAGAAGAGUAAGAAGAAAUAUAAGACCCCG GCGCCGCCACC | 2 |
| ORF of mRNA Construct (excluding the stop codon) | AUGUUCGUGUUCCUGGUGCUGCUGCCCCUGGUGAGCAGCCAGUGCG UGAACCUGACCACCCGGACCCAGCUGCCACCAGCCUACACCAACAG CUUCACCCGGGGCGUCUACUACCCCGACAAGGUGUUCCGGAGCAGC GUCCUGCACAGCACCCAGGACCUGUUCCUGCCCUUCUUCAGCAACG UGACCUGGUUCCACGCCAUCCACGUGAGCGGCACCAACGGCACCAA GCGGUUCGACAACCCCGUGCUGCCCUUCAACGACGGCGUGUACUUC GCCAGCACCGAGAAGAGCAACAUCAUCCGGGGCUGGAUCUUCGGCA CCACCCUGGACAGCAAGACCCAGAGCCUGCUGAUCGUGAAUAACGC CACCAACGUGGUGAUCAAGGUGUGCGAGUUCCAGUUCUGCAACGAC | 100 |

TABLE 15B-continued

| Antigens Linked to a Foldon Domain | | |
|---|---|---|
| | CCCUUCCUGGGCGUGUACUACCACAAGAACAACAAGAGCUGGAUGG<br>AGAGCGAGUUCCGGGUGUACAGCAGCGCCAACAACUGCACCUUCGA<br>GUACGUGAGCCAGCCCUUCCUGAUGGACCUGGAGGGCAAGCAGGGC<br>AACUUCAAGAACCUGCGGGAGUUCGUGUUCAAGAACAUCGACGGCU<br>ACUUCAAGAUCUACAGCAAGCACACCCCAAUCAACCUGGUGCGGGA<br>UCUGCCCCAGGGCUUCUCAGCCCUGGAGCCCCUGGUGGACCUGCCC<br>AUCGGCAUCAACAUCACCCGGUUCCAGACCCUGCUGGCCCUGCACC<br>GGAGCUACCUGACCCCAGGCGACAGCAGCAGCGGGUGGACAGCAGG<br>CGCGGCUGCUUACUACGUGGGCUACCUGCAGCCCCGGACCUUCCUG<br>CUGAAGUACAACGAGAACGGCACCAUCACCGACGCCGUGGACGGAG<br>GCGGAUCGGGAGGCGGACCCAACAUCACCAACCUGUGCCCCUUCGG<br>CGAGGUGUUCAACGCCACCCGGUUCGCCAGCGUGUACGCCUGGAAC<br>CGGAAGCGGAUCAGCAACUGCGUGGCCGACUACAGCGUGCUGUACA<br>ACAGCGCCAGCUUCAGCACCUUCAAGUGCUACGGCGUGAGCCCCAC<br>CAAGCUGAACGACCUGUGCUUCACCAACGUGUACGCCGACAGCUUC<br>GUGAUCCGUGGCGACGAGGUGCGGCAGAUCGCACCCGGCCAGACAG<br>GCAAGAUCGCCGACUACAACUACAAGCUGCCCGACGACUUCACCGG<br>CUGCGUGAUCGCCUGGAACAGCAACAACCUCGACAGCAAGGUGGGC<br>GGCAACUACAACUACCUGUACCGGCUGUUCCGGAAGAGCAACCUGA<br>AGCCCUUCGAGCGGGACAUCAGCACCGAGAUCUACCAAGCCGGCUC<br>CACCCCUUGCAACGGCGUGGAGGGCUUCAACUGCUACUUCCCUCUG<br>CAGAGCUACGGCUUCCAGCCCACCAACGGCGUGGGCUACCAGCCCU<br>ACCGGGUGGUGGUGCUGAGCUUCGAGCUGCUGCACGCCCCAGCCAC<br>CGUGUGUGGCCCCAAGUCUGGCGGAGGCGGCAGCGCCAUCGGCGGC<br>UACAUCCCCGAGGCCCCUAGAGACGGCCAGGCCUACGUGCGGAAGG<br>ACGGCGAGUGGGUGCUGCUGAGCACCUUCCUGGGCGGAGGCAGCAU<br>CCUGGCCAUCUACAGCACCGUGGCCAGCAGCCUGGUGCUGCUGGUG<br>AGCCUGGGCGCCAUCAGCUUC | |
| 3' UTR | UGAUAAUAGGCUGGAGCCUCGGUGGCCUAGCUUCUUGCCCCUUGGG<br>CCUCCCCCCAGCCCCUCCUCCCCUUCCUGCACCCGUACCCCCGUGG<br>UCUUUGAAUAAAGUCUGAGUGGGCGGC | 4 |
| Corresponding amino acid sequence | MFVFLVLLPLVSSQCVNLTTRTQLPPAYTNSFTRGVYYPDKVFRSS<br>VLHSTQDLFLPFFSNVTWFHAIHVSGTNGTKRFDNPVLPFNDGVYF<br>ASTEKSNIIRGWIFGTTLDSKTQSLLIVNNATNVVIKVCEFQFCND<br>PFLGVYYHKNNKSWMESEFRVYSSANNCTFEYVSQPFLMDLEGKQG<br>NFKNLREFVFKNIDGYFKIYSKHTPINLVRDLPQGFSALEPLVDLP<br>IGINITRFQTLLALHRSYLTPGDSSSGWTAGAAAYYVGYLQPRTFL<br>LKYNENGTITDAVDgggsgggPNITNLCPFGEVFNATRFASVYAWN<br>RKRISNCVADYSVLYNSASFSTFKCYGVSPTKLNDLCFTNVYADSF<br>VIRGDEVRQIAPGQTGKIADYNYKLPDDFTGCVIAWNSNNLDSKVG<br>GNYNYLYRLFRKSNLKPFERDISTEIYQAGSTPCNGVEGFNCYFPL<br>QSYGFQPTNGVGYQPYRVVVLSFELLHAPATVCGPKsggggSAIGG<br>YIPEAPRDGQAYVRKDGEWVLLSTFLGggsilaiystvasslvllv<br>slgaisf | 101 |
| PolyA tail | 100 nt | |
| SARS-CoV-2 NTD-RBD Linked to Transmembrane Domain and Foldon Domain (NTD-RBD-TM-FD) | | |
| SEQ ID NO: 102 consists of from 5' end to 3' end: 5' UTR SEQ ID NO: 2, mRNA ORF SEQ ID NO: 103 and 3' UTR SEQ ID NO: 4. | | 102 |
| Chemistry | 1-methylpseudouridine | |
| Cap | 7mG(5')ppp(5')NlmpNp | |
| 5' UTR | GGGAAAUAAGAGAGAAAAGAAGAGUAAGAAGAAAUAUAAGACCCCG<br>GCGCCGCCACC | 2 |
| ORF of mRNA Construct (excluding the stop codon) | AUGUUCGUGUUCCUGGUGCUGCUGCCCCUGGUGAGCAGCCAGUGCG<br>UGAACCUGACCACCCGGACCCAGCUGCCACCAGCCUACACCAACAG<br>CUUCACCCGGGGCGUCUACUACCCCGACAAGGUGUUCCGGAGCAGC<br>GUCCUGCACAGCACCCAGGACCUGUUCCUGCCCUUCUUCAGCAACG<br>UGACCUGGUUCCACGCCAUCCACGUGAGCGGCACCAACGGCACCAA<br>GCGGUUCGACAACCCCGUGCUGCCCUUCAACGACGGCGUGUACUUC<br>GCCAGCACCGAGAAGAGCAACAUCAUCCGGGGCUGGAUCUUCGGCA<br>CCACCCUGGACAGCAAGACCCAGAGCCUGCUGAUCGUGAAUAACGC<br>CACCAACGUGGUGAUCAAGGUGUGCGAGUUCCAGUUCUGCAACGAC<br>CCCUUCCUGGGCGUGUACUACCACAAGAACAACAAGAGCUGGAUGG<br>AGAGCGAGUUCCGGGUGUACAGCAGCGCCAACAACUGCACCUUCGA<br>GUACGUGAGCCAGCCCUUCCUGAUGGACCUGGAGGGCAAGCAGGGC<br>AACUUCAAGAACCUGCGGGAGUUCGUGUUCAAGAACAUCGACGGCU<br>ACUUCAAGAUCUACAGCAAGCACACCCCAAUCAACCUGGUGCGGGA<br>UCUGCCCCAGGGCUUCUCAGCCCUGGAGCCCCUGGUGGACCUGCCC<br>AUCGGCAUCAACAUCACCCGGUUCCAGACCCUGCUGGCCCUGCACC<br>GGAGCUACCUGACCCCAGGCGACAGCAGCAGCGGGUGGACAGCAGG | 103 |

TABLE 15B-continued

| Antigens Linked to a Foldon Domain | | |
|---|---|---|
| | CGCGGCUGCUUACUACGUGGGCUACCUGCAGCCCCGGACCUUCCUG<br>CUGAAGUACAACGAGAACGGCACCAUCACCGACGCCGUGGACGGAG<br>GCGGAUCGGGAGGCGGACCCAACAUCACCAACCUGUGCCCCUUCGG<br>CGAGGUGUUCAACGCCACCCGGUUCGCCAGCGUGUACGCCUGGAAC<br>CGGAAGCGGAUCAGCAACUGCGUGGCCGACUACAGCGUGCUGUACA<br>ACAGCGCCAGCUUCAGCACCUUCAAGUGCUACGGCGUGAGCCCCAC<br>CAAGCUGAACGACCUGUGCUUCACCAACGUGUACGCCGACAGCUUC<br>GUGAUCCGUGGCGACGAGGUGCGGCAGAUCGCACCCGGCCAGACAG<br>GCAAGAUCGCCGACUACAACUACAAGCUGCCCGACGACUUCACCGG<br>CUGCGUGAUCGCCUGGAACAGCAACAACCUCGACAGCAAGGUGGGC<br>GGCAACUACAACUACCUGUACCGGCUGUUCCGGAAGAGCAACCUGA<br>AGCCCUUCGAGCGGGACAUCAGCACCGAGAUCUACCAAGCCGGCUC<br>CACCCCUUGCAACGGCGUGGAGGGCUUCAACUGCUACUUCCCUCUG<br>CAGAGCUACGGCUUCCAGCCCACCAACGGCGUGGGCUACCAGCCCU<br>ACCGGGUGGUGGUGCUGAGCUUCGAGCUGCUGCACGCCCCAGCCAC<br>CGUGUGUGGCCCCAAGUCUGGCGGAGGCAGCAUCCUGGCCAUCUAC<br>AGCACCGUGGCCAGCAGCCUGGUGCUGCUGGUGAGCCUGGGCGCCA<br>UCAGCUUCGGCGGAGGCAGCGCCAUCGGCGGCUACAUCCCCGAGGC<br>CCCUAGAGACGGCCAGGCCUACGUGCGGAAGGACGGCGAGUGGGUG<br>CUGCUGAGCACCUUCCUGGGCAAG | |
| 3' UTR | UGAUAAUAGGCUGGAGCCUCGGUGGCCUAGCUUCUUGCCCCUUGGG<br>CCUCCCCCCAGCCCCUCCUCCCCUUCCUGCACCCGUACCCCCGUGG<br>UCUUUGAAUAAAGUCUGAGUGGGCGGC | 4 |
| Corresponding amino acid sequence | MFVFLVLLPLVSSQCVNLTTRTQLPPAYTNSFTRGVYYPDKVFRSS<br>VLHSTQDLFLPFFSNVTWFHAIHVSGTNGTKRFDNPVLPFNDGVYF<br>ASTEKSNIIRGWIFGTTLDSKTQSLLIVNNATNVVIKVCEFQFCND<br>PFLGVYYHKNNKSWMESEFRVYSSANNCTFEYVSQPFLMDLEGKQG<br>NFKNLREFVFKNIDGYFKIYSKHTPINLVRDLPQGFSALEPLVDLP<br>IGINITRFQTLLALHRSYLTPGDSSSGWTAGAAAYYVGYLQPRTFL<br>LKYNENGTITDAVDgggsgggPNITNLCPFGEVFNATRFASVYAWN<br>RKRISNCVADYSVLYNSASFSTFKCYGVSPTKLNDLCFTNVYADSF<br>VIRGDEVRQIAPGQTGKIADYNYKLPDDFTGCVIAWNSNNLDSKVG<br>GNYNYLYRLFRKSNLKPFERDISTEIYQAGSTPCNGVEGFNCYFPL<br>QSYGFQPTNGVGYQPYRVVVLSFELLHAPATVCGPKsgggsilaiy<br>stvasslvllvslgaisfgggSAIGGYIPEAPRDGQAYVRKDGEWV<br>LLSTFLGK | 104 |
| PolyA tail | 100 nt | |

| SARS-COV-2 NTD-RBD Linked to Foldon Domain | | |
|---|---|---|
| SEQ ID NO: 111 consists of from 5' end to 3' end: 5' UTR SEQ ID NO: 2, mRNA ORF SEQ ID NO: 112 and 3' UTR SEQ ID NO: 4. | | 111 |
| Chemistry | 1-methylpseudouridine | |
| Cap | 7mG(5')ppp(5')N1mpNp | |
| 5' UTR | GGGAAAUAAGAGAGAAAAGAAGAGUAAGAAGAAAUAUAAGACCCCG<br>GCGCCGCCACC | 2 |
| ORF of mRNA Construct (excluding the stop codon) | AUGUUCGUGUUCCUGGUGCUGCUGCCCCUGGUGAGCAGCCAGUGCG<br>UGAACCUGACCACCCGGACCCAGCUGCCACCAGCCUACACCAACAG<br>CUUCACCCGGGGCGUCUACUACCCCGACAAGGUGUUCCGGAGCAGC<br>GUCCUGCACAGCACCCAGGACCUGUUCCUGCCCUUCUUCAGCAACG<br>UGACCUGGUUCCACGCCAUCCACGUGAGCGGCACCAACGGCACCAA<br>GCGGUUCGACAACCCCGUGCUGCCCUUCAACGACGGCGUGUACUUC<br>GCCAGCACCGAGAAGAGCAACAUCAUCCGGGGCUGGAUCUUCGGCA<br>CCACCCUGGACAGCAAGACCCAGAGCCUGCUGAUCGUGAAUAACGC<br>CACCAACGUGGUGAUCAAGGUGUGCGAGUUCCAGUUCUGCAACGAC<br>CCCUUCCUGGGCGUGUACUACCACAAGAACAACAAGAGCUGGAUGG<br>AGAGCGAGUUCCGGGUGUACAGCAGCGCCAACAACUGCACCUUCGA<br>GUACGUGAGCCAGCCCUUCCUGAUGGACCUGGAGGGCAAGCAGGGC<br>AACUUCAAGAACCUGCGGGAGUUCGUGUUCAAGAACAUCGACGGCU<br>ACUUCAAGAUCUACAGCAAGCACACCCCAAUCAACCUGGUGCGGGA<br>UCUGCCCCAGGGCUUCUCAGCCCUGGAGCCCCUGGUGGACCUGCCC<br>AUCGGCAUCAACAUCACCCGGUUCCAGACCCUGCUGGCCCUGCACC<br>GGAGCUACCUGACCCCAGGCGACAGCAGCAGCGGGUGGACAGCAGG<br>CGCGGCUGCUUACUACGUGGGCUACCUGCAGCCCCGGACCUUCCUG<br>CUGAAGUACAACGAGAACGGCACCAUCACCGACGCCGUGGACGGAG<br>GCGGAUCGGGAGGCGGACCCAACAUCACCAACCUGUGCCCCUUCGG<br>CGAGGUGUUCAACGCCACCCGGUUCGCCAGCGUGUACGCCUGGAAC<br>CGGAAGCGGAUCAGCAACUGCGUGGCCGACUACAGCGUGCUGUACA<br>ACAGCGCCAGCUUCAGCACCUUCAAGUGCUACGGCGUGAGCCCCAC<br>CAAGCUGAACGACCUGUGCUUCACCAACGUGUACGCCGACAGCUUC<br>GUGAUCCGUGGCGACGAGGUGCGGCAGAUCGCACCCGGCCAGACAG | 112 |

TABLE 15B-continued

| Antigens Linked to a Foldon Domain | | |
|---|---|---|
| | GCAAGAUCGCCGACUACAACUACAAGCUGCCCGACGACUUCACCGG<br>CUGCGUGAUCGCCUGGAACAGCAACAACCUCGACAGCAAGGUGGGC<br>GGCAACUACAACUACCUGUACCGGCUGUUCCGGAAGAGCAACCUGA<br>AGCCCUUCGAGCGGGACAUCAGCACCGAGAUCUACCAAGCCGGCUC<br>CACCCCUUGCAACGGCGUGGAGGGCUUCAACUGCUACUUCCCUCUG<br>CAGAGCUACGGCUUCCAGCCCACCAACGGCGUGGGCUACCAGCCCU<br>ACCGGGUGGUGGUGCUGAGCUUCGAGCUGCUGCACGCCCCAGCCAC<br>CGUGUGUGGCCCCAAGUCUGGCGGAGGCGGCAGCGCCAUCGGCGGC<br>UACAUCCCCGAGGCCCCUAGAGACGGCCAGGCCUACGUGCGGAAGG<br>ACGGCGAGUGGGUGCUGCUGAGCACCUUCCUGGGC | |
| 3' UTR | UGAUAAUAGGCUGGAGCCUCGGUGGCCUAGCUUCUUGCCCCUUGGG<br>CCUCCCCCCAGCCCCUCCUCCCCUUCCUGCACCCGUACCCCCGUGG<br>UCUUUGAAUAAAGUCUGAGUGGGCGGC | 4 |
| Corresponding amino acid sequence | MFVFLVLLPLVSSQCVNLTTRTQLPPAYTNSFTRGVYYPDKVFRSS<br>VLHSTQDLFLPFFSNVTWFHAIHVSGTNGTKRFDNPVLPFNDGVYF<br>ASTEKSNIIRGWIFGTTLDSKTQSLLIVNNATNVVIKVCEFQFCND<br>PFLGVYYHKNNKSWMESEFRVYSSANNCTFEYVSQPFLMDLEGKQG<br>NFKNLREFVFKNIDGYFKIYSKHTPINLVRDLPQGFSALEPLVDLP<br>IGINITRFQTLLALHRSYLTPGDSSSGWTAGAAAYYVGYLQPRTFL<br>LKYNENGTITDAVDgggsgggPNITNLCPFGEVFNATRFASVYAWN<br>RKRISNCVADYSVLYNSASFSTFKCYGVSPTKLNDLCFTNVYADSF<br>VIRGDEVRQIAPGQTGKIADYNYKLPDDFTGCVIAWNSNNLDSKVG<br>GNYNYLYRLFRKSNLKPFERDISTEIYQAGSTPCNGVEGFNCYFPL<br>QSYGFQPTNGVGYQPYRVVVLSFELLHAPATVCGPKsggggSAIGG<br>YIPEAPRDGQAYVRKDGEWVLLSTFLG | 113 |
| PolyA tail | 100 nt | |

Encapsulin

In some embodiments, an encapsulin domain is used as a scaffold domain. Encapsulin is a protein cage nanoparticle isolated from the thermophile *Thermotoga maritima*. Encapsulin is assembled from 60 copies of identical 31 kDa monomers having a thin and icosahedral T=1 symmetric cage structure with interior and exterior diameters of 20 and 24 nm, respectively (Sutter M. et al. Nat Struct Mol Biol. 2008; 15: 939-947). Although the exact function of encapsulin in *T. maritima* is not clearly understood yet, its crystal structure has been recently solved and its function was postulated as a cellular compartment that encapsulates proteins such as DyP (Dye decolorizing peroxidase) and Flp (Ferritin like protein), which are involved in oxidative stress responses 30 (Rahmanpour R. et al. FEBS J. 2013; 280: 2097-2104). The use of encapsulin for nanoparticle construction enables both the display of protein antigen on the surface of the nanoparticle, and the enclosure of cargo such as mRNA within the nanoparticle itself. Previous encapsulin nanoparticle-based vaccines have elicited strong immune responses to both surface displayed antigen and cargo protein itself (Lagoutte P. et al. Vaccine. 2018; 36(25): 3622-3628).

An mRNA provided herein, in some embodiments, encodes an S protein domain (e.g., S1, S2, RBD, and/or NTD) linked to an encapsulin domain.

Fusion Proteins

In some embodiments, a composition of the present disclosure includes an mRNA encoding an antigenic fusion protein. Thus, the encoded antigen or antigens may include two or more proteins (e.g., protein and/or protein fragment) joined together. Alternatively, the protein to which a protein antigen is fused does not promote a strong immune response to itself, but rather to the coronavirus antigen. Antigenic fusion proteins, in some embodiments, retain the functional property from each original protein.

In some embodiments, a fusion protein comprises a receptor binding domain from a SARS-CoV-2 Spike protein.

In some embodiments, a fusion protein comprises an N-terminal domain from a SARS-CoV-2 Spike protein In some embodiments, a fusion protein comprises a transmembrane domain. The transmembrane domain may, in some embodiments, be from a virus that is not SARS-CoV-2. For example, the transmembrane domain may be from an influenza hemagglutinin transmembrane domain, which has been demonstrated to effectively anchor proteins at the cell surface.

Variants

In some embodiments, the compositions of the present disclosure include RNA that encodes a coronavirus antigen variant. Antigen variants or other polypeptide variants refers to molecules that differ in their amino acid sequence from a wild-type, native, or reference sequence. The antigen/polypeptide variants may possess substitutions, deletions, and/or insertions at certain positions within the amino acid sequence, as compared to a native or reference sequence. Ordinarily, variants possess at least 50% identity to a wild-type, native or reference sequence. In some embodiments, variants share at least 80%, or at least 90% identity with a wild-type, native, or reference sequence.

Variant antigens/polypeptides encoded by nucleic acids of the disclosure may contain amino acid changes that confer any of a number of desirable properties, e.g., that enhance their immunogenicity, enhance their expression, and/or improve their stability or PK/PD properties in a subject. Variant antigens/polypeptides can be made using routine mutagenesis techniques and assayed as appropriate to determine whether they possess the desired property. Assays to determine expression levels and immunogenicity are well known in the art and exemplary such assays are set forth in the Examples section. Similarly, PK/PD properties of a protein variant can be measured using art recognized techniques, e.g., by determining expression of antigens in a vaccinated subject over time and/or by looking at the durability of the induced immune response. The stability of protein(s) encoded by a variant nucleic acid may be measured by assaying thermal stability or stability upon urea denaturation or may be measured using in silico prediction. Methods for such experiments and in silico determinations are known in the art.

In some embodiments, a composition comprises an mRNA or an mRNA ORF that comprises a nucleotide sequence of any one of the sequences provided herein (see, e.g., Sequence Listing), or comprises a nucleotide sequence at least 80%, at least 85%, at least 90%, at least 95%, at least 96%, at least 97%, at least 98%, or at least 99% identical to a nucleotide sequence of any one of the sequences provided herein.

The term "identity" refers to a relationship between the sequences of two or more polypeptides (e.g. antigens) or polynucleotides (nucleic acids), as determined by comparing the sequences. Identity also refers to the degree of sequence relatedness between or among sequences as determined by the number of matches between strings of two or more amino acid residues or nucleic acid residues. Identity measures the percent of identical matches between the smaller of two or more sequences with gap alignments (if any) addressed by a particular mathematical model or computer program (e.g., "algorithms"). Identity of related antigens or nucleic acids can be readily calculated by known methods. "Percent (%) identity" as it applies to polypeptide or polynucleotide sequences is defined as the percentage of residues (amino acid residues or nucleic acid residues) in the candidate amino acid or nucleic acid sequence that are identical with the residues in the amino acid sequence or nucleic acid sequence of a second sequence after aligning the sequences and introducing gaps, if necessary, to achieve the maximum percent identity. Methods and computer programs for the alignment are well known in the art. It is understood that identity depends on a calculation of percent identity but may differ in value due to gaps and penalties introduced in the calculation. Generally, variants of a particular polynucleotide or polypeptide (e.g., antigen) have at least 40%, 45%, 50%, 55%, 60%, 65%, 70%, 75%, 80%, 85%, 90%, 91%, 92%, 93%, 94%, 95%, 96%, 97%, 98%, 99% but less than 100% sequence identity to that particular reference polynucleotide or polypeptide as determined by sequence alignment programs and parameters described herein and known to those skilled in the art. Such tools for alignment include those of the BLAST suite (Stephen F. Altschul, et al (1997), "Gapped BLAST and PSI-BLAST: a new generation of protein database search programs", Nucleic Acids Res. 25:3389-3402). Another popular local alignment technique is based on the Smith-Waterman algorithm (Smith, T. F. & Waterman, M. S. (1981) "Identification of common molecular subsequences." J. Mol. Biol. 147:195-197). A general global alignment technique based on dynamic programming is the Needleman-Wunsch algorithm (Needleman, S. B. & Wunsch, C. D. (1970) "A general method applicable to the search for similarities in the amino acid sequences of two proteins." J. Mol. Biol. 48:443-453). More recently a Fast Optimal Global Sequence Alignment Algorithm (FOGSAA) has been developed that purportedly produces global alignment of nucleotide and protein sequences faster than other optimal global alignment methods, including the Needleman-Wunsch algorithm.

As such, polynucleotides encoding peptides or polypeptides containing substitutions, insertions and/or additions, deletions and covalent modifications with respect to reference sequences, particularly the polypeptide (e.g., antigen) sequences disclosed herein, are included within the scope of this disclosure. For example, sequence tags or amino acids, such as one or more lysines, can be added to peptide sequences (e.g., at the N-terminal or C-terminal ends). Sequence tags can be used for peptide detection, purification or localization. Lysines can be used to increase peptide solubility or to allow for biotinylation. Alternatively, amino acid residues located at the carboxy and amino terminal regions of the amino acid sequence of a peptide or protein may optionally be deleted providing for truncated sequences. Certain amino acids (e.g., C-terminal or N-terminal residues) may alternatively be deleted depending on the use of the sequence, as for example, expression of the sequence as part of a larger sequence which is soluble or linked to a solid support. In some embodiments, sequences for (or encoding) signal sequences, termination sequences, transmembrane domains, linkers, multimerization domains (such as, e.g., foldon regions) and the like may be substituted with alternative sequences that achieve the same or a similar function. In some embodiments, cavities in the core of proteins can be filled to improve stability, e.g., by introducing larger amino acids. In other embodiments, buried hydrogen bond networks may be replaced with hydrophobic resides to improve stability. In yet other embodiments, glycosylation sites may be removed and replaced with appropriate residues. Such sequences are readily identifiable to one of skill in the art. It should also be understood that some of the sequences provided herein contain sequence tags or terminal peptide sequences (e.g., at the N-terminal or C-terminal ends) that may be deleted, for example, prior to use in the preparation of an mRNA vaccine.

As recognized by those skilled in the art, protein fragments, functional protein domains, and homologous proteins are also considered to be within the scope of coronavirus antigens of interest. For example, provided herein is any protein fragment (meaning a polypeptide sequence at least one amino acid residue shorter than a reference antigen sequence but otherwise identical) of a reference protein, provided that the fragment is immunogenic and confers a protective immune response to the coronavirus. In addition to variants that are identical to the reference protein but are truncated, in some embodiments, an antigen includes 2, 3, 4, 5, 6, 7, 8, 9, 10, or more mutations, as shown in any of the sequences provided or referenced herein. Antigens/antigenic polypeptides can range in length from about 4, 6, or 8 amino acids to full length proteins.

Stabilizing Elements

Naturally-occurring eukaryotic mRNA molecules can contain stabilizing elements, including, but not limited to untranslated regions (UTR) at their 5'-end (5' UTR) and/or at their 3'-end (3' UTR), in addition to other structural features, such as a 5'-cap structure or a 3'-poly(A) tail. Both the 5' UTR and the 3' UTR are typically transcribed from the genomic DNA and are elements of the premature mRNA. Characteristic structural features of mature mRNA, such as the 5'-cap and the 3'-poly(A) tail are usually added to the transcribed (premature) mRNA during mRNA processing.

In some embodiments, a composition includes an mRNA having an open reading frame encoding at least one antigenic polypeptide having at least one modification, at least one 5' terminal cap, and is formulated within a lipid nanoparticle. 5'-capping of polynucleotides may be completed concomitantly during the in vitro-transcription reaction using the following chemical RNA cap analogs to generate the 5'-guanosine cap structure according to manufacturer protocols: 3'-O-Me-m7G(5')ppp(5') G [the ARCA cap]; G(5')ppp(5')A; G(5')ppp(5')G; m7G(5')ppp(5')A; m7G(5')ppp(5')G (New England BioLabs, Ipswich, MA). 5'-capping of modified RNA may be completed post-transcriptionally using a Vaccinia Virus Capping Enzyme to generate the "Cap 0" structure: m7G(5')ppp(5')G (New England BioLabs, Ipswich, MA). Cap 1 structure may be generated using both Vaccinia Virus Capping Enzyme and a 2'-O methyltransferase to generate: m7G(5')ppp(5')G-2'-O-methyl. Cap 2 structure may be generated from the Cap 1 structure followed by the 2'-O-methylation of the 5'-antepenultimate nucleotide using a 2'-O methyl-transferase. Cap 3 structure may be generated from the Cap 2 structure followed by the 2'-O-methylation of the 5'-preantepenultimate nucleotide using a 2'-0 methyl-transferase. Enzymes may be derived from a recombinant source.

The 3'-poly(A) tail is typically a stretch of adenine nucleotides added to the 3'-end of the transcribed mRNA. It can, in some instances, comprise up to about 400 adenine nucleotides. In some embodiments, the length of the 3'-poly (A) tail may be an essential element with respect to the stability of the individual mRNA.

In some embodiments, a composition includes a stabilizing element. Stabilizing elements may include for instance a histone stem-loop. A stem-loop binding protein (SLBP), a 32 kDa protein has been identified. It is associated with the histone stem-loop at the 3'-end of the histone messages in both the nucleus and the cytoplasm. Its expression level is regulated by the cell cycle; it peaks during the S-phase, when histone mRNA levels are also elevated. The protein has been shown to be essential for efficient 3'-end processing of histone pre-mRNA by the U7 snRNP. SLBP continues to be associated with the stem-loop after processing, and then stimulates the translation of mature histone mRNAs into histone proteins in the cytoplasm. The RNA binding domain of SLBP is conserved through metazoa and protozoa; its binding to the histone stem-loop depends on the structure of the loop. The minimum binding site includes at least three nucleotides 5' and two nucleotides 3' relative to the stem-loop.

In some embodiments, an mRNA includes a coding region, at least one histone stem-loop, and optionally, a poly(A) sequence or polyadenylation signal. The poly(A) sequence or polyadenylation signal generally should enhance the expression level of the encoded protein. The encoded protein, in some embodiments, is not a histone protein, a reporter protein (e.g. Luciferase, GFP, EGFP, β-Galactosidase, EGFP), or a marker or selection protein (e.g. alpha-Globin, Galactokinase and Xanthine:guanine phosphoribosyl transferase (GPT)).

In some embodiments, an mRNA includes the combination of a poly(A) sequence or polyadenylation signal and at least one histone stem-loop, even though both represent alternative mechanisms in nature, acts synergistically to increase the protein expression beyond the level observed with either of the individual elements. The synergistic effect of the combination of poly(A) and at least one histone stem-loop does not depend on the order of the elements or the length of the poly(A) sequence.

In some embodiments, an mRNA does not include a histone downstream element (HDE). "Histone downstream element" (HDE) includes a purine-rich polynucleotide stretch of approximately 15 to 20 nucleotides 3' of naturally occurring stem-loops, representing the binding site for the U7 snRNA, which is involved in processing of histone pre-mRNA into mature histone mRNA. In some embodiments, the nucleic acid does not include an intron.

An mRNA may or may not contain an enhancer and/or promoter sequence, which may be modified or unmodified or which may be activated or inactivated. In some embodiments, the histone stem-loop is generally derived from histone genes and includes an intramolecular base pairing of two neighbored partially or entirely reverse complementary sequences separated by a spacer, consisting of a short sequence, which forms the loop of the structure. The unpaired loop region is typically unable to base pair with either of the stem loop elements. It occurs more often in RNA, as is a key component of many RNA secondary structures but may be present in single-stranded DNA as well. Stability of the stem-loop structure generally depends on the length, number of mismatches or bulges, and base composition of the paired region. In some embodiments, wobble base pairing (non-Watson-Crick base pairing) may result. In some embodiments, the at least one histone stem-loop sequence comprises a length of 15 to 45 nucleotides.

In some embodiments, an mRNA has one or more AU-rich sequences removed. These sequences, sometimes referred to as AURES are destabilizing sequences found in the 3'UTR. The AURES may be removed from the RNA vaccines. Alternatively, the AURES may remain in the RNA vaccine.

Signal Peptides

In some embodiments, a composition comprises an mRNA having an ORF that encodes a signal peptide fused to the coronavirus antigen. Signal peptides, comprising the N-terminal 15-60 amino acids of proteins, are typically needed for the translocation across the membrane on the secretory pathway and, thus, universally control the entry of most proteins both in eukaryotes and prokaryotes to the secretory pathway. In eukaryotes, the signal peptide of a nascent precursor protein (pre-protein) directs the ribosome to the rough endoplasmic reticulum (ER) membrane and initiates the transport of the growing peptide chain across it for processing. ER processing produces mature proteins, wherein the signal peptide is cleaved from precursor proteins, typically by a ER-resident signal peptidase of the host cell, or they remain uncleaved and function as a membrane anchor. A signal peptide may also facilitate the targeting of the protein to the cell membrane.

A signal peptide may have a length of 15-60 amino acids. For example, a signal peptide may have a length of 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 amino acids. In some embodiments, a signal peptide has a length of 20-60, 25-60, 30-60, 35-60, 40-60, 45-60, 50-60, 55-60, 15-55, 20-55, 25-55, 30-55, 35-55, 40-55, 45-55, 50-55, 15-50, 20-50, 25-50, 30-50, 35-50, 40-50, 45-50, 15-45, 20-45, 25-45, 30-45, 35-45, 40-45, 15-40, 20-40, 25-40, 30-40, 35-40, 15-35, 20-35, 25-35, 30-35, 15-30, 20-30, 25-30, 15-25, 20-25, or 15-20 amino acids.

Signal peptides from heterologous genes (which regulate expression of genes other than coronavirus antigens in nature) are known in the art and can be tested for desired properties and then incorporated into a nucleic acid of the disclosure.

Sequence Optimization

In some embodiments, an ORF encoding an antigen of the disclosure is codon optimized. Codon optimization methods are known in the art. For example, an ORF of any one or more of the sequences provided herein may be codon optimized. Codon optimization, in some embodiments, may be used to match codon frequencies in target and host organisms to ensure proper folding; bias GC content to increase mRNA stability or reduce secondary structures; minimize tandem repeat codons or base runs that may impair gene construction or expression; customize transcriptional and translational control regions; insert or remove protein trafficking sequences; remove/add post translation modification sites in encoded protein (e.g., glycosylation sites); add, remove or shuffle protein domains; insert or delete restriction sites; modify ribosome binding sites and mRNA degradation sites; adjust translational rates to allow the various domains of the protein to fold properly; or reduce or eliminate problem secondary structures within the polynucleotide. Codon optimization tools, algorithms and services are known in the art—non-limiting examples include services from GeneArt (Life Technologies), DNA2.0 (Menlo Park CA) and/or proprietary methods. In some embodiments, the open reading frame (ORF) sequence is optimized using optimization algorithms.

In some embodiments, a codon optimized sequence shares less than 95% sequence identity to a naturally-occurring or wild-type sequence ORF (e.g., a naturally-occurring or wild-type mRNA sequence encoding a coronavirus antigen). In some embodiments, a codon optimized sequence shares less than 90% sequence identity to a naturally-occurring or wild-type sequence (e.g., a naturally-occurring or wild-type mRNA sequence encoding a coronavirus antigen). In some embodiments, a codon optimized sequence shares less than 85% sequence identity to a naturally-occurring or wild-type sequence (e.g., a naturally-occurring or wild-type mRNA sequence encoding a coronavirus antigen). In some embodiments, a codon optimized sequence shares less than 80% sequence identity to a naturally-occurring or wild-type sequence (e.g., a naturally-occurring or wild-type mRNA sequence encoding a coronavirus antigen). In some embodiments, a codon optimized sequence shares less than 75% sequence identity to a naturally-occurring or wild-type sequence (e.g., a naturally-occurring or wild-type mRNA sequence encoding a coronavirus antigen).

In some embodiments, a codon optimized sequence shares between 65% and 85% (e.g., between about 67% and about 85% or between about 67% and about 80%) sequence identity to a naturally-occurring or wild-type sequence (e.g., a naturally-occurring or wild-type mRNA sequence encoding a coronavirus antigen). In some embodiments, a codon optimized sequence shares between 65% and 75% or about 80% sequence identity to a naturally-occurring or wild-type sequence (e.g., a naturally-occurring or wild-type mRNA sequence encoding a coronavirus antigen).

In some embodiments, a codon-optimized sequence encodes an antigen that is as immunogenic as, or more immunogenic than (e.g., at least 10%, at least 20%, at least 30%, at least 40%, at least 50%, at least 100%, or at least 200% more), than a coronavirus antigen encoded by a non-codon-optimized sequence.

When transfected into mammalian host cells, the modified mRNAs have a stability of between 12-18 hours, or greater than 18 hours, e.g., 24, 36, 48, 60, 72, or greater than 72 hours and are capable of being expressed by the mammalian host cells.

In some embodiments, a codon optimized RNA may be one in which the levels of G/C are enhanced. The G/C-content of nucleic acid molecules (e.g., mRNA) may influence the stability of the RNA. RNA having an increased amount of guanine (G) and/or cytosine (C) residues may be functionally more stable than mRNA containing a large amount of adenine (A) and thymine (T) or uracil (U) nucleotides. As an example, WO02/098443 discloses a pharmaceutical composition containing an mRNA stabilized by sequence modifications in the translated region. Due to the degeneracy of the genetic code, the modifications work by substituting existing codons for those that promote greater RNA stability without changing the resulting amino acid. The approach is limited to coding regions of the RNA.

Chemically Unmodified Nucleotides

In some embodiments, an mRNA is not chemically modified and comprises the standard ribonucleotides consisting of adenosine, guanosine, cytosine and uridine. In some embodiments, nucleotides and nucleosides of the present disclosure comprise standard nucleoside residues such as those present in transcribed RNA (e.g. A, G, C, or U). In some embodiments, nucleotides and nucleosides of the present disclosure comprise standard deoxyribonucleosides such as those present in DNA (e.g. dA, dG, dC, or dT).

Chemical Modifications

The compositions of the present disclosure comprise, in some embodiments, an mRNA having an open reading frame encoding a coronavirus antigen, wherein the nucleic acid comprises nucleotides and/or nucleosides that can be standard (unmodified) or modified as is known in the art. In some embodiments, nucleotides and nucleosides of the present disclosure comprise modified nucleotides or nucleosides. Such modified nucleotides and nucleosides can be naturally-occurring modified nucleotides and nucleosides or non-naturally occurring modified nucleotides and nucleosides. Such modifications can include those at the sugar, backbone, or nucleobase portion of the nucleotide and/or nucleoside as are recognized in the art.

In some embodiments, a naturally-occurring modified nucleotide or nucleotide of the disclosure is one as is generally known or recognized in the art. Non-limiting examples of such naturally occurring modified nucleotides and nucleotides can be found, inter alia, in the widely recognized MODOMICS database.

In some embodiments, a non-naturally occurring modified nucleotide or nucleoside of the disclosure is one as is generally known or recognized in the art. Non-limiting examples of such non-naturally occurring modified nucleotides and nucleosides can be found, inter alia, in published US application Nos. PCT/US2012/058519; PCT/US2013/075177; PCT/US2014/058897; PCT/US2014/058891; PCT/US2014/070413; PCT/US2015/36773; PCT/US2015/36759; PCT/US2015/36771; or PCT/IB2017/051367 all of which are incorporated by reference herein.

Hence, nucleic acids of the disclosure (e.g., DNA nucleic acids and RNA nucleic acids, such as mRNA nucleic acids) can comprise standard nucleotides and nucleosides, naturally-occurring nucleotides and nucleosides, non-naturally-occurring nucleotides and nucleosides, or any combination thereof.

Nucleic acids of the disclosure (e.g., DNA nucleic acids and RNA nucleic acids, such as mRNA nucleic acids), in some embodiments, comprise various (more than one) different types of standard and/or modified nucleotides and nucleosides. In some embodiments, a particular region of a nucleic acid contains one, two or more (optionally different) types of standard and/or modified nucleotides and nucleosides.

In some embodiments, a modified RNA nucleic acid (e.g., a modified mRNA nucleic acid), introduced to a cell or organism, exhibits reduced degradation in the cell or organism, respectively, relative to an unmodified nucleic acid comprising standard nucleotides and nucleosides.

In some embodiments, a modified RNA nucleic acid (e.g., a modified mRNA nucleic acid), introduced into a cell or organism, may exhibit reduced immunogenicity in the cell or organism, respectively (e.g., a reduced innate response) relative to an unmodified nucleic acid comprising standard nucleotides and nucleosides.

Nucleic acids (e.g., RNA nucleic acids, such as mRNA nucleic acids), in some embodiments, comprise non-natural modified nucleotides that are introduced during synthesis or post-synthesis of the nucleic acids to achieve desired functions or properties. The modifications may be present on internucleotide linkages, purine or pyrimidine bases, or sugars. The modification may be introduced with chemical synthesis or with a polymerase enzyme at the terminal of a chain or anywhere else in the chain. Any of the regions of a nucleic acid may be chemically modified.

The present disclosure provides for modified nucleosides and nucleotides of a nucleic acid (e.g., RNA nucleic acids, such as mRNA nucleic acids). A "nucleoside" refers to a compound containing a sugar molecule (e.g., a pentose or ribose) or a derivative thereof in combination with an organic base (e.g., a purine or pyrimidine) or a derivative thereof (also referred to herein as "nucleobase"). A "nucleotide" refers to a nucleoside, including a phosphate group. Modified nucleotides may by synthesized by any useful method, such as, for example, chemically, enzymatically, or recombinantly, to include one or more modified or non-natural nucleosides. Nucleic acids can comprise a region or regions of linked nucleosides. Such regions may have variable backbone linkages. The linkages can be standard phosphodiester linkages, in which case the nucleic acids would comprise regions of nucleotides.

Modified nucleotide base pairing encompasses not only the standard adenosine-thymine, adenosine-uracil, or guanosine-cytosine base pairs, but also base pairs formed between nucleotides and/or modified nucleotides comprising non-standard or modified bases, wherein the arrangement of hydrogen bond donors and hydrogen bond acceptors permits hydrogen bonding between a non-standard base and a standard base or between two complementary non-standard base structures, such as, for example, in those nucleic acids having at least one chemical modification. One example of such non-standard base pairing is the base pairing between the modified nucleotide inosine and adenine, cytosine or uracil. Any combination of base/sugar or linker may be incorporated into nucleic acids of the present disclosure.

In some embodiments, modified nucleobases in nucleic acids (e.g., RNA nucleic acids, such as mRNA nucleic acids) comprise 1-methyl-pseudouridine (m1ψ), 1-ethyl-pseudouridine (e1ψ), 5-methoxy-uridine (mo5U), 5-methyl-cytidine (m5C), and/or pseudouridine (y). In some embodiments, modified nucleobases in nucleic acids (e.g., RNA nucleic acids, such as mRNA nucleic acids) comprise 5-methoxymethyl uridine, 5-methylthio uridine, 1-methoxymethyl pseudouridine, 5-methyl cytidine, and/or 5-methoxy cytidine. In some embodiments, the polyribonucleotide includes a combination of at least two (e.g., 2, 3, 4 or more) of any of the aforementioned modified nucleobases, including but not limited to chemical modifications.

In some embodiments, an mRNA of the disclosure comprises 1-methyl-pseudouridine (m1ψ) substitutions at one or more or all uridine positions of the nucleic acid.

In some embodiments, an mRNA of the disclosure comprises 1-methyl-pseudouridine (m1ψ) substitutions at one or more or all uridine positions of the nucleic acid and 5-methyl cytidine substitutions at one or more or all cytidine positions of the nucleic acid.

In some embodiments, an mRNA of the disclosure comprises pseudouridine (ψ) substitutions at one or more or all uridine positions of the nucleic acid.

In some embodiments, an mRNA of the disclosure comprises pseudouridine (ψ) substitutions at one or more or all uridine positions of the nucleic acid and 5-methyl cytidine substitutions at one or more or all cytidine positions of the nucleic acid.

In some embodiments, an mRNA of the disclosure comprises uridine at one or more or all uridine positions of the nucleic acid.

In some embodiments, mRNAs are uniformly modified (e.g., fully modified, modified throughout the entire sequence) for a particular modification. For example, a nucleic acid can be uniformly modified with 1-methyl-pseudouridine, meaning that all uridine residues in the mRNA sequence are replaced with 1-methyl-pseudouridine. Similarly, a nucleic acid can be uniformly modified for any type of nucleoside residue present in the sequence by replacement with a modified residue such as those set forth above.

The nucleic acids of the present disclosure may be partially or fully modified along the entire length of the molecule. For example, one or more or all or a given type of nucleotide (e.g., purine or pyrimidine, or any one or more or all of A, G, U, C) may be uniformly modified in a nucleic acid of the disclosure, or in a predetermined sequence region thereof (e.g., in the mRNA including or excluding the poly(A) tail). In some embodiments, all nucleotides X in a nucleic acid of the present disclosure (or in a sequence region thereof) are modified nucleotides, wherein X may be any one of nucleotides A, G, U, C, or any one of the combinations A+G, A+U, A+C, G+U, G+C, U+C, A+G+U, A+G+C, G+U+C or A+G+C.

The nucleic acid may contain from about 1% to about 100% modified nucleotides (either in relation to overall nucleotide content, or in relation to one or more types of nucleotide, i.e., any one or more of A, G, U or C) or any intervening percentage (e.g., from 1% to 20%, from 1% to 25%, from 1% to 50%, from 1% to 60%, from 1% to 70%, from 1% to 80%, from 1% to 90%, from 1% to 95%, from 10% to 20%, from 10% to 25%, from 10% to 50%, from 10% to 60%, from 10% to 70%, from 10% to 80%, from 10% to 90%, from 10% to 95%, from 10% to 100%, from 20% to 25%, from 20% to 50%, from 20% to 60%, from 20% to 70%, from 20% to 80%, from 20% to 90%, from 20% to 95%, from 20% to 100%, from 50% to 60%, from 50% to 70%, from 50% to 80%, from 50% to 90%, from 50% to 95%, from 50% to 100%, from 70% to 80%, from 70% to 90%, from 70% to 95%, from 70% to 100%, from 80% to 90%, from 80% to 95%, from 80% to 100%, from 90% to 95%, from 90% to 100%, and from 95% to 100%). It will be understood that any remaining percentage is accounted for by the presence of unmodified A, G, U, or C.

The mRNAs may contain at a minimum 1% and at maximum 100% modified nucleotides, or any intervening percentage, such as at least 5% modified nucleotides, at least 10% modified nucleotides, at least 25% modified nucleotides, at least 50% modified nucleotides, at least 80% modified nucleotides, or at least 90% modified nucleotides. For example, the nucleic acids may contain a modified pyrimidine such as a modified uracil or cytosine. In some embodiments, at least 5%, at least 10%, at least 25%, at least 50%, at least 80%, at least 90% or 100% of the uracil in the nucleic acid is replaced with a modified uracil (e.g., a 5-substituted uracil). The modified uracil can be replaced by a compound having a single unique structure or can be replaced by a plurality of compounds having different structures (e.g., 2, 3, 4 or more unique structures). In some embodiments, at least 5%, at least 10%, at least 25%, at least 50%, at least 80%, at least 90% or 100% of the cytosine in the nucleic acid is replaced with a modified cytosine (e.g., a 5-substituted cytosine). The modified cytosine can be replaced by a compound having a single unique structure or can be replaced by a plurality of compounds having different structures (e.g., 2, 3, 4 or more unique structures).

Untranslated Regions (UTRs)

The mRNAs of the present disclosure may comprise one or more regions or parts which act or function as an untranslated region. Where mRNAs are designed to encode at least one antigen of interest, the nucleic may comprise one or more of these untranslated regions (UTRs).

Wild-type untranslated regions of a nucleic acid are transcribed but not translated. In mRNA, the 5' UTR starts at the transcription start site and continues to the start codon but does not include the start codon; whereas, the 3' UTR starts immediately following the stop codon and continues until the transcriptional termination signal. There is growing body of evidence about the regulatory roles played by the UTRs in terms of stability of the nucleic acid molecule and translation. The regulatory features of a UTR can be incorporated into the polynucleotides of the present disclosure to, among other things, enhance the stability of the molecule. The specific features can also be incorporated to ensure controlled down-regulation of the transcript in case they are misdirected to undesired organs sites. A variety of 5'UTR and 3'UTR sequences are known and available in the art.

A 5' UTR is region of an mRNA that is directly upstream (5') from the start codon (the first codon of an mRNA transcript translated by a ribosome). A 5' UTR does not encode a protein (is non-coding). Natural 5'UTRs have features that play roles in translation initiation. They harbor signatures like Kozak sequences which are commonly known to be involved in the process by which the ribosome initiates translation of many genes. Kozak sequences have the consensus CCR(A/G)CCAUGG (SEQ ID NO: 128), where R is a purine (adenine or guanine) three bases upstream of the start codon (AUG), which is followed by another 'G'0.5'UTR also have been known to form secondary structures which are involved in elongation factor binding.

In some embodiments of the disclosure, a 5' UTR is a heterologous UTR, i.e., is a UTR found in nature associated with a different ORF. In another embodiment, a 5' UTR is a synthetic UTR, i.e., does not occur in nature. Synthetic UTRs include UTRs that have been mutated to improve their properties, e.g., which increase gene expression as well as those which are completely synthetic. Exemplary 5' UTRs include *Xenopus* or human derived α-globin or b-globin (U.S. Pat. Nos. 8,278,063; 9,012,219), human cytochrome b-245 a polypeptide, and hydroxysteroid (17b) dehydrogenase, and Tobacco etch virus (U.S. Pat. Nos. 8,278,063, 9,012,219). CMV immediate-early 1 (IE1) gene (US20140206753, WO2013/185069), the sequence GGGAUCCUACC (SEQ ID NO: 129) (WO2014144196) may also be used. In another embodiment, 5' UTR of a TOP gene is a 5' UTR of a TOP gene lacking the 5' TOP motif (the oligopyrimidine tract) (e.g., WO/2015101414, WO2015101415, WO/2015/062738, WO2015024667, WO2015024667; 5' UTR element derived from ribosomal protein Large 32 (L32) gene (WO/2015101414, WO2015101415, WO/2015/062738), 5' UTR element derived from the 5'UTR of an hydroxysteroid (17-0) dehydrogenase 4 gene (HSD17B4) (WO2015024667), or a 5' UTR element derived from the 5' UTR of ATP5A1 (WO2015024667) can be used. In some embodiments, an internal ribosome entry site (IRES) is used instead of a 5' UTR.

In some embodiments, a 5' UTR of the present disclosure comprises a sequence selected from SEQ ID NO: 131 and SEQ ID NO: 2.

A 3' UTR is region of an mRNA that is directly downstream (3?) from the stop codon (the codon of an mRNA transcript that signals a termination of translation). A 3' UTR does not encode a protein (is non-coding). Natural or wild type 3' UTRs are known to have stretches of adenosines and uridines embedded in them. These AU rich signatures are particularly prevalent in genes with high rates of turnover. Based on their sequence features and functional properties, the AU rich elements (AREs) can be separated into three classes (Chen et al, 1995): Class I AREs contain several dispersed copies of an AUUUA motif within U-rich regions. C-Myc and MyoD contain class I AREs. Class II AREs possess two or more overlapping UUAUUUA(U/A)(U/A) (SEQ ID NO: 130) nonamers. Molecules containing this type of AREs include GM-CSF and TNF-α. Class III ARES are less well defined. These U rich regions do not contain an AUUUA motif. c-Jun and Myogenin are two well-studied examples of this class. Most proteins binding to the AREs are known to destabilize the messenger, whereas members of the ELAV family, most notably HuR, have been documented to increase the stability of mRNA. HuR binds to AREs of all the three classes. Engineering the HuR specific binding sites into the 3' UTR of nucleic acid molecules will lead to HuR binding and thus, stabilization of the message in vivo.

Introduction, removal or modification of 3' UTR AU rich elements (AREs) can be used to modulate the stability of nucleic acids (e.g., RNA) of the disclosure. When engineering specific nucleic acids, one or more copies of an ARE can be introduced to make nucleic acids of the disclosure less stable and thereby curtail translation and decrease production of the resultant protein. Likewise, AREs can be identified and removed or mutated to increase the intracellular stability and thus increase translation and production of the resultant protein. Transfection experiments can be conducted in relevant cell lines, using nucleic acids of the disclosure and protein production can be assayed at various time points post-transfection. For example, cells can be transfected with different ARE-engineering molecules and by using an ELISA kit to the relevant protein and assaying protein produced at 6 hour, 12 hour, 24 hour, 48 hour, and 7 days post-transfection.

Figure 4:
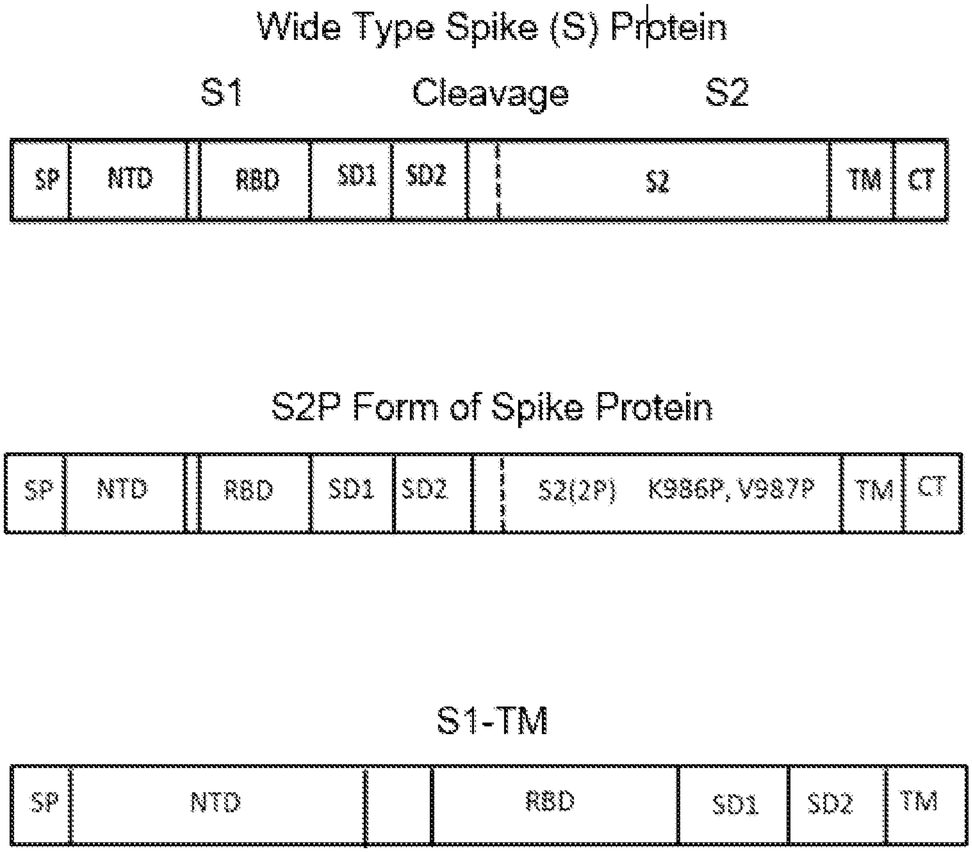
FIG. 4 shows exemplary linear designs of the antigens encoded by the mRNAs described in Examples 4-6.

3' UTRs may be heterologous or synthetic. With respect to 3' UTRs, globin UTRs, including *Xenopus* P-globin UTRs and human s-globin UTRs are known in the art (U.S. Pat. Nos. 8,278,063, 9,012,219, US20110086907). A modified P-globin construct with enhanced stability in some cell types by cloning two sequential human P-globin 3'UTRs head to tail has been developed and is well known in the art (US2012/0195936, WO2014/071963). Additionally, a2-globin, al-globin, UTRs and mutants thereof are also known in the art (WO2015101415, WO2015024667). Other 3' UTRs described in the mRNA constructs in the non-patent literature include CYBA (Ferizi et al., 2015) and albumin (Thess et al., 2015). Other exemplary 3' UTRs include that of bovine or human growth hormone (wild type or modified) (WO2013/185069, US20140206753, WO2014152774), rabbit p globin and hepatitis B virus (HBV), α-globin 3' UTR and Viral VEEV 3' UTR sequences are also known in the art. In some embodiments, the sequence UUUGAAUU (WO2014144196) is used. In some embodiments, 3' UTRs of human and mouse ribosomal protein are used. Other examples include rps9 3'UTR (WO2015101414), FIG. 4 (WO2015101415), and human albumin 7 (WO2015101415).

In some embodiments, a 3' UTR of the present disclosure comprises a sequence selected from SEQ ID NO: 132 and SEQ ID NO: 4.

Those of ordinary skill in the art will understand that 5'UTRs that are heterologous or synthetic may be used with any desired 3' UTR sequence. For example, a heterologous 5'UTR may be used with a synthetic 3'UTR with a heterologous 3" UTR.

Non-UTR sequences may also be used as regions or subregions within a nucleic acid. For example, introns or portions of introns sequences may be incorporated into regions of nucleic acid of the disclosure. Incorporation of intronic sequences may increase protein production as well as nucleic acid levels.

Combinations of features may be included in flanking regions and may be contained within other features. For example, the ORF may be flanked by a 5' UTR which may contain a strong Kozak translational initiation signal and/or a 3' UTR which may include an oligo(dT) sequence for templated addition of a poly-A tail. 5' UTR may comprise a first polynucleotide fragment and a second polynucleotide fragment from the same and/or different genes such as the 5' UTRs described in US Patent Application Publication No. 20100293625 and PCT/US2014/069155, herein incorporated by reference in its entirety.

It should be understood that any UTR from any gene may be incorporated into the regions of a nucleic acid. Furthermore, multiple wild-type UTRs of any known gene may be utilized. It is also within the scope of the present disclosure to provide artificial UTRs which are not variants of wild type regions. These UTRs or portions thereof may be placed in the same orientation as in the transcript from which they were selected or may be altered in orientation or location. Hence a 5' or 3' UTR may be inverted, shortened, lengthened, made with one or more other 5' UTRs or 3' UTRs. As used herein, the term "altered" as it relates to a UTR sequence, means that the UTR has been changed in some way in relation to a reference sequence. For example, a 3' UTR or 5' UTR may be altered relative to a wild-type or native UTR by the change in orientation or location as taught above or may be altered by the inclusion of additional nucleotides, deletion of nucleotides, swapping or transposition of nucleotides. Any of these changes producing an "altered" UTR (whether 3' or 5') comprise a variant UTR.

In some embodiments, a double, triple or quadruple UTR such as a 5' UTR or 3' UTR may be used. As used herein, a "double" UTR is one in which two copies of the same UTR are encoded either in series or substantially in series. For example, a double beta-globin 3' UTR may be used as described in US Patent publication 20100129877, the contents of which are incorporated herein by reference in its entirety.

It is also within the scope of the present disclosure to have patterned UTRs. As used herein "patterned UTRs" are those UTRs which reflect a repeating or alternating pattern, such as ABABAB or AABBAABBAABB or ABCABCABC or variants thereof repeated once, twice, or more than 3 times. In these patterns, each letter, A, B, or C represent a different UTR at the nucleotide level.

In some embodiments, flanking regions are selected from a family of transcripts whose proteins share a common function, structure, feature or property. For example, polypeptides of interest may belong to a family of proteins which are expressed in a particular cell, tissue or at some time during development. The UTRs from any of these genes may be swapped for any other UTR of the same or different family of proteins to create a new polynucleotide. As used herein, a "family of proteins" is used in the broadest sense to refer to a group of two or more polypeptides of interest which share at least one function, structure, feature, localization, origin, or expression pattern.

The untranslated region may also include translation enhancer elements (TEE). As a non-limiting example, the TEE may include those described in US Application No. 20090226470, herein incorporated by reference in its entirety, and those known in the art.

In Vitro Transcription of RNA cDNA encoding the polynucleotides described herein may be transcribed using an in vitro transcription (IVT) system. In vitro transcription of RNA is known in the art and is described in International Publication WO 2014/152027, which is incorporated by reference herein in its entirety. In some embodiments, the RNA of the present disclosure is prepared in accordance with any one or more of the methods described in WO 2018/053209 and WO 2019/036682, each of which is incorporated by reference herein.

In some embodiments, the RNA transcript is generated using a non-amplified, linearized DNA template in an in vitro transcription reaction to generate the RNA transcript. In some embodiments, the template DNA is isolated DNA. In some embodiments, the template DNA is cDNA. In some embodiments, the cDNA is formed by reverse transcription of an mRNA, for example, but not limited to coronavirus mRNA. In some embodiments, cells, e.g., bacterial cells, e.g., *E. coli*, e.g., DH-1 cells are transfected with the plasmid DNA template. In some embodiments, the transfected cells are cultured to replicate the plasmid DNA which is then isolated and purified. In some embodiments, the DNA template includes an RNA polymerase promoter, e.g., a T7 promoter located 5' to and operably linked to the gene of interest.

In some embodiments, an in vitro transcription template encodes a 5' untranslated (UTR) region, contains an open reading frame, and encodes a 3' UTR and a poly(A) tail. The particular nucleic acid sequence composition and length of an in vitro transcription template will depend on the mRNA encoded by the template.

A "5' untranslated region" (UTR) refers to a region of an mRNA that is directly upstream (i.e., 5') from the start codon (i.e., the first codon of an mRNA transcript translated by a ribosome) that does not encode a polypeptide. When RNA transcripts are being generated, the 5' UTR may comprise a promoter sequence. Such promoter sequences are known in the art. It should be understood that such promoter sequences will not be present in a vaccine of the disclosure.

A "3' untranslated region" (UTR) refers to a region of an mRNA that is directly downstream (i.e., 3') from the stop codon (i.e., the codon of an mRNA transcript that signals a termination of translation) that does not encode a polypeptide.

An "open reading frame" is a continuous stretch of DNA beginning with a start codon (e.g., methionine (ATG)), and ending with a stop codon (e.g., TAA, TAG or TGA) and encodes a polypeptide.

A "poly(A) tail" is a region of mRNA that is downstream, e.g., directly downstream (i.e., 3'), from the 3' UTR that contains multiple, consecutive adenosine monophosphates. A poly(A) tail may contain 10 to 300 adenosine monophosphates. For example, a poly(A) tail may contain 10, 20, 30, 40, 50, 60, 70, 80, 90, 100, 110, 120, 130, 140, 150, 160, 170, 180, 190, 200, 210, 220, 230, 240, 250, 260, 270, 280, 290 or 300 adenosine monophosphates. In some embodiments, a poly(A) tail contains 50 to 250 adenosine monophosphates. In a relevant biological setting (e.g., in cells, in vivo) the poly(A) tail functions to protect mRNA from enzymatic degradation, e.g., in the cytoplasm, and aids in transcription termination, and/or export of the mRNA from the nucleus and translation.

In some embodiments, a nucleic acid includes 200 to 3,000 nucleotides. For example, a nucleic acid may include 200 to 500, 200 to 1000, 200 to 1500, 200 to 3000, 500 to 1000, 500 to 1500, 500 to 2000, 500 to 3000, 1000 to 1500, 1000 to 2000, 1000 to 3000, 1500 to 3000, or 2000 to 3000 nucleotides).

An in vitro transcription system typically comprises a transcription buffer, nucleotide triphosphates (NTPs), an RNase inhibitor and a polymerase.

The NTPs may be manufactured in house, may be selected from a supplier, or may be synthesized as described herein. The NTPs may be selected from, but are not limited to, those described herein including natural and unnatural (modified) NTPs.

Any number of RNA polymerases or variants may be used in the method of the present disclosure. The polymerase may be selected from, but is not limited to, a phage RNA polymerase, e.g., a T7 RNA polymerase, a T3 RNA polymerase, a SP6 RNA polymerase, and/or mutant polymerases such as, but not limited to, polymerases able to incorporate modified nucleic acids and/or modified nucleotides, including chemically modified nucleic acids and/or nucleotides. Some embodiments exclude the use of DNase.

In some embodiments, the RNA transcript is capped via enzymatic capping. In some embodiments, the RNA comprises 5' terminal cap, for example, 7mG(5')ppp(5')NlmpNp.

Chemical Synthesis Solid-phase chemical synthesis. Nucleic acids the present disclosure may be manufactured in whole or in part using solid phase techniques. Solid-phase chemical synthesis of nucleic acids is an automated method wherein molecules are immobilized on a solid support and synthesized step by step in a reactant solution. Solid-phase synthesis is useful in site-specific introduction of chemical modifications in the nucleic acid sequences.

Liquid Phase Chemical Synthesis. The synthesis of nucleic acids of the present disclosure by the sequential addition of monomer building blocks may be carried out in a liquid phase.

Combination of Synthetic Methods. The synthetic methods discussed above each has its own advantages and limitations. Attempts have been conducted to combine these methods to overcome the limitations. Such combinations of methods are within the scope of the present disclosure. The use of solid-phase or liquid-phase chemical synthesis in combination with enzymatic ligation provides an efficient way to generate long chain nucleic acids that cannot be obtained by chemical synthesis alone.

Ligation of Nucleic Acid Regions or Subregions Assembling nucleic acids by a ligase may also be used. DNA or RNA ligases promote intermolecular ligation of the 5' and 3' ends of polynucleotide chains through the formation of a phosphodiester bond. Nucleic acids such as chimeric polynucleotides and/or circular nucleic acids may be prepared by ligation of one or more regions or subregions. DNA fragments can be joined by a ligase catalyzed reaction to create recombinant DNA with different functions. Two oligodeoxynucleotides, one with a 5' phosphoryl group and another with a free 3' hydroxyl group, serve as substrates for a DNA ligase.

Purification

Purification of the nucleic acids described herein may include, but is not limited to, nucleic acid clean-up, quality assurance and quality control. Clean-up may be performed by methods known in the arts such as, but not limited to, AGENCOURT® beads (Beckman Coulter Genomics, Danvers, MA), poly-T beads, LNATM oligo-T capture probes (EXIQON® Inc, Vedbaek, Denmark) or HPLC based purification methods such as, but not limited to, strong anion exchange HPLC, weak anion exchange HPLC, reverse phase HPLC (RP-HPLC), and hydrophobic interaction HPLC (HIC-HPLC). The term "purified" when used in relation to a nucleic acid such as a "purified nucleic acid" refers to one that is separated from at least one contaminant. A "contaminant" is any substance that makes another unfit, impure or inferior. Thus, a purified nucleic acid (e.g., DNA and RNA) is present in a form or setting different from that in which it is found in nature, or a form or setting different from that which existed prior to subjecting it to a treatment or purification method.

A quality assurance and/or quality control check may be conducted using methods such as, but not limited to, gel electrophoresis, UV absorbance, or analytical HPLC.

In some embodiments, the nucleic acids may be sequenced by methods including, but not limited to reverse-transcriptase-PCR.

Quantification

In some embodiments, the nucleic acids of the present disclosure may be quantified in exosomes or when derived from one or more bodily fluid. Bodily fluids include peripheral blood, serum, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, cowper's fluid or pre-ejaculatory fluid, sweat, fecal matter, hair, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates, blastocyl cavity fluid, and umbilical cord blood. Alternatively, exosomes may be retrieved from an organ selected from the group consisting of lung, heart, pancreas, stomach, intestine, bladder, kidney, ovary, testis, skin, colon, breast, prostate, brain, esophagus, liver, and placenta.

Assays may be performed using construct specific probes, cytometry, qRT-PCR, real-time PCR, PCR, flow cytometry, electrophoresis, mass spectrometry, or combinations thereof while the exosomes may be isolated using immunohistochemical methods such as enzyme linked immunosorbent assay (ELISA) methods. Exosomes may also be isolated by size exclusion chromatography, density gradient centrifugation, differential centrifugation, nanomembrane ultrafiltration, immunoabsorbent capture, affinity purification, microfluidic separation, or combinations thereof.

These methods afford the investigator the ability to monitor, in real time, the level of nucleic acids remaining or delivered. This is possible because the nucleic acids of the present disclosure, in some embodiments, differ from the endogenous forms due to the structural or chemical modifications.

In some embodiments, the nucleic acid may be quantified using methods such as, but not limited to, ultraviolet visible spectroscopy (UV/Vis). A non-limiting example of a UV/Vis spectrometer is a NANODROP® spectrometer (ThermoFisher, Waltham, MA). The quantified nucleic acid may be analyzed in order to determine if the nucleic acid may be of proper size, check that no degradation of the nucleic acid has occurred. Degradation of the nucleic acid may be checked by methods such as, but not limited to, agarose gel electrophoresis, HPLC based purification methods such as, but not limited to, strong anion exchange HPLC, weak anion exchange HPLC, reverse phase HPLC (RP-HPLC), and hydrophobic interaction HPLC (HIC-HPLC), liquid chromatography-mass spectrometry (LCMS), capillary electrophoresis (CE) and capillary gel electrophoresis (CGE).

Lipid Nanoparticles (LNPs)

In some embodiments, the mRNA of the disclosure is formulated in a lipid nanoparticle (LNP). Lipid nanoparticles typically comprise ionizable cationic lipid, non-cationic lipid, sterol and PEG lipid components along with the nucleic acid cargo of interest. The lipid nanoparticles of the disclosure can be generated using components, compositions, and methods as are generally known in the art, see for example PCT/US2016/052352; PCT/US2016/068300; PCT/US2017/037551; PCT/US2015/027400; PCT/US2016/047406; PCT/US2016000129; PCT/US2016/014280; PCT/US2016/014280; PCT/US2017/038426; PCT/US2014/027077; PCT/US2014/055394; PCT/US2016/52117; PCT/US2012/069610; PCT/US2017/027492; PCT/US2016/059575 and PCT/US2016/069491 all of which are incorporated by reference herein in their entirety.

Vaccines of the present disclosure are typically formulated in lipid nanoparticle. In some embodiments, the lipid nanoparticle comprises at least one ionizable cationic lipid, at least one non-cationic lipid, at least one sterol, and/or at least one polyethylene glycol (PEG)-modified lipid.

In some embodiments, the lipid nanoparticle comprises 40-50 mol % ionizable lipid, optionally 45-50 mol %, for example, 45-46 mol %, 46-47 mol %, 47-48 mol %, 48-49 mol %, or 49-50 mol % for example about 45 mol %, 45.5 mol %, 46 mol %, 46.5 mol %, 47 mol %, 47.5 mol %, 48 mol %, 48.5 mol %, 49 mol %, or 49.5 mol %.

In some embodiments, the lipid nanoparticle comprises 30-45 mol % sterol, optionally 35-40 mol %, for example, 30-31 mol %, 31-32 mol %, 32-33 mol %, 33-34 mol %, 35-35 mol %, 35-36 mol %, 36-37 mol %, 38-38 mol %, 38-39 mol %, or 39-40 mol %.

In some embodiments, the lipid nanoparticle comprises 5-15 mol % helper lipid, optionally 10-12 mol %, for example, 5-6 mol %, 6-7 mol %, 7-8 mol %, 8-9 mol %, 9-10 mol %, 10-11 mol %, 11-12 mol %, 12-13 mol %, 13-14 mol %, or 14-15 mol %.

In some embodiments, the lipid nanoparticle comprises 1-5% PEG lipid, optionally 1-3 mol %, for example 1.5 to 2.5 mol %, 1-2 mol %, 2-3 mol %, 3-4 mol %, or 4-5 mol %.

In some embodiments, the lipid nanoparticle comprises 20-60 mol % ionizable cationic lipid. For example, the lipid nanoparticle may comprise 20-50 mol %, 20-40 mol %, 20-30 mol %, 30-60 mol %, 30-50 mol %, 30-40 mol %, 40-60 mol %, 40-50 mol %, or 50-60 mol % ionizable cationic lipid. In some embodiments, the lipid nanoparticle comprises 20 mol %, 30 mol %, 40 mol %, 50 mol %, or 60 mol % ionizable cationic lipid. In some embodiments, the lipid nanoparticle comprises 35 mol %, 36 mol %, 37 mol %, 38 mol %, 39 mol %, 40 mol %, 41 mol %, 42 mol %, 43 mol %, 44 mol %, 45 mol %, 46 mol %, 47 mol %, 48 mol %, 49 mol %, 50 mol %, 51 mol %, 52 mol %, 53 mol %, 54 mol %, or 55 mol % ionizable cationic lipid.

In some embodiments, the lipid nanoparticle comprises 5-25 mol % non-cationic lipid. For example, the lipid nanoparticle may comprise 5-20 mol %, 5-15 mol %, 5-10 mol %, 10-25 mol %, 10-20 mol %, 10-25 mol %, 15-25 mol %, 15-20 mol %, or 20-25 mol % non-cationic lipid.

In some embodiments, the lipid nanoparticle comprises 5 mol %, 10 mol %, 15 mol %, 20 mol %, or 25 mol % non-cationic lipid.

In some embodiments, the lipid nanoparticle comprises 25-55 mol % sterol. For example, the lipid nanoparticle may comprise 25-50 mol %, 25-45 mol %, 25-40 mol %, 25-35 mol %, 25-30 mol %, 30-55 mol %, 30-50 mol %, 30-45 mol %, 30-40 mol %, 30-35 mol %, 35-55 mol %, 35-50 mol %, 35-45 mol %, 35-40 mol %, 40-55 mol %, 40-50 mol %, 40-45 mol %, 45-55 mol %, 45-50 mol %, or 50-55 mol % sterol. In some embodiments, the lipid nanoparticle comprises 25 mol %, 30 mol %, 35 mol %, 40 mol %, 45 mol %, 50 mol %, or 55 mol % sterol.

In some embodiments, the lipid nanoparticle comprises 0.5-15 mol % PEG-modified lipid. For example, the lipid nanoparticle may comprise 0.5-10 mol %, 0.5-5 mol %, 1-15 mol %, 1-10 mol %, 1-5 mol %, 2-15 mol %, 2-10 mol %, 2-5 mol %, 5-15 mol %, 5-10 mol %, or 10-15 mol %.

In some embodiments, the lipid nanoparticle comprises 0.5 mol %, 1 mol %, 2 mol %, 3 mol %, 4 mol %, 5 mol %, 6 mol %, 7 mol %, 8 mol %, 9 mol %, 10 mol %, 11 mol %, 12 mol %, 13 mol %, 14 mol %, or 15 mol % PEG-modified lipid.

In some embodiments, the lipid nanoparticle comprises 20-60 mol % ionizable cationic lipid, 5-25 mol % non-cationic lipid, 25-55 mol % sterol, and 0.5-15 mol % PEG-modified lipid.

In some embodiments, an ionizable cationic lipid of the disclosure comprises a compound of Formula (I):

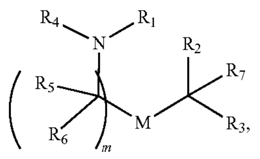

(I)

or a salt or isomer thereof, wherein:

$R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, $—(CH_2)_nQ$, $—(CH_2)_nCHQR$, —CHQR, $—CQ(R)_2$, and unsubstituted $C_{1-6}$ alkyl, where Q is selected from a carbocycle, heterocycle, —OR, $—O(CH_2)_nN(R)_2$, —C(O)OR, —OC(O)R, $—CX_3$, $—CX_2H$, $—CXH_2$, —CN, $—N(R)_2$, $—C(O)N(R)_2$, —N(R)C(O)R, $—N(R)S(O)_2R$, $—N(R)C(O)N(R)_2$, $—N(R)C(S)N(R)_2$, $—N(R)R_8$, $—O(CH_2)_nOR$, $—N(R)C(=NR_9)N(R)_2$, $—N(R)C(=CHR_9)N(R)_2$, $—OC(O)N(R)_2$, —N(R)C(O)OR, —N(OR)C(O)R, $—N(OR)S(O)_2R$, —N(OR)C(O)OR, $—N(OR)C(O)N(R)_2$, $—N(OR)C(S)N(R)_2$, $—N(OR)C(=NR_9)N(R)_2$, $—N(OR)C(=CHR_9)N(R)_2$, $—C(=NR_9)N(R)_2$, $—C(=NR_9)R$, —C(O)N(R)OR, and $—C(R)N(R)_2C(O)OR$, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, $—S(O)_2—$, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, $—S(O)_2R$, $—S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13.

In some embodiments, a subset of compounds of Formula (I) includes those in which when $R_4$ is $—(CH_2)_nQ$, $—(CH_2)n$ CHQR, —CHQR, or $—CQ(R)_2$, then (i) Q is not $—N(R)_2$ when n is 1, 2, 3, 4 or 5, or (ii) Q is not 5, 6, or 7-membered heterocycloalkyl when n is 1 or 2.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, $—(CH_2)_nQ$, $—(CH_2)_nCHQR$, —CHQR, $—CQ(R)_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, $—O(CH_2)_nN(R)_2$, —C(O)OR, —OC(O)R, $—CX_3$, $—CX_2H$, $—CXH_2$, —CN, $—C(O)N(R)_2$, —N(R)C(O)R, $—N(R)S(O)_2R$, $—N(R)C(O)N(R)_2$, $—N(R)C(S)N(R)_2$, $—CRN(R)_2C(O)OR$, $—N(R)R_8$, $—O(CH_2)_nOR$, $—N(R)C(=NR_9)N(R)_2$, $—N(R)C(=CHR_9)N(R)_2$, $—OC(O)N(R)_2$, —N(R)C(O)OR, —N(OR)C(O)R, $—N(OR)S(O)_2R$, —N(OR)C(O)OR, $—N(OR)C(O)N(R)_2$, $—N(OR)C(S)N(R)_2$, $—N(OR)C(=NR_9)N(R)_2$, $—N(OR)C(=CHR_9)N(R)_2$, $—C(=NR_9)N(R)_2$, $—C(=NR_9)R$, —C(O)N(R)OR, and a 5- to 14-membered heterocycloalkyl having one or more heteroatoms selected from N, O, and S which is substituted with one or more substituents selected from oxo (=O), OH, amino, mono- or di-alkylamino, and $C_{1-3}$ alkyl, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, $—S(O)_2—$, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, $—S(O)_2R$, $—S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, $—(CH_2)_nQ$, $—(CH_2)_nCHQR$, —CHQR, $—CQ(R)_2$, and unsubstituted $C_{1-6}$ alkyl, where Q is selected from a $C_{3-6}$ carbocycle, a 5- to 14-membered heterocycle having one or more heteroatoms selected from N, O, and S, —OR, $—O(CH_2)_nN(R)_2$, —C(O)OR, —OC(O)R, $—CX_3$, $—CX_2H$, $—CXH_2$, —CN, $—C(O)N(R)_2$, —N(R)C(O)R, $—N(R)S(O)_2R$, $—N(R)C(O)N(R)_2$, $—N(R)C(S)N(R)_2$, $—CRN(R)_2C(O)OR$, $—N(R)R_8$, $—O(CH_2)_nOR$, $—N(R)C(=NR_9)N(R)_2$, $—N(R)C(=CHR_9)N(R)_2$, $—OC(O)N(R)_2$, —N(R)C(O) OR, —N(OR)C(O)R, $—N(OR)S(O)_2R$, —N(OR)C(O)OR, $—N(OR)C(O)N(R)_2$, $—N(OR)C(S)N(R)_2$, $—N (OR)C(=NR_9)N(R)_2$, $—N(OR)C(=CHR_9)N(R)_2$, $—C(=NR_9)R$, —C(O)N(R)OR, and $—C(=NR_9)N(R)_2$, and each n is independently selected from 1, 2, 3, 4, and 5; and when Q is a 5- to 14-membered heterocycle and (i) $R_4$ is $—(CH_2)_nQ$ in which n is 1 or 2, or (ii) $R_4$ is $—(CH_2)_nCHQR$ in which n is 1, or (iii) $R_4$ is —CHQR, and $—CQ(R)_2$, then Q is either a 5- to 14-membered heteroaryl or 8- to 14-membered heterocycloalkyl;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, $—S(O)_2—$, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —$S(O)_2R$, —$S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_nQ$, —$(CH_2)$·CHQR, —CHQR, —CQ$(R)_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —$O(CH_2)_nN(R)_2$, —C(O)OR, —OC(O)R, —$CX_3$, —$CX_2H$, —$CXH_2$, —CN, —C(O)$N(R)_2$, —N(R)C(O)R, —N(R)$S(O)_2R$, —N(R)C(O)$N(R)_2$, —N(R)C(S)$N(R)_2$, —CRN$(R)_2$C(O)OR, —N(R)$R_8$, —$O(CH_2)_nOR$, —N(R)C(=$NR_9$)$N(R)_2$, —N(R)C(=$CHR_9$)$N(R)_2$, —OC(O)$N(R)_2$, —N(R)C(O)OR, —N(OR)C(O)R, —N(OR)$S(O)_2R$, —N(OR)C(O)OR, —N(OR)C(O)$N(R)_2$, —N(OR)C(S)$N(R)_2$, —N(OR)C(=$NR_9$)$N(R)_2$, —N(OR)C(=$CHR_9$)$N(R)_2$, —C(=$NR_9$)R, —C(O)N(R)OR, and —C(=$NR_9$)$N(R)_2$, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —$S(O)_2R$, —$S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{2-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is —$(CH_2)_nQ$ or —$(CH_2)_n$CHQR, where Q is —N$(R)_2$, and n is selected from 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of —$(CH_2)_nQ$, —$(CH_2)$·CHQR, —CHQR, and —CQ$(R)_2$, where Q is —N$(R)_2$, and n is selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, a subset of compounds of Formula (I) includes those of Formula (IA)

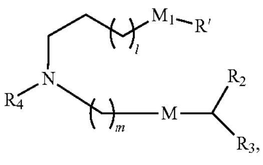

or a salt or isomer thereof, wherein 1 is selected from 1, 2, 3, 4, and 5; m is selected from 5, 6, 7, 8, and 9; $M_1$ is a bond or M'; $R_4$ is unsubstituted $C_{1-3}$ alkyl, or —$(CH_2)_n$Q, in which Q is OH, —NHC(S)N$(R)_2$, —NHC(O)N$(R)_2$, —N(R)C(O)R, —N(R)S$(O)_2$R, —N(R)$R_8$, —NHC(=N$R_9$)N$(R)_2$, —NHC(=CH$R_9$)N$(R)_2$, —OC(O)N$(R)_2$, —N(R)C(O)OR, heteroaryl or heterocycloalkyl; M and M' are independently selected from —C(O)O—, —OC(O)—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl.

In some embodiments, a subset of compounds of Formula (I) includes those of Formula (II)

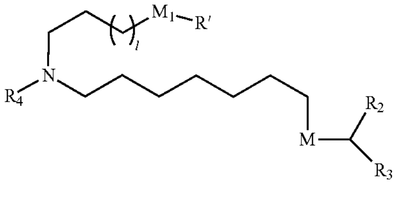

or a salt or isomer thereof, wherein 1 is selected from 1, 2, 3, 4, and 5; $M_1$ is a bond or M'; $R_4$ is unsubstituted $C_{1-3}$ alkyl, or —$(CH_2)_n$Q, in which n is 2, 3, or 4, and Q is OH, —NHC(S)N$(R)_2$, —NHC(O)N$(R)_2$, —N(R)C(O)R, —N(R)S$(O)_2$R, —N(R)$R_8$, —NHC(=N$R_9$)N$(R)_2$, —NHC(=CH$R_9$)N$(R)_2$, —OC(O)N$(R)_2$, —N(R)C(O)OR, heteroaryl or heterocycloalkyl; M and M' are independently selected from —C(O)O—, —OC(O)—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl.

In some embodiments, a subset of compounds of Formula (I) includes those of Formula (IIa), (IIb), (IIc), or (IIe):

(IIa)

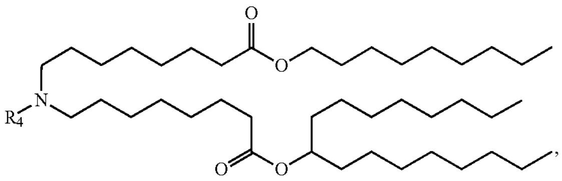

(IIb)

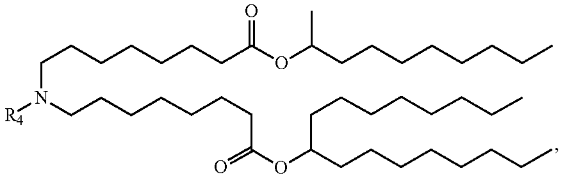

(IIc)

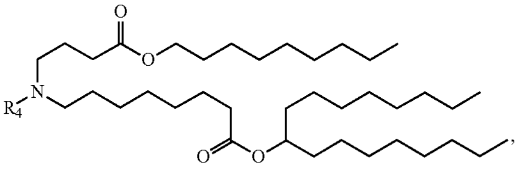

, or (IIe)

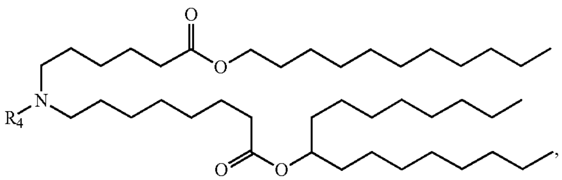

or a salt or isomer thereof, wherein $R_4$ is as described herein.

In some embodiments, a subset of compounds of Formula (I) includes those of Formula (IId):

(IId)

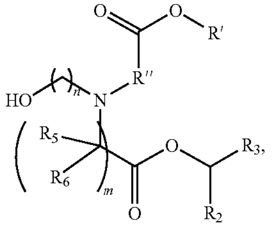

or a salt or isomer thereof, wherein n is 2, 3, or 4; and m, R', R", and $R_2$ through $R_6$ are as described herein. For example, each of $R_2$ and $R_3$ may be independently selected from the group consisting of $C_{5-14}$ alkyl and $C_{5-14}$ alkenyl.

In some embodiments, an ionizable cationic lipid of the disclosure comprises a compound having structure:

(Compound I)

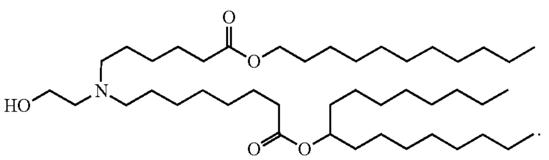

In some embodiments, an ionizable cationic lipid of the disclosure comprises a compound having structure:

(Compound II)

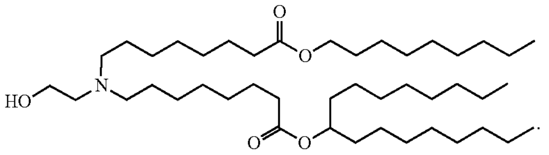

In some embodiments, a non-cationic lipid of the disclosure comprises 1,2-distearoyl-sn-glycero-3-phosphocholine (DSPC), 1,2-dioleoyl-sn-glycero-3-phosphoethanolamine (DOPE), 1,2-dilinoleoyl-sn-glycero-3-phosphocholine (DLPC), 1,2-dimyristoyl-sn-gly cero-phosphocholine (DMPC), 1,2-dioleoyl-sn-glycero-3-phosphocholine (DOPC), 1,2-dipalmitoyl-sn-glycero-3-phosphocholine (DPPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2 cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), sphingomyelin, and mixtures thereof.

In some embodiments, a PEG modified lipid of the disclosure comprises a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and mixtures thereof. In some embodiments, the PEG-modified lipid is DMG-PEG, PEG-c-DOMG (also referred to as PEG-DOMG), PEG-DSG and/or PEG-DPG.

In some embodiments, a sterol of the disclosure comprises cholesterol, fecosterol, sitosterol, ergosterol, campesterol, stigmasterol, brassicasterol, tomatidine, ursolic acid, alpha-tocopherol, and mixtures thereof.

In some embodiments, a LNP of the disclosure comprises an ionizable cationic lipid of Compound 1, wherein the non-cationic lipid is DSPC, the structural lipid that is cholesterol, and the PEG lipid is DMG-PEG.

In some embodiments, the lipid nanoparticle comprises 45-55 mole percent (mol %) ionizable cationic lipid. For example, lipid nanoparticle may comprise 45, 46, 47, 48, 49, 50, 51, 52, 53, 54, or 55 mol % ionizable cationic lipid.

In some embodiments, the lipid nanoparticle comprises 5-15 mol %, 5-10 mol %, or 10-15 mol % DSPC. For example, the lipid nanoparticle may comprise 5, 6, 7, 8, 9, 10, 11, 12, 13, 14, or 15 mol % DSPC.

In some embodiments, the lipid nanoparticle comprises 35-40 mol % cholesterol. For example, the lipid nanoparticle may comprise 35, 35.5, 36, 36.5, 37, 37.5, 38, 38.5, 39, 39.5, or 40 mol % cholesterol.

In some embodiments, the lipid nanoparticle comprises 1-2 mol %, 1-3 mol %, 1-4 mol %, or 1-5 mol % DMG-PEG. For example, the lipid nanoparticle may comprise 1, 1.5, 2, 2.5, 3, or 3.5 mol % DMG-PEG.

In some embodiments, the lipid nanoparticle comprises 50 mol % ionizable cationic lipid, 10 mol % DSPC, 38.5 mol % cholesterol, and 1.5 mol % DMG-PEG.

In some embodiments, the lipid nanoparticle comprises 49 mol % ionizable cationic lipid, 10 mol % DSPC, 38.5 mol % cholesterol, and 2.5 mol % DMG-PEG.

In some embodiments, the lipid nanoparticle comprises 49 mol % ionizable cationic lipid, 11 mol % DSPC, 38.5 mol % cholesterol, and 1.5 mol % DMG-PEG.

In some embodiments, the lipid nanoparticle comprises 48 mol % ionizable cationic lipid, 11 mol % DSPC, 38.5 mol % cholesterol, and 2.5 mol % DMG-PEG.

In some embodiments, an LNP of the disclosure comprises an N:P ratio of from about 2:1 to about 30:1.

In some embodiments, an LNP of the disclosure comprises an N:P ratio of about 6:1.

In some embodiments, an LNP of the disclosure comprises an N:P ratio of about 3:1.

In some embodiments, an LNP of the disclosure comprises a wt/wt ratio of the ionizable cationic lipid component to the RNA of from about 10:1 to about 100:1.

In some embodiments, an LNP of the disclosure comprises a wt/wt ratio of the ionizable cationic lipid component to the RNA of about 20:1.

In some embodiments, an LNP of the disclosure comprises a wt/wt ratio of the ionizable cationic lipid component to the RNA of about 10:1.

In some embodiments, an LNP of the disclosure has a mean diameter from about 50 nm to about 150 nm.

In some embodiments, an LNP of the disclosure has a mean diameter from about 70 nm to about 120 nm.

Multivalent Vaccines

The compositions, as provided herein, may include RNA or multiple RNAs encoding two or more antigens of the same or different species. In some embodiments, composition includes an mRNA or multiple mRNAs encoding two or more coronavirus antigens. In some embodiments, the RNA may encode 1, 2, 3, 4, 5, 6, 7, 8, 9, 10, 11, 12, or more coronavirus antigens.

In some embodiments, two or more different mRNA encoding antigens may be formulated in the same lipid nanoparticle. In other embodiments, two or more different RNA encoding antigens may be formulated in separate lipid nanoparticles (each RNA formulated in a single lipid nanoparticle). The lipid nanoparticles may then be combined and administered as a single vaccine composition (e.g., comprising multiple RNA encoding multiple antigens) or may be administered separately.

Combination Vaccines

The compositions, as provided herein, may include an mRNA or multiple RNAs encoding two or more antigens of the same or different viral strains. Also provided herein are combination vaccines that include RNA encoding one or more coronavirus and one or more antigen(s) of a different organism. Thus, the vaccines of the present disclosure may be combination vaccines that target one or more antigens of the same strain/species, or one or more antigens of different strains/species, e.g., antigens which induce immunity to organisms which are found in the same geographic areas where the risk of coronavirus infection is high or organisms to which an individual is likely to be exposed to when exposed to a coronavirus.

Pharmaceutical Formulations

Provided herein are compositions (e.g., pharmaceutical compositions), methods, kits and reagents for prevention or treatment of coronavirus in humans and other mammals, for example. The compositions provided herein can be used as therapeutic or prophylactic agents. They may be used in medicine to prevent and/or treat a coronavirus infection.

In some embodiments, the coronavirus vaccine containing RNA as described herein can be administered to a subject (e.g., a mammalian subject, such as a human subject), and the mRNAs are translated in vivo to produce an antigenic polypeptide (antigen).

An "effective amount" of a composition (e.g., comprising RNA) is based, at least in part, on the target tissue, target cell type, means of administration, physical characteristics of the RNA (e.g., length, nucleotide composition, and/or extent of modified nucleosides), other components of the vaccine, and other determinants, such as age, body weight, height, sex and general health of the subject. Typically, an effective amount of a composition provides an induced or boosted immune response as a function of antigen production in the cells of the subject. In some embodiments, an effective amount of the composition containing mRNA having at least one chemical modifications are more efficient than a composition containing a corresponding unmodified polynucleotide encoding the same antigen or a peptide antigen. Increased antigen production may be demonstrated by increased cell transfection (the percentage of cells transfected with the RNA vaccine), increased protein translation and/or expression from the polynucleotide, decreased nucleic acid degradation (as demonstrated, for example, by increased duration of protein translation from a modified polynucleotide), or altered antigen specific immune response of the host cell.

The term "pharmaceutical composition" refers to the combination of an active agent with a carrier, inert or active, making the composition especially suitable for diagnostic or therapeutic use in vivo or ex vivo. A "pharmaceutically acceptable carrier," after administered to or upon a subject, does not cause undesirable physiological effects. The carrier in the pharmaceutical composition must be "acceptable" also in the sense that it is compatible with the active ingredient and can be capable of stabilizing it. One or more solubilizing agents can be utilized as pharmaceutical carriers for delivery of an active agent. Examples of a pharmaceutically acceptable carrier include, but are not limited to, biocompatible vehicles, adjuvants, additives, and diluents to achieve a composition usable as a dosage form. Examples of other carriers include colloidal silicon oxide, magnesium stearate, cellulose, and sodium lauryl sulfate. Additional suitable pharmaceutical carriers and diluents, as well as pharmaceutical necessities for their use, are described in Remington's Pharmaceutical Sciences.

In some embodiments, the compositions (comprising polynucleotides and their encoded polypeptides) in accordance with the present disclosure may be used for treatment or prevention of a coronavirus infection. A composition may be administered prophylactically or therapeutically as part of an active immunization scheme to healthy individuals or early in infection during the incubation phase or during active infection after onset of symptoms. In some embodiments, the amount of RNA provided to a cell, a tissue or a subject may be an amount effective for immune prophylaxis.

A composition may be administered with other prophylactic or therapeutic compounds. As a non-limiting example, a prophylactic or therapeutic compound may be an adjuvant or a booster. As used herein, when referring to a prophylactic composition, such as a vaccine, the term "booster" refers to an extra administration of the prophylactic (vaccine) composition. A booster (or booster vaccine) may be given after an earlier administration of the prophylactic composition. The time of administration between the initial administration of the prophylactic composition and the booster may be, but is not limited to, 1 minute, 2 minutes, 3 minutes, 4 minutes, 5 minutes, 6 minutes, 7 minutes, 8 minutes, 9 minutes, 10 minutes, 15 minutes, 20 minutes 35 minutes, 40 minutes, 45 minutes, 50 minutes, 55 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 36 hours, 2 days, 3 days, 4 days, 5 days, 6 days, 1 week, 10 days, 2 weeks, 3 weeks, 1 month, 2 months, 3 months, 4 months, 5 months, 6 months, 7 months, 8 months, 9 months, 10 months, 11 months, 1 year, 18 months, 2 years, 3 years, 4 years, 5 years, 6 years, 7 years, 8 years, 9 years, 10 years, 11 years, 12 years, 13 years, 14 years, 15 years, 16 years, 17 years, 18 years, 19 years, 20 years, 25 years, 30 years, 35 years, 40 years, 45 years, 50 years, 55 years, 60 years, 65 years, 70 years, 75 years, 80 years, 85 years, 90 years, 95 years or more than 99 years. In exemplary embodiments, the time of administration between the initial administration of the prophylactic composition and the booster may be, but is not limited to, 1 week, 2 weeks, 3 weeks, 1 month, 2 months, 3 months, 6 months or 1 year.

In some embodiments, a composition may be administered intramuscularly, intranasally or intradermally, similarly to the administration of inactivated vaccines known in the art.

A composition may be utilized in various settings depending on the prevalence of the infection or the degree or level of unmet medical need. As a non-limiting example, the RNA vaccines may be utilized to treat and/or prevent a variety of infectious disease. RNA vaccines have superior properties in that they produce much larger antibody titers, better neutralizing immunity, produce more durable immune responses, and/or produce responses earlier than commercially available vaccines.

Provided herein are pharmaceutical compositions including RNA and/or complexes optionally in combination with one or more pharmaceutically acceptable excipients.

The RNA may be formulated or administered alone or in conjunction with one or more other components. For example, a composition may comprise other components including, but not limited to, adjuvants.

In some embodiments, a composition does not include an adjuvant (they are adjuvant free).

An RNA may be formulated or administered in combination with one or more pharmaceutically-acceptable excipients. In some embodiments, vaccine compositions comprise at least one additional active substance, such as, for example, a therapeutically-active substance, a prophylactically-active substance, or a combination of both. Vaccine compositions may be sterile, pyrogen-free or both sterile and pyrogen-free. General considerations in the formulation and/or manufacture of pharmaceutical agents, such as vaccine compositions, may be found, for example, in Remington: The Science and Practice of Pharmacy 21st ed., Lippincott Williams & Wilkins, 2005 (incorporated herein by reference in its entirety).

In some embodiments, a composition is administered to humans, human patients or subjects. For the purposes of the present disclosure, the phrase "active ingredient" generally refers to the RNA vaccines or the polynucleotides contained therein, for example, mRNA encoding antigens.

Formulations of the vaccine compositions described herein may be prepared by any method known or hereafter developed in the art of pharmacology. In general, such preparatory methods include the step of bringing the active ingredient (e.g., mRNA) into association with an excipient and/or one or more other accessory ingredients, and then, if necessary and/or desirable, dividing, shaping and/or packaging the product into a desired single- or multi-dose unit.

Relative amounts of the active ingredient, the pharmaceutically acceptable excipient, and/or any additional ingredients in a pharmaceutical composition in accordance with the disclosure will vary, depending upon the identity, size, and/or condition of the subject treated and further depending upon the route by which the composition is to be administered. By way of example, the composition may comprise between 0.1% and 100%, e.g., between 0.5 and 50%, between 1-30%, between 5-80%, at least 80% (w/w) active ingredient.

In some embodiments, an mRNA is formulated using one or more excipients to: (1) increase stability; (2) increase cell transfection; (3) permit the sustained or delayed release (e.g., from a depot formulation); (4) alter the biodistribution (e.g., target to specific tissues or cell types); (5) increase the translation of encoded protein in vivo; and/or (6) alter the release profile of encoded protein (antigen) in vivo. In addition to traditional excipients such as any and all solvents, dispersion media, diluents, or other liquid vehicles, dispersion or suspension aids, surface active agents, isotonic agents, thickening or emulsifying agents, preservatives, excipients can include, without limitation, lipidoids, liposomes, lipid nanoparticles, polymers, lipoplexes, core-shell nanoparticles, peptides, proteins, cells transfected with the RNA (e.g., for transplantation into a subject), hyaluronidase, nanoparticle mimics and combinations thereof.

Dosing/Administration

Provided herein are compositions (e.g., RNA vaccines), methods, kits and reagents for prevention and/or treatment of coronavirus infection in humans and other mammals. Immunizing compositions can be used as therapeutic or prophylactic agents. In some embodiments, compositions are used to provide prophylactic protection from coronavirus infection. In some embodiments, compositions are used to treat a coronavirus infection. In some embodiments, embodiments, compositions are used in the priming of immune effector cells, for example, to activate peripheral blood mononuclear cells (PBMCs) ex vivo, which are then infused (re-infused) into a subject.

A subject may be any mammal, including non-human primate and human subjects. Typically, a subject is a human subject.

In some embodiments, a composition (e.g., RNA a vaccine) is administered to a subject (e.g., a mammalian subject, such as a human subject) in an effective amount to induce an antigen-specific immune response. The RNA encoding the coronavirus antigen is expressed and translated in vivo to produce the antigen, which then stimulates an immune response in the subject.

Prophylactic protection from a coronavirus can be achieved following administration of a composition of the present disclosure. Immunizing compositions can be administered once, twice, three times, four times or more but it is likely sufficient to administer the vaccine once (optionally followed by a single booster). It is possible, although less desirable, to administer a composition to an infected individual to achieve a therapeutic response. Dosing may need to be adjusted accordingly.

A method of eliciting an immune response in a subject against a coronavirus antigen (or multiple antigens) is provided in aspects of the present disclosure. In some embodiments, a method involves administering to the subject a composition comprising a mRNA having an open reading frame encoding a coronavirus antigen, thereby inducing in the subject an immune response specific to the coronavirus antigen, wherein anti-antigen antibody titer in the subject is increased following vaccination relative to anti-antigen antibody titer in a subject vaccinated with a prophylactically effective dose of a traditional vaccine against the antigen. An "anti-antigen antibody" is a serum antibody the binds specifically to the antigen.

A prophylactically effective dose is an effective dose that prevents infection with the virus at a clinically acceptable level. In some embodiments, the effective dose is a dose listed in a package insert for the vaccine. A traditional vaccine, as used herein, refers to a vaccine other than the mRNA vaccines of the present disclosure. For instance, a traditional vaccine includes, but is not limited, to live microorganism vaccines, killed microorganism vaccines, subunit vaccines, protein antigen vaccines, DNA vaccines, virus like particle (VLP) vaccines, etc. In exemplary embodiments, a traditional vaccine is a vaccine that has achieved regulatory approval and/or is registered by a national drug regulatory body, for example the Food and Drug Administration (FDA) in the United States or the European Medicines Agency (EMA).

In some embodiments, the anti-antigen antibody titer in the subject is increased 1 log to 10 log following vaccination relative to anti-antigen antibody titer in a subject vaccinated with a prophylactically effective dose of a traditional vaccine against the coronavirus or an unvaccinated subject. In some embodiments, the anti-antigen antibody titer in the subject is increased 1 log, 2 log, 3 log, 4 log, 5 log, or 10 log following vaccination relative to anti-antigen antibody titer in a subject vaccinated with a prophylactically effective dose of a traditional vaccine against the coronavirus or an unvaccinated subject.

A method of eliciting an immune response in a subject against a coronavirus is provided in other aspects of the disclosure. The method involves administering to the subject a composition comprising an mRNA comprising an open reading frame encoding a coronavirus antigen, thereby inducing in the subject an immune response specific to the coronavirus, wherein the immune response in the subject is equivalent to an immune response in a subject vaccinated with a traditional vaccine against the coronavirus at 2 times to 100 times the dosage level relative to the composition.

In some embodiments, the immune response in the subject is equivalent to an immune response in a subject vaccinated with a traditional vaccine at twice the dosage level relative to a composition of the present disclosure. In some embodiments, the immune response in the subject is equivalent to an immune response in a subject vaccinated with a traditional vaccine at three times the dosage level relative to a composition of the present disclosure. In some embodiments, the immune response in the subject is equivalent to an immune response in a subject vaccinated with a traditional vaccine at 4 times, 5 times, 10 times, 50 times, or 100 times the dosage level relative to a composition of the present disclosure. In some embodiments, the immune response in the subject is equivalent to an immune response in a subject vaccinated with a traditional vaccine at 10 times to 1000 times the dosage level relative to a composition of the present disclosure. In some embodiments, the immune response in the subject is equivalent to an immune response in a subject vaccinated with a traditional vaccine at 100 times to 1000 times the dosage level relative to a composition of the present disclosure.

In other embodiments, the immune response is assessed by determining [protein] antibody titer in the subject. In other embodiments, the ability of serum or antibody from an immunized subject is tested for its ability to neutralize viral uptake or reduce coronavirus transformation of human B lymphocytes. In other embodiments, the ability to promote a robust T cell response(s) is measured using art recognized techniques.

Other aspects the disclosure provide methods of eliciting an immune response in a subject against a coronavirus by administering to the subject composition comprising an mRNA having an open reading frame encoding a coronavirus antigen, thereby inducing in the subject an immune response specific to the coronavirus antigen, wherein the immune response in the subject is induced 2 days to 10 weeks earlier relative to an immune response induced in a subject vaccinated with a prophylactically effective dose of a traditional vaccine against the coronavirus. In some embodiments, the immune response in the subject is induced in a subject vaccinated with a prophylactically effective dose of a traditional vaccine at 2 times to 100 times the dosage level relative to a composition of the present disclosure.

In some embodiments, the immune response in the subject is induced 2 days, 3 days, 1 week, 2 weeks, 3 weeks, 5 weeks, or 10 weeks earlier relative to an immune response induced in a subject vaccinated with a prophylactically effective dose of a traditional vaccine.

Also provided herein are methods of eliciting an immune response in a subject against a coronavirus by administering to the subject an mRNA having an open reading frame encoding a first antigen, wherein the RNA does not include a stabilization element, and wherein an adjuvant is not co-formulated or co-administered with the vaccine.

A composition may be administered by any route that results in a therapeutically effective outcome. These include, but are not limited, to intradermal, intramuscular, intranasal, and/or subcutaneous administration. The present disclosure provides methods comprising administering RNA vaccines to a subject in need thereof. The exact amount required will vary from subject to subject, depending on the species, age, and general condition of the subject, the severity of the disease, the particular composition, its mode of administration, its mode of activity, and the like. The RNA is typically formulated in dosage unit form for ease of administration and uniformity of dosage. It will be understood, however, that the total daily usage of the RNA may be decided by the attending physician within the scope of sound medical judgment. The specific therapeutically effective, prophylactically effective, or appropriate imaging dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The effective amount of the RNA, as provided herein, may be as low as 20 μg, administered for example as a single dose or as two 10 μg doses. In some embodiments, the effective amount is a total dose of 20 μg-300 μg or 25 μg-300 μg. For example, the effective amount may be a total dose of 20 μg, 25 μg, 30 μg, 35 μg, 40 μg, 45 μg, 50 μg, 55 μg, 60 μg, 65 μg, 70 μg, 75 μg, 80 μg, 85 μg, 90 μg, 95 μg, 100 μg, 110 μg, 120 μg, 130 μg, 140 μg, 150 μg, 160 μg, 170 μg, 180 μg, 190 μg, 200 μg, 250 μg, or 300 μg. In some embodiments, the effective amount is a total dose of 20 μg. In some embodiments, the effective amount is a total dose of 25 μg. In some embodiments, the effective amount is a total dose of 50 μg. In some embodiments, the effective amount is a total dose of 75 μg. In some embodiments, the effective amount is a total dose of 100 μg. In some embodiments, the effective amount is a total dose of 150 μg. In some embodiments, the effective amount is a total dose of 200 μg. In some embodiments, the effective amount is a total dose of 250 μg. In some embodiments, the effective amount is a total dose of 300 μg.

The RNA described herein can be formulated into a dosage form described herein, such as an intranasal, intratracheal, or injectable (e.g., intravenous, intraocular, intravitreal, intramuscular, intradermal, intracardiac, intraperitoneal, and subcutaneous).

Vaccine Efficacy

Some aspects of the present disclosure provide formulations of the compositions (e.g., RNA vaccines), wherein the RNA is formulated in an effective amount to produce an antigen specific immune response in a subject (e.g., production of antibodies specific to a coronavirus antigen). "An effective amount" is a dose of the RNA effective to produce an antigen-specific immune response. Also provided herein are methods of inducing an antigen-specific immune response in a subject.

As used herein, an immune response to a vaccine or LNP of the present disclosure is the development in a subject of a humoral and/or a cellular immune response to a (one or more) coronavirus protein(s) present in the vaccine. For purposes of the present disclosure, a "humoral" immune response refers to an immune response mediated by antibody molecules, including, e.g., secretory (IgA) or IgG molecules, while a "cellular" immune response is one mediated by T-lymphocytes (e.g., CD4+ helper and/or CD8+ T cells (e.g., CTLs) and/or other white blood cells. One important aspect of cellular immunity involves an antigen-specific response by cytolytic T-cells (CTLs). CTLs have specificity for peptide antigens that are presented in association with proteins encoded by the major histocompatibility complex (MHC) and expressed on the surfaces of cells. CTLs help induce and promote the destruction of intracellular microbes or the lysis of cells infected with such microbes. Another aspect of cellular immunity involves and antigen-specific response by helper T-cells. Helper T-cells act to help stimulate the function and focus the activity nonspecific effector cells against cells displaying peptide antigens in association with MHC molecules on their surface. A cellular immune response also leads to the production of cytokines, chemokines, and other such molecules produced by activated T-cells and/or other white blood cells including those derived from CD4+ and CD8+ T-cells.

In some embodiments, the antigen-specific immune response is characterized by measuring an anti-coronavirus antigen antibody titer produced in a subject administered a composition as provided herein. An antibody titer is a measurement of the amount of antibodies within a subject, for example, antibodies that are specific to a particular antigen or epitope of an antigen. Antibody titer is typically expressed as the inverse of the greatest dilution that provides a positive result. Enzyme-linked immunosorbent assay (ELISA) is a common assay for determining antibody titers, for example.

A variety of serological tests can be used to measure antibody against encoded antigen of interest, for example, SAR-CoV-2 virus or SAR-CoV-2 viral antigen, e.g., SAR-CoV-2 spike or S protein, of domain thereof. These tests include the hemagglutination-inhibition test, complement fixation test, fluorescent antibody test, enzyme-linked immunosorbent assay (ELISA), and plaque reduction neutralization test (PRNT). Each of these tests measures different antibody activities. In exemplary embodiments, A plaque reduction neutralization test, or PRNT (e.g., PRNT50 or PRNT90) is used as a serological correlate of protection. PRNT measures the biological parameter of in vitro virus neutralization and is the most serologically virus-specific test among certain classes of viruses, correlating well to serum levels of protection from virus infection.

The basic design of the PRNT allows for virus-antibody interaction to occur in a test tube or microtiter plate, and then measuring antibody effects on viral infectivity by plating the mixture on virus-susceptible cells, preferably cells of mammalian origin. The cells are overlaid with a semi-solid media that restricts spread of progeny virus. Each virus that initiates a productive infection produces a localized area of infection (a plaque), that can be detected in a variety of ways. Plaques are counted and compared back to the starting concentration of virus to determine the percent reduction in total virus infectivity. In PRNT, the serum sample being tested is usually subjected to serial dilutions prior to mixing with a standardized amount of virus. The concentration of virus is held constant such that, when added to susceptible cells and overlaid with semi-solid media, individual plaques can be discerned and counted. In this way, PRNT end-point titers can be calculated for each serum sample at any selected percent reduction of virus activity.

In functional assays intended to assess vaccinal immunogenicity, the serum sample dilution series for antibody titration should ideally start below the "seroprotective" threshold titer. Regarding SARS-CoV-2 neutralizing antibodies, the "seroprotective" threshold titer remains unknown; but a seropositivity threshold of 1:10 can be considered a seroprotection threshold in certain embodiments.

PRNT end-point titers are expressed as the reciprocal of the last serum dilution showing the desired percent reduction in plaque counts. The PRNT titer can be calculated based on a 50% or greater reduction in plaque counts (PRNT50). A PRNT50 titer is preferred over titers using higher cut-offs (e.g., PRNT90) for vaccine sera, providing more accurate results from the linear portion of the titration curve.

There are several ways to calculate PRNT titers. The simplest and most widely used way to calculate titers is to count plaques and report the titer as the reciprocal of the last serum dilution to show >50% reduction of the input plaque count as based on the back-titration of input plaques. Use of curve fitting methods from several serum dilutions may permit calculation of a more precise result. There are a variety of computer analysis programs available for this (e.g., SPSS or GraphPad Prism).

In some embodiments, an antibody titer is used to assess whether a subject has had an infection or to determine whether immunizations are required. In some embodiments, an antibody titer is used to determine the strength of an autoimmune response, to determine whether a booster immunization is needed, to determine whether a previous vaccine was effective, and to identify any recent or prior infections. In accordance with the present disclosure, an antibody titer may be used to determine the strength of an immune response induced in a subject by a composition (e.g., RNA vaccine).

In some embodiments, an anti-coronavirus antigen antibody titer produced in a subject is increased by at least 1 log relative to a control. For example, anti-coronavirus antigen antibody titer produced in a subject may be increased by at least 1.5, at least 2, at least 2.5, or at least 3 log relative to a control. In some embodiments, the anti-coronavirus antigen antibody titer produced in the subject is increased by 1, 1.5, 2, 2.5 or 3 log relative to a control. In some embodiments, the anti-coronavirus antigen antibody titer produced in the subject is increased by 1-3 log relative to a control. For example, the anti-coronavirus antigen antibody titer produced in a subject may be increased by 1-1.5, 1-2, 1-2.5, 1-3, 1.5-2, 1.5-2.5, 1.5-3, 2-2.5, 2-3, or 2.5-3 log relative to a control.

In some embodiments, the anti-coronavirus antigen antibody titer produced in a subject is increased at least 2 times relative to a control. For example, the anti-coronavirus antigen antibody titer produced in a subject may be increased at least 3 times, at least 4 times, at least 5 times, at least 6 times, at least 7 times, at least 8 times, at least 9 times, or at least 10 times relative to a control. In some embodiments, the anti-coronavirus antigen antibody titer produced in the subject is increased 2, 3, 4, 5, 6, 7, 8, 9, or 10 times relative to a control. In some embodiments, the anti-coronavirus antigen antibody titer produced in a subject is increased 2-10 times relative to a control. For example, the anti-coronavirus antigen antibody titer produced in a subject may be increased 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9, or 9-10 times relative to a control.

In some embodiments, an antigen-specific immune response is measured as a ratio of geometric mean titer (GMT), referred to as a geometric mean ratio (GMR), of serum neutralizing antibody titers to coronavirus. A geometric mean titer (GMT) is the average antibody titer for a group of subjects calculated by multiplying all values and taking the nth root of the number, where n is the number of subjects with available data.

A control, in some embodiments, is an anti-coronavirus antigen antibody titer produced in a subject who has not been administered a composition (e.g., RNA vaccine). In some embodiments, a control is an anti-coronavirus antigen antibody titer produced in a subject administered a recombinant or purified protein vaccine. Recombinant protein vaccines typically include protein antigens that either have been produced in a heterologous expression system (e.g., bacteria or yeast) or purified from large amounts of the pathogenic organism.

In some embodiments, the ability of a composition (e.g., RNA vaccine) to be effective is measured in a murine model. For example, a composition may be administered to a murine model and the murine model assayed for induction of neutralizing antibody titers. Viral challenge studies may also be used to assess the efficacy of a vaccine of the present disclosure. For example, a composition may be administered to a murine model, the murine model challenged with virus, and the murine model assayed for survival and/or immune response (e.g., neutralizing antibody response, T cell response (e.g., cytokine response)).

In some embodiments, an effective amount of a composition (e.g., RNA vaccine) is a dose that is reduced compared to the standard of care dose of a recombinant protein vaccine. A "standard of care," as provided herein, refers to a medical or psychological treatment guideline and can be general or specific. "Standard of care" specifies appropriate treatment based on scientific evidence and collaboration between medical professionals involved in the treatment of a given condition. It is the diagnostic and treatment process that a physician/clinician should follow for a certain type of patient, illness or clinical circumstance. A "standard of care dose," as provided herein, refers to the dose of a recombinant or purified protein vaccine, or a live attenuated or inactivated vaccine, or a VLP vaccine, that a physician/clinician or other medical professional would administer to a subject to treat or prevent coronavirus infection or a related condition, while following the standard of care guideline for treating or preventing coronavirus infection or a related condition.

In some embodiments, the anti-coronavirus antigen antibody titer produced in a subject administered an effective amount of a composition is equivalent to an anti-coronavirus antigen antibody titer produced in a control subject administered a standard of care dose of a recombinant or purified protein vaccine, or a live attenuated or inactivated vaccine, or a VLP vaccine.

Vaccine efficacy may be assessed using standard analyses (see, e.g., Weinberg et al., J Infect Dis. 2010 Jun. 1; 201(11):1607-10). For example, vaccine efficacy may be measured by double-blind, randomized, clinical controlled trials. Vaccine efficacy may be expressed as a proportionate reduction in disease attack rate (AR) between the unvaccinated (ARU) and vaccinated (ARV) study cohorts and can be calculated from the relative risk (RR) of disease among the vaccinated group with use of the following formulas:

$$\text{Efficacy}=(\text{ARU}-\text{ARV})/\text{ARU}\times 100; \text{ and}$$

$$\text{Efficacy}=(1-\text{RR})\times 100.$$

Likewise, vaccine effectiveness may be assessed using standard analyses (see, e.g., Weinberg et al., J Infect Dis. 2010 Jun. 1; 201(11):1607-10). Vaccine effectiveness is an assessment of how a vaccine (which may have already proven to have high vaccine efficacy) reduces disease in a population. This measure can assess the net balance of benefits and adverse effects of a vaccination program, not just the vaccine itself, under natural field conditions rather than in a controlled clinical trial. Vaccine effectiveness is proportional to vaccine efficacy (potency) but is also affected by how well target groups in the population are immunized, as well as by other non-vaccine-related factors that influence the 'real-world' outcomes of hospitalizations, ambulatory visits, or costs. For example, a retrospective case control analysis may be used, in which the rates of vaccination among a set of infected cases and appropriate controls are compared. Vaccine effectiveness may be expressed as a rate difference, with use of the odds ratio (OR) for developing infection despite vaccination:

$$\text{Effectiveness}=(1-\text{OR})\times 100.$$

In some embodiments, efficacy of the composition (e.g., RNA vaccine) is at least 60% relative to unvaccinated control subjects. For example, efficacy of the composition may be at least 65%, at least 70%, at least 75%, at least 80%, at least 85%, at least 95%, at least 98%, or 100% relative to unvaccinated control subjects.

Sterilizing Immunity. Sterilizing immunity refers to a unique immune status that prevents effective pathogen infection into the host. In some embodiments, the effective amount of a composition of the present disclosure is sufficient to provide sterilizing immunity in the subject for at least 1 year. For example, the effective amount of a composition of the present disclosure is sufficient to provide sterilizing immunity in the subject for at least 2 years, at least 3 years, at least 4 years, or at least 5 years. In some embodiments, the effective amount of a composition of the present disclosure is sufficient to provide sterilizing immunity in the subject at an at least 5-fold lower dose relative to control. For example, the effective amount may be sufficient to provide sterilizing immunity in the subject at an at least 10-fold lower, 15-fold, or 20-fold lower dose relative to a control.

Detectable Antigen. In some embodiments, the effective amount of a composition of the present disclosure is sufficient to produce detectable levels of coronavirus antigen as measured in serum of the subject at 1-72 hours post administration.

Titer. An antibody titer is a measurement of the number of antibodies within a subject, for example, antibodies that are specific to a particular antigen (e.g., an anti-coronavirus antigen). Antibody titer is typically expressed as the inverse of the greatest dilution that provides a positive result. Enzyme-linked immunosorbent assay (ELISA) is a common assay for determining antibody titers, for example.

In some embodiments, the effective amount of a composition of the present disclosure is sufficient to produce a 1,000-10,000 neutralizing antibody titer produced by neutralizing antibody against the coronavirus antigen as measured in serum of the subject at 1-72 hours post administration. In some embodiments, the effective amount is sufficient to produce a 1,000-5,000 neutralizing antibody titer produced by neutralizing antibody against the coronavirus antigen as measured in serum of the subject at 1-72 hours post administration. In some embodiments, the effective amount is sufficient to produce a 5,000-10,000 neutralizing antibody titer produced by neutralizing antibody against the coronavirus antigen as measured in serum of the subject at 1-72 hours post administration.

In some embodiments, the neutralizing antibody titer is at least 100 $NT_{50}$. For example, the neutralizing antibody titer may be at least 200, 300, 400, 500, 600, 700, 800, 900 or 1000 $NT_{50}$. In some embodiments, the neutralizing antibody titer is at least 10,000 $NT_{50}$.

In some embodiments, the neutralizing antibody titer is at least 100 neutralizing units per milliliter (NU/mL). For example, the neutralizing antibody titer may be at least 200, 300, 400, 500, 600, 700, 800, 900 or 1000 NU/mL. In some embodiments, the neutralizing antibody titer is at least 10,000 NU/mL.

In some embodiments, an anti-coronavirus antigen antibody titer produced in the subject is increased by at least 1 log relative to a control. For example, an anti-coronavirus antigen antibody titer produced in the subject may be increased by at least 2, 3, 4, 5, 6, 7, 8, 9 or 10 log relative to a control.

In some embodiments, an anti-coronavirus antigen antibody titer produced in the subject is increased at least 2 times relative to a control. For example, an anti-coronavirus antigen antibody titer produced in the subject is increased by at least 3, 4, 5, 6, 7, 8, 9 or 10 times relative to a control.

In some embodiments, a geometric mean, which is the nth root of the product of n numbers, is generally used to describe proportional growth. Geometric mean, in some embodiments, is used to characterize antibody titer produced in a subject.

A control may be, for example, an unvaccinated subject, or a subject administered a live attenuated viral vaccine, an inactivated viral vaccine, or a protein subunit vaccine.

Additional Embodiments

Additional embodiments of the present disclosure are encompassed by the following numbered paragraphs:

1. A messenger ribonucleic acid (mRNA) comprising an open reading frame encoding a fusion protein comprising a receptor binding domain (RBD) of a SARS-CoV-2 Spike protein and a protein transmembrane domain.
2. The mRNA of paragraph 1, wherein the protein transmembrane domain is an influenza hemagglutinin transmembrane domain.
3. The mRNA of paragraph 2, wherein the fusion protein comprises an amino acid sequence having at least 80% identity to the amino acid sequence of SEQ ID NO: 77.
4. The mRNA of paragraph 3, wherein the fusion protein comprises an amino acid sequence having at least 85%, at least 90%, at least 95%, at least 96%, at least 97%, at least 98%, or at least 99% identity to the amino acid sequence of SEQ ID NO: 77.
5. The mRNA of paragraph 4, wherein the fusion protein comprises the amino acid sequence of SEQ ID NO: 77.
6. The mRNA of any one of the preceding paragraphs, wherein the open reading frame comprises a nucleotide sequence having at least 70% identity to the nucleotide sequence of SEQ ID NO: 76.
7. The mRNA of paragraph 6, wherein the open reading frame comprises a nucleotide sequence having at least 75%, at least 80%, at least 90%, at least 95%, at least 96%, at least 97%, at least 98%, or at least 99% identity to the nucleotide sequence of SEQ ID NO: 76.
8. The mRNA of paragraph 7, wherein the open reading frame comprises the nucleotide sequence of SEQ ID NO: 76.
9. A messenger ribonucleic acid (mRNA) comprising an open reading frame encoding a fusion protein comprising an amino (N)-terminal domain (NTD) of a SARS-CoV-2 Spike protein and a transmembrane domain.
10. The mRNA of paragraph 9, wherein the transmembrane domain is an influenza hemagglutinin transmembrane domain.
11. The mRNA of paragraph 10, wherein the fusion protein comprises an amino acid sequence having at least 80% identity to the amino acid sequence of SEQ ID NO: 47.
12. The mRNA of paragraph 11, wherein the fusion protein comprises an amino acid sequence having at least 85%, at least 90%, at least 95%, at least 96%, at least 97%, at least 98%, or at least 99% identity to the amino acid sequence of SEQ ID NO: 47.
13. The mRNA of paragraph 12, wherein the fusion protein comprises the amino acid sequence of SEQ ID NO: 47.
14. The mRNA of any one of the preceding paragraphs, wherein the open reading frame comprises a nucleotide sequence having at least 70% identity to the nucleotide sequence of SEQ ID NO: 46.
15. The mRNA of paragraph 14, wherein the open reading frame comprises a nucleotide sequence having at least 75%, at least 80%, at least 90%, at least 95%, at least 96%, at least 97%, at least 98%, or at least 99% identity to the nucleotide sequence of SEQ ID NO: 46.
16. The mRNA of paragraph 15, wherein the open reading frame comprises the nucleotide sequence of SEQ ID NO: 46.
17. A messenger ribonucleic acid (mRNA) comprising an open reading frame encoding a fusion protein comprising an amino (N)-terminal domain of a SARS-CoV-2 Spike protein linked to a receptor binding domain of a SARS-CoV-2 Spike protein.
18. The mRNA of paragraph 17, wherein the fusion protein further comprises a transmembrane domain.
19. The mRNA of paragraph 18, wherein the fusion protein comprises an amino acid sequence having at least 80% identity to the amino acid sequence of SEQ ID NO: 92.
20. The mRNA of paragraph 18, wherein the fusion protein comprises an amino acid sequence having at least 85%, at least 90%, at least 95%, at least 96%, at least 97%, at least 98%, or at least 99% identity to the amino acid sequence of SEQ ID NO: 92.
21. The mRNA of paragraph 20, wherein the fusion protein comprises the amino acid sequence of SEQ ID NO: 92.
22. The mRNA of any one of the preceding paragraphs, wherein the open reading frame comprises a nucleotide sequence having at least 70% identity to the nucleotide sequence of SEQ ID NO: 91.
23. The mRNA of paragraph 22, wherein the open reading frame comprises a nucleotide sequence having at least 75%, at least 80%, at least 90%, at least 95%, at least 96%, at least 97%, at least 98%, or at least 99% identity to the nucleotide sequence of SEQ ID NO: 91.
24. The mRNA of paragraph 23, wherein the open reading frame comprises the nucleotide sequence of SEQ ID NO: 91.
25. The mRNA of any one of the preceding paragraphs further comprising a 5' untranslated region (UTR), optionally comprising the nucleotide sequence of SEQ ID NO: 131 or 2.
26. The mRNA of any one of the preceding paragraphs further comprising a 3' untranslated region (UTR), optionally comprising the nucleotide sequence of SEQ ID NO: 132 or 4.
27. The mRNA of any one of the preceding paragraphs further comprising a 5' cap, optionally 7mG(5')ppp(5')NlmpNp.
28. The mRNA of any one of the preceding paragraphs further comprising a polyA tail, optionally having a length of about 100 nucleotides.
29. The mRNA of any one of the preceding paragraphs, wherein the mRNA comprises a chemical modification, optionally 1-methylpseudouridine.
30. A composition comprising the mRNA of any one of paragraphs 1-29.
31. A composition comprising the mRNA of any one of paragraphs 1-8 and the mRNA of any one of paragraphs 9-16.
32. A composition comprising the mRNA of any one of paragraphs 17-29.
33. A composition comprising:
    (a) a messenger ribonucleic acid (mRNA) comprising an open reading frame encoding a fusion protein comprising a receptor binding domain (RBD) of a SARS-CoV-2 Spike protein and a protein transmembrane domain; and (b) an mRNA comprising an open reading frame encoding a fusion protein comprising an amino (N)-terminal domain of a SARS-CoV-2 Spike protein and a transmembrane domain.

34. The composition of paragraph 33 wherein the protein transmembrane domain is an influenza hemagglutinin transmembrane domain.

35. The composition of paragraph 34, wherein the fusion protein of (a) comprises an amino acid sequence having at least 80% identity to the amino acid sequence of SEQ ID NO: 77.

36. The composition of paragraph 35, wherein the fusion protein of (a) comprises an amino acid sequence having at least 85%, at least 90%, at least 95%, at least 96%, at least 97%, at least 98%, or at least 99% identity to the amino acid sequence of SEQ ID NO: 77.

37. The composition of paragraph 36, wherein the fusion protein of (a) comprises the amino acid sequence of SEQ ID NO: 77.

38. The composition of any one of paragraphs 34-37, wherein the open reading frame of (a) comprises a nucleotide sequence having at least 70% identity to the nucleotide sequence of SEQ ID NO: 76.

39. The composition of paragraph 38 wherein the open reading frame of (a) comprises a nucleotide sequence having at least 75%, at least 80%, at least 90%, at least 95%, at least 96%, at least 97%, at least 98%, or at least 99% identity to the nucleotide sequence of SEQ ID NO: 76.

40. The composition of paragraph 39, wherein the open reading frame of (a) comprises the nucleotide sequence of SEQ ID NO: 76.

41. The composition of any one of paragraphs 34-40, wherein the fusion protein of (b) comprises an amino acid sequence having at least 80% identity to the amino acid sequence of SEQ ID NO: 47.

42. The composition of paragraph 41, wherein the fusion protein of (b) comprises an amino acid sequence having at least 85%, at least 90%, at least 95%, at least 96%, at least 97%, at least 98%, or at least 99% identity to the amino acid sequence of SEQ ID NO: 47.

43. The composition of paragraph 42, wherein the fusion protein of (b) comprises the amino acid sequence of SEQ ID NO: 47.

44. The composition of any one of paragraphs 34-43, wherein the open reading frame of (b) comprises a nucleotide sequence having at least 70% identity to the nucleotide sequence of SEQ ID NO: 46.

45. The composition of paragraph 44, wherein the open reading frame of (b) comprises a nucleotide sequence having at least 75%, at least 80%, at least 90%, at least 95%, at least 96%, at least 97%, at least 98%, or at least 99% identity to the nucleotide sequence of SEQ ID NO: 46.

46. The composition of paragraph 45, wherein the open reading frame of (b) comprises the nucleotide sequence of SEQ ID NO: 46.

47. The composition of any one of paragraphs 33-46, wherein the ratio of the mRNA of (a) to the mRNA of (b) is about 1:1.

48. The mRNA of any one of paragraphs 1-29 formulated in a lipid nanoparticle.

49. The composition of any one of paragraphs 30-47 further comprising a lipid nanoparticle.

50. The composition of paragraph 49, wherein the mRNA is formulated in the lipid nanoparticle.

51. The composition of any one of paragraphs 33-47, wherein the mRNA of (a) is formulated in a lipid nanoparticle and the mRNA of (b) is formulated in a lipid nanoparticle.

52. The composition of paragraph 51, wherein the mRNA of (a) and (b) are in the same lipid nanoparticle or wherein each of the mRNA of (a) and (b) is formulated in a separate nanoparticle, relative to each other.

53. The mRNA of paragraph 48 or the composition of any one of paragraphs 49-52, wherein the lipid nanoparticle comprises a cationic lipid.

54. The mRNA or composition of paragraph 53, wherein the lipid nanoparticle further comprises a neutral lipid.

55. The mRNA or composition of paragraph 53 or 54, wherein the lipid nanoparticle further comprises a sterol.

56. The mRNA or composition of any one of paragraphs 53-55, wherein the lipid nanoparticle further comprises a polyethylene glycol (PEG)-modified lipid.

57. The mRNA or composition of any one of paragraphs 53-56, wherein the lipid nanoparticle comprises an ionizable cationic lipid, a neutral lipid, a sterol, and a PEG-modified lipid.

58. The mRNA or composition of paragraph 57, wherein the ionizable cationic lipid is heptadecan-9-yl 8 ((2 hydroxyethyl)(6 oxo 6-(undecyloxy)hexyl)amino)octanoate (Compound 1).

59. The mRNA or composition of paragraph 57 or 58, wherein the neutral lipid is 1,2 distearoyl-sn-glycero-3-phosphocholine (DSPC).

60. The mRNA or composition of any one of paragraphs 57-59, wherein the sterol is cholesterol.

61. The mRNA or composition of any one of paragraphs 57-60, wherein the PEG-modified lipid is 1,2 dimyristoyl-sn-glycerol, methoxypolyethyleneglycol (PEG2000 DMG).

62. The mRNA or composition of any one of paragraphs 57-61, wherein the lipid nanoparticle comprises 20-60 mol % ionizable cationic lipid, 5-25 mol % neutral lipid, 25-55 mol % sterol, and 0.5-15 mol % PEG-modified lipid.

63. The mRNA or composition of paragraph 62, wherein the lipid nanoparticle comprises:

47 mol % ionizable cationic lipid; 11.5 mol % neutral lipid; 38.5 mol % sterol; and 3.0 mol % PEG-modified lipid;

48 mol % ionizable cationic lipid; 11 mol % neutral lipid; 38.5 mol % sterol; and 2.5 mol % PEG-modified lipid;

49 mol % ionizable cationic lipid; 10.5 mol % neutral lipid; 38.5 mol % sterol; and 2.0 mol % PEG-modified lipid;

50 mol % ionizable cationic lipid; 10 mol % neutral lipid; 38.5 mol % sterol; and 1.5 mol % PEG-modified lipid; or 51 mol % ionizable cationic lipid; 9.5 mol % neutral lipid; 38.5 mol % sterol; and 1.0 mol % PEG-modified lipid.

64. The mRNA or composition of paragraph 63, wherein the lipid nanoparticle comprises:

47 mol % Compound 1; 11.5 mol % DSPC; 38.5 mol % cholesterol; and 3.0 mol % PEG2000 DMG;

48 mol % Compound 1; 11 mol % DSPC; 38.5 mol % cholesterol; and 2.5 mol % PEG2000 DMG;

49 mol % Compound 1; 10.5 mol % DSPC; 38.5 mol % cholesterol; and 2.0 mol % PEG2000 DMG;

50 mol % Compound 1; 10 mol % DSPC; 38.5 mol % cholesterol; and 1.5 mol % PEG2000 DMG; or 51 mol % Compound 1; 9.5 mol % DSPC; 38.5 mol % cholesterol; and 1.0 mol % PEG2000 DMG.

65. A method comprising administering to a subject the mRNA or the composition of any one of the preceding paragraphs in an amount effective to induce in the subject a neutralizing antibody response against SARS-CoV-2.

66. A method comprising administering to a subject the mRNA or the composition of any one of the preceding paragraphs in an amount effective to induce in the subject a T cell immune response against SARS-CoV-2.

67. A messenger ribonucleic acid (mRNA) comprising an open reading frame (ORF) that encodes a coronavirus antigen capable of inducing an immune response, such as a neutralizing antibody response, to a SARS-CoV-2, wherein the antigen comprises a protein fragment or a functional protein domain of a SARS-CoV-2, optionally wherein the RNA is formulated in a lipid nanoparticle.

68. The mRNA of paragraph 67, wherein the antigen is a functional protein domain.

69. The mRNA of paragraph 68, wherein the protein domain is an N-terminal domain (NTD) of a SARS-CoV-2 Spike protein.

70. The mRNA of paragraph 69, wherein the NTD is linked to a transmembrane domain, optionally an influenza hemagglutinin transmembrane domain.

71. The mRNA of paragraph 70, wherein the antigen comprises an amino acid sequence having at least 80%, at least 85%, at least 90%, at least 95%, at least 96%, at least 97%, at least 98%, or at least 99% identity to the amino acid sequence of SEQ ID NO: 47, optionally wherein the antigen comprises the amino acid sequence of SEQ ID NO: 47.

72. The mRNA of paragraph 70 or 71, wherein the open reading frame comprises a nucleotide sequence having at least 70%, least 75%, at least 80%, at least 90%, at least 95%, at least 96%, at least 97%, at least 98%, or at least 99% identity to the nucleotide sequence of SEQ ID NO: 46, optionally wherein the open reading frame comprises the nucleotide sequence of SEQ ID NO: 46.

73. The mRNA of paragraph 68, wherein the protein domain is a receptor binding domain (RBD) of a SARS-CoV-2 Spike protein.

74. The mRNA of paragraph 73, wherein the RBD is soluble.

75. The mRNA of paragraph 74, wherein the antigen comprises an amino acid sequence having at least 80%, at least 85%, at least 90%, at least 95%, at least 96%, at least 97%, at least 98%, or at least 99% identity to the amino acid sequence of SEQ ID NO: 62, optionally wherein the antigen comprises the amino acid sequence of SEQ ID NO: 62.

76. The mRNA of paragraph 74 or 75, wherein the open reading frame comprises a nucleotide sequence having at least 70%, least 75%, at least 80%, at least 90%, at least 95%, at least 96%, at least 97%, at least 98%, or at least 99% identity to the nucleotide sequence of SEQ ID NO: 61, optionally wherein the open reading frame comprises the nucleotide sequence of SEQ ID NO: 61.

77. The mRNA of paragraph 73, wherein the RBD is linked to a transmembrane domain, optionally an influenza hemagglutinin transmembrane domain.

78. The mRNA of paragraph 77, wherein the antigen comprises an amino acid sequence having at least 80%, at least 85%, at least 90%, at least 95%, at least 96%, at least 97%, at least 98%, or at least 99% identity to the amino acid sequence of SEQ ID NO: 77, optionally wherein the antigen comprises the amino acid sequence of SEQ ID NO: 77.

79. The mRNA of paragraph 77 or 78, wherein the open reading frame comprises a nucleotide sequence having at least 70%, least 75%, at least 80%, at least 90%, at least 95%, at least 96%, at least 97%, at least 98%, or at least 99% identity to the nucleotide sequence of SEQ ID NO: 76, optionally wherein the open reading frame comprises the nucleotide sequence of SEQ ID NOs: 76.

80. The mRNA of paragraph 69, wherein the NTD is linked to an RBD of a SARS-CoV-2 Spike protein to form an NTD-RBD fusion protein.

81. The mRNA of paragraph 80, wherein the NTD-RBD fusion is linked to a transmembrane domain (TM), optionally an influenza hemagglutinin transmembrane domain, to form an NTD-RBD-TM protein.

82. The mRNA of paragraph 81, wherein the antigen comprises an amino acid sequence having at least 80%, at least 85%, at least 90%, at least 95%, at least 96%, at least 97%, at least 98%, or at least 99% identity to the amino acid sequence of SEQ ID NO: 92, optionally wherein the antigen comprises the amino acid sequence of SEQ ID NO: 92.

83. The mRNA of paragraph 81 or 82, wherein the open reading frame comprises a nucleotide sequence having at least 70%, least 75%, at least 80%, at least 90%, at least 95%, at least 96%, at least 97%, at least 98%, or at least 99% identity to the nucleotide sequence of SEQ ID NO: 91, optionally wherein the open reading frame comprises the nucleotide sequence of SEQ ID NO: 91.

84. The mRNA of paragraph 80, wherein the NTD-RBD fusion comprises a C-terminal truncation.

85. The mRNA of paragraph 84, wherein the antigen comprises an amino acid sequence having at least 80%, at least 85%, at least 90%, at least 95%, at least 96%, at least 97%, at least 98%, or at least 99% identity to the amino acid sequence of SEQ ID NO: 107, optionally wherein the antigen comprises the amino acid sequence of SEQ ID NO: 107.

86. The mRNA of paragraph 84 or 85, wherein the open reading frame comprises a nucleotide sequence having at least 70%, least 75%, at least 80%, at least 90%, at least 95%, at least 96%, at least 97%, at least 98%, or at least 99% identity to the nucleotide sequence of SEQ ID NO: 106, optionally wherein the open reading frame comprises the nucleotide sequence of SEQ ID NO: 106.

87. The mRNA of any one of the preceding paragraphs, wherein the NTD and/or RBD includes an extended region.

88. The mRNA of paragraph 87, wherein the antigen comprises an amino acid sequence having at least 80%, at least 85%, at least 90%, at least 95%, at least 96%, at least 97%, at least 98%, or at least 99% identity to the amino acid sequence of any one of SEQ ID NOs: 59, 86, 89, 116, 119, or 122, optionally wherein the antigen comprises the amino acid sequence of any one of SEQ ID NOs: 59, 86, 89, 116, 119, or 122.

89. The mRNA of paragraph 87 or 88, wherein the open reading frame comprises a nucleotide sequence having at least 70%, least 75%, at least 80%, at least 90%, at least 95%, at least 96%, at least 97%, at least 98%, or at least 99% identity to the nucleotide sequence of any one of SEQ ID NOs: 58, 85, 88, 115, 118, or 121, optionally wherein the open reading frame comprises the nucleotide sequence of any one of SEQ ID NOs: 58, 85, 88, 115, 118, or 121.

90. The mRNA of paragraph 68, wherein the protein domain is an S1 subunit domain of a SARS-CoV-2 Spike protein.

91. The mRNA of paragraph 90, wherein the S1 subunit is soluble.

92. The mRNA of paragraph 91, wherein the antigen comprises an amino acid sequence having at least 80%, at least 85%, at least 90%, at least 95%, at least 96%, at least 97%, at least 98%, or at least 99% identity to the amino acid sequence of SEQ ID NO: 5, optionally wherein the antigen comprises the amino acid sequence of SEQ ID NO: 5.

93. The mRNA of paragraph 91 or 92, wherein the open reading frame comprises a nucleotide sequence having at least 70%, least 75%, at least 80%, at least 90%, at least 95%, at least 96%, at least 97%, at least 98%, or at least 99% identity to the nucleotide sequence of SEQ ID NO: 3, optionally wherein the open reading frame comprises the nucleotide sequence of SEQ ID NO: 3.

94. The mRNA of paragraph 90, wherein the S1 subunit is linked to a transmembrane domain, optionally an influenza hemagglutinin transmembrane domain.

95. The mRNA of paragraph 94, wherein the antigen comprises an amino acid sequence having at least 80%, at least 85%, at least 90%, at least 95%, at least 96%, at least 97%, at least 98%, or at least 99% identity to the amino acid sequence of SEQ ID NO: 17, optionally wherein the antigen comprises the amino acid sequence of SEQ ID NO: 17.

96. The mRNA of paragraph 94 or 95, wherein the open reading frame comprises a nucleotide sequence having at least 70%, least 75%, at least 80%, at least 90%, at least 95%, at least 96%, at least 97%, at least 98%, or at least 99% identity to the nucleotide sequence of SEQ ID NO: 16, optionally wherein the open reading frame comprises the nucleotide sequence of SEQ ID NO: 16.

97. The mRNA of paragraph 90, wherein the S1 subunit has been modified to remove a RBD or a portion of a RBD of S protein.

98. The mRNA of paragraph 97, wherein the antigen comprises an amino acid sequence having at least 80%, at least 85%, at least 90%, at least 95%, at least 96%, at least 97%, at least 98%, or at least 99% identity to the amino acid sequence of any one of SEQ ID NOs: 20, 23, 26, 29, 32 or 35, optionally wherein the antigen comprises the amino acid sequence of any one of SEQ ID NOs: 20, 23, 26, 29, 32, or 35.

99. The mRNA of paragraph 97 or 98, wherein the open reading frame comprises a nucleotide sequence having at least 70%, least 75%, at least 80%, at least 90%, at least 95%, at least 96%, at least 97%, at least 98%, or at least 99% identity to the nucleotide sequence of any one of SEQ ID NOs: 19, 22, 25, 28, 41, or 34, optionally wherein the open reading frame comprises the nucleotide sequence of any one of SEQ ID NOs: 19, 22, 25, 28, 31, or 34.

100. The mRNA of paragraph 90, wherein the S1 subunit is linked to an S2 subunit of an S protein.

101. The mRNA of paragraph 100, wherein the S2 subunit is from a SARS-CoV-2 S protein and in some embodiments wherein the S2 subunit comprises an open reading frame comprising a nucleotide sequence having at least 70%, least 75%, at least 80%, at least 90%, at least 95%, at least 96%, at least 97%, at least 98%, or at least 99% identity to the nucleotide sequence of SEQ ID NO: 145, optionally wherein the open reading frame comprises the nucleotide sequence of SEQ ID NOs: 145.

102. The mRNA of paragraph 101, wherein the S1 subunit is from an HKU1 S protein.

103. The mRNA of paragraph 102, wherein the antigen comprises an amino acid sequence having at least 80%, at least 85%, at least 90%, at least 95%, at least 96%, at least 97%, at least 98%, or at least 99% identity to the amino acid sequence of SEQ ID NO: 38, optionally wherein the antigen comprises the amino acid sequence of SEQ ID NO: 38.

104. The mRNA of paragraph 102 or 103, wherein the open reading frame comprises a nucleotide sequence having at least 70%, least 75%, at least 80%, at least 90%, at least 95%, at least 96%, at least 97%, at least 98%, or at least 99% identity to the nucleotide sequence of SEQ ID NO: 37, optionally wherein the open reading frame comprises the nucleotide sequence of SEQ ID NO: 37.

105. The mRNA of paragraph 101, wherein the S1 subunit is from an OC43 S protein.

106. The mRNA of paragraph 105, wherein the antigen comprises an amino acid sequence having at least 80%, at least 85%, at least 90%, at least 95%, at least 96%, at least 97%, at least 98%, or at least 99% identity to the amino acid sequence of SEQ ID NO: 41, optionally wherein the antigen comprises the amino acid sequence of SEQ ID NO: 41.

107. The mRNA of paragraph 105 or 106, wherein the open reading frame comprises a nucleotide sequence having at least 70%, least 75%, at least 80%, at least 90%, at least 95%, at least 96%, at least 97%, at least 98%, or at least 99% identity to the nucleotide sequence of SEQ ID NO: 40, optionally wherein the open reading frame comprises the nucleotide sequence of SEQ ID NO: 40.

108. The mRNA of any one of the preceding paragraphs, wherein the antigen further comprises a scaffold domain, optionally selected from ferritin, lumazine synthetase and a foldon.

109. The mRNA of paragraph 108, wherein the scaffold domain is ferritin.

110. The mRNA of paragraph 109, wherein the antigen comprises an amino acid sequence having at least 80%, at least 85%, at least 90%, at least 95%, at least 96%, at least 97%, at least 98%, or at least 99% identity to the amino acid sequence of SEQ ID NO: 8 or 65, optionally wherein the antigen comprises the amino acid sequence of SEQ ID NO: 8 or 65.

111. The mRNA of paragraph 109 or 110, wherein the open reading frame comprises a nucleotide sequence having at least 70%, least 75%, at least 80%, at least 90%, at least 95%, at least 96%, at least 97%, at least 98%, or at least 99% identity to the nucleotide sequence of SEQ ID NO: 7 or 64, optionally wherein the open reading frame comprises the nucleotide sequence of SEQ ID NO: 7 or 64.

112. The mRNA of paragraph 108, wherein the scaffold domain is lumazine synthetase.

113. The mRNA of paragraph 112, wherein the antigen comprises an amino acid sequence having at least 80%, at least 85%, at least 90%, at least 95%, at least 96%, at least 97%, at least 98%, or at least 99% identity to the amino acid sequence of any one of SEQ ID NOs: 11, 14, 68, or 71, optionally wherein the antigen comprises the amino acid sequence of any one of SEQ ID NOs: 11, 14, 68, or 71.

114. The mRNA of paragraph 112 or 113, wherein the open reading frame comprises a nucleotide sequence having at least 70%, least 75%, at least 80%, at least 90%, at least 95%, at least 96%, at least 97%, at least 98%, or at least 99% identity to the nucleotide sequence of any one of SEQ ID NOs: 10, 13, 67, or 70, optionally wherein the open reading frame comprises the nucleotide sequence of any one of SEQ ID NOs: 10, 13, 67, or 70.

115. The mRNA of paragraph 108, wherein the scaffold domain is a foldon.

116. The mRNA of paragraph 115, wherein the antigen comprises an amino acid sequence having at least 80%, at least 85%, at least 90%, at least 95%, at least 96%, at least 97%, at least 98%, or at least 99% identity to the amino acid sequence of any one of SEQ ID NOs: 44, 50, 74, 80, 83, 101, 104 or 113, optionally wherein the antigen comprises the amino acid sequence of any one of SEQ ID NOs: 44, 50, 74, 80, 83, 101, 104 or 113.

117. The mRNA of paragraph 115 or 116, wherein the open reading frame comprises a nucleotide sequence having at least 70%, least 75%, at least 80%, at least 90%, at least 95%, at least 96%, at least 97%, at least 98%, or at least 99% identity to the nucleotide sequence of any one of SEQ ID NOs: 43, 49, 73, 79, 82, 100, 103, or 112, optionally wherein the open reading frame comprises the nucleotide sequence of any one of SEQ ID NOs: 43, 49, 73, 79, 82, 100, 103, or 112.

118. The mRNA of any one of the preceding paragraphs, wherein the antigen further comprising a trafficking signal, optionally selected from macrophage markers, optionally CD86, CD11B and/or VSVGct.

119. The mRNA of paragraph 118, wherein the antigen comprises an amino acid sequence having at least 80%, at least 85%, at least 90%, at least 95%, at least 96%, at least 97%, at least 98%, or at least 99% identity to the amino acid sequence of any one of SEQ ID NOs: 95, 98, or 110, optionally wherein the antigen comprises the amino acid sequence of any one of SEQ ID NOs: 95, 98, or 110.

120. The mRNA of paragraph 118 or 119, wherein the open reading frame comprises a nucleotide sequence having at least 70%, least 75%, at least 80%, at least 90%, at least 95%, at least 96%, at least 97%, at least 98%, or at least 99% identity to the nucleotide sequence of any one of SEQ ID NOs: 94, 97, or 109, optionally wherein the open reading frame comprises the nucleotide sequence of any one of SEQ ID NOs: 94, 97, or 109.

121. The mRNA of any one of paragraphs 67-120 formulated in a lipid nanoparticle.

122. The mRNA of paragraph 121, wherein the lipid nanoparticle comprises a cationic lipid, optionally an ionizable cationic lipid, a neutral lipid, a sterol, and/or a polyethylene glycol (PEG)-modified lipid.

123. The mRNA or composition of paragraph 108, wherein the ionizable cationic lipid is heptadecan-9-yl 8 ((2 hydroxyethyl)(6 oxo 6-(undecyloxy)hexyl) amino)octanoate (Compound 1), the neutral lipid is 1,2 distearoyl-sn-glycero-3-phosphocholine (DSPC), the sterol is cholesterol, and/or the PEG-modified lipid is 1,2 dimyristoyl-sn-glycerol, methoxypolyethyleneglycol (PEG2000 DMG).

124. The mRNA or composition of any one of paragraphs 121-123, wherein the lipid nanoparticle comprises 20-60 mol % ionizable cationic lipid, 5-25 mol % neutral lipid, 25-55 mol % sterol, and 0.5-15 mol % PEG-modified lipid.

125. The mRNA or composition of paragraph 124, wherein the lipid nanoparticle comprises:
   - 47 mol % ionizable cationic lipid; 11.5 mol % neutral lipid; 38.5 mol % sterol; and 3.0 mol % PEG-modified lipid;
   - 48 mol % ionizable cationic lipid; 11 mol % neutral lipid; 38.5 mol % sterol; and 2.5 mol % PEG-modified lipid;
   - 49 mol % ionizable cationic lipid; 10.5 mol % neutral lipid; 38.5 mol % sterol; and 2.0 mol % PEG-modified lipid;
   - 50 mol % ionizable cationic lipid; 10 mol % neutral lipid; 38.5 mol % sterol; and 1.5 mol % PEG-modified lipid; or
   - 51 mol % ionizable cationic lipid; 9.5 mol % neutral lipid; 38.5 mol % sterol; and 1.0 mol % PEG-modified lipid.

126. The mRNA or composition of paragraph 125, wherein the lipid nanoparticle comprises:
   - 47 mol % Compound 1; 11.5 mol % DSPC; 38.5 mol % cholesterol; and 3.0 mol % PEG2000 DMG;
   - 48 mol % Compound 1; 11 mol % DSPC; 38.5 mol % cholesterol; and 2.5 mol % PEG2000 DMG;
   - 49 mol % Compound 1; 10.5 mol % DSPC; 38.5 mol % cholesterol; and 2.0 mol % PEG2000 DMG;
   - 50 mol % Compound 1; 10 mol % DSPC; 38.5 mol % cholesterol; and 1.5 mol % PEG2000 DMG; or
   - 51 mol % Compound 1; 9.5 mol % DSPC; 38.5 mol % cholesterol; and 1.0 mol % PEG2000 DMG.

127. A method comprising administering to a subject the mRNA of any one of the paragraphs 67-126 in an amount effective to induce in the subject a neutralizing antibody response against SARS-CoV-2.

128. A method comprising administering to a subject the mRNA of any one of the paragraphs 67-126 in an amount effective to induce in the subject a T cell immune response against SARS-CoV-2.

EXAMPLES

Example 1. Expression Data

The mRNAs used in the present study were used to express key neutralizing domains of the SARS-CoV-2 coronavirus spike (S) protein and assess whether these neutralizing protein domains may be more efficient at inducing protective immunity when used individually or in combination as an immunogenic composition or vaccine to protect people from infection by the live and spreading natural virus. The linear designs of the proteins encoded by the mRNAs are shown in FIG. 2. The proteins all also contain a carboxy (C) terminal transmembrane domain (TM) derived from the hemagglutinin (HA) of influenza.

Both the NTD and RBD are known to be sites for binding of antibodies that manifest neutralizing virus activity. RBD in the case of SARS-CoV-2 is the receptor binding site of the spike protein and binds the angiotensin-converting enzyme 2 (ACE2). The amino (N) terminal domain, NTD, the function of which is not thoroughly understood, seems to have a role in binding sugar moieties and in facilitating the conformational transition of the spike protein from prefusion to a post fusion conformation. See Zhou H, Chen Y, Zhang S, et al. *Nat Commun.* 2019; 10(1): 3068. Regardless, both the NTD and RBD domains induce high binding antibody and neutralizing antibody titers as discussed below.

Expression data for the mRNA RBD-TM vaccine ("SARS-CoV-2 RBD-TM"; SEQ ID NOs: 75-77), the mRNA NTD-TM vaccine ("SARS-CoV-2 NTD-TM"; SEQ ID NOs: 45-47), and mRNA NTD-RBD-TM ("SARS-CoV-1 NTD-RBD-TM"; SEQ ID NOs: 90-92) vaccine is shown in Tables 16 and 17 using an antibody specific for the receptor binding domain (RBD) of SARS-CoV-2 Spike protein (mAb1) and for the N-terminal domain (NTD) of SARS-CoV-2 Spike protein (Ab2). Table 16 shows the average fold difference (over dilution range) in MFI*Freq compared to WT SARS-CoV-2 Spike protein mRNA (Table 16) at 24 hours (hr), 48 hr, and 72 hr.

TABLE 16

Total Antigen Expression (MFI * Freq) Fold Change Compared to S2P Protein

| | Monoclonal Antibody (mAb) | Wild Type (WT) S mRNA | RBD-TM mRNA | NTD-TM mRNA | NTD-RBD-TM mRNA | blank |
|---|---|---|---|---|---|---|
| 24 hour (hr) | 1 - specific to RBD | 1.8 | 30.6 | 0.0 | 10.4 | 0.0 |
| 24 hr | 2 - specific to NTD | 0.7 | 0.0 | 9.7 | 2.5 | 0.0 |
| 48 hr | 1 | 1.2 | 40.1 | 0.0 | 7.3 | 0.0 |
| 48 hr | 2 | 0.8 | 0.0 | 19.0 | 6.0 | 0.0 |
| 72 hr | 1 | 0.8 | 32.5 | 0.1 | 11.6 | 0.0 |
| 72 hr | 2 | 0.7 | 0 | 14.4 | 4.1 | 0.0 |

RBD = receptor binding domain
NTD = N-terminal domain
TM = transmembrane domain

Example 2. Immunogenicity Data and Neutralization Data at Day 21 Following a Single Dose mRNA NTD-TM and mRNA RBD-TM (described in Example 1) were administered to mice at the following doses: 0.001 μg, 0.01 μg, 0.1 μg, or 1 μg (N=8). mRNA NTD-RBD-TM (described in Example 1) were administered to mice at the following doses: 0.1 μg or 1 μg (N=8). A 50:50 mixture of the mRNA NTD-TM and mRNA RBD-TM was administered to mice, which contained 0.1 μg of each mRNA for a total of 0.2 μg mRNA, or 1 μg of each mRNA for a total of 2 μg mRNA (N=8). SARS-CoV-2 Spike protein-specific IgG titers (Table 17), SARS-CoV-2 RBD-specific IgG titers (Table 18), and SARS-CoV-2 NTD-specific IgG titers (Table 19) were then measured by ELISA at Day 21 post vaccination. The data is provided in Tables 17-19. The 0.1 g dose of mRNA NTD-RBD-TM and 0.2 μg dose of a 50:50 mixture of mRNA NTD-TM and mRNA RBD-TM compositions, elicited observable NTD-specific and RBD-specific IgG titers, and the 0.1 μg doses of RBD-TM and NTD-TM elicited measurable IgG titers against RBD and NTD antigens, respectively.

TABLE 17

SARS-CoV-2 S1/S2 spike protein-specific IgG titers - Mean Values

| Micrograms (per mRNA construct) | RBD-TM | NTD-TM | NTD-RBD-TM | 50:50 mix |
|---|---|---|---|---|
| 0.001 | 13 | 13 | — | — |
| 0.01 | 13 | 13 | — | — |
| 0.1 | 13 | 13 | 13 | 19 |
| 1 | 225 | 13 | 379 | 707 |

Average of N = 8; PBS only = 1.1

TABLE 18

RBD domain-specific IgG titers - Mean Values

| Micrograms (per mRNA construct) | RBD-TM | NTD-RBD-TM | 50:50 mix |
|---|---|---|---|
| 0.001 | 15 | — | — |
| 0.01 | 14 | — | — |
| 0.1 | 75 | 209 | 266 |
| 1 | 1947 | 7710 | 15530 |

Average of N = 8; PBS only = 1.1

TABLE 19

NTD domain-specific IgG titers - Mean Values

| Micrograms (per mRNA construct) | NTD-TM | NTD-RBD-TM | 50:50 mix |
|---|---|---|---|
| 0.001 | 13 | — | — |
| 0.01 | 14 | — | — |
| 0.1 | 30 | 20 | 38 |
| 1 | 620 | 848 | 1075 |

Average of N = 8; PBS only = 1.1

Figure 7:
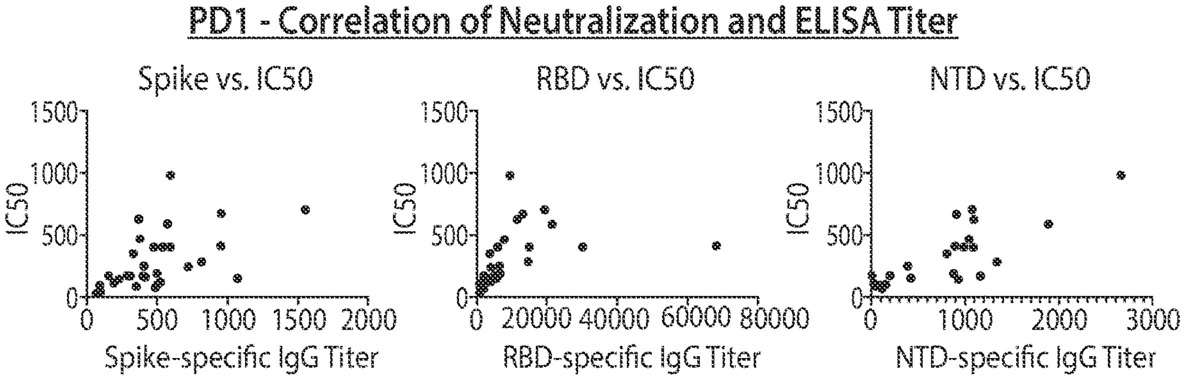
FIG. 7 shows correlations of neutralization and ELISA titers.

Neutralization titers from serum of mice vaccinated with the 1 μg dose of RBD-TM and NTD-RBD-TM compositions and the 2 μg dose of the 50:50 mixture of NTD-TM and RBD-TM compositions were measured and the correlation between ELISA titers and neutralization titers was analyzed (FIG. 7).

The titers elicited by 1 μg dose of the NTD-RBD-TM composition or 2 μg of the 50:50 mixture of NTD-TM and RBD-TM compositions were greater than those elicited by the 1 μg dose of RBD-TM composition (Table 20). Significant correlations exist between neutralization titers and ELISA titers of Spike-specific IgG, RBD-specific IgG, and NTD-specific IgG (FIG. 7).

TABLE 20

Neutralization Titers - Mean Values

| Micrograms (per mRNA construct) | RBD-TM | NTD-RBD-TM | 50:50 mix |
|---|---|---|---|
| 1 | 238 | 504 | — |
| 2 | — | — | 421 |

Average of N = 8; PBS only = 1.1

Recombinant VSVΔG-based SARS-CoV-2 Pseudovirus Neutralization Assay Codon-optimized wild-type or D614G spike gene (Wuhan-Hu-1 strain; NC_045512.2) was cloned into pCAGGS vector. To generate VSVΔG-based SARS-CoV-2 pseudovirus, BHK-21/WI-2 cells were transfected with the spike expression plasmid and infected VSVΔG-firefly-luciferase as previously described (Whitt, 2010). A549-hACE2-TMPRSS2 cells were used as target cells for VSVΔG-based SARS-CoV-2 pseudovirus neutralization assay. Lentivirus encoding hACE2-P2A-TMPRSS2 was made to generate A549-hACE2-TMPRSS2 cells which were maintained in DMEM supplemented with 10% fetal bovine serum and 1 μg/mL puromycin. A549-hACE2-TMPRSS2 cells were infected by pseudovirus for 1 hr at 37 Celsius. The inoculum virus or virus-antibody mix was removed after infection. 18 hr later, equal volume of One-Glo reagent (Promega; E6120) was added to culture medium for readout using BMG PHERastar-FS plate reader. The neutralization procedure and data analysis are same as mentioned above in the lentivirus-based pseudovirus neutralization assay. See Whitt, M. A. (2010). Journal of Virological Methods 169, 365-374.

Example 3. Immunogenicity Data at Day 36 Following Two Doses

The same doses of the mRNA vaccines described in Example 2 were again administered to mice as booster doses on Day 22 post-vaccination with the first dose. The titers of antibodies generated after the booster dose to each of RBD antigen, NTD antigen, wildtype (WT) Spike (S) protein and S2P protein (S protein having a double proline mutations to stabilize the prefusion conformation) were measured by ELISA from day 36 serum and shown below. The 50:50 mixture of the two immunogenic compositions of RBD-TM and NTD-TM encoded by mRNA in an LNP were administered at 2 μg or 0.2 μg total mRNA to mice as a booster dose on day 22 and the titers were determined on day 36. See Table 21.

The WT S protein titers shown in Table 21 by mice immunized with RBD-TM, NTD-TM, or the NTD-RBD-TM encoded by mRNA in an LNP indicated that two doses were superior at all doses tested in inducing antibodies that could recognize and bind to SARS-CoV-2 WT S protein.

TABLE 21

SARS-CoV-2 WT S-specific IgG titers - Geometric Mean Values

| Micrograms (mRNA construct) | RBD-TM | NTD-TM | NTD-RBD-TM |
|---|---|---|---|
| | Day 21 (GMT) Titers | | |
| 0.001 | 13 | 13 | — |
| 0.01 | 13 | 13 | — |
| 0.1 | 13 | 13 | 14 |
| 1 | 225 | 13 | 379 |
| | Day 36 (GMT) Titers | | |
| 0.001 | 13 | 13 | — |
| 0.01 | 295 | 13 | — |
| 0.1 | 1,017 | 39 | 3879 |
| 1 | 27,674 | 6317 | 24,413 |

Average of N = 8; PBS only = 1.1

The serum from mice immunized with two doses of RBD-TM, NTD-TM, or the NTD-RBD-TM encoded by mRNA in an LNP and were further analyzed for the ability of the antibodies to recognize and bind SARS-CoV-2 S2P protein. The titers to SARS-CoV-2 S2P protein were determined by ELISA using the S2P as the antigen on the plate and are shown below in Table 22. Each of these immunogens induced much higher antibody titers when S2P was the antigen versus when WT S protein was the ELISA antigen. Compare Table 21 and Table 22.

TABLE 22

SARS-CoV-2 S2P-specific IgG titers - Geometric Mean Values

| Micrograms (mRNA construct) | RBD-TM | NTD-TM | NTD-RBD-TM |
|---|---|---|---|
| | Day 36 (GMT) Titers | | |
| 0.001 | 88 | 16 | — |
| 0.01 | 1,416 | 280 | — |
| 0.1 | 3,892 | 11,687 | 25,298 |
| 1 | 107,611 | 192,040 | 223,140 |

Average of N = 8; PBS only = 1.1

In Table 23, the immunogen was the 50:50 mix of RBD-TM and NTD-TM encoded by mRNA in an LNP and the titers to WT S, RBD, NTD, and S2P were determined after one dose (day 21) and two doses (day 36). These results show dramatically increased titers when the immunogen is the combination of RBD-TM and NTD-TM in a 50:50 mix compared to the antibody titers induced by the individual antigens at the same doses. The 50:50 mix induced good titers to the immunizing antigens, but surprisingly even better titers to the WT S protein and extremely higher titers to the S2P protein. See Table 23.

TABLE 23

SARS-CoV-2 Antigen-specific IgG titers - Geometric Mean Values

| Immunogen Micrograms (mRNA) 50:50 mix | Detection antigen on ELISA plate | | | |
|---|---|---|---|---|
| RBD-TM LNP NTD-TM LNP | Anti-Spike Protein IgG | Anti-RBD IgG | Anti-NTD IgG | Anti-S2P IgG |
| Day 21 (GMT) Titers | | | | |
| 0.2 | 19 | 266 | 38 | 4,869 |
| 2 | 707 | 15,530 | 1,075 | 52,936 |
| Day 36 (GMT) Titers | | | | |
| 0.2 | 7,259 | 15,957 | 4,869 | 74,718 |
| 2 | 75,871 | 186,740 | 52,936 | 2,726,948 |

Average of N = 8; PBS only = 1.1

Table 24 shows the results of an immunization with each of RBD-TM and NTD-TM as mRNA encoding those antigens. The geometric mean titers were measured for groups of 8 mice using the protein encoded by the mRNA immunogen as the antigen on the ELISA plate. Again, both immunogenic compositions induced high titers to the immunizing antigen when the antigen is administered as mRNA formulated in an LNP. In this case, two doses produced superior antibody responses at all concentrations. However, on a per microgram (μg) basis the 50:50 mix of these antigens induced about a 10-fold higher antibody response than when the antigens are administered singly. Compare Table 23 and Table 24.

TABLE 24

| SARS-CoV-2 RBD and NTD Domain Specific IgG titers - Geometric Mean Values | | |
|---|---|---|
| Micrograms (mRNA construct) | RBD-TM Antigen on plate | NTD-TM Antigen on plate |
| | Day 21 (GMT) Titers | |
| 0.001 | 15 | 13 |
| 0.01 | 14 | 14 |
| 0.1 | 75 | 30 |
| 1 | 1,947 | 620 |
| | Day 36 (GMT) Titers | |
| 0.001 | 25 | 13 |
| 0.01 | 1,357 | 123 |
| 0.1 | 4,678 | 6898 |
| 1 | 84,385 | 46,516 |

Average of N = 8; PBS only = 1.1

The fusion protein comprising NTD linked to RBD and encoded by mRNA in an LNP was administered as an immunogenic composition to groups of 8 mice at 0.1 and 1 μg doses at days 1 and 21. See Table 25 below. Even the mRNA encoding the fusion protein version of NTD-RBD-TM induced very good titers to the individual domains that were higher than when a single domain was the immunizing antigen. The titers to the S2P protein were about 8-fold higher than the titers to WT S protein. See Table 25.

TABLE 25

| SARS-CoV-2 NTD-RBD-TM Domain Specific IgG titers - Geometric Mean Values | | | | |
|---|---|---|---|---|
| Micrograms Immunogen NTD-RBD-TM (mRNA construct) | RBD-TM Antigen on plate | NTD-TM Antigen on plate | WT Spike Antigen on plate | S2P Antigen on plate |
| | | Day 21 (GMT) Titers | | |
| 0.1 | 209 | 20 | 13 | NA |
| 1 | 7,710 | 848 | 379 | NA |
| | | Day 36 (GMT) Titers | | |
| 0.1 | 5,769 | 2,875 | 3,878 | 25,298 |
| 1 | 111,747 | 41,876 | 24,413 | 223,140 |

Average of N = 8; PBS only = 1.1

Neutralization data are shown in Table 26. The S1-666-TM encoded by mRNA is an antigen using the S1 subdomain, specifically residues 1-666 of SARS-CoV-2 spike protein attached to a transmembrane domain.

TABLE 26

| Mean Neutralization Titers on Day 36 after Two Immunizations on Days 1 and 22. | | | | | |
|---|---|---|---|---|---|
| Micrograms (per mRNA construct) | S1-666-TM | 50:50 Mix of NTD-TM & RBD-TM | RBD-TM | NTD-TM | NTD-RBD-TM |
| 0.001 | — | — | 40 | 40 | — |
| 0.01 | 508 | — | 70.5 | 40 | — |
| 0.1 | 11,561 | 1,336 | 260 | 205 | 865 |
| 1.0 | — | 25,208 | 7,402 | 4,669 | 57,891 |

Average of N = 8; PBS only = 1.1

Example 4. Immunogenicity of S1-666-TM

The S1-666-TM (or S1 residues 1-666 of spike protein S) encoded by mRNA in an LNP was administered to mice as a prime immunization on day 1, and as booster dose on day 22 for 0.01 μg, and 0.1 μg (N=8) groups. The titers of antibodies generated after the booster dose to each of mRNA RBD, mRNA NTD, and mRNA wildtype (WT) Spike (S) protein (FIG. 1) were measured by ELISA from days 21 (pre-boost) and 36 (post boost) serum and shown below in Table 27.

The WT S protein titers shown in Table 27 by mice immunized with S1-666-TM encoded by mRNA in an LNP indicated that two doses were superior at all doses tested in inducing antibodies that could recognize and bind to SARS-CoV-2 WT S protein. Surprisingly, the induced titers weres highest when measured against the S2P version of the spike protein even though the 2P mutation is not found in S1, because the 2P mutation occurs in S2 and S2 is not present in the immunogen. Similar to other constructs, the NTD titers require the second dose to become elevated.

TABLE 27

| SARS-CoV-2 Antigen-specific IgG titers - Geometric Mean Values | | | | |
|---|---|---|---|---|
| Immunogen | Detection antigen on ELISA plate | | | |
| Micrograms (mRNA) S1-666-TM | Anti-Spike Protein IgG | Anti-RBD IgG | Anti-NTD IgG | Anti-S2P IgG |
| Day 21 (GMT) Titers | | | | |
| 0.01 | 13 | 30 | 13 | NA |
| 0.1 | 175 | 868 | 49 | NA |
| Day 36 (GMT) Titers | | | | |
| 0.01 | 2,450 | 12,952 | 112 | 186,561 |
| 0.1 | 17,066 | 69,969 | 9,015 | 874,609 |

Average of N = 8; PBS only = 1.1

Example 5. Immunogenicity of RBD-TM, NTD-TM, NTD-RBD-TM, and 50:50 Mixture of NTD-TM/RBD-TM Compositions at Day 36 after Two Doses In this repeat experiment, the same doses of the mRNA vaccines described in the examples above were again administered to mice as booster doses on Day 22 post-vaccination with the first dose. SARS-CoV-2 Spike protein-specific IgG titers, SARS-CoV-2 S2P protein-specific IgG titers, SARS-CoV-2 RBD-specific IgG titers, and SARS-CoV-2 NTD-specific IgG titers (were then measured by ELISA at Day 36 post-vaccination with the first dose.

Results showed that 1 μg and 0.1 μg doses of mRNA RBD-TM, mRNA NTD-TM, mRNA NTD-RBD-TM compositions, and 50:50 mixtures containing 1 μg or 0.1 μg each of mRNA RBD-TM and mRNA NTD-TM compositions, elicited high ELISA titers towards SARS-CoV-2 Spike or SARS-CoV-2 S2P proteins.

Example 6. Immunogenicity Studies

The immunogenicity of a 50:50 mixture of mRNA NTD-TM and mRNA RBD-TM was administered to mice at the follow doses: 0.2 μg or 2 μg total mRNA (0.1 μg or 1 μg of each mRNA) (N=8). A prime dose was administered on Day 1, and a boost dose was administered on Day 22. On Day 36, ELISA was used to assess antibody binding to SARS-CoV-2 stabilized prefusion spike protein (SARS-CoV-2 pre-S). The following vaccine compositions including mRNA NTD-RBD-TM, mRNA RBD-TM and mRNA NTD-TM were administered to mice at the following doses: 0.1 μg and 0.01 μg (N=8). The GMT data was determined and shown below in Table 28.

TABLE 28

SARS-CoV-2 Spike Titers induced by S Protein Domain Fusions and Combinations

| Vaccination Immunogen | Dose μg mRNA | Day 21 GMT Titer 3 weeks post dose 1 S2P coated on plates | Day 36 GMT Titer 3 weeks post dose 2 S2P coated on plates |
|---|---|---|---|
| 50:50 mix RBD-TM NTD-TM | 1 | 5,913 | 301,881 |
| 50:50 mix RBD-TM NTD-TM | 0.1 | 71 | 13,423 |
| NTD-RBD-TM | 1.0 | 3,329 | 177,499 |
| NTD-RBD-TM | 0.1 | 80 | 48947 |
| RBD-TM | 1.0 | 3198 | 593,730 |
| RBD-TM | 0.1 | 73 | 31,090 |
| NTD-TM | 1.0 | 593 | 74,777 |
| NTD-TM | 0.1 | 21 | 23,916 |

Example 7. Determination of the Ratio of IgG2a and IgG1 for NTD-RBD-TM

Figure 8A:
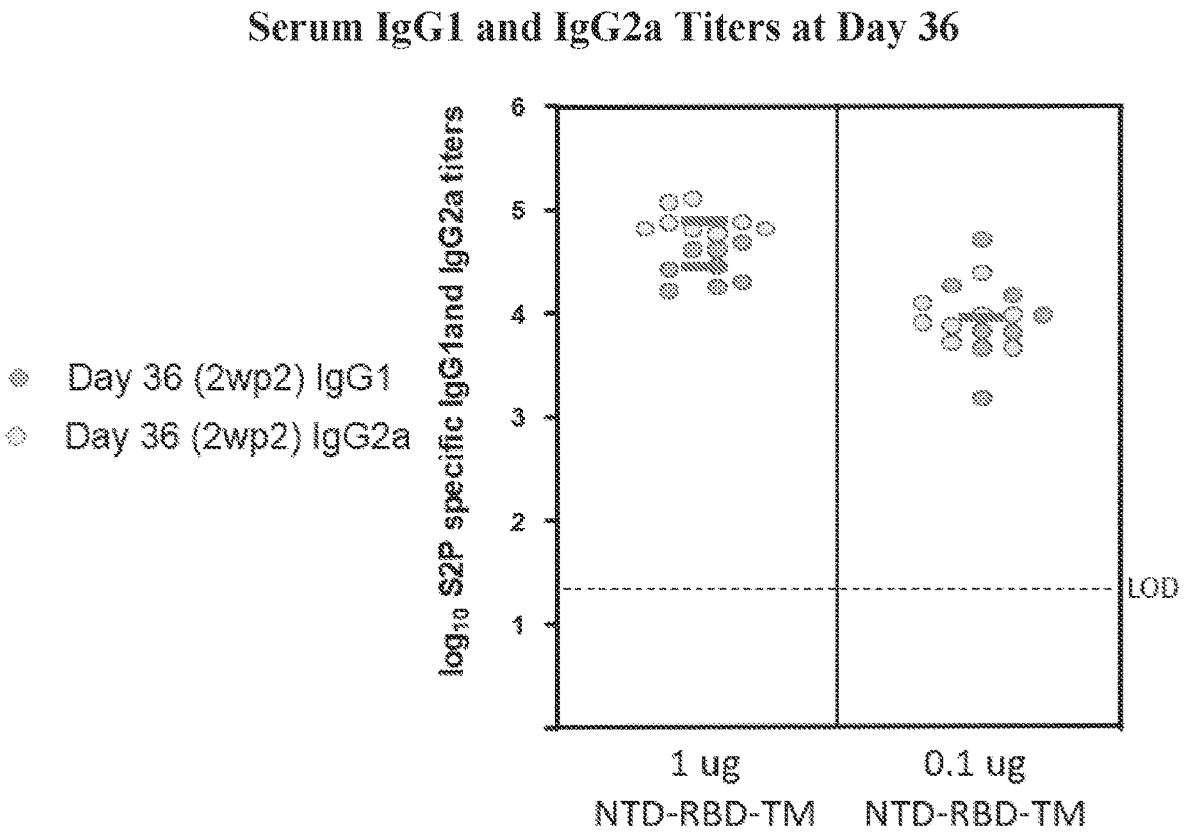
FIGS. 8A-8C show serum IgG1 and IgG2a Titers at Day 36 following a Day 1 prime and Day 21 boost dose in mice with mRNA encoding NTD-RBD-TM in an LNP.
Figure 8B:
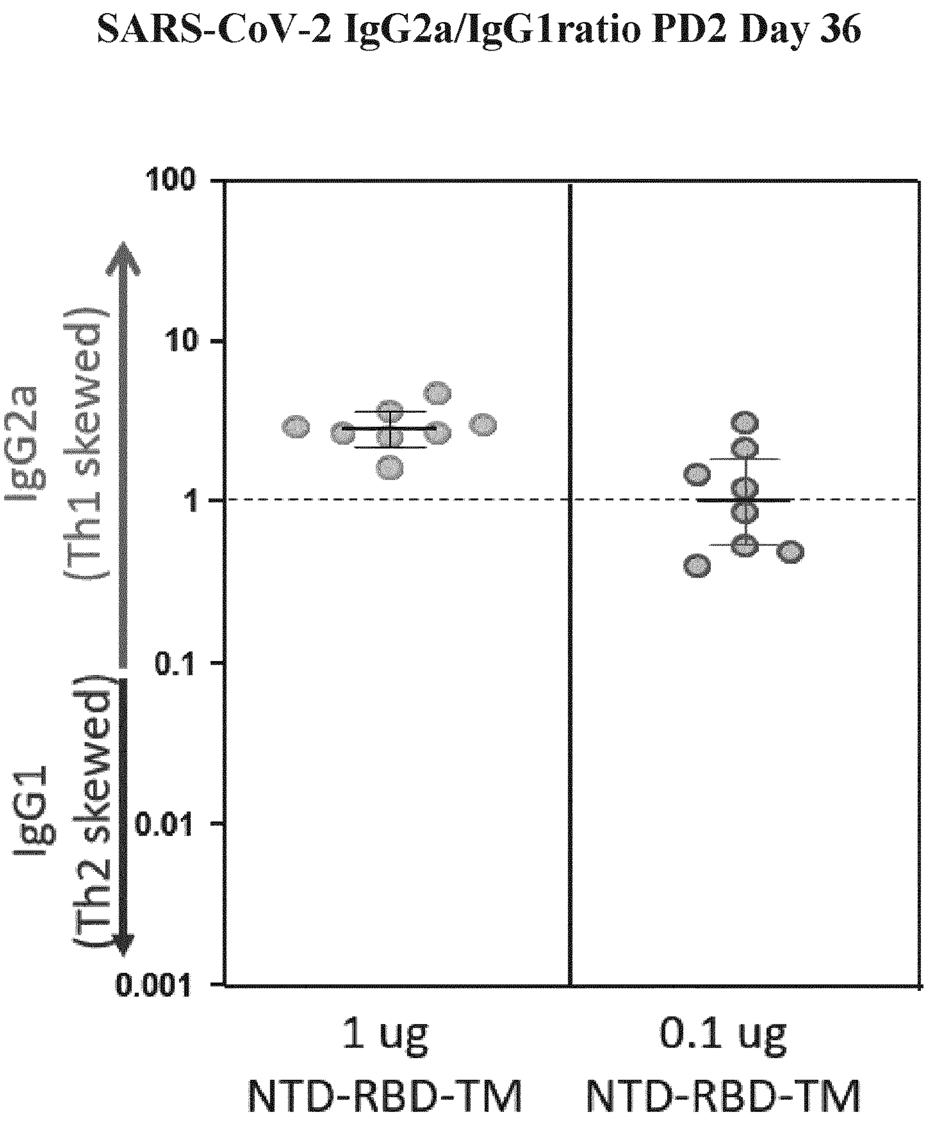
Figure 8C:
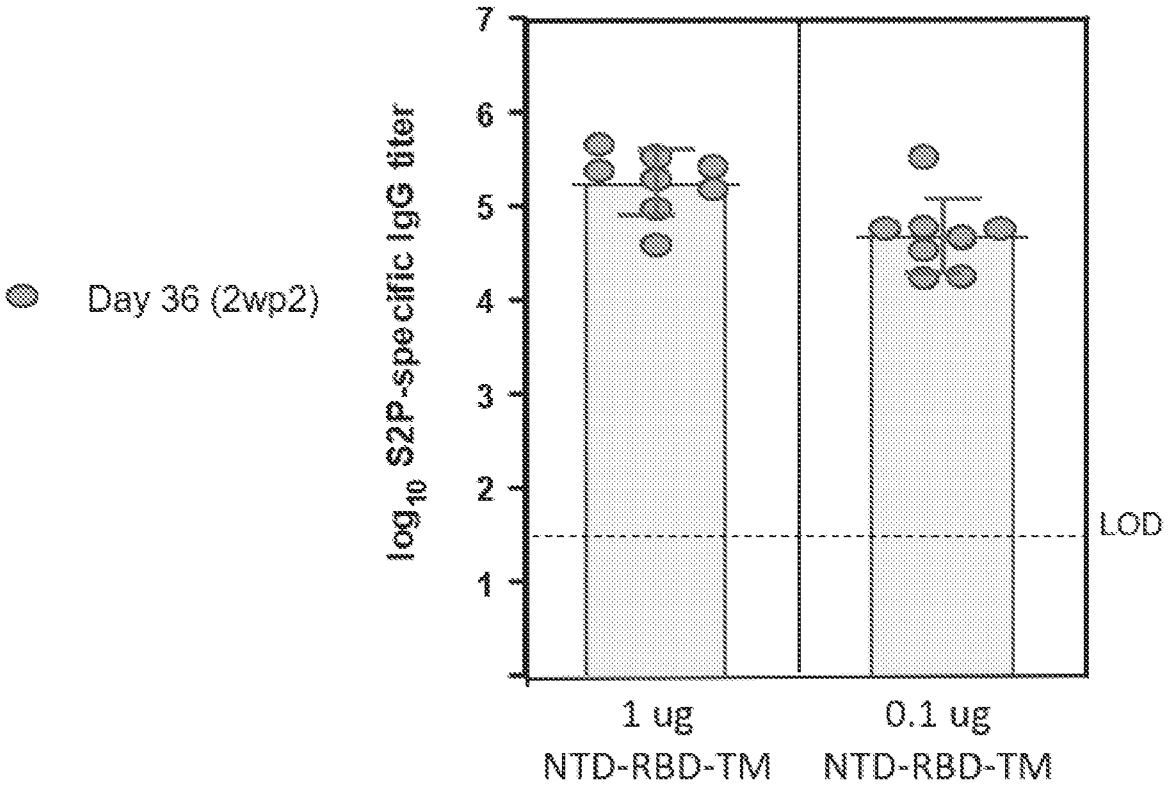

The compositions of NTD-RBD-TM, mRNA NTD-RBD-TM were administered to mice at the following doses: 0.1 μg and 1 μg. A prime dose was administered on Day 1, and a boost dose was administered on Day 22. On Day 36, S2P specific IgG1 and IgG2a titers were assessed. See FIGS. 8A-8C. By day 36, the titer of IgG2a was higher than the amount of IgG1 at both dose levels. See FIG. 8A. To determine whether the T cell response is skewed toward either a Th1 or a Th2 type of response, we plotted the ration of IgG2a/IgG1 at the day 36 timepoint. As shown in FIG. 8B, the NTD-RBD-TM composition induces an antibody within the Th1 type of response. Th2 type response is disfavored in vaccine development because of an association with driving disease enhancement.

Example 8. Immunogenocity Studies

The mRNAs listed in Table 29 were administered to mice at the following doses: 0.1 μg and 1 μg (N=8). A prime dose was administered on Day 1, and a boost dose was administered on Day 22. Serum IgG tiers were assayed on S2P coated plates on Day 21 and Day 36. Results are shown in Table 29.

TABLE 29

| Formulation/Material | Dose (μg) | Day 21 | Day 36 |
|---|---|---|---|
| PBS | | 1.097 | 1.097 |
| NTD-RBD-TM | 1 | 4.237 | 6.036 |
| | 0.1 | 2.711 | 5.106 |
| S1-666-TM (SEQ ID NO: 16) | 1 | 4.224 | 5.704 |
| | 0.1 | 1.944 | 4.633 |
| mix (50:50) NTD-EXT-F43C-TM | 1 | 3.939 | 5.442 |
| (SEQ ID NO: 55) + RBD-Q563D-EXT-TM (SEQ ID NO: 88) | 0.1 | 1.867 | 4.342 |
| NTD-EXT-RBD-EXT-TM (SEQ ID NO: 121) | 1 | 4.541 | 6.001 |
| | 0.1 | 3.694 | 4.885 |
| S1-594-TM (SEQ ID NO: 22) | 1 | 4.027 | 5.517 |
| | 0.1 | 3.313 | 4.780 |
| S1-594-PolyG-DS-TM (SEQ ID NO: 28) | 1 | 3.974 | 5.531 |
| | 0.1 | 2.551 | 4.425 |
| S2-TM (SEQ ID NO: 145) | 1 | 1.989 | 4.058 |
| | 0.1 | 1.097 | 2.015 |
| RBD-NTD-TM (SEQ ID NO: 139) | 1 | 4.523 | 6.062 |
| | 0.1 | 3.453 | 5.222 |
| NTD-PADRE-RBD-TM (SEQ ID NO: 142) | 1 | 4.489 | 6.040 |
| | 0.1 | 3.386 | 5.301 |

Additional Sequences

It should be understood that any of the mRNA sequences described herein may include a 5' UTR and/or a 3' UTR. The UTR sequences may be selected from the following sequences, or other known UTR sequences may be used. It should also be understood that any of the mRNA constructs described herein may further comprise a poly(A) tail and/or cap (e.g., 7mG(5')ppp(5')NlmpNp). Further, while many of the mRNAs and encoded antigen sequences described herein include a signal peptide and/or a peptide tag (e.g., C-terminal His tag), it should be understood that the indicated signal peptide and/or peptide tag may be substituted for a different signal peptide and/or peptide tag, or the signal peptide and/or peptide tag may be omitted.

5' UTR: GGGAAAUAAGAGAGAAAAGAAGAGUAAGAAGAAAUAUAAGAGCCACC (SEQ ID NO: 131)

5' UTR: GGGAAAUAAGAGAGAAAAGAAGAGUAAGAAGAAAUAUAAGACCCCGGCGCCGCCACC (SEQ ID NO: 2)

3' UTR:
UGAUAAUAGGCUGGAGCCUCGGUGGCCAUGCUUCUUGCCCCUUGGGCCUCCCCCCAGCCCCUCCUCCCCUUCCUGCAC
CCGUACCCCCGUGGUCUUUGAAUAAAGUCUGAGUGGGCGGC (SEQ ID NO: 132)

3' UTR:
UGAUAAUAGGCUGGAGCCUCGGUGGCCUAGCUUCUUGCCCCUUGGGCCUCCCCCCAGCCCCUCCUCCCCUUCCUGCAC
CCGUACCCCCGUGGUCUUUGAAUAAAGUCUGAGUGGGCGGC (SEQ ID NO: 4)

-continued

SARS-CoV-2 Wild Type Spike (S) Protein

| | | |
|---|---|---|
| SEQ ID NO: 123 consists of from 5' end to 3' end: 5' UTR SEQ ID NO: 2, mRNA ORF SEQ ID NO: 124, and 3' UTR SEQ ID NO: 4. | | 123 |
| Chemistry | 1-methylpseudouridine | |
| Cap | 7mG(5')ppp(5')NlmpNp | |
| 5' UTR | GGGAAAUAAGAGAGAAAAGAAGAGUAAGAAGAAAUAUAAGACCCCG<br>GCGCCGCCACC | 2 |
| ORF of mRNA Construct (excluding the stop codon) | AUGUUCGUGUUCCUGGUGCUGCUGCCCCUGGUGAGCAGCCAGUGCG<br>UGAACCUGACCACCCGGACCCAGCUGCCACCAGCCUACACCAACAG<br>CUUCACCCGGGGCGUCUACUACCCCGACAAGGUGUUCCGGAGCAGC<br>GUCCUGCACAGCACCCAGGACCUGUUCCUGCCCUUCUUCAGCAACG<br>UGACCUGGUUCCACGCCAUCCACGUGAGCGGCACCAACGGCACCAA<br>GCGGUUCGACAACCCCGUGCUGCCCUUCAACGACGGCGUGUACUUC<br>GCCAGCACCGAGAAGAGCAACAUCAUCCGGGGCUGGAUCUUCGGCA<br>CCACCCUGGACAGCAAGACCCAGAGCCUGCUGAUCGUGAAUAACGC<br>CACCAACGUGGUGAUCAAGGUGUGCGAGUUCCAGUUCUGCAACGAC<br>CCCUUCCUGGGCGUGUACUACCACAAGAACAACAAGAGCUGGAUGG<br>AGAGCGAGUUCCGGGUGUACAGCAGCGCCAACAACUGCACCUUCGA<br>GUACGUGAGCCAGCCCUUCCUGAUGGACCUGGAGGGCAAGCAGGGC<br>AACUUCAAGAACCUGCGGGAGUUCGUGUUCAAGAACAUCGACGGCU<br>ACUUCAAGAUCUACAGCAAGCACACCCCAAUCAACCUGGUGCGGGA<br>UCUGCCCCAGGGCUUCUCAGCCCUGGAGCCCCUGGUGGACCUGCCC<br>AUCGGCAUCAACAUCACCCGGUUCCAGACCCUGCUGGCCCUGCACC<br>GGAGCUACCUGACCCCAGGCGACAGCAGCAGCGGGUGGACAGCAGG<br>CGCGGCUGCUUACUACGUGGGCUACCUGCAGCCCCGGACCUUCCUG<br>CUGAAGUACAACGAGAACGGCACCAUCACCGACGCCGUGGACUGCG<br>CCCUGGACCCUCUGAGCGAGACCAAGUGCACCCUGAAGAGCUUCAC<br>CGUGGAGAAGGGCAUCUACCAGACCAGCAACUUCCGGGUGCAGCCC<br>ACCGAGAGCAUCGUGCGGUUCCCCAACAUCACCAACCUGUGCCCCU<br>UCGGCGAGGUGUUCAACGCCACCCGGUUCGCCAGCGUGUACGCCUG<br>GAACCGGAAGCGGAUCAGCAACUGCGUGGCCGACUACAGCGUGCUG<br>UACAACAGCGCCAGCUUCAGCACCUUCAAGUGCUACGGCGUGAGCC<br>CCACCAAGCUGAACGACCUGUGCUUCACCAACGUGUACGCCGACAG<br>CUUCGUGAUCCGUGGCGACGAGGUGCGGCAGAUCGCACCCGGCCAG<br>ACAGGCAAGAUCGCCGACUACAACUACAAGCUGCCCGACGACUUCA<br>CCGGCUGCGUGAUCGCCUGGAACAGCAACAACCUCGACAGCAAGGU<br>GGGCGGCAACUACAACUACCUGUACCGGCUGUUCCGGAAGAGCAAC<br>CUGAAGCCCUUCGAGCGGGACAUCAGCACCGAGAUCUACCAAGCCG<br>GCUCCACCCCUUGCAACGGCGUGGAGGGCUUCAACUGCUACUUCCC<br>UCUGCAGAGCUACGGCUUCCAGCCCACCAACGGCGUGGGCUACCAG<br>CCCUACCGGGUGGUGGUGCUGAGCUUCGAGCUGCUGCACGCCCCAG<br>CCACCGUGUGUGGCCCCAAGAAGAGCACCAACCUGGUGAAGAACAA<br>GUGCGUGAACUUCAACUUCAACGGCCUUACCGGCACCGGCGUGCUG<br>ACCGAGAGCAACAAGAAAUUCCUGCCCUUUCAGCAGUUCGGCCGGG<br>ACAUCGCCGACACCACCGACGCUGUGCGGGAUCCCCAGACCCUGGA<br>GAUCCUGGACAUCACCCCUUGCAGCUUCGGCGGCGUGAGCGUGAUC<br>ACCCCAGGCACCAACACCAGCAACCAGGUGGCCGUGCUGUACCAGG<br>ACGUGAACUGCACCGAGGUGCCCGUGGCCAUCCACGCCGACCAGCU<br>GACACCCACCUGGCGGGUCUACAGCACCGGCAGCAACGUGUUCCAG<br>ACCCGGGCCGGUUGCCUGAUCGGCGCCGAGCACGUGAACAACAGCU<br>ACGAGUGCGACAUCCCCAUCGGCGCCGGCAUCUGUGCCAGCUACCA<br>GACCCAGACCAAUUCACCCCGGAGGGCAAGGAGCGUGGCCAGCCAG<br>AGCAUCAUCGCCUACACCAUGAGCCUGGGCGCCGAGAACAGCGUGG<br>CCUACAGCAACAACAGCAUCGCCAUCCCCACCAACUUCACCAUCAG<br>CGUGACCACCGAGAUUCUGCCCGUGAGCAUGACCAAGACCAGCGUG<br>GACUGCACCAUGUACAUCUGCGGCGACAGCACCGAGUGCAGCAACC<br>UGCUGCUGCAGUACGGCAGCUUCUGCACCCAGCUGAACCGGGCCCU<br>GACCGGCAUCGCCGUGGAGCAGGACAAGAACACCCAGGAGGUGUUC<br>GCCCAGGUGAAGCAGAUCUACAAGACCCCUCCCAUCAAGGACUUCG<br>GCGGCUUCAACUUCAGCCAGAUCCUGCCCGACCCCAGCAAGCCCAG<br>CAAGCGGAGCUUCAUCGAGGACCUGCUGUUCAACAAGGUGACCCUA<br>GCCGACGCCGGCUUCAUCAAGCAGUACGGCGACUGCCUCGGCGACA<br>UAGCCGCCCGGGACCUGAUCUGCGCCCAGAAGUUCAACGGCCUGAC<br>CGUGCUGCCUCCCCUGCUGACCGACGAGAUGAUCGCCCAGUACACC<br>AGCGCCCUGUUAGCCGGAACCAUCACCAGCGGCUGGACUUUCGGCG<br>CUGGAGCCGCUCUGCAGAUCCCCUUCGCCAUGCAGAUGGCCUACCG<br>GUUCAACGGCAUCGGCGUGACCCAGAACGUGCUGUACGAGAACCAG<br>AAGCUGAUCGCCAACCAGUUCAACAGCGCCAUCGGCAAGAUCCAGG<br>ACAGCCUGAGCAGCACCGCUAGCGCCCUGGGCAAGCUGCAGGACGU<br>GGUGAACCAGAACGCCCAGGCCCUGAACACCCUGGUGAAGCAGCUG<br>AGCAGCAACUUCGGCGCCAUCAGCAGCGUGCUGAACGACAUCCUGA<br>GCCGGCUGGACAAGGUGGAGGCCGAGGUGCAGAUCGACCGGCUGAU<br>CACUGGCCGGCUGCAGAGCCUGCAGACCUACGUGACCCAGCAGCUG | 124 |

-continued

| | | |
|---|---|---|
| | AUCCGGGCCGCCGAGAUUCGGGCCAGCGCCAACCUGGCCGCCACCA<br>AGAUGAGCGAGUGCGUGCUGGGCCAGAGCAAGCGGGUGGACUUCUG<br>CGGCAAGGGCUACCACCUGAUGAGCUUUCCCCAGAGCGCACCCCAC<br>GGAGUGGUGUUCCUGCACGUGACCUACGUGCCCGCCCAGGAGAAGA<br>ACUUCACCACCGCCCCAGCCAUCUGCCACGACGGCAAGGCCCACUU<br>UCCCCGGGAGGGCGUGUUCGUGAGCAACGGCACCCACUGGUUCGUG<br>ACCCAGCGGAACUUCUACGAGCCCCAGAUCAUCACCACCGACAACA<br>CCUUCGUGAGCGGCAACUGCGACGUGGUGAUCGGCAUCGUGAACAA<br>CACCGUGUACGAUCCCCUGCAGCCCGAGCUGGACAGCUUCAAGGAG<br>GAGCUGGACAAGUACUUCAAGAAUCACACCAGCCCCGACGUGGACC<br>UGGGCGACAUCAGCGGCAUCAACGCCAGCGUGGUGAACAUCCAGAA<br>GGAGAUCGAUCGGCUGAACGAGGUGGCCAAGAACCUGAACGAGAGC<br>CUGAUCGACCUGCAGGAGCUGGGCAAGUACGAGCAGUACAUCAAGU<br>GGCCCUGGUACAUCUGGCUGGGCUUCAUCGCCGGCCUGAUCGCCAU<br>CGUGAUGGUGACCAUCAUGCUGUGCUGCAUGACCAGCUGCUGCAGC<br>UGCCUGAAGGGCUGUUGCAGCUGCGGCAGCUGCUGCAAGUUCGACG<br>AGGACGACAGCGAGCCCGUGCUGAAGGGCGUGAAGCUGCACUACAC<br>C | |
| 3' UTR | UGAUAAUAGGCUGGAGCCUCGGUGGCCUAGCUUCUUGCCCCUUGGG<br>CCUCCCCCCAGCCCCUCCUCCCCUUCCUGCACCCGUACCCCCGUGG<br>UCUUUGAAUAAAGUCUGAGUGGGCGGC | 4 |
| Corresponding amino acid sequence | MFVFLVLLPLVSSQCVNLTTRTQLPPAYTNSFTRGVYYPDKVFRSS<br>VLHSTQDLFLPFFSNVTWFHAIHVSGTNGTKRFDNPVLPFNDGVYF<br>ASTEKSNIIRGWIFGTTLDSKTQSLLIVNNATNVVIKVCEFQFCND<br>PFLGVYYHKNNKSWMESEFRVYSSANNCTFEYVSQPFLMDLEGKQG<br>NFKNLREFVFKNIDGYFKIYSKHTPINLVRDLPQGFSALEPLVDLP<br>IGINITRFQTLLALHRSYLTPGDSSSGWTAGAAAYYVGYLQPRTFL<br>LKYNENGTITDAVDCALDPLSETKCTLKSFTVEKGIYQTSNFRVQP<br>TESIVRFPNITNLCPFGEVENATRFASVYAWNRKRISNCVADYSVL<br>YNSASFSTFKCYGVSPTKLNDLCFTNVYADSFVIRGDEVRQIAPGQ<br>TGKIADYNYKLPDDFTGCVIAWNSNNLDSKVGGNYNYLYRLFRKSN<br>LKPFERDISTEIYQAGSTPCNGVEGFNCYFPLQSYGFQPTNGVGYQ<br>PYRVVVLSFELLHAPATVCGPKKSTNLVKNKCVNFNFNGLTGTGVL<br>TESNKKFLPFQQFGRDIADTTDAVRDPQTLEILDITPCSFGGVSVI<br>TPGTNTSNQVAVLYQDVNCTEVPVAIHADQLTPTWRVYSTGSNVFQ<br>TRAGCLIGAEHVNNSYECDIPIGAGICASYQTQTNSPRRARSVASQ<br>SIIAYTMSLGAENSVAYSNNSIAIPTNFTISVTTEILPVSMTKTSV<br>DCTMYICGDSTECSNLLLQYGSFCTQLNRALTGIAVEQDKNTQEVF<br>AQVKQTYKTPPIKDFGGFNFSQILPDPSKPSKRSFIEDLLFNKVTL<br>ADAGFIKQYGDCLGDIAARDLICAQKFNGLTVLPPLLTDEMIAQYT<br>SALLAGTITSGWTFGAGAALQIPFAMQMAYRENGIGVTQNVLYENQ<br>KLIANQFNSAIGKIQDSLSSTASALGKLQDVVNQNAQALNTLVKQL<br>SSNFGAISSVLNDILSRLDKVEAEVQIDRLITGRLQSLQTYVTQQL<br>IRAAEIRASANLAATKMSECVLGQSKRVDFCGKGYHLMSFPQSAPH<br>GVVFLHVTYVPAQEKNFTTAPAICHDGKAHFPREGVFVSNGTHWFV<br>TQRNFYEPQIITTDNTFVSGNCDVVIGIVNNTVYDPLQPELDSFKE<br>ELDKYFKNHTSPDVDLGDISGINASVVNIQKEIDRLNEVAKNLNES<br>LIDLQELGKYEQYIKWPWYIWLGFIAGLIAIVMVTIMLCCMTSCCS<br>CLKGCCSCGSCCKFDEDDSEPVLKGVKLHYT | 125 |
| PolyA tail | 100 nt | |

It should also be understood that any one of the open reading frames and/or corresponding amino acid sequences described herein may include or exclude a signal sequence.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The terms "about" and "substantially" preceding a numerical value mean±10% of the recited numerical value.

Where a range of values is provided, each value between the upper and lower ends of the range are specifically contemplated and described herein.

The entire contents of International Application Nos. PCT/US2015/02740, PCT/US2016/043348, PCT/US2016/043332, PCT/US2016/058327, PCT/US2016/058324, PCT/US2016/058314, PCT/US2016/058310, PCT/US2016/058321, PCT/US2016/058297, PCT/US2016/058319, and PCT/US2016/058314 are incorporated herein by reference.

What is claimed is:

1. A vaccine comprising a messenger ribonucleic acid (mRNA) in a lipid nanoparticle (LNP), wherein the mRNA in the vaccine comprises an open reading frame (ORF) encoding a fusion protein comprising a N-terminal domain (NTD) of a SARS-CoV-2 Spike protein linked via a first linker to a receptor binding domain (RBD) of the SARS-CoV-2 Spike protein, wherein the RBD is linked via a second linker to a transmembrane domain (TD).

2. The vaccine of claim 1, wherein the ORF comprises nucleosides consisting of 1-methylpseudouridine, adenosine, guanosine, and cytidine.

3. The vaccine of claim 2, wherein the TD is an influenza hemagglutinin transmembrane domain.

4. The vaccine of claim 3, wherein the first linker is a glycine-serine (GS) linker and the second linker is a GS linker.

5. The vaccine of claim 4, wherein the first linker comprises an amino acid sequence comprising GGGS (SEQ ID NO: 136) and wherein the second linker comprises an amino acid sequence comprising GGGS (SEQ ID NO: 136).

6. The vaccine of claim 5, wherein the amino acid sequence of the second linker comprises SGGGS (SEQ ID NO: 138).

7. The vaccine of claim 3, wherein the LNP comprises a molar ratio of about 20-60 mol % ionizable cationic lipid, 5-25 mol % neutral lipid, 25-55 mol % sterol, and 0.5-15 mol % PEG-modified lipid.

8. The vaccine of claim 7, wherein the ionizable cationic lipid comprises a compound of Formula (I):

(I)

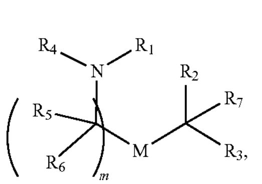

or a salt or isomer thereof, wherein:

$R_1$ is selected from the group consisting of $C_{5-30}$ alkyl, $C_{5-20}$ alkenyl, and-R"M'R';

$R_2$ and $R_3$ are independently selected from the group consisting of $C_{1-14}$ alkyl and $C_{2-14}$ alkenyl;

$R_4$ is $—(CH_2)_nQ$, wherein Q is —OR, and n is selected from 1, 2, 3, 4, and 5;

each $R_5$ is H;

each $R_6$ is H;

M and M' are independently selected from —C(O)O— and —OC(O)—;

$R_7$ is H;

R is H;

R' is selected from the group consisting of $C_{1-18}$ alkyl and $C_{2-18}$ alkenyl;

R" is selected from the group consisting of $C_{3-14}$ alkyl and $C_{3-14}$ alkenyl; and m is selected from 5, 6, 7, 8, 9, 10, 11, 12, and 13.

9. The vaccine of claim 1, wherein the RBD comprises an amino acid sequence at least 85% identical to amino acids 21-220 of SEQ ID NO: 77.

10. The vaccine of claim 9, wherein the NTD comprises an amino acid sequence at least 85% identical to amino acids 14-290 of SEQ ID NO: 92.

11. The vaccine of claim 10, wherein the TD comprises an amino acid sequence comprising ILAIYSTVASSLVLL-VSLGAISF (amino acids 226-248 of SEQ ID NO: 77).

12. A vaccine comprising a messenger ribonucleic acid (mRNA) in a lipid nanoparticle (LNP), wherein the mRNA in the vaccine comprises an open reading frame (ORF) encoding a fusion protein comprising a N-terminal domain (NTD) of a SARS-CoV-2 Spike protein linked to a receptor binding motif (RBM) of the SARS-CoV-2 Spike protein via a first GS linker, wherein the RBM is linked to a transmembrane domain (TD) via a second GS linker, and wherein the open reading frame comprises nucleosides consisting of 1-methylpseudouridine, adenosine, guanosine, and cytidine.

13. The vaccine of claim 12, wherein the fusion protein comprises a receptor binding domain (RBD) comprising the RBM.

14. The vaccine of claim 13, wherein the RBD comprises an amino acid sequence at least 85% identical to a RBD domain of SEQ ID NO: 92.

15. The vaccine of claim 14, wherein the TD is an influenza hemagglutinin TD.

16. The vaccine of claim 15, wherein the second GS linker comprises SGGGS (SEQ ID NO: 138).

17. The vaccine of claim 16, wherein the first GS linker comprises GGGSGGG (SEQ ID NO: 135).

18. The vaccine of claim 17, wherein the NTD comprises an amino acid sequence at least 85% identical to a NTD domain of SEQ ID NO: 92.

19. The vaccine of claim 12, wherein the fusion protein comprises an amino acid sequence at least 85% identical to SEQ ID NO: 92.

20. The vaccine of claim 19, wherein the LNP comprises a molar ratio of about 20-60 mol % ionizable cationic lipid, 5-25 mol % neutral lipid, 25-55 mol % sterol, and 0.5-15 mol % PEG-modified lipid.

* * * * *